(12) United States Patent
Gaiger et al.

(10) Patent No.: US 7,915,393 B2
(45) Date of Patent: Mar. 29, 2011

(54) COMPOSITIONS AND METHODS FOR WT1 SPECIFIC IMMUNOTHERAPY

(75) Inventors: Alexander Gaiger, Vienna (AT); Patricia D. McNeill, Federal Way, WA (US); Nomalie Jaya, Tucson, AZ (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 12/470,408

(22) Filed: May 21, 2009

(65) Prior Publication Data

US 2009/0312403 A1 Dec. 17, 2009

Related U.S. Application Data

(63) Continuation of application No. 10/427,717, filed on Apr. 30, 2003, now Pat. No. 7,553,494, which is a continuation-in-part of application No. 10/286,333, filed on Oct. 30, 2002, now abandoned, which is a continuation-in-part of application No. 10/244,830, filed on Sep. 16, 2002, now abandoned, which is a continuation-in-part of application No. 10/195,835, filed on Jul. 12, 2002, now Pat. No. 7,655,249, which is a continuation-in-part of application No. 10/125,635, filed on Apr. 16, 2002, now abandoned, which is a continuation-in-part of application No. 10/002,603, filed on Oct. 30, 2001, which is a continuation-in-part of application No. 09/938,864, filed on Aug. 24, 2001, now abandoned.

(51) Int. Cl.
| | |
|---|---|
| C12N 15/11 | (2006.01) |
| C12N 15/12 | (2006.01) |
| C12N 15/63 | (2006.01) |
| C12N 15/70 | (2006.01) |
| C12N 5/10 | (2006.01) |
| A61K 48/00 | (2006.01) |

(52) U.S. Cl. ............... 536/23.1; 514/44 R; 536/23.4; 536/23.5; 435/320.1; 435/325; 435/252.3; 435/254.11; 435/252.33

(58) Field of Classification Search .................. None
See application file for complete search history.

(56) References Cited

U.S. PATENT DOCUMENTS

| | | | |
|---|---|---|---|
| 5,350,840 A | 9/1994 | Call et al. | 536/23.1 |
| 5,622,835 A | 4/1997 | Herlyn et al. | 435/328 |
| 5,633,142 A | 5/1997 | Herlyn et al. | 435/7.23 |
| 5,670,317 A | 9/1997 | Ladanyi et al. | 435/6 |
| 5,679,356 A | 10/1997 | Bonnem et al. | 424/278.1 |
| 5,693,522 A | 12/1997 | Chada et al. | 435/2.402 |
| 5,726,288 A | 3/1998 | Call et al. | 530/350 |
| 6,034,235 A | 3/2000 | Sugiyama et al. | 536/24.5 |
| 6,096,313 A | 8/2000 | Jäger et al. | 424/184.1 |
| 6,277,832 B1 | 8/2001 | Sugiyama et al. | 514/44 |
| 6,316,599 B1 | 11/2001 | Call et al. | 530/387.7 |
| 6,818,751 B1 | 11/2004 | Xu et al. | 536/23.1 |
| 7,063,854 B1 | 6/2006 | Gaiger et al. | 424/277.1 |
| 7,115,272 B1 | 10/2006 | Gaiger et al. | 424/277.1 |
| 7,144,581 B2 | 12/2006 | Gaiger et al. | 424/277.1 |
| 7,316,924 B2 | 1/2008 | Bron et al. | 435/320.1 |
| 7,329,410 B1 | 2/2008 | Gaiger et al. | 424/277.1 |
| 2003/0039635 A1 | 2/2003 | Gaiger et al. | 424/93.2 |
| 2003/0072767 A1 | 4/2003 | Gaiger et al. | 424/185.1 |

FOREIGN PATENT DOCUMENTS

| | | |
|---|---|---|
| EP | 1004319 A1 | 5/2000 |
| EP | 1103564 A1 | 5/2001 |
| JP | 06-128299 | 5/1994 |
| JP | 11-89596 A | 4/1999 |
| JP | 11-89599 A | 4/1999 |
| WO | WO 91/07509 | 5/1991 |
| WO | WO 94/21287 | 9/1994 |
| WO | WO95/06725 | 3/1995 |
| WO | WO95/29995 | 11/1995 |
| WO | WO 96/38176 | 12/1996 |
| WO | WO 99/03506 | 1/1999 |
| WO | 99/51753 A1 | 10/1999 |
| WO | WO99/58135 | 11/1999 |
| WO | WO 00/06602 | 2/2000 |
| WO | WO 00/18795 | 4/2000 |
| WO | WO 00/26249 | 5/2000 |
| WO | WO 01/25273 | 4/2001 |
| WO | WO 01/60970 | 8/2001 |
| WO | WO 01/62920 | 8/2001 |
| WO | WO 01/72786 | 10/2001 |
| WO | WO 01/94629 | 12/2001 |
| WO | WO 02/00677 | 1/2002 |
| WO | WO 02/28414 | 4/2002 |
| WO | WO 03/037060 | 5/2003 |

OTHER PUBLICATIONS

Aaronson and Todaro, "Development of 3t3-like lines from Balb/c mouse embryo cultures: transformation susceptibility to SV40," *J. Cell. Physiol.* 72(2):141-148, Oct. 1968.

Adachi et al., "Midkine as a novel target gene for the Wilms' tumor suppressor gene (WT1)," *Oncogene* 13: 2197-2203, 1996.

Algar et al., "A WT1 antisense oligonucleotide inhibits proliferation and induces apoptosis in myeloid leukaemia cell lines," *Oncogene* 12: 1005-1014, 1996.

Altman et al., "Phenotypic analysis of antigen-specific T lymphocytes," *Science* 274:94-96, Oct. 4, 1996.

Appel, R.D. et al., "A new generation of information retrieval tools for biologists: the example of the ExPASy WWW server," *Trends in Biochemical Sciences* 19(6): 258-260, Jun. 1994.

Armstrong et al., "The expression of the Wilms' tumour gene, WT1, in the developing mammalian embryo," *Mechanisms of Development* 40: 85-97, 1992.

Bellantuono et al., "Selective elimination of leukemic progenitors by allorestricted CTL specific for WILMS Tumor Antigen-1 (WT-1)," *Blood*, 94(10):532A-533A, Nov. 15, 1999.

(Continued)

*Primary Examiner* — Ron Schwadron
(74) *Attorney, Agent, or Firm* — Seed IP Law Group PLLC

(57) ABSTRACT

Compositions and methods for the therapy of malignant diseases, such as leukemia and cancer, are disclosed. The compositions comprise one or more of a WT1 polynucleotide, a WT1 polypeptide, an antigen-presenting cell presenting a WT1 polypeptide, an antibody that specifically binds to a WT1 polypeptide; or a T cell that specifically reacts with a WT1 polypeptide. Such compositions may be used, for example, for the prevention and treatment of metastatic diseases.

18 Claims, 43 Drawing Sheets

OTHER PUBLICATIONS

Bergmann et al., "High Levels of Wilms' Tumor Gene (wt1) mRNA in Acute Myeloid Leukemias Are Associated With a Worse Long-Term Outcome," *Blood* 90(3): 1217-1225, 1997.

Bergmann et al., "Wilms Tumor Gene Expression in Acute Myeloid Leukemias," *Leukemia and Lymphoma* 25: 435-443, 1997.

Blaudeck, N. et al., "Specificity of Signal Peptide Recognition in Tat-Dependent Bacterial Protein Translocation," *Journal of Bacteriology* 183(2): 604-610, Jan. 2001.

Boon, T., "Tumor Antigens Recognized by Cytolytic T Lymphocytes: Present Perspectives for Specific Immunotherapy," *Int. J. Cancer* 54: 177-180, 1993.

Brenner et al., "RNA polymerase chain reaction detects different levels of four alternatively spliced *WT1* transcripts in Wilms' tumors," *Oncogene* 7: 1431-1433, 1992.

Brieger et al., "The Expression of the Wilms' Tumor Gene in Acute Myelocytic Leukemias as Possible Marker for Leukemic Blast Cells," *Leukemia* 8(12): 2138-2143, 1994.

Brieger et al., "The Wilms' tumor gene is frequently expressed in acute myeloblastic leukemias and may provide a marker for residual blast cells detectable by PCR," *Annals of Oncology* 6: 811-816, 1995.

Buckler et al., "Isolation, Characterization, and Expression of the Murine Wilms' Tumor Gene (WT1) During Kidney Development," *Molecular and Cellular Biology* 11: 1707-1712, 1991.

Call et al., "Isolation and Characterization of a Zinc Finger Polypeptide Gene at the Human Chromosome 11 Wilms' Tumor Locus," *Cell* 60: 509-520, 1990.

Carapeti et al., "Dominant-negative mutations of the Wilms' tumour predisposing gene (WT1) are infrequent in CML blast crisis and de novo acute leukaemia," *Eur. J. Haematol.* 58: 346-349, 1997.

Charles et al., "Expression of the Wilms' tumour gene WT1 in the developing human and in paediatric renal tumours: an immunohistochemical study," *J. Clin. Pathol.: Mol. Pathol.* 50: 138-144, 1997.

Charles et al., "Immunohistochemical detection of the Wilms' tumour gene WT1 in desmoplastic small round cell tumour," *Histopathology* 30: 312-314, 1997.

Chen et al., "T-cells for tumor therapy can be obtained from antigen-loaded sponge implants," *Cancer Research* 54(4):1065-1070, Feb. 15, 1994.

Chesebro et al., "Characterization of Ia8 antigen, THY-1.2 antigen, complemnt receptors, and virus production in a group of murine virus-induced leukemia cell lines," *The Journal of Immunology* 117(4):1267-1274, Oct. 1976.

Crawford et al., "Detection of antigen-specific T cells with multivalent soluble class II MHC covalent peptide complexes," *Immunity* 8:675-682, Jun. 1998.

De Bruijn et al., "Peptide loading of empty major histocompatibility complex molecules on RMA-S cells allows the induction of primary cytotoxic T lymphocyte responses," *Eur J Immunol* 21(12):2963-2970, Dec. 1991.

Deavin et al., "Statistical comparison of established T-cell eptiope predictors against a large database of human and murine antigens," *Molecular Immunology*, 33(2):145-155, 1996.

Drummond et al., "Repression of the Insulin-Like Growth Factor Gene by the Wilms Tumor Suppressor WT1," *Science* 257: 674-677, 1992.

Feller and de la Cruz, "Tsites (Version 1.1) A computer program to determine T cell epitopes using four predictive algorithms," *Nature* 349: 720-721, 1991.

Foster et al., "Characterization of prostatic epithelial cell lines derived from transgenic adenocarcinoma of the mouse prostate (TRAMP) model," *Cancer Research* 57(16):3325-3330, Aug. 15, 1997.

Frazier et al., "Expression of the Tumor Suppressor Gene WT1 in Both Human and Mouse Bone Marrow," *Blood* 86: 4704-4706, 1995 (letter).

Gaiger et al., "Immunity to WT1 in animal models and leukemia pateints," *Blood*, 94(10):78, Nov. 15, 1999.

Gaiger et al., "Immunity to WT1 in the animal model and in patients with acute myeloid leukemia," *Blood* 96(4):1480-1489, Aug. 15, 2000.

Gaiger et al., "WT1: A new leukemia and cancer antigen A," *Proceedings of the Annual Meeting of the American Association for Cancer Research*, 40:424, 1999.

Gillis and Smith, "Long term culture of tumour-specific cytotoxic T cells," *Nature* 268:154-156, Jul. 14, 1977.

Glynn et al., "Cross-resistance to the transplantation of syngeneic friend, moloney, and rauscher virus-induced tumors," *Cancer Research* 28(3):434-439, Mar. 1968.

Goodyer et al., "Repression of the retinoic acid receptor-$\alpha$ gene by the Wilms' tumor suppressor gene product, wt1," *Oncogene* 10: 1125-1129, 1995.

Haber et al., "A dominant mutation in the Wilms tumor gene *WT1* cooperates with the viral oncogene *E1A* in transformation of primary kidney cells," *Proc. Natl. Acad. Sci. USA* 89: 6010-6014, 1992.

Haber et al., "Alternative splicing and genomic structure of the Wilms tumor gene *WT1*," *Proc. Natl. Acad. Sci. USA* 88: 9618-9622, 1991.

Haber et al., "An Internal Deletion within an 11p13 Zinc Finger Gene Contributes to the Development of Wilms' Tumor," *Cell* 61: 1257-1269, 1990.

Hamilton et al., "High affinity binding sites for the Wilms' tumour suppressor protein WT1," *Nucleic Acids Research* 23(2): 277-284, 1995.

Harrington et al., "Inhibition of Colony-stimulating Factor-1 Promoter Activity by the Product of the Wilms' Tumor Locus," *The Journal of Biological Chemistry* 268(28): 21271-21275, 1993.

Horibata and Harris, "Mouse myelomas and lyphomas in culture," *Experimental Cell Research* 60:61-77, 1970.

Huang et al., "Tissue, Developmental, and Tumor-Specific Expression of Divergent Transcripts in Wilms Tumor," *Science* 250: 991-994, 1990.

Inoue et al., "Aberrant Overexpression of the Wilms Tumor Gene (WT1) in Human Leukemia," *Blood* 89(4): 1405-1412, 1997.

Inoue et al., "Long-Term Follow-Up of Minimal Residual Disease in Leukemia Patients by Monitoring WT1 (Wilms Tumor Gene) Expression Levels," *Blood* 88: 2267-2278, 1996.

Inoue et al., "Wilms' Tumor Gene (WT1) Competes With Differentiation-Inducing Signal in Hematopoetic Progenitor Cells," *Blood* 91(8): 2969-2976, 1998.

Inoue et al., "WT1 as a New Prognostic Factor and a New Marker for the Detection of Minimal Residual Disease in Acute Leukemia," *Blood* 84: 3071-3079, 1994.

King-Underwood and Pritchard-Jones, "Wilms' Tumor (*WT1*) Gene Mutations Occur Mainly in Acute Myeloid Leukemia and May Confer Drug Resistance," *Blood* 91(8): 2961-2968, 1998.

King-Underwood et al., "Mutations in the Wilms' Tumor Gene WT1 in Leukemias," *Blood* 91: 2961-2968, 1998.

Kreidberg et al., "WT-1 Is Required for Early Kidney Development," *Cell* 74: 679-691, 1993.

Kudoh et al., "Constitutive expression of the Wilms tumor suppressor gene WT1 in F9 embryonal carcinoma cells induces apoptotic cell death in response to retinoic acid," *Oncogene* 13: 1431-1439, 1996.

Kudoh et al., "$G_1$ phase arrest induced by Wilms tumor protein WT1 is abrogated by cyclin/CDK complexes," *Proc. Natl. Acad. Sci. USA* 92: 4517-4521, 1995.

Kwok and Higuchi, "Avoiding false positives with PCR," *Nature* 339:237-238, May 18, 1989.

Larsson et al., "Subnuclear Localization of WT1 in Splicing or Transcription Factor Domains Is Regulated by Alternative Splicing," *Cell* 81: 391-401, 1995.

Ljunggren et al., "Empty MHC class I molecules come out in the cold," *Nature* 346:476-480, Aug. 2, 1990.

Lozzio and Lozzio, "Human chronic myelogenous leukemia cell-line with positive Philadelphia chromosome," *Blood* 45(3):321-334, Mar. 1975.

Luo et al., "The tumor suppressor gene WT1 inhibits *ras*-mediated transformation," *Oncogene* 11: 743-750, 1995.

Madden et al., "Transcriptional Repression Mediated by the WT1 Wilms Tumor Gene Product," *Science* 253: 1550-1552, 1991.

Maurer et al., "The Wilms' tumor gene is expressed in a subset of CD34 progenitors and downregulated early in the course of differentiation in vitro," *Experimental Hematology* 25: 945-950, 1997.

Menke et al., "Wilms' Tumor 1 splice variants have opposite effects on the tumorigenicity of adenovirus-transformed baby-rat kidney cells," *Oncogene* 12: 537-546, 1996.

Menssen et al., "Detection By Monoclonal Antibodies Of The Wilms' Tumor (WT1) Nuclear Protein In Patients With Acute Leukemia," *Int. J. Cancer* 70: 518-523, 1997.

Menssen et al., "Presence of Wilms' tumor gene (*wt1*) transcripts and the WT1 nuclear protein in the majority of human acute leukemias," *Leukemia* 9: 1060-1067, 1995.

Menssen et al., "Wilms' Tumor Gene Expression in Human CD34 Hematopoietic Progenitors During Fetal Development and Early Clonogenic Growth," *Blood* 89(9): 3486-3487, 1997 (letter).

Miwa et al., "Expression of the Wilms' Tumor Gene (WT1) in Human Leukemias," *Leukemia* 6(5): 405-409, 1992.

Miyagi et al., "Expression of the Candidate Wilms' Tumor Gene, *WT1*, in Human Leukemia Cells," *Leukemia* 7(7): 970-977, 1993.

Morris et al., "Characterization of the zinc finger protein encoded by the WT1 Wilms' tumor locus," *Oncogene* 6: 2339-2348, 1991.

Mundlos et al., "Nuclear localization of the protein encoded by the Wilms' tumor gene *WT1* in embryonic and adult tissues," *Development* 119: 1329-1341, 1993.

Murata et al., "The Wilms tumor suppressor gene WT1 induces G1 arrest and apoptosis in myeloblastic leukemia M1 cells," *FEBS Letters* 409: 41-45, 1997.

Nakagama et al., "Sequence and Structural Requirements for High-Affinity DNA Binding by the WT1 Gene Product," *Molecular and Cellular Biology* 15(3): 1489-1498, 1995.

Nichols et al., "WT1 Induces Expression of Insulin-like Growth Factor 2 in Wilms' Tumor Cells," *Cancer Research* 55: 4540-4543, 1995.

Ogawa et al., "Successful donor leukocyte transfusion at molecular relapse for a patient with acute myeloid leukemia who was treated with allogeneic bone marrow transplantation: importance of the monitoring of minimal residual disease by WT1 assay," *Bone Marrow Transplantation* 21: 525-527, 1998.

Old et al., "Antigenic properties of chemically induced tumors," *Annals of the New York Academy of Sciences* 101:80-107, Nov. 20, 1962.

Osaka et al., "WT1 Contributes to Leukemogenesis: Expression Patterns in 7,12-Dimethylbenz[a]Anthracene (DMBA)-Induced Leukemia," *International Journal of Cancer* 72: 696-699, 1997.

Parker et al., "Scheme for Ranking Potential HLA-A2 Binding Peptides Based on Independent Binding of Individual Peptide Side-Chains," *Journal of Immunology* 152: 163-175, 1994.

Patek et al., "Transformed cell lines susceptible or resistant to in vivo surveillance against tumorigenesis," *Nature* 276:510-511, Nov. 30, 1978.

Patmasiriwat et al., "Expression pattern of WT1 and GATA-1 in AML with chromosome 16q22 abnormalities," *Leukemia* 10: 1127-1133, 1996.

Peitsch, M.C., "ProMod and Swiss-Model: Internet-based tools for automated comparative protein modelling," *Biochemical Society Transactions* 24(1): 274-279, Feb. 1996.

Pelletier et al., "Expression of the Wilms' tumor gene WT1 in the murine urogenital system," *Genes & Development* 5: 1345-1356, 1991.

Pelletier et al., "Germline Mutations in the Wilms' Tumor Suppressor Gene Are Associated with Abnormal Urogenital Development in Denys-Drash Syndrome," *Cell* 67: 437-447, 1991.

Phelan et al., "Wilms' Tumor Gene, *WT1*, mRNA Is Down-regulated during Induction of Erythroid and Megakaryocytic Differentiation of K562 Cells," *Cell Growth & Differentiation* 5: 677-686, 1994.

Pogue et al., "Amino-terminal alteration of the HLA-A*0201-restricted human immunodeficiency virus pol peptide increases complex stability and *in vitro* immunogenicity," *Proc. Natl. Acad. Sci. USA* 92: 8166-8170, 1995.

Pritchard-Jones et al., "The candidate Wilms' tumour gene is involved in genitourinary development," *Nature* 346: 194-197, 1990.

Pritchard-Jones et al., "The Wilms tumour (WT1) gene is mutated in a secondary leukaemia in a WAGR patient," *Human Molecular Genetics* 3(9): 1633-1637, 1994.

Rackley et al., "Expression of the Wilms' Tumor Suppressor Gene *WT1* during Mouse Embryogenesis," *Cell Growth & Differentiation* 4: 1023-1031, 1993.

Ramani and Cowell, "The Expression Pattern Of Wilms' Tumour Gene (*WT1*) Product In Normal Tissues And Paediatric Renal Tumours," *Journal Of Pathology* 179: 162-168, 1996.

Rammensee, H. et al., "SYFPEITHI: database for MHC ligands and peptide motifs," *Immunogenetics* 50(3-4): 213-219, Nov. 1999.

Rauscher et al., "Binding of the Wilms' Tumor Locus Zinc Finger Protein to the EGR-1 Consensus Sequence," *Science* 250: 1259-1262, 1990.

Rauscher et al., "Characterization of monoclonal antibodies directed to the amino-terminus of the WT1, Wilms' tumor suppressor," *Hybridoma*, 17(2):191-198, Apr. 1998.

Rauscher, "The WT1 Wilms tumor gene product: a developmentally regulated transcription factor in the kidney that functions as a tumor suppressor," *FASEB J.* 7: 896-903, 1993.

Reddy et al., "WT1-mediated Transcriptional Activation Is Inhibited by Dominant Negative Mutant Proteins," *The Journal of Biological Chemistry* 270(18): 10878-10884, 1995.

Rothbard and Taylor, "A sequence pattern common to T cell epitopes," *EMBO Journal*, 7(1):93-100, 1988.

Rupprecht et al., "The Wilms' Tumor Suppressor Gene WT1 Is Negatively Autoregulated," *The Journal of Biological Chemistry* 269(8): 6198-6206, 1994.

Sadovnikova et al., "Generation of human tumor-reactive cytotoxic T-cells against peptides presented by non-self HLA class I molecules," *Eur.J. Immunol.*, 28:193-200, 1998.

Santini, Claire-Lise et al., "Translocation of Jellyfish Green Fluorescent Protein via the Tat System of *Escherichia coli* and Change of Its Periplasmic Localization in Response to Osmotic Up-shock," *Journal of Biological Chemistry* 276(11): 8159-8164, Mar. 16, 2001.

Schmid et al., "Prognostic significance of WT1 gene expression at diagnosis in adult *de novo* acute myeloid leukemia," *Leukemia* 11: 639-643, 1997.

Sekiya et al., "Downregulation of Wilms' Tumor Gene (wt1) During Myelomonocytic Differentiation in HL60 Cells," *Blood* 83(7): 1876-1882, 1994.

Sharma et al., "Molecular Cloning of Rat Wilms' Tumor Complementary DNA and a Study of Messenger RNA Expression in the Urogenital System and the Brain," *Cancer Research* 52: 6407-6412, 1992.

Silberstein et al., "Altered expression of the WT1 Wilms tumor suppressor gene in human breast cancer," *Proc. Natl. Acad. Sci. USA* 94: 8132-8137, 1997.

Skeiky et al., "Cloning, expression, and immunological evaluation of two putative secreted serine protease antigens of Mycobacterium tuberculosis," *Infection and Immunity* 67(8):3998-4007, Aug. 1999.

Slavin and Strober, "Spontaneous murine B-cell leukaemia," *Nature* 272:624-626, Apr. 13, 1978.

Svedberg et al., "Constitutive expression of the Wilms' tumor gene (WT1) in the leukemic cell line U937 blocks parts of the differentiation program," *Oncogene* 15: 1-8, 1997.

Tadokoro et al., "Genomic Organization of the Human WT1 Gene," *Jpn. J. Cancer Res.* 83: 1198-1203, 1992.

Tadokoro et al., "Intragenic homozygous deletion of the *WT1* gene in Wilms' tumor," *Oncogene* 7: 1215-1221, 1992.

Tadokoro et al., "PCR Detection of 9 Polymorphisms in the WT1 Gene," *Human Molecular Genetics* 2(12): 2205-2206, 1993.

Tadokoro et al., "Taql RFLPs at the Wilms' tumor gene (WT1)," *Nucleic Acids Research* 19(9): 2514, 1991.

Telerman et al., "Identification of the cellular protein encoded by the human Wilms' tumor (WT1) gene," *Oncogene* 7: 2545-2548, 1992.

Toes et al., "Efficient tumor eradication by adoptively transferred cytotoxic T-cell clones in allogeneic hosts," *Int. J. Cancer*, 66:686-691, 1996.

Tsurutani et al., "cDNA cloning and developmental expression of the porcine homologue of *WT1*," *Gene* 211(2): 215-220, 1998.

Wang et al., "A second transcriptionally active DNA-binding site for the Wilms tumor gene product, WT1," *Proc. Natl. Acad. Sci. USA* 90: 8896-8900, 1993.

Wang et al., "The Wilms' Tumor Gene Product WT1 Activates or Suppresses Transcription through Separate Functional Domains," *The Journal of Biological Chemistry* 268(13): 9172-9175, 1993.

Wang et al., "The Wilms' Tumor Gene Product, WT1, Represses Transcription of the Platelet-derived Growth Factor A-chain Gene," *The Journal of Biological Chemistry* 267(31): 21999-22002, 1992.

Wang et al., "WT1, the Wilms' tumor suppressor gene product, represses transcription through an interactive nuclear protein," *Oncogene* 10(6): 1243-1247, 1995.

Watson et al., "Leukemia viruses associated with mouse myeloma cells," *Proceeding of the National Academy of Sciences* 66(2):344-351, Jun. 1970.

Werner et al., "Inhibition of Cellular Proliferation by the Wilms' Tumor Suppressor WT1 Is Associated with Suppression of Insulin-Like Growth Factor I Receptor Gene Expression," *Molecular and Cellular Biology* 15: 3516-3522, 1995.

Wu et al., "GATA-1 Transactivates the WT1 Hematopoietic Specific Enhancer," *The Journal of Biological Chemistry* 270(11): 5944-5949, 1995.

Wu, L.F. et al., "Bacterial Twin-Arginine Signal Peptide-Dependent Protein Translocation Pathway: Evolution and Mechanism," *J. Mol. Microbiol. Biotechnol.* 2(2): 179-189, Apr. 2000.

Yamagami et al., "Growth Inhibition of Human Leukemic Cells by WT1 (Wilms Tumor Gene) Antisene Oligodeoxynucleotides: Implications for the Involvement of WT1 in Leukemogenesis," *Blood* 87(7): 2878-2884, 1996.

Oka, Y. et al., "Wilms Tumor Gene Peptide—Based Immunotherapy for Patients with Overt Leukemia from Myelodysplastic Syndrome (MDS) or MDS with Myelofibrosis," *International Journal of Hematology* 78: 56-61, 2003.

GenBank Database, Accession No. A39692, Feb. 16, 1997.
GenBank Database, Accession No. AAA36810, Jun. 15, 1990.
GenBank Database, Accession No. AAA62825, Oct. 27, 1994.
GenBank Database, Accession No. AAB33427, May 12, 1995.
GenBank Database, Accession No. AAB33443, Jul. 11, 1995.
GenBank Database, Accession No. AAC60039, Nov. 8, 1996.
GenBank Database, Accession No. BAA94794, Apr. 21, 2000.
GenBank Database, Accession No. CAA35956, May 29, 1991.
GenBank Database, Accession No. CAA43819, Dec. 3, 1993.
GenBank Database, Accession No. CAA59736, Feb. 13, 1996.
GenBank Database, Accession No. I51960, Nov. 5, 1999.
GenBank Database, Accession No. M30393, Jun. 15, 1990.
GenBank Database, Accession No. NM_000378, Nov. 5, 2000.
GenBank Database, Accession No. NM_024424, Mar. 20, 2001.
GenBank Database, Accession No. NM_024426, Mar. 20, 2001.
GenBank Database, Accession No. NP_000369, Nov. 5, 2000.
GenBank Database, Accession No. NP_077742, Mar. 20, 2001.
GenBank Database, Accession No. NP_077743, Mar. 20, 2001.
GenBank Database, Accession No. NP_077744, Mar. 20, 2001.
GenBank Database, Accession No. NP_113722, Apr. 6, 2003.
GenBank Database, Accession No. O62651, Nov. 1, 1998.
GenBank Database, Accession No. P50902, Oct. 1, 1996.
GenBank Database, Accession No. S75264, Jul. 11, 1995.
GenBank Database, Accession No. X51630, May 29, 1991.
Derwent Geneseq Database, Accession No. AAT45130, Aug. 19, 1997.
Derwent Geneseq Database, Accession No. AAT45131, Aug. 20, 1997.
Derwent Geneseq Database, Accession No. AAT45132, Aug. 20, 1997.
Derwent Geneseq Database, Accession No. AAT45133, Aug. 20, 1997.
Derwent Geneseq Database, Accession No. AAT45134, Aug. 20, 1997.
Derwent Geneseq Database, Accession No. AAT45135, Aug. 20, 1997.
Derwent Geneseq Database, Accession No. AAT45136, Aug. 20, 1997.
Derwent Geneseq Database, Accession No. AAT45137, Aug. 20, 1997.
Derwent Geneseq Database, Accession No. AAT45138, Aug. 20, 1997.
Derwent Geneseq Database, Accession No. AAT45139, Aug. 20, 1997.
Derwent Geneseq Database, Accession No. AAT45140, Aug. 20, 1997.
Derwent Geneseq Database, Accession No. AAT45141, Aug. 20, 1997.
Derwent Geneseq Database, Accession No. AAT45142, Aug. 20, 1997.
Derwent Geneseq Database, Accession No. AAT97855, Mar. 9, 1998.
Derwent Geneseq Database, Accession No. AAT97856, Mar. 9, 1998.
Derwent Geneseq Database, Accession No. AAT97857, Mar. 9, 1998.
Derwent Geneseq Database, Accession No. AAT97858, Mar. 9, 1998.
Derwent Geneseq Database, Accession No. AAT97859, Mar. 9, 1998.
Derwent Geneseq Database, Accession No. AAT97860, Mar. 9, 1998.
Derwent Geneseq Database, Accession No. AAT97861, Mar. 9, 1998.
Derwent Geneseq Database, Accession No. AAT97862, Mar. 9, 1998.
Derwent Geneseq Database, Accession No. AAT97863, Mar. 9, 1998.
Derwent Geneseq Database, Accession No. AAT97864, Mar. 9, 1998.
Derwent Geneseq Database, Accession No. AAT97865, Mar. 9, 1998.
Derwent Geneseq Database, Accession No. AAT97866, Mar. 9, 1998.
Derwent Geneseq Database, Accession No. AAT97867, Mar. 9, 1998.
Derwent Geneseq Database, Accession No. AAT97868, Mar. 9, 1998.
Derwent Geneseq Database, Accession No. AAX15839, May 11, 1999.
Derwent Geneseq Database, Accession No. AAX15840, May 11, 1999.
Derwent Geneseq Database, Accession No. AAX15841, May 11, 1999.
Derwent Geneseq Database, Accession No. AAX15842, May 11, 1999.
Derwent Geneseq Database, Accession No. AAX15843, May 11, 1999.
Derwent Geneseq Database, Accession No. AAX15844, May 11, 1999.
Derwent Geneseq Database, Accession No. AAX15845, May 11, 1999.
Derwent Geneseq Database, Accession No. AAX15846, May 11, 1999.
Derwent Geneseq Database, Accession No. AAX15847, May 11, 1999.
Derwent Geneseq Database, Accession No. AAX15848, May 11, 1999.
Derwent Geneseq Database, Accession No. AAX15849, May 11, 1999.
Derwent Geneseq Database, Accession No. AAX15850, May 11, 1999.
Derwent Geneseq Database, Accession No. AAX15851, May 11, 1999.
Derwent Geneseq Database, Accession No. AAX15852, May 11, 1999.
Derwent Geneseq Database, Accession No. AAX15853, May 11, 1999.
Derwent Geneseq Database, Accession No. AAX15854, May 11, 1999.
Derwent Geneseq Database, Accession No. AAX15855, May 11, 1999.
Derwent Geneseq Database, Accession No. AAX23927, Jun. 25, 1999.

Derwent Geneseq Database, Accession No. AAX23928, Jun. 25, 1999.
Derwent Geneseq Database, Accession No. AAX23929, Jun. 25, 1999.
Derwent Geneseq Database, Accession No. AAX23930, Jun. 25, 1999.
Derwent Geneseq Database, Accession No. AAX23931, Jun. 25, 1999.
Derwent Geneseq Database, Accession No. AAX34315, Jul. 6, 1999.
Derwent Geneseq Database, Accession No. AAX34316, Jul. 6, 1999.
Derwent Geneseq Database, Accession No. AAX34317, Jul. 6, 1999.
Derwent Geneseq Database, Accession No. AAX34318, Jul. 6, 1999.
Derwent Geneseq Database, Accession No. AAX34319, Jul. 6, 1999.
Derwent Geneseq Database, Accession No. AAX34320, Jul. 6, 1999.
Derwent Geneseq Database, Accession No. AAX34321, Jul. 6, 1999.
Derwent Geneseq Database, Accession No. AAY80196, May 24, 2000.
Derwent Geneseq Database, Accession No. AAY80197, May 24, 2000.
Derwent Geneseq Database, Accession No. AAY80198, May 24, 2000.
Derwent Geneseq Database, Accession No. AAY80199, May 24, 2000.
Derwent Geneseq Database, Accession No. AAY80200, May 24, 2000.
Derwent Geneseq Database, Accession No. AAY80201, May 24, 2000.
Derwent Geneseq Database, Accession No. AAY80202, May 24, 2000.
Derwent Geneseq Database, Accession No. AAY80203, May 24, 2000.
Derwent Geneseq Database, Accession No. ABP42234, Aug. 22, 2002.
Gaiger, A. and Cheever, M.A., "Compositions and Methods for WT1 Specific Immunotherapy," U.S. Appl. No. 09/164,223, filed Sep. 30, 1998.
Gaiger, A. and Cheever, M.A., "Compositions and Methods for WT1 Specific Immunotherapy," U.S. Appl. No. 09/276,484, filed Mar. 25, 1999.
Gaiger, A. and Cheever, M.A., "Compositions and Methods for WT1 Specific Immunotherapy," U.S. Appl. No. 09/684,361, filed Oct. 6, 2000.
Gaiger, A. and Cheever, M.A., "Compositions and Methods for WT1 Specific Immunotherapy," U.S. Appl. No. 09/685,830, filed Oct. 9, 2000.
Gaiger, A. et al., "Compositions and Methods for WT1 Specific Immunotherapy," U.S. Appl. No. 09/785,019, filed Feb. 15, 2001.
TrEMBL Database Accession No. Q93046, Feb. 2, 1997.
Tsuboi, A. et al., "Cytotoxic T-Lymphocyte Responses Elicited to Wilms' Tumor Gene WT1 Product by DNA Vaccination," *Journal of Clinical Immunology* 20(3): 195-202, 2000.
Grosenbach, D.W. et al., "Synergy of Vaccines Strategies to Amplify Antigen-specific Immune Responses and Antitumor Effects," *Cancer Research* 61: 4497-4505, Jun. 1, 2001.
Hale, R.S. et al., "Codon Optimization of the Gene Encoding a Domain from Human Type 1 Neurofibromin Protein Results in a Threefold Improvement in Expression Level in *Escherichia coli*," *Protein Expression and Purification* 12: 185-188, 1998.
Oka, Y. et al., "Cancer Immunotherapy Targeting Wilms' Tumor Gene WT1 Product," *The Journal of Immunology* 164: 1873-1880, 2000.
Oka, Y. et al., "Human cytotoxic T-lymphocyte responses specific for peptides of the wild-type Wilms' tumor gene (*WT1*) product," *Immunogenetics* 51: 99-107, 2000.
Corixa Corporation, Ribi Adjuvant System (RAS), "Research Adjuvant Fact Sheet," 2005, pp. 1-2.
Genbank Database, Accession No. NM_024425, Sep. 14, 2008.
Genbank Database, Accession No. P19544, Jul. 1, 2008.
Genbank Database, Accession No. P22561, Jun. 10, 2008.
Genbank Database, Accession No. P49952, Jun. 10, 2008.
Genbank Database, Accession No. 574529, May 16, 1995.
Derwent Geneseq Database, Accession No. AAG78443, Apr. 12, 2002.
Derwent Geneseq Database, Accession No. AAG78444, Apr. 12, 2002.
Derwent Geneseq Database, Accession No. AAG78446, Apr. 12, 2002.
Derwent Geneseq Database, Accession No. AAH99946, Apr. 12, 2002.
Derwent Geneseq Database, Accession No. AAQ12020, Mar. 25, 2003.
Derwent Geneseq Database, Accession No. AAR12240, Mar. 25, 2003.
Derwent Geneseq Database, Accession No. AAR85065, Feb. 2, 1996.
Derwent Geneseq Database, Accession No. AAR85066, Feb. 2, 1996.
Derwent Geneseq Database, Accession No. AAS13085, Dec. 17, 2001.
Derwent Geneseq Database, Accession No. AAT02461, Feb. 2, 1996.
Derwent Geneseq Database, Accession No. AAT02462, Feb. 2, 1996.
Derwent Geneseq Database, Accession No. AAT97869, Mar. 9, 1998.
Derwent Geneseq Database, Accession No. AAT97870, Mar. 9, 1998.
Derwent Geneseq Database, Accession No. AAU08555, Dec. 17, 2001.
Derwent Geneseq Database, Accession No. AAV17060, Jun. 1, 1998.
Derwent Geneseq Database, Accession No. AAW34972, Mar. 9, 1998.
Derwent Geneseq Database, Accession No. AAW47173, Jun. 1, 1998.
Derwent Geneseq Database, Accession No. AAW47175, Jun. 1, 1998.
Derwent Geneseq Database, Accession No. AAW47176, Jun. 1, 1998.
Derwent Geneseq Database, Accession No. ABL65410, May 15, 2002.
Pardoll, D.M., "New strategies for enhancing the immunogenicity of tumors," *Current Opinion in Immunology* 5:719-725, 1993.
Rammensee, H.-G. et al., "MHC ligands and peptide motifs: first listing," *Immunogenetics* 41:178-228, 1995.
Shu, Q. et al., "Effects of various adjuvants on efficacy of a vaccine against *Streptococcus bovis* and *Lactobacillus* spp in cattle," *American Journal of Veterinary Research* 61(7):839-843, Jul. 2000.
Van Brunt, J. (ed.), Pharmalicensing.com, "Biotech's old soldiers—Signals," Nov. 15, 2005, pp. 1-12, accessed Jan. 18, 2007.
Wikipedia, "Lipid A," Mar. 20, 2006, p. 1.
Ye, Y. et al., "Regulation of WT1 by phosphorylation: inhibition of DNA binding, alteration of transcriptional activity and cellular translocation," *The EMBO Journal* 15(20):5606-5615, 1996.
Yewdell, J.W. et al., "Immunodominance in major histocompatibility complex class I-restricted T lymphocyte responses," *Annu. Rev. Immunol.* 17:51-88, 1999.
Rivera, M.N. et al., "Wilm's Tumour: Connecting Tumorigenesis and Organ Development in the Kidney," *Nature Reviews Cancer* 5: 699-712, Sep. 2005.
Wagner, K-D. et al., "The complex life of WT1," *Journal of Cell Science* 116(9): 1653-1658, 2003.
Berks, "A common export pathway for proteins binding complex redox cofactors?" *Molecular Microbiology* 22(3):393-404, 1996.
Robinson, "The Twin-Arginine Translocation System: A Novel Means of Transporting Folded Proteins in Chloroplasts and Bacteria," *Biol. Chem.* 381:89-93, Feb. 2000.

HU: MGSDVRDLNALLPAVPSLGGGGGCALPVSGAAQWAPVLDFAPPGASAYGSL
MO: MGSDVRDLNALLPAVSSLGGGGGCGLPVSGAAQWAPVLDFAPPGASAYGSL

HU: GGPAPPPAPPPPPPPPHSFIKQEPSWGGAEPHEEQCLSAFTVHFSGQFTGTAG
MO: GGPAPPPAPPPPPPPPHSFIKQEPSWGGAEPHEEQCLSAFTLHFSGQFTGTAG

HU: ACRYGPFGPPPPSQASSGQARMFPNAPYLPSCLESQPAIRNQGYSTVTFDGTPS
MO: ACRYGPFGPPPPSQASSGQARMFPNAPYLPSCLESQPTIRNQGYSTVTFDGAPS

HU: YGHTPSHHAAQFPNHSFKHEDPMGQQGSLGEQQYSVPPPVYGCHTPTDSCTG
MO: YGHTPSHHAAQFPNHSFKHEDPMGQQGSLGEQQYSVPPPVYGCHTPTDSCTG

HU: SQALLLRTPYSSDNLYQMTSQLECMTWNQMNLGATLKGVAAGSSSSVKWTE
MO: SQALLLRTPYSSDNLYQMTSQLECMTWNQMNLGATLKGMAAGSSSSVKWTE

HU: GQSNHSTGYESDNHTTPILCGAQYRIHTHGVFRGIQDVRRVPGVAPTLVRSAS
MO: GQSNHGIGYESDNHTAPILCGAQYRIHTHGVFRGIQDVRRVSGVAPTLVRSAS

HU: ETSEKRPFMCAYPGCNKRYFKLSHLQMHSRKHTGEKPYQCDFKDCERRFSR
MO: ETSEKRPFMCAYPGCNKRYFKLSHLQMHSRKHTGEKPYQCDFKDCERRFSR

HU: SDQLKRHQRRHTGVKPFQCKTCQRKFSRSDHLKTHTRTHTGKTSEKPFSCR
MO: SDQLKRHQRRHTGVKPFQCKTCQRKFSRSDHLKTHTRTHTGKTSEKPFSCR

HU: WPSCQKKFARSDELVRHHNMHQRNMTKLQLAL
MO: WHSCQKKFARSDELVRHHNMHQRNMTKLHVAL

*Fig. 1*

```
             5         10        15        20        25        30        35        40        45        50        55        60        65        70        75
             MGSDVRDLNALLPAVPSLGGGGGCALPVSGAAQWAPVLDFAPPGASAYGSLGGPAPPPAPPPPPPPPHSFIKQE
             .....AAAAAAAAAAAAAAAAAAA......AAAAAA.........AAAAAAAAAAAA...................
             ............................RRRR..........................................
             ...........................................................................
             ...........................................................................
             ...........................................................................

80        85        90        95       100       105       110       115       120       125       130       135       140       145       150
             PSWGGAEPHEEQCLSAFTVHFSGQFTGTAGACRYGPFGPPPPSQASSGQARMFPNAPYLPSCLESQPAIRNQGYS
             ..............AAA......AAAA..................AAA......AAAAAA............
             .....................RRRR....................RRRRR.......................
             ............................DDDDDDDD....................................
             ...........................................................................

155       160       165       170       175       180       185       190       195       200       205       210       215       220       225
             TVTFDGTPSYGHTPSHHAAQFPNHSFKHEDPMGQQGSLGEQQYSVPPPVYGCHTPTDSCTGSQALLLRTPYSSDN
             ...............AAAAA.............................AAAAAA..............AA
             ................RRRR......................................................
             ....................................................DDDDDDDDDDDDDD...
             ...........................................................................

230       235       240       245       250       255       260       265       270       275       280       285       290       295       300
             LYQMTSQLECMTWNQMNLGATLKGVAAGSSSSVKWTEGQSNHSTGYESDNHTTPILCGAQYRIHTHGVFRGIQDV
             AAAAAAAA...........AAA.AAA.....................................AAAAAAAAAA
             ...........RRRRRRRRRR.....RRRR.................................RRRR.....
             DDDDDD.........DDDDDDDDDDD................................................
             ..........................................................ddddd........

305       310       315       320       325       330       335       340       345       350       355       360       365       370       375
             RRVPGVAPTLVRSASEFSEKRPFMCAYPGCNKRYFKLSHLQMHSRKHTGEKPYQCDFKDCERRFSRSDQLKRHQR
             AAAAA..AAAAAAAAAAA.............................................AAAA.AAAAAAAAA.
             ....RRRRR....................RRRR.........................................
             .......DDDDDD..............................................................
             ...........................................................................

380       385       390       395       400       405       410       415       420       425       430       435       440       445       450
             RHTGVKPFQCKTCQRKFSRSDHLKTHTRTHTGKTSEKPFSCRWPSCQKKFARSDELVRHHNMHQRNMTKLQLAL
             ............AAAA.AAAA..AA.....AAAA..........AAA....AAAAAAAA...AAA........
             .....................................................RRRR..RRRR..........
             ...........................................................................
             .............ddddddddddd..................................................
```

*Fig. 8A*

```
        5   10   15   20   25   30   35   40   45   50   55   60   65   70   75
MGSDVRDLNALLPAVSSLGGGGGCGLPVSGAAQWAPVLDFAPPGASAYGSLGGPAPPPAPPPPPPPPHSFIKQE
.....AAAAAAAAAAAAAAAAAA.......AAAAAA.........AAAAAAAAAAAA...................
.........................RRRR..............................................
............................................................................
............................................................................
............................................................................

80   85   90   95   100  105  110  115  120  125  130  135  140  145  150
PSWGGAEPHEEQCLSAFTLHFSGQFTGTAGACRYGPFGPPPPSQASSGQARMFPNAPYLPSCLESQPTIRNQGYS
.....................AAAA....................AAA......AAAAAA................
..........................RRRR....................RRRRR...................
.................................DDDDDDDD...................................
............................................................................

155  160  165  170  175  180  185  190  195  200  205  210  215  220  225
TVTFDGAPSYGHTPSHHAAQFPNI-SFKHEDPMGQQGSLGEQQYSVPPPVYGCHTPTDSCTGSQALLLRTPYSSDN
..............AAAAA..........................AAAAAA...............AA
.............RRRR..........................................................
........................................................DDDDDDDDDDDDD...
............................................................................

230  235  240  245  250  255  260  265  270  275  280  285  290  295  300
LYQMTSQLECMTWNQMNLGATLKGMAAGSSSSVKWTEGQSNHGIGYESDNHTAPILCGAQYRIHTHGVFRGIQDV
AAAAAAAA............AAA.AAA............................AAAAAAAAAAA
...............RRRRRRRRRR.....RRRR............................RRRR.....
DDDDDD...........DDDDDDDDDDD...............................................
........................................................ddddd.........

305  310  315  320  325  330  335  340  345  350  355  360  365  370  375
RRVSGVAPTLVRSASETSEKRPFMCAYPGCNKRYFKLSHLQMHSRKHTGEKPYQCDFKDCERRFSRSDQLKRHQR
AAAAA..AAAAAAAAAAA................................................AAAA.AAAAAAAAA.
....RRRRR.........................RRRR....................................
..DDDDDDDDDD................................................................
............................................................................

380  385  390  395  400  405  410  415  420  425  430  435  440  445  450
RHTGVKPFQCKTCQRKFSRSDHLKTHTRTHTGKTSEKPFSCRWHSCQKKFARSDELVRHHNMHQRNMTKLHVAL
............AAAA.AAAA..AA.....AAAA.........AA....AAAAAAAA...AAAA.......
..............................................RRRR..RRRR................
............................................................................
................ddddcdddddd..............................................
```

*Fig. 8B*

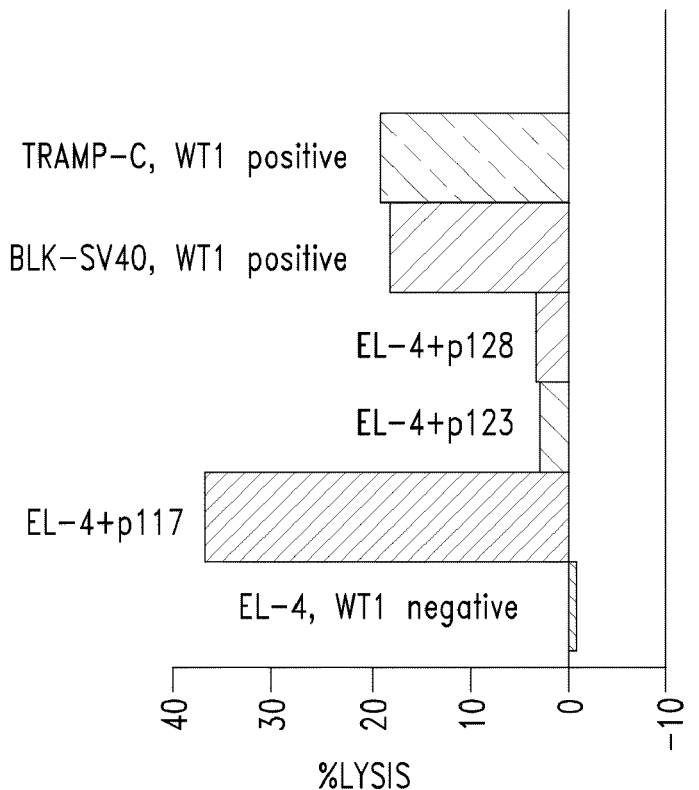
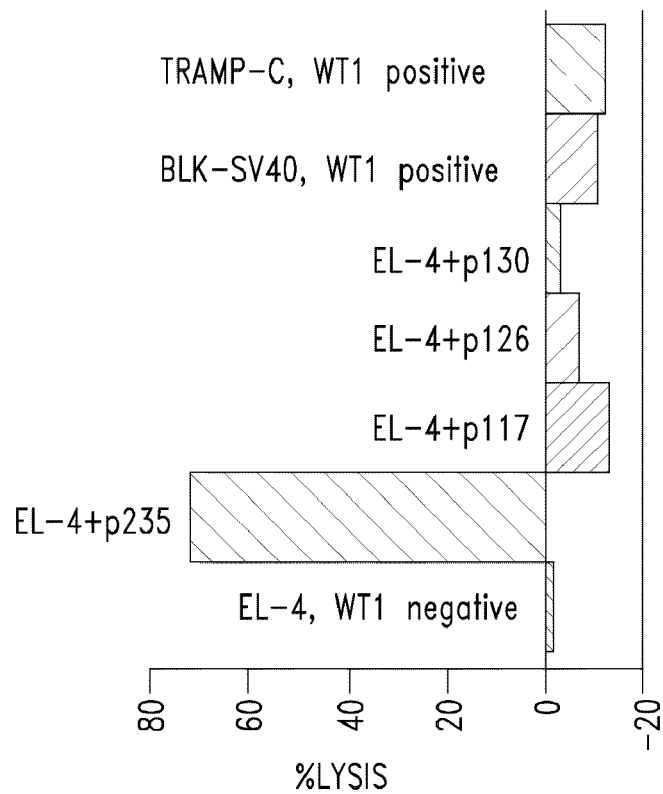
Fig. 11B
Fig. 11A

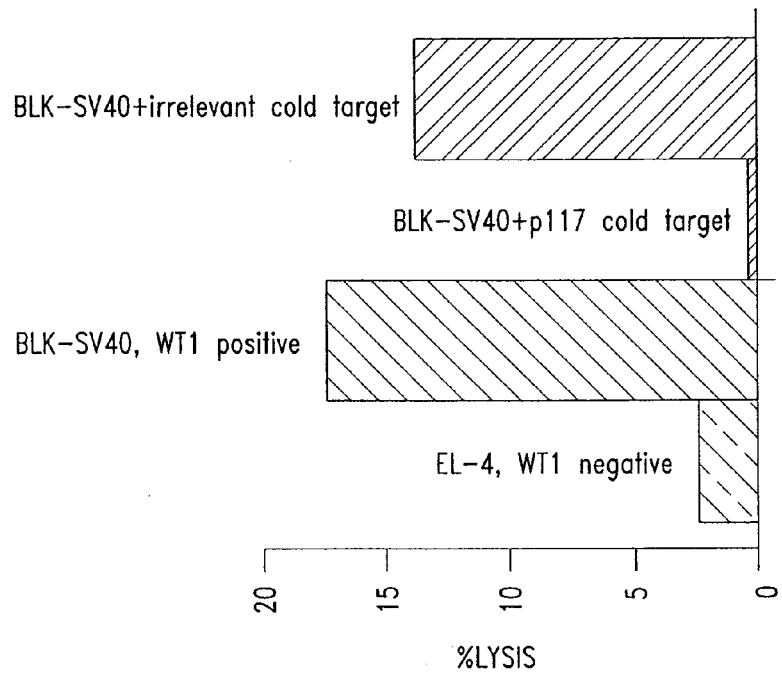
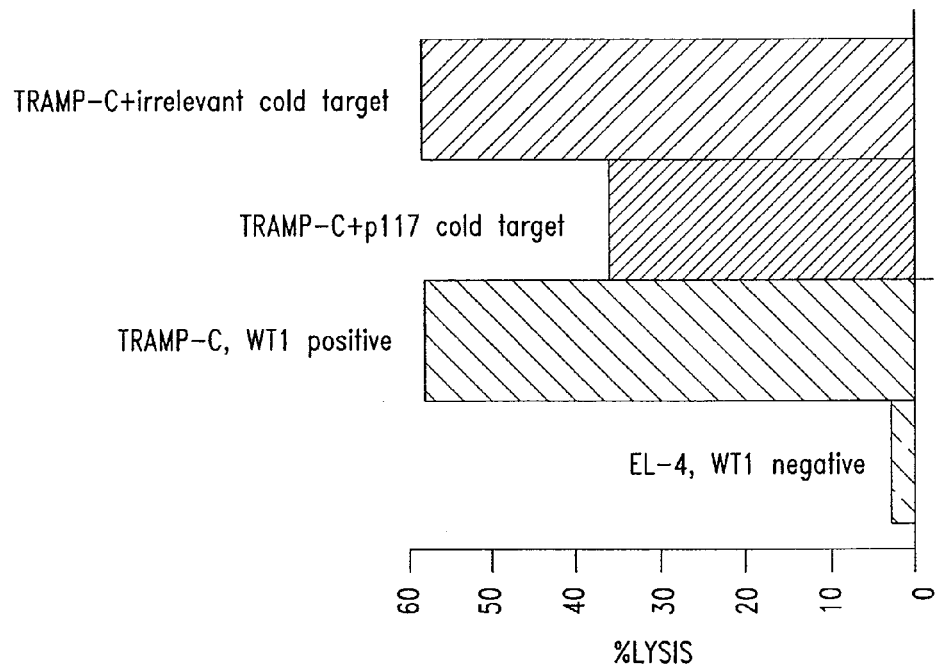

TABLE 1: Characteristics of Recombinant WT1 Proteins Used for Serological Analysis

| NAME | Recombinant Protein | WT1 Amino Acid Position | Molecular Weight |
|---|---|---|---|
| WT1/full-length | Ral2-WT1 full length fusion protein | aa 1-449 | 85kDa |
| WT1/N-terminus | TRX-WT1 N-terminus fusion protein | aa 1-249 | 60kDa |
| WT1/C-terminus | WT1 C-terminus protein | aa 267-449 | 50kDa |

*Fig. 18*

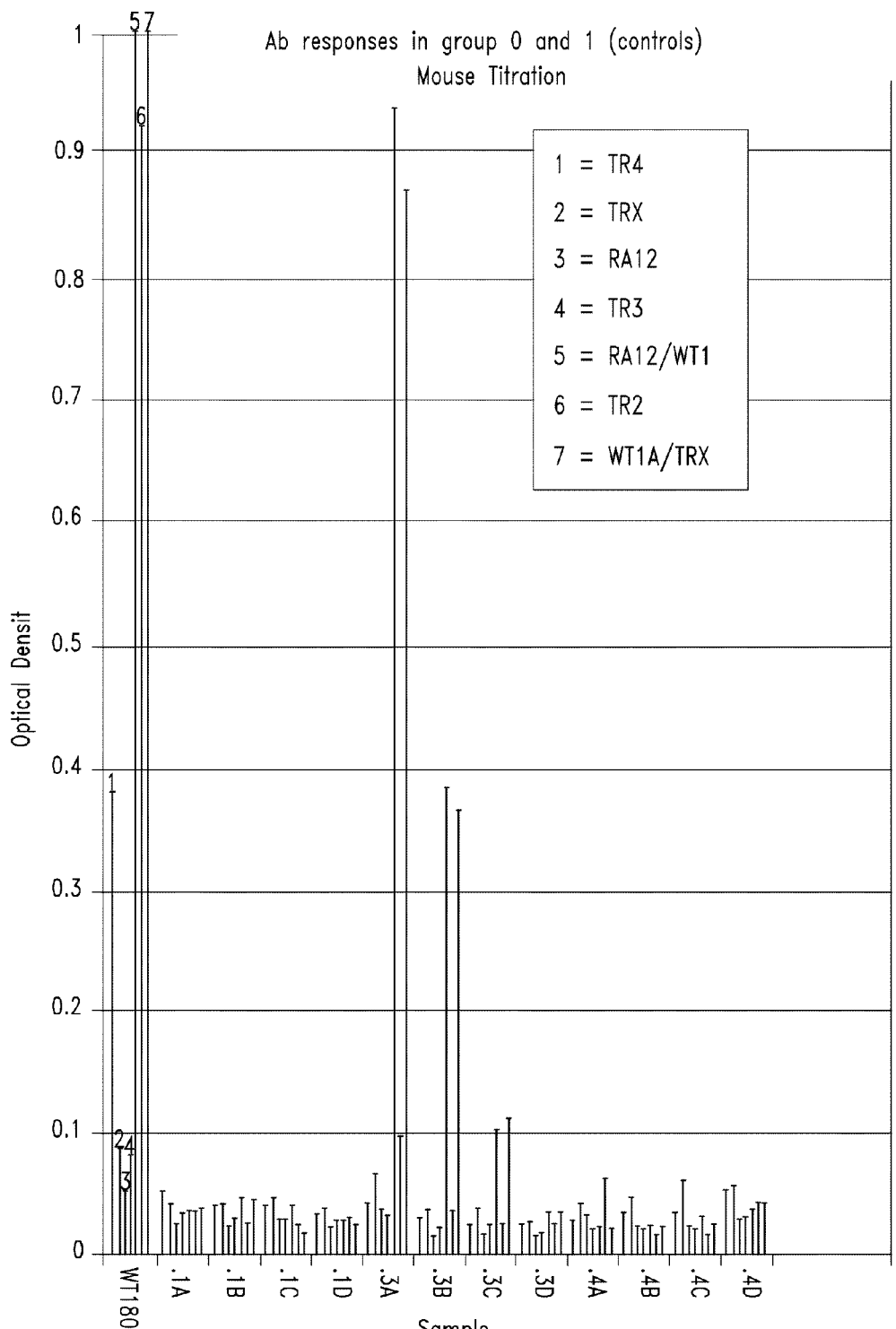
Fig. 19A1  Control groups. A: 1:500 Dilution, B: 1:2000, C: 1:8000, D: 1:16000

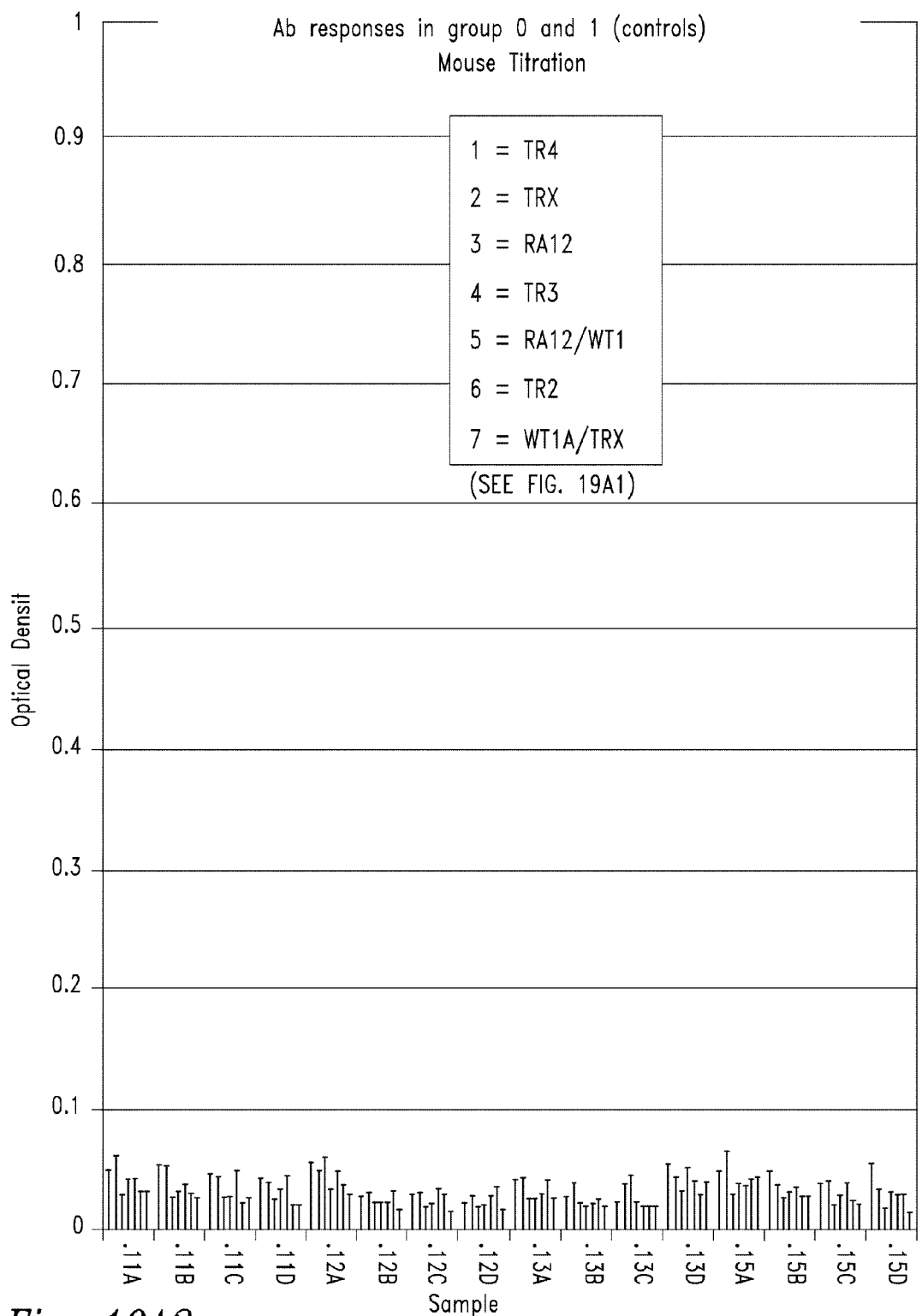
Fig. 19A2  Control groups. A: 1:500 Dilution, B: 1:2000, C: 1:8000, D: 1:16000

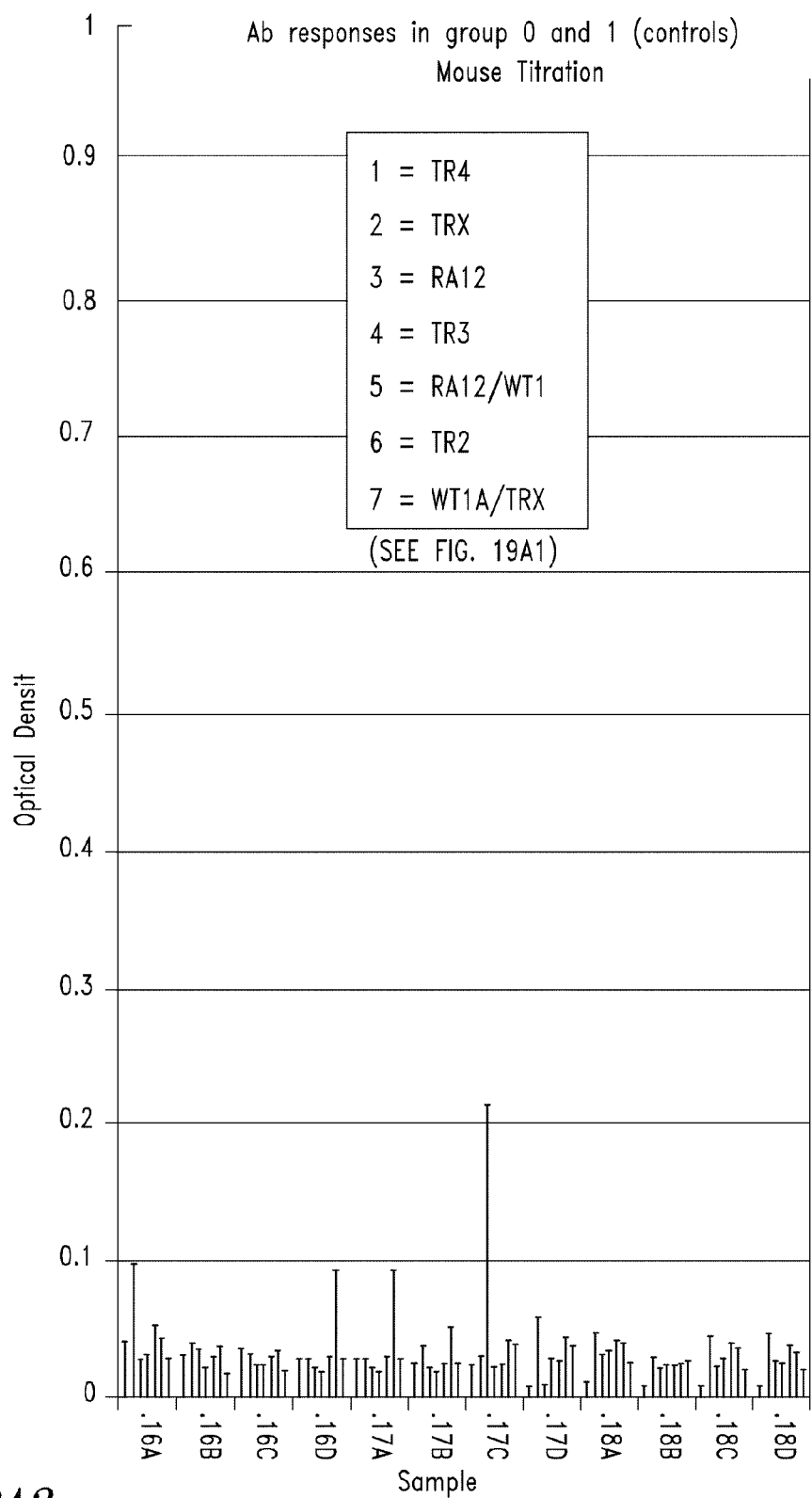
Fig. 19A3  Control groups. A: 1:500 Dilution, B: 1:2000, C: 1:8000, D: 1:16000

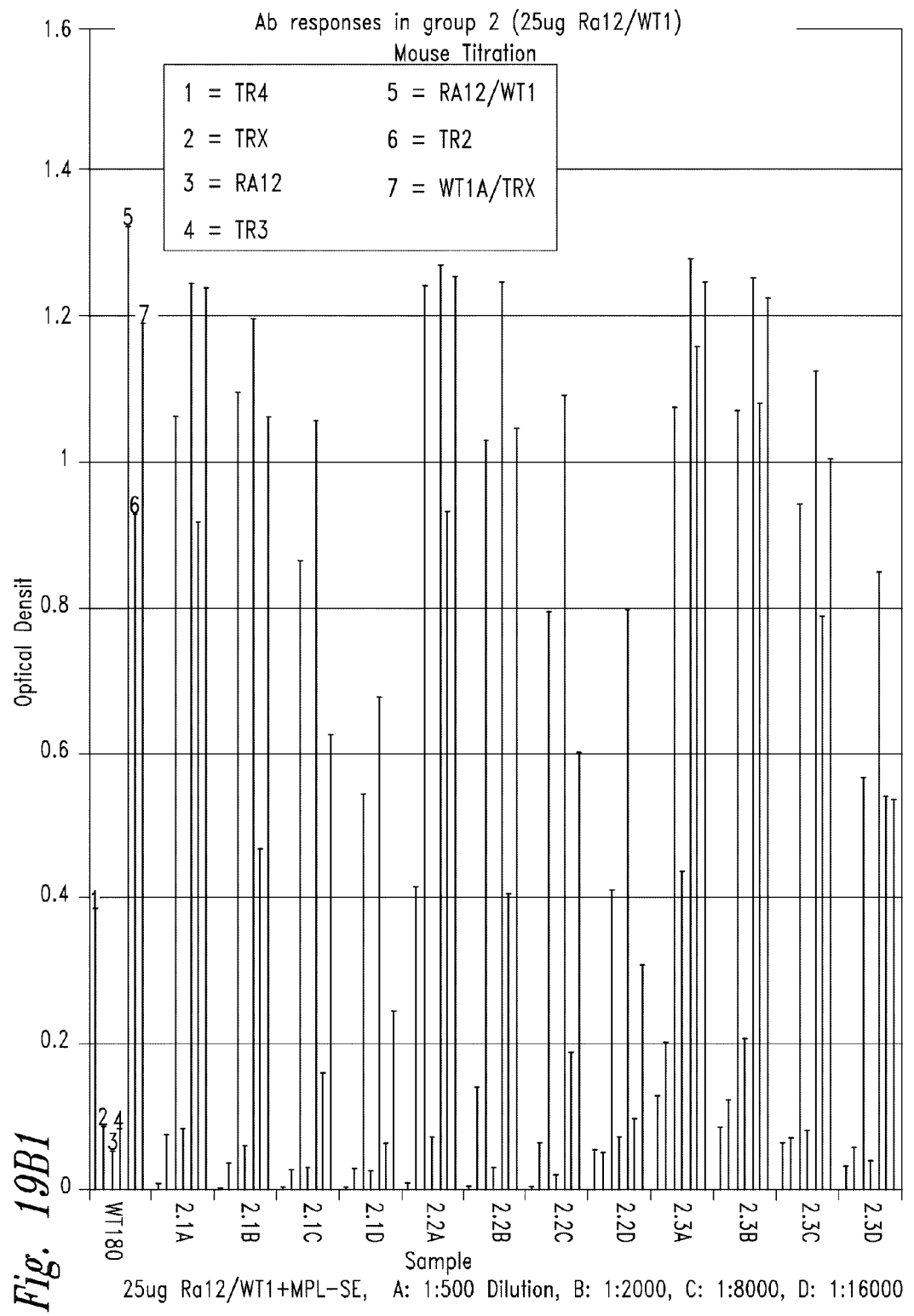
Fig. 19B1

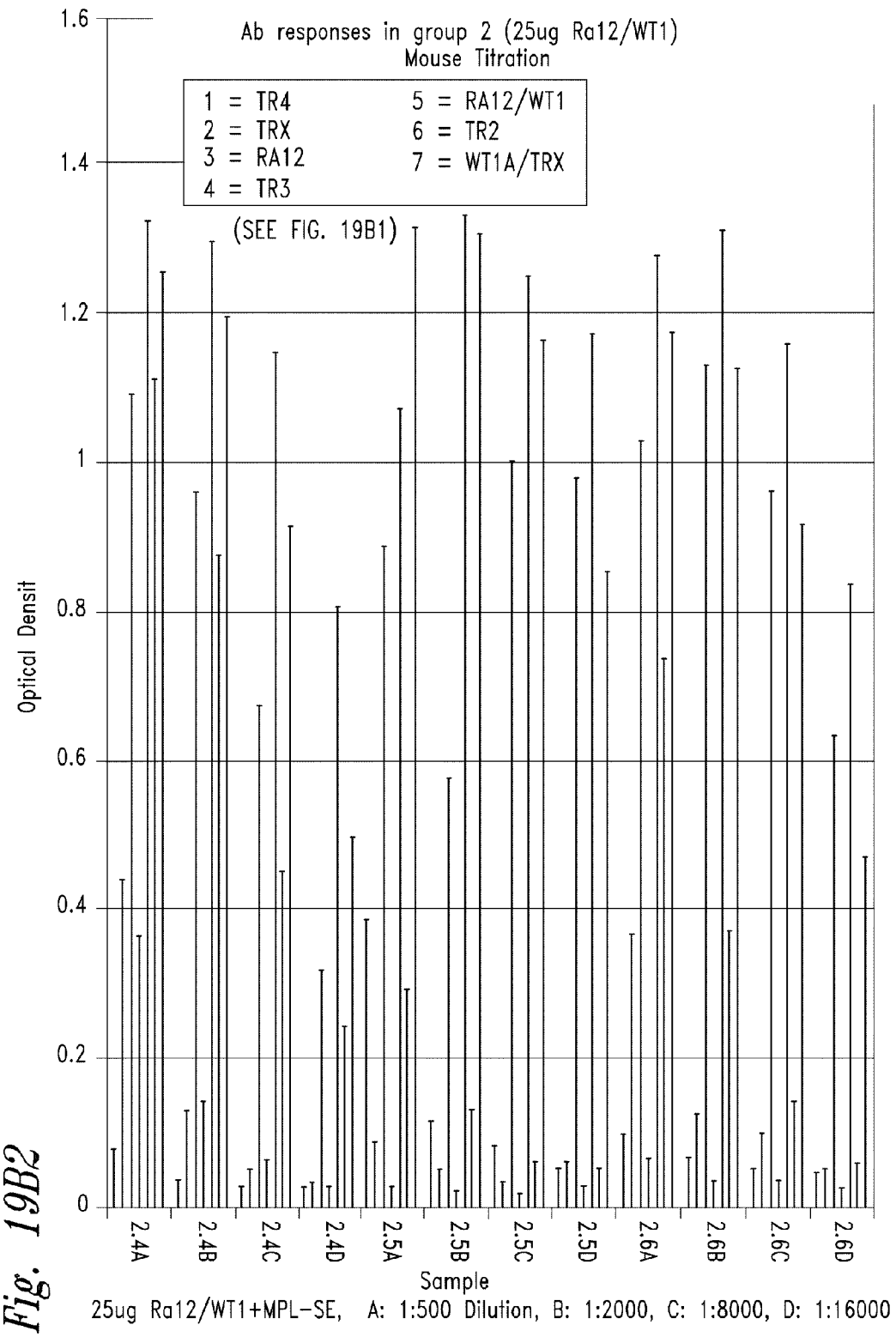
Fig. 19B2

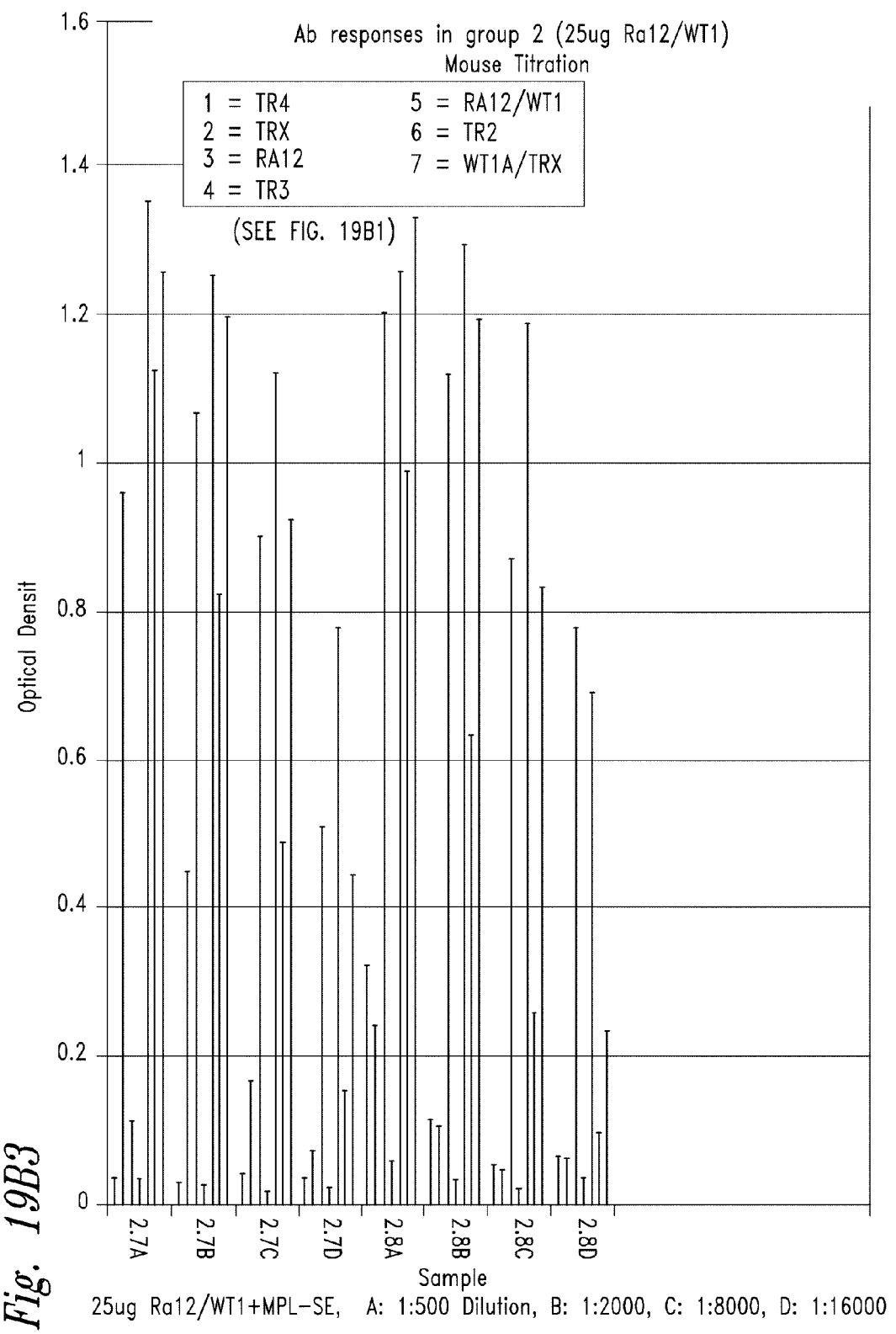

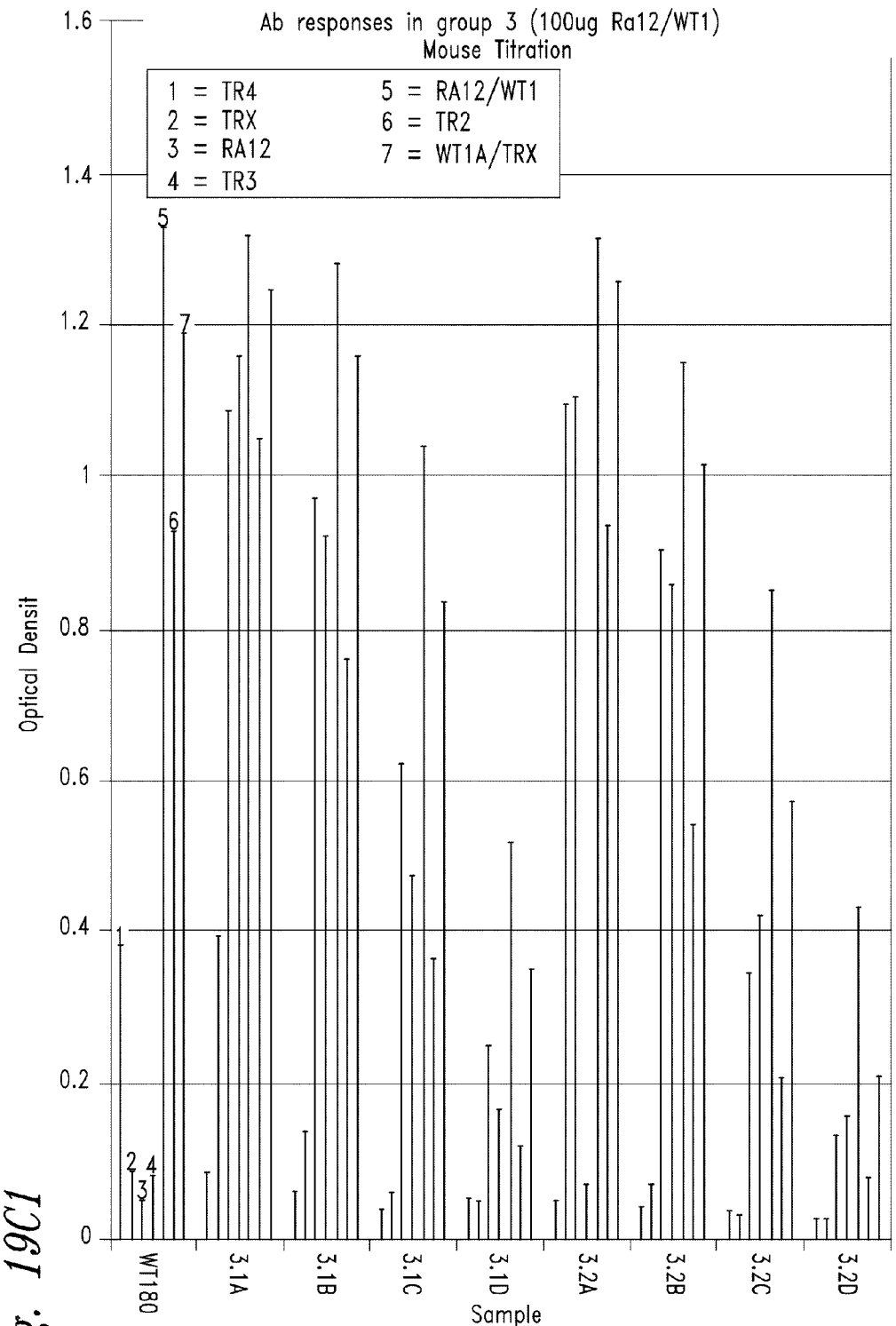
Fig. 19C1

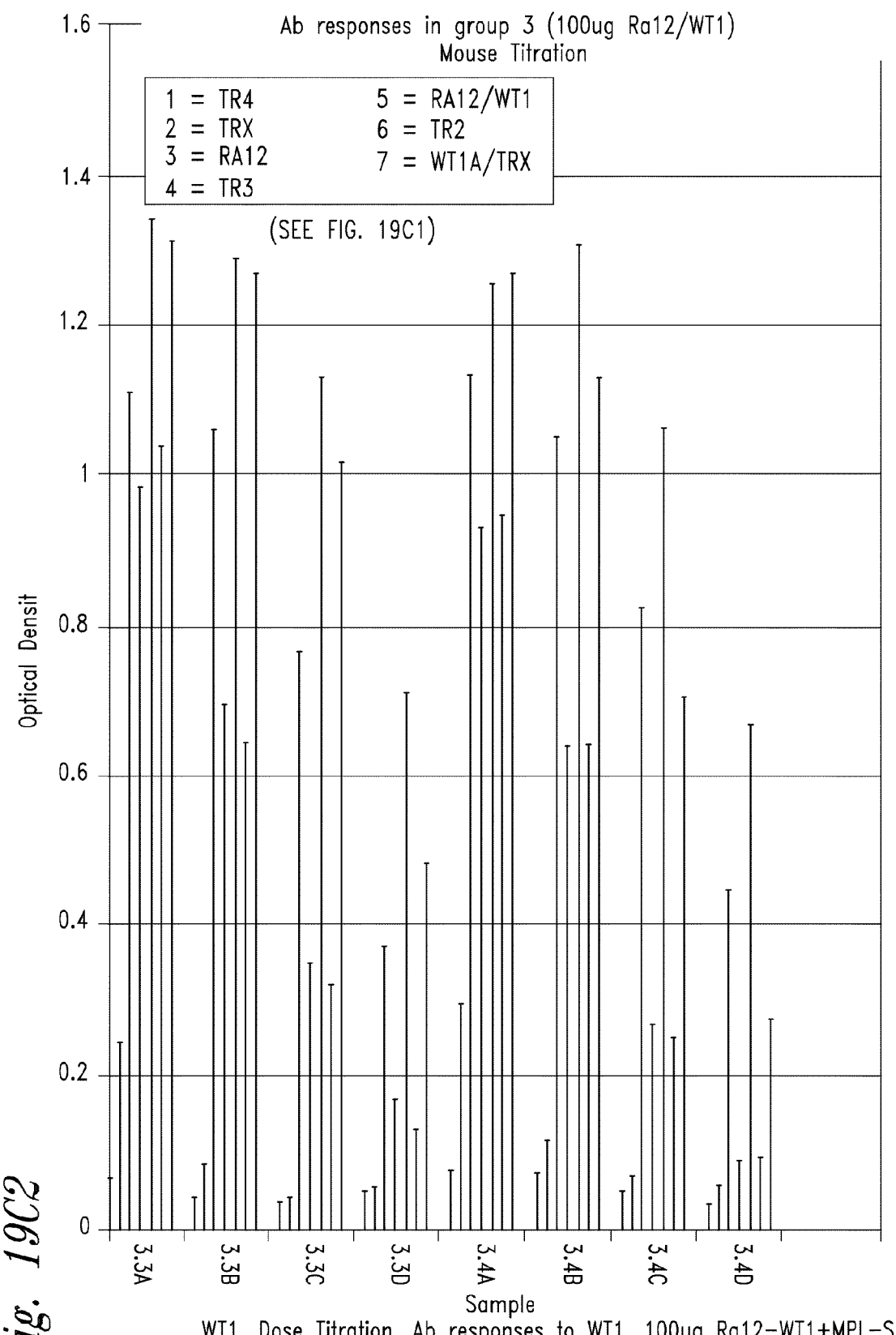
Fig. 19C2

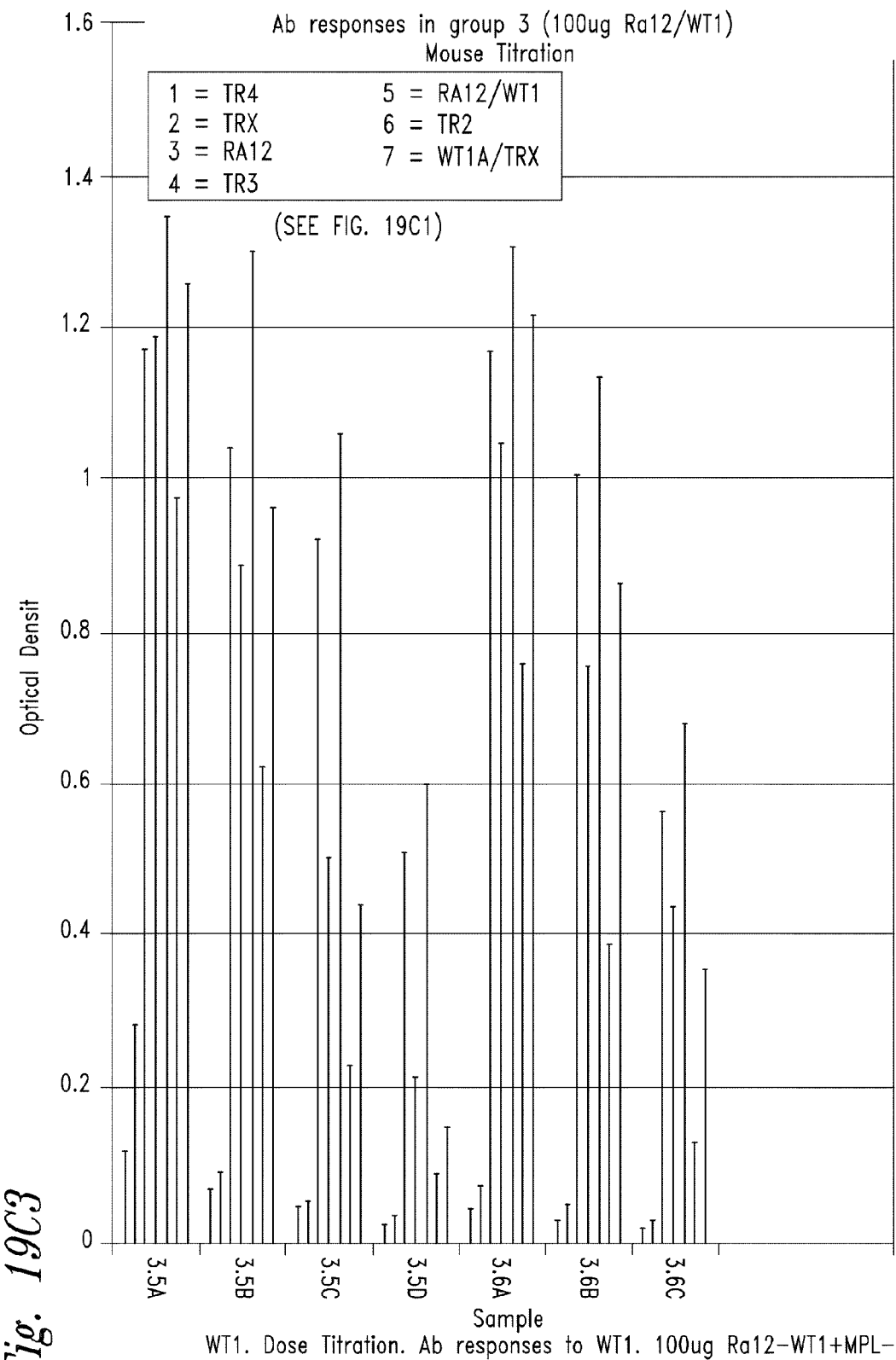
Fig. 19C3

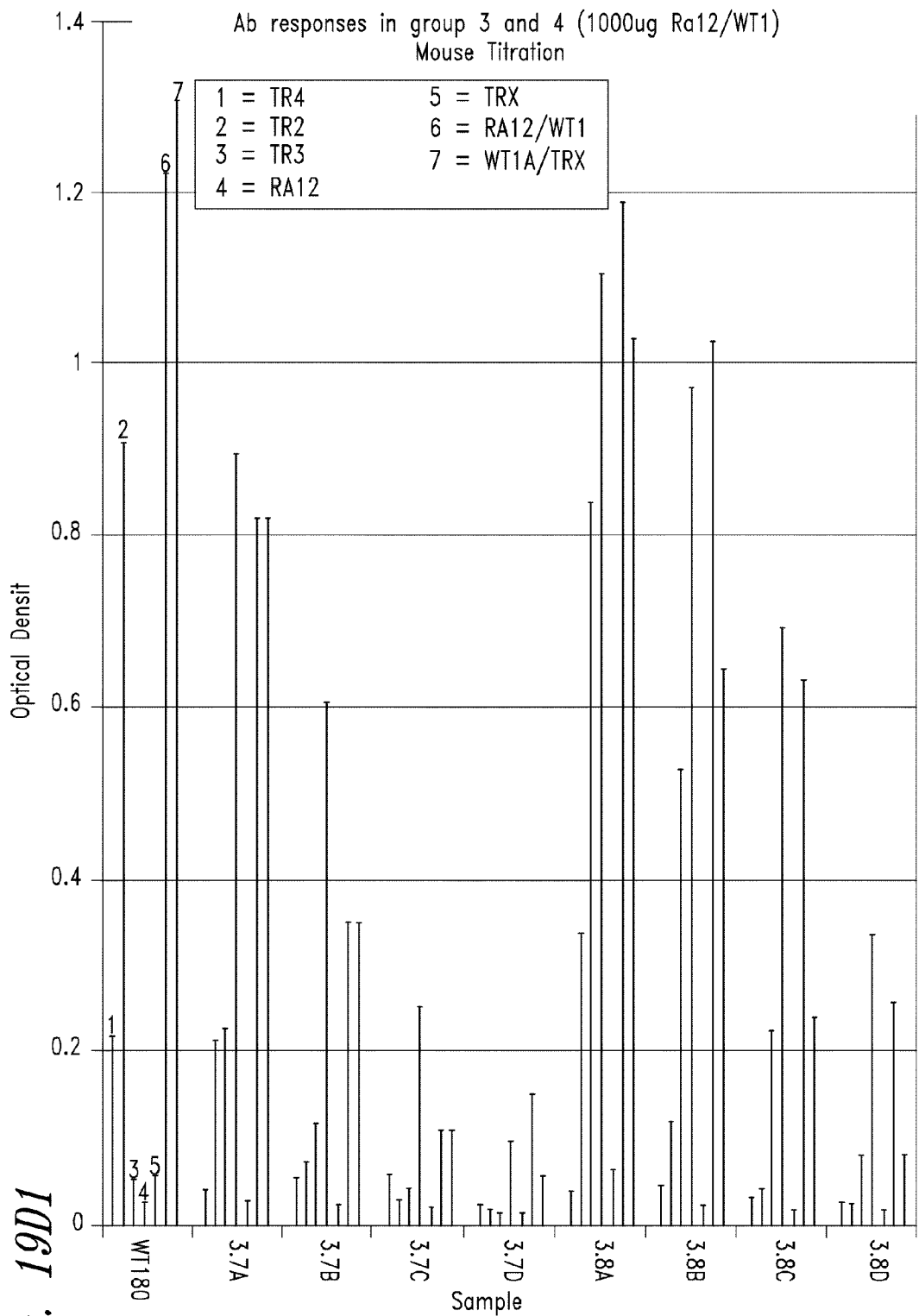

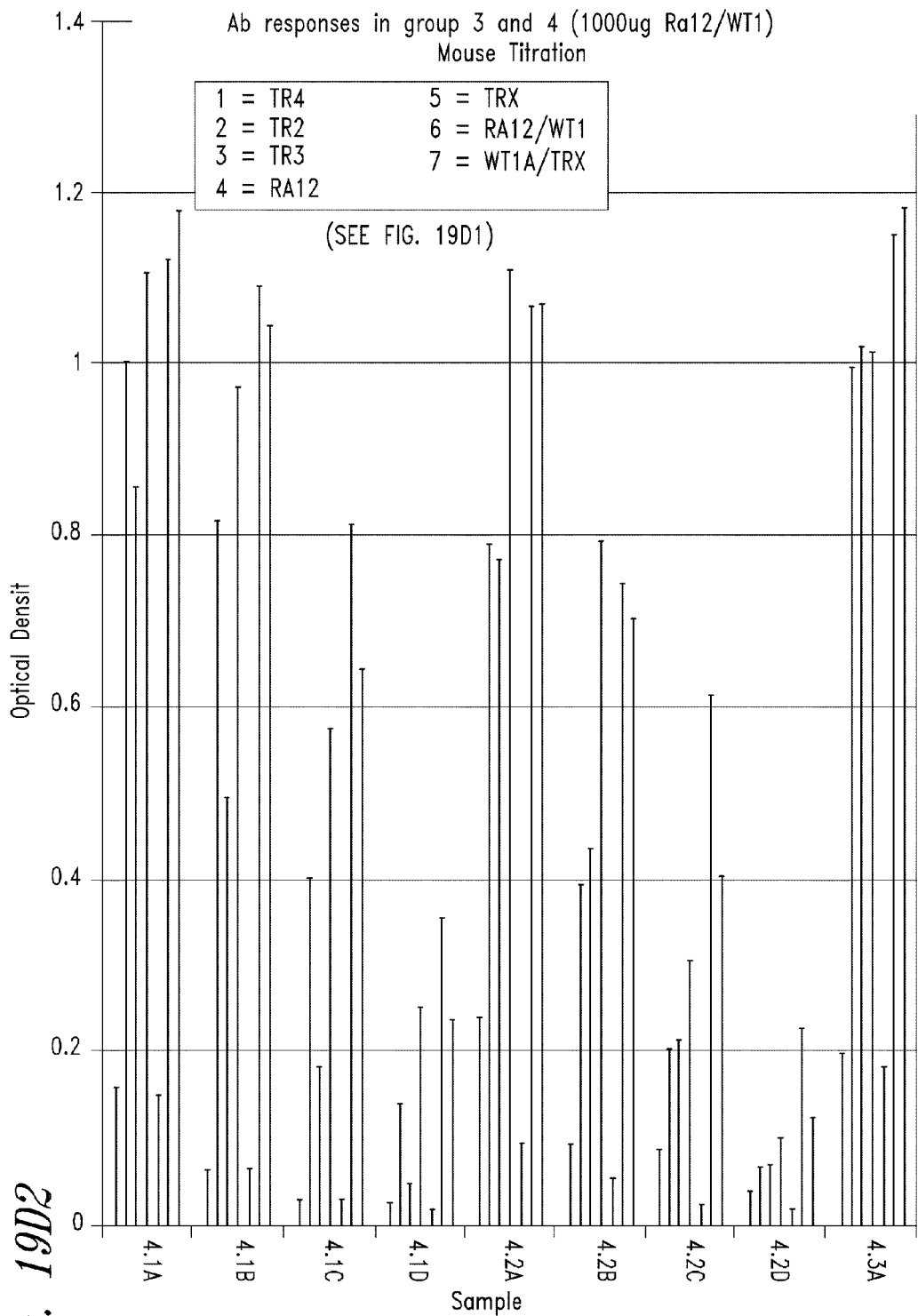
Fig. 19D2

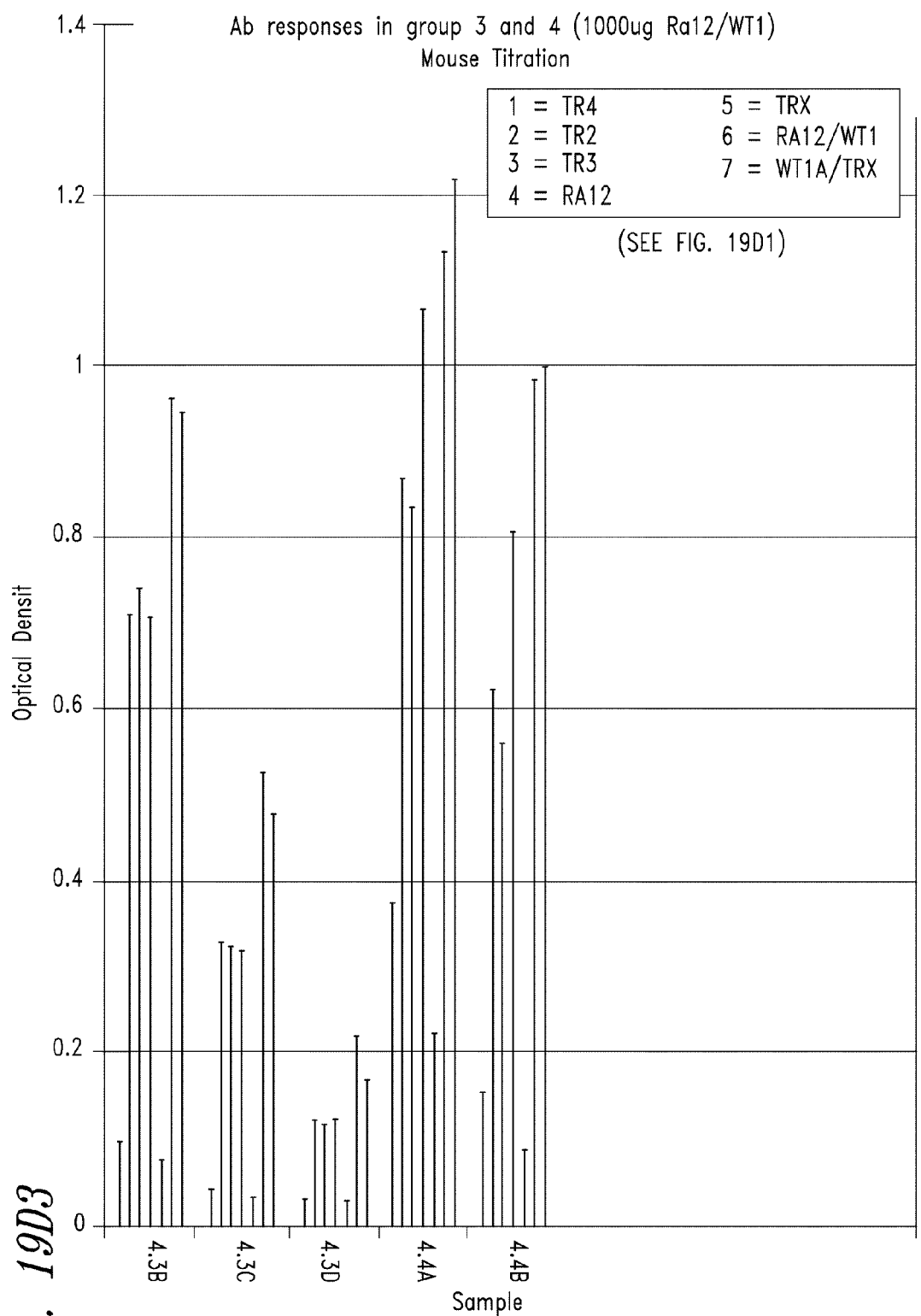
Fig. 19D3
WT1. Dose Titration. Ab responses to WT1. 1000ug Ra12-WT1+MPL-SE.
A: 1:500 Dilution, B: 1:2000, C: 1:8000, D: 1:16000

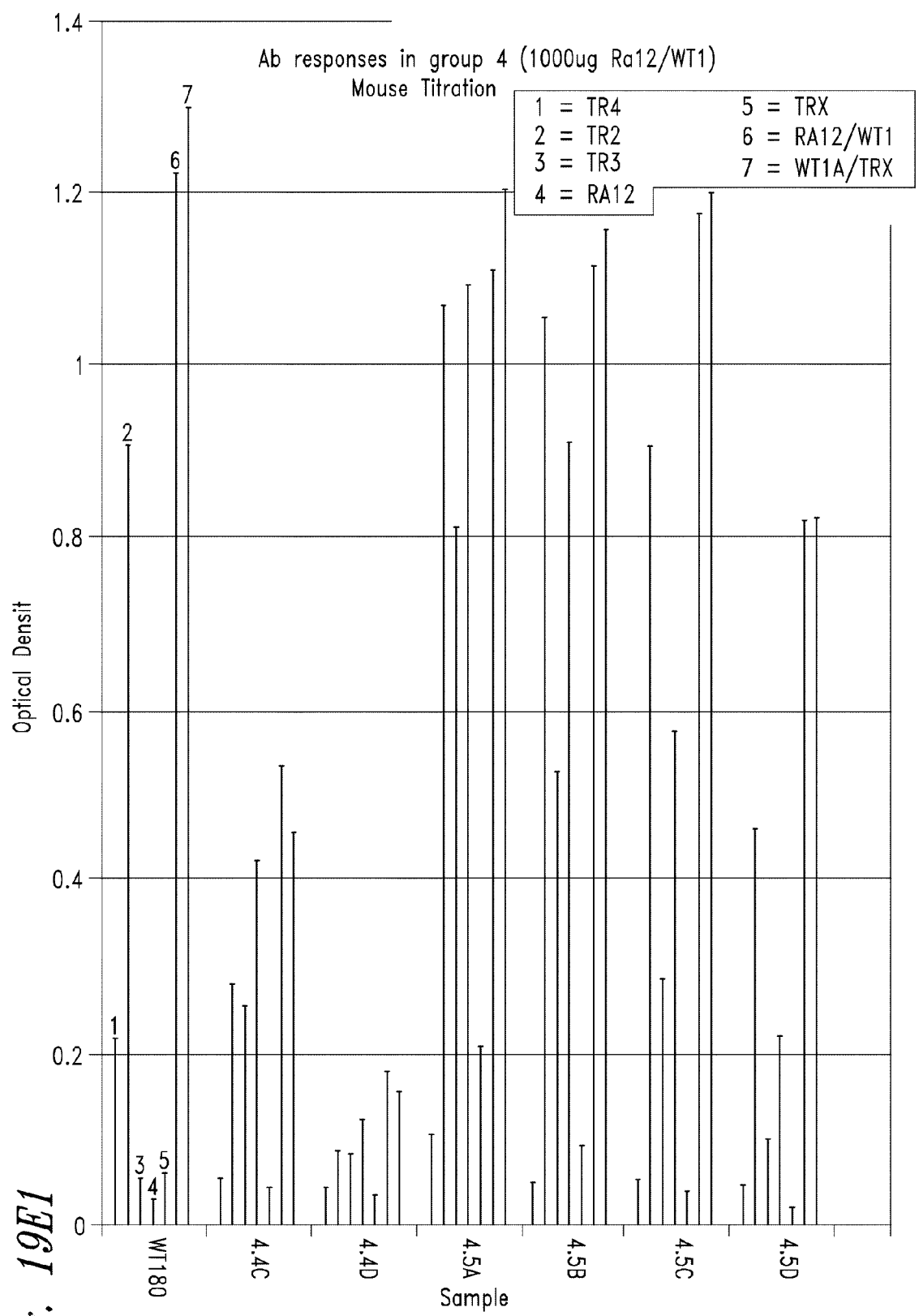

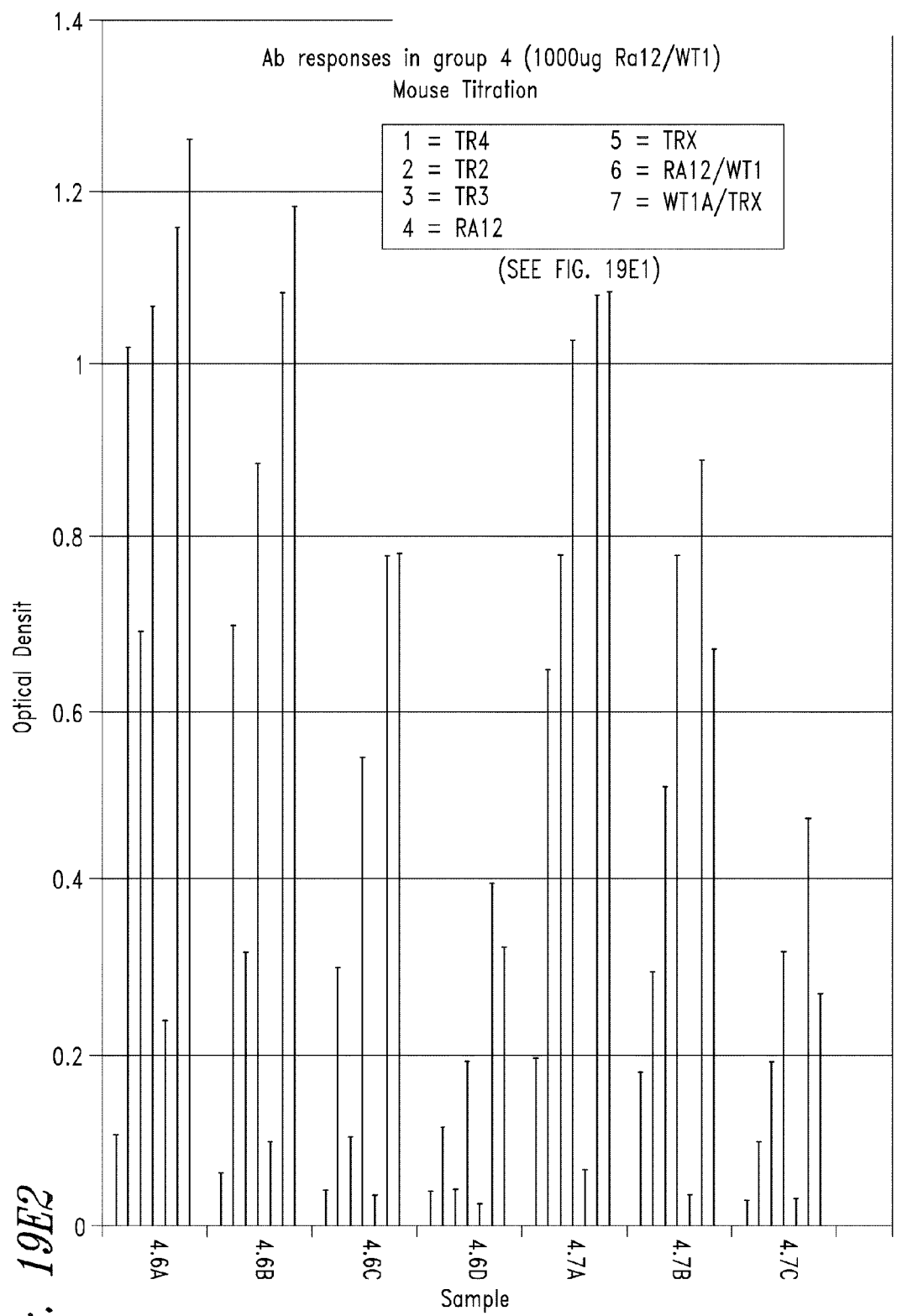
Fig. 19E2
WT1. Dose Titration. Ab responses to WT1. 1000ug Ra12-WT1+MPL-SE.
A: 1:500 Dilution, B: 1:2000, C: 1:8000, D: 1:16000

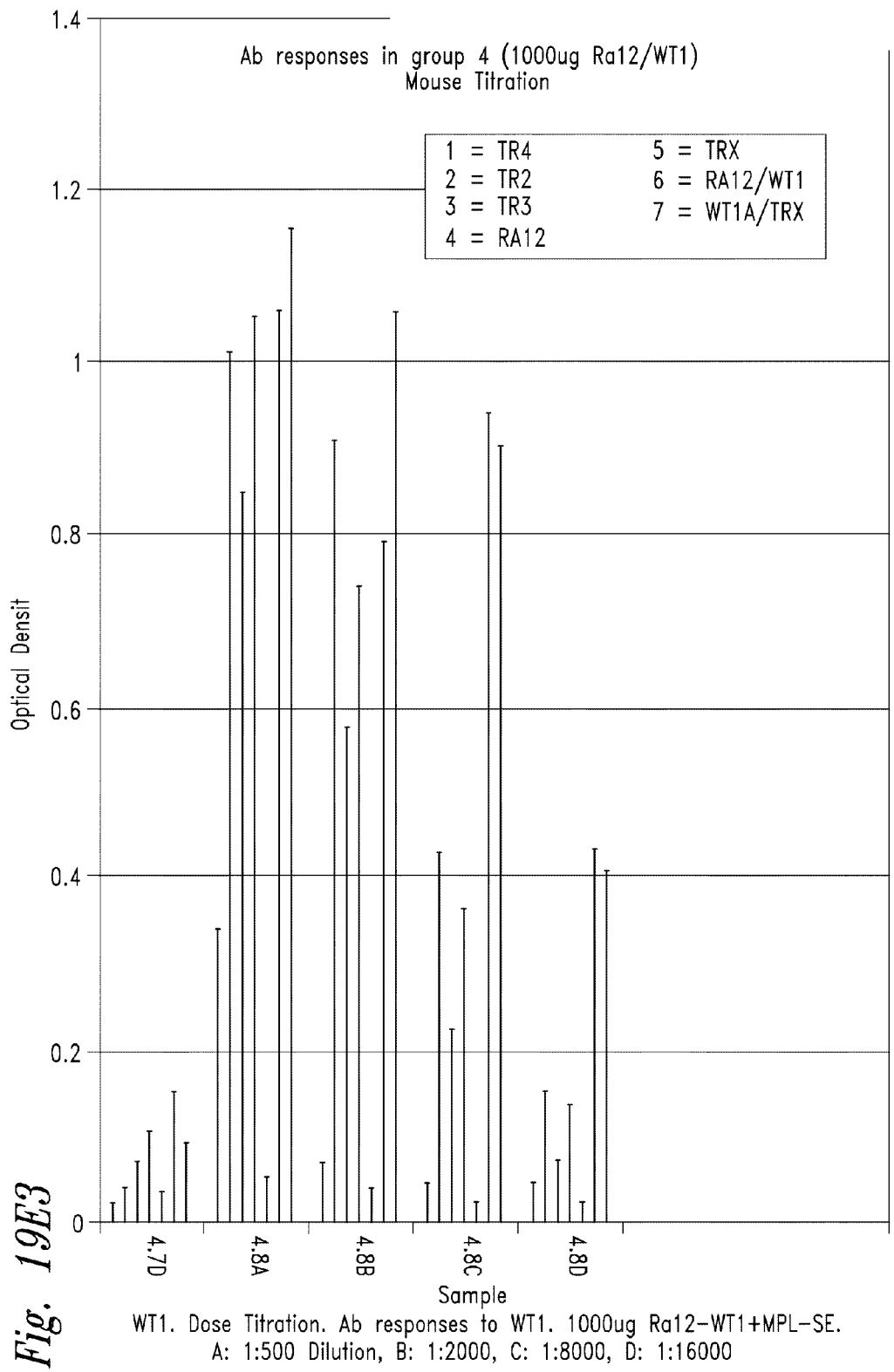
Fig. 19E3

WT1 expression in human DC following adeno WT1 and Vaccinia WT1 infection
Control (uninfected human DC)
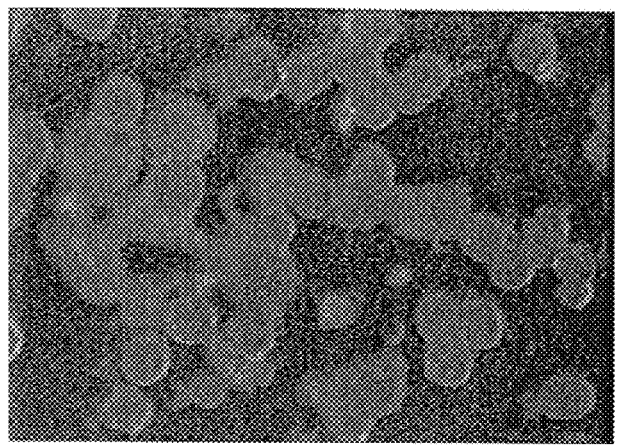
Adeno WT1 (infected human DC)
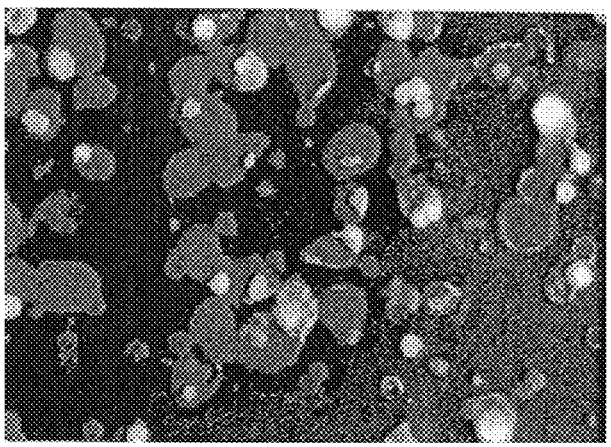
Vaccinia WT1 (infected human DC)
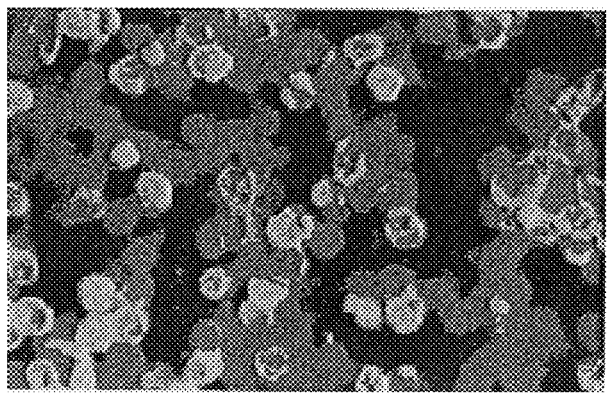
Fig. 21

WT1 can be expressed reproducible in human DC following adeno WT1 infection and is not induced by a control Adeno infection
Control
(Adeno EGFP
infected human DC)
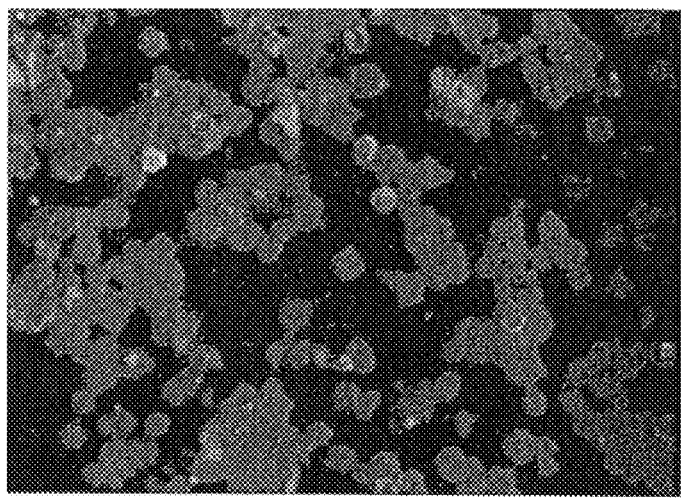
Vaccinia WT1
(infected human DC)
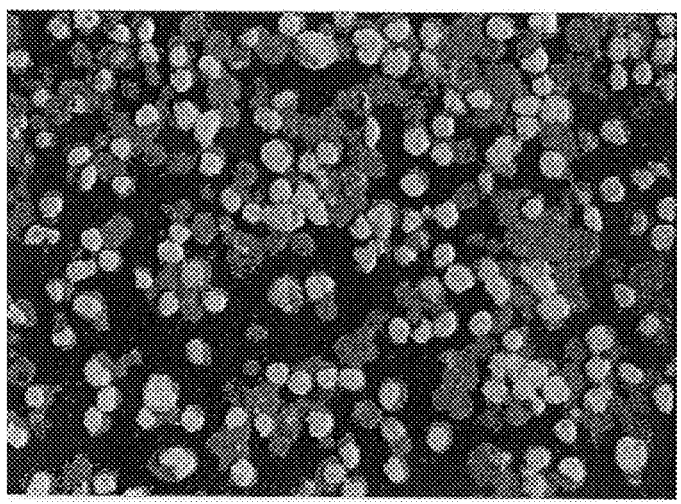
*Fig. 22*

WT-1 F cDNA 2-281

```
GGCTCCGACGTTCGGGACCTGAACGCACTGCTGCCGGCAGTTCCGTCCCTGGGTGGTGGTGGTGGTTGCGCACTGCCGGTTAGCGGTGCAGCACAGTGGG
CTCCGGTTCTGGACTTCGCACCGCCGGGTGCATCCGCATACGGTTCCCTGGGTGGTCCGGCACCGCCGCCGGCACCGCCGCCGCCGCCGCCGCCGCCGCC
GCACTCCTTCATCAAACAGGAACCGAGCTGGGGTGGTGCAGAACCGCACGAAGAACAGTGCCTGAGCGCATTCACCGTTCACTTCTCCGGCCAGTTCACT
GGCACAGCCGGAGCCTGTCGCTACGGGCCCTTCGGTCCTCCTCCGCCCAGCCAGGCGTCATCCGCCCAGGCCAGGATGTTTCCTAACGCGCCCTACCTGC
CCAGCTGCCTCGAGAGCCAGCCCGCTATTCGCAATCAGGGTTACAGCACGGTCACCTTCGACGGGACGCCCAGCTACGGTCACACGCCCTCGCACCATGC
GGCGCAGTTCCCCAACCACTCATTCAAGCATGAGGATCCCATGGGCCAGCAGGGCTCGCTGGGTGAGCAGCAGTACTCGGTGCCGCCCCCGGTCTATGGC
TGCCACACCCCCACCGACAGCTGCACCGGCAGCCAGGCCTTTGCTGCTGAGGACGCCCTACAGCAGTGACAATTTATACCAAATGACATCCCAGCTTGAAT
GCATGACCTGGAATCAGATGAACTTAGGAGCCACCTTAAAGGGCCACAGCACAGGGTACGAGAGCGATAACCACACAACGCCCATCCTCTGCGGAGCCCA
ATACAGAATACACACGCACGGTGTCTTCAGAGGCATTCAGTGA
```

WT-1 F amino acid 2-281

```
GSDVRDLNALLPAVPSLGGGGGCALPVSGAAQWAPVLDFAPPGASAYGSLGGPAPPPAPPPPPPPPHSFIKQEPSWGGAEPHEEQCLSAFTVHFSGQFT
GTAGACRYGPFGPPPPSQASSGQARMFPNAPYLPSCLESQPAIRNQGYSTVTFDGTPSYGHTPSHHAAQFPNHSFKHEDPYGQQGSLGEQQYSVPPPVYG
CHTPTDSCTGSQALLLRTPYSSDNLYQMTSQLECMTWNQMNLGATLKGHSTGYESDNHTTPILCGAQYRIHTHGVFRGIQ
```

*Fig. 24*

SEQUENCE LISTING

```
<160> NUMBER OF SEQ ID NOS: 511

<210> SEQ ID NO 1
<211> LENGTH: 17
<212> TYPE: PRT
<213> ORGANISM: Homo sapien

<400> SEQUENCE: 1

Arg Asp Leu Asn Ala Leu Leu Pro Ala Val Pro Ser Leu Gly Gly Gly
1               5                   10                  15
```

Gly

```
<210> SEQ ID NO 2
<211> LENGTH: 23
<212> TYPE: PRT
<213> ORGANISM: Homo sapien

<400> SEQUENCE: 2
```

Pro Ser Gln Ala Ser Ser Gly Gln Ala Arg Met Phe Pro Asn Ala Pro
 1               5                  10                  15

Tyr Leu Pro Ser Cys Leu Glu
            20

```
<210> SEQ ID NO 3
<211> LENGTH: 23
<212> TYPE: PRT
<213> ORGANISM: Mus musculus

<400> SEQUENCE: 3
```

Pro Ser Gln Ala Ser Ser Gly Gln Ala Arg Met Phe Pro Asn Ala Pro
 1               5                  10                  15

Tyr Leu Pro Ser Cys Leu Glu
            20

```
<210> SEQ ID NO 4
<211> LENGTH: 19
<212> TYPE: PRT
<213> ORGANISM: Homo sapien

<400> SEQUENCE: 4
```

Gly Ala Thr Leu Lys Gly Val Ala Ala Gly Ser Ser Ser Ser Val Lys
 1               5                  10                  15

Trp Thr Glu

```
<210> SEQ ID NO 5
<211> LENGTH: 22
<212> TYPE: DNA
<213> ORGANISM: Homo sapien

<400> SEQUENCE: 5
```
gagagtcaga cttgaaagca gt                                        22

```
<210> SEQ ID NO 6
<211> LENGTH: 20
<212> TYPE: DNA
<213> ORGANISM: Homo sapien

<400> SEQUENCE: 6
```
ctgagcctca gcaaatgggc                                           20

```
<210> SEQ ID NO 7
<211> LENGTH: 27
<212> TYPE: DNA
<213> ORGANISM: Homo sapien

<400> SEQUENCE: 7
```
gagcatgcat gggctccgac gtgcggg                                   27

```
<210> SEQ ID NO 8
<211> LENGTH: 25
<212> TYPE: DNA
<213> ORGANISM: Homo sapien

<400> SEQUENCE: 8
```

-continued

```
ggggtaccca ctgaacggtc cccga                                          25
```

<210> SEQ ID NO 9
<211> LENGTH: 18
<212> TYPE: DNA
<213> ORGANISM: Mus musculus

<400> SEQUENCE: 9

```
tccgagccgc acctcatg                                                  18
```

<210> SEQ ID NO 10
<211> LENGTH: 18
<212> TYPE: DNA
<213> ORGANISM: Mus musculus

<400> SEQUENCE: 10

```
gcctgggatg ctggactg                                                  18
```

<210> SEQ ID NO 11
<211> LENGTH: 27
<212> TYPE: DNA
<213> ORGANISM: Mus musculus

<400> SEQUENCE: 11

```
gagcatgcga tgggttccga cgtgcgg                                        27
```

<210> SEQ ID NO 12
<211> LENGTH: 29
<212> TYPE: DNA
<213> ORGANISM: Mus musculus

<400> SEQUENCE: 12

```
ggggtacctc aaagcgccac gtggagttt                                      29
```

<210> SEQ ID NO 13
<211> LENGTH: 17
<212> TYPE: PRT
<213> ORGANISM: Mus musculus

<400> SEQUENCE: 13

Arg Asp Leu Asn Ala Leu Leu Pro Ala Val Ser Ser Leu Gly Gly Gly
 1               5                  10                  15

Gly

<210> SEQ ID NO 14
<211> LENGTH: 19
<212> TYPE: PRT
<213> ORGANISM: Mus musculus

<400> SEQUENCE: 14

Gly Ala Thr Leu Lys Gly Met Ala Ala Gly Ser Ser Ser Ser Val Lys
 1               5                  10                  15

Trp Thr Glu

<210> SEQ ID NO 15
<211> LENGTH: 15
<212> TYPE: PRT
<213> ORGANISM: Homo sapien

<400> SEQUENCE: 15

Arg Ile His Thr His Gly Val Phe Arg Gly Ile Gln Asp Val Arg
 1               5                  10                  15

```
<210> SEQ ID NO 16
<211> LENGTH: 15
<212> TYPE: PRT
<213> ORGANISM: Mus musculus

<400> SEQUENCE: 16

Arg Ile His Thr His Gly Val Phe Arg Gly Ile Gln Asp Val Arg
 1               5                  10                  15

<210> SEQ ID NO 17
<211> LENGTH: 14
<212> TYPE: PRT
<213> ORGANISM: Mus musculus

<400> SEQUENCE: 17

Val Arg Arg Val Ser Gly Val Ala Pro Thr Leu Val Arg Ser
 1               5                  10

<210> SEQ ID NO 18
<211> LENGTH: 14
<212> TYPE: PRT
<213> ORGANISM: Homo sapien

<400> SEQUENCE: 18

Val Arg Arg Val Pro Gly Val Ala Pro Thr Leu Val Arg Ser
 1               5                  10

<210> SEQ ID NO 19
<211> LENGTH: 15
<212> TYPE: PRT
<213> ORGANISM: Homo sapien

<400> SEQUENCE: 19

Cys Gln Lys Lys Phe Ala Arg Ser Asp Glu Leu Val Arg His His
 1               5                  10                  15

<210> SEQ ID NO 20
<211> LENGTH: 15
<212> TYPE: PRT
<213> ORGANISM: Mus musculus

<400> SEQUENCE: 20

Cys Gln Lys Lys Phe Ala Arg Ser Asp Glu Leu Val Arg His His
 1               5                  10                  15

<210> SEQ ID NO 21
<211> LENGTH: 21
<212> TYPE: DNA
<213> ORGANISM: Mus musculus

<400> SEQUENCE: 21
cccaggctgc aataagagat a                                              21

<210> SEQ ID NO 22
<211> LENGTH: 21
<212> TYPE: DNA
<213> ORGANISM: Mus musculus

<400> SEQUENCE: 22
atgttgtgat ggcggaccaa t                                              21

<210> SEQ ID NO 23
<211> LENGTH: 20
<212> TYPE: DNA
<213> ORGANISM: Homo sapien
```

-continued

<400> SEQUENCE: 23
gtggggcgcc ccaggcacca                                             20

<210> SEQ ID NO 24
<211> LENGTH: 24
<212> TYPE: DNA
<213> ORGANISM: Homo sapien

<400> SEQUENCE: 24
gtccttaatg ctacgcacga tttc                                        24

<210> SEQ ID NO 25
<211> LENGTH: 21
<212> TYPE: DNA
<213> ORGANISM: Homo sapien

<400> SEQUENCE: 25
ggcatctgag accagtgaga a                                           21

<210> SEQ ID NO 26
<211> LENGTH: 21
<212> TYPE: DNA
<213> ORGANISM: Homo sapien

<400> SEQUENCE: 26
gctgtcccac ttacagatgc a                                           21

<210> SEQ ID NO 27
<211> LENGTH: 21
<212> TYPE: DNA
<213> ORGANISM: Homo sapien

<400> SEQUENCE: 27
tcaaagcgcc agctggagtt t                                           21

<210> SEQ ID NO 28
<211> LENGTH: 9
<212> TYPE: PRT
<213> ORGANISM: Homo sapien

<400> SEQUENCE: 28

Ala Ala Gly Ser Ser Ser Ser Val Lys
 1               5

<210> SEQ ID NO 29
<211> LENGTH: 9
<212> TYPE: PRT
<213> ORGANISM: Homo sapien

<400> SEQUENCE: 29

Ala Ala Gln Phe Pro Asn His Ser Phe
 1               5

<210> SEQ ID NO 30
<211> LENGTH: 9
<212> TYPE: PRT
<213> ORGANISM: Homo sapien

<400> SEQUENCE: 30

Ala Glu Pro His Glu Glu Gln Cys Leu
 1               5

<210> SEQ ID NO 31

```
<211> LENGTH: 9
<212> TYPE: PRT
<213> ORGANISM: Homo sapien

<400> SEQUENCE: 31

Ala Gly Ala Cys Arg Tyr Gly Pro Phe
1               5

<210> SEQ ID NO 32
<211> LENGTH: 9
<212> TYPE: PRT
<213> ORGANISM: Homo sapien

<400> SEQUENCE: 32

Ala Gly Ser Ser Ser Ser Val Lys Trp
1               5

<210> SEQ ID NO 33
<211> LENGTH: 9
<212> TYPE: PRT
<213> ORGANISM: Homo sapien

<400> SEQUENCE: 33

Ala Ile Arg Asn Gln Gly Tyr Ser Thr
1               5

<210> SEQ ID NO 34
<211> LENGTH: 9
<212> TYPE: PRT
<213> ORGANISM: Homo sapien

<400> SEQUENCE: 34

Ala Leu Leu Pro Ala Val Pro Ser Leu
1               5

<210> SEQ ID NO 35
<211> LENGTH: 9
<212> TYPE: PRT
<213> ORGANISM: Homo sapien

<400> SEQUENCE: 35

Ala Leu Leu Pro Ala Val Ser Ser Leu
1               5

<210> SEQ ID NO 36
<211> LENGTH: 9
<212> TYPE: PRT
<213> ORGANISM: Homo sapien

<400> SEQUENCE: 36

Ala Gln Phe Pro Asn His Ser Phe Lys
1               5

<210> SEQ ID NO 37
<211> LENGTH: 9
<212> TYPE: PRT
<213> ORGANISM: Homo sapien

<400> SEQUENCE: 37

Ala Gln Trp Ala Pro Val Leu Asp Phe
1               5

<210> SEQ ID NO 38
<211> LENGTH: 9
<212> TYPE: PRT
<213> ORGANISM: Homo sapien
```

```
<400> SEQUENCE: 38

Ala Arg Met Phe Pro Asn Ala Pro Tyr
 1               5

<210> SEQ ID NO 39
<211> LENGTH: 9
<212> TYPE: PRT
<213> ORGANISM: Homo sapien

<400> SEQUENCE: 39

Ala Arg Ser Asp Glu Leu Val Arg His
 1               5

<210> SEQ ID NO 40
<211> LENGTH: 9
<212> TYPE: PRT
<213> ORGANISM: Homo sapien

<400> SEQUENCE: 40

Ala Ser Ser Gly Gln Ala Arg Met Phe
 1               5

<210> SEQ ID NO 41
<211> LENGTH: 9
<212> TYPE: PRT
<213> ORGANISM: Homo sapien

<400> SEQUENCE: 41

Ala Tyr Gly Ser Leu Gly Gly Pro Ala
 1               5

<210> SEQ ID NO 42
<211> LENGTH: 9
<212> TYPE: PRT
<213> ORGANISM: Homo sapien

<400> SEQUENCE: 42

Ala Tyr Pro Gly Cys Asn Lys Arg Tyr
 1               5

<210> SEQ ID NO 43
<211> LENGTH: 9
<212> TYPE: PRT
<213> ORGANISM: Homo sapien

<400> SEQUENCE: 43

Cys Ala Leu Pro Val Ser Gly Ala Ala
 1               5

<210> SEQ ID NO 44
<211> LENGTH: 9
<212> TYPE: PRT
<213> ORGANISM: Homo sapien

<400> SEQUENCE: 44

Cys Ala Tyr Pro Gly Cys Asn Lys Arg
 1               5

<210> SEQ ID NO 45
<211> LENGTH: 9
<212> TYPE: PRT
<213> ORGANISM: Homo sapien

<400> SEQUENCE: 45
```

```
Cys His Thr Pro Thr Asp Ser Cys Thr
1               5
```

<210> SEQ ID NO 46
<211> LENGTH: 9
<212> TYPE: PRT
<213> ORGANISM: Homo sapien

<400> SEQUENCE: 46

```
Cys Lys Thr Cys Gln Arg Lys Phe Ser
1               5
```

<210> SEQ ID NO 47
<211> LENGTH: 9
<212> TYPE: PRT
<213> ORGANISM: Homo sapien

<400> SEQUENCE: 47

```
Cys Leu Glu Ser Gln Pro Ala Ile Arg
1               5
```

<210> SEQ ID NO 48
<211> LENGTH: 9
<212> TYPE: PRT
<213> ORGANISM: Homo sapien

<400> SEQUENCE: 48

```
Cys Leu Ser Ala Phe Thr Val His Phe
1               5
```

<210> SEQ ID NO 49
<211> LENGTH: 9
<212> TYPE: PRT
<213> ORGANISM: Homo sapien

<400> SEQUENCE: 49

```
Cys Met Thr Trp Asn Gln Met Asn Leu
1               5
```

<210> SEQ ID NO 50
<211> LENGTH: 9
<212> TYPE: PRT
<213> ORGANISM: Homo sapien

<400> SEQUENCE: 50

```
Cys Arg Trp Pro Ser Cys Gln Lys Lys
1               5
```

<210> SEQ ID NO 51
<211> LENGTH: 9
<212> TYPE: PRT
<213> ORGANISM: Homo sapien

<400> SEQUENCE: 51

```
Cys Arg Tyr Gly Pro Phe Gly Pro Pro
1               5
```

<210> SEQ ID NO 52
<211> LENGTH: 9
<212> TYPE: PRT
<213> ORGANISM: Homo sapien

<400> SEQUENCE: 52

```
Cys Thr Gly Ser Gln Ala Leu Leu Leu
1               5
```

<210> SEQ ID NO 53
<211> LENGTH: 9
<212> TYPE: PRT
<213> ORGANISM: Homo sapien

<400> SEQUENCE: 53

Asp Glu Leu Val Arg His His Asn Met
1               5

<210> SEQ ID NO 54
<211> LENGTH: 9
<212> TYPE: PRT
<213> ORGANISM: Homo sapien

<400> SEQUENCE: 54

Asp Phe Ala Pro Pro Gly Ala Ser Ala
1               5

<210> SEQ ID NO 55
<211> LENGTH: 9
<212> TYPE: PRT
<213> ORGANISM: Homo sapien

<400> SEQUENCE: 55

Asp Phe Lys Asp Cys Glu Arg Arg Phe
1               5

<210> SEQ ID NO 56
<211> LENGTH: 9
<212> TYPE: PRT
<213> ORGANISM: Homo sapien

<400> SEQUENCE: 56

Asp Gly Thr Pro Ser Tyr Gly His Thr
1               5

<210> SEQ ID NO 57
<211> LENGTH: 9
<212> TYPE: PRT
<213> ORGANISM: Homo sapien

<400> SEQUENCE: 57

Asp His Leu Lys Thr His Thr Arg Thr
1               5

<210> SEQ ID NO 58
<211> LENGTH: 9
<212> TYPE: PRT
<213> ORGANISM: Homo sapien

<400> SEQUENCE: 58

Asp Leu Asn Ala Leu Leu Pro Ala Val
1               5

<210> SEQ ID NO 59
<211> LENGTH: 9
<212> TYPE: PRT
<213> ORGANISM: Homo sapien

<400> SEQUENCE: 59

Asp Pro Met Gly Gln Gln Gly Ser Leu
1               5

<210> SEQ ID NO 60
<211> LENGTH: 9

```
<212> TYPE: PRT
<213> ORGANISM: Homo sapien

<400> SEQUENCE: 60

Asp Gln Leu Lys Arg His Gln Arg Arg
1               5

<210> SEQ ID NO 61
<211> LENGTH: 9
<212> TYPE: PRT
<213> ORGANISM: Homo sapien

<400> SEQUENCE: 61

Asp Ser Cys Thr Gly Ser Gln Ala Leu
1               5

<210> SEQ ID NO 62
<211> LENGTH: 9
<212> TYPE: PRT
<213> ORGANISM: Homo sapien

<400> SEQUENCE: 62

Asp Val Arg Asp Leu Asn Ala Leu Leu
1               5

<210> SEQ ID NO 63
<211> LENGTH: 9
<212> TYPE: PRT
<213> ORGANISM: Homo sapien

<400> SEQUENCE: 63

Asp Val Arg Arg Val Pro Gly Val Ala
1               5

<210> SEQ ID NO 64
<211> LENGTH: 9
<212> TYPE: PRT
<213> ORGANISM: Homo sapien

<400> SEQUENCE: 64

Glu Asp Pro Met Gly Gln Gln Gly Ser
1               5

<210> SEQ ID NO 65
<211> LENGTH: 9
<212> TYPE: PRT
<213> ORGANISM: Homo sapien

<400> SEQUENCE: 65

Glu Glu Gln Cys Leu Ser Ala Phe Thr
1               5

<210> SEQ ID NO 66
<211> LENGTH: 9
<212> TYPE: PRT
<213> ORGANISM: Homo sapien

<400> SEQUENCE: 66

Glu Lys Pro Tyr Gln Cys Asp Phe Lys
1               5

<210> SEQ ID NO 67
<211> LENGTH: 9
<212> TYPE: PRT
<213> ORGANISM: Homo sapien
```

```
<400> SEQUENCE: 67

Glu Lys Arg Pro Phe Met Cys Ala Tyr
1               5

<210> SEQ ID NO 68
<211> LENGTH: 9
<212> TYPE: PRT
<213> ORGANISM: Homo sapien

<400> SEQUENCE: 68

Glu Pro His Glu Glu Gln Cys Leu Ser
1               5

<210> SEQ ID NO 69
<211> LENGTH: 9
<212> TYPE: PRT
<213> ORGANISM: Homo sapien

<400> SEQUENCE: 69

Glu Gln Cys Leu Ser Ala Phe Thr Val
1               5

<210> SEQ ID NO 70
<211> LENGTH: 9
<212> TYPE: PRT
<213> ORGANISM: Homo sapien

<400> SEQUENCE: 70

Glu Ser Asp Asn His Thr Ala Pro Ile
1               5

<210> SEQ ID NO 71
<211> LENGTH: 9
<212> TYPE: PRT
<213> ORGANISM: Homo sapien

<400> SEQUENCE: 71

Glu Ser Asp Asn His Thr Thr Pro Ile
1               5

<210> SEQ ID NO 72
<211> LENGTH: 9
<212> TYPE: PRT
<213> ORGANISM: Homo sapien

<400> SEQUENCE: 72

Glu Ser Gln Pro Ala Ile Arg Asn Gln
1               5

<210> SEQ ID NO 73
<211> LENGTH: 9
<212> TYPE: PRT
<213> ORGANISM: Homo sapien

<400> SEQUENCE: 73

Glu Thr Ser Glu Lys Arg Pro Phe Met
1               5

<210> SEQ ID NO 74
<211> LENGTH: 9
<212> TYPE: PRT
<213> ORGANISM: Homo sapien

<400> SEQUENCE: 74

Phe Ala Pro Pro Gly Ala Ser Ala Tyr
```

<210> SEQ ID NO 75
<211> LENGTH: 9
<212> TYPE: PRT
<213> ORGANISM: Homo sapien

<400> SEQUENCE: 75

Phe Ala Arg Ser Asp Glu Leu Val Arg
 1               5

<210> SEQ ID NO 76
<211> LENGTH: 9
<212> TYPE: PRT
<213> ORGANISM: Homo sapien

<400> SEQUENCE: 76

Phe Gly Pro Pro Pro Pro Ser Gln Ala
 1               5

<210> SEQ ID NO 77
<211> LENGTH: 9
<212> TYPE: PRT
<213> ORGANISM: Homo sapien

<400> SEQUENCE: 77

Phe Lys Asp Cys Glu Arg Arg Phe Ser
 1               5

<210> SEQ ID NO 78
<211> LENGTH: 9
<212> TYPE: PRT
<213> ORGANISM: Homo sapien

<400> SEQUENCE: 78

Phe Lys Leu Ser His Leu Gln Met His
 1               5

<210> SEQ ID NO 79
<211> LENGTH: 9
<212> TYPE: PRT
<213> ORGANISM: Homo sapien

<400> SEQUENCE: 79

Phe Pro Asn Ala Pro Tyr Leu Pro Ser
 1               5

<210> SEQ ID NO 80
<211> LENGTH: 9
<212> TYPE: PRT
<213> ORGANISM: Homo sapien

<400> SEQUENCE: 80

Phe Gln Cys Lys Thr Cys Gln Arg Lys
 1               5

<210> SEQ ID NO 81
<211> LENGTH: 9
<212> TYPE: PRT
<213> ORGANISM: Homo sapien

<400> SEQUENCE: 81

Phe Arg Gly Ile Gln Asp Val Arg Arg
 1               5

<210> SEQ ID NO 82
<211> LENGTH: 9
<212> TYPE: PRT
<213> ORGANISM: Homo sapien

<400> SEQUENCE: 82

Phe Ser Gly Gln Phe Thr Gly Thr Ala
1               5

<210> SEQ ID NO 83
<211> LENGTH: 9
<212> TYPE: PRT
<213> ORGANISM: Homo sapien

<400> SEQUENCE: 83

Phe Ser Arg Ser Asp Gln Leu Lys Arg
1               5

<210> SEQ ID NO 84
<211> LENGTH: 9
<212> TYPE: PRT
<213> ORGANISM: Homo sapien

<400> SEQUENCE: 84

Phe Thr Gly Thr Ala Gly Ala Cys Arg
1               5

<210> SEQ ID NO 85
<211> LENGTH: 9
<212> TYPE: PRT
<213> ORGANISM: Homo sapien

<400> SEQUENCE: 85

Phe Thr Val His Phe Ser Gly Gln Phe
1               5

<210> SEQ ID NO 86
<211> LENGTH: 9
<212> TYPE: PRT
<213> ORGANISM: Homo sapien

<400> SEQUENCE: 86

Gly Ala Ala Gln Trp Ala Pro Val Leu
1               5

<210> SEQ ID NO 87
<211> LENGTH: 9
<212> TYPE: PRT
<213> ORGANISM: Homo sapien

<400> SEQUENCE: 87

Gly Ala Glu Pro His Glu Glu Gln Cys
1               5

<210> SEQ ID NO 88
<211> LENGTH: 9
<212> TYPE: PRT
<213> ORGANISM: Homo sapien

<400> SEQUENCE: 88

Gly Ala Thr Leu Lys Gly Val Ala Ala
1               5

<210> SEQ ID NO 89
<211> LENGTH: 9
<212> TYPE: PRT

<213> ORGANISM: Homo sapien

<400> SEQUENCE: 89

Gly Cys Ala Leu Pro Val Ser Gly Ala
1               5

<210> SEQ ID NO 90
<211> LENGTH: 9
<212> TYPE: PRT
<213> ORGANISM: Homo sapien

<400> SEQUENCE: 90

Gly Cys Asn Lys Arg Tyr Phe Lys Leu
1               5

<210> SEQ ID NO 91
<211> LENGTH: 9
<212> TYPE: PRT
<213> ORGANISM: Homo sapien

<400> SEQUENCE: 91

Gly Glu Lys Pro Tyr Gln Cys Asp Phe
1               5

<210> SEQ ID NO 92
<211> LENGTH: 9
<212> TYPE: PRT
<213> ORGANISM: Homo sapien

<400> SEQUENCE: 92

Gly Gly Gly Gly Cys Ala Leu Pro Val
1               5

<210> SEQ ID NO 93
<211> LENGTH: 9
<212> TYPE: PRT
<213> ORGANISM: Homo sapien

<400> SEQUENCE: 93

Gly Gly Pro Ala Pro Pro Pro Ala Pro
1               5

<210> SEQ ID NO 94
<211> LENGTH: 9
<212> TYPE: PRT
<213> ORGANISM: Homo sapien

<400> SEQUENCE: 94

Gly His Thr Pro Ser His His Ala Ala
1               5

<210> SEQ ID NO 95
<211> LENGTH: 9
<212> TYPE: PRT
<213> ORGANISM: Homo sapien

<400> SEQUENCE: 95

Gly Lys Thr Ser Glu Lys Pro Phe Ser
1               5

<210> SEQ ID NO 96
<211> LENGTH: 9
<212> TYPE: PRT
<213> ORGANISM: Homo sapien

<400> SEQUENCE: 96

Gly Pro Phe Gly Pro Pro Pro Ser
1               5

<210> SEQ ID NO 97
<211> LENGTH: 9
<212> TYPE: PRT
<213> ORGANISM: Homo sapien

<400> SEQUENCE: 97

Gly Pro Pro Pro Ser Gln Ala Ser
1               5

<210> SEQ ID NO 98
<211> LENGTH: 9
<212> TYPE: PRT
<213> ORGANISM: Homo sapien

<400> SEQUENCE: 98

Gly Gln Ala Arg Met Phe Pro Asn Ala
1               5

<210> SEQ ID NO 99
<211> LENGTH: 9
<212> TYPE: PRT
<213> ORGANISM: Homo sapien

<400> SEQUENCE: 99

Gly Gln Phe Thr Gly Thr Ala Gly Ala
1               5

<210> SEQ ID NO 100
<211> LENGTH: 9
<212> TYPE: PRT
<213> ORGANISM: Homo sapien

<400> SEQUENCE: 100

Gly Gln Ser Asn His Ser Thr Gly Tyr
1               5

<210> SEQ ID NO 101
<211> LENGTH: 9
<212> TYPE: PRT
<213> ORGANISM: Homo sapien

<400> SEQUENCE: 101

Gly Ser Asp Val Arg Asp Leu Asn Ala
1               5

<210> SEQ ID NO 102
<211> LENGTH: 9
<212> TYPE: PRT
<213> ORGANISM: Homo sapien

<400> SEQUENCE: 102

Gly Ser Gln Ala Leu Leu Leu Arg Thr
1               5

<210> SEQ ID NO 103
<211> LENGTH: 9
<212> TYPE: PRT
<213> ORGANISM: Homo sapien

<400> SEQUENCE: 103

Gly Val Phe Arg Gly Ile Gln Asp Val
1               5

```
<210> SEQ ID NO 104
<211> LENGTH: 9
<212> TYPE: PRT
<213> ORGANISM: Homo sapien

<400> SEQUENCE: 104

Gly Val Lys Pro Phe Gln Cys Lys Thr
1               5

<210> SEQ ID NO 105
<211> LENGTH: 9
<212> TYPE: PRT
<213> ORGANISM: Homo sapien

<400> SEQUENCE: 105

Gly Tyr Glu Ser Asp Asn His Thr Ala
1               5

<210> SEQ ID NO 106
<211> LENGTH: 9
<212> TYPE: PRT
<213> ORGANISM: Homo sapien

<400> SEQUENCE: 106

Gly Tyr Glu Ser Asp Asn His Thr Thr
1               5

<210> SEQ ID NO 107
<211> LENGTH: 9
<212> TYPE: PRT
<213> ORGANISM: Homo sapien

<400> SEQUENCE: 107

His Glu Glu Gln Cys Leu Ser Ala Phe
1               5

<210> SEQ ID NO 108
<211> LENGTH: 9
<212> TYPE: PRT
<213> ORGANISM: Homo sapien

<400> SEQUENCE: 108

His His Asn Met His Gln Arg Asn Met
1               5

<210> SEQ ID NO 109
<211> LENGTH: 9
<212> TYPE: PRT
<213> ORGANISM: Homo sapien

<400> SEQUENCE: 109

His Gln Arg Arg His Thr Gly Val Lys
1               5

<210> SEQ ID NO 110
<211> LENGTH: 9
<212> TYPE: PRT
<213> ORGANISM: Homo sapien

<400> SEQUENCE: 110

His Ser Phe Lys His Glu Asp Pro Met
1               5

<210> SEQ ID NO 111
```

```
<211> LENGTH: 9
<212> TYPE: PRT
<213> ORGANISM: Homo sapien

<400> SEQUENCE: 111

His Ser Arg Lys His Thr Gly Glu Lys
1               5

<210> SEQ ID NO 112
<211> LENGTH: 9
<212> TYPE: PRT
<213> ORGANISM: Homo sapien

<400> SEQUENCE: 112

His Thr Gly Glu Lys Pro Tyr Gln Cys
1               5

<210> SEQ ID NO 113
<211> LENGTH: 9
<212> TYPE: PRT
<213> ORGANISM: Homo sapien

<400> SEQUENCE: 113

His Thr His Gly Val Phe Arg Gly Ile
1               5

<210> SEQ ID NO 114
<211> LENGTH: 9
<212> TYPE: PRT
<213> ORGANISM: Homo sapien

<400> SEQUENCE: 114

His Thr Arg Thr His Thr Gly Lys Thr
1               5

<210> SEQ ID NO 115
<211> LENGTH: 9
<212> TYPE: PRT
<213> ORGANISM: Homo sapien

<400> SEQUENCE: 115

His Thr Thr Pro Ile Leu Cys Gly Ala
1               5

<210> SEQ ID NO 116
<211> LENGTH: 9
<212> TYPE: PRT
<213> ORGANISM: Homo sapien

<400> SEQUENCE: 116

Ile Leu Cys Gly Ala Gln Tyr Arg Ile
1               5

<210> SEQ ID NO 117
<211> LENGTH: 9
<212> TYPE: PRT
<213> ORGANISM: Homo sapien

<400> SEQUENCE: 117

Ile Arg Asn Gln Gly Tyr Ser Thr Val
1               5

<210> SEQ ID NO 118
<211> LENGTH: 9
<212> TYPE: PRT
<213> ORGANISM: Homo sapien
```

<400> SEQUENCE: 118

Lys Asp Cys Glu Arg Arg Phe Ser Arg
 1               5

<210> SEQ ID NO 119
<211> LENGTH: 9
<212> TYPE: PRT
<213> ORGANISM: Homo sapien

<400> SEQUENCE: 119

Lys Phe Ala Arg Ser Asp Glu Leu Val
 1               5

<210> SEQ ID NO 120
<211> LENGTH: 9
<212> TYPE: PRT
<213> ORGANISM: Homo sapien

<400> SEQUENCE: 120

Lys Phe Ser Arg Ser Asp His Leu Lys
 1               5

<210> SEQ ID NO 121
<211> LENGTH: 9
<212> TYPE: PRT
<213> ORGANISM: Homo sapien

<400> SEQUENCE: 121

Lys His Glu Asp Pro Met Gly Gln Gln
 1               5

<210> SEQ ID NO 122
<211> LENGTH: 9
<212> TYPE: PRT
<213> ORGANISM: Homo sapien

<400> SEQUENCE: 122

Lys Lys Phe Ala Arg Ser Asp Glu Leu
 1               5

<210> SEQ ID NO 123
<211> LENGTH: 9
<212> TYPE: PRT
<213> ORGANISM: Homo sapien

<400> SEQUENCE: 123

Lys Pro Phe Ser Cys Arg Trp Pro Ser
 1               5

<210> SEQ ID NO 124
<211> LENGTH: 9
<212> TYPE: PRT
<213> ORGANISM: Homo sapien

<400> SEQUENCE: 124

Lys Pro Tyr Gln Cys Asp Phe Lys Asp
 1               5

<210> SEQ ID NO 125
<211> LENGTH: 9
<212> TYPE: PRT
<213> ORGANISM: Homo sapien

<400> SEQUENCE: 125

```
Lys Gln Glu Pro Ser Trp Gly Gly Ala
1               5

<210> SEQ ID NO 126
<211> LENGTH: 9
<212> TYPE: PRT
<213> ORGANISM: Homo sapien

<400> SEQUENCE: 126

Lys Arg His Gln Arg Arg His Thr Gly
1               5

<210> SEQ ID NO 127
<211> LENGTH: 9
<212> TYPE: PRT
<213> ORGANISM: Homo sapien

<400> SEQUENCE: 127

Lys Arg Tyr Phe Lys Leu Ser His Leu
1               5

<210> SEQ ID NO 128
<211> LENGTH: 9
<212> TYPE: PRT
<213> ORGANISM: Homo sapien

<400> SEQUENCE: 128

Lys Thr Cys Gln Arg Lys Phe Ser Arg
1               5

<210> SEQ ID NO 129
<211> LENGTH: 9
<212> TYPE: PRT
<213> ORGANISM: Homo sapien

<400> SEQUENCE: 129

Lys Thr Ser Glu Lys Pro Phe Ser Cys
1               5

<210> SEQ ID NO 130
<211> LENGTH: 9
<212> TYPE: PRT
<213> ORGANISM: Homo sapien

<400> SEQUENCE: 130

Leu Asp Phe Ala Pro Pro Gly Ala Ser
1               5

<210> SEQ ID NO 131
<211> LENGTH: 9
<212> TYPE: PRT
<213> ORGANISM: Homo sapien

<400> SEQUENCE: 131

Leu Glu Cys Met Thr Trp Asn Gln Met
1               5

<210> SEQ ID NO 132
<211> LENGTH: 9
<212> TYPE: PRT
<213> ORGANISM: Homo sapien

<400> SEQUENCE: 132

Leu Glu Ser Gln Pro Ala Ile Arg Asn
1               5
```

```
<210> SEQ ID NO 133
<211> LENGTH: 9
<212> TYPE: PRT
<213> ORGANISM: Homo sapien

<400> SEQUENCE: 133

Leu Gly Ala Thr Leu Lys Gly Val Ala
1               5

<210> SEQ ID NO 134
<211> LENGTH: 9
<212> TYPE: PRT
<213> ORGANISM: Homo sapien

<400> SEQUENCE: 134

Leu Gly Gly Gly Gly Gly Cys Ala Leu
1               5

<210> SEQ ID NO 135
<211> LENGTH: 9
<212> TYPE: PRT
<213> ORGANISM: Homo sapien

<400> SEQUENCE: 135

Leu Lys Gly Val Ala Ala Gly Ser Ser
1               5

<210> SEQ ID NO 136
<211> LENGTH: 9
<212> TYPE: PRT
<213> ORGANISM: Homo sapien

<400> SEQUENCE: 136

Leu Lys Arg His Gln Arg Arg His Thr
1               5

<210> SEQ ID NO 137
<211> LENGTH: 9
<212> TYPE: PRT
<213> ORGANISM: Homo sapien

<400> SEQUENCE: 137

Leu Lys Thr His Thr Arg Thr His Thr
1               5

<210> SEQ ID NO 138
<211> LENGTH: 9
<212> TYPE: PRT
<213> ORGANISM: Homo sapien

<400> SEQUENCE: 138

Leu Pro Val Ser Gly Ala Ala Gln Trp
1               5

<210> SEQ ID NO 139
<211> LENGTH: 9
<212> TYPE: PRT
<213> ORGANISM: Homo sapien

<400> SEQUENCE: 139

Leu Gln Met His Ser Arg Lys His Thr
1               5

<210> SEQ ID NO 140
<211> LENGTH: 9
```

```
<212> TYPE: PRT
<213> ORGANISM: Homo sapien

<400> SEQUENCE: 140

Leu Arg Thr Pro Tyr Ser Ser Asp Asn
 1               5

<210> SEQ ID NO 141
<211> LENGTH: 9
<212> TYPE: PRT
<213> ORGANISM: Homo sapien

<400> SEQUENCE: 141

Leu Ser His Leu Gln Met His Ser Arg
 1               5

<210> SEQ ID NO 142
<211> LENGTH: 9
<212> TYPE: PRT
<213> ORGANISM: Homo sapien

<400> SEQUENCE: 142

Met Cys Ala Tyr Pro Gly Cys Asn Lys
 1               5

<210> SEQ ID NO 143
<211> LENGTH: 9
<212> TYPE: PRT
<213> ORGANISM: Homo sapien

<400> SEQUENCE: 143

Met His Gln Arg Asn Met Thr Lys Leu
 1               5

<210> SEQ ID NO 144
<211> LENGTH: 9
<212> TYPE: PRT
<213> ORGANISM: Homo sapien

<400> SEQUENCE: 144

Asn Ala Pro Tyr Leu Pro Ser Cys Leu
 1               5

<210> SEQ ID NO 145
<211> LENGTH: 9
<212> TYPE: PRT
<213> ORGANISM: Homo sapien

<400> SEQUENCE: 145

Asn Lys Arg Tyr Phe Lys Leu Ser His
 1               5

<210> SEQ ID NO 146
<211> LENGTH: 9
<212> TYPE: PRT
<213> ORGANISM: Homo sapien

<400> SEQUENCE: 146

Asn Leu Gly Ala Thr Leu Lys Gly Val
 1               5

<210> SEQ ID NO 147
<211> LENGTH: 9
<212> TYPE: PRT
<213> ORGANISM: Homo sapien
```

```
<400> SEQUENCE: 147

Asn Leu Tyr Gln Met Thr Ser Gln Leu
 1               5

<210> SEQ ID NO 148
<211> LENGTH: 9
<212> TYPE: PRT
<213> ORGANISM: Homo sapien

<400> SEQUENCE: 148

Asn Met His Gln Arg Asn Met Thr Lys
 1               5

<210> SEQ ID NO 149
<211> LENGTH: 9
<212> TYPE: PRT
<213> ORGANISM: Homo sapien

<400> SEQUENCE: 149

Asn Met Thr Lys Leu Gln Leu Ala Leu
 1               5

<210> SEQ ID NO 150
<211> LENGTH: 9
<212> TYPE: PRT
<213> ORGANISM: Homo sapien

<400> SEQUENCE: 150

Asn Gln Gly Tyr Ser Thr Val Thr Phe
 1               5

<210> SEQ ID NO 151
<211> LENGTH: 9
<212> TYPE: PRT
<213> ORGANISM: Homo sapien

<400> SEQUENCE: 151

Asn Gln Met Asn Leu Gly Ala Thr Leu
 1               5

<210> SEQ ID NO 152
<211> LENGTH: 9
<212> TYPE: PRT
<213> ORGANISM: Homo sapien

<400> SEQUENCE: 152

Pro Ala Ile Arg Asn Gln Gly Tyr Ser
 1               5

<210> SEQ ID NO 153
<211> LENGTH: 9
<212> TYPE: PRT
<213> ORGANISM: Homo sapien

<400> SEQUENCE: 153

Pro Gly Ala Ser Ala Tyr Gly Ser Leu
 1               5

<210> SEQ ID NO 154
<211> LENGTH: 9
<212> TYPE: PRT
<213> ORGANISM: Homo sapien

<400> SEQUENCE: 154

Pro His Glu Glu Gln Cys Leu Ser Ala
```

```
<210> SEQ ID NO 155
<211> LENGTH: 9
<212> TYPE: PRT
<213> ORGANISM: Homo sapien

<400> SEQUENCE: 155

Pro Ile Leu Cys Gly Ala Gln Tyr Arg
1               5

<210> SEQ ID NO 156
<211> LENGTH: 9
<212> TYPE: PRT
<213> ORGANISM: Homo sapien

<400> SEQUENCE: 156

Pro Pro Pro Pro His Ser Phe Ile Lys
1               5

<210> SEQ ID NO 157
<211> LENGTH: 9
<212> TYPE: PRT
<213> ORGANISM: Homo sapien

<400> SEQUENCE: 157

Pro Pro Pro Pro Pro His Ser Phe Ile
1               5

<210> SEQ ID NO 158
<211> LENGTH: 9
<212> TYPE: PRT
<213> ORGANISM: Homo sapien

<400> SEQUENCE: 158

Pro Pro Pro Pro Pro Pro His Ser Phe
1               5

<210> SEQ ID NO 159
<211> LENGTH: 9
<212> TYPE: PRT
<213> ORGANISM: Homo sapien

<400> SEQUENCE: 159

Pro Ser Cys Gln Lys Lys Phe Ala Arg
1               5

<210> SEQ ID NO 160
<211> LENGTH: 9
<212> TYPE: PRT
<213> ORGANISM: Homo sapien

<400> SEQUENCE: 160

Gln Ala Leu Leu Leu Arg Thr Pro Tyr
1               5

<210> SEQ ID NO 161
<211> LENGTH: 9
<212> TYPE: PRT
<213> ORGANISM: Homo sapien

<400> SEQUENCE: 161

Gln Ala Ser Ser Gly Gln Ala Arg Met
1               5
```

```
<210> SEQ ID NO 162
<211> LENGTH: 9
<212> TYPE: PRT
<213> ORGANISM: Homo sapien

<400> SEQUENCE: 162

Gln Cys Asp Phe Lys Asp Cys Glu Arg
1               5

<210> SEQ ID NO 163
<211> LENGTH: 9
<212> TYPE: PRT
<213> ORGANISM: Homo sapien

<400> SEQUENCE: 163

Gln Cys Lys Thr Cys Gln Arg Lys Phe
1               5

<210> SEQ ID NO 164
<211> LENGTH: 9
<212> TYPE: PRT
<213> ORGANISM: Homo sapien

<400> SEQUENCE: 164

Gln Asp Val Arg Arg Val Pro Gly Val
1               5

<210> SEQ ID NO 165
<211> LENGTH: 9
<212> TYPE: PRT
<213> ORGANISM: Homo sapien

<400> SEQUENCE: 165

Gln Phe Thr Gly Thr Ala Gly Ala Cys
1               5

<210> SEQ ID NO 166
<211> LENGTH: 9
<212> TYPE: PRT
<213> ORGANISM: Homo sapien

<400> SEQUENCE: 166

Gln Gly Ser Leu Gly Glu Gln Gln Tyr
1               5

<210> SEQ ID NO 167
<211> LENGTH: 9
<212> TYPE: PRT
<213> ORGANISM: Homo sapien

<400> SEQUENCE: 167

Gln Leu Glu Cys Met Thr Trp Asn Gln
1               5

<210> SEQ ID NO 168
<211> LENGTH: 9
<212> TYPE: PRT
<213> ORGANISM: Homo sapien

<400> SEQUENCE: 168

Gln Met Asn Leu Gly Ala Thr Leu Lys
1               5

<210> SEQ ID NO 169
<211> LENGTH: 9
<212> TYPE: PRT
```

<213> ORGANISM: Homo sapien

<400> SEQUENCE: 169

Gln Met Thr Ser Gln Leu Glu Cys Met
1               5

<210> SEQ ID NO 170
<211> LENGTH: 9
<212> TYPE: PRT
<213> ORGANISM: Homo sapien

<400> SEQUENCE: 170

Gln Pro Ala Ile Arg Asn Gln Gly Tyr
1               5

<210> SEQ ID NO 171
<211> LENGTH: 9
<212> TYPE: PRT
<213> ORGANISM: Homo sapien

<400> SEQUENCE: 171

Gln Gln Tyr Ser Val Pro Pro Pro Val
1               5

<210> SEQ ID NO 172
<211> LENGTH: 9
<212> TYPE: PRT
<213> ORGANISM: Homo sapien

<400> SEQUENCE: 172

Gln Arg Lys Phe Ser Arg Ser Asp His
1               5

<210> SEQ ID NO 173
<211> LENGTH: 9
<212> TYPE: PRT
<213> ORGANISM: Homo sapien

<400> SEQUENCE: 173

Gln Arg Asn Met Thr Lys Leu Gln Leu
1               5

<210> SEQ ID NO 174
<211> LENGTH: 9
<212> TYPE: PRT
<213> ORGANISM: Homo sapien

<400> SEQUENCE: 174

Gln Trp Ala Pro Val Leu Asp Phe Ala
1               5

<210> SEQ ID NO 175
<211> LENGTH: 9
<212> TYPE: PRT
<213> ORGANISM: Homo sapien

<400> SEQUENCE: 175

Gln Tyr Arg Ile His Thr His Gly Val
1               5

<210> SEQ ID NO 176
<211> LENGTH: 9
<212> TYPE: PRT
<213> ORGANISM: Homo sapien

<400> SEQUENCE: 176

```
Gln Tyr Ser Val Pro Pro Val Tyr
1               5

<210> SEQ ID NO 177
<211> LENGTH: 9
<212> TYPE: PRT
<213> ORGANISM: Homo sapien

<400> SEQUENCE: 177

Arg Asp Leu Asn Ala Leu Leu Pro Ala
1               5

<210> SEQ ID NO 178
<211> LENGTH: 9
<212> TYPE: PRT
<213> ORGANISM: Homo sapien

<400> SEQUENCE: 178

Arg Phe Ser Arg Ser Asp Gln Leu Lys
1               5

<210> SEQ ID NO 179
<211> LENGTH: 9
<212> TYPE: PRT
<213> ORGANISM: Homo sapien

<400> SEQUENCE: 179

Arg Gly Ile Gln Asp Val Arg Arg Val
1               5

<210> SEQ ID NO 180
<211> LENGTH: 9
<212> TYPE: PRT
<213> ORGANISM: Homo sapien

<400> SEQUENCE: 180

Arg His His Asn Met His Gln Arg Asn
1               5

<210> SEQ ID NO 181
<211> LENGTH: 9
<212> TYPE: PRT
<213> ORGANISM: Homo sapien

<400> SEQUENCE: 181

Arg His Gln Arg His Thr Gly Val
1               5

<210> SEQ ID NO 182
<211> LENGTH: 9
<212> TYPE: PRT
<213> ORGANISM: Homo sapien

<400> SEQUENCE: 182

Arg Ile His Thr His Gly Val Phe Arg
1               5

<210> SEQ ID NO 183
<211> LENGTH: 9
<212> TYPE: PRT
<213> ORGANISM: Homo sapien

<400> SEQUENCE: 183

Arg Lys Phe Ser Arg Ser Asp His Leu
1               5
```

<210> SEQ ID NO 184
<211> LENGTH: 9
<212> TYPE: PRT
<213> ORGANISM: Homo sapien

<400> SEQUENCE: 184

Arg Lys His Thr Gly Glu Lys Pro Tyr
1               5

<210> SEQ ID NO 185
<211> LENGTH: 9
<212> TYPE: PRT
<213> ORGANISM: Homo sapien

<400> SEQUENCE: 185

Arg Met Phe Pro Asn Ala Pro Tyr Leu
1               5

<210> SEQ ID NO 186
<211> LENGTH: 9
<212> TYPE: PRT
<213> ORGANISM: Homo sapien

<400> SEQUENCE: 186

Arg Asn Met Thr Lys Leu Gln Leu Ala
1               5

<210> SEQ ID NO 187
<211> LENGTH: 9
<212> TYPE: PRT
<213> ORGANISM: Homo sapien

<400> SEQUENCE: 187

Arg Arg Phe Ser Arg Ser Asp Gln Leu
1               5

<210> SEQ ID NO 188
<211> LENGTH: 9
<212> TYPE: PRT
<213> ORGANISM: Homo sapien

<400> SEQUENCE: 188

Arg Arg His Thr Gly Val Lys Pro Phe
1               5

<210> SEQ ID NO 189
<211> LENGTH: 9
<212> TYPE: PRT
<213> ORGANISM: Homo sapien

<400> SEQUENCE: 189

Arg Arg Val Pro Gly Val Ala Pro Thr
1               5

<210> SEQ ID NO 190
<211> LENGTH: 9
<212> TYPE: PRT
<213> ORGANISM: Homo sapien

<400> SEQUENCE: 190

Arg Ser Ala Ser Glu Thr Ser Glu Lys
1               5

<210> SEQ ID NO 191

```
<211> LENGTH: 9
<212> TYPE: PRT
<213> ORGANISM: Homo sapien

<400> SEQUENCE: 191

Arg Ser Asp Glu Leu Val Arg His His
 1               5

<210> SEQ ID NO 192
<211> LENGTH: 9
<212> TYPE: PRT
<213> ORGANISM: Homo sapien

<400> SEQUENCE: 192

Arg Ser Asp His Leu Lys Thr His Thr
 1               5

<210> SEQ ID NO 193
<211> LENGTH: 9
<212> TYPE: PRT
<213> ORGANISM: Homo sapien

<400> SEQUENCE: 193

Arg Ser Asp Gln Leu Lys Arg His Gln
 1               5

<210> SEQ ID NO 194
<211> LENGTH: 9
<212> TYPE: PRT
<213> ORGANISM: Homo sapien

<400> SEQUENCE: 194

Arg Thr Pro Tyr Ser Ser Asp Asn Leu
 1               5

<210> SEQ ID NO 195
<211> LENGTH: 9
<212> TYPE: PRT
<213> ORGANISM: Homo sapien

<400> SEQUENCE: 195

Arg Val Pro Gly Val Ala Pro Thr Leu
 1               5

<210> SEQ ID NO 196
<211> LENGTH: 9
<212> TYPE: PRT
<213> ORGANISM: Homo sapien

<400> SEQUENCE: 196

Arg Trp Pro Ser Cys Gln Lys Lys Phe
 1               5

<210> SEQ ID NO 197
<211> LENGTH: 9
<212> TYPE: PRT
<213> ORGANISM: Homo sapien

<400> SEQUENCE: 197

Ser Ala Ser Glu Thr Ser Glu Lys Arg
 1               5

<210> SEQ ID NO 198
<211> LENGTH: 9
<212> TYPE: PRT
<213> ORGANISM: Homo sapien
```

```
<400> SEQUENCE: 198

Ser Cys Leu Glu Ser Gln Pro Ala Ile
1               5

<210> SEQ ID NO 199
<211> LENGTH: 9
<212> TYPE: PRT
<213> ORGANISM: Homo sapien

<400> SEQUENCE: 199

Ser Cys Leu Glu Ser Gln Pro Thr Ile
1               5

<210> SEQ ID NO 200
<211> LENGTH: 9
<212> TYPE: PRT
<213> ORGANISM: Homo sapien

<400> SEQUENCE: 200

Ser Cys Gln Lys Lys Phe Ala Arg Ser
1               5

<210> SEQ ID NO 201
<211> LENGTH: 9
<212> TYPE: PRT
<213> ORGANISM: Homo sapien

<400> SEQUENCE: 201

Ser Cys Arg Trp Pro Ser Cys Gln Lys
1               5

<210> SEQ ID NO 202
<211> LENGTH: 9
<212> TYPE: PRT
<213> ORGANISM: Homo sapien

<400> SEQUENCE: 202

Ser Cys Thr Gly Ser Gln Ala Leu Leu
1               5

<210> SEQ ID NO 203
<211> LENGTH: 9
<212> TYPE: PRT
<213> ORGANISM: Homo sapien

<400> SEQUENCE: 203

Ser Asp Glu Leu Val Arg His His Asn
1               5

<210> SEQ ID NO 204
<211> LENGTH: 9
<212> TYPE: PRT
<213> ORGANISM: Homo sapien

<400> SEQUENCE: 204

Ser Asp Asn His Thr Thr Pro Ile Leu
1               5

<210> SEQ ID NO 205
<211> LENGTH: 9
<212> TYPE: PRT
<213> ORGANISM: Homo sapien

<400> SEQUENCE: 205
```

```
Ser Asp Asn Leu Tyr Gln Met Thr Ser
1               5
```

<210> SEQ ID NO 206
<211> LENGTH: 9
<212> TYPE: PRT
<213> ORGANISM: Homo sapien

<400> SEQUENCE: 206

```
Ser Asp Val Arg Asp Leu Asn Ala Leu
1               5
```

<210> SEQ ID NO 207
<211> LENGTH: 9
<212> TYPE: PRT
<213> ORGANISM: Homo sapien

<400> SEQUENCE: 207

```
Ser Glu Lys Pro Phe Ser Cys Arg Trp
1               5
```

<210> SEQ ID NO 208
<211> LENGTH: 9
<212> TYPE: PRT
<213> ORGANISM: Homo sapien

<400> SEQUENCE: 208

```
Ser Glu Lys Arg Pro Phe Met Cys Ala
1               5
```

<210> SEQ ID NO 209
<211> LENGTH: 9
<212> TYPE: PRT
<213> ORGANISM: Homo sapien

<400> SEQUENCE: 209

```
Ser Glu Thr Ser Glu Lys Arg Pro Phe
1               5
```

<210> SEQ ID NO 210
<211> LENGTH: 9
<212> TYPE: PRT
<213> ORGANISM: Homo sapien

<400> SEQUENCE: 210

```
Ser Phe Ile Lys Gln Glu Pro Ser Trp
1               5
```

<210> SEQ ID NO 211
<211> LENGTH: 9
<212> TYPE: PRT
<213> ORGANISM: Homo sapien

<400> SEQUENCE: 211

```
Ser Gly Ala Ala Gln Trp Ala Pro Val
1               5
```

<210> SEQ ID NO 212
<211> LENGTH: 9
<212> TYPE: PRT
<213> ORGANISM: Homo sapien

<400> SEQUENCE: 212

```
Ser Gly Gln Ala Arg Met Phe Pro Asn
1               5
```

```
<210> SEQ ID NO 213
<211> LENGTH: 9
<212> TYPE: PRT
<213> ORGANISM: Homo sapien

<400> SEQUENCE: 213

Ser His His Ala Ala Gln Phe Pro Asn
1               5

<210> SEQ ID NO 214
<211> LENGTH: 9
<212> TYPE: PRT
<213> ORGANISM: Homo sapien

<400> SEQUENCE: 214

Ser Leu Gly Glu Gln Gln Tyr Ser Val
1               5

<210> SEQ ID NO 215
<211> LENGTH: 9
<212> TYPE: PRT
<213> ORGANISM: Homo sapien

<400> SEQUENCE: 215

Ser Leu Gly Gly Gly Gly Gly Cys Ala
1               5

<210> SEQ ID NO 216
<211> LENGTH: 9
<212> TYPE: PRT
<213> ORGANISM: Homo sapien

<400> SEQUENCE: 216

Ser Gln Ala Ser Ser Gly Gln Ala Arg
1               5

<210> SEQ ID NO 217
<211> LENGTH: 9
<212> TYPE: PRT
<213> ORGANISM: Homo sapien

<400> SEQUENCE: 217

Ser Ser Asp Asn Leu Tyr Gln Met Thr
1               5

<210> SEQ ID NO 218
<211> LENGTH: 9
<212> TYPE: PRT
<213> ORGANISM: Homo sapien

<400> SEQUENCE: 218

Ser Val Pro Pro Pro Val Tyr Gly Cys
1               5

<210> SEQ ID NO 219
<211> LENGTH: 9
<212> TYPE: PRT
<213> ORGANISM: Homo sapien

<400> SEQUENCE: 219

Thr Cys Gln Arg Lys Phe Ser Arg Ser
1               5

<210> SEQ ID NO 220
<211> LENGTH: 9
```

```
<212> TYPE: PRT
<213> ORGANISM: Homo sapien

<400> SEQUENCE: 220

Thr Asp Ser Cys Thr Gly Ser Gln Ala
1               5

<210> SEQ ID NO 221
<211> LENGTH: 9
<212> TYPE: PRT
<213> ORGANISM: Homo sapien

<400> SEQUENCE: 221

Thr Glu Gly Gln Ser Asn His Ser Thr
1               5

<210> SEQ ID NO 222
<211> LENGTH: 9
<212> TYPE: PRT
<213> ORGANISM: Homo sapien

<400> SEQUENCE: 222

Thr Gly Lys Thr Ser Glu Lys Pro Phe
1               5

<210> SEQ ID NO 223
<211> LENGTH: 9
<212> TYPE: PRT
<213> ORGANISM: Homo sapien

<400> SEQUENCE: 223

Thr Gly Ser Gln Ala Leu Leu Leu Arg
1               5

<210> SEQ ID NO 224
<211> LENGTH: 9
<212> TYPE: PRT
<213> ORGANISM: Homo sapien

<400> SEQUENCE: 224

Thr Gly Thr Ala Gly Ala Cys Arg Tyr
1               5

<210> SEQ ID NO 225
<211> LENGTH: 9
<212> TYPE: PRT
<213> ORGANISM: Homo sapien

<400> SEQUENCE: 225

Thr Gly Tyr Glu Ser Asp Asn His Thr
1               5

<210> SEQ ID NO 226
<211> LENGTH: 9
<212> TYPE: PRT
<213> ORGANISM: Homo sapien

<400> SEQUENCE: 226

Thr Leu Val Arg Ser Ala Ser Glu Thr
1               5

<210> SEQ ID NO 227
<211> LENGTH: 9
<212> TYPE: PRT
<213> ORGANISM: Homo sapien
```

```
<400> SEQUENCE: 227

Thr Pro Ile Leu Cys Gly Ala Gln Tyr
 1               5

<210> SEQ ID NO 228
<211> LENGTH: 9
<212> TYPE: PRT
<213> ORGANISM: Homo sapien

<400> SEQUENCE: 228

Thr Pro Ser His His Ala Ala Gln Phe
 1               5

<210> SEQ ID NO 229
<211> LENGTH: 9
<212> TYPE: PRT
<213> ORGANISM: Homo sapien

<400> SEQUENCE: 229

Thr Pro Ser Tyr Gly His Thr Pro Ser
 1               5

<210> SEQ ID NO 230
<211> LENGTH: 9
<212> TYPE: PRT
<213> ORGANISM: Homo sapien

<400> SEQUENCE: 230

Thr Pro Thr Asp Ser Cys Thr Gly Ser
 1               5

<210> SEQ ID NO 231
<211> LENGTH: 9
<212> TYPE: PRT
<213> ORGANISM: Homo sapien

<400> SEQUENCE: 231

Thr Pro Tyr Ser Ser Asp Asn Leu Tyr
 1               5

<210> SEQ ID NO 232
<211> LENGTH: 9
<212> TYPE: PRT
<213> ORGANISM: Homo sapien

<400> SEQUENCE: 232

Thr Ser Glu Lys Pro Phe Ser Cys Arg
 1               5

<210> SEQ ID NO 233
<211> LENGTH: 9
<212> TYPE: PRT
<213> ORGANISM: Homo sapien

<400> SEQUENCE: 233

Thr Ser Glu Lys Arg Pro Phe Met Cys
 1               5

<210> SEQ ID NO 234
<211> LENGTH: 9
<212> TYPE: PRT
<213> ORGANISM: Homo sapien

<400> SEQUENCE: 234

Thr Ser Gln Leu Glu Cys Met Thr Trp
```

<210> SEQ ID NO 235
<211> LENGTH: 9
<212> TYPE: PRT
<213> ORGANISM: Homo sapien

<400> SEQUENCE: 235

Thr Val His Phe Ser Gly Gln Phe Thr
1               5

<210> SEQ ID NO 236
<211> LENGTH: 9
<212> TYPE: PRT
<213> ORGANISM: Homo sapien

<400> SEQUENCE: 236

Val Ala Ala Gly Ser Ser Ser Ser Val
1               5

<210> SEQ ID NO 237
<211> LENGTH: 9
<212> TYPE: PRT
<213> ORGANISM: Homo sapien

<400> SEQUENCE: 237

Val Ala Pro Thr Leu Val Arg Ser Ala
1               5

<210> SEQ ID NO 238
<211> LENGTH: 9
<212> TYPE: PRT
<213> ORGANISM: Homo sapien

<400> SEQUENCE: 238

Val Phe Arg Gly Ile Gln Asp Val Arg
1               5

<210> SEQ ID NO 239
<211> LENGTH: 9
<212> TYPE: PRT
<213> ORGANISM: Homo sapien

<400> SEQUENCE: 239

Val Lys Pro Phe Gln Cys Lys Thr Cys
1               5

<210> SEQ ID NO 240
<211> LENGTH: 9
<212> TYPE: PRT
<213> ORGANISM: Homo sapien

<400> SEQUENCE: 240

Val Lys Trp Thr Glu Gly Gln Ser Asn
1               5

<210> SEQ ID NO 241
<211> LENGTH: 9
<212> TYPE: PRT
<213> ORGANISM: Homo sapien

<400> SEQUENCE: 241

Val Leu Asp Phe Ala Pro Pro Gly Ala
1               5

```
<210> SEQ ID NO 242
<211> LENGTH: 9
<212> TYPE: PRT
<213> ORGANISM: Homo sapien

<400> SEQUENCE: 242

Val Pro Gly Val Ala Pro Thr Leu Val
 1               5

<210> SEQ ID NO 243
<211> LENGTH: 9
<212> TYPE: PRT
<213> ORGANISM: Homo sapien

<400> SEQUENCE: 243

Val Arg His His Asn Met His Gln Arg
 1               5

<210> SEQ ID NO 244
<211> LENGTH: 9
<212> TYPE: PRT
<213> ORGANISM: Homo sapien

<400> SEQUENCE: 244

Val Thr Phe Asp Gly Thr Pro Ser Tyr
 1               5

<210> SEQ ID NO 245
<211> LENGTH: 9
<212> TYPE: PRT
<213> ORGANISM: Homo sapien

<400> SEQUENCE: 245

Trp Asn Gln Met Asn Leu Gly Ala Thr
 1               5

<210> SEQ ID NO 246
<211> LENGTH: 9
<212> TYPE: PRT
<213> ORGANISM: Homo sapien

<400> SEQUENCE: 246

Trp Pro Ser Cys Gln Lys Lys Phe Ala
 1               5

<210> SEQ ID NO 247
<211> LENGTH: 9
<212> TYPE: PRT
<213> ORGANISM: Homo sapien

<400> SEQUENCE: 247

Trp Thr Glu Gly Gln Ser Asn His Ser
 1               5

<210> SEQ ID NO 248
<211> LENGTH: 9
<212> TYPE: PRT
<213> ORGANISM: Homo sapien

<400> SEQUENCE: 248

Tyr Phe Lys Leu Ser His Leu Gln Met
 1               5

<210> SEQ ID NO 249
<211> LENGTH: 9
<212> TYPE: PRT
```

<213> ORGANISM: Homo sapien

<400> SEQUENCE: 249

Tyr Gly His Thr Pro Ser His His Ala
1               5

<210> SEQ ID NO 250
<211> LENGTH: 9
<212> TYPE: PRT
<213> ORGANISM: Homo sapien

<400> SEQUENCE: 250

Tyr Pro Gly Cys Asn Lys Arg Tyr Phe
1               5

<210> SEQ ID NO 251
<211> LENGTH: 9
<212> TYPE: PRT
<213> ORGANISM: Homo sapien

<400> SEQUENCE: 251

Tyr Gln Met Thr Ser Gln Leu Glu Cys
1               5

<210> SEQ ID NO 252
<211> LENGTH: 9
<212> TYPE: PRT
<213> ORGANISM: Homo sapien

<400> SEQUENCE: 252

Tyr Arg Ile His Thr His Gly Val Phe
1               5

<210> SEQ ID NO 253
<211> LENGTH: 9
<212> TYPE: PRT
<213> ORGANISM: Homo sapien

<400> SEQUENCE: 253

Tyr Ser Ser Asp Asn Leu Tyr Gln Met
1               5

<210> SEQ ID NO 254
<211> LENGTH: 9
<212> TYPE: PRT
<213> ORGANISM: Mus musculus

<400> SEQUENCE: 254

Ala Glu Pro His Glu Glu Gln Cys Leu
1               5

<210> SEQ ID NO 255
<211> LENGTH: 9
<212> TYPE: PRT
<213> ORGANISM: Mus musculus

<400> SEQUENCE: 255

Ala Leu Leu Pro Ala Val Ser Ser Leu
1               5

<210> SEQ ID NO 256
<211> LENGTH: 9
<212> TYPE: PRT
<213> ORGANISM: Mus musculus

<400> SEQUENCE: 256

Ala Tyr Gly Ser Leu Gly Gly Pro Ala
1               5

<210> SEQ ID NO 257
<211> LENGTH: 9
<212> TYPE: PRT
<213> ORGANISM: Mus musculus

<400> SEQUENCE: 257

Ala Tyr Pro Gly Cys Asn Lys Arg Tyr
1               5

<210> SEQ ID NO 258
<211> LENGTH: 9
<212> TYPE: PRT
<213> ORGANISM: Mus musculus

<400> SEQUENCE: 258

Cys Met Thr Trp Asn Gln Met Asn Leu
1               5

<210> SEQ ID NO 259
<211> LENGTH: 9
<212> TYPE: PRT
<213> ORGANISM: Mus musculus

<400> SEQUENCE: 259

Cys Thr Gly Ser Gln Ala Leu Leu Leu
1               5

<210> SEQ ID NO 260
<211> LENGTH: 9
<212> TYPE: PRT
<213> ORGANISM: Mus musculus

<400> SEQUENCE: 260

Asp Gly Ala Pro Ser Tyr Gly His Thr
1               5

<210> SEQ ID NO 261
<211> LENGTH: 9
<212> TYPE: PRT
<213> ORGANISM: Mus musculus

<400> SEQUENCE: 261

Asp Leu Asn Ala Leu Leu Pro Ala Val
1               5

<210> SEQ ID NO 262
<211> LENGTH: 9
<212> TYPE: PRT
<213> ORGANISM: Mus musculus

<400> SEQUENCE: 262

Asp Pro Met Gly Gln Gln Gly Ser Leu
1               5

<210> SEQ ID NO 263
<211> LENGTH: 9
<212> TYPE: PRT
<213> ORGANISM: Mus musculus

<400> SEQUENCE: 263

Asp Ser Cys Thr Gly Ser Gln Ala Leu
1               5

<210> SEQ ID NO 264
<211> LENGTH: 9
<212> TYPE: PRT
<213> ORGANISM: Mus musculus

<400> SEQUENCE: 264

Asp Val Arg Asp Leu Asn Ala Leu Leu
1               5

<210> SEQ ID NO 265
<211> LENGTH: 9
<212> TYPE: PRT
<213> ORGANISM: Mus musculus

<400> SEQUENCE: 265

Glu Gln Cys Leu Ser Ala Phe Thr Leu
1               5

<210> SEQ ID NO 266
<211> LENGTH: 9
<212> TYPE: PRT
<213> ORGANISM: Mus musculus

<400> SEQUENCE: 266

Glu Ser Asp Asn His Thr Ala Pro Ile
1               5

<210> SEQ ID NO 267
<211> LENGTH: 9
<212> TYPE: PRT
<213> ORGANISM: Mus musculus

<400> SEQUENCE: 267

Phe Pro Asn Ala Pro Tyr Leu Pro Ser
1               5

<210> SEQ ID NO 268
<211> LENGTH: 9
<212> TYPE: PRT
<213> ORGANISM: Mus musculus

<400> SEQUENCE: 268

Gly Cys Asn Lys Arg Tyr Phe Lys Leu
1               5

<210> SEQ ID NO 269
<211> LENGTH: 9
<212> TYPE: PRT
<213> ORGANISM: Mus musculus

<400> SEQUENCE: 269

Gly Gln Ala Arg Met Phe Pro Asn Ala
1               5

<210> SEQ ID NO 270
<211> LENGTH: 9
<212> TYPE: PRT
<213> ORGANISM: Mus musculus

<400> SEQUENCE: 270

Gly Val Phe Arg Gly Ile Gln Asp Val
1               5

<210> SEQ ID NO 271

```
<211> LENGTH: 9
<212> TYPE: PRT
<213> ORGANISM: Mus musculus

<400> SEQUENCE: 271

Gly Tyr Glu Ser Asp Asn His Thr Ala
 1               5

<210> SEQ ID NO 272
<211> LENGTH: 9
<212> TYPE: PRT
<213> ORGANISM: Mus musculus

<400> SEQUENCE: 272

His Ser Phe Lys His Glu Asp Pro Met
 1               5

<210> SEQ ID NO 273
<211> LENGTH: 9
<212> TYPE: PRT
<213> ORGANISM: Mus musculus

<400> SEQUENCE: 273

His Thr His Gly Val Phe Arg Gly Ile
 1               5

<210> SEQ ID NO 274
<211> LENGTH: 9
<212> TYPE: PRT
<213> ORGANISM: Mus musculus

<400> SEQUENCE: 274

Ile Leu Cys Gly Ala Gln Tyr Arg Ile
 1               5

<210> SEQ ID NO 275
<211> LENGTH: 9
<212> TYPE: PRT
<213> ORGANISM: Mus musculus

<400> SEQUENCE: 275

Lys Phe Ala Arg Ser Asp Glu Leu Val
 1               5

<210> SEQ ID NO 276
<211> LENGTH: 9
<212> TYPE: PRT
<213> ORGANISM: Mus musculus

<400> SEQUENCE: 276

Lys Arg Tyr Phe Lys Leu Ser His Leu
 1               5

<210> SEQ ID NO 277
<211> LENGTH: 9
<212> TYPE: PRT
<213> ORGANISM: Mus musculus

<400> SEQUENCE: 277

Lys Thr Ser Glu Lys Pro Phe Ser Cys
 1               5

<210> SEQ ID NO 278
<211> LENGTH: 9
<212> TYPE: PRT
<213> ORGANISM: Mus musculus
```

<400> SEQUENCE: 278

Leu Glu Cys Met Thr Trp Asn Gln Met
1               5

<210> SEQ ID NO 279
<211> LENGTH: 9
<212> TYPE: PRT
<213> ORGANISM: Mus musculus

<400> SEQUENCE: 279

Leu Gly Gly Gly Gly Cys Gly Leu
1               5

<210> SEQ ID NO 280
<211> LENGTH: 9
<212> TYPE: PRT
<213> ORGANISM: Mus musculus

<400> SEQUENCE: 280

Leu Gln Met His Ser Arg Lys His Thr
1               5

<210> SEQ ID NO 281
<211> LENGTH: 9
<212> TYPE: PRT
<213> ORGANISM: Mus musculus

<400> SEQUENCE: 281

Met His Gln Arg Asn Met Thr Lys Leu
1               5

<210> SEQ ID NO 282
<211> LENGTH: 9
<212> TYPE: PRT
<213> ORGANISM: Mus musculus

<400> SEQUENCE: 282

Asn Ala Pro Tyr Leu Pro Ser Cys Leu
1               5

<210> SEQ ID NO 283
<211> LENGTH: 9
<212> TYPE: PRT
<213> ORGANISM: Mus musculus

<400> SEQUENCE: 283

Asn Leu Gly Ala Thr Leu Lys Gly Met
1               5

<210> SEQ ID NO 284
<211> LENGTH: 9
<212> TYPE: PRT
<213> ORGANISM: Mus musculus

<400> SEQUENCE: 284

Asn Leu Tyr Gln Met Thr Ser Gln Leu
1               5

<210> SEQ ID NO 285
<211> LENGTH: 9
<212> TYPE: PRT
<213> ORGANISM: Mus musculus

<400> SEQUENCE: 285

```
Asn Met Thr Lys Leu His Val Ala Leu
1               5

<210> SEQ ID NO 286
<211> LENGTH: 9
<212> TYPE: PRT
<213> ORGANISM: Mus musculus

<400> SEQUENCE: 286

Asn Gln Met Asn Leu Gly Ala Thr Leu
1               5

<210> SEQ ID NO 287
<211> LENGTH: 9
<212> TYPE: PRT
<213> ORGANISM: Mus musculus

<400> SEQUENCE: 287

Pro Gly Ala Ser Ala Tyr Gly Ser Leu
1               5

<210> SEQ ID NO 288
<211> LENGTH: 9
<212> TYPE: PRT
<213> ORGANISM: Mus musculus

<400> SEQUENCE: 288

Gln Ala Ser Ser Gly Gln Ala Arg Met
1               5

<210> SEQ ID NO 289
<211> LENGTH: 9
<212> TYPE: PRT
<213> ORGANISM: Mus musculus

<400> SEQUENCE: 289

Gln Met Thr Ser Gln Leu Glu Cys Met
1               5

<210> SEQ ID NO 290
<211> LENGTH: 9
<212> TYPE: PRT
<213> ORGANISM: Mus musculus

<400> SEQUENCE: 290

Gln Gln Tyr Ser Val Pro Pro Pro Val
1               5

<210> SEQ ID NO 291
<211> LENGTH: 9
<212> TYPE: PRT
<213> ORGANISM: Mus musculus

<400> SEQUENCE: 291

Gln Tyr Arg Ile His Thr His Gly Val
1               5

<210> SEQ ID NO 292
<211> LENGTH: 9
<212> TYPE: PRT
<213> ORGANISM: Mus musculus

<400> SEQUENCE: 292

Gln Tyr Ser Val Pro Pro Pro Val Tyr
1               5
```

<210> SEQ ID NO 293
<211> LENGTH: 9
<212> TYPE: PRT
<213> ORGANISM: Mus musculus

<400> SEQUENCE: 293

Arg Met Phe Pro Asn Ala Pro Tyr Leu
1               5

<210> SEQ ID NO 294
<211> LENGTH: 9
<212> TYPE: PRT
<213> ORGANISM: Mus musculus

<400> SEQUENCE: 294

Arg Thr Pro Tyr Ser Ser Asp Asn Leu
1               5

<210> SEQ ID NO 295
<211> LENGTH: 9
<212> TYPE: PRT
<213> ORGANISM: Mus musculus

<400> SEQUENCE: 295

Arg Val Ser Gly Val Ala Pro Thr Leu
1               5

<210> SEQ ID NO 296
<211> LENGTH: 9
<212> TYPE: PRT
<213> ORGANISM: Mus musculus

<400> SEQUENCE: 296

Ser Cys Leu Glu Ser Gln Pro Thr Ile
1               5

<210> SEQ ID NO 297
<211> LENGTH: 9
<212> TYPE: PRT
<213> ORGANISM: Mus musculus

<400> SEQUENCE: 297

Ser Cys Gln Lys Lys Phe Ala Arg Ser
1               5

<210> SEQ ID NO 298
<211> LENGTH: 9
<212> TYPE: PRT
<213> ORGANISM: Mus musculus

<400> SEQUENCE: 298

Ser Asp Val Arg Asp Leu Asn Ala Leu
1               5

<210> SEQ ID NO 299
<211> LENGTH: 9
<212> TYPE: PRT
<213> ORGANISM: Mus musculus

<400> SEQUENCE: 299

Ser Leu Gly Glu Gln Gln Tyr Ser Val
1               5

<210> SEQ ID NO 300
<211> LENGTH: 9

<212> TYPE: PRT
<213> ORGANISM: Mus musculus

<400> SEQUENCE: 300

Thr Cys Gln Arg Lys Phe Ser Arg Ser
1               5

<210> SEQ ID NO 301
<211> LENGTH: 9
<212> TYPE: PRT
<213> ORGANISM: Mus musculus

<400> SEQUENCE: 301

Thr Glu Gly Gln Ser Asn His Gly Ile
1               5

<210> SEQ ID NO 302
<211> LENGTH: 9
<212> TYPE: PRT
<213> ORGANISM: Mus musculus

<400> SEQUENCE: 302

Thr Leu His Phe Ser Gly Gln Phe Thr
1               5

<210> SEQ ID NO 303
<211> LENGTH: 9
<212> TYPE: PRT
<213> ORGANISM: Mus musculus

<400> SEQUENCE: 303

Thr Leu Val Arg Ser Ala Ser Glu Thr
1               5

<210> SEQ ID NO 304
<211> LENGTH: 9
<212> TYPE: PRT
<213> ORGANISM: Mus musculus

<400> SEQUENCE: 304

Val Leu Asp Phe Ala Pro Pro Gly Ala
1               5

<210> SEQ ID NO 305
<211> LENGTH: 9
<212> TYPE: PRT
<213> ORGANISM: Mus musculus

<400> SEQUENCE: 305

Trp Asn Gln Met Asn Leu Gly Ala Thr
1               5

<210> SEQ ID NO 306
<211> LENGTH: 9
<212> TYPE: PRT
<213> ORGANISM: Mus musculus

<400> SEQUENCE: 306

Tyr Phe Lys Leu Ser His Leu Gln Met
1               5

<210> SEQ ID NO 307
<211> LENGTH: 9
<212> TYPE: PRT
<213> ORGANISM: Mus musculus

```
<400> SEQUENCE: 307

Tyr Gln Met Thr Ser Gln Leu Glu Cys
 1               5

<210> SEQ ID NO 308
<211> LENGTH: 9
<212> TYPE: PRT
<213> ORGANISM: Mus musculus

<400> SEQUENCE: 308

Tyr Ser Ser Asp Asn Leu Tyr Gln Met
 1               5

<210> SEQ ID NO 309
<211> LENGTH: 6
<212> TYPE: PRT
<213> ORGANISM: Homo sapien

<400> SEQUENCE: 309

Gly Ala Ala Gln Trp Ala
 1               5

<210> SEQ ID NO 310
<211> LENGTH: 12
<212> TYPE: PRT
<213> ORGANISM: Homo sapien

<400> SEQUENCE: 310

Ala Ser Ala Tyr Gly Ser Leu Gly Gly Pro Ala Pro
 1               5                  10

<210> SEQ ID NO 311
<211> LENGTH: 15
<212> TYPE: PRT
<213> ORGANISM: Homo sapien

<400> SEQUENCE: 311

Ala Phe Thr Val His Phe Ser Gly Gln Phe Thr Gly Thr Ala Gly
 1               5                  10                  15

<210> SEQ ID NO 312
<211> LENGTH: 5
<212> TYPE: PRT
<213> ORGANISM: Homo sapien

<400> SEQUENCE: 312

His Ala Ala Gln Phe
 1               5

<210> SEQ ID NO 313
<211> LENGTH: 32
<212> TYPE: PRT
<213> ORGANISM: Homo sapien

<400> SEQUENCE: 313

Cys His Thr Pro Thr Asp Ser Cys Thr Gly Ser Gln Ala Leu Leu Leu
 1               5                  10                  15

Arg Thr Pro Tyr Ser Ser Asp Asn Leu Tyr Gln Met Thr Ser Gln Leu
                20                  25                  30

<210> SEQ ID NO 314
<211> LENGTH: 32
<212> TYPE: PRT
<213> ORGANISM: Homo sapien
```

```
<400> SEQUENCE: 314

Arg Ile His Thr His Gly Val Phe Arg Gly Ile Gln Asp Val Arg Arg
  1               5                  10                  15

Val Pro Gly Val Ala Pro Thr Leu Val Arg Ser Ala Ser Glu Thr Ser
             20                  25                  30

<210> SEQ ID NO 315
<211> LENGTH: 4
<212> TYPE: PRT
<213> ORGANISM: Homo sapien

<400> SEQUENCE: 315

Arg Tyr Phe Lys
  1

<210> SEQ ID NO 316
<211> LENGTH: 14
<212> TYPE: PRT
<213> ORGANISM: Homo sapien

<400> SEQUENCE: 316

Glu Arg Arg Phe Ser Arg Ser Asp Gln Leu Lys Arg His Gln
  1               5                  10

<210> SEQ ID NO 317
<211> LENGTH: 22
<212> TYPE: PRT
<213> ORGANISM: Homo sapien

<400> SEQUENCE: 317

Gln Arg Lys Phe Ser Arg Ser Asp His Leu Lys Thr His Thr Arg Thr
  1               5                  10                  15

His Thr Gly Lys Thr Ser
             20

<210> SEQ ID NO 318
<211> LENGTH: 21
<212> TYPE: PRT
<213> ORGANISM: Homo sapien

<400> SEQUENCE: 318

Cys Gln Lys Lys Phe Ala Arg Ser Asp Glu Leu Val Arg His His Asn
  1               5                  10                  15

Met His Gln Arg Asn
             20

<210> SEQ ID NO 319
<211> LENGTH: 449
<212> TYPE: PRT
<213> ORGANISM: Homo sapien

<400> SEQUENCE: 319

Met Gly Ser Asp Val Arg Asp Leu Asn Ala Leu Leu Pro Ala Val Pro
  1               5                  10                  15

Ser Leu Gly Gly Gly Gly Gly Cys Ala Leu Pro Val Ser Gly Ala Ala
             20                  25                  30

Gln Trp Ala Pro Val Leu Asp Phe Ala Pro Gly Ala Ser Ala Tyr
             35                  40                  45

Gly Ser Leu Gly Gly Pro Ala Pro Pro Ala Pro Pro Pro Pro Pro
     50                  55                  60

Pro Pro Pro Pro His Ser Phe Ile Lys Gln Glu Pro Ser Trp Gly Gly
 65                  70                  75                  80
```

```
Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 320
<211> LENGTH: 449
<212> TYPE: PRT
<213> ORGANISM: Mus musculus

<400> SEQUENCE: 320
```

-continued

```
Met Gly Ser Asp Val Arg Asp Leu Asn Ala Leu Leu Pro Ala Val Ser
 1               5                  10                  15

Ser Leu Gly Gly Gly Gly Cys Gly Leu Pro Val Ser Gly Ala Ala
             20                  25                  30

Gln Trp Ala Pro Val Leu Asp Phe Ala Pro Pro Gly Ala Ser Ala Tyr
             35                  40                  45

Gly Ser Leu Gly Gly Pro Ala Pro Pro Ala Pro Pro Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Leu His Phe
                 85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Thr Ile
    130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
            260                 265                 270

Ser Asp Asn His Thr Ala Pro Ile Leu Cys Gly Ala Gln Tyr Arg Ile
            275                 280                 285

His Thr His Gly Val Phe Arg Gly Ile Gln Asp Val Arg Arg Val Ser
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430
```

```
Arg His His Asn Met His Gln Arg Asn Met Thr Lys Leu His Val Ala
        435                 440                 445

Leu

<210> SEQ ID NO 321
<211> LENGTH: 9
<212> TYPE: PRT
<213> ORGANISM: Homo sapien and Mus musculus

<400> SEQUENCE: 321

Pro Ser Gln Ala Ser Ser Gly Gln Ala
1               5

<210> SEQ ID NO 322
<211> LENGTH: 9
<212> TYPE: PRT
<213> ORGANISM: Homo sapien and Mus musculus

<400> SEQUENCE: 322

Ser Ser Gly Gln Ala Arg Met Phe Pro
1               5

<210> SEQ ID NO 323
<211> LENGTH: 9
<212> TYPE: PRT
<213> ORGANISM: Homo sapien and Mus musculus

<400> SEQUENCE: 323

Gln Ala Arg Met Phe Pro Asn Ala Pro
1               5

<210> SEQ ID NO 324
<211> LENGTH: 9
<212> TYPE: PRT
<213> ORGANISM: Homo sapien and Mus musculus

<400> SEQUENCE: 324

Met Phe Pro Asn Ala Pro Tyr Leu Pro
1               5

<210> SEQ ID NO 325
<211> LENGTH: 9
<212> TYPE: PRT
<213> ORGANISM: Homo sapien and Mus musculus

<400> SEQUENCE: 325

Pro Asn Ala Pro Tyr Leu Pro Ser Cys
1               5

<210> SEQ ID NO 326
<211> LENGTH: 9
<212> TYPE: PRT
<213> ORGANISM: Homo sapien and Mus musculus

<400> SEQUENCE: 326

Ala Pro Tyr Leu Pro Ser Cys Leu Glu
1               5

<210> SEQ ID NO 327
<211> LENGTH: 1029
<212> TYPE: DNA
<213> ORGANISM: Homo sapiens

<400> SEQUENCE: 327
```

```
atgcagcatc accaccatca ccacatgagc gataaaatta ttcacctgac tgacgacagt    60
tttgacacgg atgtactcaa agcggacggg gcgatcctcg tcgatttctg ggcagagtgg   120
tgcggtccgt gcaaaatgat cgccccgatt ctggatgaaa tcgctgacga atatcagggc   180
aaactgaccg ttgcaaaact gaacatcgat caaaaccctg gcactgcgcc gaaatatggc   240
atccgtggta tcccgactct gctgctgttc aaaaacggtg aagtggcggc aaccaaagtg   300
ggtgcactgt ctaaaggtca gttgaaagag ttcctcgacg ctaacctggc cggttctggt   360
tctggccata tgcagcatca ccaccatcac cacgtgtcta tcgaaggtcg tgctagctct   420
ggtggcagcg gtctggttcc gcgtggtagc tctggttcgg gggacgacga cgacaaatct   480
agtaggcaca gcacagggta cgagagcgat aaccacacaa cgcccatcct ctgcggagcc   540
caatacagaa tacacacgca cggtgtcttc agaggcattc aggatgtgcg acgtgtgcct   600
ggagtagccc cgactcttgt acggtcggca tctgagacca gtgagaaacg ccccttcatg   660
tgtgcttacc caggctgcaa taagagatat tttaagctgt cccacttaca gatgcacagc   720
aggaagcaca ctggtgagaa accataccag tgtgacttca aggactgtga acgaaggttt   780
tttcgttcag accagctcaa aagacaccaa aggagacata caggtgtgaa accattccag   840
tgtaaaactt gtcagcgaaa gttctcccgg tccgaccacc tgaagaccca caccaggact   900
catacaggtg aaaagccctt cagctgtcgg tggccaagtt gtcagaaaaa gtttgcccgg   960
tcagatgaat tagtccgcca tcacaacatg catcagagaa acatgaccaa actccagctg  1020
gcgctttga                                                         1029

<210> SEQ ID NO 328
<211> LENGTH: 1233
<212> TYPE: DNA
<213> ORGANISM: Homo sapiens

<400> SEQUENCE: 328
atgcagcatc accaccatca ccacatgagc gataaaatta ttcacctgac tgacgacagt    60
tttgacacgg atgtactcaa agcggacggg gcgatcctcg tcgatttctg ggcagagtgg   120
tgcggtccgt gcaaaatgat cgccccgatt ctggatgaaa tcgctgacga atatcagggc   180
aaactgaccg ttgcaaaact gaacatcgat caaaaccctg gcactgcgcc gaaatatggc   240
atccgtggta tcccgactct gctgctgttc aaaaacggtg aagtggcggc aaccaaagtg   300
ggtgcactgt ctaaaggtca gttgaaagag ttcctcgacg ctaacctggc cggttctggt   360
tctggccata tgcagcatca ccaccatcac cacgtgtcta tcgaaggtcg tgctagctct   420
ggtggcagcg gtctggttcc gcgtggtagc tctggttcgg gggacgacga cgacaaatct   480
agtaggggct ccgacgttcg tgacctgaac gcactgctgc cggcagttcc gtccctgggt   540
ggtggtggtg gttgcgcact gccggttagc ggtgcagcac agtgggctcc ggttctggac   600
ttcgcaccgc cgggtgcatc cgcatacggt tccctgggtg tccggcacc gccgccggca   660 ccgccgccgc cgccgccgcc gccgccgcac tccttcatca acaggaacc gagctgggt   720 ggtgcagaac cgcacgaaga acagtgcctg agcgcattca ccgttcactt ctccggccag   780
ttcactggca cagccggagc ctgtcgctac gggcccttcg gtcctcctcc gcccagccag   840
gcgtcatccg gccaggccag gatgtttcct aacgcgccct acctgcccag ctgcctcgag   900
agccagcccg ctattcgcaa tcagggttac agcacggtca ccttcgacgg gacgcccagc   960
tacggtcaca cgccctcgca ccatgcggcg cagttcccca accactcatt caagcatgag  1020
gatcccatgg gccagcaggg ctcgctgggt gagcagcagt actcggtgcc gccccggtc   1080
```

| tatggctgcc acaccccac cgacagctgc accggcagcc aggctttgct gctgaggacg | 1140 |
| ccctacagca gtgacaattt ataccaaatg acatcccagc ttgaatgcat gacctggaat | 1200 |
| cagatgaact taggagccac cttaaagggc tga | 1233 |

<210> SEQ ID NO 329
<211> LENGTH: 1776
<212> TYPE: DNA
<213> ORGANISM: Homo sapiens

<400> SEQUENCE: 329

| atgcagcatc accaccatca ccacatgagc gataaaatta ttcacctgac tgacgacagt | 60 |
| tttgacacgg atgtactcaa agcggacggg gcgatcctcg tcgatttctg ggcagagtgg | 120 |
| tgcggtccgt gcaaaatgat cgccccgatt ctggatgaaa tcgctgacga atatcagggc | 180 |
| aaactgaccg ttgcaaaact gaacatcgat caaaaccctg gcactgcgcc gaaatatggc | 240 |
| atccgtggta tcccgactct gctgctgttc aaaaacggtg aagtggcggc aaccaaagtg | 300 |
| ggtgcactgt ctaaaggtca gttgaaagag ttcctcgacg ctaacctggc cggttctggt | 360 |
| tctggccata tgcagcatca ccaccatcac cacgtgtcta tcgaaggtcg tgctagctct | 420 |
| ggtggcagcg gtctggttcc gcgtggtagc tctggttcgg gggacgacga cgacaaatct | 480 |
| agtaggatgg gctccgacgt tcgtgacctg aacgcactgc tgccggcagt tccgtccctg | 540 |
| ggtggtggtg gtggttgcgc actgccggtt agcggtgcag cacagtgggc tccggttctg | 600 |
| gacttcgcac cgccgggtgc atccgcatac ggttccctgg gtggtccggc accgccgccg | 660 |
| gcaccgccgc cgccgccgcc gccgccgccg cactccttca tcaaacagga accgagctgg | 720 |
| ggtggtgcag aaccgcacga agaacagtgc ctgagcgcat tcaccgttca cttctccggc | 780 |
| cagttcactg gcacagccgg agcctgtcgc tacgggccct tcggtcctcc tccgcccagc | 840 |
| caggcgtcat ccggccaggc caggatgttt cctaacgcgc cctacctgcc cagctgcctc | 900 |
| gagagccagc ccgctattcg caatcagggt tacagcacgg tcaccttcga cgggacgccc | 960 |
| agctacggtc acacgccctc gcaccatgcg gcgcagttcc ccaaccactc attcaagcat | 1020 |
| gaggatccca tgggccagca gggctcgctg ggtgagcagc agtactcggt gccgccccg | 1080 |
| gtctatggct gccacacccc caccgacagc tgcaccggca gccaggcttt gctgctgagg | 1140 |
| acgccctaca gcagtgacaa tttataccaa atgcatccc agcttgaatg catgacctgg | 1200 |
| aatcagatga acttaggagc caccttaaag gccacagca gggtacga gagcgataac | 1260 |
| cacacaacgc ccatcctctg cggagcccaa tacagaatac acacgcacgg tgtcttcaga | 1320 |
| ggcattcagg atgtgcgacg tgtgcctgga gtagccccga ctcttgtacg gtcggcatct | 1380 |
| gagaccagtg agaaacgccc cttcatgtgt gcttacccag gctgcaataa gagatatttt | 1440 |
| aagctgtccc acttacagat gcacagcagg aagcacactg gtgagaaacc ataccagtgt | 1500 |
| gacttcaagg actgtgaacg aaggttttt cgttcagacc agctcaaaag acaccaaagg | 1560 |
| agacatacag gtgtgaaacc attccagtgt aaaacttgtc agcgaaagtt ctcccggtcc | 1620 |
| gaccacctga agacccacac caggactcat acaggtgaaa agcccttcag ctgtcggtgg | 1680 |
| ccaagttgtc agaaaaagtt tgcccggtca gatgaattag tccgccatca caacatgcat | 1740 |
| cagagaaaca tgaccaaact ccagctggcg ctttga | 1776 |

<210> SEQ ID NO 330
<211> LENGTH: 771
<212> TYPE: DNA
<213> ORGANISM: Homo sapiens

```
<400> SEQUENCE: 330
atgcagcatc accaccatca ccacggctcc gacgttcgtg acctgaacgc actgctgccg      60
gcagttccgt ccctgggtgg tggtggtggt tgcgcactgc cggttagcgg tgcagcacag     120
tgggctccgg ttctggactt cgcaccgccg ggtgcatccg catacggttc cctgggtggt     180
ccggcaccgc cgccggcacc gccgccgccg ccgccgccgc cgccgcactc cttcatcaaa     240
caggaaccga gctggggtgg tgcagaaccg cacgaagaac agtgcctgag cgcattcacc     300
gttcacttct ccggccagtt cactggcaca gccggagcct gtcgctacgg gcccttcggt     360
cctcctccgc ccagccaggc gtcatccggc caggccagga tgtttcctaa cgcgccctac     420
ctgcccagct gcctcgagag ccagcccgct attcgcaatc agggttacag cacggtcacc     480
ttcgacggga cgcccagcta cggtcacacg ccctcgcacc atgcggcgca gttccccaac     540
cactcattca agcatgagga tcccatgggc cagcagggct cgctgggtga gcagcagtac     600
tcggtgccgc cccggtcta tggctgccac acccccaccg acagctgcac cggcagccag     660
gctttgctgc tgaggacgcc ctacagcagt gacaattat accaaatgac atcccagctt     720
gaatgcatga cctggaatca gatgaactta ggagccacct taaagggctg a              771

<210> SEQ ID NO 331
<211> LENGTH: 567
<212> TYPE: DNA
<213> ORGANISM: Homo sapiens

<400> SEQUENCE: 331
atgcagcatc accaccatca ccaccacagc acagggtacg agagcgataa ccacacaacg      60
cccatcctct gcggagccca atacagaata cacacgcacg tgtcttcag aggcattcag     120 gatgtgcgac gtgtgcctgg agtagccccg actcttgtac ggtcggcatc tgagaccagt     180
gagaaacgcc ccttcatgtg tgcttaccca ggctgcaata agagatattt taagctgtcc     240
cacttacaga tgcacagcag gaagcacact ggtgagaaac ataccagtg tgacttcaag     300 gactgtgaac gaaggttttt tcgttcagac cagctcaaaa gacaccaaag gagacataca     360
ggtgtgaaac cattccagtg taaaacttgt cagcgaaagt tctcccggtc cgaccacctg     420
aagacccaca ccaggactca tacaggtgaa aagcccttca gctgtcggtg gccaagttgt     480
cagaaaaagt ttgcccggtc agatgaatta gtccgccatc acaacatgca tcagagaaac     540
atgaccaaac tccagctggc gctttga                                          567

<210> SEQ ID NO 332
<211> LENGTH: 342
<212> TYPE: PRT
<213> ORGANISM: Homo sapiens

<400> SEQUENCE: 332

Met Gln His His His His His His Met Ser Asp Lys Ile Ile His Leu
                 5                  10                  15

Thr Asp Ser Phe Asp Thr Asp Val Leu Lys Ala Asp Gly Ala Ile
             20                  25                  30

Leu Val Asp Phe Trp Ala Glu Trp Cys Gly Pro Cys Lys Met Ile Ala
         35                  40                  45

Pro Ile Leu Asp Glu Ile Ala Asp Glu Tyr Gln Gly Lys Leu Thr Val
     50                  55                  60

Ala Lys Leu Asn Ile Asp Gln Asn Pro Gly Thr Ala Pro Lys Tyr Gly
 65                  70                  75                  80

Ile Arg Gly Ile Pro Thr Leu Leu Leu Phe Lys Asn Gly Glu Val Ala
```

85                  90                  95
Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His
            115                 120                 125

His His His Val Ser Ile Glu Gly Arg Ala Ser Ser Gly Gly Ser Gly
            130                 135                 140

Leu Val Pro Arg Gly Ser Ser Gly Ser Gly Asp Asp Asp Lys Ser
145                 150                 155                 160

Ser Arg His Ser Thr Gly Tyr Glu Ser Asp Asn His Thr Thr Pro Ile
                165                 170                 175

Leu Cys Gly Ala Gln Tyr Arg Ile His Thr His Gly Val Phe Arg Gly
            180                 185                 190

Ile Gln Asp Val Arg Arg Val Pro Gly Val Ala Pro Thr Leu Val Arg
            195                 200                 205

Ser Ala Ser Glu Thr Ser Glu Lys Arg Pro Phe Met Cys Ala Tyr Pro
210                 215                 220

Gly Cys Asn Lys Arg Tyr Phe Lys Leu Ser His Leu Gln Met His Ser
225                 230                 235                 240

Arg Lys His Thr Gly Glu Lys Pro Tyr Gln Cys Asp Phe Lys Asp Cys
                245                 250                 255

Glu Arg Arg Phe Phe Arg Ser Asp Gln Leu Lys Arg His Gln Arg Arg
            260                 265                 270

His Thr Gly Val Lys Pro Phe Gln Cys Lys Thr Cys Gln Arg Lys Phe
            275                 280                 285

Ser Arg Ser Asp His Leu Lys Thr His Thr Arg Thr His Thr Gly Glu
290                 295                 300

Lys Pro Phe Ser Cys Arg Trp Pro Ser Cys Gln Lys Phe Ala Arg
305                 310                 315                 320

Ser Asp Glu Leu Val Arg His His Asn Met His Gln Arg Asn Met Thr
                325                 330                 335

Lys Leu Gln Leu Ala Leu
            340

<210> SEQ ID NO 333
<211> LENGTH: 410
<212> TYPE: PRT
<213> ORGANISM: Homo sapiens

<400> SEQUENCE: 333

Met Gln His His His His His Met Ser Asp Lys Ile Ile His Leu
                5                   10                  15

Thr Asp Asp Ser Phe Asp Thr Asp Val Leu Lys Ala Asp Gly Ala Ile
            20                  25                  30

Leu Val Asp Phe Trp Ala Glu Trp Cys Gly Pro Cys Lys Met Ile Ala
            35                  40                  45

Pro Ile Leu Asp Glu Ile Ala Asp Glu Tyr Gln Gly Lys Leu Thr Val
            50                  55                  60

Ala Lys Leu Asn Ile Asp Gln Asn Pro Gly Thr Ala Pro Lys Tyr Gly
65                  70                  75                  80

Ile Arg Gly Ile Pro Thr Leu Leu Leu Phe Lys Asn Gly Glu Val Ala
                85                  90                  95

Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His

```
                115                 120                 125
His His His Val Ser Ile Glu Gly Arg Ala Ser Ser Gly Ser Gly
            130                 135                 140
Leu Val Pro Arg Gly Ser Gly Ser Gly Asp Asp Asp Lys Ser
145                 150                 155                 160
Ser Arg Gly Ser Asp Val Arg Asp Leu Asn Ala Leu Leu Pro Ala Val
                165                 170                 175
Pro Ser Leu Gly Gly Gly Gly Cys Ala Leu Pro Val Ser Gly Ala
            180                 185                 190
Ala Gln Trp Ala Pro Val Leu Asp Phe Ala Pro Pro Gly Ala Ser Ala
                195                 200                 205
Tyr Gly Ser Leu Gly Gly Pro Ala Pro Pro Ala Pro Pro Pro
            210                 215                 220
Pro Pro Pro Pro Pro His Ser Phe Ile Lys Gln Glu Pro Ser Trp Gly
225                 230                 235                 240
Gly Ala Glu Pro His Glu Glu Gln Cys Leu Ser Ala Phe Thr Val His
                245                 250                 255
Phe Ser Gly Gln Phe Thr Gly Thr Ala Gly Ala Cys Arg Tyr Gly Pro
            260                 265                 270
Phe Gly Pro Pro Pro Ser Gln Ala Ser Ser Gly Gln Ala Arg Met
                275                 280                 285
Phe Pro Asn Ala Pro Tyr Leu Pro Ser Cys Leu Glu Ser Gln Pro Ala
            290                 295                 300
Ile Arg Asn Gln Gly Tyr Ser Thr Val Thr Phe Asp Gly Thr Pro Ser
305                 310                 315                 320
Tyr Gly His Thr Pro Ser His His Ala Ala Gln Phe Pro Asn His Ser
                325                 330                 335
Phe Lys His Glu Asp Pro Met Gly Gln Gln Gly Ser Leu Gly Glu Gln
            340                 345                 350
Gln Tyr Ser Val Pro Pro Val Tyr Gly Cys His Thr Pro Thr Asp
                355                 360                 365
Ser Cys Thr Gly Ser Gln Ala Leu Leu Leu Arg Thr Pro Tyr Ser Ser
370                 375                 380
Asp Asn Leu Tyr Gln Met Thr Ser Gln Leu Glu Cys Met Thr Trp Asn
385                 390                 395                 400
Gln Met Asn Leu Gly Ala Thr Leu Lys Gly
                405                 410

<210> SEQ ID NO 334
<211> LENGTH: 591
<212> TYPE: PRT
<213> ORGANISM: Homo sapiens

<400> SEQUENCE: 334

Met Gln His His His His His Met Ser Asp Lys Ile Ile His Leu
                5                  10                  15
Thr Asp Asp Ser Phe Asp Thr Asp Val Leu Lys Ala Asp Gly Ala Ile
            20                  25                  30
Leu Val Asp Phe Trp Ala Glu Trp Cys Gly Pro Cys Lys Met Ile Ala
                35                  40                  45
Pro Ile Leu Asp Glu Ile Ala Asp Glu Tyr Gln Gly Lys Leu Thr Val
            50                  55                  60
Ala Lys Leu Asn Ile Asp Gln Asn Pro Gly Thr Ala Pro Lys Tyr Gly
65                  70                  75                  80
Ile Arg Gly Ile Pro Thr Leu Leu Leu Phe Lys Asn Gly Glu Val Ala
```

```
                    85                  90                  95
Ala Thr Lys Val Gly Ala Leu Ser Lys Gly Gln Leu Lys Glu Phe Leu
                100                 105                 110

Asp Ala Asn Leu Ala Gly Ser Gly Ser Gly His Met Gln His His His
            115                 120                 125

His His His Val Ser Ile Glu Gly Arg Ala Ser Ser Gly Gly Ser Gly
        130                 135                 140

Leu Val Pro Arg Gly Ser Ser Gly Ser Gly Asp Asp Asp Asp Lys Ser
145                 150                 155                 160

Ser Arg Met Gly Ser Asp Val Arg Asp Leu Asn Ala Leu Leu Pro Ala
                165                 170                 175

Val Pro Ser Leu Gly Gly Gly Gly Cys Ala Leu Pro Val Ser Gly
            180                 185                 190

Ala Ala Gln Trp Ala Pro Val Leu Asp Phe Ala Pro Pro Gly Ala Ser
        195                 200                 205

Ala Tyr Gly Ser Leu Gly Gly Pro Ala Pro Pro Ala Pro Pro Pro
    210                 215                 220

Pro Pro Pro Pro Pro His Ser Phe Ile Lys Gln Glu Pro Ser Trp
225                 230                 235                 240

Gly Gly Ala Glu Pro His Glu Glu Gln Cys Leu Ser Ala Phe Thr Val
                245                 250                 255

His Phe Ser Gly Gln Phe Thr Gly Thr Ala Gly Ala Cys Arg Tyr Gly
            260                 265                 270

Pro Phe Gly Pro Pro Pro Ser Gln Ala Ser Ser Gly Gln Ala Arg
        275                 280                 285

Met Phe Pro Asn Ala Pro Tyr Leu Pro Ser Cys Leu Glu Ser Gln Pro
    290                 295                 300

Ala Ile Arg Asn Gln Gly Tyr Ser Thr Val Thr Phe Asp Gly Thr Pro
305                 310                 315                 320

Ser Tyr Gly His Thr Pro Ser His His Ala Ala Gln Phe Pro Asn His
                325                 330                 335

Ser Phe Lys His Glu Asp Pro Met Gly Gln Gln Gly Ser Leu Gly Glu
            340                 345                 350

Gln Gln Tyr Ser Val Pro Pro Val Tyr Gly Cys His Thr Pro Thr
        355                 360                 365

Asp Ser Cys Thr Gly Ser Gln Ala Leu Leu Leu Arg Thr Pro Tyr Ser
    370                 375                 380

Ser Asp Asn Leu Tyr Gln Met Thr Ser Gln Leu Glu Cys Met Thr Trp
385                 390                 395                 400

Asn Gln Met Asn Leu Gly Ala Thr Leu Lys Gly His Ser Thr Gly Tyr
                405                 410                 415

Glu Ser Asp Asn His Thr Thr Pro Ile Leu Cys Gly Ala Gln Tyr Arg
            420                 425                 430

Ile His Thr His Gly Val Phe Arg Gly Ile Gln Asp Val Arg Arg Val
        435                 440                 445

Pro Gly Val Ala Pro Thr Leu Val Arg Ser Ala Ser Glu Thr Ser Glu
    450                 455                 460

Lys Arg Pro Phe Met Cys Ala Tyr Pro Gly Cys Asn Lys Arg Tyr Phe
465                 470                 475                 480

Lys Leu Ser His Leu Gln Met His Ser Arg Lys His Thr Gly Glu Lys
                485                 490                 495

Pro Tyr Gln Cys Asp Phe Lys Asp Cys Glu Arg Arg Phe Phe Arg Ser
            500                 505                 510
```

-continued

```
Asp Gln Leu Lys Arg His Gln Arg Arg His Thr Gly Val Lys Pro Phe
            515                 520                 525
Gln Cys Lys Thr Cys Gln Arg Lys Phe Ser Arg Ser Asp His Leu Lys
    530                 535                 540
Thr His Thr Arg Thr His Thr Gly Glu Lys Pro Phe Ser Cys Arg Trp
545                 550                 555                 560
Pro Ser Cys Gln Lys Lys Phe Ala Arg Ser Asp Glu Leu Val Arg His
                565                 570                 575
His Asn Met His Gln Arg Asn Met Thr Lys Leu Gln Leu Ala Leu
                580                 585                 590

<210> SEQ ID NO 335
<211> LENGTH: 256
<212> TYPE: PRT
<213> ORGANISM: Homo sapiens

<400> SEQUENCE: 335

Met Gln His His His His His His Gly Ser Asp Val Arg Asp Leu Asn
                5                   10                  15
Ala Leu Leu Pro Ala Val Pro Ser Leu Gly Gly Gly Gly Cys Ala
            20                  25                  30
Leu Pro Val Ser Gly Ala Ala Gln Trp Ala Pro Val Leu Asp Phe Ala
        35                  40                  45
Pro Pro Gly Ala Ser Ala Tyr Gly Ser Leu Gly Gly Pro Ala Pro Pro
    50                  55                  60
Pro Ala Pro Pro Pro Pro Pro Pro Pro His Ser Phe Ile Lys
65                  70                  75                  80
Gln Glu Pro Ser Trp Gly Gly Ala Glu Pro His Glu Glu Gln Cys Leu
                85                  90                  95
Ser Ala Phe Thr Val His Phe Ser Gly Gln Phe Thr Gly Thr Ala Gly
            100                 105                 110
Ala Cys Arg Tyr Gly Pro Phe Gly Pro Pro Pro Ser Gln Ala Ser
        115                 120                 125
Ser Gly Gln Ala Arg Met Phe Pro Asn Ala Pro Tyr Leu Pro Ser Cys
    130                 135                 140
Leu Glu Ser Gln Pro Ala Ile Arg Asn Gln Gly Tyr Ser Thr Val Thr
145                 150                 155                 160
Phe Asp Gly Thr Pro Ser Tyr Gly His Thr Pro Ser His His Ala Ala
                165                 170                 175
Gln Phe Pro Asn His Ser Phe Lys His Glu Asp Pro Met Gly Gln Gln
            180                 185                 190
Gly Ser Leu Gly Glu Gln Gln Tyr Ser Val Pro Pro Val Tyr Gly
        195                 200                 205
Cys His Thr Pro Thr Asp Ser Cys Thr Gly Ser Gln Ala Leu Leu Leu
    210                 215                 220
Arg Thr Pro Tyr Ser Ser Asp Asn Leu Tyr Gln Met Thr Ser Gln Leu
225                 230                 235                 240
Glu Cys Met Thr Trp Asn Gln Met Asn Leu Gly Ala Thr Leu Lys Gly
                245                 250                 255

<210> SEQ ID NO 336
<211> LENGTH: 188
<212> TYPE: PRT
<213> ORGANISM: Homo sapiens

<400> SEQUENCE: 336

Met Gln His His His His His His Ser Thr Gly Tyr Glu Ser Asp
```

```
                  5                   10                  15
Asn His Thr Thr Pro Ile Leu Cys Gly Ala Gln Tyr Arg Ile His Thr
                  20                  25                  30

His Gly Val Phe Arg Gly Ile Gln Asp Val Arg Arg Val Pro Gly Val
            35                  40                  45

Ala Pro Thr Leu Val Arg Ser Ala Ser Glu Thr Ser Glu Lys Arg Pro
 50                  55                  60

Phe Met Cys Ala Tyr Pro Gly Cys Asn Lys Arg Tyr Phe Lys Leu Ser
 65                  70                  75                  80

His Leu Gln Met His Ser Arg Lys His Thr Gly Glu Lys Pro Tyr Gln
                 85                  90                  95

Cys Asp Phe Lys Asp Cys Glu Arg Arg Phe Phe Arg Ser Asp Gln Leu
            100                 105                 110

Lys Arg His Gln Arg Arg His Thr Gly Val Lys Pro Phe Gln Cys Lys
        115                 120                 125

Thr Cys Gln Arg Lys Phe Ser Arg Ser Asp His Leu Lys Thr His Thr
    130                 135                 140

Arg Thr His Thr Gly Glu Lys Pro Phe Ser Cys Arg Trp Pro Ser Cys
145                 150                 155                 160

Gln Lys Lys Phe Ala Arg Ser Asp Glu Leu Val Arg His His Asn Met
                165                 170                 175

His Gln Arg Asn Met Thr Lys Leu Gln Leu Ala Leu
            180                 185

<210> SEQ ID NO 337
<211> LENGTH: 324
<212> TYPE: DNA
<213> ORGANISM: Homo sapiens

<400> SEQUENCE: 337
atgcagcatc accaccatca ccacggttcc gacgtgcggg acctgaacgc actgctgccg      60
gcagttccat ccctgggtgg cggtggaggc tgcgcactgc cggttagcgg tgcagcacag     120
tgggctccag ttctggactt cgcaccgcct ggtgcatccg catacggttc cctgggtggt     180
ccagcacctc cgcccgcaac gccccaccg cctccaccgc cccgcactc cttcatcaaa       240 caggaaccta gctggggtgg tgcagaaccg cacgaagaac agtgcctgag cgcattctga     300
gaattctgca gatatccatc acac                                            324

<210> SEQ ID NO 338
<211> LENGTH: 462
<212> TYPE: DNA
<213> ORGANISM: Homo sapiens

<400> SEQUENCE: 338
atgcagcatc accaccatca ccaccacgaa gaacagtgcc tgagcgcatt caccgttcac      60
ttctccggcc agttcactgg cacagccgga gcctgtcgct acgggcccctt cggtcctcct    120 ccgcccagcc aggcgtcatc cggccaggcc aggatgtttc ctaacgcgcc ctacctgccc     180
agctgcctcg agagccagcc cgctattcgc aatcaggggtt acagcacggt caccttcgac   240
gggacgccca gctacggtca cacgccctcg caccatgcgg cgcagttccc caaccactca     300
ttcaagcatg aggatcccat gggccagcag ggctcgctgg gtgagcagca gtactcggtg     360
ccgcccccgg tctatggctg ccacacccccc accgacagct gcaccggcag ccaggctttg    420
ctgctgagga cgccctacag cagtgacaat ttatactgat ga                        462
```

```
<210> SEQ ID NO 339
<211> LENGTH: 405
<212> TYPE: DNA
<213> ORGANISM: Homo sapiens

<400> SEQUENCE: 339
atgcagcatc accaccatca ccaccaggct ttgctgctga ggacgcccta cagcagtgac      60
aatttatacc aaatgacatc ccagcttgaa tgcatgacct ggaatcagat gaacttagga     120
gccaccttaa agggccacag cacagggtac gagagcgata ccacacaac gcccatcctc     180 tgcggagccc aatacagaat acacacgcac ggtgtcttca gaggcattca ggatgtgcga     240
cgtgtgcctg gagtagcccc gactcttgta cggtcggcat ctgagaccag tgagaaacgc     300
cccttcatgt gtgcttaccc aggctgcaat aagagatatt ttaagctgtc ccacttacag     360
atgcacagca ggaagcacac tggtgagaaa ccataccagt gatga                    405

<210> SEQ ID NO 340
<211> LENGTH: 339
<212> TYPE: DNA
<213> ORGANISM: Homo sapiens

<400> SEQUENCE: 340
atgcagcatc accaccatca ccaccacagc aggaagcaca ctggtgagaa accataccag      60
tgtgacttca aggactgtga acgaaggttt tttcgttcag accagctcaa aagacaccaa     120
aggagacata caggtgtgaa accattccag tgtaaaactt gtcagcgaaa gttctcccgg     180
tccgaccacc tgaagaccca caccaggact catacaggtg aaaagccctt cagctgtcgg     240
tggccaagtt gtcagaaaaa gtttgcccgg tcagatgaat tagtccgcca tcacaacatg     300
catcagagaa acatgaccaa actccagctg gcgctttga                           339

<210> SEQ ID NO 341
<211> LENGTH: 1110
<212> TYPE: DNA
<213> ORGANISM: Homo sapiens

<400> SEQUENCE: 341
atgcagcatc accaccatca ccaccactcc ttcatcaaac aggaaccgag ctggggtggt      60
gcagaaccgc acgaagaaca gtgcctgagc gcattcaccg ttcacttctc cggccagttc     120
actggcacag ccggagcctg tcgctacggg cccttcggtc ctcctccgcc cagccaggcg     180
tcatccggcc aggccaggat gtttcctaac gcgccctacc tgcccagctg cctcgagagc     240
cagcccgcta ttcgcaatca gggttacagc acggtcacct tcgacgggac gcccagctac     300
ggtcacacgc cctcgcacca tgcggcgcag ttccccaacc actcattcaa gcatgaggat     360
cccatgggcc agcagggctc gctgggtgag cagcagtact cggtgccgcc ccggtctat     420 ggctgccaca ccccccaccga cagctgcacc ggcagccagg cttgctgct gaggacgccc     480 tacagcagtg acaatttata ccaaatgaca tcccagcttg aatgcatgac ctggaatcag     540
atgaacttag gagccacctt aaagggccac agcacaggt acgagagcga taaccacaca     600
acgcccatcc tctgcggagc ccaatacaga atacacacgc acggtgtctt cagaggcatt     660
caggatgtgc gacgtgtgcc tggagtagcc ccgactcttg tacggtcggc atctgagacc     720
agtgagaaac gccccttcat gtgtgcttac ccaggctgca ataagagata ttttaagctg     780
tcccacttac agatgcacag caggaagcac actggtgaga accataccag gtgtgacttc     840
aaggactgtg aacgaaggtt ttttcgttca gaccagctca aaagacacca aaggagacat     900
acaggtgtga accattccag tgtaaaaact tgtcagcgaa agttctcccg gtccgaccac     960
```

```
ctgaagaccc acaccaggac tcatacaggt gaaaagccct tcagctgtcg gtggccaagt    1020
tgtcagaaaa agtttgcccg gtcagatgaa ttagtccgcc atcacaacat gcatcagaga    1080
aacatgacca aactccagct ggcgctttga                                     1110
```

<210> SEQ ID NO 342
<211> LENGTH: 99
<212> TYPE: PRT
<213> ORGANISM: Homo sapiens

<400> SEQUENCE: 342

```
Met Gln His His His His His His Gly Ser Asp Val Arg Asp Leu Asn
                  5                  10                  15
Ala Leu Leu Pro Ala Val Pro Ser Leu Gly Gly Gly Gly Cys Ala
             20                  25                  30
Leu Pro Val Ser Gly Ala Ala Gln Trp Ala Pro Val Leu Asp Phe Ala
         35                  40                  45
Pro Pro Gly Ala Ser Ala Tyr Gly Ser Leu Gly Gly Pro Ala Pro Pro
     50                  55                  60
Pro Ala Pro Pro Pro Pro Pro Pro Pro His Ser Phe Ile Lys
 65                  70                  75                  80
Gln Glu Pro Ser Trp Gly Gly Ala Glu Pro His Glu Glu Gln Cys Leu
                 85                  90                  95
Ser Ala Phe
```

<210> SEQ ID NO 343
<211> LENGTH: 152
<212> TYPE: PRT
<213> ORGANISM: Homo sapiens

<400> SEQUENCE: 343

```
Met Gln His His His His His His Glu Glu Gln Cys Leu Ser Ala
                  5                  10                  15
Phe Thr Val His Phe Ser Gly Gln Phe Thr Gly Thr Ala Gly Ala Cys
             20                  25                  30
Arg Tyr Gly Pro Phe Gly Pro Pro Pro Ser Gln Ala Ser Ser Gly
         35                  40                  45
Gln Ala Arg Met Phe Pro Asn Ala Pro Tyr Leu Pro Ser Cys Leu Glu
     50                  55                  60
Ser Gln Pro Ala Ile Arg Asn Gln Gly Tyr Ser Thr Val Thr Phe Asp
 65                  70                  75                  80
Gly Thr Pro Ser Tyr Gly His Thr Pro Ser His His Ala Ala Gln Phe
                 85                  90                  95
Pro Asn His Ser Phe Lys His Glu Asp Pro Met Gly Gln Gln Gly Ser
                100                 105                 110
Leu Gly Glu Gln Gln Tyr Ser Val Pro Pro Val Tyr Gly Cys His
            115                 120                 125
Thr Pro Thr Asp Ser Cys Thr Gly Ser Gln Ala Leu Leu Leu Arg Thr
        130                 135                 140
Pro Tyr Ser Ser Asp Asn Leu Tyr
145                 150
```

<210> SEQ ID NO 344
<211> LENGTH: 133
<212> TYPE: PRT
<213> ORGANISM: Homo sapiens

<400> SEQUENCE: 344

Met Gln His His His His His Gln Ala Leu Leu Leu Arg Thr Pro
               5                   10                  15

Tyr Ser Ser Asp Asn Leu Tyr Gln Met Thr Ser Gln Leu Glu Cys Met
               20                  25                  30

Thr Trp Asn Gln Met Asn Leu Gly Ala Thr Leu Lys Gly His Ser Thr
           35                  40                  45

Gly Tyr Glu Ser Asp Asn His Thr Thr Pro Ile Leu Cys Gly Ala Gln
50                  55                  60

Tyr Arg Ile His Thr His Gly Val Phe Arg Gly Ile Gln Asp Val Arg
65                  70                  75                  80

Arg Val Pro Gly Val Ala Pro Thr Leu Val Arg Ser Ala Ser Glu Thr
               85                  90                  95

Ser Glu Lys Arg Pro Phe Met Cys Ala Tyr Pro Gly Cys Asn Lys Arg
               100                 105                 110

Tyr Phe Lys Leu Ser His Leu Gln Met His Ser Arg Lys His Thr Gly
               115                 120                 125

Glu Lys Pro Tyr Gln
130

<210> SEQ ID NO 345
<211> LENGTH: 112
<212> TYPE: PRT
<213> ORGANISM: Homo sapiens

<400> SEQUENCE: 345

Met Gln His His His His His His Ser Arg Lys His Thr Gly Glu
               5                   10                  15

Lys Pro Tyr Gln Cys Asp Phe Lys Asp Cys Glu Arg Arg Phe Phe Arg
               20                  25                  30

Ser Asp Gln Leu Lys Arg His Gln Arg Arg His Thr Gly Val Lys Pro
           35                  40                  45

Phe Gln Cys Lys Thr Cys Gln Arg Lys Phe Ser Arg Ser Asp His Leu
50                  55                  60

Lys Thr His Thr Arg Thr His Thr Gly Glu Lys Pro Phe Ser Cys Arg
65                  70                  75                  80

Trp Pro Ser Cys Gln Lys Lys Phe Ala Arg Ser Asp Glu Leu Val Arg
               85                  90                  95

His His Asn Met His Gln Arg Asn Met Thr Lys Leu Gln Leu Ala Leu
               100                 105                 110

<210> SEQ ID NO 346
<211> LENGTH: 369
<212> TYPE: PRT
<213> ORGANISM: Homo sapiens

<400> SEQUENCE: 346

Met Gln His His His His His His Ser Phe Ile Lys Gln Glu Pro
               5                   10                  15

Ser Trp Gly Gly Ala Glu Pro His Glu Glu Gln Cys Leu Ser Ala Phe
               20                  25                  30

Thr Val His Phe Ser Gly Gln Phe Thr Gly Thr Ala Gly Ala Cys Arg
           35                  40                  45

Tyr Gly Pro Phe Gly Pro Pro Pro Ser Gln Ala Ser Ser Gly Gln
50                  55                  60

Ala Arg Met Phe Pro Asn Ala Pro Tyr Leu Pro Ser Cys Leu Glu Ser
65                  70                  75                  80

```
Gln Pro Ala Ile Arg Asn Gln Gly Tyr Ser Thr Val Thr Phe Asp Gly
                 85                  90                  95

Thr Pro Ser Tyr Gly His Thr Pro Ser His His Ala Ala Gln Phe Pro
            100                 105                 110

Asn His Ser Phe Lys His Glu Asp Pro Met Gly Gln Gln Gly Ser Leu
        115                 120                 125

Gly Glu Gln Gln Tyr Ser Val Pro Pro Val Tyr Gly Cys His Thr
    130                 135                 140

Pro Thr Asp Ser Cys Thr Gly Ser Gln Ala Leu Leu Leu Arg Thr Pro
145                 150                 155                 160

Tyr Ser Ser Asp Asn Leu Tyr Gln Met Thr Ser Gln Leu Glu Cys Met
                165                 170                 175

Thr Trp Asn Gln Met Asn Leu Gly Ala Thr Leu Lys Gly His Ser Thr
            180                 185                 190

Gly Tyr Glu Ser Asp Asn His Thr Thr Pro Ile Leu Cys Gly Ala Gln
        195                 200                 205

Tyr Arg Ile His Thr His Gly Val Phe Arg Gly Ile Gln Asp Val Arg
    210                 215                 220

Arg Val Pro Gly Val Ala Pro Thr Leu Val Arg Ser Ala Ser Glu Thr
225                 230                 235                 240

Ser Glu Lys Arg Pro Phe Met Cys Ala Tyr Pro Gly Cys Asn Lys Arg
                245                 250                 255

Tyr Phe Lys Leu Ser His Leu Gln Met His Ser Arg Lys His Thr Gly
            260                 265                 270

Glu Lys Pro Tyr Gln Cys Asp Phe Lys Asp Cys Glu Arg Arg Phe Phe
        275                 280                 285

Arg Ser Asp Gln Leu Lys Arg His Gln Arg Arg His Thr Gly Val Lys
    290                 295                 300

Pro Phe Gln Cys Lys Thr Cys Gln Arg Lys Phe Ser Arg Ser Asp His
305                 310                 315                 320

Leu Lys Thr His Thr Arg Thr His Thr Gly Glu Lys Pro Phe Ser Cys
                325                 330                 335

Arg Trp Pro Ser Cys Gln Lys Lys Phe Ala Arg Ser Asp Glu Leu Val
            340                 345                 350

Arg His His Asn Met His Gln Arg Asn Met Thr Lys Leu Gln Leu Ala
        355                 360                 365

Leu

<210> SEQ ID NO 347
<211> LENGTH: 21
<212> TYPE: DNA
<213> ORGANISM: Artificial Sequence
<220> FEATURE:
<223> OTHER INFORMATION: Primer

<400> SEQUENCE: 347
ggctccgacg tgcgggacct g                                              21

<210> SEQ ID NO 348
<211> LENGTH: 30
<212> TYPE: DNA
<213> ORGANISM: Artificial Sequence
<220> FEATURE:
<223> OTHER INFORMATION: Primer

<400> SEQUENCE: 348
gaattctcaa agcgccagct ggagtttggt                                     30
```

```
<210> SEQ ID NO 349
<211> LENGTH: 21
<212> TYPE: DNA
<213> ORGANISM: Artificial Sequence
<220> FEATURE:
<223> OTHER INFORMATION: Primer

<400> SEQUENCE: 349
ggctccgacg tgcgggacct g                                           21

<210> SEQ ID NO 350
<211> LENGTH: 30
<212> TYPE: DNA
<213> ORGANISM: Artificial Sequence
<220> FEATURE:
<223> OTHER INFORMATION: Primer

<400> SEQUENCE: 350
gaattctcaa agcgccagct ggagtttggt                                  30

<210> SEQ ID NO 351
<211> LENGTH: 21
<212> TYPE: DNA
<213> ORGANISM: Artificial Sequence
<220> FEATURE:
<223> OTHER INFORMATION: Primer

<400> SEQUENCE: 351
cacagcacag ggtacgagag c                                           21

<210> SEQ ID NO 352
<211> LENGTH: 30
<212> TYPE: DNA
<213> ORGANISM: Artificial Sequence
<220> FEATURE:
<223> OTHER INFORMATION: Primer

<400> SEQUENCE: 352
gaattctcaa agcgccagct ggagtttggt                                  30

<210> SEQ ID NO 353
<211> LENGTH: 29
<212> TYPE: DNA
<213> ORGANISM: Artificial Sequence
<220> FEATURE:
<223> OTHER INFORMATION: Primer

<400> SEQUENCE: 353
cacgaagaac agtgcctgag cgcattcac                                   29

<210> SEQ ID NO 354
<211> LENGTH: 32
<212> TYPE: DNA
<213> ORGANISM: Artificial Sequence
<220> FEATURE:
<223> OTHER INFORMATION: Primer

<400> SEQUENCE: 354
ccggcgaatt catcagtata aattgtcact gc                               32

<210> SEQ ID NO 355
<211> LENGTH: 24
<212> TYPE: DNA
<213> ORGANISM: Artificial Sequence
<220> FEATURE:
<223> OTHER INFORMATION: Primer
```

<400> SEQUENCE: 355
caggctttgc tgctgaggac gccc                                          24

<210> SEQ ID NO 356
<211> LENGTH: 34
<212> TYPE: DNA
<213> ORGANISM: Artificial Sequence
<220> FEATURE:
<223> OTHER INFORMATION: Primer

<400> SEQUENCE: 356
cacggagaat tcatcactgg tatggtttct cacc                               34

<210> SEQ ID NO 357
<211> LENGTH: 28
<212> TYPE: DNA
<213> ORGANISM: Artificial Sequence
<220> FEATURE:
<223> OTHER INFORMATION: Primer

<400> SEQUENCE: 357
cacagcagga agcacactgg tgagaaac                                      28

<210> SEQ ID NO 358
<211> LENGTH: 30
<212> TYPE: DNA
<213> ORGANISM: Artificial Sequence
<220> FEATURE:
<223> OTHER INFORMATION: Primer

<400> SEQUENCE: 358
ggatatctgc agaattctca aagcgccagc                                    30

<210> SEQ ID NO 359
<211> LENGTH: 22
<212> TYPE: DNA
<213> ORGANISM: Artificial Sequence
<220> FEATURE:
<223> OTHER INFORMATION: Primer

<400> SEQUENCE: 359
cactccttca tcaaacagga ac                                            22

<210> SEQ ID NO 360
<211> LENGTH: 30
<212> TYPE: DNA
<213> ORGANISM: Artificial Sequence
<220> FEATURE:
<223> OTHER INFORMATION: Primer

<400> SEQUENCE: 360
ggatatctgc agaattctca aagcgccagc                                    30

<210> SEQ ID NO 361
<211> LENGTH: 33
<212> TYPE: DNA
<213> ORGANISM: Artificial Sequence
<220> FEATURE:
<223> OTHER INFORMATION: Primer

<400> SEQUENCE: 361
ggttccgacg tgcgggacct gaacgcactg ctg                                33

<210> SEQ ID NO 362
<211> LENGTH: 40
<212> TYPE: DNA

```
<213> ORGANISM: Artificial Sequence
<220> FEATURE:
<223> OTHER INFORMATION: Primer

<400> SEQUENCE: 362
ctgccggcag cagtgcgttc aggtcccgca cgtcggaacc                              40

<210> SEQ ID NO 363
<211> LENGTH: 35
<212> TYPE: DNA
<213> ORGANISM: Artificial Sequence
<220> FEATURE:
<223> OTHER INFORMATION: Primer

<400> SEQUENCE: 363
ccggcagttc catccctggg tggcggtgga ggctg                                   35

<210> SEQ ID NO 364
<211> LENGTH: 38
<212> TYPE: DNA
<213> ORGANISM: Artificial Sequence
<220> FEATURE:
<223> OTHER INFORMATION: Primer

<400> SEQUENCE: 364
cggcagtgcg cagcctccac cgccacccag ggatggaa                                38

<210> SEQ ID NO 365
<211> LENGTH: 35
<212> TYPE: DNA
<213> ORGANISM: Artificial Sequence
<220> FEATURE:
<223> OTHER INFORMATION: Primer

<400> SEQUENCE: 365
cgcactgccg gttagcggtg cagcacagtg ggctc                                   35

<210> SEQ ID NO 366
<211> LENGTH: 33
<212> TYPE: DNA
<213> ORGANISM: Artificial Sequence
<220> FEATURE:
<223> OTHER INFORMATION: Primer

<400> SEQUENCE: 366
cagaactgga gcccactgtg ctgcaccgct aac                                     33

<210> SEQ ID NO 367
<211> LENGTH: 38
<212> TYPE: DNA
<213> ORGANISM: Artificial Sequence
<220> FEATURE:
<223> OTHER INFORMATION: Primer

<400> SEQUENCE: 367
cagttctgga cttcgcaccg cctggtgcat ccgcatac                                38

<210> SEQ ID NO 368
<211> LENGTH: 39
<212> TYPE: DNA
<213> ORGANISM: Artificial Sequence
<220> FEATURE:
<223> OTHER INFORMATION: Primer

<400> SEQUENCE: 368
cagggaaccg tatgcggatg caccaggcgg tgcgaagtc                               39
```

<210> SEQ ID NO 369
<211> LENGTH: 38
<212> TYPE: DNA
<213> ORGANISM: Artificial Sequence
<220> FEATURE:
<223> OTHER INFORMATION: Primer

<400> SEQUENCE: 369
ggttccctgg gtggtccagc acctccgccc gcaacgcc                           38

<210> SEQ ID NO 370
<211> LENGTH: 38
<212> TYPE: DNA
<213> ORGANISM: Artificial Sequence
<220> FEATURE:
<223> OTHER INFORMATION: Primer

<400> SEQUENCE: 370
ggcggtgggg gcgttgcggg cggaggtgct ggaccacc                           38

<210> SEQ ID NO 371
<211> LENGTH: 40
<212> TYPE: DNA
<213> ORGANISM: Artificial Sequence
<220> FEATURE:
<223> OTHER INFORMATION: Primer

<400> SEQUENCE: 371
cccaccgcct ccaccgcccc cgcactcctt catcaaacag                         40

<210> SEQ ID NO 372
<211> LENGTH: 39
<212> TYPE: DNA
<213> ORGANISM: Artificial Sequence
<220> FEATURE:
<223> OTHER INFORMATION: Primer

<400> SEQUENCE: 372
ctaggttcct gtttgatgaa ggagtgcggg ggcggtgga                          39

<210> SEQ ID NO 373
<211> LENGTH: 38
<212> TYPE: DNA
<213> ORGANISM: Artificial Sequence
<220> FEATURE:
<223> OTHER INFORMATION: Primer

<400> SEQUENCE: 373
gaacctagct ggggtggtgc agaaccgcac gaagaaca                           38

<210> SEQ ID NO 374
<211> LENGTH: 39
<212> TYPE: DNA
<213> ORGANISM: Artificial Sequence
<220> FEATURE:
<223> OTHER INFORMATION: Primer

<400> SEQUENCE: 374
ctcaggcact gttcttcgtg cggttctgca ccaccccag                          39

<210> SEQ ID NO 375
<211> LENGTH: 32
<212> TYPE: DNA
<213> ORGANISM: Artificial Sequence
<220> FEATURE:
<223> OTHER INFORMATION: Primer

```
<400> SEQUENCE: 375
gtgcctgagc gcattctgag aattctgcag at                                    32

<210> SEQ ID NO 376
<211> LENGTH: 34
<212> TYPE: DNA
<213> ORGANISM: Artificial Sequence
<220> FEATURE:
<223> OTHER INFORMATION: Primer

<400> SEQUENCE: 376
gtgtgatgga tatctgcaga attctcagaa tgcg                                  34

<210> SEQ ID NO 377
<211> LENGTH: 1292
<212> TYPE: DNA
<213> ORGANISM: Homo sapiens
<220> FEATURE:
<221> NAME/KEY: misc_feature
<222> LOCATION: 253,256,517,518,520,521,522,743,753,754,
      758
<223> OTHER INFORMATION: n = A,T,C or G

<400> SEQUENCE: 377
atgggctccg acgttcgtga cctgagcgcg ctgctgccgg cagttccgtc cctgggtgat      60
ggtggtggtt gcgcactgcc ggttagcggt gcagcacagt gggctccggt tctggacttc     120
gcaccgccgg gtgcatccgc acacggtccc ctgggtggtc cggcgccgcc gtcggcaccg     180
ccgccgccgc cgccgccgcc gccgcactcc ttcatcaaac agggaccgag ctggggtggc     240
gcggaactgc ackaakaaca gtacctgagc gcgttcaccg ttcactcctc cggtcaggtt     300
cactggcacg gccggggcct gtcgctacgg gcccctcggc cccctccgc ccagccaggc      360 gtcatccggc caggccagga tgtctcctag cgcgccctgc ctgcccagcc gcctcgagag     420
ccagcccgct acccgcaatc ggggctacag cacggtcacc ttcgacgggg cgtccggcta     480
cggtcacacg ccctcgcacc atgcggcgca gttctcsmar yyactcgtta ggcgtgagga     540
tcccatgggc cagcagggtc cgctgggtga gcagcagtgc tcggcgccgc ccccggcctg     600
tggccgccac accccgccg acagctgcgc cggcagccag gctttgctgc tgagggcgcc      660
ctgtagcagc gacggtttat accaagtgac gtcccagctt gagtgcatgg cctggagtca     720
gatgagcctc ggggccgcct tamcgggcca cakyacargg tacgagagcg atgatcacac     780
aacgcccggc ctctgcggag cccaatacag aatacacacg cacggtgcct tcaggggcgt     840
tcagggtgtg cgccgtgtgc ctggagtagc cccgactctt gtacggtcgg catctgaggc     900
cagtgaggaa cgcccctca tgtgtgctta cccaggctgc aataggaggt atctgaagct      960
gccccgctta cagatgcacg gtaggaagca cgctggtgag agaccatacc agtgtgactt    1020
caaggactgt ggacggaggt ttttctgctc agaccggctc aaaagacacc aggggaggca    1080
tacagatgtg aagccattcc agcgtaagac ctgtcagcga gggttctccc ggcccaacca    1140
cctgaagacc cacgccagga ctcatgcagg tgaaaagccc cccagctgtc ggtggtcaga    1200
ttgtcagaga aagcctgccc ggtcaagtga gttggtccgc catcgcgaca tgcatcagag    1260
gggcatgacc gaactccagc tggcgctttg aa                                  1292

<210> SEQ ID NO 378
<211> LENGTH: 1291
<212> TYPE: DNA
<213> ORGANISM: Homo sapiens

<400> SEQUENCE: 378
```

```
atgggctccg acgttcgtga cctaaacgca ctgctgccgg cagttccgtc cccgggtggt    60
ggtggtggtt gcgcactgcc ggttagcggt gcaacacagt gggctccggt tctggacttc   120
gtaccgccgg gtgcgcctgt atgcggttcc ctgggtggcc cggcaccgcc gccagcgccg   180
ccgccgctgc cgccgccgcc gtcgcactcc ttcaccaaac aggaaccgag ttggggtggt   240
acagagccgc acgcaggaca gggccggagc gcactcgtcg ctcactcctc cggccagttc   300
actggcacag ccggagcctg tcgctacggg cccttcggtc ctcctccgcc cagccaggcg   360
tcatccggcc aggccaggat gtttcctaac gcgccctacc tgcccagctg cctcgagagc   420
cagcccgcta ttcgcaatca gggttacagc acggtcacct tcgacgggac gcccagctac   480
ggtcacacgc cctcgcacca tgcggcgcag ttccccaacc actcatccaa gcatgaggac   540
cccatgggcc agcagggctc gccgggtgag cagcagtact cggcgccgcc cccggtctgc   600
ggctgccgca cccccaccgg cagctgcacc ggcagccagg cttTgctgct gagggcgccc   660
tacagcggtg gcgatctaca ccaaacgaca tcccagcttg acacatggc  ctggaatcag   720
acgaacttag gagccacctt aaagggccac ggcacaggTg acgagagcga tgaccacaca   780
acgcccatcc tctgcggaac ccagtacagg atacgcgcgc gcggcgtcct ccggggtact   840
caggatgtgc ggtgtgtgcc tggggtggcc ccgactcttg tgcggtcggc atctgagacc   900
agtgagaagc gcccctcat  gtgtgcctac ccaggctgca ataagagaca ctttaagccg   960
tcccgcttgc gggtgcgcgg cagggagcgc actggtgaga accatacca  gcgcgacttc  1020
aaggaccgtg gacgagggct tctccgtcca gaccagctca aaaggcacca gaggggcat   1080
acaggtgtga aacctctcca gtgtgaagct tgacggcgga ggccccccg  acccggccac  1140
ctgaaggtcc acaccaggac ccatacaggt ggagagccct tcagttgtcg gtggccaagt  1200
tgtcaggaga gtctgcccg  ccagatgaa  tcagcccgcc gtcataacat gcatcagaga  1260
aacatgacca aactccagct ggcgctttga a                                  1291

<210> SEQ ID NO 379
<211> LENGTH: 1281
<212> TYPE: DNA
<213> ORGANISM: Homo sapiens

<400> SEQUENCE: 379
atgggctccg acgttcgtga cctgagtgca ttgctaccga cggccccgtc cctgggtggt    60
ggcggtgact gcacactgcc ggttagcggt acagcacagt gggctccggt cccggcctcc   120
gcaccgccgg gcgcatccgc atacgattcc ctgggtggcc cggcaccgcc gccggcgccg   180
ccgccgccgc cgccgccgcc gccgcactcc tgcggcgaac aggggccgag ctggggtggt   240
gcagaaccgc gcgaggggca atgcctgagt gcgcccgccg tccgcttctc cggccggttc   300
accggcacag tcggagcctg tcgctatggg cccctcggtc ctcctccgcc cagccaggcg   360
ccatccggcc agaccaggat gttgcccagc gcgccctatc tgtcgagttg cctcaggagc   420
cggtccgcta tccgtagtca gggtcgcagc acggcacctt cagcggggcg cccagctatg   480
gcacccaccc tcgcaccacc ggcgcagtcc cactactccc aacatggggt cctacatggg   540
ccagcagggc tcgctgggtg agcagcagta ctcggtgccg ccccccggtct atggctgcca   600
cacccccacc gacagctgca ccggcagcca ggctttgctg ctgaggacgc cctacagcag   660
tgacaattta taccaaatga catcccagct tgaatgcatg acctggaatc agatgaactt   720
aggagccacc ttaaagggcc acagcacagg gtacgagagc gataaccaca caacgcccat   780
cctctgcgga gcccaataca gaatacacac gcacggtgtc ttcagaggca ttcaggatgt   840
```

```
gcgacgtgtg cctggagtag ccccgactct tgtacggtag cacctgagac cagtgagaac    900
gccccttggt gtgtgttacc ggggctgcag taagggtat tttaagccgt cccacttacg     960
ggtgcacagc aggaagcgca ttggtgagac gccacgccag tgcgactcca agggccgtgg   1020
acgagggcct ctccgttcgg gaccagccca agggacacca aggagacat acaggtacgc    1080 aaccactcca gtgtaaggct tgtcagcgaa ggttcccccg gtccgaccac ctgagggccc   1140
acgccagggc ccacacgggt gggaagcccc tcagctgccg gtggccaagc tgccagagag   1200
ggttcgccca gtcagacgaa ttagtccgtc atcacaacat gtatcagcga aacatgacta   1260
aactccagct ggcgctttga a                                             1281

<210> SEQ ID NO 380
<211> LENGTH: 3020
<212> TYPE: DNA
<213> ORGANISM: Homo sapiens

<400> SEQUENCE: 380
gttcaaggca gcgcccacac ccgggggctc tccgcaaccc gaccgcctgt ccgctccccc     60
acttcccgcc ctccctccca cctactcatt cacccaccca cccacccaga gccgggacgg    120
cagcccaggc gcccgggccc cgccgtctcc tcgccgcgat cctggacttc ctcttgctgc    180
aggacccggc ttccacgtgt gtcccggagc cggcgtctca gcacacgctc cgctccgggc    240
ctgggtgcct acagcagcca gagcagcagg gagtccggga cccgggcggc atctgggcca    300
agttaggcgc cgccgaggcc agcgctgaac gtctccaggg ccggaggagc cgcggggcgt    360
ccgggtctga gcctcagcaa atgggctccg acgtgcggga cctgaacgcg ctgctgcccg    420
ccgtcccctc cctgggtggc ggcggcggct gtgccctgcc tgtgagcggc gcggcgcagt    480
gggcgccggt gctggacttt gcgccccgg gcgcttcggc ttacgggtcg ttgggcggcc     540
ccgcgccgcc accggctccg ccgccacccc gccgccgcc gcctcactcc ttcatcaaac    600
aggagccgag ctggggcggc gcggagccgc acaggagca gtgcctgagc gccttcactg    660
tccacttttc cggccagttc actggcacag ccggagcctg tcgctacggg cccttcggtc    720
ctcctccgcc cagccaggcg tcatccggcc aggccaggat gtttcctaac gcgccctacc   780
tgcccagctg cctcgagagc cagcccgcta ttcgcaatca gggttacagc acggtcacct    840
tcgacgggac gcccagctac ggtcacacgc cctcgcacca tgcggcgcag ttccccaacc    900
actcattcaa gcatgaggat ccatggggcc agcagggctc gctgggtgag cagcagtact    960
cggtgccgcc cccggtctat ggctgccaca ccccccaccga cagctgcacc ggcagccagg   1020
cttgtgctct gaggacgccc tacagcagtg acaatttata ccaaatgaca tcccagcttg   1080
aatgcatgac ctggaatcag atgaacttag gagccaccct aaagggagtt gctgctggga   1140
gctccagctc agtgaaatgg acagaagggc agagcaacca cagcacaggg tacgagagcg   1200
ataaccacac aacgcccatc ctctgcggag cccaatacag aatacacacg cacggtgtct   1260
tcagaggcat tcaggatgtg cgacgtgtgc ctggagtagc cccgactctt gtacggtcgg   1320
catctgagac cagtgagaaa cgccccttca tgtgtgctta cccaggctgc aataagagat   1380
attttaagct gtcccactta cagatgcaca gcaggaagca cactggtgag aaaccatacc   1440
agtgtgactt caaggactgt gaacgaaggt tttctcgttc agaccagctc aaaagacacc   1500
aaaggagaca tacaggtgtg aaaccattcc agtgtaaaac ttgtcagcga agttctccc    1560 ggtccgacca cctgaagacc cacaccagga ctcatacagg taaaacaagt gaaaagccct   1620
tcagctgtcg gtggccaagt tgtcagaaaa agtttgcccg gtcagatgaa ttagtccgcc   1680
```

| | |
|---|---|
| atcacaacat gcatcagaga aacatgacca aactccagct ggcgctttga ggggtctccc | 1740 |
| tcggggaccg ttcagtgtcc caggcagcac agtgtgtgaa ctgctttcaa gtctgactct | 1800 |
| ccactcctcc tcactaaaaa ggaaacttca gttgatcttc ttcatccaac ttccaagaca | 1860 |
| agataccggt gcttctggaa actaccaggt gtgcctggaa gagttggtct ctgccctgcc | 1920 |
| tacttttagt tgactcacag gccctggaga agcagctaac aatgtctggt tagttaaaag | 1980 |
| cccattgcca tttggtctgg attttctact gtaagaagag ccatagctga tcatgtcccc | 2040 |
| ctgacccttc ccttcttttt ttatgctcgt tttcgctggg gatggaatta ttgtaccatt | 2100 |
| ttctatcatg gaatatttat aggccagggc atgtgtatgt gtctgctaat gtaaactttg | 2160 |
| tcatggtttc catttactaa cagcaacagc aagaaataaa tcagagagca aggcatcggg | 2220 |
| ggtgaatctt gtctaacatt cccgaggtca gccaggctgc taacctggaa agcaggatgt | 2280 |
| agttctgcca ggcaactttt aaagctcatg catttcaagc agctgaagaa agaatcagaa | 2340 |
| ctaaccagta cctctgtata gaaatctaaa agaattttac cattcagtta attcaatgtg | 2400 |
| aacactggca cactgctctt aagaaactat gaagatctga gattttttttg tgtatgtttt | 2460 |
| tgactctttt gagtggtaat catatgtgtc tttatagatg tacataccte cttgcacaaa | 2520 |
| tggagggggaa ttcattttca tcactgggac tgtccttagt gtataaaaac catgctggta | 2580 |
| tatgcttca agttgtaaaa atgaaagtga ctttaaaaga aaataggggga tggtccagga | 2640 |
| tctccactga taagactgtt tttaagtaac ttaaggacct ttgggtctac aagtatatgt | 2700 |
| gaaaaaatg agacttactg ggtgaggaaa tccattgttt aaagatggtc gtgtgtgtgt | 2760 |
| gtgtgtgtgt gtgtgtgttg tgttgtgttt tgttttttaa gggagggaat ttattattta | 2820 |
| ccgttgcttg aaattactgt gtaaatatat gtctgataat gatttgctct ttgacaacta | 2880 |
| aaattaggac tgtataagta ctagatgcat cactgggtgt tgatcttaca agatattgat | 2940 |
| gataacactt aaaattgtaa cctgcatttt tcactttgct ctcaattaaa gtctattcaa | 3000 |
| aaggaaaaaa aaaaaaaaaa | 3020 |

<210> SEQ ID NO 381
<211> LENGTH: 1291
<212> TYPE: DNA
<213> ORGANISM: Homo sapiens

<400> SEQUENCE: 381

| | |
|---|---|
| atgggctccg acgttcgtga cctgaacgca ctgctgccgg cagttccgtc cctgggtggt | 60 |
| ggtggtggtt gcgcactgcc ggttagcggt gcagcacagt gggctccggt tctggacttc | 120 |
| gcaccgccgg gtgcatccgc atacggttcc ctgggtggtc cggcaccgcc gccggcaccg | 180 |
| ccgccgccgc cgccgccgcc gccgcactcc ttcatcaaac aggaaccgag ctggggtggt | 240 |
| gcagaaccgc acgaagaaca gtgcctgagc gcattcaccg ttcacttctc cggccagttc | 300 |
| actggcacag ccggagcctg tcgctacggg cccttcggtc ctcctccgcc cagccaggcg | 360 |
| tcatccggcc aggccaggat gtttcctaac gcgccctacc tgcccagctg cctcgagagc | 420 |
| cagcccgcta ttcgcaatca gggttacagc acggtcacct tcgacgggac gcccagctac | 480 |
| ggtcacacgc cctcgcacca tgcggcgcag ttcccaacc actcattcaa gcatgaggat | 540 |
| cccatgggcc agcagggctc gctggtgag cagcagtact cggtgccgcc cccggtctat | 600 |
| ggctgccaca ccccaccga cagctgcacc ggcagccagg cttgctgct gaggacgccc | 660 |
| tacagcagtg acaatttata ccaaatgaca tcccagcttg aatgcatgac ctggaatcag | 720 |
| atgaacttag gagccaccct taaagggcca cagcacaggt acgagagcga taaccacaca | 780 |

```
acgcccatcc tctgcggagc ccaatacaga atacacacgc acggtgtctt cagaggcatt      840
caggatgtgc gacgtgtgcc tggagtagcc ccgactcttg tacggtcggc atctgagacc      900
agtgagaaac gcccccttcat gtgtgcttac ccaggctgca ataagagata ttttaagctg      960
tcccacttac agatgcacag caggaagcac actggtgaga aaccatacca gtgtgacttc      1020
aaggactgtg aacgaaggtt ttttcgttca gaccagctca aaagacacca aaggagacat      1080
acaggtgtga aaccattcca gtgtaaaact tgtcagcgaa agttctcccg gtccgaccac      1140
ctgaagaccc acaccaggac tcatacaggt gaaaagccct tcagctgtcg gtggccaagt      1200
tgtcagaaaa agtttgcccg gtcagatgaa ttagtccgcc atcacaacat gcatcagaga      1260
aacatgacca aactccagct ggcgctttga g                                     1291
```

<210> SEQ ID NO 382
<211> LENGTH: 1491
<212> TYPE: DNA
<213> ORGANISM: Homo sapiens

<400> SEQUENCE: 382

```
atggcggccc ccggcgcccg gcggtcgctg ctcctgctgc tgctggcagg ccttgcacat      60
ggcgcctcag cactctttga ggatctaatg ggctccgacg ttcgtgacct gaacgcactg      120
ctgccggcag ttccgtccct gggtggtggt ggtggttgcg cactgccggt tagcggtgca      180
gcacagtggg ctccggttct ggacttcgca ccgccgggtg catccgcata cggttccctg      240
ggtggtccgg caccgccgcc ggcaccgccg ccgccgccgc cgccgcactc cttcatcaaa      300
caggaaccga gctggggtgg tgcagaaccg cacgaagaac agtgcctgag cgcattcacc      360
gttcacttct ccggccagtt cactggcaca gccgagcct gtcgctacgg gcccttcggt      420
cctcctccgc ccagccaggc gtcatccggc caggccagga tgtttcctaa cgcgccctac      480
ctgcccagct gcctcgagag ccagcccgct attcgcaatc agggttacag cacggtcacc      540
ttcgacggga cgcccagcta cggtcacacg ccctcgcacc atgcggcgca gttccccaac      600
cactcattca gcatgagga tcccatgggc cagcagggcc cgctgggtga gcagcagtac      660
tcggtgccgc ccccggtcta tggctgccac accccaccg acagctgcac cggcagccag      720
gctttgctgc tgaggacgcc ctacagcagt gacaatttat accaaatgac atcccagctt      780
gaatgcatga cctggaatca gatgaactta ggagccacct taaagggcca cagcacaggg      840
tacgagagcg ataaccacac aacgcccatc tctgcggag cccaatacag aatacacacg       900
cacggtgtct tcagaggcat tcaggatgtg cgacgtgtgc ctggagtagc cccgactctt      960
gtacggtcgg catctgagac cagtgagaaa cgcccccttca tgtgtgctta cccaggctgc      1020
aataagagat attttaagct gtcccactta cagatgcaca gcaggaagca cactggtgag      1080
aaaccatacc agtgtgactt caaggactgt aacgaaggt ttttcgttc agaccagctc       1140 aaaagacacc aaaggagaca tacaggtgtg aaaccattcc agtgtaaaac ttgtcagcga      1200
aagttctccc ggtccgacca cctgaagacc cacaccagga ctcatacagg tgaaaagccc      1260
ttcagctgtc ggtggccaag ttgtcagaaa agtttgcccc ggtcagatga attagtccgc      1320
catcacaaca tgcatcagag aaacatgacc aaactccagc tggcgcttct taacaacatg      1380
ttgatcccca ttgctgtggg cggtgccctg gcagggctgg tcctcatcgt cctcattgcc      1440
tacctcattg gcaggaagag gagtcacgcc ggctatcaga ccatctagtg a               1491
```

<210> SEQ ID NO 383
<211> LENGTH: 1251

```
<212> TYPE: DNA
<213> ORGANISM: Homo sapiens

<400> SEQUENCE: 383
atggcgcccc gcagcgcccg gcgacccctg ctgctgctac tgcctgttgc tgctgctcgg      60
cctcatgcat tgtcgtcagc agccatgttt atggtgaaaa atggcaacgg gaccgcgtgc     120
ataatggcca acttctctgc tgccttctca gtgaactacg acaccaagag tggcccaag      180 aacatgacct ttgacctgcc atcagatgcc acagtggtgc tcaaccgcag ctcctgtgga     240
aaagagaaca cttctgaccc cagtctcgtg attgcttttg aagaggaca tacactcact      300 ctcaatttca cgagaaatgc aacacgttac agcgttcagc tcatgagttt tgtttataac     360
ttgtcagaca cacacctttt ccccaatgcg agctccaaag aaatcaagac tgtggaatct     420
ataactgaca tcagggcaga tatagataaa aaatacagat gtgttagtgg cacccaggtc     480
cacatgaaca acgtgaccgt aacgctccat gatgccacca tccaggcgta cctttccaac     540
agcagcttca gcggggaga cacacgctgt gaacaagaca ggccttcccc aaccacagcg     600
ccccctgcgc cacccagccc ctcgccctca ccgtgccca agagcccctc tgtggacaag     660
tacaacgtga gcggcaccaa cgggacctgc ctgctggcca gcatggggct gcagctgaac     720
ctcacctatg agaggaagga caacacgacg gtgacaaggc ttctcaacat caaccccaac     780
aagacctcgg ccagcgggag ctgcggcgcc cacctggtga ctctggagct gcacagcgag     840
ggcaccaccg tcctgctctt ccagttcggg atgaatgcaa gttctagccg gttttttccta   900 caaggaatcc agttgaatac aattcttcct gacgccagag accctgcctt taaagctgcc    960
aacggctccc tgcgagcgct gcaggccaca gtcggcaatt cctacaagtg caacgcggag   1020
gagcacgtcc gtgtcacgaa ggcgttttca gtcaatatat tcaaagtgtg ggtccaggct   1080
ttcaaggtgg aaggtggcca gtttggctct gtggaggagt gtctgctgga cgagaacagc   1140
acgctgatcc ccatcgctgt gggtggtgcc ctggcggggc tggtcctcat cgtcctcatc   1200
gcctacctcg tcggcaggaa gaggagtcac gcaggctacc agactatcta g            1251

<210> SEQ ID NO 384
<211> LENGTH: 228
<212> TYPE: DNA
<213> ORGANISM: Homo sapiens

<400> SEQUENCE: 384
atgcagatct tcgtgaagac tctgactggt aagaccatca ccctcgaggt ggagcccagt     60
gacaccatcg agaatgtcaa ggcaaagatc caagataagg aaggcattcc tcctgatcag    120
cagaggttga tctttgccgg aaaacagctg gaagatggtc gtaccctgtc tgactacaac    180
atccagaaag agtccacctt gcacctggta ctccgtctca gaggtggg               228

<210> SEQ ID NO 385
<211> LENGTH: 1515
<212> TYPE: DNA
<213> ORGANISM: Homo sapiens

<400> SEQUENCE: 385
atgcagatct tcgtgaagac cctgaccggc aagaccatca ccctggaagt ggagcccagt     60
gacaccatcg aaaatgtgaa ggccaagatc caggataaag aaggcatccc tccgaccag    120 cagaggctca tctttgcagg caagcagcta gaagatggcc gcactctttc tgactacaac    180
atccagaagg agtcgaccct gcacctggtc cttcgcctga gggtgcat gggctccgac     240 gttcgtgacc tgaacgcact gctgccggca gttccgtccc tgggtggtgg tggtggttgc    300
```

```
gcactgccgg ttagcggtgc agcacagtgg gctccggttc tggacttcgc accgccgggt    360
gcatccgcat acggttccct gggtggtccg gcaccgccgc cggcaccgcc gccgccgccg    420
ccgccgccgc actccttcat caaacaggaa ccgagctggg gtggtgcaga accgcacgaa    480
gaacagtgcc tgagcgcatt caccgttcac ttctccggcc agttcactgg cacagccgga    540
gcctgtcgct acgggccctt cggtcctcct ccgcccagcc aggcgtcatc cggccaggcc    600
aggatgtttc ctaacgcgcc ctatctgccc agctgcctcg agagccagcc cgctattcgc    660
aatcagggtt acagcacggt caccttcgac gggacgccca gctacggtca cacgccctcg    720
caccatgcgg cgcagttccc caaccactca ttcaagcatg aggatccat  gggccagcag    780 ggctcgctgg gtgagcagca gtactcggtg ccgccccgg  tctatggctg ccacaccccc    840
accgacagct gcaccggcag ccaggctttg ctgctgagga cgccctacag cagtgacaat    900
ttataccaaa tgacatccca gcttgaatgc atgacctgga atcagatgaa cttaggagcc    960
accttaaagg gccacagcac agggtacgag agcgataacc acacaacgcc catcctctgc   1020
ggagcccaat acagaataca cacgcacggt gtcttcagag gcattcagga tgtgcgacgt   1080
gtgcctggag tagccccgac tcttgtacgg tcggcatctg agaccagtga gaaacgcccc   1140
ttcatgtgtg cttacccagg ctgcaataag agatatttta gctgtcccca cttacagatg   1200
cacagcagga agcacactgg tgagaaacca taccagtgtg acttcaagga ctgtgaacga   1260
aggttttttc gttcagacca gctcaaaaga caccaaagga gacatacagg tgtgaaacca   1320
ttccagtgta aaacttgtca gcgaaagttc tcccggtccg accacctgaa gacccacacc   1380
aggactcata caggtgaaaa gcccttcagc tgtcggtggc caagttgtca gaaaaagttt   1440
gcccggtcag atgaattagt ccgccatcac aacatgcatc agagaaacat gaccaaactc   1500
cagctggcgc tttga                                                    1515

<210> SEQ ID NO 386
<211> LENGTH: 648
<212> TYPE: DNA
<213> ORGANISM: Homo sapiens

<400> SEQUENCE: 386
atgcactcct tcatcaaaca ggaaccgagc tggggtggtg cagaaccgca cgaagaacag     60
tgcctgagcg cattcaccgt tcacttctcc ggccagttca ctggcacagc cggagcctgt    120
cgctacgggc ccttcggtcc tcctccgccc agccaggcgt catccggcca ggccaggatg    180
tttcctaacg cgcctacct  gcccagctgc ctcgagagcc agcccgctat tcgcaatcag    240
ggttacagca cggtcacctt cgacgggacg cccagctacg gtcacacgcc ctcgcaccat    300
gcggcgcagt tccccaacca ctcattcaag catgaggatc ccatgggcca gcagggctcg    360
ctgggtgagc agcagtactc ggtgccgccc ccggtctatg gctgccacac ccccaccgac    420
agctgcaccg gcagccaggc tttgctgctg aggacgccct acagcagtga catttatac    480 caaatgacat cccagcttga atgcatgacc tggaatcaga tgaacttagg agccaccttt  540
aagggccaca gcacagggta cgagagcgat aaccacacaa cgcccatcct ctgcggagcc    600
caatacagaa tacacacgca cggtgtcttc agaggcattc agtgatga               648

<210> SEQ ID NO 387
<211> LENGTH: 1089
<212> TYPE: DNA
<213> ORGANISM: Homo sapiens

<400> SEQUENCE: 387
```

```
atgcactcct tcatcaaaca ggaaccgagc tggggtggtg cagaaccgca cgaagaacag    60
tgcctgagcg cattcaccgt tcacttctcc ggccagttca ctggcacagc cggagcctgt   120
cgctacgggc ccttcggtcc tcctccgccc agccaggcgt catccggcca ggccaggatg   180
tttcctaacg cgccctacct gcccagctgc ctcgagagcc agcccgctat tcgcaatcag   240
ggttacagca cggtcacctt cgacgggacg cccagctacg gtcacacgcc ctcgcaccat   300
gcggcgcagt tccccaacca ctcattcaag catgaggatc ccatgggcca gcagggctcg   360
ctgggtgagc agcagtactc ggtgccgccc ccggtctatg gctgccacac ccccaccgac   420
agctgcaccg gcagccaggc tttgctgctg aggacgccct acagcagtga caatttatac   480
caaatgacat cccagcttga atgcatgacc tggaatcaga tgaacttagg agccaccttq   540 aagggccaca gcacagggta cgagagcgat aaccacacaa cgcccatcct ctgcggagcc   600
caatacagaa tacacacgca cggtgtcttc agaggcattc aggatgtgcg acgtgtgcct   660
ggagtagccc cgactcttgt acggtcggca tctgagacca gtgagaaacg ccccttcatg   720
tgtgcttacc caggctgcaa taagagatat tttaagctgt cccacttaca gatgcacagc   780
aggaagcaca ctggtgagaa accataccag tgtgacttca aggactgtga acgaaggttt   840
tttcgttcag accagctcaa aagacaccaa aggagacata caggtgtgaa accattccag   900
tgtaaaactt gtcagcgaaa gttctcccgg tccgaccacc tgaagaccca caccaggact   960
catacaggtg aaaagccctt cagctgtcgg tggccaagtt gtcagaaaaa gtttgcccgg  1020
tcagatgaat tagtccgcca tcacaacatg catcagagaa acatgaccaa actccagctg  1080
gcgcttttga                                                          1089

<210> SEQ ID NO 388
<211> LENGTH: 1035
<212> TYPE: DNA
<213> ORGANISM: Homo sapiens

<400> SEQUENCE: 388
atgacggccg cgtccgataa cttccagctg tcccagggtg ggcagggatt cgccattccg    60
atcgggcagg cgatggcgat cgcgggccag atcaagcttc ccaccgttca tatcgggcct   120
accgccttcc tcggcttggg tgttgtcgac aacaacggca acggcgcacg agtccaacgc   180
gtggtcggga gcgctccggc ggcaagtctc ggcatctcca ccggcgacgt gatcaccgcg   240
gtcgacggcg ctccgatcaa ctcggccacc gcgatggcgg acgcgcttaa cgggcatcat   300
cccggtgacg tcatctcggt gacctggcaa accaagtcgg gcggcacgcg tacagggaac   360
gtgacattgg ccgagggacc cccggccgaa ttccactcct tcatcaaaca ggaaccgagc   420
tggggtggtg cagaaccgca cgaagaacag tgcctgagcg cattcaccgt tcacttctcc   480
ggccagttca ctggcacagc cggagcctgt cgctacgggc ccttcggtcc tcctccgccc   540
agccaggcgt catccggcca ggccaggatg tttcctaacg cgccctacct gcccagctgc   600
ctcgagagcc agcccgctat tcgcaatcag ggttacagca cggtcacctt cgacgggacg   660
cccagctacg gtcacacgcc ctcgcaccat gcggcgcagt tccccaacca ctcattcaag   720
catgaggatc ccatgggcca gcagggctcg ctgggtgagc agcagtactc ggtgccgccc   780
ccggtctatg gctgccacac ccccaccgac agctgcaccg gcagccaggc tttgctgctg   840
aggacgccct acagcagtga caatttatac caaatgacat cccagcttga atgcatgacc   900
tggaatcaga tgaacttagg agccaccttq aagggccaca gcacagggta cgagagcgat   960
aaccacacaa cgcccatcct ctgcggagcc caatacagaa tacacacgca cggtgtcttc  1020
```

```
agaggcattc agtga                                                  1035

<210> SEQ ID NO 389
<211> LENGTH: 1263
<212> TYPE: DNA
<213> ORGANISM: Homo sapiens

<400> SEQUENCE: 389
atgacggccg cgtccgataa cttccagctg tcccagggtg ggcagggatt cgccattccg   60
atcgggcagg cgatggcgat cgcgggccag atcaagcttc ccaccgttca tatcgggcct  120
accgccttcc tcggcttggg tgttgtcgac aacaacggca acggcgcacg agtccaacgc  180
gtggtcggga gcgctccggc ggcaagtctc ggcatctcca ccggcgacgt gatcaccgcg  240
gtcgacggcg ctccgatcaa ctcggccacc gcgatggcgg acgcgcttaa cgggcatcat  300
cccggtgacg tcatctcggt gacctggcaa accaagtcgg gcggcacgcg tacagggaac  360
gtgacattgg ccgagggacc cccggccgaa ttccgctgg tgccgcgcgg cagcccgatg   420
ggctccgacg ttcgggacct gaacgcactg ctgccggcag ttccgtccct gggtggtggt  480
ggtggttgcg cactgccggt tagcggtgca gcacagtggg ctccggttct ggacttcgca  540
ccgccgggtg catccgcata cggttccctg gtggtccgg caccgccgcc ggcaccgccg   600
ccgccgccgc cgccgccgcc gcactccttc atcaaacagg aaccgagctg gggtggtgca  660
gaaccgcacg aagaacagtg cctgagcgca ttcaccgttc acttctccgg ccagttcact  720
ggcacagccg agcctgtcg ctacgggccc ttcggtcctc ctccgcccag ccaggcgtca   780
tccggccagg ccaggatgtt tcctaacgcg ccctacctgc ccagctgcct cgagagccag  840
cccgctattc gcaatcaggg ttacagcacg gtcaccttcg acgggacgcc cagctacggt  900
cacacgccct cgcaccatgc ggcgcagttc cccaaccact cattcaagca tgaggatccc  960
atgggccagc agggctcgct gggtgagcag cagtactcgg tgccgccccc ggtctatggc 1020
tgccacaccc ccaccgacag ctgcaccggc agccaggctt tgctgctgag gacgccctac 1080
agcagtgaca atttataccc aatgacatcc cagcttgaat gcatgacctg gaatcagatg 1140
aacttaggag ccaccttaaa gggccacagc acagggtacg agagcgataa ccacacaacg 1200
cccatcctct gcggagccca atacagaata cacgcgcacg gtgtcttcag aggcattcag 1260
tga                                                               1263

<210> SEQ ID NO 390
<211> LENGTH: 1707
<212> TYPE: DNA
<213> ORGANISM: Homo sapiens

<400> SEQUENCE: 390
atgacggccg cgtccgataa cttccagctg tcccagggtg ggcagggatt cgccattccg   60
atcgggcagg cgatggcgat cgcgggccag atcaagcttc ccaccgttca tatcgggcct  120
accgccttcc tcggcttggg tgttgtcgac aacaacggca acggcgcacg agtccaacgc  180
gtggtcggga gcgctccggc ggcaagtctc ggcatctcca ccggcgacgt gatcaccgcg  240
gtcgacggcg ctccgatcaa ctcggccacc gcgatggcgg acgcgcttaa cgggcatcat  300
cccggtgacg tcatctcggt gacctggcaa accaagtcgg gcggcacgcg tacagggaac  360
gtgacattgg ccgagggacc cccggccgaa ttccgctgg tgccgcgcgg cagcccgatg   420
ggctccgacg ttcgggacct gaacgcactg ctgccggcag ttccgtccct gggtggtggt  480
ggtggttgcg cactgccggt tagcggtgca gcacagtggg ctccggttct ggacttcgca  540
```

```
ccgccgggtg catccgcata cggttccctg ggtggtccgg caccgccgcc ggcaccgccg    600
ccgccgccgc cgccgccgcc gcactccttc atcaaacagg aaccgagctg ggtggtgca    660 gaaccgcacg aagaacagtg cctgagcgca ttcaccgttc acttctccgg ccagttcact    720
ggcacagccg agcctgtcgc ctacgggccc ttcggtcctc ctccgcccag ccaggcgtca    780
tccggccagg ccaggatgtt tcctaacgcg ccctacctgc ccagctgcct cgagagccag    840
cccgctattc gcaatcaggg ttacagcacg gtcaccttcg acgggacgcc cagctacggt    900
cacacgccct cgcaccatgc ggcgcagttc cccaaccact cattcaagca tgaggatccc    960
atgggccagc agggctcgct gggtgagcag cagtactcgg tgccgccccc ggtctatggc   1020
tgccacaccc ccaccgacag ctgcaccggc agccaggctt tgctgctgag gacgccctac   1080
agcagtgaca atttatacca aatgacatcc cagcttgaat gcatgacctg aatcagatg   1140 aacttaggag ccaccttaaa gggccacagc acagggtacg agagcgataa ccacacaacg   1200
cccatcctct gcggagccca atacagaata cacacgcacg tgtcttcag aggcattcag   1260 gatgtgcgac gtgtgcctgg agtagccccg actcttgtac ggtcggcatc tgagaccagt   1320
gagaaacgcc ccttcatgtg tgcttaccca ggctgcaata agagatattt taagctgtcc   1380
cacttacaga tgcacagcag gaagcacact ggtgagaaac cataccagtg tgacttcaag   1440
gactgtgaac gaaggttttt tcgttcagac cagctcaaaa gacaccaaag gagacataca   1500
ggtgtgaaac cattccagtg taaaacttgt cagcgaaagt tctcccggtc cgaccacctg   1560
aagacccaca ccaggactca tacaggtgaa aagcccttca gctgtcggtg gccaagttgt   1620
cagaaaaagt ttgcccggtc agatgaatta gtccgccatc acaacatgca tcagagaaac   1680
atgaccaaac tccagctggc gctttga                                      1707
```

<210> SEQ ID NO 391
<211> LENGTH: 344
<212> TYPE: PRT
<213> ORGANISM: Homo sapiens

<400> SEQUENCE: 391

```
Met Thr Ala Ala Ser Asp Asn Phe Gln Leu Ser Gln Gly Gly Gln Gly
                5                   10                  15

Phe Ala Ile Pro Ile Gly Gln Ala Met Ala Ile Ala Gly Gln Ile Lys
            20                  25                  30

Leu Pro Thr Val His Ile Gly Pro Thr Ala Phe Leu Gly Leu Gly Val
        35                  40                  45

Val Asp Asn Asn Gly Asn Gly Ala Arg Val Gln Arg Val Val Gly Ser
    50                  55                  60

Ala Pro Ala Ala Ser Leu Gly Ile Ser Thr Gly Asp Val Ile Thr Ala
65                  70                  75                  80

Val Asp Gly Ala Pro Ile Asn Ser Ala Thr Ala Met Ala Asp Ala Leu
                85                  90                  95

Asn Gly His His Pro Gly Asp Val Ile Ser Val Thr Trp Gln Thr Lys
            100                 105                 110

Ser Gly Gly Thr Arg Thr Gly Asn Val Thr Leu Ala Glu Gly Pro Pro
        115                 120                 125

Ala Glu Phe His Ser Phe Ile Lys Gln Glu Pro Ser Trp Gly Gly Ala
    130                 135                 140

Glu Pro His Glu Glu Gln Cys Leu Ser Ala Phe Thr Val His Phe Ser
145                 150                 155                 160

Gly Gln Phe Thr Gly Thr Ala Gly Ala Cys Arg Tyr Gly Pro Phe Gly
```

-continued

```
                165                 170                 175
Pro Pro Pro Pro Ser Gln Ala Ser Ser Gly Gln Ala Arg Met Phe Pro
            180                 185                 190

Asn Ala Pro Tyr Leu Pro Ser Cys Leu Glu Ser Gln Pro Ala Ile Arg
        195                 200                 205

Asn Gln Gly Tyr Ser Thr Val Thr Phe Asp Gly Thr Pro Ser Tyr Gly
    210                 215                 220

His Thr Pro Ser His His Ala Ala Gln Phe Pro Asn His Ser Phe Lys
225                 230                 235                 240

His Glu Asp Pro Met Gly Gln Gln Gly Ser Leu Gly Glu Gln Gln Tyr
                245                 250                 255

Ser Val Pro Pro Val Tyr Gly Cys His Thr Pro Thr Asp Ser Cys
            260                 265                 270

Thr Gly Ser Gln Ala Leu Leu Leu Arg Thr Pro Tyr Ser Ser Asp Asn
        275                 280                 285

Leu Tyr Gln Met Thr Ser Gln Leu Glu Cys Met Thr Trp Asn Gln Met
    290                 295                 300

Asn Leu Gly Ala Thr Leu Lys Gly His Ser Thr Gly Tyr Glu Ser Asp
305                 310                 315                 320

Asn His Thr Thr Pro Ile Leu Cys Gly Ala Gln Tyr Arg Ile His Thr
                325                 330                 335

His Gly Val Phe Arg Gly Ile Gln
            340

<210> SEQ ID NO 392
<211> LENGTH: 568
<212> TYPE: PRT
<213> ORGANISM: Homo sapiens

<400> SEQUENCE: 392

Met Thr Ala Ala Ser Asp Asn Phe Gln Leu Ser Gln Gly Gly Gln Gly
                  5                  10                  15

Phe Ala Ile Pro Ile Gly Gln Ala Met Ala Ile Ala Gly Gln Ile Lys
             20                  25                  30

Leu Pro Thr Val His Ile Gly Pro Thr Ala Phe Leu Gly Leu Gly Val
         35                  40                  45

Val Asp Asn Asn Gly Asn Gly Ala Arg Val Gln Arg Val Val Gly Ser
     50                  55                  60

Ala Pro Ala Ala Ser Leu Gly Ile Ser Thr Gly Asp Val Ile Thr Ala
 65                  70                  75                  80

Val Asp Gly Ala Pro Ile Asn Ser Ala Thr Ala Met Ala Asp Ala Leu
                 85                  90                  95

Asn Gly His His Pro Gly Asp Val Ile Ser Val Thr Trp Gln Thr Lys
            100                 105                 110

Ser Gly Gly Thr Arg Thr Gly Asn Val Thr Leu Ala Glu Gly Pro Pro
        115                 120                 125

Ala Glu Phe Pro Leu Val Pro Arg Gly Ser Pro Met Gly Ser Asp Val
    130                 135                 140

Arg Asp Leu Asn Ala Leu Leu Pro Ala Val Pro Ser Leu Gly Gly Gly
145                 150                 155                 160

Gly Gly Cys Ala Leu Pro Val Ser Gly Ala Ala Gln Trp Ala Pro Val
                165                 170                 175

Leu Asp Phe Ala Pro Pro Gly Ala Ser Ala Tyr Gly Ser Leu Gly Gly
            180                 185                 190

Pro Ala Pro Pro Pro Ala Pro Pro Pro Pro Pro Pro Pro Pro Pro His
```

```
                195                 200                 205
Ser Phe Ile Lys Gln Glu Pro Ser Trp Gly Gly Ala Glu Pro His Glu
210                 215                 220

Glu Gln Cys Leu Ser Ala Phe Thr Val His Phe Ser Gly Gln Phe Thr
225                 230                 235                 240

Gly Thr Ala Gly Ala Cys Arg Tyr Gly Pro Phe Gly Pro Pro Pro Pro
                245                 250                 255

Ser Gln Ala Ser Ser Gly Gln Ala Arg Met Phe Pro Asn Ala Pro Tyr
            260                 265                 270

Leu Pro Ser Cys Leu Glu Ser Gln Pro Ala Ile Arg Asn Gln Gly Tyr
        275                 280                 285

Ser Thr Val Thr Phe Asp Gly Thr Pro Ser Tyr Gly His Thr Pro Ser
    290                 295                 300

His His Ala Ala Gln Phe Pro Asn His Ser Phe Lys His Glu Asp Pro
305                 310                 315                 320

Met Gly Gln Gln Gly Ser Leu Gly Glu Gln Gln Tyr Ser Val Pro Pro
                325                 330                 335

Pro Val Tyr Gly Cys His Thr Pro Thr Asp Ser Cys Thr Gly Ser Gln
            340                 345                 350

Ala Leu Leu Leu Arg Thr Pro Tyr Ser Ser Asp Asn Leu Tyr Gln Met
        355                 360                 365

Thr Ser Gln Leu Glu Cys Met Thr Trp Asn Gln Met Asn Leu Gly Ala
    370                 375                 380

Thr Leu Lys Gly His Ser Thr Gly Tyr Glu Ser Asp Asn His Thr Thr
385                 390                 395                 400

Pro Ile Leu Cys Gly Ala Gln Tyr Arg Ile His Thr His Gly Val Phe
                405                 410                 415

Arg Gly Ile Gln Asp Val Arg Val Pro Gly Val Ala Pro Thr Leu
            420                 425                 430

Val Arg Ser Ala Ser Glu Thr Ser Glu Lys Arg Pro Phe Met Cys Ala
        435                 440                 445

Tyr Pro Gly Cys Asn Lys Arg Tyr Phe Lys Leu Ser His Leu Gln Met
    450                 455                 460

His Ser Arg Lys His Thr Gly Glu Lys Pro Tyr Gln Cys Asp Phe Lys
465                 470                 475                 480

Asp Cys Glu Arg Arg Phe Phe Arg Ser Asp Gln Leu Lys Arg His Gln
                485                 490                 495

Arg Arg His Thr Gly Val Lys Pro Phe Gln Cys Lys Thr Cys Gln Arg
            500                 505                 510

Lys Phe Ser Arg Ser Asp His Leu Lys Thr His Thr Arg Thr His Thr
        515                 520                 525

Gly Glu Lys Pro Phe Ser Cys Arg Trp Pro Ser Cys Gln Lys Lys Phe
    530                 535                 540

Ala Arg Ser Asp Glu Leu Val Arg His His Asn Met His Gln Arg Asn
545                 550                 555                 560

Met Thr Lys Leu Gln Leu Ala Leu
                565

<210> SEQ ID NO 393
<211> LENGTH: 420
<212> TYPE: PRT
<213> ORGANISM: Homo sapiens

<400> SEQUENCE: 393

Met Thr Ala Ala Ser Asp Asn Phe Gln Leu Ser Gln Gly Gly Gln Gly
```

```
              5                  10                 15
Phe Ala Ile Pro Ile Gly Gln Ala Met Ala Ile Ala Gly Gln Ile Lys
                20                 25                 30

Leu Pro Thr Val His Ile Gly Pro Thr Ala Phe Leu Gly Leu Gly Val
            35                 40                 45

Val Asp Asn Asn Gly Asn Gly Ala Arg Val Gln Arg Val Val Gly Ser
 50                 55                 60

Ala Pro Ala Ala Ser Leu Gly Ile Ser Thr Gly Asp Val Ile Thr Ala
 65                 70                 75                 80

Val Asp Gly Ala Pro Ile Asn Ser Ala Thr Ala Met Ala Asp Ala Leu
                85                 90                 95

Asn Gly His His Pro Gly Asp Val Ile Ser Val Thr Trp Gln Thr Lys
                100                105                110

Ser Gly Gly Thr Arg Thr Gly Asn Val Thr Leu Ala Glu Gly Pro Pro
            115                120                125

Ala Glu Phe Pro Leu Val Pro Arg Gly Ser Pro Met Gly Ser Asp Val
            130                135                140

Arg Asp Leu Asn Ala Leu Leu Pro Ala Val Pro Ser Leu Gly Gly Gly
145                150                155                160

Gly Gly Cys Ala Leu Pro Val Ser Gly Ala Ala Gln Trp Ala Pro Val
                165                170                175

Leu Asp Phe Ala Pro Pro Gly Ala Ser Ala Tyr Gly Ser Leu Gly Gly
                180                185                190

Pro Ala Pro Pro Pro Ala Pro Pro Pro Pro Pro Pro Pro Pro Pro His
                195                200                205

Ser Phe Ile Lys Gln Glu Pro Ser Trp Gly Gly Ala Glu Pro His Glu
    210                215                220

Glu Gln Cys Leu Ser Ala Phe Thr Val His Phe Ser Gly Gln Phe Thr
225                230                235                240

Gly Thr Ala Gly Ala Cys Arg Tyr Gly Pro Phe Gly Pro Pro Pro Pro
                245                250                255

Ser Gln Ala Ser Ser Gly Gln Ala Arg Met Phe Pro Asn Ala Pro Tyr
                260                265                270

Leu Pro Ser Cys Leu Glu Ser Gln Pro Ala Ile Arg Asn Gln Gly Tyr
            275                280                285

Ser Thr Val Thr Phe Asp Gly Thr Pro Ser Tyr Gly His Thr Pro Ser
            290                295                300

His His Ala Ala Gln Phe Pro Asn His Ser Phe Lys His Glu Asp Pro
305                310                315                320

Met Gly Gln Gln Gly Ser Leu Gly Glu Gln Gln Tyr Ser Val Pro Pro
                325                330                335

Pro Val Tyr Gly Cys His Thr Pro Thr Asp Ser Cys Thr Gly Ser Gln
                340                345                350

Ala Leu Leu Leu Arg Thr Pro Tyr Ser Ser Asp Asn Leu Tyr Gln Met
            355                360                365

Thr Ser Gln Leu Glu Cys Met Thr Trp Asn Gln Met Asn Leu Gly Ala
370                375                380

Thr Leu Lys Gly His Ser Thr Gly Tyr Glu Ser Asp Asn His Thr Thr
385                390                395                400

Pro Ile Leu Cys Gly Ala Gln Tyr Arg Ile His Thr His Gly Val Phe
                405                410                415

Arg Gly Ile Gln
            420
```

```
<210> SEQ ID NO 394
<211> LENGTH: 362
<212> TYPE: PRT
<213> ORGANISM: Homo sapiens

<400> SEQUENCE: 394

Met His Ser Phe Ile Lys Gln Glu Pro Ser Trp Gly Gly Ala Glu Pro
                 5                  10                  15

His Glu Glu Gln Cys Leu Ser Ala Phe Thr Val His Phe Ser Gly Gln
             20                  25                  30

Phe Thr Gly Thr Ala Gly Ala Cys Arg Tyr Gly Pro Phe Gly Pro Pro
         35                  40                  45

Pro Pro Ser Gln Ala Ser Ser Gly Gln Ala Arg Met Phe Pro Asn Ala
     50                  55                  60

Pro Tyr Leu Pro Ser Cys Leu Glu Ser Gln Pro Ala Ile Arg Asn Gln
 65                  70                  75                  80

Gly Tyr Ser Thr Val Thr Phe Asp Gly Thr Pro Ser Tyr Gly His Thr
                 85                  90                  95

Pro Ser His His Ala Ala Gln Phe Pro Asn His Ser Phe Lys His Glu
            100                 105                 110

Asp Pro Met Gly Gln Gln Gly Ser Leu Gly Glu Gln Gln Tyr Ser Val
        115                 120                 125

Pro Pro Pro Val Tyr Gly Cys His Thr Pro Thr Asp Ser Cys Thr Gly
    130                 135                 140

Ser Gln Ala Leu Leu Leu Arg Thr Pro Tyr Ser Ser Asp Asn Leu Tyr
145                 150                 155                 160

Gln Met Thr Ser Gln Leu Glu Cys Met Thr Trp Asn Gln Met Asn Leu
                165                 170                 175

Gly Ala Thr Leu Lys Gly His Ser Thr Gly Tyr Glu Ser Asp Asn His
            180                 185                 190

Thr Thr Pro Ile Leu Cys Gly Ala Gln Tyr Arg Ile His Thr His Gly
        195                 200                 205

Val Phe Arg Gly Ile Gln Asp Val Arg Arg Val Pro Gly Val Ala Pro
    210                 215                 220

Thr Leu Val Arg Ser Ala Ser Glu Thr Ser Glu Lys Arg Pro Phe Met
225                 230                 235                 240

Cys Ala Tyr Pro Gly Cys Asn Lys Arg Tyr Phe Lys Leu Ser His Leu
                245                 250                 255

Gln Met His Ser Arg Lys His Thr Gly Glu Lys Pro Tyr Gln Cys Asp
            260                 265                 270

Phe Lys Asp Cys Glu Arg Arg Phe Phe Arg Ser Asp Gln Leu Lys Arg
        275                 280                 285

His Gln Arg Arg His Thr Gly Val Lys Pro Phe Gln Cys Lys Thr Cys
    290                 295                 300

Gln Arg Lys Phe Ser Arg Ser Asp His Leu Lys Thr His Thr Arg Thr
305                 310                 315                 320

His Thr Gly Glu Lys Pro Phe Ser Cys Arg Trp Pro Ser Cys Gln Lys
                325                 330                 335

Lys Phe Ala Arg Ser Asp Glu Leu Val Arg His His Asn Met His Gln
            340                 345                 350

Arg Asn Met Thr Lys Leu Gln Leu Ala Leu
        355                 360

<210> SEQ ID NO 395
<211> LENGTH: 214
```

```
<212> TYPE: PRT
<213> ORGANISM: Homo sapiens

<400> SEQUENCE: 395

Met His Ser Phe Ile Lys Gln Glu Pro Ser Trp Gly Gly Ala Glu Pro
                  5                  10                  15

His Glu Glu Gln Cys Leu Ser Ala Phe Thr Val His Phe Ser Gly Gln
             20                  25                  30

Phe Thr Gly Thr Ala Gly Ala Cys Arg Tyr Gly Pro Phe Gly Pro Pro
         35                  40                  45

Pro Pro Ser Gln Ala Ser Ser Gly Gln Ala Arg Met Phe Pro Asn Ala
     50                  55                  60

Pro Tyr Leu Pro Ser Cys Leu Glu Ser Gln Pro Ala Ile Arg Asn Gln
65                  70                  75                  80

Gly Tyr Ser Thr Val Thr Phe Asp Gly Thr Pro Ser Tyr Gly His Thr
                 85                  90                  95

Pro Ser His His Ala Ala Gln Phe Pro Asn His Ser Phe Lys His Glu
            100                 105                 110

Asp Pro Met Gly Gln Gln Gly Ser Leu Gly Glu Gln Gln Tyr Ser Val
        115                 120                 125

Pro Pro Pro Val Tyr Gly Cys His Thr Pro Thr Asp Ser Cys Thr Gly
    130                 135                 140

Ser Gln Ala Leu Leu Leu Arg Thr Pro Tyr Ser Ser Asp Asn Leu Tyr
145                 150                 155                 160

Gln Met Thr Ser Gln Leu Glu Cys Met Thr Trp Asn Gln Met Asn Leu
                165                 170                 175

Gly Ala Thr Leu Lys Gly His Ser Thr Gly Tyr Glu Ser Asp Asn His
            180                 185                 190

Thr Thr Pro Ile Leu Cys Gly Ala Gln Tyr Arg Ile His Thr His Gly
        195                 200                 205

Val Phe Arg Gly Ile Gln
    210

<210> SEQ ID NO 396
<211> LENGTH: 30
<212> TYPE: DNA
<213> ORGANISM: Artificial Sequence
<220> FEATURE:
<223> OTHER INFORMATION: PCR primer

<400> SEQUENCE: 396
gacgaaagca tatgcactcc ttcatcaaac                                    30

<210> SEQ ID NO 397
<211> LENGTH: 31
<212> TYPE: DNA
<213> ORGANISM: Artificial Sequence
<220> FEATURE:
<223> OTHER INFORMATION: PCR primer

<400> SEQUENCE: 397
cgcgtgaatt catcactgaa tgcctctgaa g                                  31

<210> SEQ ID NO 398
<211> LENGTH: 31
<212> TYPE: DNA
<213> ORGANISM: Artificial Sequence
<220> FEATURE:
<223> OTHER INFORMATION: PCR primer

<400> SEQUENCE: 398
```

```
cgataagcat atgacggccg cgtccgataa c                                    31

<210> SEQ ID NO 399
<211> LENGTH: 31
<212> TYPE: DNA
<213> ORGANISM: Artificial Sequence
<220> FEATURE:
<223> OTHER INFORMATION: PCR primer

<400> SEQUENCE: 399
cgcgtgaatt catcactgaa tgcctctgaa g                                    31

<210> SEQ ID NO 400
<211> LENGTH: 31
<212> TYPE: DNA
<213> ORGANISM: Artificial Sequence
<220> FEATURE:
<223> OTHER INFORMATION: PCR primer

<400> SEQUENCE: 400
cgataagcat atgacggccg cgtccgataa c                                    31

<210> SEQ ID NO 401
<211> LENGTH: 28
<212> TYPE: DNA
<213> ORGANISM: Artificial Sequence
<220> FEATURE:
<223> OTHER INFORMATION: PCR primer

<400> SEQUENCE: 401
gtctgcagcg gccgctcaaa gcgccagc                                        28

<210> SEQ ID NO 402
<211> LENGTH: 30
<212> TYPE: DNA
<213> ORGANISM: Artificial Sequence
<220> FEATURE:
<223> OTHER INFORMATION: PCR primer

<400> SEQUENCE: 402
gacgaaagca tatgcactcc ttcatcaaac                                      30

<210> SEQ ID NO 403
<211> LENGTH: 28
<212> TYPE: DNA
<213> ORGANISM: Artificial Sequence
<220> FEATURE:
<223> OTHER INFORMATION: PCR primer

<400> SEQUENCE: 403
gtctgcagcg gccgctcaaa gcgccagc                                        28

<210> SEQ ID NO 404
<211> LENGTH: 449
<212> TYPE: PRT
<213> ORGANISM: Homo sapiens

<400> SEQUENCE: 404

Met Gly Ser Asp Val Arg Asp Leu Asn Ala Leu Leu Pro Ala Val Pro
 1               5                   10                  15

Ser Leu Gly Gly Gly Gly Gly Cys Ala Leu Pro Val Ser Gly Ala Ala
             20                  25                  30

Gln Trp Ala Pro Val Leu Asp Phe Ala Pro Pro Gly Ala Ser Ala Tyr
         35                  40                  45
```

Gly Ser Leu Gly Gly Pro Ala Pro Pro Ala Pro Pro Pro Pro
        50                  55                  60

Pro Pro Pro His Ser Phe Ile Lys Gln Glu Pro Ser Trp Gly Gly
65              70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
                100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Pro Val Tyr Gly Cys His Thr Pro Thr Asp Ser
                195                 200                 205

Cys Thr Gly Ser Gln Ala Leu Leu Leu Arg Thr Pro Tyr Ser Ser Asp
        210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Gly Ser Ser Ser
                245                 250                 255

Ser Val Lys Trp Thr Glu Gly Gln Ser Asn His Ser Thr Gly Tyr Glu
        260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
                435                 440                 445

Leu

<210> SEQ ID NO 405
<211> LENGTH: 428

```
<212> TYPE: PRT
<213> ORGANISM: Homo sapiens

<400> SEQUENCE: 405
```

| | | | | | | | | | | | | | | |
|---|---|---|---|---|---|---|---|---|---|---|---|---|---|---|
| Met | Gly | Ser | Asp | Val | Arg | Asp | Leu | Asn | Ala | Leu | Leu | Pro | Ala | Pro |
| 1 | | | | 5 | | | | | 10 | | | | | 15 |
| Ser | Pro | Gly | Gly | Gly | Gly | Cys | Ala | Leu | Pro | Val | Ser | Gly | Ala | Thr |
| | | | 20 | | | | | 25 | | | | | 30 | |
| Gln | Trp | Ala | Pro | Val | Leu | Asp | Phe | Val | Pro | Pro | Gly | Ala | Pro | Val | Cys |
| | | 35 | | | | | 40 | | | | | 45 | | | |
| Gly | Ser | Leu | Gly | Gly | Pro | Ala | Pro | Pro | Ala | Pro | Pro | Leu | Pro |
| | 50 | | | | | 55 | | | | | 60 | | | |
| Pro | Pro | Pro | Ser | His | Ser | Phe | Thr | Lys | Gln | Glu | Pro | Ser | Trp | Gly | Gly |
| 65 | | | | | 70 | | | | | 75 | | | | | 80 |
| Thr | Glu | Pro | His | Ala | Gly | Gln | Gly | Arg | Ser | Ala | Leu | Val | Ala | His | Ser |
| | | | | 85 | | | | | 90 | | | | | 95 | |
| Ser | Gly | Gln | Phe | Thr | Gly | Thr | Ala | Gly | Ala | Cys | Arg | Tyr | Gly | Pro | Phe |
| | | | | 100 | | | | | 105 | | | | | 110 | |
| Gly | Pro | Pro | Pro | Pro | Ser | Gln | Ala | Ser | Ser | Gly | Gln | Ala | Arg | Met | Phe |
| | | | 115 | | | | | 120 | | | | | 125 | | |
| Pro | Asn | Ala | Pro | Tyr | Leu | Pro | Ser | Cys | Leu | Glu | Ser | Gln | Pro | Ala | Ile |
| | 130 | | | | | 135 | | | | | 140 | | | | |
| Arg | Asn | Gln | Gly | Tyr | Ser | Thr | Val | Thr | Phe | Asp | Gly | Thr | Pro | Ser | Tyr |
| 145 | | | | | 150 | | | | | 155 | | | | | 160 |
| Gly | His | Thr | Pro | Ser | His | His | Ala | Ala | Gln | Phe | Pro | Asn | His | Ser | Ser |
| | | | | 165 | | | | | 170 | | | | | 175 | |
| Lys | His | Glu | Asp | Pro | Met | Gly | Gln | Gln | Gly | Ser | Pro | Gly | Glu | Gln | Gln |
| | | | 180 | | | | | 185 | | | | | 190 | | |
| Tyr | Ser | Ala | Pro | Pro | Val | Cys | Gly | Cys | Arg | Thr | Pro | Thr | Gly | Ser |
| | | 195 | | | | | 200 | | | | | 205 | | | |
| Cys | Thr | Gly | Ser | Gln | Ala | Leu | Leu | Leu | Arg | Ala | Pro | Tyr | Ser | Gly | Gly |
| | 210 | | | | | 215 | | | | | 220 | | | | |
| Asp | Leu | His | Gln | Thr | Thr | Ser | Gln | Leu | Gly | His | Met | Ala | Trp | Asn | Gln |
| 225 | | | | | 230 | | | | | 235 | | | | | 240 |
| Thr | Asn | Leu | Gly | Ala | Thr | Leu | Lys | Gly | His | Gly | Thr | Gly | Tyr | Glu | Ser |
| | | | | 245 | | | | | 250 | | | | | 255 | |
| Asp | Asp | His | Thr | Thr | Pro | Ile | Leu | Cys | Gly | Thr | Gln | Tyr | Arg | Ile | Arg |
| | | | 260 | | | | | 265 | | | | | 270 | | |
| Ala | Arg | Gly | Val | Leu | Arg | Gly | Thr | Gln | Asp | Val | Arg | Cys | Val | Pro | Gly |
| | | 275 | | | | | 280 | | | | | 285 | | | |
| Val | Ala | Pro | Thr | Leu | Val | Arg | Ser | Ala | Ser | Glu | Thr | Ser | Glu | Lys | Arg |
| | 290 | | | | | 295 | | | | | 300 | | | | |
| Pro | Leu | Met | Cys | Ala | Tyr | Pro | Gly | Cys | Asn | Lys | Arg | His | Phe | Lys | Pro |
| 305 | | | | | 310 | | | | | 315 | | | | | 320 |
| Ser | Arg | Leu | Arg | Val | Arg | Gly | Arg | Glu | Arg | Thr | Gly | Glu | Lys | Pro | Tyr |
| | | | | 325 | | | | | 330 | | | | | 335 | |
| Gln | Arg | Asp | Phe | Lys | Asp | Arg | Gly | Arg | Gly | Leu | Leu | Arg | Pro | Asp | Gln |
| | | | 340 | | | | | 345 | | | | | 350 | | |
| Leu | Lys | Arg | His | Gln | Arg | Gly | His | Thr | Gly | Val | Lys | Pro | Leu | Gln | Cys |
| | | 355 | | | | | 360 | | | | | 365 | | | |
| Glu | Ala | Arg | Arg | Arg | Pro | Pro | Arg | Pro | Gly | His | Leu | Lys | Val | His | Thr |
| | 370 | | | | | 375 | | | | | 380 | | | | |
| Arg | Thr | His | Thr | Gly | Gly | Glu | Pro | Phe | Ser | Cys | Arg | Trp | Pro | Ser | Cys |
| 385 | | | | | 390 | | | | | 395 | | | | | 400 |

-continued

```
Gln Glu Lys Ser Ala Arg Pro Asp Glu Ser Ala Arg Arg His Asn Met
            405                 410                 415

His Gln Arg Asn Met Thr Lys Leu Gln Leu Ala Leu
            420                 425

<210> SEQ ID NO 406
<211> LENGTH: 414
<212> TYPE: PRT
<213> ORGANISM: Homo sapiens
<220> FEATURE:
<221> NAME/KEY: VARIANT
<222> LOCATION: 85, 86, 172, 173, 242, 245, 246, 247
<223> OTHER INFORMATION: Xaa = Any Amino Acid

<400> SEQUENCE: 406

Met Gly Ser Asp Val Arg Asp Leu Ser Ala Leu Leu Pro Ala Val Pro
 1               5                  10                  15

Ser Leu Gly Asp Gly Gly Gly Cys Ala Leu Pro Val Ser Gly Ala Ala
                20                  25                  30

Gln Trp Ala Pro Val Leu Asp Phe Ala Pro Pro Gly Ala Ser Ala His
            35                  40                  45

Gly Pro Leu Gly Gly Pro Ala Pro Pro Ser Ala Pro Pro Pro Pro Pro
        50                  55                  60

Pro Pro Pro Pro His Ser Phe Ile Lys Gln Gly Pro Ser Trp Gly Gly
 65                  70                  75                  80

Ala Glu Leu His Xaa Xaa Gln Tyr Leu Ser Ala Phe Thr Val His Ser
                85                  90                  95

Ser Gly Gln Val His Trp His Gly Arg Gly Leu Ser Leu Arg Ala Pro
                100                 105                 110

Arg Pro Pro Ser Ala Gln Pro Gly Val Ile Arg Pro Gly Gln Asp Val
            115                 120                 125

Ser Arg Ala Leu Pro Ala Gln Pro Pro Arg Glu Pro Ala Arg Tyr Pro
130                 135                 140

Gln Ser Gly Leu Gln His Gly His Leu Arg Arg Gly Val Arg Leu Arg
145                 150                 155                 160

Ser His Ala Leu Ala Pro Cys Gly Ala Val Leu Xaa Xaa Thr Arg Ala
                165                 170                 175

Gly Ser His Gly Pro Ala Gly Ser Ala Gly Ala Ala Val Leu Gly Ala
            180                 185                 190

Ala Pro Gly Leu Trp Pro Pro His Pro Arg Arg Gln Leu Arg Arg Gln
            195                 200                 205

Pro Gly Phe Ala Ala Glu Gly Ala Leu Gln Arg Arg Phe Ile Pro Ser
210                 215                 220

Asp Val Pro Ala Val His Gly Leu Glu Ser Asp Glu Pro Arg Gly Arg
225                 230                 235                 240

Leu Xaa Gly Pro Xaa Xaa Xaa Val Arg Glu Arg Ser His Asn Ala Arg
                245                 250                 255

Pro Leu Arg Ser Pro Ile Gln Asn Thr His Ala Arg Cys Leu Gln Gly
            260                 265                 270

Arg Ser Gly Cys Ala Pro Cys Ala Trp Ser Ser Pro Asp Ser Cys Thr
        275                 280                 285

Val Gly Ile Gly Gln Gly Thr Pro Pro His Val Cys Leu Pro Arg Leu
    290                 295                 300

Gln Glu Val Ser Glu Ala Ala Pro Leu Thr Asp Ala Arg Glu Ala Arg
305                 310                 315                 320

Trp Glu Thr Ile Pro Val Leu Gln Gly Leu Trp Thr Glu Val Phe Leu
                325                 330                 335
```

-continued

```
Leu Arg Pro Ala Gln Lys Thr Pro Gly Glu Ala Tyr Arg Cys Glu Ala
            340                 345                 350

Ile Pro Ala Asp Leu Ser Ala Arg Val Leu Pro Ala Gln Pro Pro Glu
            355                 360                 365

Asp Pro Arg Gln Asp Ser Cys Arg Lys Ala Pro Gln Leu Ser Val Val
370                 375                 380

Arg Leu Ser Glu Lys Ala Cys Pro Val Lys Val Gly Pro Pro Ser Arg
385                 390                 395                 400

His Ala Ser Glu Gly His Asp Arg Thr Pro Ala Gly Ala Leu
                405                 410

<210> SEQ ID NO 407
<211> LENGTH: 417
<212> TYPE: PRT
<213> ORGANISM: Homo sapiens

<400> SEQUENCE: 407

Met Gly Ser Asp Val Arg Asp Leu Ser Ala Leu Leu Pro Thr Ala Pro
1               5                   10                  15

Ser Leu Gly Gly Gly Asp Cys Thr Leu Pro Val Ser Gly Thr Ala
            20                  25                  30

Gln Trp Ala Pro Val Pro Ala Ser Ala Pro Gly Ala Ser Ala Tyr
            35                  40                  45

Asp Ser Leu Gly Gly Pro Ala Pro Pro Ala Pro Pro Pro Pro
50                  55                  60

Pro Pro Pro Pro His Ser Cys Gly Glu Gln Pro Ser Trp Gly Gly
65                  70                  75                  80

Ala Glu Pro Arg Glu Gly Gln Cys Leu Ser Ala Pro Val Arg Phe
                85                  90                  95

Ser Gly Arg Phe Thr Gly Thr Val Gly Ala Cys Arg Tyr Gly Pro Leu
            100                 105                 110

Gly Pro Pro Pro Ser Gln Ala Pro Ser Gly Gln Thr Arg Met Leu
            115                 120                 125

Pro Ser Ala Pro Tyr Leu Ser Ser Cys Leu Arg Ser Arg Ser Ala Ile
            130                 135                 140

Arg Ser Gln Gly Arg Ser Thr Ala Pro Ser Ala Gly Arg Pro Ala Met
145                 150                 155                 160

Ala Pro Thr Leu Ala Pro Pro Ala Gln Ser His Tyr Ser Gln His Gly
                165                 170                 175

Val Leu His Gly Pro Ala Gly Leu Ala Gly Ala Ala Val Leu Gly Ala
            180                 185                 190

Ala Pro Gly Leu Trp Leu Pro His Pro His Arg Gln Leu His Arg Gln
            195                 200                 205

Pro Gly Phe Ala Ala Glu Asp Ala Leu Gln Gln Gln Phe Ile Pro Asn
210                 215                 220

Asp Ile Pro Ala Met His Asp Leu Glu Ser Asp Glu Leu Arg Ser His
225                 230                 235                 240

Leu Lys Gly Pro Gln His Arg Val Arg Glu Arg Pro His Asn Ala His
                245                 250                 255

Pro Leu Arg Ser Pro Ile Gln Asn Thr His Ala Arg Cys Leu Gln Arg
            260                 265                 270

His Ser Gly Cys Ala Thr Cys Ala Trp Ser Ser Pro Asp Ser Cys Thr
            275                 280                 285

Val Ala Pro Glu Thr Ser Glu Asn Ala Pro Trp Cys Val Leu Pro Gly
290                 295                 300
```

```
Leu Gln Gly Val Phe Ala Val Pro Leu Thr Gly Ala Gln Gln Glu Ala
305                 310                 315                 320

His Trp Asp Ala Thr Pro Val Arg Leu Gln Gly Pro Trp Thr Arg Ala
                325                 330                 335

Ser Pro Phe Gly Thr Ser Pro Arg Asp Thr Lys Gly Asp Ile Gln Val
            340                 345                 350

Arg Asn His Ser Ser Val Arg Leu Val Ser Glu Gly Ser Pro Gly Pro
                355                 360                 365

Thr Thr Gly Pro Thr Pro Gly Pro Thr Arg Val Gly Ser Pro Ser Ala
        370                 375                 380

Ala Gly Gly Gln Ala Ala Arg Glu Gly Ser Pro Ser Gln Thr Asn Ser
385                 390                 395                 400

Val Ile Thr Thr Cys Ile Ser Glu Thr Leu Asn Ser Ser Trp Arg Phe
                405                 410                 415

Glu

<210> SEQ ID NO 408
<211> LENGTH: 429
<212> TYPE: PRT
<213> ORGANISM: Homo sapiens

<400> SEQUENCE: 408

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro Pro Pro
50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly His Ser Thr Gly Tyr Glu Ser
                245                 250                 255
```

```
Asp Asn His Thr Thr Pro Ile Leu Cys Gly Ala Gln Tyr Arg Ile His
            260                 265                 270

Thr His Gly Val Phe Arg Gly Ile Gln Asp Val Arg Val Pro Gly
        275                 280                 285

Val Ala Pro Thr Leu Val Arg Ser Ala Ser Glu Thr Ser Glu Lys Arg
290                 295                 300

Pro Phe Met Cys Ala Tyr Pro Gly Cys Asn Lys Arg Tyr Phe Lys Leu
305                 310                 315                 320

Ser His Leu Gln Met His Ser Arg Lys His Thr Gly Glu Lys Pro Tyr
                325                 330                 335

Gln Cys Asp Phe Lys Asp Cys Glu Arg Arg Phe Ser Asp Gln
                340                 345                 350

Leu Lys Arg His Gln Arg Arg His Thr Gly Val Lys Pro Phe Gln Cys
            355                 360                 365

Lys Thr Cys Gln Arg Lys Phe Ser Arg Ser Asp His Leu Lys Thr His
            370                 375                 380

Thr Arg Thr His Thr Gly Glu Lys Pro Phe Ser Cys Arg Trp Pro Ser
385                 390                 395                 400

Cys Gln Lys Lys Phe Ala Arg Ser Asp Glu Leu Val Arg His His Asn
                405                 410                 415

Met His Gln Arg Asn Met Thr Lys Leu Gln Leu Ala Leu
                420                 425

<210> SEQ ID NO 409
<211> LENGTH: 495
<212> TYPE: PRT
<213> ORGANISM: Homo sapiens

<400> SEQUENCE: 409

Met Ala Ala Pro Gly Ala Arg Arg Ser Leu Leu Leu Leu Leu Leu Ala
1               5                   10                  15

Gly Leu Ala His Gly Ala Ser Ala Leu Phe Glu Asp Leu Met Gly Ser
                20                  25                  30

Asp Val Arg Asp Leu Asn Ala Leu Leu Pro Ala Val Pro Ser Leu Gly
            35                  40                  45

Gly Gly Gly Gly Cys Ala Leu Pro Val Ser Gly Ala Ala Gln Trp Ala
        50                  55                  60

Pro Val Leu Asp Phe Ala Pro Pro Gly Ala Ser Ala Tyr Gly Ser Leu
65                  70                  75                  80

Gly Gly Pro Ala Pro Pro Ala Pro Pro Pro Pro Pro Pro His
                85                  90                  95

Ser Phe Ile Lys Gln Glu Pro Ser Trp Gly Gly Ala Glu Pro His Glu
                100                 105                 110

Glu Gln Cys Leu Ser Ala Phe Thr Val His Phe Ser Gly Gln Phe Thr
            115                 120                 125

Gly Thr Ala Gly Ala Cys Arg Tyr Gly Pro Phe Gly Pro Pro Pro
        130                 135                 140

Ser Gln Ala Ser Ser Gly Gln Ala Arg Met Phe Pro Asn Ala Pro Tyr
145                 150                 155                 160

Leu Pro Ser Cys Leu Glu Ser Gln Pro Ala Ile Arg Asn Gln Gly Tyr
                165                 170                 175

Ser Thr Val Thr Phe Asp Gly Thr Pro Ser Tyr Gly His Thr Pro Ser
                180                 185                 190

His His Ala Ala Gln Phe Pro Asn His Ser Phe Lys His Glu Asp Pro
            195                 200                 205
```

Met Gly Gln Gln Gly Ser Leu Gly Glu Gln Gln Tyr Ser Val Pro Pro
    210                 215                 220

Pro Val Tyr Gly Cys His Thr Pro Thr Asp Ser Cys Thr Gly Ser Gln
225                 230                 235                 240

Ala Leu Leu Leu Arg Thr Pro Tyr Ser Ser Asp Asn Leu Tyr Gln Met
                245                 250                 255

Thr Ser Gln Leu Glu Cys Met Thr Trp Asn Gln Met Asn Leu Gly Ala
                260                 265                 270

Thr Leu Lys Gly His Ser Thr Gly Tyr Glu Ser Asp Asn His Thr Thr
            275                 280                 285

Pro Ile Leu Cys Gly Ala Gln Tyr Arg Ile His Thr His Gly Val Phe
        290                 295                 300

Arg Gly Ile Gln Asp Val Arg Val Pro Gly Val Ala Pro Thr Leu
305                 310                 315                 320

Val Arg Ser Ala Ser Glu Thr Ser Glu Lys Arg Pro Phe Met Cys Ala
                325                 330                 335

Tyr Pro Gly Cys Asn Lys Arg Tyr Phe Lys Leu Ser His Leu Gln Met
                340                 345                 350

His Ser Arg Lys His Thr Gly Glu Lys Pro Tyr Gln Cys Asp Phe Lys
            355                 360                 365

Asp Cys Glu Arg Arg Phe Phe Arg Ser Asp Gln Leu Lys Arg His Gln
    370                 375                 380

Arg Arg His Thr Gly Val Lys Pro Phe Gln Cys Lys Thr Cys Gln Arg
385                 390                 395                 400

Lys Phe Ser Arg Ser Asp His Leu Lys Thr His Thr Arg Thr His Thr
                405                 410                 415

Gly Glu Lys Pro Phe Ser Cys Arg Trp Pro Ser Cys Gln Lys Lys Phe
            420                 425                 430

Ala Arg Ser Asp Glu Leu Val Arg His His Asn Met His Gln Arg Asn
        435                 440                 445

Met Thr Lys Leu Gln Leu Ala Leu Leu Asn Asn Met Leu Ile Pro Ile
    450                 455                 460

Ala Val Gly Gly Ala Leu Ala Gly Leu Val Leu Ile Val Leu Ile Ala
465                 470                 475                 480

Tyr Leu Ile Gly Arg Lys Arg Ser His Ala Gly Tyr Gln Thr Ile
                485                 490                 495

<210> SEQ ID NO 410
<211> LENGTH: 504
<212> TYPE: PRT
<213> ORGANISM: Homo sapiens

<400> SEQUENCE: 410

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Ala Met Gly Ser Asp
65                  70                  75                  80

Val Arg Asp Leu Asn Ala Leu Leu Pro Ala Val Pro Ser Leu Gly Gly
                85                  90                  95

```
Gly Gly Gly Cys Ala Leu Pro Val Ser Gly Ala Ala Gln Trp Ala Pro
            100                 105                 110

Val Leu Asp Phe Ala Pro Pro Gly Ala Ser Ala Tyr Gly Ser Leu Gly
            115                 120                 125

Gly Pro Ala Pro Pro Ala Pro Pro Pro Pro Pro Pro Pro Pro Pro His
130                 135                 140

Ser Phe Ile Lys Gln Glu Pro Ser Trp Gly Gly Ala Glu Pro His Glu
145                 150                 155                 160

Glu Gln Cys Leu Ser Ala Phe Thr Val His Phe Ser Gly Gln Phe Thr
                165                 170                 175

Gly Thr Ala Gly Ala Cys Arg Tyr Gly Pro Phe Gly Pro Pro Pro Pro
            180                 185                 190

Ser Gln Ala Ser Ser Gly Gln Ala Arg Met Phe Pro Asn Ala Pro Tyr
            195                 200                 205

Leu Pro Ser Cys Leu Glu Ser Gln Pro Ala Ile Arg Asn Gln Gly Tyr
            210                 215                 220

Ser Thr Val Thr Phe Asp Gly Thr Pro Ser Tyr Gly His Thr Pro Ser
225                 230                 235                 240

His His Ala Ala Gln Phe Pro Asn His Ser Phe Lys His Glu Asp Pro
                245                 250                 255

Met Gly Gln Gln Gly Ser Leu Gly Glu Gln Gln Tyr Ser Val Pro Pro
            260                 265                 270

Pro Val Tyr Gly Cys His Thr Pro Thr Asp Ser Cys Thr Gly Ser Gln
            275                 280                 285

Ala Leu Leu Leu Arg Thr Pro Tyr Ser Ser Asp Asn Leu Tyr Gln Met
290                 295                 300

Thr Ser Gln Leu Glu Cys Met Thr Trp Asn Gln Met Asn Leu Gly Ala
305                 310                 315                 320

Thr Leu Lys Gly His Ser Thr Gly Tyr Glu Ser Asp Asn His Thr Thr
                325                 330                 335

Pro Ile Leu Cys Gly Ala Gln Tyr Arg Ile His Thr His Gly Val Phe
            340                 345                 350

Arg Gly Ile Gln Asp Val Arg Arg Val Pro Gly Val Ala Pro Thr Leu
            355                 360                 365

Val Arg Ser Ala Ser Glu Thr Ser Glu Lys Arg Pro Phe Met Cys Ala
370                 375                 380

Tyr Pro Gly Cys Asn Lys Arg Tyr Phe Lys Leu Ser His Leu Gln Met
385                 390                 395                 400

His Ser Arg Lys His Thr Gly Glu Lys Pro Tyr Gln Cys Asp Phe Lys
                405                 410                 415

Asp Cys Glu Arg Arg Phe Phe Arg Ser Asp Gln Leu Lys Arg His Gln
            420                 425                 430

Arg Arg His Thr Gly Val Lys Pro Phe Gln Cys Lys Thr Cys Gln Arg
            435                 440                 445

Lys Phe Ser Arg Ser Asp His Leu Lys Thr His Thr Arg Thr His Thr
            450                 455                 460

Gly Glu Lys Pro Phe Ser Cys Arg Trp Pro Ser Cys Gln Lys Lys Phe
465                 470                 475                 480

Ala Arg Ser Asp Glu Leu Val Arg His His Asn Met His Gln Arg Asn
                485                 490                 495

Met Thr Lys Leu Gln Leu Ala Leu
            500

<210> SEQ ID NO 411
```

```
<211> LENGTH: 10
<212> TYPE: PRT
<213> ORGANISM: Homo sapiens

<400> SEQUENCE: 411

Val Leu Asp Phe Ala Pro Pro Gly Ala Ser
 1               5                  10

<210> SEQ ID NO 412
<211> LENGTH: 15
<212> TYPE: PRT
<213> ORGANISM: Homo sapiens

<400> SEQUENCE: 412

Gln Trp Ala Pro Val Leu Asp Phe Ala Pro Pro Gly Ala Ser Ala
 1               5                  10                  15

<210> SEQ ID NO 413
<211> LENGTH: 15
<212> TYPE: PRT
<213> ORGANISM: Homo sapiens

<400> SEQUENCE: 413

Val Leu Asp Phe Ala Pro Pro Gly Ala Ser Ala Tyr Gly Ser Leu
 1               5                  10                  15

<210> SEQ ID NO 414
<211> LENGTH: 9
<212> TYPE: PRT
<213> ORGANISM: Artificial Sequence
<220> FEATURE:
<223> OTHER INFORMATION: Synthetic peptide

<400> SEQUENCE: 414

Ile Leu Asp Phe Ala Pro Pro Gly Ala
 1               5

<210> SEQ ID NO 415
<211> LENGTH: 9
<212> TYPE: PRT
<213> ORGANISM: Artificial Sequence
<220> FEATURE:
<223> OTHER INFORMATION: Synthetic peptide

<400> SEQUENCE: 415

Leu Leu Asp Phe Ala Pro Pro Gly Ala
 1               5

<210> SEQ ID NO 416
<211> LENGTH: 9
<212> TYPE: PRT
<213> ORGANISM: Artificial Sequence
<220> FEATURE:
<223> OTHER INFORMATION: Synthetic peptide

<400> SEQUENCE: 416

Phe Leu Asp Phe Ala Pro Pro Gly Ala
 1               5

<210> SEQ ID NO 417
<211> LENGTH: 9
<212> TYPE: PRT
<213> ORGANISM: Artificial Sequence
<220> FEATURE:
<223> OTHER INFORMATION: Synthetic peptide

<400> SEQUENCE: 417
```

```
Lys Leu Asp Phe Ala Pro Pro Gly Ala
1               5

<210> SEQ ID NO 418
<211> LENGTH: 9
<212> TYPE: PRT
<213> ORGANISM: Artificial Sequence
<220> FEATURE:
<223> OTHER INFORMATION: Synthetic peptide

<400> SEQUENCE: 418

Met Leu Asp Phe Ala Pro Pro Gly Ala
1               5

<210> SEQ ID NO 419
<211> LENGTH: 9
<212> TYPE: PRT
<213> ORGANISM: Artificial Sequence
<220> FEATURE:
<223> OTHER INFORMATION: Synthetic peptide

<400> SEQUENCE: 419

Tyr Leu Asp Phe Ala Pro Pro Gly Ala
1               5

<210> SEQ ID NO 420
<211> LENGTH: 9
<212> TYPE: PRT
<213> ORGANISM: Artificial Sequence
<220> FEATURE:
<223> OTHER INFORMATION: Synthetic peptide

<400> SEQUENCE: 420

Val Met Asp Phe Ala Pro Pro Gly Ala
1               5

<210> SEQ ID NO 421
<211> LENGTH: 9
<212> TYPE: PRT
<213> ORGANISM: Artificial Sequence
<220> FEATURE:
<223> OTHER INFORMATION: Synthetic peptide

<400> SEQUENCE: 421

Val Leu Asp Glu Ala Pro Pro Gly Ala
1               5

<210> SEQ ID NO 422
<211> LENGTH: 9
<212> TYPE: PRT
<213> ORGANISM: Artificial Sequence
<220> FEATURE:
<223> OTHER INFORMATION: Synthetic peptide

<400> SEQUENCE: 422

Val Leu Asp Lys Ala Pro Pro Gly Ala
1               5

<210> SEQ ID NO 423
<211> LENGTH: 9
<212> TYPE: PRT
<213> ORGANISM: Artificial Sequence
<220> FEATURE:
<223> OTHER INFORMATION: Synthetic peptide

<400> SEQUENCE: 423

Val Leu Asp Phe Ala Val Pro Gly Ala
1               5
```

```
<210> SEQ ID NO 424
<211> LENGTH: 9
<212> TYPE: PRT
<213> ORGANISM: Artificial Sequence
<220> FEATURE:
<223> OTHER INFORMATION: Synthetic peptide

<400> SEQUENCE: 424

Val Leu Asp Phe Ala Pro Pro Lys Ala
 1               5

<210> SEQ ID NO 425
<211> LENGTH: 9
<212> TYPE: PRT
<213> ORGANISM: Artificial Sequence
<220> FEATURE:
<223> OTHER INFORMATION: Synthetic peptide

<400> SEQUENCE: 425

Val Leu Asp Phe Ala Pro Pro Gly Val
 1               5

<210> SEQ ID NO 426
<211> LENGTH: 9
<212> TYPE: PRT
<213> ORGANISM: Artificial Sequence
<220> FEATURE:
<223> OTHER INFORMATION: Synthetic peptide

<400> SEQUENCE: 426

Val Leu Asp Phe Ala Pro Pro Gly Leu
 1               5

<210> SEQ ID NO 427
<211> LENGTH: 9
<212> TYPE: PRT
<213> ORGANISM: Artificial Sequence
<220> FEATURE:
<223> OTHER INFORMATION: Synthetic peptide

<400> SEQUENCE: 427

Phe Leu Asp Glu Ala Pro Pro Gly Ala
 1               5

<210> SEQ ID NO 428
<211> LENGTH: 9
<212> TYPE: PRT
<213> ORGANISM: Artificial Sequence
<220> FEATURE:
<223> OTHER INFORMATION: Synthetic peptide

<400> SEQUENCE: 428

Lys Leu Asp Glu Ala Pro Pro Gly Ala
 1               5

<210> SEQ ID NO 429
<211> LENGTH: 9
<212> TYPE: PRT
<213> ORGANISM: Artificial Sequence
<220> FEATURE:
<223> OTHER INFORMATION: Synthetic peptide

<400> SEQUENCE: 429

Tyr Leu Asp Glu Ala Pro Pro Gly Ala
 1               5
```

```
<210> SEQ ID NO 430
<211> LENGTH: 9
<212> TYPE: PRT
<213> ORGANISM: Artificial Sequence
<220> FEATURE:
<223> OTHER INFORMATION: Synthetic peptide

<400> SEQUENCE: 430

Phe Leu Asp Lys Ala Pro Pro Gly Ala
 1               5

<210> SEQ ID NO 431
<211> LENGTH: 9
<212> TYPE: PRT
<213> ORGANISM: Artificial Sequence
<220> FEATURE:
<223> OTHER INFORMATION: Synthetic peptide

<400> SEQUENCE: 431

Lys Leu Asp Lys Ala Pro Pro Gly Ala
 1               5

<210> SEQ ID NO 432
<211> LENGTH: 9
<212> TYPE: PRT
<213> ORGANISM: Artificial Sequence
<220> FEATURE:
<223> OTHER INFORMATION: Synthetic peptide

<400> SEQUENCE: 432

Tyr Leu Asp Lys Ala Pro Pro Gly Ala
 1               5

<210> SEQ ID NO 433
<211> LENGTH: 9
<212> TYPE: PRT
<213> ORGANISM: Artificial Sequence
<220> FEATURE:
<223> OTHER INFORMATION: Synthetic peptide

<400> SEQUENCE: 433

Phe Leu Asp Phe Ala Pro Pro Gly Val
 1               5

<210> SEQ ID NO 434
<211> LENGTH: 9
<212> TYPE: PRT
<213> ORGANISM: Artificial Sequence
<220> FEATURE:
<223> OTHER INFORMATION: Synthetic peptide

<400> SEQUENCE: 434

Lys Leu Asp Phe Ala Pro Pro Gly Val
 1               5

<210> SEQ ID NO 435
<211> LENGTH: 9
<212> TYPE: PRT
<213> ORGANISM: Artificial Sequence
<220> FEATURE:
<223> OTHER INFORMATION: Synthetic peptide

<400> SEQUENCE: 435

Tyr Leu Asp Phe Ala Pro Pro Gly Val
 1               5

<210> SEQ ID NO 436
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 436

Phe Leu Asp Phe Ala Pro Pro Gly Leu
 1               5

<210> SEQ ID NO 437
<211> LENGTH: 9
<212> TYPE: PRT
<213> ORGANISM: Artificial Sequence
<220> FEATURE:
<223> OTHER INFORMATION: Synthetic peptide

<400> SEQUENCE: 437

Lys Leu Asp Phe Ala Pro Pro Gly Leu
 1               5

<210> SEQ ID NO 438
<211> LENGTH: 9
<212> TYPE: PRT
<213> ORGANISM: Artificial Sequence
<220> FEATURE:
<223> OTHER INFORMATION: Synthetic peptide

<400> SEQUENCE: 438

Tyr Leu Asp Phe Ala Pro Pro Gly Leu
 1               5

<210> SEQ ID NO 439
<211> LENGTH: 9
<212> TYPE: PRT
<213> ORGANISM: Artificial Sequence
<220> FEATURE:
<223> OTHER INFORMATION: Synthetic peptide

<400> SEQUENCE: 439

Phe Leu Asp Glu Ala Pro Pro Gly Val
 1               5

<210> SEQ ID NO 440
<211> LENGTH: 9
<212> TYPE: PRT
<213> ORGANISM: Artificial Sequence
<220> FEATURE:
<223> OTHER INFORMATION: Synthetic peptide

<400> SEQUENCE: 440

Lys Leu Asp Glu Ala Pro Pro Gly Val
 1               5

<210> SEQ ID NO 441
<211> LENGTH: 9
<212> TYPE: PRT
<213> ORGANISM: Artificial Sequence
<220> FEATURE:
<223> OTHER INFORMATION: Synthetic peptide

<400> SEQUENCE: 441

Tyr Leu Asp Glu Ala Pro Pro Gly Val
 1               5

<210> SEQ ID NO 442
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 442

Phe Leu Asp Glu Ala Pro Pro Gly Leu
 1               5

<210> SEQ ID NO 443
<211> LENGTH: 9
<212> TYPE: PRT
<213> ORGANISM: Artificial Sequence
<220> FEATURE:
<223> OTHER INFORMATION: Synthetic peptide

<400> SEQUENCE: 443

Lys Leu Asp Glu Ala Pro Pro Gly Leu
 1               5

<210> SEQ ID NO 444
<211> LENGTH: 9
<212> TYPE: PRT
<213> ORGANISM: Artificial Sequence
<220> FEATURE:
<223> OTHER INFORMATION: Synthetic peptide

<400> SEQUENCE: 444

Tyr Leu Asp Glu Ala Pro Pro Gly Leu
 1               5

<210> SEQ ID NO 445
<211> LENGTH: 9
<212> TYPE: PRT
<213> ORGANISM: Artificial Sequence
<220> FEATURE:
<223> OTHER INFORMATION: Synthetic peptide

<400> SEQUENCE: 445

Val Leu Asp Phe Ala Gly Pro Gly Ala
 1               5

<210> SEQ ID NO 446
<211> LENGTH: 9
<212> TYPE: PRT
<213> ORGANISM: Artificial Sequence
<220> FEATURE:
<223> OTHER INFORMATION: Synthetic peptide

<400> SEQUENCE: 446

Val Leu Asp Phe Ala Thr Pro Gly Ala
 1               5

<210> SEQ ID NO 447
<211> LENGTH: 9
<212> TYPE: PRT
<213> ORGANISM: Artificial Sequence
<220> FEATURE:
<223> OTHER INFORMATION: Synthetic peptide

<400> SEQUENCE: 447

Val Leu Asp Phe Ala Thr Pro Gly Val
 1               5

<210> SEQ ID NO 448
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 448

Val Leu Asp Phe Ala Thr Pro Gly Leu
1               5

<210> SEQ ID NO 449
<211> LENGTH: 9
<212> TYPE: PRT
<213> ORGANISM: Artificial Sequence
<220> FEATURE:
<223> OTHER INFORMATION: Synthetic peptide

<400> SEQUENCE: 449

Val Leu Asp Phe Ala Thr Pro Gly Ser
1               5

<210> SEQ ID NO 450
<211> LENGTH: 9
<212> TYPE: PRT
<213> ORGANISM: Artificial Sequence
<220> FEATURE:
<223> OTHER INFORMATION: Synthetic peptide

<400> SEQUENCE: 450

Val Leu Asp Phe Ala Thr Pro Gly Ala
1               5

<210> SEQ ID NO 451
<211> LENGTH: 9
<212> TYPE: PRT
<213> ORGANISM: Homo sapiens

<400> SEQUENCE: 451

Ala Leu Leu Pro Ala Val Pro Ser Leu
1               5

<210> SEQ ID NO 452
<211> LENGTH: 969
<212> TYPE: DNA
<213> ORGANISM: Homo sapiens

<400> SEQUENCE: 452
atgaacaaca acgacctgtt ccaggcttct cgtcgtcgtt tcctggctca gctgggtggt      60
ctgaccgttg ctggtatgct gggtccgtct ctgctgaccc gcgtcgtgc taccgctgct     120
cacggctccg acgttcggga cctgaacgca ctgctgccgg cagttccgtc cctgggtggt     180
ggtggtggtt gcgcactgcc ggttagcggt gcagcacagt gggctccggt tctggacttc     240
gcaccgccgg gtgcatccgc atacggttcc ctgggtggtc cggcaccgcc gccggcaccg     300
ccgccgccgc cgccgccgcc gccgcactcc ttcatcaaac aggaaccgag ctggggtggt     360
gcagaaccgc acgaagaaca gtgcctgagc gcattcaccg ttcacttctc cggccagttc     420
actggcacag ccggagcctg tcgctacggg cccttcggtc ctcctccgcc cagccaggcg     480
tcatccggcc aggccaggat gtttcctaac gcgccctacc tgcccagctg cctcgagagc     540
cagcccgcta ttcgcaatca gggttacagc acggtcacct tcgacgggac gcccagctac     600
ggtcacacgc cctcgcacca tgcggcgcag ttccccaacc actcattcaa gcatgaggat     660
cccatgggcc agcagggctc gctgggtgag cagcagtact cggtgccgcc ccggtctat     720
ggctgccaca ccccaccga cagctgcacc ggcagccagg cttgctgct gaggacgccc     780
tacagcagtg acaatttata ccaaatgaca tcccagcttg aatgcatgac ctggaatcag     840
atgaacttag gagccacctt aaagggccac agcacagggt acgagagcga taaccacaca     900

```
acgcccatcc tctgcggagc ccaatacaga atacacacgc acgtgtcttc cagaggcatt      960
cagtgatga                                                              969
```

<210> SEQ ID NO 453
<211> LENGTH: 1410
<212> TYPE: DNA
<213> ORGANISM: Homo sapiens

<400> SEQUENCE: 453

```
atgaacaaca acgacctgtt ccaggcttct cgtcgtcgtt tcctggctca gctgggtggt       60
ctgaccgttg ctggtatgct gggtccgtct ctgctgaccc cgcgtcgtgc taccgctgct      120
cacggctccg acgtgcggga cctgaacgca ctgctgccgg cagttccgtc cctgggtggt      180
ggtggtggtt gcgcactgcc ggttagcggt gcagcacagt gggctccggt tctggacttc      240
gcaccgccgg tgcatccgc atacggttcc ctgggtggtc cggcaccgcc gccggcaccg      300
ccgccgccgc cgccgccgcc gccgcactcc ttcatcaaac aggaaccgag ctggggtggt      360
gcagaaccgc acgaagaaca gtgcctgagc gcattcaccg ttcacttctc cggccagttc      420
actggcacag ccggagcctg tcgctacggg cccttcggtc ctcctccgcc cagccaggcg      480
tcatccggcc aggccaggat gtttcctaac gcgccctacc tgcccagctg cctcgagagc      540
cagcccgcta ttcgcaatca gggttacagc acggtcacct tcgacgggac gcccagctac      600
ggtcacacgc cctcgcacca tgcggcgcag ttccccaacc actcattcaa gcatgaggat      660
cccatgggcc agcagggctc gctgggtgag cagcagtact cggtgccgcc ccggtctat      720 ggctgccaca ccccaccga cagctgcacc ggcagccagg ctttgctgct gaggacgccc      780
tacagcagtg acaatttata ccaaatgaca tcccagcttg aatgcatgac ctggaatcag      840
atgaacttag gagccacctt aaagggccac agcacagggt acgagagcga taaccacaca      900
acgcccatcc tctgcggagc ccaatacaga atacacacgc acgtgtcttc cagaggcatt      960
caggatgtgc gacgtgtgcc tggagtagcc ccgactcttg tacggtcggc atctgagacc     1020
agtgagaaac gcccccttcat gtgtgcttac ccaggctgca ataagagata tttaagctg     1080 tcccacttac agatgcacag caggaagcac actggtgaga accataccaa gtgtgacttc     1140
aaggactgtg aacgaaggtt ttttcgttca gaccagctca aaagacacca aaggagacat     1200
acaggtgtga aaccattcca gtgtaaaact tgtcagcgaa agttctcccg gtccgaccac     1260
ctgaagaccc acaccaggac tcatacaggt gaaaagccct tcagctgtcg gtggccaagt     1320
tgtcagaaaa agtttgcccg gtcagatgaa ttagtccgcc atcacaacat gcatcagaga     1380
aacatgacca aactccagct ggcgctttga                                     1410
```

<210> SEQ ID NO 454
<211> LENGTH: 469
<212> TYPE: PRT
<213> ORGANISM: Homo sapiens

<400> SEQUENCE: 454

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala His Gly Ser Asp Val Arg Asp Leu
        35                  40                  45

Asn Ala Leu Leu Pro Ala Val Pro Ser Leu Gly Gly Gly Gly Gly Cys
    50                  55                  60

```
Ala Leu Pro Val Ser Gly Ala Ala Gln Trp Ala Pro Val Leu Asp Phe
 65                  70                  75                  80

Ala Pro Pro Gly Ala Ser Ala Tyr Gly Ser Leu Gly Gly Pro Ala Pro
                 85                  90                  95

Pro Pro Ala Pro Pro Pro Pro Pro Pro Pro Pro His Ser Phe Ile
            100                 105                 110

Lys Gln Glu Pro Ser Trp Gly Gly Ala Glu Pro His Glu Glu Gln Cys
            115                 120                 125

Leu Ser Ala Phe Thr Val His Phe Ser Gly Gln Phe Thr Gly Thr Ala
            130                 135                 140

Gly Ala Cys Arg Tyr Gly Pro Phe Gly Pro Pro Pro Ser Gln Ala
145                 150                 155                 160

Ser Ser Gly Gln Ala Arg Met Phe Pro Asn Ala Pro Tyr Leu Pro Ser
                165                 170                 175

Cys Leu Glu Ser Gln Pro Ala Ile Arg Asn Gln Gly Tyr Ser Thr Val
            180                 185                 190

Thr Phe Asp Gly Thr Pro Ser Tyr Gly His Thr Pro Ser His His Ala
            195                 200                 205

Ala Gln Phe Pro Asn His Ser Phe Lys His Glu Asp Pro Met Gly Gln
210                 215                 220

Gln Gly Ser Leu Gly Glu Gln Gln Tyr Ser Val Pro Pro Pro Val Tyr
225                 230                 235                 240

Gly Cys His Thr Pro Thr Asp Ser Cys Thr Gly Ser Gln Ala Leu Leu
                245                 250                 255

Leu Arg Thr Pro Tyr Ser Ser Asp Asn Leu Tyr Gln Met Thr Ser Gln
                260                 265                 270

Leu Glu Cys Met Thr Trp Asn Gln Met Asn Leu Gly Ala Thr Leu Lys
            275                 280                 285

Gly His Ser Thr Gly Tyr Glu Ser Asp Asn His Thr Thr Pro Ile Leu
            290                 295                 300

Cys Gly Ala Gln Tyr Arg Ile His Thr His Gly Val Phe Arg Gly Ile
305                 310                 315                 320

Gln Asp Val Arg Arg Val Pro Gly Val Ala Pro Thr Leu Val Arg Ser
                325                 330                 335

Ala Ser Glu Thr Ser Glu Lys Arg Pro Phe Met Cys Ala Tyr Pro Gly
                340                 345                 350

Cys Asn Lys Arg Tyr Phe Lys Leu Ser His Leu Gln Met His Ser Arg
                355                 360                 365

Lys His Thr Gly Glu Lys Pro Tyr Gln Cys Asp Phe Lys Asp Cys Glu
            370                 375                 380

Arg Arg Phe Phe Arg Ser Asp Gln Leu Lys Arg His Gln Arg Arg His
385                 390                 395                 400

Thr Gly Val Lys Pro Phe Gln Cys Lys Thr Cys Gln Arg Lys Phe Ser
                405                 410                 415

Arg Ser Asp His Leu Lys Thr His Thr Arg Thr His Thr Gly Glu Lys
                420                 425                 430

Pro Phe Ser Cys Arg Trp Pro Ser Cys Gln Lys Lys Phe Ala Arg Ser
            435                 440                 445

Asp Glu Leu Val Arg His His Asn Met His Gln Arg Asn Met Thr Lys
            450                 455                 460

Leu Gln Leu Ala Leu
465
```

```
<210> SEQ ID NO 455
<211> LENGTH: 321
<212> TYPE: PRT
<213> ORGANISM: Homo sapiens

<400> SEQUENCE: 455

Met Asn Asn Asn Asp Leu Phe Gln Ala Ser Arg Arg Arg Phe Leu Ala
                 5                  10                  15

Gln Leu Gly Gly Leu Thr Val Ala Gly Met Leu Gly Pro Ser Leu Leu
             20                  25                  30

Thr Pro Arg Arg Ala Thr Ala Ala His Gly Ser Asp Val Arg Asp Leu
         35                  40                  45

Asn Ala Leu Leu Pro Ala Val Pro Ser Leu Gly Gly Gly Gly Gly Cys
     50                  55                  60

Ala Leu Pro Val Ser Gly Ala Ala Gln Trp Ala Pro Val Leu Asp Phe
65                  70                  75                  80

Ala Pro Pro Gly Ala Ser Ala Tyr Gly Ser Leu Gly Gly Pro Ala Pro
                 85                  90                  95

Pro Pro Ala Pro Pro Pro Pro Pro Pro Pro Pro His Ser Phe Ile
            100                 105                 110

Lys Gln Glu Pro Ser Trp Gly Gly Ala Glu Pro His Glu Glu Gln Cys
        115                 120                 125

Leu Ser Ala Phe Thr Val His Phe Ser Gly Gln Phe Thr Gly Thr Ala
    130                 135                 140

Gly Ala Cys Arg Tyr Gly Pro Phe Gly Pro Pro Pro Ser Gln Ala
145                 150                 155                 160

Ser Ser Gly Gln Ala Arg Met Phe Pro Asn Ala Pro Tyr Leu Pro Ser
                165                 170                 175

Cys Leu Glu Ser Gln Pro Ala Ile Arg Asn Gln Gly Tyr Ser Thr Val
            180                 185                 190

Thr Phe Asp Gly Thr Pro Ser Tyr Gly His Thr Pro Ser His His Ala
        195                 200                 205

Ala Gln Phe Pro Asn His Ser Phe Lys His Glu Asp Pro Met Gly Gln
    210                 215                 220

Gln Gly Ser Leu Gly Glu Gln Gln Tyr Ser Val Pro Pro Pro Val Tyr
225                 230                 235                 240

Gly Cys His Thr Pro Thr Asp Ser Cys Thr Gly Ser Gln Ala Leu Leu
                245                 250                 255

Leu Arg Thr Pro Tyr Ser Ser Asp Asn Leu Tyr Gln Met Thr Ser Gln
            260                 265                 270

Leu Glu Cys Met Thr Trp Asn Gln Met Asn Leu Gly Ala Thr Leu Lys
        275                 280                 285

Gly His Ser Thr Gly Tyr Glu Ser Asp Asn His Thr Thr Pro Ile Leu
    290                 295                 300

Cys Gly Ala Gln Tyr Arg Ile His Thr His Gly Val Phe Arg Gly Ile
305                 310                 315                 320

Gln

<210> SEQ ID NO 456
<211> LENGTH: 24
<212> TYPE: DNA
<213> ORGANISM: Artificial Sequence
<220> FEATURE:
<223> OTHER INFORMATION: PCR primer

<400> SEQUENCE: 456
ggctccgacg tgcgggacct gaac                                               24
```

<210> SEQ ID NO 457
<211> LENGTH: 31
<212> TYPE: DNA
<213> ORGANISM: Artificial Sequence
<220> FEATURE:
<223> OTHER INFORMATION: PCR primer

<400> SEQUENCE: 457
cgcgtgaatt catcactgaa tgcctctgaa g                            31

<210> SEQ ID NO 458
<211> LENGTH: 21
<212> TYPE: DNA
<213> ORGANISM: Artificial Sequence
<220> FEATURE:
<223> OTHER INFORMATION: PCR primer

<400> SEQUENCE: 458
ggctccgacg tgcgggacct g                                       21

<210> SEQ ID NO 459
<211> LENGTH: 30
<212> TYPE: DNA
<213> ORGANISM: Artificial Sequence
<220> FEATURE:
<223> OTHER INFORMATION: PCR primer

<400> SEQUENCE: 459
gaattctcaa agcgccagct ggagtttggt                              30

<210> SEQ ID NO 460
<211> LENGTH: 843
<212> TYPE: DNA
<213> ORGANISM: Homo sapiens

<400> SEQUENCE: 460
ggctccgacg ttcgggacct gaacgcactg ctgccggcag ttccgtccct gggtggtggt    60
ggtggttgcg cactgccggt tagcggtgca gcacagtggg ctccggttct ggacttcgca   120
ccgccgggtg catccgcata cggttccctg ggtggtccgg caccgccgcc ggcaccgccg   180
ccgccgccgc cgccgccgcc gcactccttc atcaaacagg aaccgagctg gggtggtgca   240
gaaccgcacg aagaacagtg cctgagcgca ttcaccgttc acttctccgg ccagttcact   300
ggcacagccg agcctgtcg ctacgggccc ttcggtcctc ctccgcccag ccaggcgtca   360
tccggccagg ccaggatgtt tcctaacgcg ccctacctgc ccagctgcct cgagagccag   420
cccgctattc gcaatcaggg ttacagcacg gtcaccttcg acgggacgcc cagctacggt   480
cacacgccct cgcaccatgc ggcgcagttc cccaaccact cattcaagca tgaggatccc   540
atgggccagc agggctcgct gggtgagcag cagtactcgg tgccgccccc ggtctatggc   600
tgccacaccc ccaccgacag ctgcaccggc agccaggctt tgctgctgag gacgccctac   660
agcagtgaca atttataccaa aatgacatcc cagcttgaat gcatgacctg gaatcagatg   720
aacttaggag ccaccttaaa gggccacagc acagggtacg agagcgataa ccacacaacg   780
cccatcctct gcggagccca atacagaata cacacgcacg gtgtcttcag aggcattcag   840
tga                                                                843

<210> SEQ ID NO 461
<211> LENGTH: 280
<212> TYPE: PRT
<213> ORGANISM: Homo sapiens

<400> SEQUENCE: 461

Gly Ser Asp Val Arg Asp Leu Asn Ala Leu Leu Pro Ala Val Pro Ser
1               5                   10                  15
Leu Gly Gly Gly Gly Cys Ala Leu Pro Val Ser Gly Ala Ala Gln
            20                  25                  30
Trp Ala Pro Val Leu Asp Phe Ala Pro Pro Gly Ala Ser Ala Tyr Gly
            35                  40                  45
Ser Leu Gly Gly Pro Ala Pro Pro Ala Pro Pro Pro Pro Pro
    50                  55                  60
Pro Pro Pro His Ser Phe Ile Lys Gln Glu Pro Ser Trp Gly Gly Ala
65                  70                  75                  80
Glu Pro His Glu Glu Gln Cys Leu Ser Ala Phe Thr Val His Phe Ser
                85                  90                  95
Gly Gln Phe Thr Gly Thr Ala Gly Ala Cys Arg Tyr Gly Pro Phe Gly
            100                 105                 110
Pro Pro Pro Pro Ser Gln Ala Ser Ser Gly Gln Ala Arg Met Phe Pro
        115                 120                 125
Asn Ala Pro Tyr Leu Pro Ser Cys Leu Glu Ser Gln Pro Ala Ile Arg
130                 135                 140
Asn Gln Gly Tyr Ser Thr Val Thr Phe Asp Gly Thr Pro Ser Tyr Gly
145                 150                 155                 160
His Thr Pro Ser His His Ala Ala Gln Phe Pro Asn His Ser Phe Lys
                165                 170                 175
His Glu Asp Pro Met Gly Gln Gln Gly Ser Leu Gly Glu Gln Gln Tyr
            180                 185                 190
Ser Val Pro Pro Pro Val Tyr Gly Cys His Thr Pro Thr Asp Ser Cys
        195                 200                 205
Thr Gly Ser Gln Ala Leu Leu Leu Arg Thr Pro Tyr Ser Ser Asp Asn
    210                 215                 220
Leu Tyr Gln Met Thr Ser Gln Leu Glu Cys Met Thr Trp Asn Gln Met
225                 230                 235                 240
Asn Leu Gly Ala Thr Leu Lys Gly His Ser Thr Gly Tyr Glu Ser Asp
                245                 250                 255
Asn His Thr Thr Pro Ile Leu Cys Gly Ala Gln Tyr Arg Ile His Thr
            260                 265                 270
His Gly Val Phe Arg Gly Ile Gln
        275                 280

<210> SEQ ID NO 462
<211> LENGTH: 876
<212> TYPE: DNA
<213> ORGANISM: Homo sapiens

<400> SEQUENCE: 462
atgggctccg acgtgcggga cctgaacgca ctgctgccgg cagttccgtc cctgggtggt    60
ggtggtggtt gcgcactgcc ggttagcggt gcagcacagt gggctccggt tctggacttc   120
gcaccgccgg gtgcatccgc atacggttcc ctggtggtc cggcaccgcc gccggcaccg   180
ccgccgccgc cgccgccgcc gccgcactcc ttcatcaaac aggaaccgag ctggggtggt   240
gcagaaccgc acgaagaaca gtgcctgagc gcattcaccg ttcacttctc cggccagttc   300
actggcacag ccggagcctg tcgctacggg cccttcggtc ctcctccgcc cagccaggcg   360
tcatccggcc aggccaggat gtttcctaac gcgccctacc tgcccagctg cctcgagagc   420
cagcccgcta ttcgcaatca gggttacagc acggtcacct cgacgggac gcccagctac   480

```
ggtcacacgc cctcgcacca tgcggcgcag ttccccaacc actcattcaa gcatgaggat      540
cccatgggcc agcagggctc gctgggtgag cagcagtact cggtgccgcc cccggtctat      600
ggctgccaca cccccaccga cagctgcacc ggcagccagg cttTGCTgct gaggacgccc      660
```

```
ggctgccaca cccccaccga cagctgcacc ggcagccagg cTTtgctgct gaggacgccc      660
tacagcagtg acaatttata ccaaatgaca tcccagcttg aatgcatgac ctggaatcag      720
atgaacttag agccacctt aaagggccac agcacagggt acgagagcga taaccacaca       780
acgcccatcc tctgcggagc ccaatacaga atacacacgc acggtgtctt cagaggcatt      840
cagcatcatc accatcatca tcaccatcac cattag                                876

<210> SEQ ID NO 463
<211> LENGTH: 846
<212> TYPE: DNA
<213> ORGANISM: Homo sapiens

<400> SEQUENCE: 463
atgggctccg acgtgcggga cctgaacgca ctgctgccgg cagttccgtc cctgggtggt       60
ggtggtggtt gcgcactgcc ggttagcggt gcagcacagt gggctccggt tctggacttc      120
gcaccgccgg gtcatccgc atacggttcc ctgggtggtc cggcaccgcc gccggcaccg      180
ccgccgccgc cgccgccgcc gccgcactcc ttcatcaaac aggaaccgag ctggggtggt      240
gcagaaccgc acgaagaaca gtgcctgagc gcattcaccg ttcacttctc cggccagttc      300
actggcacag ccggagcctg tcgctacggg cccttcggtc ctcctccgcc cagccaggcg      360
tcatccggcc aggccaggat gtttcctaac gcgccctacc tgcccagctg cctcgagagc      420
cagcccgcta ttcgcaatca gggttacagc acggtcacct tcgacgggac gcccagctac      480
ggtcacacgc cctcgcacca tgcggcgcag ttccccaacc actcattcaa gcatgaggat      540
cccatgggcc agcagggctc gctgggtgag cagcagtact cggtgccgcc cccggtctat      600
ggctgccaca cccccaccga cagctgcacc ggcagccagg cttTGCTgct gaggacgccc      660
tacagcagtg acaatttata ccaaatgaca tcccagcttg aatgcatgac ctggaatcag      720
atgaacttag agccacctt aaagggccac agcacagggt acgagagcga taaccacaca       780
acgcccatcc tctgcggagc ccaatacaga atacacacgc acggtgtctt cagaggcatt      840
cagtag                                                                846

<210> SEQ ID NO 464
<211> LENGTH: 291
<212> TYPE: PRT
<213> ORGANISM: Homo sapiens

<400> SEQUENCE: 464

Met Gly Ser Asp Val Arg Asp Leu Asn Ala Leu Leu Pro Ala Val Pro
                 5                  10                  15

Ser Leu Gly Gly Gly Gly Gly Cys Ala Leu Pro Val Ser Gly Ala Ala
             20                  25                  30

Gln Trp Ala Pro Val Leu Asp Phe Ala Pro Pro Gly Ala Ser Ala Tyr
         35                  40                  45

Gly Ser Leu Gly Gly Pro Ala Pro Pro Ala Pro Pro Pro Pro
     50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
```

```
                    100                 105                 110
Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
        130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly His Ser Thr Gly Tyr Glu Ser
                245                 250                 255

Asp Asn His Thr Thr Pro Ile Leu Cys Gly Ala Gln Tyr Arg Ile His
            260                 265                 270

Thr His Gly Val Phe Arg Gly Ile Gln His His His His His His
        275                 280                 285

His His His
    290

<210> SEQ ID NO 465
<211> LENGTH: 281
<212> TYPE: PRT
<213> ORGANISM: Homo sapiens

<400> SEQUENCE: 465

Met Gly Ser Asp Val Arg Asp Leu Asn Ala Leu Leu Pro Ala Val Pro
                5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
```

```
                        180                 185                 190
Tyr Ser Val Pro Pro Val Tyr Gly Cys His Thr Pro Thr Asp Ser
            195                 200                 205
Cys Thr Gly Ser Gln Ala Leu Leu Leu Arg Thr Pro Tyr Ser Ser Asp
            210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly His Ser Thr Gly Tyr Glu Ser
                245                 250                 255
Asp Asn His Thr Thr Pro Ile Leu Cys Gly Ala Gln Tyr Arg Ile His
                260                 265                 270
Thr His Gly Val Phe Arg Gly Ile Gln
            275                 280
```

<210> SEQ ID NO 466
<211> LENGTH: 36
<212> TYPE: DNA
<213> ORGANISM: Artificial Sequence
<220> FEATURE:
<223> OTHER INFORMATION: PCR primer

<400> SEQUENCE: 466
cggctctaga gccgccacca tgggctccga cgtgcg                    36

<210> SEQ ID NO 467
<211> LENGTH: 37
<212> TYPE: DNA
<213> ORGANISM: Artificial Sequence
<220> FEATURE:
<223> OTHER INFORMATION: PCR primer

<400> SEQUENCE: 467
cggctctaga ctactgaatg cctctgaaga caccgtg                   37

<210> SEQ ID NO 468
<211> LENGTH: 67
<212> TYPE: DNA
<213> ORGANISM: Artificial Sequence
<220> FEATURE:
<223> OTHER INFORMATION: PCR primer

<400> SEQUENCE: 468
cggctctaga ctaatggtga tggtgatgat gatggtgatg atgctgaatg cctctgaaga    60
caccgtg                                                              67

<210> SEQ ID NO 469
<211> LENGTH: 882
<212> TYPE: DNA
<213> ORGANISM: Homo sapiens

<400> SEQUENCE: 469
atgaacaata acgatctgtt tcaggcgagc cgccacggct ccgacgttcg ggacctgaac    60
gcactgctgc cggcagttcc gtccctgggt ggtggtggtg gttgcgcact gccggttagc   120
ggtgcagcac agtgggctcc ggttctggac ttcgcaccgc cgggtgcatc cgcatacggt   180
tccctgggtg gtccggcacc gccgccggca ccgccgccgc cgccgccgcc gccgccgcac   240
tccttcatca acaggaacc gagctggggt ggtgcagaac cgcacgaaga cagtgcctg    300 agcgcattca ccgttcactt ctccggcag ttcactggca cagccggagc ctgtcgctac   360
gggcccttcg gtcctcctcc gcccagccag gcgtcatccg ccaggccag gatgtttcct   420
```

```
aacgcgccct acctgcccag ctgcctcgag agccagcccg ctattcgcaa tcagggttac    480
agcacggtca ccttcgacgg gacgcccagc tacggtcaca cgccctcgca ccatgcggcg    540
cagttcccca accactcatt caagcatgag gatcccatgg gccagcaggg ctcgctgggt    600
gagcagcagt actcggtgcc gcccccggtc tatggctgcc acaccccccac cgacagctgc    660 accggcagcc aggctttgct gctgaggacg ccctacagca gtgacaattt ataccaaatg    720
acatcccagc ttgaatgcat gacctggaat cagatgaact taggagccac cttaaagggc    780
cacagcacag ggtacgagag cgataaccac acaacgccca tcctctgcgg agcccaatac    840
agaatacaca cgcacggtgt cttcagaggc attcagtgat ga                       882
```

<210> SEQ ID NO 470
<211> LENGTH: 292
<212> TYPE: PRT
<213> ORGANISM: Homo sapiens

<400> SEQUENCE: 470

```
Met Asn Asn Asn Asp Leu Phe Gln Ala Ser Arg His Gly Ser Asp Val
                 5                  10                  15

Arg Asp Leu Asn Ala Leu Leu Pro Ala Val Pro Ser Leu Gly Gly Gly
             20                  25                  30

Gly Gly Cys Ala Leu Pro Val Ser Gly Ala Ala Gln Trp Ala Pro Val
         35                  40                  45

Leu Asp Phe Ala Pro Pro Gly Ala Ser Ala Tyr Gly Ser Leu Gly Gly
     50                  55                  60

Pro Ala Pro Pro Ala Pro Pro Pro Pro Pro Pro Pro His
65                  70                  75                  80

Ser Phe Ile Lys Gln Glu Pro Ser Trp Gly Gly Ala Glu Pro His Glu
                 85                  90                  95

Glu Gln Cys Leu Ser Ala Phe Thr Val His Phe Ser Gly Gln Phe Thr
            100                 105                 110

Gly Thr Ala Gly Ala Cys Arg Tyr Gly Pro Phe Gly Pro Pro Pro Pro
        115                 120                 125

Ser Gln Ala Ser Ser Gly Gln Ala Arg Met Phe Pro Asn Ala Pro Tyr
    130                 135                 140

Leu Pro Ser Cys Leu Glu Ser Gln Pro Ala Ile Arg Asn Gln Gly Tyr
145                 150                 155                 160

Ser Thr Val Thr Phe Asp Gly Thr Pro Ser Tyr Gly His Thr Pro Ser
                165                 170                 175

His His Ala Ala Gln Phe Pro Asn His Ser Phe Lys His Glu Asp Pro
            180                 185                 190

Met Gly Gln Gln Gly Ser Leu Gly Glu Gln Gln Tyr Ser Val Pro Pro
        195                 200                 205

Pro Val Tyr Gly Cys His Thr Pro Thr Asp Ser Cys Thr Gly Ser Gln
    210                 215                 220

Ala Leu Leu Leu Arg Thr Pro Tyr Ser Ser Asp Asn Leu Tyr Gln Met
225                 230                 235                 240

Thr Ser Gln Leu Glu Cys Met Thr Trp Asn Gln Met Asn Leu Gly Ala
                245                 250                 255

Thr Leu Lys Gly His Ser Thr Gly Tyr Glu Ser Asp Asn His Thr Thr
            260                 265                 270

Pro Ile Leu Cys Gly Ala Gln Tyr Arg Ile His Thr His Gly Val Phe
        275                 280                 285

Arg Gly Ile Gln
    290
```

<210> SEQ ID NO 471
<211> LENGTH: 5315
<212> TYPE: DNA
<213> ORGANISM: E Coli

<400> SEQUENCE: 471

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | ccccctatttg | tttatttttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatccttttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccagggggaa | acgcctggta | tctttatagt | cctgtcgggt | ttcgccacct | ctgacttgag | 2040 |
| cgtcgatttt | tgtgatgctc | gtcagggggg | cggagcctat | ggaaaaacgc | cagcaacgcg | 2100 |
| gcctttttac | ggttcctggc | cttttgctgg | ccttttgctc | acatgttctt | tcctgcgtta | 2160 |

```
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggca taatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
```

```
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc aacagtccc     4800 ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccgccac gatgcgtccg gcgtagagga tcgagatctc gatcccgcga     4980
aattaatacg actcactata ggggaattgt gagcggataa caattcccct ctagaaataa    5040
ttttgtttaa ctttaagaag gagatataca tatgaacaat aacgatctgt ttcaggcgag    5100
ccgccacgtg aatgaccaag aattctgcag atatccatca cactggcggc cgctcgagca    5160
ccaccaccac caccactgag atccggctgc taacaaagcc cgaaaggaag ctgagttggc    5220
tgctgccacc gctgagcaat aactagcata accccttggg gcctctaaac gggtcttgag    5280
gggttttttg ctgaaaggag gaactatatc cggat                              5315
```

<210> SEQ ID NO 472
<211> LENGTH: 828
<212> TYPE: DNA
<213> ORGANISM: Homo sapiens

<400> SEQUENCE: 472

```
atgcagcatc accaccatca ccacggttcg gatgtacgcg atctgaacgc gcttcttccg      60
gcggtcccaa gcttgggcgg gggaggtgga tgcgccctgc ccgtgagcgg cgccgcgcaa    120
tgggccccgg tccttgattt tgctccgccg gtgcgagcg catacggctc tctgggcggg    180
ccccattcat tcatcaaaca ggagcccagc tggggtggcg ccgaacctca tgaagaacaa    240
tgtctgtctg cttttaccgt acattttca ggccagttta ccggaactgc cggtgcatgt     300
cgctatggcc cattcggtcc gccgccaccg tcacaagcct cttcgggaca gcccgcatg    360 tttccgaatg caccctacct gccgtcttgt ctggaaagcc aacccgcgat ccgtaaccaa    420
ggctacagca ccgtcacgtt tgatggtacc ccgagctatg gtcatacgcc gagtcatcat    480
gcagcacagt tcccgaacca ctcgttcaaa cacgaagatc ctatgggcca gcagggtagt    540
ctgggcgaac aacagtatag cgtcccacca ccagtttatg gttgccatac cccaacggat    600
tcctgtactg gtagccaagc gctcctgctc cgcacccct attcttctga taatctctat    660
cagatgacca gccaactgga atgtatgacg tggaaccaaa tgaacctggg cgcaaccctg    720
aaaggccaca gtaccggcta tgagtcagat aaccacacaa cacccatttt gtgcggcgct    780
caatatcgta ttcatacca tggcgttttt cgcggtattc agtgatga                   828
```

<210> SEQ ID NO 473
<211> LENGTH: 811
<212> TYPE: DNA
<213> ORGANISM: Homo sapiens

<400> SEQUENCE: 473

```
atgggttcgg atgtacgcga tctgaacgcg cttcttccgg cggtcccaag cttgggcggg      60
ggaggtggat gcgccctgcc cgtgagcggg ccgcgcaat gggccccggt ccttgattt     120 gctccgccgg gtgcgagcgc atacggctct ctgggcgggc ccattcatt catcaaacag     180 gagcccagct ggggtggcgc cgaacctcat gaagaacaat gtctgtctgc ttttaccgta    240 cattttcag gccagtttac cggaactgcc ggtgcatgtc gctatggccc attcggtccg     300
```

```
ccgccaccgt cacaagcctc ttcgggacaa gcccgcatgt ttccgaatgc accctacctg    360
ccgtcttgtc tggaaagcca acccgcgatc cgtaaccaag gctacagcac cgtcacgttt    420
gatggtaccc cgagctatgg tcatacgccg agtcatcatg cagcacagtt cccgaaccac    480
tcgttcaaac acgaagatcc tatgggccag cagggtagtc tgggcgaaca acagtatagc    540
gtcccaccac cagtttatgg ttgccatacc ccaacggatt cctgtactgg tagccaagcg    600
ctcctgctcc gcaccccta ttcttctgat aatctctatc agatgaccag ccaactggaa    660
tgtatgacgt ggaaccaaat gaacctgggc gcaaccctga aggccacag taccggctat    720 gagtcagata accacacaac acccattttg tgcggcgctc aatatcgtat tcatacccat    780
ggcgtttttc gcggtattca gtgatgaatt c                                    811

<210> SEQ ID NO 474
<211> LENGTH: 844
<212> TYPE: DNA
<213> ORGANISM: Homo sapiens

<400> SEQUENCE: 474
atgaacaata acgatctgtt tcaggcgagc cgccacggtt cggatgtacg cgatctgaac     60
gcgcttcttc cggcggtccc aagcttgggc gggggaggtg gatgcgccct gccgtgagc    120 ggcgccgcgc aatgggcccc ggtccttgat tttgctccgc cgggtgcgag cgcatacggc    180
tctctgggcg ggccccattc attcatcaaa caggagccca gctggggtgg cgccgaacct    240
catgaagaac aatgtctgtc tgcttttacc gtacattttt caggccagtt taccggaact    300
gccggtgcat gtcgctatgg cccattcggt ccgccgccac cgtcacaagc ctcttcggga    360
caagcccgca tgtttccgaa tgcaccctac ctgccgtctt gtctggaaag ccaacccgcg    420
atccgtaacc aaggctacag caccgtcacg tttgatggta ccccgagcta tggtcatacg    480
ccgagtcatc atgcagcaca gttcccgaac cactcgttca acacgaagda tcctatgggc    540
cagcagggta gtctgggcga acaacagtat agcgtcccac caccagttta tggttgccat    600
accccaacgg attcctgtac tggtagccaa gcgctcctgc tccgcacccc ctattcttct    660
gataatctct atcagatgac cagccaactg gaatgtatga cgtggaacca aatgaacctg    720
ggcgcaaccc tgaaaggcca cagtaccggc tatgagtcag ataaccacac aacacccatt    780
ttgtgcggcg ctcaatatcg tattcatacc catggcgttt ttcgcggtat tcagtgatga    840
attc                                                                 844

<210> SEQ ID NO 475
<211> LENGTH: 927
<212> TYPE: DNA
<213> ORGANISM: Homo sapiens

<400> SEQUENCE: 475
atgaacaata acgatctctt ccaagcttcc cgtcgtcgtt tcctggcgca gctcggcggc     60
cttaccgtgg ccgtatgct gggtccgtcg ctttttaacac cgcgccgcgc aaccgccgct    120
catggttcgg atgtacgcga tctgaacgcg cttcttccgg cggtcccaag cttgggcggg    180
ggaggtggat cgccctgcc cgtgagcggc cgcgcaat gggccccggt ccttgatttt    240
gctccgccgg gtgcgagcgc ataccggctct ctgggcgggc ccattcatt catcaaacag    300 gagcccagct ggggtggcgc cgaacctcat gaagaacaat gtctgtctgc ttttaccgta    360 cattttttcag gccagtttac cggaactgcc ggtgcatgtc gctatggccc attcggtccg    420
ccgccaccgt cacaagcctc ttcgggacaa gcccgcatgt ttccgaatgc accctacctg    480
```

-continued

| | |
|---|---|
| ccgtcttgtc tggaaagcca acccgcgatc cgtaaccaag gctacagcac cgtcacgttt | 540 |
| gatggtaccc cgagctatgg tcatacgccg agtcatcatg cagcacagtt cccgaaccac | 600 |
| tcgttcaaac acgaagatcc tatgggccag cagggtagtc tgggcgaaca acagtatagc | 660 |
| gtcccaccac cagtttatgg ttgccatacc ccaacggatt cctgtactgg tagccaagcg | 720 |
| ctcctgctcc gcaccccta ttcttctgat aatctctatc agatgaccag ccaactggaa | 780 |
| tgtatgacgt ggaaccaaat gaacctgggc gcaaccctga aggccacag taccggctat | 840 |
| gagtcagata accacacaac acccattttg tgcggcgctc aatatcgtat tcatacccat | 900 |
| ggcgtttttc gcggtattca gtgatga | 927 |

<210> SEQ ID NO 476
<211> LENGTH: 936
<212> TYPE: DNA
<213> ORGANISM: Homo sapiens

<400> SEQUENCE: 476

| | |
|---|---|
| atgaacaata acgatctctt ccaagcttcc cgtcgtcgtt tcctggcgca gctcggcggc | 60 |
| cttaccgtgg ccggtatgct gggtccgtcg cttttaacac cgcgccgcgc aaccgccgct | 120 |
| catggttcgg atgtacgcga tctgaacgcg cttcttccgg cggtcccaag cttgggcggg | 180 |
| ggaggtggat gcgccctgcc cgtgagcggc gccgcgcaat gggcccggt ccttgatttt | 240 |
| gctccgccgg gtgcgagcgc atacggctct ctgggcgggc ccgggcaaat tcattcattc | 300 |
| atcaaacagg agcccagctg gggtggcgcc gaacctcatg aagaacaatg tctgtctgct | 360 |
| tttaccgtac attttcagg ccagtttacc ggaactgccg gtgcatgtcg ctatggccca | 420 |
| ttcggtccgc cgccaccgtc acaagcctct tcgggacaag cccgcatgtt ccgaatgca | 480 |
| ccctacctgc cgtcttgtct ggaaagccaa cccgcgatcc gtaaccaagg ctacagcacc | 540 |
| gtcacgtttg atggtacccc gagctatggt catacgccga gtcatcatgc agcacagttc | 600 |
| ccgaaccact cgttcaaaca cgaagatcct atgggccagc agggtagtct gggcgaacaa | 660 |
| cagtatagcg tcccaccacc agtttatggt tgccataccc caacggattc ctgtactggt | 720 |
| agccaagcgc tcctgctccg cacccctat tcttctgata atctctatca gatgaccagc | 780 |
| caactggaat gtatgacgtg gaaccaaatg aacctgggcg caaccctgaa aggccacagt | 840 |
| accggctatg agtcagataa ccacacaaca cccattttgt gcggcgctca atatcgtatt | 900 |
| catacccatg gcgtttttcg cggtattcag tgatga | 936 |

<210> SEQ ID NO 477
<211> LENGTH: 969
<212> TYPE: DNA
<213> ORGANISM: Homo sapiens

<400> SEQUENCE: 477

| | |
|---|---|
| atgaacaata acgatctctt ccaagcttcc cgtcgtcgtt tcctggcgca gctcggcggc | 60 |
| cttaccgtgg ccggtatgct gggtccgtcg cttttaacac cgcgccgcgc aaccgccgct | 120 |
| catggttcgg atgtacgcga tctgaacgcg cttcttccgg cggtcccaag cttgggcggg | 180 |
| ggaggtggat gcgccctgcc cgtgagcggc gccgcgcaat gggcccggt ccttgatttt | 240 |
| gctccgccgg gtgcgagcgc atacggctct ctgggcggtc cggcacctcc tccagcaccg | 300 |
| cctccaccgc caccgccgcc gccgcattca ttcatcaaac aggagcccag ctggggtggc | 360 |
| gccgaacctc atgaagaaca atgtctgtct gcttttaccg tacattttc aggccagttt | 420 |
| accggaactg ccggtgcatg tcgctatggc ccattcggtc cgccgccacc gtcacaagcc | 480 |

-continued

```
tcttcgggac aagcccgcat gtttccgaat gcaccctacc tgccgtcttg tctggaaagc    540
caacccgcga tccgtaacca aggctacagc accgtcacgt ttgatggtac cccgagctat    600
ggtcatacgc cgagtcatca tgcagcacag ttcccgaacc actcgttcaa acacgaagat    660
cctatgggcc agcagggtag tctgggcgaa caacagtata gcgtcccacc accagtttat    720
ggttgccata ccccaacgga ttcctgtact ggtagccaag cgctcctgct ccgcaccccc    780
tattcttctg ataatctcta tcagatgacc agccaactgg aatgtatgac gtggaaccaa    840
atgaacctgg gcgcaaccct gaaaggccac agtaccggct atgagtcaga taaccacaca    900
acacccattt tgtgcggcgc tcaatatcgt attcataccc atggcgtttt tcgcggtatt    960
cagtgatga                                                            969
```

<210> SEQ ID NO 478
<211> LENGTH: 267
<212> TYPE: PRT
<213> ORGANISM: Homo sapiens

<400> SEQUENCE: 478

```
Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro His Ser Phe Ile Lys Gln Glu Pro Ser Trp
    50                  55                  60

Gly Gly Ala Glu Pro His Glu Glu Gln Cys Leu Ser Ala Phe Thr Val
65                  70                  75                  80

His Phe Ser Gly Gln Phe Thr Gly Thr Ala Gly Ala Cys Arg Tyr Gly
                85                  90                  95

Pro Phe Gly Pro Pro Pro Ser Gln Ala Ser Ser Gly Gln Ala Arg
            100                 105                 110

Met Phe Pro Asn Ala Pro Tyr Leu Pro Ser Cys Leu Glu Ser Gln Pro
        115                 120                 125

Ala Ile Arg Asn Gln Gly Tyr Ser Thr Val Thr Phe Asp Gly Thr Pro
    130                 135                 140

Ser Tyr Gly His Thr Pro Ser His His Ala Ala Gln Phe Pro Asn His
145                 150                 155                 160

Ser Phe Lys His Glu Asp Pro Met Gly Gln Gln Gly Ser Leu Gly Glu
                165                 170                 175

Gln Gln Tyr Ser Val Pro Pro Val Tyr Gly Cys His Thr Pro Thr
            180                 185                 190

Asp Ser Cys Thr Gly Ser Gln Ala Leu Leu Leu Arg Thr Pro Tyr Ser
        195                 200                 205

Ser Asp Asn Leu Tyr Gln Met Thr Ser Gln Leu Glu Cys Met Thr Trp
    210                 215                 220

Asn Gln Met Asn Leu Gly Ala Thr Leu Lys Gly His Ser Thr Gly Tyr
225                 230                 235                 240

Glu Ser Asp Asn His Thr Thr Pro Ile Leu Cys Gly Ala Gln Tyr Arg
                245                 250                 255

Ile His Thr His Gly Val Phe Arg Gly Ile Gln
            260                 265
```

<210> SEQ ID NO 479

```
<211> LENGTH: 321
<212> TYPE: PRT
<213> ORGANISM: Homo sapiens

<400> SEQUENCE: 479

Met Asn Asn Asp Leu Phe Gln Ala Ser Arg Arg Phe Leu Ala
                5                  10                 15

Gln Leu Gly Gly Leu Thr Val Ala Gly Met Leu Gly Pro Ser Leu Leu
                20                 25                 30

Thr Pro Arg Arg Ala Thr Ala Ala His Gly Ser Asp Val Arg Asp Leu
                35                 40                 45

Asn Ala Leu Leu Pro Ala Val Pro Ser Leu Gly Gly Gly Gly Cys
 50                 55                 60

Ala Leu Pro Val Ser Gly Ala Ala Gln Trp Ala Pro Val Leu Asp Phe
 65                 70                 75                 80

Ala Pro Pro Gly Ala Ser Ala Tyr Gly Ser Leu Gly Gly Pro Ala Pro
                85                 90                 95

Pro Pro Ala Pro Pro Pro Pro Pro Pro Pro His Ser Phe Ile
                100                105                110

Lys Gln Glu Pro Ser Trp Gly Gly Ala Glu Pro His Glu Glu Gln Cys
                115                120                125

Leu Ser Ala Phe Thr Val His Phe Ser Gly Gln Phe Thr Gly Thr Ala
 130                135                140

Gly Ala Cys Arg Tyr Gly Pro Phe Gly Pro Pro Pro Ser Gln Ala
145                150                155                160

Ser Ser Gly Gln Ala Arg Met Phe Pro Asn Ala Pro Tyr Leu Pro Ser
                165                170                175

Cys Leu Glu Ser Gln Pro Ala Ile Arg Asn Gln Gly Tyr Ser Thr Val
                180                185                190

Thr Phe Asp Gly Thr Pro Ser Tyr Gly His Thr Pro Ser His His Ala
                195                200                205

Ala Gln Phe Pro Asn His Ser Phe Lys His Glu Asp Pro Met Gly Gln
 210                215                220

Gln Gly Ser Leu Gly Glu Gln Gln Tyr Ser Val Pro Pro Pro Val Tyr
225                230                235                240

Gly Cys His Thr Pro Thr Asp Ser Cys Thr Gly Ser Gln Ala Leu Leu
                245                250                255

Leu Arg Thr Pro Tyr Ser Ser Asp Asn Leu Tyr Gln Met Thr Ser Gln
                260                265                270

Leu Glu Cys Met Thr Trp Asn Gln Met Asn Leu Gly Ala Thr Leu Lys
                275                280                285

Gly His Ser Thr Gly Tyr Glu Ser Asp Asn His Thr Thr Pro Ile Leu
                290                295                300

Cys Gly Ala Gln Tyr Arg Ile His Thr His Gly Val Phe Arg Gly Ile
305                310                315                320

Gln

<210> SEQ ID NO 480
<211> LENGTH: 274
<212> TYPE: PRT
<213> ORGANISM: Homo sapiens

<400> SEQUENCE: 480

Met Gln His His His His His His Gly Ser Asp Val Arg Asp Leu Asn
                5                  10                 15

Ala Leu Leu Pro Ala Val Pro Ser Leu Gly Gly Gly Gly Cys Ala
```

-continued

```
                20                  25                  30
Leu Pro Val Ser Gly Ala Ala Gln Trp Ala Pro Val Leu Asp Phe Ala
                35                  40                  45
Pro Pro Gly Ala Ser Ala Tyr Gly Ser Leu Gly Pro His Ser Phe
        50                  55                  60
Ile Lys Gln Glu Pro Ser Trp Gly Ala Glu Pro His Glu Glu Gln
65                  70                  75                  80
Cys Leu Ser Ala Phe Thr Val His Phe Ser Gly Gln Phe Thr Gly Thr
                85                  90                  95
Ala Gly Ala Cys Arg Tyr Gly Pro Phe Gly Pro Pro Pro Ser Gln
            100                 105                 110
Ala Ser Ser Gly Gln Ala Arg Met Phe Pro Asn Ala Pro Tyr Leu Pro
            115                 120                 125
Ser Cys Leu Glu Ser Gln Pro Ala Ile Arg Asn Gln Gly Tyr Ser Thr
            130                 135                 140
Val Thr Phe Asp Gly Thr Pro Ser Tyr Gly His Thr Pro Ser His His
145                 150                 155                 160
Ala Ala Gln Phe Pro Asn His Ser Phe Lys His Glu Asp Pro Met Gly
                165                 170                 175
Gln Gln Gly Ser Leu Gly Glu Gln Gln Tyr Ser Val Pro Pro Pro Val
            180                 185                 190
Tyr Gly Cys His Thr Pro Thr Asp Ser Cys Thr Gly Ser Gln Ala Leu
            195                 200                 205
Leu Leu Arg Thr Pro Tyr Ser Ser Asp Asn Leu Tyr Gln Met Thr Ser
        210                 215                 220
Gln Leu Glu Cys Met Thr Trp Asn Gln Met Asn Leu Gly Ala Thr Leu
225                 230                 235                 240
Lys Gly His Ser Thr Gly Tyr Glu Ser Asp Asn His Thr Thr Pro Ile
                245                 250                 255
Leu Cys Gly Ala Gln Tyr Arg Ile His Thr His Gly Val Phe Arg Gly
            260                 265                 270
Ile Gln

<210> SEQ ID NO 481
<211> LENGTH: 310
<212> TYPE: PRT
<213> ORGANISM: Homo sapiens

<400> SEQUENCE: 481

Met Asn Asn Asn Asp Leu Phe Gln Ala Ser Arg Arg Arg Phe Leu Ala
                5                   10                  15
Gln Leu Gly Gly Leu Thr Val Ala Gly Met Leu Gly Pro Ser Leu Leu
            20                  25                  30
Thr Pro Arg Arg Ala Thr Ala Ala His Gly Ser Asp Val Arg Asp Leu
        35                  40                  45
Asn Ala Leu Leu Pro Ala Val Pro Ser Leu Gly Gly Gly Gly Cys
    50                  55                  60
Ala Leu Pro Val Ser Gly Ala Ala Gln Trp Ala Pro Val Leu Asp Phe
65                  70                  75                  80
Ala Pro Pro Gly Ala Ser Ala Tyr Gly Ser Leu Gly Pro Gly Gln
                85                  90                  95
Ile His Ser Phe Ile Lys Gln Glu Pro Ser Trp Gly Ala Glu Pro
            100                 105                 110
His Glu Glu Gln Cys Leu Ser Ala Phe Thr Val His Phe Ser Gly Gln
        115                 120                 125
```

```
Phe Thr Gly Thr Ala Gly Ala Cys Arg Tyr Gly Pro Phe Gly Pro Pro
            130                 135                 140

Pro Pro Ser Gln Ala Ser Ser Gly Gln Ala Arg Met Phe Pro Asn Ala
145                 150                 155                 160

Pro Tyr Leu Pro Ser Cys Leu Glu Ser Gln Pro Ala Ile Arg Asn Gln
                165                 170                 175

Gly Tyr Ser Thr Val Thr Phe Asp Gly Thr Pro Ser Tyr Gly His Thr
            180                 185                 190

Pro Ser His His Ala Ala Gln Phe Pro Asn His Ser Phe Lys His Glu
        195                 200                 205

Asp Pro Met Gly Gln Gln Gly Ser Leu Gly Glu Gln Gln Tyr Ser Val
    210                 215                 220

Pro Pro Pro Val Tyr Gly Cys His Thr Pro Thr Asp Ser Cys Thr Gly
225                 230                 235                 240

Ser Gln Ala Leu Leu Leu Arg Thr Pro Tyr Ser Ser Asp Asn Leu Tyr
                245                 250                 255

Gln Met Thr Ser Gln Leu Glu Cys Met Thr Trp Asn Gln Met Asn Leu
            260                 265                 270

Gly Ala Thr Leu Lys Gly His Ser Thr Gly Tyr Glu Ser Asp Asn His
        275                 280                 285

Thr Thr Pro Ile Leu Cys Gly Ala Gln Tyr Arg Ile His Thr His Gly
    290                 295                 300

Val Phe Arg Gly Ile Gln
305                 310

<210> SEQ ID NO 482
<211> LENGTH: 307
<212> TYPE: PRT
<213> ORGANISM: Homo sapiens

<400> SEQUENCE: 482

Met Asn Asn Asn Asp Leu Phe Gln Ala Ser Arg Arg Arg Phe Leu Ala
                5                   10                  15

Gln Leu Gly Gly Leu Thr Val Ala Gly Met Leu Gly Pro Ser Leu Leu
            20                  25                  30

Thr Pro Arg Arg Ala Thr Ala Ala His Gly Ser Asp Val Arg Asp Leu
        35                  40                  45

Asn Ala Leu Leu Pro Ala Val Pro Ser Leu Gly Gly Gly Gly Gly Cys
    50                  55                  60

Ala Leu Pro Val Ser Gly Ala Ala Gln Trp Ala Pro Val Leu Asp Phe
65                  70                  75                  80

Ala Pro Pro Gly Ala Ser Ala Tyr Gly Ser Leu Gly Gly Pro His Ser
                85                  90                  95

Phe Ile Lys Gln Glu Pro Ser Trp Gly Gly Ala Glu Pro His Glu Glu
            100                 105                 110

Gln Cys Leu Ser Ala Phe Thr Val His Phe Ser Gly Gln Phe Thr Gly
        115                 120                 125

Thr Ala Gly Ala Cys Arg Tyr Gly Pro Phe Gly Pro Pro Pro Pro Ser
    130                 135                 140

Gln Ala Ser Ser Gly Gln Ala Arg Met Phe Pro Asn Ala Pro Tyr Leu
145                 150                 155                 160

Pro Ser Cys Leu Glu Ser Gln Pro Ala Ile Arg Asn Gln Gly Tyr Ser
                165                 170                 175

Thr Val Thr Phe Asp Gly Thr Pro Ser Tyr Gly His Thr Pro Ser His
            180                 185                 190
```

```
His Ala Ala Gln Phe Pro Asn His Ser Phe Lys His Glu Asp Pro Met
        195                 200                 205
Gly Gln Gln Gly Ser Leu Gly Glu Gln Gln Tyr Ser Val Pro Pro Pro
    210                 215                 220
Val Tyr Gly Cys His Thr Pro Thr Asp Ser Cys Thr Gly Ser Gln Ala
225                 230                 235                 240
Leu Leu Leu Arg Thr Pro Tyr Ser Ser Asp Asn Leu Tyr Gln Met Thr
                245                 250                 255
Ser Gln Leu Glu Cys Met Thr Trp Asn Gln Met Asn Leu Gly Ala Thr
            260                 265                 270
Leu Lys Gly His Ser Thr Gly Tyr Glu Ser Asp Asn His Thr Thr Pro
        275                 280                 285
Ile Leu Cys Gly Ala Gln Tyr Arg Ile His Thr His Gly Val Phe Arg
    290                 295                 300
Gly Ile Gln
305

<210> SEQ ID NO 483
<211> LENGTH: 278
<212> TYPE: PRT
<213> ORGANISM: Homo sapiens

<400> SEQUENCE: 483

Met Asn Asn Asn Asp Leu Phe Gln Ala Ser Arg His Gly Ser Asp Val
                5                   10                  15
Arg Asp Leu Asn Ala Leu Leu Pro Ala Val Pro Ser Leu Gly Gly Gly
            20                  25                  30
Gly Gly Cys Ala Leu Pro Val Ser Gly Ala Ala Gln Trp Ala Pro Val
        35                  40                  45
Leu Asp Phe Ala Pro Pro Gly Ala Ser Ala Tyr Gly Ser Leu Gly Gly
    50                  55                  60
Pro His Ser Phe Ile Lys Gln Glu Pro Ser Trp Gly Gly Ala Glu Pro
65                  70                  75                  80
His Glu Glu Gln Cys Leu Ser Ala Phe Thr Val His Phe Ser Gly Gln
                85                  90                  95
Phe Thr Gly Thr Ala Gly Ala Cys Arg Tyr Gly Pro Phe Gly Pro Pro
                100                 105                 110
Pro Pro Ser Gln Ala Ser Ser Gly Gln Ala Arg Met Phe Pro Asn Ala
        115                 120                 125
Pro Tyr Leu Pro Ser Cys Leu Glu Ser Gln Pro Ala Ile Arg Asn Gln
    130                 135                 140
Gly Tyr Ser Thr Val Thr Phe Asp Gly Thr Pro Ser Tyr Gly His Thr
145                 150                 155                 160
Pro Ser His His Ala Ala Gln Phe Pro Asn His Ser Phe Lys His Glu
                165                 170                 175
Asp Pro Met Gly Gln Gln Gly Ser Leu Gly Glu Gln Gln Tyr Ser Val
                180                 185                 190
Pro Pro Pro Val Tyr Gly Cys His Thr Pro Thr Asp Ser Cys Thr Gly
            195                 200                 205
Ser Gln Ala Leu Leu Leu Arg Thr Pro Tyr Ser Ser Asp Asn Leu Tyr
        210                 215                 220
Gln Met Thr Ser Gln Leu Glu Cys Met Thr Trp Asn Gln Met Asn Leu
225                 230                 235                 240
Gly Ala Thr Leu Lys Gly His Ser Thr Gly Tyr Glu Ser Asp Asn His
                245                 250                 255
```

Thr Thr Pro Ile Leu Cys Gly Ala Gln Tyr Arg Ile His Thr His Gly
            260                 265                 270

Val Phe Arg Gly Ile Gln
        275

<210> SEQ ID NO 484
<211> LENGTH: 30
<212> TYPE: DNA
<213> ORGANISM: Artificial Sequence
<220> FEATURE:
<223> OTHER INFORMATION: PCR primer

<400> SEQUENCE: 484
ggctccgacg ttcgggacct gaacgcactg                                    30

<210> SEQ ID NO 485
<211> LENGTH: 31
<212> TYPE: DNA
<213> ORGANISM: Artificial Sequence
<220> FEATURE:
<223> OTHER INFORMATION: PCR primer

<400> SEQUENCE: 485
ctgcagaatt catcactgaa tgcctctgaa g                                  31

<210> SEQ ID NO 486
<211> LENGTH: 27
<212> TYPE: DNA
<213> ORGANISM: Artificial Sequence
<220> FEATURE:
<223> OTHER INFORMATION: Oligonucleotide used in construction of the TAT
      "Stumpy" vector.

<400> SEQUENCE: 486
tatgaacaat aacgatctgt ttcaggc                                       27

<210> SEQ ID NO 487
<211> LENGTH: 23
<212> TYPE: DNA
<213> ORGANISM: Artificial Sequence
<220> FEATURE:
<223> OTHER INFORMATION: Oligonucleotide used in construction of the TAT
      "Stumpy" vector.

<400> SEQUENCE: 487
ctgaaacaga tcgttattgt tca                                           23

<210> SEQ ID NO 488
<211> LENGTH: 29
<212> TYPE: DNA
<213> ORGANISM: Artificial Sequence
<220> FEATURE:
<223> OTHER INFORMATION: Oligonucleotide used in construction of the TAT
      "Stumpy" vector.

<400> SEQUENCE: 488
aattcttggt cattcacgtg gcggctcgc                                     29

<210> SEQ ID NO 489
<211> LENGTH: 23
<212> TYPE: DNA
<213> ORGANISM: Artificial Sequence
<220> FEATURE:
<223> OTHER INFORMATION: Oligonucleotide used in construction of the TAT
      "Stumpy" vector.

<400> SEQUENCE: 489
gagccgccac gtgaatgacc aag                                   23

<210> SEQ ID NO 490
<211> LENGTH: 31
<212> TYPE: DNA
<213> ORGANISM: Artificial Sequence
<220> FEATURE:
<223> OTHER INFORMATION: PCR primer

<400> SEQUENCE: 490
caagcgctca tgagcccgaa gtggcgagcc c                          31

<210> SEQ ID NO 491
<211> LENGTH: 32
<212> TYPE: DNA
<213> ORGANISM: Artificial Sequence
<220> FEATURE:
<223> OTHER INFORMATION: PCR primer

<400> SEQUENCE: 491
cataaatttg cccgggcccg cccagagagc cg                         32

<210> SEQ ID NO 492
<211> LENGTH: 23
<212> TYPE: DNA
<213> ORGANISM: Artificial Sequence
<220> FEATURE:
<223> OTHER INFORMATION: PCR primer

<400> SEQUENCE: 492
cattcattca tcaaacagga gcc                                   23

<210> SEQ ID NO 493
<211> LENGTH: 26
<212> TYPE: DNA
<213> ORGANISM: Artificial Sequence
<220> FEATURE:
<223> OTHER INFORMATION: PCR primer

<400> SEQUENCE: 493
ccattaagaa ttcatcactg aatacc                                26

<210> SEQ ID NO 494
<211> LENGTH: 25
<212> TYPE: DNA
<213> ORGANISM: Artificial Sequence
<220> FEATURE:
<223> OTHER INFORMATION: PCR primer

<400> SEQUENCE: 494
ggttcggatg tacgcgatct gaacg                                 25

<210> SEQ ID NO 495
<211> LENGTH: 26
<212> TYPE: DNA
<213> ORGANISM: Artificial Sequence
<220> FEATURE:
<223> OTHER INFORMATION: PCR primer

<400> SEQUENCE: 495
caaagaattc atcactgaat accgcg                                26

<210> SEQ ID NO 496
<211> LENGTH: 33
<212> TYPE: DNA
<213> ORGANISM: Artificial Sequence

```
<220> FEATURE:
<223> OTHER INFORMATION: PCR primer

<400> SEQUENCE: 496
gcttttggca tatgggttcg gatgtacgcg atc                                      33

<210> SEQ ID NO 497
<211> LENGTH: 26
<212> TYPE: DNA
<213> ORGANISM: Artificial Sequence
<220> FEATURE:
<223> OTHER INFORMATION: PCR primer

<400> SEQUENCE: 497
caaagaattc atcactgaat accgcg                                              26

<210> SEQ ID NO 498
<211> LENGTH: 882
<212> TYPE: DNA
<213> ORGANISM: Homo sapiens

<400> SEQUENCE: 498
atgaacaata acgatctgtt tcaggcgagc cgccacggtt cggatgtacg cgatctgaac         60
gcgcttcttc cggcggtccc aagcttgggc gggggaggtg gatgcgccct gcccgtgagc        120
ggcgccgcgc aatgggcccc ggtccttgat tttgctccgc cgggtgcgag cgcatacggc        180
tctctgggcg gtccggcacc tcctccagca ccgcctccac cgccaccgcc gccgccgcat        240
tcattcatca aacaggagcc cagctggggt ggcgccgaac ctcatgaaga acaatgtctg        300
tctgctttta ccgtacattt ttcaggccag tttaccggaa ctgccggtgc atgtcgctat        360
ggcccattcg gtccgccgcc accgtcacaa gcctcttcgg acaagcccg catgtttccg         420 aatgcaccct acctgccgtc ttgtctggaa agccaacccg cgatccgtaa ccaaggctac        480
agcaccgtca cgtttgatgg tacccccgagc tatggtcata cgccgagtca tcatgcagca      540
cagttcccga ccactcgtt caaacacgaa gatcctatgg ccagcaggg tagtctgggc         600 gaacaacagt atagcgtccc accaccagtt tatggttgcc atacccccaac ggattcctgt      660 actggtagcc aagcgctcct gctccgcacc ccctattctt ctgataatct ctatcagatg       720
accagccaac tggaatgtat gacgtggaac caaatgaacc tgggcgcaac cctgaaaggc       780
cacagtaccg gctatgagtc agataaccac acaacaccca ttttgtgcgg cgctcaatat      840
cgtattcata cccatggcgt ttttcgcggt attcagtgat ga                         882

<210> SEQ ID NO 499
<211> LENGTH: 292
<212> TYPE: PRT
<213> ORGANISM: Homo sapiens

<400> SEQUENCE: 499

Met Asn Asn Asn Asp Leu Phe Gln Ala Ser Arg His Gly Ser Asp Val
 1               5                  10                  15

Arg Asp Leu Asn Ala Leu Leu Pro Ala Val Pro Ser Leu Gly Gly Gly
             20                  25                  30

Gly Gly Cys Ala Leu Pro Val Ser Gly Ala Ala Gln Trp Ala Pro Val
         35                  40                  45

Leu Asp Phe Ala Pro Pro Gly Ala Ser Ala Tyr Gly Ser Leu Gly Gly
     50                  55                  60

Pro Ala Pro Pro Pro Ala Pro Pro Pro Pro Pro Pro Pro Pro Pro His
 65                  70                  75                  80
```

-continued

```
Ser Phe Ile Lys Gln Glu Pro Ser Trp Gly Gly Ala Glu Pro His Glu
            85                  90                  95

Glu Gln Cys Leu Ser Ala Phe Thr Val His Phe Ser Gly Gln Phe Thr
        100                 105                 110

Gly Thr Ala Gly Ala Cys Arg Tyr Gly Pro Phe Gly Pro Pro Pro Pro
    115                 120                 125

Ser Gln Ala Ser Ser Gly Gln Ala Arg Met Phe Pro Asn Ala Pro Tyr
130                 135                 140

Leu Pro Ser Cys Leu Glu Ser Gln Pro Ala Ile Arg Asn Gln Gly Tyr
145                 150                 155                 160

Ser Thr Val Thr Phe Asp Gly Thr Pro Ser Tyr Gly His Thr Pro Ser
                165                 170                 175

His His Ala Ala Gln Phe Pro Asn His Ser Phe Lys His Glu Asp Pro
            180                 185                 190

Met Gly Gln Gln Gly Ser Leu Gly Glu Gln Gln Tyr Ser Val Pro Pro
        195                 200                 205

Pro Val Tyr Gly Cys His Thr Pro Thr Asp Ser Cys Thr Gly Ser Gln
    210                 215                 220

Ala Leu Leu Leu Arg Thr Pro Tyr Ser Ser Asp Asn Leu Tyr Gln Met
225                 230                 235                 240

Thr Ser Gln Leu Glu Cys Met Thr Trp Asn Gln Met Asn Leu Gly Ala
                245                 250                 255

Thr Leu Lys Gly His Ser Thr Gly Tyr Glu Ser Asp Asn His Thr Thr
            260                 265                 270

Pro Ile Leu Cys Gly Ala Gln Tyr Arg Ile His Thr His Gly Val Phe
        275                 280                 285

Arg Gly Ile Gln
        290
```

<210> SEQ ID NO 500
<211> LENGTH: 25
<212> TYPE: DNA
<213> ORGANISM: Artificial Sequence
<220> FEATURE:
<223> OTHER INFORMATION: PCR primer

<400> SEQUENCE: 500
ggttcggatg tacgcgatct gaacg                                   25

<210> SEQ ID NO 501
<211> LENGTH: 26
<212> TYPE: DNA
<213> ORGANISM: Artificial Sequence
<220> FEATURE:
<223> OTHER INFORMATION: PCR primer

<400> SEQUENCE: 501
caaagaattc atcactgaat accgcg                                  26

<210> SEQ ID NO 502
<211> LENGTH: 270
<212> TYPE: PRT
<213> ORGANISM: Homo sapiens

<400> SEQUENCE: 502

```
Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30
```

| | | | | | | | | | | | |
|---|---|---|---|---|---|---|---|---|---|---|---|
|Gln|Trp|Ala|Pro|Val|Leu|Asp|Phe|Ala|Pro|Pro|Gly|Ala|Ser|Ala|Tyr|
| |35| | | |40| | | |45| | | | | | |
|Gly|Ser|Leu|Gly|Gly|Pro|Gly|Gln|Ile|His|Ser|Phe|Ile|Lys|Gln|Glu|
|50| | | | |55| | | | |60| | | | | |
|Pro|Ser|Trp|Gly|Gly|Ala|Glu|Pro|His|Glu|Glu|Gln|Cys|Leu|Ser|Ala|
|65| | | | |70| | | | |75| | | | |80|
|Phe|Thr|Val|His|Phe|Ser|Gly|Gln|Phe|Thr|Gly|Thr|Ala|Gly|Ala|Cys|
| | | | |85| | | | |90| | | | |95| |
|Arg|Tyr|Gly|Pro|Phe|Gly|Pro|Pro|Pro|Ser|Gln|Ala|Ser|Ser|Gly|
| | | |100| | | | |105| | | | |110| | |
|Gln|Ala|Arg|Met|Phe|Pro|Asn|Ala|Pro|Tyr|Leu|Pro|Ser|Cys|Leu|Glu|
| | | |115| | | | |120| | | | |125| | |
|Ser|Gln|Pro|Ala|Ile|Arg|Asn|Gln|Gly|Tyr|Ser|Thr|Val|Thr|Phe|Asp|
| |130| | | | |135| | | | |140| | | | |
|Gly|Thr|Pro|Ser|Tyr|Gly|His|Thr|Pro|Ser|His|His|Ala|Ala|Gln|Phe|
|145| | | | |150| | | | |155| | | | |160|
|Pro|Asn|His|Ser|Phe|Lys|His|Glu|Asp|Pro|Met|Gly|Gln|Gln|Gly|Ser|
| | | | |165| | | | |170| | | | |175| |
|Leu|Gly|Glu|Gln|Gln|Tyr|Ser|Val|Pro|Pro|Val|Tyr|Gly|Cys|His|
| | | |180| | | | |185| | | | |190| | |
|Thr|Pro|Thr|Asp|Ser|Cys|Thr|Gly|Ser|Gln|Ala|Leu|Leu|Arg|Thr|
| | | |195| | | | |200| | | | |205| | |
|Pro|Tyr|Ser|Ser|Asp|Asn|Leu|Tyr|Gln|Met|Thr|Ser|Gln|Leu|Glu|Cys|
| | | |210| | | | |215| | | | |220| | |
|Met|Thr|Trp|Asn|Gln|Met|Asn|Leu|Gly|Ala|Thr|Leu|Lys|Gly|His|Ser|
|225| | | | |230| | | | |235| | | | |240|
|Thr|Gly|Tyr|Glu|Ser|Asp|Asn|His|Thr|Thr|Pro|Ile|Leu|Cys|Gly|Ala|
| | | | |245| | | | |250| | | | |255| |
|Gln|Tyr|Arg|Ile|His|Thr|His|Gly|Val|Phe|Arg|Gly|Ile|Gln|
| | | |260| | | | |265| | | | |270| | |

<210> SEQ ID NO 503
<211> LENGTH: 5400
<212> TYPE: DNA
<213> ORGANISM: E. coli

<400> SEQUENCE: 503

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggattt tgccgatttc ggcctattgg ttaaaaatg agctgattta      420
acaaaatttt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaagccg tttctgtaat gaaggagaaa      660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
```

```
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggaa acgcctggta tctttatagt cctgtcgggt ttcgccacct ctgacttgag   2040
cgtcgatttt tgtgatgctc gtcaggggg cggagcctat ggaaaaacgc cagcaacgcg   2100
gccttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca gggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
```

```
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg cgcgcattg     3840 cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatataca tatgaacaac aacgacctgt tccaggcttc    5100
tcgtcgtcgt ttcctggctc agctgggtgg tctgaccgtt gctggtatgc tgggtccgtc    5160
tctgctgacc ccgcgtcgtg ctaccgctgc tcacgtgccc atctgaattc tgcagatatc    5220
catcacactg gcggccgctc gagcaccacc accaccacca ctgagatccg gctgctaaca    5280
aagcccgaaa ggaagctgag ttggctgctg ccaccgctga gcaataacta gcataacccc    5340
ttggggcctc taaacgggtc ttgaggggtt ttttgctgaa aggaggaact atatccggat    5400
```

<210> SEQ ID NO 504
<211> LENGTH: 39
<212> TYPE: PRT
<213> ORGANISM: E. coli
<220> FEATURE:
<221> NAME/KEY: VARIANT
<222> LOCATION: 31, 32, 33, 34, 35, 36, 37, 38, 39
<223> OTHER INFORMATION: Xaa = Any Amino Acid

<400> SEQUENCE: 504

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Xaa Xaa
            20                  25                  30

Xaa Xaa Xaa Xaa Xaa Xaa Xaa
        35

<210> SEQ ID NO 505
<211> LENGTH: 816
<212> TYPE: DNA
<213> ORGANISM: Homo sapiens

<400> SEQUENCE: 505

```
atgggttcgg atgtacgcga tctgaacgcg cttcttccgg cggtcccaag cttgggcggg    60
ggaggtggat gcgccctgcc cgtgagcggc gccgcgcaat gggccccggt ccttgatttt   120
gctccgccgg gtgcgagcgc ataccggtct ctgggcgggc ccgggcaaat tcattcattc   180
atcaaacagg agcccagctg gggtggcgcc gaacctcatg aagaacaatg tctgtctgct   240
tttaccgtac attttccagg ccagtttacc ggaactgccg gtgcatgtcg ctatggccca   300
ttcggtccgc cgccaccgtc acaagcctct tcgggacaag cccgcatgtt tccgaatgca   360
ccctacctgc cgtcttgtct ggaaagccaa cccgcgatcc gtaaccaagg ctacagcacc   420
gtcacgtttg atggtacccc gagctatggt catacgccga gtcatcatgc agcacagttc   480
ccgaaccact cgttcaaaca cgaagatcct atgggccagc agggtagtct gggcgaacaa   540
cagtatagcg tcccaccacc agtttatggt tgccataccc aacggattc ctgtactggt   600
agccaagcgc tcctgctccg caccccctat tcttctgata atctctatca gatgaccagc   660
caactggaat gtatgacgtg gaaccaaatg aacctgggcg caaccctgaa aggccacagt   720
accggctatg agtcagataa ccacacaaca cccattttgt gcggcgctca atatcgtatt   780
catacccatg gcgttttcg cggtattcag tgatga                              816
```

<210> SEQ ID NO 506
<211> LENGTH: 12
<212> TYPE: PRT
<213> ORGANISM: Homo sapiens

<400> SEQUENCE: 506

Met Asn Asn Asn Asp Leu Phe Gln Ala Ser Arg His
1               5                   10

<210> SEQ ID NO 507
<211> LENGTH: 31880
<212> TYPE: DNA
<213> ORGANISM: Homo sapiens

<400> SEQUENCE: 507

```
catcatcaat aatataccttt attttggatt gaagccaata tgataatgag ggggtggagt    60
ttgtgacgtg gcgcggggcg tgggaacggg gcgggtgacg tagtagtgtg gcggaagtgt   120
gatgttgcaa gtgtggcgga acacatgtaa gcgacggatg tggcaaaagt gacgtttttg   180
gtgtgcgccg gtgtacacag gaagtgacaa ttttcgcgcg gttttaggcg gatgttgtag   240
taaatttggg cgtaaccgag taagatttgg ccatttttcgc gggaaaactg aataagagga   300
agtgaaatct gaataatttt gtgttactca tagcgcgtaa tactgtaata gtaatcaatt   360
```

```
acggggtcat tagttcatag cccatatatg gagttccgcg ttacataact tacggtaaat    420
ggcccgcctg gctgaccgcc caacgacccc cgcccattga cgtcaataat gacgtatgtt    480
cccatagtaa cgccaatagg gactttccat tgacgtcaat gggtggagta tttacggtaa    540
actgcccact tggcagtaca tcaagtgtat catatgccaa gtacgccccc tattgacgtc    600
aatgacggta atggcccgcc tggcattat gcccagtaca tgaccttatg gactttcct    660 acttggcagt acatctacgt attagtcatc gctattacca tggtgatgcg gttttggcag    720
tacatcaatg ggcgtggata gcggtttgac tcacggggat ttccaagtct ccaccccatt    780
gacgtcaatg ggagtttgtt ttggcaccaa aatcaacggg actttccaaa atgtcgtaac    840
aactccgccc cattgacgca aatgggcggt aggcgtgtac ggtgggaggt ctatataagc    900
agagctggtt tagtgaaccg tcagatccgc tagagatctg gtaccgtcga cgcggccgct    960
cgagcctaag cttctagagc cgccaccatg ggctccgacg ttcgggacct gaacgcactg   1020
ctgccggcag ttccgtccct gggtggtggt ggtggttgcg cactgccggt tagcggtgca   1080
gcacagtggg ctccggttct ggacttcgca ccgccgggtg catccgcata cggttccctg   1140
ggtggtccgg caccgccgcc ggcaccgccg ccgccgccgc cgccgccgcc gcactccttc   1200
atcaaacagg aaccgagctg gggtggtgca gaaccgcacg aagaacagtg cctgagcgca   1260
ttcaccgttc acttctccgg ccagttcact ggcacagccg gagcctgtcg ctacgggccc   1320
ttcggtcctc ctccgcccag ccaggcgtca tccggccagg ccaggatgtt tcctaacgcg   1380
ccctacctgc ccagctgcct cgagagccag cccgctattc gcaatcaggg ttacagcacg   1440
gtcaccttcg acgggacgcc cagctacggt cacacgccct cgcaccatgc ggcgcagttc   1500
cccaaccact cattcaagca tgaggatccc atgggccagc agggctcgct gggtgagcag   1560
cagtactcgg tgccgccccc ggtctatggc tgccacaccc ccaccgacag ctgcaccggc   1620
agccaggctt tgctgctgag gacgccctac agcagtgaca atttatacca aatgacatcc   1680
cagcttgaat gcatgacctg gaatcagatg aacttaggag ccaccttaaa gggccacagc   1740
acagggtacg agagcgataa ccacacaacg cccatcctct gcggagccca atacagaata   1800
cacacgcacg gtgtcttcag aggcattcag tgatctagat aagatatccg atccaccgga   1860
tctagataac tgatcataat cagccatacc acatttgtag aggttttact tgctttaaaa   1920
aacctcccac acctccccct gaacctgaaa cataaaatga atgcaattgt tgttgttaac   1980
ttgtttattg cagcttataa tggttacaaa taaagcaata gcatcacaaa tttcacaaat   2040
aaagcatttt tttcactgca ttctagttgt ggtttgtcca aactcatcaa tgtatcttaa   2100
cgcggatctg ggcgtggtta agggtgggaa agaatatata aggtgggggt cttatgtagt   2160
tttgtatctg ttttgcagca gccgccgccg ccatgagcac caactcgttt gatggaagca   2220
ttgtgagctc atatttgaca acgcgcatgc ccccatgggc cggggtgcgt cagaatgtga   2280
tgggctccag cattgatggt cgccccgtcc tgcccgcaaa ctctactacc ttgacctacg   2340
agaccgtgtc tggaacgccg ttggagactg cagcctccgc cgccgcttca gccgctgcag   2400
ccaccgcccg cgggattgtg actgactttg ctttcctgag cccgcttgca agcagtgcag   2460
cttcccgttc atccgcccgc gatgacaagt tgacggctct tttggcacaa ttggattctt   2520
tgacccggga acttaatgtc gtttctcagc agctgttgga tctgcgccag caggtttctg   2580
ccctgaaggc ttcctcccct cccaatgcgg tttaaaacat aaataaaaaa ccagactctg   2640
tttggatttg gatcaagcaa gtgtcttgct gtctttattt aggggttttg cgcgcgcggt   2700
aggcccggga ccagcggtct cggtcgttga gggtcctgtg tattttttcc aggacgtggt   2760
```

```
aaaggtgact ctggatgttc agatacatgg gcataagccc gtctctgggg tggaggtagc    2820
accactgcag agcttcatgc tgcggggtgg tgttgtagat gatccagtcg tagcaggagc    2880
gctgggcgtg gtgcctaaaa atgtctttca gtagcaagct gattgccagg ggcaggccct    2940
tggtgtaagt gtttacaaag cggttaagct gggatgggtg catacgtggg gatatgagat    3000
gcatcttgga ctgtattttt aggttggcta tgttcccagc catatccctc cggggattca    3060
tgttgtgcag aaccaccagc acagtgtatc cggtgcactt gggaaatttg tcatgtagct    3120
tagaaggaaa tgcgtggaag aacttggaga cgcccttgtg acctccaaga ttttccatgc    3180
attcgtccat aatgatggca atgggcccac gggcggcggc ctgggcgaag atatttctgg    3240
gatcactaac gtcatagttg tgttccagga tgagatcgtc ataggccatt tttacaaagc    3300
gcgggcggag ggtgccagac tgcggtataa tggttccatc cggcccaggg gcgtagttac    3360
cctcacagat ttgcatttcc cacgctttga gttcagatgg ggggatcatg tctacctgcg    3420
gggcgatgaa gaaaacggtt tccggggtag gggagatcag ctgggaagaa agcaggttcc    3480
tgagcagctg cgacttaccg cagccggtgg gcccgtaaat cacacctatt accggctgca    3540
actggtagtt aagagagctg cagctgccgt catccctgag caggggggcc acttcgttaa    3600
gcatgtccct gactcgcatg ttttccctga ccaaatccgc cagaaggcgc tcgccgccca    3660
gcgatagcag ttcttgcaag gaagcaaagt ttttcaacgg tttgagaccg tccgccgtag    3720
gcatgctttt gagcgtttga ccaagcagtt ccaggcggtc ccacagctcg gtcacctgct    3780
ctacggcatc tcgatccagc atatctcctc gtttcgcggg ttggggcggc tttcgctgta    3840
cggcagtagt cggtgctcgt ccagacgggc caggtcatg tctttccacg ggcgcagggt    3900
cctcgtcagc gtagtctggg tcacggtgaa ggggtgcgct ccgggctgcg cgctggccag    3960
ggtgcgcttg aggctggtcc tgctggtgct gaagcgctgc cggtcttcgc cctgcgcgtc    4020
ggccaggtag catttgacca tggtgtcata gtccagcccc tccgcggcgt ggcccttggc    4080
gcgcagcttg cccttggagg aggcgccgca cgaggggcag tgcagacttt tgagggcgta    4140
gagcttgggc gcgagaaata ccgattccgg ggagtaggca tccgcgccgc aggcccgca    4200 gacggtctcg cattccacga gccaggtgag ctctggccgt tcggggtcaa aaaccaggtt    4260 tccccccatgc tttttgatgc gtttcttacc tctggtttcc atgagccggt gtccacgctc    4320
ggtgacgaaa aggctgtccg tgtccccgta tacagacttg agaggcctgt cctcgagcgg    4380
tgttccgcgg tcctcctcgt atagaaactc ggaccactct gagacaaagg ctcgcgtcca    4440
ggccagcacg aaggaggcta agtgggaggg gtagcggtcg ttgtccacta gggggtccac    4500
tcgctccagg gtgtgaagac acatgtcgcc ctcttcggca tcaaggaagg tgattggttt    4560
gtaggtgtag gccacgtgac cgggtgttcc tgaagggggg ctataaaagg gggtgggggc    4620
gcgttcgtcc tcactctctt ccgcatcgct gtctgcgagg gccagctgtt ggggtgagta    4680
ctccctctga aaagcgggca tgacttctgc gctaagattg tcagtttcca aaaacgagga    4740
ggatttgata ttcacctggc ccgcggtgat gcctttgagg gtggccgcat ccatctggtc    4800
agaaaagaca atctttttgt tgtcaagctt ggtggcaaac gacccgtaga gggcgttgga    4860
cagcaacttg gcgatggagc gcagggtttg gtttttgtcg cgatcggcgc gctccttggc    4920
cgcgatgttt agctgcacgt attcgcgcgc aacgcaccgc cattcgggaa agacggtggt    4980
gcgctcgtcg gcaccaggt gcacgcgcca accgcggttg tgcagggtga caaggtcaac    5040
gctggtggct acctctccgc gtaggcgctc gttggtccag cagaggcggc cgcccttgcg    5100
cgagcagaat ggcggtaggg ggtctagctg cgtctcgtcc gggggtctg cgtccacggt    5160
```

```
aaagacccccg ggcagcaggc gcgcgtcgaa gtagtctatc ttgcatcctt gcaagtctag   5220
cgcctgctgc catgcgcggg cggcaagcgc gcgctcgtat gggttgagtg ggggaccccca   5280 tggcatgggg tgggtgagcg cggaggcgta catgccgcaa atgtcgtaaa cgtagagggg   5340
ctctctgagt attccaagat atgtagggta gcatcttcca ccgcggatgc tggcgcgcac   5400
gtaatcgtat agttcgtgcg agggagcgag gaggtcggga ccgaggttgc tacgggcggg   5460
ctgctctgct cggaagacta tctgcctgaa gatggcatgt gagttggatg atatggttgg   5520
acgctggaag acgttgaagc tggcgtctgt gagacctacc gcgtcacgca cgaaggaggc   5580
gtaggagtcg cgcagcttgt tgaccagctc ggcggtgacc tgcacgtcta gggcgcagta   5640
gtccagggtt tccttgatga tgtcatactt atcctgtccc ttttttttcc acagctcgcg   5700
gttgaggaca aactcttcgc ggtctttcca gtactcttgg atcggaaacc cgtcggcctc   5760
cgaacggtaa gagcctagca gtagaactg gttgacggcc tggtaggcgc agcatcccett   5820 ttctacgggt agcgcgtatg cctgcgcggc cttccggagc gaggtgtggg tgagcgcaaa   5880
ggtgtccctg accatgactt tgaggtactg gtatttgaag tcagtgtcgt cgcatccgcc   5940
ctgctcccag agcaaaaagt ccgtgcgctt tttggaacgc ggatttggca gggcgaaggt   6000
gacatcgttg aagagtatct ttcccgcgcg aggcataaag ttgcgtgtga tgcggaaggg   6060
tcccggcacc tcgaacggt tgttaattac ctgggcggcg agcacgatct cgtcaaagcc   6120
gttgatgttg tgcccacaa tgtaaagttc caagaagcgc gggatgccct tgatggaagg   6180
caatttttta agttcctcgt aggtgagctc ttcaggggag ctgagcccgt gctctgaaag   6240
ggcccagtct gcaagatgag ggttggaagc gacgaatgag ctccacaggt cacgggccat   6300
tagcatttgc aggtggtcgc gaaaggtcct aaactggcga cctatggcca ttttttctgg   6360
ggtgatgcag tagaaggtaa gcgggtcttg ttcccagcgg tcccatccaa ggttcgcggc   6420
taggtctcgc gcggcagtca ctagaggctc atctccgccg aacttcatga ccagcatgaa   6480
gggcacgagc tgcttcccaa aggcccccat ccaagtatag gtctctacat cgtaggtgac   6540
aaagagacgc tcggtgcgag gatgcgagcc gatcgggaag aactggatct cccgccacca   6600
attggaggag tggctattga tgtggtgaaa gtagaagtcc ctgcgacggg ccgaacactc   6660
gtgctggctt ttgtaaaaac gtgcgcagta ctggcagcgg tgcacgggct gtacatcctg   6720
cacgaggttg acctgacgac cgcgcacaag gaagcagagt gggaatttga gcccctcgcc   6780
tggcgggttt ggctggtggt cttctacttc ggctgcttgt ccttgaccgt ctggctgctc   6840 gagggagtt acggtggatc ggaccaccac gccgcgcgag cccaaagtcc agatgtccgc   6900
gcgcggcggt cggagcttga tgacaacatc gcgcagatgg gagctgtcca tggtctggag   6960
ctcccgcggc gtcaggtcag gcgggagctc ctgcaggttt acctcgcata gacgggtcag   7020
ggcgcgggct agatccaggt gatacctaat ttccaggggc tggttggtgg cggcgtcgat   7080
ggcttgcaag aggccgcatc cccgcggcgc gactacggta ccgcgcggcg ggcggtgggc   7140 cgcggggtg tccttggatg atgcatctaa aagcggtgac gcgggcgagc ccccggaggt   7200 aggggggct ccggacccgc cgggagaggg ggcagggca cgtcggcgcc gcgcgcgggc   7260
aggagctggt gctgcgcgcg taggttgctg gcgaacgcga cgacgcgcg gttgatctcc   7320 tgaatctggc gcctctgcgt gaagacgacg ggcccgtga gcttgaacct gaaagagagt   7380
tcgacagaat caatttcggt gtcgttgacg gcggcctggc gcaaaatctc ctgcacgtct   7440
cctgagttgt cttgataggc gatctccgcc atgaactgct cgatctcttc ctcctggaga   7500
tctccgcgtc cggctcgctc cacggtggcg gcgaggtcgt tggaaatgcg ggccatgagc   7560
```

```
tgcgagaagg cgttgaggcc tccctcgttc cagacgcggc tgtagaccac gcccccttcg  7620
gcatcgcggg cgcgcatgac cacctgcgcg agattgagct ccacgtgccg ggcgaagacg  7680
gcgtagtttc gcaggcgctg aaagaggtag ttgagggtgg tggcggtgtg ttctgccacg  7740
aagaagtaca taacccagcg tcgcaacgtg gattcgttga tatcccccaa ggcctcaagg  7800
cgctccatgg cctcgtagaa gtccacggcg aagttgaaaa actggagtt gcgcgccgac  7860 acggttaact cctcctccag aagacggatg agctcggcga cagtgtcgcg cacctcgcgc  7920
tcaaaggcta caggggcctc ttcttcttct tcaatctcct cttccataag ggcctcccct  7980
tcttcttctt ctggcggcgg tgggggaggg gggacacggg ggcgacgacg gcgcaccggg  8040
aggcggtcga caaagcgctc gatcatctcc ccgcggcgac ggcgcatggt ctcggtgacg  8100
gcgcggccgt tctcgcgggg gcgcagttgg aagacgccgc ccgtcatgtc ccggttatgg  8160
gttggcgggg ggctgccatg cggcagggat acggcgctaa cgatgcatct caacaattgt  8220
tgtgtaggta ctccgccgcc gagggacctg agcgagtccg catcgaccgg atcggaaaac  8280
ctctcgagaa aggcgtctaa ccagtcacag tcgcaaggta ggctgagcac cgtggcgggc  8340
ggcagcgggc ggcggtcggg gttgtttctg cggaggtgc tgctgatgat gtaattaaag  8400
taggcggtct tgagacggcg gatggtcgac agaagcacca tgtccttggg tccggcctgc  8460
tgaatgcgca ggcggtcggc catgccccag gcttcgtttt gacatcggcg caggtctttg  8520
tagtagtctt gcatgagcct ttctaccggc acttcttctt ctccttcctc ttgtcctgca  8580
tctcttgcat ctatcgctgc ggcggcgcg gagtttggcc gtaggtggcg ccctcttcct  8640
cccatgcgtg tgaccccgaa gcccctcatc ggctgaagca gggctaggtc ggcgacaacg  8700
cgctcggcta atatgccctg ctgcacctgc gtgagggtag actggaagtc atccatgtcc  8760
acaaagcggt ggtatgcgcc cgtgttgatg gtgtaagtgc agttggccat aacggaccag  8820
ttaacggtct ggtgacccgg ctgcgagagc tcggtgtacc tgagacgcga gtaagccctc  8880
gagtcaaata cgtagtcgtt gcaagtccgc accaggtact ggtatcccac caaaaagtgc  8940
ggcggcggct ggcggtagag gggccagcgt agggtggccg gggctccggg ggcgagatct  9000
tccaacataa ggcgatgata tccgtagatg tacctggaca tccaggtgat gccggcggcg  9060
gtggtggagg cgcgcggaaa gtcgcggacg cggttccaga tgttgcgcag cggcaaaaag  9120
tgctccatgg tcgggacgct ctggccggtc aggcgcgcgc aatcgttgac gctctagcgt  9180
gcaaaaggag agcctgtaag cgggcactct tccgtggtct ggtggataaa ttcgcaaggg  9240
tatcatggcg gacgaccggg gttcgagccc cgtatccggc cgtccgccgt gatccatgcg  9300
gttaccgccc gcgtgtcgaa cccaggtgtg cgacgtcaga caacggggga gtgctccttt  9360
tggcttcctt ccaggcgcgg cggctgctgc gctagctttt ttggccactg gccgcgcgca  9420
gcgtaagcgg ttaggctgga aagcgaaagc attaagtggc tcgctccctg tagccggagg  9480
gttattttcc aagggttgag tcgcgggacc cccggttcga gtctcggacc ggccggactg  9540
cggcgaacgg gggtttgcct ccccgtcatg caagacccccg cttgcaaatt cctccggaaa  9600
cagggacgag cccctttttt gcttttccca gatgcatccg gtgctgcggc agatgcgccc  9660
ccctcctcag cagcggcaag agcaagagca gcggcagaca tgcagggcac cctcccctcc  9720
tcctaccgcg tcaggagggg cgacatccgc ggttgacgcg gcagcagatg gtgattacga  9780 accccgcgg cgccgggccc ggcactacct ggacttggag gagggcgagg gcctggcgcg  9840
gctaggagcg ccctctcctg agcggcaccc aaggggtgcag ctgaagcgtg atacgcgtga  9900
ggcgtacgtg ccgcggcaga acctgtttcg cgaccgcgag ggagaggagc ccgaggagat  9960
```

```
gcgggatcga aagttccacg cagggcgcga gctgcggcat ggcctgaatc gcgagcggtt    10020
gctgcgcgag gaggactttg agcccgacgc gcgaaccggg attagtcccg cgcgcgcaca    10080
cgtggcggcc gccgacctgg taaccgcata cgagcagacg gtgaaccagg agattaactt    10140
tcaaaaaagc tttaacaacc acgtgcgtac gcttgtggcg cgcgaggagg tggctatagg    10200
actgatgcat ctgtgggact ttgtaagcgc gctggagcaa aacccaaata gcaagccgct    10260
catggcgcag ctgttcctta tagtgcagca cagcagggac aacgaggcat tcagggatgc    10320
gctgctaaac atagtagagc ccgagggccg ctggctgctc gatttgataa acatcctgca    10380
gagcatagtg gtgcaggagc gcagcttgag cctggctgac aaggtggccg ccatcaacta    10440
ttccatgctt agcctgggca agttttacgc ccgcaagata taccatcccc cttacgttcc    10500
catagacaag gaggtaaaga tcgaggggtt ctacatgcgc atggcgctga aggtgcttac    10560
cttgagcgac gacctgggcg tttatcgcaa cgagcgcatc cacaaggccg tgagcgtgag    10620
ccggcggcgc gagctcagcg accgcgagct gatgcacagc ctgcaaaggg ccctggctgg    10680
cacgggcagc ggcgatagag aggccgagtc ctactttgac gcgggcgctg acctgcgctg    10740
ggccccaagc cgacgcgccc tggaggcagc tggggccgga cctgggctgg cggtggcacc    10800
cgcgcgcgct ggcaacgtcg gcggcgtgga ggaatatgac gaggacgatg agtacgagcc    10860
agaggacggc gagtactaag cggtgatgtt tctgatcaga tgatgcaaga cgcaacggac    10920
ccggcggtgc gggcggcgct gcagagccag ccgtccggcc ttaactccac ggacgactgg    10980
cgccaggtca tggaccgcat catgtcgctg actgcgcgca atcctgacgc gttccggcag    11040
cagccgcagg ccaaccggct ctccgcaatt ctggaagcgg tggtcccggc gcgcgcaaac    11100
cccacgcacg agaaggtgct ggcgatcgta aacgcgctgg ccgaaaacag gccatccgg    11160
cccgacgagg ccggcctggt ctacgacgcg ctgcttcagc gcgtggctcg ttacaacagc    11220
ggcaacgtgc agaccaacct ggaccggctg gtggggatg tgcgcgaggc cgtgggcgcag    11280
cgtgagcgcg cgcagcagca gggcaacctg ggctccatgg ttgcactaaa cgccttcctg    11340
agtacacagc ccgccaacgt gccgcggga caggaggact acaccaactt tgtgagcgca    11400
ctgcggctaa tggtgactga gacaccgcaa agtgaggtgt accagtctgg gccagactat    11460
tttttccaga ccagtagaca aggcctgcag accgtaaacc tgagccaggc tttcaaaaac    11520
ttgcaggggc tgtgggggt gcgggctccc acaggcgacc gcgcgaccgt gtctagcttg    11580
ctgacgccca actcgcgcct gttgctgctg ctaatagcgc ccttcacgga cagtggcagc    11640
gtgtcccggg acacatacct aggtcacttg ctgacactgt accgcgaggc cataggtcag    11700
gcgcatgtgg acgagcatac tttccaggag attacaagtg tcagccgcgc gctggggcag    11760
gaggacacgg cagcctggaa ggcaaccca aactacctgc tgaccaaccg gcggcagaag    11820
atcccctcgt tgcacagttt aaacagcgag gaggagcgca ttttgcgcta cgtgcagcag    11880
agcgtgagcc ttaacctgat gcgcgacggg gtaacgccca cgtggcgct ggacatgacc    11940
gcgcgcaaca tggaacccggg catgtatgcc tcaaaccggc cgtttatcaa ccgcctaatg    12000
gactacttgc atcgcgcggc cgccgtgaac cccgagtatt tcaccaatgc catcttgaac    12060
ccgcactggc taccgcccc tggttttctac accgggggat tcgaggtgcc cgagggtaac    12120
gatggattcc tctgggacga catagacgac agcgtgtttt ccccgcaacc gcagaccctg    12180
ctagagttgc aacagcgcga gcaggcagag gcggcgctgc gaaaggaaag cttccgcagg    12240
ccaagcagct tgtccgatct aggcgctgcg ggccccgcgt cagatgctag tagcccattt    12300
ccaagcttga tagggtctct taccagcact cgcaccaccc gcccgcgcct gctgggcgag    12360
```

```
gaggagtacc taaacaactc gctgctgcag ccgcagcgcg aaaaaaacct gcctccggca   12420
tttcccaaca acgggataga gagcctagtg gacaagatga gtagatggaa gacgtacgcg   12480
caggagcaca gggacgtgcc aggcccgcgc ccgcccaccc gtcgtcaaag gcacgaccgt   12540
cagcggggtc tggtgtggga ggacgatgac tcggcagacg acagcagcgt cctggatttg   12600
ggagggagtg gcaacccgtt tgcgcacctt cgcccaggc tggggagaat gttttaaaaa   12660 aaaaaagca tgatgcaaaa taaaaaactc accaaggcca tggcaccgag cgttggtttt   12720
cttgtattcc ccttagtatg cggcgcgcg cgatgtatga ggaaggtcct cctccctcct   12780
acgagagtgt ggtgagcgcg gcgccagtgg cggcggcgct gggttctccc ttcgatgctc   12840
ccctggaccc gccgtttgtg cctccgcggt acctgcggcc taccgggggg agaaacagca   12900
tccgttactc tgagttggca cccctattcg acaccacccg tgtgtacctg gtggacaaca   12960
agtcaacgga tgtggcatcc ctgaactacc agaacgacca cagcaacttt ctgaccacgg   13020
tcattcaaaa caatgactac agcccggggg aggcaagcac acagaccatc aatcttgacg   13080
accggtcgca ctggggcggc gacctgaaaa ccatcctgca taccaacatg ccaaatgtga   13140
acgagttcat gtttaccaat aagtttaagg cgcgggtgat ggtgtcgcgc ttgcctacta   13200
aggacaatca ggtggagctg aaatacgagt gggtggagtt cacgctgccc gagggcaact   13260
actccgagac catgaccata gacctatga acaacgcgat cgtggagcac tacttgaaag   13320
tgggcagaca gaacggggtt ctggaaagcg acatcggggt aaagtttgac cccgcaact   13380 tcagactggg gtttgacccc gtcactggtc ttgtcatgcc tggggtatat acaaacgaag   13440
ccttccatcc agacatcatt ttgctgccag gatgcggggt ggacttcacc cacagccgcc   13500
tgagcaactt gttgggcatc cgcaagcggc aaccccttcca ggagggcttt aggatcacct   13560
acgatgatct ggagggtggt aacattcccg cactgttgga tgtggacgcc taccaggcga   13620
gcttgaaaga tgacaccgaa cagggcgggg gtggcgcagg cggcagcaac agcagtggca   13680
gcggcgcgga agagaactcc aacgcggcag ccgcggcaat gcagccggtg gaggacatga   13740
acgatcatgc cattcgcggc gacacctttg ccacacgggc tgaggagaag cgcgctgagg   13800
ccgaagcagc ggccgaagct gccgcccccg ctgcgcaacc cgaggtcgag aagcctcaga   13860
agaaaccggt gatcaaaccc ctgacagagg acagcaagaa acgcagttac aacctaataa   13920
gcaatgacag caccttcacc cagtaccgca gctggtacct tgcatacaac tacggcgacc   13980
ctcagaccgg aatccgctca tggaccctgc tttgcactcc tgacgtaacc tgcggctcgg   14040
agcaggtcta ctggtcgttg ccagacatga tgcaagaccc cgtgaccttc cgctccacgc   14100
gccagatcag caactttccg gtggtgggcg ccgagctgtt gccgtgcac tccaagagct   14160 tctacaacga ccaggccgtc tactcccaac tcatccgcca gtttacctct ctgacccacg   14220
tgttcaatcg cttttcccgag aaccagattt tggcgcgccc gccagcccc accatcacca   14280 ccgtcagtga aaacgttcct gctctcacag atcacgggac gctaccgctg cgcaacagca   14340
tcggaggagt ccagcgagtg accattactg acgccgacgc ccgcacctgc ccctacgttt   14400
acaaggccct gggcatagtc tcgccgcgcg tcctatcgag ccgcacttttt tgagcaagca   14460 tgtccatcct tatatcgccc agcaataaca caggctgggg cctgcgcttc ccaagcaaga   14520
tgtttggcgg ggccaagaag cgctccgacc aacacccagt gcgcgtgcgc gggcactacc   14580
gcgcgccctg ggggcgcgcac aaaacgcggc gcactgggcg caccaccgtc gatgacgcca   14640
tcgacgcggt ggtggaggag gcgcgcaact acacgcccac gccgccacca gtgtccacag   14700
tggacgcggc cattcagacc gtggtgcgcg gagcccggcg ctatgctaaa atgaagagac   14760
```

```
ggcggaggcg cgtagcacgt cgccaccgcc gccgacccgg cactgccgcc caacgcgcgg   14820
cggcggccct gcttaaccgc gcacgtcgca ccggccgacg ggcggccatg cgggccgctc   14880
gaaggctggc cgcgggtatt gtcactgtgc cccccaggtc caggcgacga gcggccgccg   14940
cagcagccgc ggccattagt gctatgactc agggtcgcag gggcaacgtg tattgggtgc   15000
gcgactcggt tagcggcctg cgcgtgcccg tgcgcacccg ccccccgcgc aactagattg   15060
caagaaaaaa ctacttagac tcgtactgtt gtatgtatcc agcggcggcg gcgcgcaacg   15120
aagctatgtc caagcgcaaa atcaaagaag agatgctcca ggtcatcgcg ccggagatct   15180
atggcccccc gaagaaggaa gagcaggatt acaagccccg aaagctaaag cgggtcaaaa   15240
agaaaaagaa agatgatgat gatgaacttg acgacgaggt ggaactgctg cacgctaccg   15300
cgcccaggcg acgggtacag tggaaaggtc gacgcgtaaa acgtgttttg cgacccggca   15360
ccaccgtagt ctttacgccc ggtgagcgct ccacccgcac ctacaagcgc gtgtatgatg   15420
aggtgtacgg cgacgaggac ctgcttgagc aggccaacga gcgcctcggg gagtttgcct   15480
acggaaagcg gcataaggac atgctggcgt tgccgctgga cgagggcaac caacacccta   15540
gcctaaagcc cgtaacactg cagcaggtgc tgcccgcgct tgcaccgtcc gaagaaaagc   15600
gcggcctaaa gcgcgagtct ggtgacttgg cacccaccgt gcagctgatg gtacccaagc   15660
gccagcgact ggaagatgtc ttggaaaaaa tgaccgtgga acctgggctg agcccgagg   15720 tccgcgtgcg gccaatcaag caggtggcgc cgggactggg cgtgcagacc gtggacgttc   15780
agatacccac taccagtagc accagtattg ccaccgccac agagggcatg gagacacaaa   15840
cgtccccggt tgcctcagcg gtggcggatg ccgcggtgca ggcggtcgct gcggccgcgt   15900
ccaagacctc tacggaggtg caaacggacc cgtggatgtt tcgcgtttca gccccccggc   15960
gcccgcgccg ttcgaggaag tacggcgccg ccagcgcgct actgcccgaa tatgccctac   16020
atccttccat tgcgcctacc cccggctatc gtggctacac ctaccgcccc agaagacgag   16080
caactacccg acgccgaacc accactggaa cccgccgccg ccgtcgccgt cgccagcccg   16140
tgctggcccc gatttccgtg cgcagggtgg ctcgcgaagg aggcaggacc ctggtgctgc   16200
caacagcgcg ctaccacccc agcatcgttt aaaagccggt ctttgtggtt cttgcagata   16260
tggccctcac ctgccgcctc cgtttcccgg tgccgggatt ccgaggaaga atgcaccgta   16320
ggaggggcat ggccggccac ggcctgacgg gcggcatgcg tcgtgcgcac caccggcggc   16380
ggcgcgcgtc gcaccgtcgc atgcgcggcg gtatcctgcc cctccttatt ccactgatcg   16440
ccgcggcgat tggcgccgtg cccggaattg catccgtggc cttgcaggcg cagagacact   16500
gattaaaaac aagttgcatg tggaaaaatc aaaataaaaa gtctggactc tcacgctcgc   16560
ttggtcctgt aactattttg tagaatggaa gacatcaact ttgcgtctct ggccccgcga   16620
cacggctcgc gcccgttcat gggaaactgg caagatatcg gcaccagcaa tatgagcggt   16680
ggcgccttca gctgggctc gctgtggagc ggcattaaaa atttcggttc caccgttaag   16740
aactatggca gcaaggcctg gaacagcagc acaggccaga tgctgaggga taagttgaaa   16800
gagcaaaatt tccaacaaaa ggtggtagat ggcctggcct ctggcattag cggggtggtg   16860
gacctggcca accaggcagt gcaaaataag attaacagta agcttgatcc ccgccctccc   16920
gtagaggagc ctccaccggc cgtggagaca gtgtctccag aggggcgtgg cgaaaagcgt   16980
ccgcgccccg acagggaaga aactctggtg acgcaaatag acgagcctcc ctcgtacgag   17040
gaggcactaa agcaaggcct gcccaccacc cgtcccatcg cgcccatggc taccggagtg   17100
ctgggccagc acacacccgt aacgctggac ctgcctcccc ccgccgacac ccagcagaaa   17160
```

```
cctgtgctgc caggcccgac cgccgttgtt gtaacccgtc ctagccgcgc gtccctgcgc    17220
cgcgccgcca gcggtccgcg atcgttgcgg cccgtagcca gtggcaactg gcaaagcaca    17280
ctgaacagca tcgtgggtct gggggtgcaa tccctgaagc gccgacgatg cttctgatag    17340
ctaacgtgtc gtatgtgtgt catgtatgcg tccatgtcgc cgccagagga gctgctgagc    17400
cgccgcgcgc ccgcttttcca agatggctac cccttcgatg atgccgcagt ggtcttacat   17460
gcacatctcg ggccaggacg cctcggagta cctgagcccc gggctggtgc agtttgcccg    17520
cgccaccgag acgtacttca gcctgaataa caagtttaga aaccccacgg tggcgcctac    17580
gcacgacgtg accacagacc ggtcccagcg tttgacgctg cggttcatcc ctgtggaccg    17640
tgaggatact cgctactcgt acaaggcgcg gttcaccta gctgtgggtg ataaccgtgt     17700
gctggacatg gcttccacgt actttgacat ccgcggcgtg ctggacaggg cccctacttt    17760
taagccctac tctggcactg cctacaacgc cctggctccc aagggtgccc caaatccttg    17820
cgaatgggat gaagctgcta ctgctcttga aataaaccta gaagaagagg acgatgacaa    17880
cgaagacgaa gtagacgagc aagctgagca gcaaaaaact cacgtatttg gcaggcgcc    17940
ttattctggt ataaatatta caaggaggg tattcaaata ggtgtcgaag gtcaaacacc     18000
taaatatgcc gataaaacat ttcaacctga acctcaaata ggagaatctc agtggtacga    18060
aacagaaatt aatcatgcag ctgggagagt cctaaaaaag actacccaa tgaaaccatg     18120
ttacggttca tatgcaaaac ccacaaatga aaatggaggg caaggcattc ttgtaaagca    18180
acaaaatgga aagctagaaa gtcaagtgga aatgcaattt ttctcaacta ctgaggcagc    18240
cgcaggcaat ggtgataact tgactcctaa agtggtattg tacagtgaag atgtagatat    18300
agaaaccccca gacactcata tttcttacat gcccactatt aaggaaggta actcacgaga    18360
actaatgggc caacaatcta tgcccaacag gcctaattac attgctttta gggacaattt    18420
tattggtcta atgtattaca acagcacggg taatatgggt gttctggcgg ccaagcatc    18480
gcagttgaat gctgttgtag atttgcaaga cagaaacaca gagctttcat accagctttt    18540
gcttgattcc attggtgata gaccaggta ctttttctatg tggaatcagg ctgttgacag    18600
ctatgatcca gatgttagaa ttattgaaaa tcatggaact gaagatgaac ttccaaatta    18660
ctgctttcca ctgggaggtg tgattaatac agagactctt accaaggtaa aacctaaaac    18720
aggtcaggaa aatggatggg aaaaagatgc tacagaattt tcagataaaa atgaaataag    18780
agttggaaat aattttgcca tggaaatcaa tctaaatgcc aacctgtgga gaaatttcct    18840
gtactccaac atagcgctgt atttgcccga caagctaaag tacagtcctt ccaacgtaaa    18900
aattctgat aacccaaaca cctacgacta catgaacaag cgagtggtgg ctcccgggct    18960
agtggactgc tacattaacc ttggagcacg ctggtcccctt gactatatgg acaacgtcaa    19020
cccatttaac caccaccgca atgctggcct gcgctaccgc tcaatgttgc tgggcaatgg    19080
tcgctatgtg cccttccaca tccaggtgcc tcagaagttc tttgccatta aaaacctcct    19140
tctcctgccg ggctcataca cctacgagtg gaacttcagg aaggatgtta acatggttct    19200
gcagagctcc ctaggaaatg acctaagggt tgacggagcc agcattaagt ttgatagcat    19260
ttgcctttac gccaccttct tcccccatggc ccacaacacc gcctccacgc ttgaggccat    19320
gcttagaaac gacaccaacg accagtcctt taacgactat ctctccgccg ccaacatgct    19380
ctaccctata cccgccaacg ctaccaacgt gcccatatcc atcccctccc gcaactgggc    19440
ggctttccgc ggctgggcct tcacgcgcct taagactaag gaaacccat cactgggctc     19500
gggctacgac ccttattaca cctactctgg ctctataccc tacctagatg gaaccttta    19560
```

```
cctcaaccac acctttaaga aggtggccat tacctttgac tcttctgtca gctggcctgg    19620
caatgaccgc ctgcttaccc ccaacgagtt tgaaattaag cgctcagttg acggggaggg    19680
ttacaacgtt gcccagtgta acatgaccaa agactggttc ctggtacaaa tgctagctaa    19740
ctataacatt ggctaccagg gcttctatat cccagagagc tacaaggacc gcatgtactc    19800
cttctttaga aacttccagc ccatgagccg tcaggtggtg gatgatacta aatacaagga    19860
ctaccaacag gtgggcatcc tacaccaaca caacaactct ggatttgttg gctaccttgc    19920
ccccaccatg cgcgaaggac aggcctaccc tgctaacttc ccctatccgc ttataggcaa    19980
gaccgcagtt gacagcatta cccagaaaaa gtttctttgc gatcgcaccc tttggcgcat    20040
cccattctcc agtaaccttta tgtccatggg cgcactcaca gacctgggcc aaaaccttct    20100
ctacgccaac tccgcccacg cgctagacat gacttttgag gtggatccca tggacgagcc    20160
caccttctt tatgttttgt ttgaagtctt tgacgtggtc cgtgtgcacc agccgcaccg    20220
cggcgtcatc gaaaccgtgt acctgcgcac gcccttctcg gccggcaacg ccacaacata    20280
aagaagcaag caacatcaac aacagctgcc gccatgggct ccagtgagca ggaactgaaa    20340
gccattgtca aagatcttgg ttgtgggcca tattttttgg gcacctatga caagcgcttt    20400
ccaggctttg tttctccaca caagctcgcc tgcgccatag tcaatacggc cggtcgcgag    20460
actggggcg tacactggat ggcctttgcc tggaacccgc actcaaaaac atgctacctc    20520
tttgagccct ttggcttttc tgaccagcga ctcaagcagg tttaccagtt tgagtacgag    20580
tcactcctgc gccgtagcgc cattgcttct tcccccgacc gctgtataac gctggaaaag    20640
tccacccaaa gcgtacaggg gcccaactcg gccgcctgtg gactattctg ctgcatgttt    20700
ctccacgcct ttgccaactg gccccaaaact cccatggatc acaaccccac catgaacctt    20760
attaccgggg tacccaactc catgctcaac agtccccagg tacagcccac cctgcgtcgc    20820
aaccaggaac agctctacag cttcctggag cgccactcgc cctacttccg cagccacagt    20880
gcgcagatta ggagcgccac ttcttttttgt cacttgaaaa acatgtaaaa ataatgtact    20940
agagacactt tcaataaagg caaatgcttt tatttgtaca ctctcgggtg attatttacc    21000
cccacccttg ccgtctgcgc cgtttaaaaa tcaaaggggt tctgccgcgc atcgctatgc    21060
gccactggca gggacacgtt gcgatactgg tgtttagtgc tccacttaaa ctcaggcaca    21120
accatccgcg gcagctcggt gaagttttca ctccacaggc tgcgcaccat caccaacgcg    21180
tttagcaggt cgggcgccga tatcttgaag tcgcagttgg ggcctccgcc ctgcgcgcgc    21240
gagttgcgat acacagggtt gcagcactgg aacactatca gcgccgggtg gtgcacgctg    21300
gccagcacgc tcttgtcgga gatcagatcc gcgtccaggt cctccgcgtt gctcagggcg    21360
aacggagtca actttggtag ctgccttccc aaaaagggcg cgtgcccagg ctttgagttg    21420
cactcgcacc gtagtggcat caaaaggtga ccgtgcccgg tctgggcgtt aggatacagc    21480
gcctgcataa aagccttgat ctgcttaaaa gccacctgag cctttgcgcc ttcagagaag    21540
aacatgccgc aagacttgcc ggaaaactga ttggccggac aggccgcgtc gtgcacgcag    21600
caccttgcgt cggtgttgga gatctgcacc acatttcggc cccaccggtt cttcacgatc    21660
ttggccttgc tagactgctc cttcagcgcg cgctgcccgt tttcgctcgt cacatccatt    21720
tcaatcacgt gctccttatt tatcataatg cttccgtgta gacacttaag ctcgccttcg    21780
atctcagcgc agcggtgcag ccacaacgcg cagcccgtgg gctcgtgatg cttgtaggtc    21840
acctctgcaa acgactgcag gtacgcctgc aggaatcgcc ccatcatcgt cacaaaggtc    21900
ttgttgctgg tgaaggtcag ctgcaacccg cggtgctcct cgttcagcca ggtcttgcat    21960
```

```
acggccgcca gagcttccac ttggtcaggc agtagtttga agttcgcctt tagatcgtta   22020
tccacgtggt acttgtccat cagcgcgcgc gcagcctcca tgcccttctc ccacgcagac   22080
acgatcggca cactcagcgg gttcatcacc gtaatttcac tttccgcttc gctgggctct   22140
tcctcttcct cttgcgtccg cataccacgc gccactgggt cgtcttcatt cagccgccgc   22200
actgtgcgct tacctccttt gccatgcttg attagcaccg gtgggttgct gaaacccacc   22260
atttgtagcg ccacatcttc tctttcttcc tcgctgtcca cgattacctc tggtgatggc   22320
gggcgctcgg gcttgggaga agggcgcttc ttttcttct tgggcgcaat ggccaaatcc   22380
gccgccgagg tcgatggccg cgggctgggt gtgcgcggca ccagcgcgtc ttgtgatgag   22440
tcttcctcgt cctcggactc gatacgccgc ctcatccgct tttttggggg cgcccgggga   22500
ggcggcggcg acgggacgg ggacgacacg tcctccatgg ttgggggacg tcgcgccgca   22560
ccgcgtccgc gctcggggt ggtttcgcgc tgctcctctt cccgactggc catttccttc   22620
tcctataggc agaaaagat catggagtca gtcgagaaga aggacagcct aaccgccccc   22680
tctgagttcg ccaccaccgc ctccaccgat gccgccaacg cgcctaccac cttccccgtc   22740
gaggcacccc cgcttgagga ggaggaagtg attatcgagc aggacccagg ttttgtaagc   22800
gaagacgacg aggaccgctc agtaccaaca gaggataaaa agcaagacca ggacaacgca   22860
gaggcaaacg aggaacaagt cgggcggggg gacgaaaggc atggcgacta cctagatgtg   22920
ggagacgacg tgctgttgaa gcatctgcag cgccagtgcg ccattatctg cgacgcgttg   22980
caagagcgca gcgatgtgcc cctcgccata gcggatgtca gccttgccta cgaacgccac   23040
ctattctcac cgcgcgtacc ccccaaacgc caagaaaacg gcacatgcga gcccaacccg   23100
cgcctcaact tctaccccgt atttgccgtg ccagaggtgc ttgccaccta tcacatcttt   23160
ttccaaaact gcaagatacc cctatcctgc cgtgccaacc gcagccgagc ggacaagcag   23220
ctggccttgc ggcagggcgc tgtcatacct gatatcgcct cgctcaacga agtgccaaaa   23280
atctttgagg gtcttggacg cgacgagaag cgcgcggcaa acgctctgca acaggaaaac   23340
agcgaaaatg aaagtcactc tggagtgttg gtggaactcg agggtgacaa cgcgcgccta   23400
gccgtactaa aacgcagcat cgaggtcacc cactttgcct acccggcact taacctaccc   23460
cccaaggtca tgagcacagt catgagtgag ctgatcgtgc gccgtgcgca gcccctggag   23520
agggatgcaa atttgcaaga acaaacagag gagggcctac ccgcagttgg cgacgagcag   23580
ctagcgcgct ggcttcaaac gcgcgagcct gccgacttgg aggagcgacg caaactaatg   23640
atggccgcag tgctcgttac cgtggagctt gagtgcatgc agcggttctt tgctgacccg   23700
gagatgcagc gcaagctaga ggaaacattg cactacacct ttcgacaggg ctacgtacgc   23760
caggcctgca gatctccaa cgtggagctc tgcaacctgg tctcctacct tggaattttg   23820
cacgaaaacc gccttgggca aaacgtgctt cattccacgc tcaagggcga ggcgcgccgc   23880
gactacgtcc gcgactgcgt ttacttattt ctatgctaca cctggcagac ggccatgggc   23940
gtttggcagc agtgcttgga ggagtgcaac ctcaaggagc tgcagaaact gctaaagcaa   24000
aacttgaagg acctatggac ggccttcaac gagcgctccg tggccgcgca cctggcggac   24060
atcattttcc ccgaacgcct gcttaaaacc ctgcaacagg gtctgccaga cttccaccagt   24120 caaagcatgt tgcagaactt taggaacttt atcctagagc gctcaggaat cttgcccgcc   24180
acctgctgtg cacttcctag cgactttgtg cccattaagt accgcgaatg ccctccgccg   24240 cttggggcc actgctacct tctgcagcta gccaactacc ttgcctacca ctctgacata   24300
atggaagacg tgagcggtga cggtctactg gagtgtcact gtcgctgcaa cctatgcacc   24360
```

```
ccgcaccgct ccctggtttg caattcgcag ctgcttaacg aaagtcaaat tatcggtacc   24420
tttgagctgc agggtccctc gcctgacgaa aagtccgcgg ctccggggtt gaaactcact   24480
ccggggctgt ggacgtcggc ttaccttcgc aaatttgtac ctgaggacta ccacgcccac   24540
gagattaggt tctacgaaga ccaatcccgc ccgcctaatg cggagcttac cgcctgcgtc   24600
attacccagg gccacattct tggccaattg caagccatca acaaagcccg ccaagagttt   24660
ctgctacgaa agggacgggg ggtttacttg gaccccagt ccggcgagga gctcaaccca   24720 atcccccgc cgccgcagcc ctatcagcag cagccgcggg cccttgcttc caggatggc   24780 acccaaaaag aagctgcagc tgccgccgcc acccacggac gaggaggaat actgggacag   24840
tcaggcagag gaggttttgg acgaggagga ggaggacatg atggaagact gggagagcct   24900
agacgaggaa gcttccgagg tcgaagaggt gtcagacgaa acaccgtcac cctcggtcgc   24960
attcccctcg ccggcgcccc agaaatcggc aaccggttcc agcatggcta caacctccgc   25020
tcctcaggcg ccgccggcac tgcccgttcg ccgacccaac cgtagatggg acaccactgg   25080
aaccagggcc ggtaagtcca agcagccgcc gccgttagcc caagagcaac aacagcgcca   25140
aggctaccgc tcatggcgcg ggcacaagaa cgccatagtt gcttgcttgc aagactgtgg   25200
gggcaacatc tccttcgccc gccgctttct tctctaccat cacggcgtgg ccttcccccg   25260
taacatcctg cattactacc gtcatctcta cagcccatac tgcaccggcg gcagcggcag   25320
caacagcagc ggccacacag aagcaaaggc gaccggatag caagactctg acaaagccca   25380
agaaatccac agcggcggca gcagcaggag gaggagcgct gcgtctggcg cccaacgaac   25440
ccgtatcgac ccgcgagctt agaaacagga ttttttcccac tctgtatgct atatttcaac   25500
agagcagggg ccaagaacaa gagctgaaaa taaaaaacag gtctctgcga tccctcaccc   25560
gcagctgcct gtatcacaaa agcgaagatc agcttcggcg cacgctggaa gacgcggagg   25620
ctctcttcag taaatactgc gcgctgactc ttaaggacta gtttcgcgcc ctttctcaaa   25680
tttaagcgcg aaaactacgt catctccagc ggccacaccc ggcgccagca cctgttgtca   25740
gcgccattat gagcaaggaa attcccacgc cctacatgtg gagttaccag ccacaaatgg   25800
gacttgcggc tggagctgcc caagactact caacccgaat aaactacatg agcgcgggac   25860
cccacatgat atcccgggtc aacggaatac gcgcccaccg aaaccgaatt ctcctggaac   25920
aggcggctat taccaccaca cctcgtaata accttaatcc ccgtagttgg cccgctgccc   25980
tggtgtacca ggaaagtccc gctcccacca ctgtggtact tcccagagac gcccaggccg   26040
aagttcagat gactaactca ggggcgcagc ttgcgggcgg ctttcgtcac agggtgcggt   26100
cgcccgggca gggtataact cacctgacaa tcagagggcg aggtattcag ctcaacgacg   26160
agtcggtgag ctcctcgctt ggtctccgtc cggacgggac atttcagatc ggcggcgccg   26220
gccgctcttc attcacgcct cgtcaggcaa tcctaactct gcagacctcg tcctctgagc   26280
cgcgctctgg aggcattgga actctgcaat ttattgagga gtttgtgcca tcggtctact   26340 ttaaccccctt ctcgggacct cccgccacT atccggatca atttattcct aactttgacg   26400
cggtaaagga ctcggcggac ggctacgact gaatgttaag tggagaggca gagcaactgc   26460
gcctgaaaca cctggtccac tgtcgccgcc acaagtgctt tgcccgcgac tccggtgagt   26520
tttgctactt tgaattgccc gaggatcata tcgagggccc ggcgcacggc gtccggctta   26580
ccgcccaggg agagcttgcc cgtagcctga ttcgggagtt tacccagcgc cccctgctag   26640
ttgagcggga caggggaccc tgtgttctca ctgtgatttg caactgtcct aaccctggat   26700
tacatcaaga tcctctagtt aatgtcaggt cgcctaagtc gattaactag agtacccggg   26760
```

```
gatcttattc cctttaacta ataaaaaaaa ataataaagc atcacttact taaaatcagt   26820
tagcaaattt ctgtccagtt tattcagcag cacctccttg ccctcctccc agctctggta   26880
ttgcagcttc ctcctggctg caaactttct ccacaatcta aatggaatgt cagtttcctc   26940
ctgttcctgt ccatccgcac ccactatctt catgttgttg cagatgaagc gcgcaagacc   27000
gtctgaagat accttcaacc ccgtgtatcc atatgacacg gaaaccggtc tccaactgt    27060 gccttttctt actcctccct ttgtatcccc caatgggttt caagagagtc cccctggggt   27120
actctctttg cgcctatccg aacctctagt tacctccaat ggcatgcttg cgctcaaaat   27180
gggcaacggc ctctctctgg acgaggccgg caaccttacc tcccaaaatg taaccactgt   27240
gagcccacct ctcaaaaaaa ccaagtcaaa cataaacctg gaaatatctg caccccctcac  27300 agttacctca gaagccctaa ctgtggctgc cgccgcacct ctaatggtcg cgggcaacac   27360
actcaccatg caatcacagg ccccgctaac cgtgcacgac tccaaactta gcattgccac   27420
ccaaggaccc ctcacagtgt cagaaggaaa gctagccctg caaacatcag gcccctcac   27480 caccaccgat agcagtaccc ttactatcac tgcctcaccc cctctaacta ctgccactgg   27540
tagcttgggc attgacttga agagcccat ttatacacaa aatggaaaac taggactaaa    27600
gtacggggct cctttgcatg taacagacga cctaaacact ttgaccgtag caactggtcc   27660
aggtgtgact attaataata cttccttgca aactaaagtt actggagcct gggttttga    27720 ttcacaaggc aatatgcaac ttaatgtagc aggaggacta aggattgatt ctcaaaacag   27780
acgccttata cttgatgtta gttatccgtt tgatgctcaa aaccaactaa atctaagact   27840
aggacagggc cctcttttta taaactcagc ccacaacttg gatattaact acaacaaagg   27900
cctttacttg tttacagctt caaacaattc caaaaagctt gaggttaacc taagcactgc   27960
caaggggttg atgtttgacg ctacagccat agccattaat gcaggagatg ggcttgaatt   28020
tggttcacct aatgcaccaa acacaaatcc cctcaaaaca aaaattggcc atggcctaga   28080
atttgattca aacaaggcta tggttcctaa actaggaact ggccttagtt ttgacagcac   28140
aggtgccatt acagtaggaa acaaaaataa tgataagcta actttgtgga ccacaccagc   28200
tccatctcct aactgtagac taaatgcaga gaaagatgct aaactcactt tggtcttaac   28260
aaaatgtggc agtcaaatac ttgctacagt ttcagttttg gctgttaaag gcagtttggc   28320
tccaatatct ggaacagttc aaagtgctca tcttattata agatttgacg aaaatggagt   28380
gctactaaac aattccttcc tggacccaga atattggaac tttagaaatg gagatcttac   28440
tgaaggcaca gcctatacaa acgctgttgg atttatgcct aacctatcag cttatccaaa   28500
atctcacggt aaaactgcca aaagtaacat tgtcagtcaa gtttacttaa acggagacaa   28560
aactaaacct gtaacactaa ccattacact aaacggtaca caggaaacag gagacacaac   28620
tccaagtgca tactctatgt cattttcatg ggactggtct ggccacaact acattaatga   28680
aatatttgcc acatcctctt cactttttc atacattgcc caagaataaa gaatcgtttg    28740
tgttatgttt caacgtgttt attttcaat tgcagaaaat ttcaagtcat ttttcattca   28800
gtagtatagc cccaccacca catagcttat acagatcacc gtaccttaat caaactcaca   28860
gaaccctagt attcaacctg ccacctccct cccaacacac agagtacaca gtcctttctc   28920
cccggctggc cttaaaaagc atcatatcat gggtaacaga catattctta ggtgttatat   28980
tccacacggt ttcctgtcga gccaaacgct catcagtgat attaataaac tccccgggca   29040
gctcacttaa gttcatgtcg ctgtccagct gctgagccac aggctgctgt ccaacttgcg   29100
gttgcttaac gggcggcgaa ggagaagtcc acgcctacat gggggtagag tcataatcgt   29160
```

```
gcatcaggat agggcggtgg tgctgcagca gcgcgcgaat aaactgctgc cgccgccgct   29220
ccgtcctgca ggaatacaac atggcagtgg tctcctcagc gatgattcgc accgcccgca   29280
gcataaggcg ccttgtcctc cgggcacagc agcgcaccct gatctcactt aaatcagcac   29340
agtaactgca gcacagcacc acaatattgt tcaaaatccc acagtgcaag gcgctgtatc   29400
caaagctcat ggcggggacc acagaaccca cgtggccatc ataccacaag cgcaggtaga   29460
ttaagtggcg acccctcata aacacgctgg acataaacat tacctctttt ggcatgttgt   29520
aattcaccac ctcccggtac catataaacc tctgattaaa catggcgcca tccaccacca   29580
tcctaaacca gctggccaaa acctgcccgc cggctataca ctgcagggaa ccgggactgg   29640
aacaatgaca gtggagagcc caggactcgt aaccatggat catcatgctc gtcatgatat   29700
caatgttggc acaacacagg cacacgtgca tacacttcct caggattaca agctcctccc   29760
gcgttagaac catatcccag ggaacaaccc attcctgaat cagcgtaaat cccacactgc   29820
agggaagacc tcgcacgtaa ctcacgttgt gcattgtcaa agtgttacat tcgggcagca   29880
gcggatgatc ctccagtatg gtagcgcggg tttctgtctc aaaggaggt agacgatccc   29940 tactgtacga agtgcgccga gacaaccgag atcgtgttgg tcgtagtgtc atgccaaatg   30000
gaacgccgga cgtagtcata tttcctgaag caaaaccagg tgcgggcgtg acaaacagat   30060
ctgcgtctcc ggtctcgccg cttagatcgc tctgtgtagt agttgtagta tatccactct   30120
ctcaaagcat ccaggcgccc cctggcttcg ggttctatgt aaactccttc atgcgccgct   30180
gccctgataa catccaccac cgcagaataa gccacaccca gccaacctac acattcgttc   30240
tgcgagtcac acacgggagg agcgggaaga gctggaagaa ccatgttttt tttttttattc   30300 caaaagatta tccaaaacct caaaatgaag atctattaag tgaacgcgct cccctccggt   30360
ggcgtggtca aactctacag ccaaagaaca gataatggca tttgtaagat gttgcacaat   30420
ggcttccaaa aggcaaacgg ccctcacgtc caagtggacg taaaggctaa acccttcagg   30480
gtgaatctcc tctataaaca ttccagcacc ttcaaccatg cccaaataat tctcatctcg   30540
ccaccttctc aatatatctc taagcaaatc ccgaatatta agtccggcca ttgtaaaaat   30600
ctgctccaga gcgccctcca ccttcagcct caagcagcga atcatgattg caaaaattca   30660
ggttcctcac agacctgtat aagattcaaa agcggaacat taacaaaaat accgcgatcc   30720
cgtaggtccc ttcgcagggc cagctgaaca taatcgtgca ggtctgcacg gaccagcgcg   30780
gccacttccc cgccaggaac catgacaaaa gaacccacac tgattatgac acgcatactc   30840
ggagctatgc taaccagcgt agccccgatg taagcttgtt gcatgggcgg cgatataaaa   30900
tgcaaggtgc tgctcaaaaa atcaggcaaa gcctcgcgca aaaagaaag cacatcgtag   30960 tcatgctcat gcagataaag gcaggtaagc tccggaacca ccacagaaaa agacaccatt   31020
tttctctcaa acatgtctgc gggtttctgc ataaaataa aataaaataa caaaaaaaca   31080
tttaaacatt agaagcctgt cttacaacag gaaaaacaac ccttataagc ataagacgga   31140
ctacggccat gccggcgtga ccgtaaaaaa actggtcacc gtgattaaaa agcaccaccg   31200
acagctcctc ggtcatgtcc ggagtcataa tgtaagactc ggtaaacaca tcaggttgat   31260
tcacatcggt cagtgctaaa aagcgaccga aatagcccgg gggaatacat acccgcaggc   31320
gtagagacaa cattacagcc cccataggag gtataacaaa attaatagga gagaaaaaca   31380
cataaacacc tgaaaaaccc tcctgcctag gcaaaatagc accctcccgc tccagaacaa   31440
catacagcgc ttccacagcg gcagccataa cagtcagcct taccagtaaa aagaaaacc   31500 tattaaaaaa acaccactcg acacggcacc agctcaatca gtcacagtgt aaaaaagggc   31560
```

```
caagtgcaga gcgagtatat ataggactaa aaaatgacgt aacggttaaa gtccacaaaa    31620
aacacccaga aaaccgcacg cgaacctacg cccagaaacg aaagccaaaa aacccacaac    31680
ttcctcaaat cgtcacttcc gttttcccac gttacgtcac ttcccatttt aagaaaacta    31740
caattcccaa cacatacaag ttactccgcc ctaaaaccta cgtcacccgc cccgttccca    31800
cgccccgcgc cacgtcacaa actccacccc ctcattatca tattggcttc aatccaaaat    31860
aaggtatatt attgatgatg                                                31880

<210> SEQ ID NO 508
<211> LENGTH: 846
<212> TYPE: DNA
<213> ORGANISM: Homo sapiens

<400> SEQUENCE: 508
atgggctccg acgttcggga cctgaacgca ctgctgccgg cagttccgtc cctgggtggt      60
ggtggtggtt gcgcactgcc ggttagcggt gcagcacagt gggctccggt tctggacttc     120
gcaccgccgg gtgcatccgc atacggttcc ctgggtggtc cggcaccgcc gccggcaccg     180
ccgccgccgc cgccgccgcc gccgcactcc ttcatcaaac aggaaccgag ctggggtggt     240
gcagaaccgc acgaagaaca gtgcctgagc gcattcaccg ttcacttctc cggccagttc     300
actggcacag ccggagcctg tcgctacggg cccttcggtc ctcctccgcc cagccaggcg     360
tcatccggcc aggccaggat gtttcctaac gcgccctacc tgcccagctg cctcgagagc     420
cagcccgcta ttcgcaatca gggttacagc acggtcacct tcgacgggac gcccagctac     480
ggtcacacgc cctcgcacca tgcggcgcag ttccccaacc actcattcaa gcatgaggat     540
cccatgggcc agcagggctc gctgggtgag cagcagtact cggtgccgcc cccggtctat     600
ggctgccaca ccccccaccga cagctgcacc ggcagccagg cttgctgct gaggacgccc     660 tacagcagtg acaatttata ccaaatgaca tcccagcttg aatgcatgac ctggaatcag     720
atgaacttag gagccacctt aaagggccac agcacagggt acgagagcga taaccacaca     780
acgcccatcc tctgcggagc ccaatacaga atacacacgc acggtgtctt cagaggcatt     840
cagtga                                                                846

<210> SEQ ID NO 509
<211> LENGTH: 15
<212> TYPE: PRT
<213> ORGANISM: Homo sapiens

<400> SEQUENCE: 509

Ala Arg Met Phe Pro Asn Ala Pro Tyr Leu Pro Ser Cys Leu Glu
 1               5                  10                  15

<210> SEQ ID NO 510
<211> LENGTH: 16
<212> TYPE: PRT
<213> ORGANISM: Homo sapiens

<400> SEQUENCE: 510

Asp Asn Leu Tyr Gln Met Thr Ser Gln Leu Glu Cys Met Thr Trp Asn
 1               5                  10                  15

<210> SEQ ID NO 511
<211> LENGTH: 15
```

```
<212> TYPE: PRT
<213> ORGANISM: Homo sapiens

<400> SEQUENCE: 511

Met Thr Ser Gln Leu Glu Cys Met Thr Trp Asn Gln Met Asn Leu
1               5                   10                  15
```

COMPOSITIONS AND METHODS FOR WT1 SPECIFIC IMMUNOTHERAPY

CROSS-REFERENCE TO RELATED APPLICATIONS

This application is a continuation of U.S. patent application Ser. No. 10/427,717, filed Apr. 30, 2003, now issued as U.S. Pat. No. 7,553,494, on Jun. 30, 2009; which is a continuation-in-part of U.S. patent application Ser. No. 10/286,333, filed Oct. 30, 2002, now abandoned; which is a continuation-in-part of U.S. patent application Ser. No. 10/244,830, filed Sep. 16, 2002, now abandoned; which is a continuation-in-part of U.S. patent application Ser. No. 10/195,835, filed Jul. 12, 2002, now issued as U.S. Pat. No. 7,655,249, on Feb. 2, 2010; which is a continuation-in-part of U.S. patent application Ser. No. 10/125,635, filed Apr. 16, 2002, now abandoned; which is a continuation-in-part of U.S. patent application Ser. No. 10/002,603, filed Oct. 30, 2001, now; which is a continuation-in-part of U.S. patent application Ser. No. 09/938,864, filed Aug. 24, 2001, now abandoned; which applications are incorporated herein by reference in their entirety.

STATEMENT REGARDING FEDERALLY SPONSORED RESEARCH OR DEVELOPMENT

This invention was made in part with government support under NIH SBIR Phase I grant number IR43CA81752-01A1. The Government may have certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 210121_610C5_SEQUENCE_LISTING.txt. The text file is 280 KB, was created on May 21, 2009, and is being submitted electronically via EFS-Web.

BACKGROUND OF THE INVENTION

1. Field of the Invention

The present invention relates generally to the immunotherapy of malignant diseases such as leukemia and cancers. The invention is more specifically related to compositions for generating or enhancing an immune response to WT1, and to the use of such compositions for preventing and/or treating malignant diseases.

2. Description of the Related Art

Cancer and leukemia are significant health problems in the United States and throughout the world. Although advances have been made in detection and treatment of such diseases, no vaccine or other universally successful method for prevention or treatment of cancer and leukemia is currently available. Management of the diseases currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and the high mortality continues to be observed in many cancer patients.

Immunotherapies have the potential to substantially improve cancer and leukemia treatment and survival. Recent data demonstrate that leukemia can be cured by immunotherapy in the context of bone marrow transplantation (e.g., donor lymphocyte infusions). Such therapies may involve the generation or enhancement of an immune response to a tumor-associated antigen (TAA). However, to date relatively few TAAs are known and the generation of an immune response against such antigens has, with rare exception, not been shown to be therapeutically beneficial.

Accordingly, there is a need in the art for improved methods for leukemia and cancer prevention and therapy. The present invention fulfills these needs and further provides other related advantages.

BRIEF SUMMARY OF THE INVENTION

Briefly stated, this invention provides compositions and methods for the diagnosis and therapy of diseases such as leukemia and cancer. In one aspect, the present invention provides polypeptides comprising an immunogenic portion of a native WT1, or a variant thereof that differs in one or more substitutions, deletions, additions and/or insertions such that the ability of the variant to react with antigen-specific antisera and/or T-cell lines or clones is not substantially diminished. Within certain embodiments of the present invention, the polypeptide comprises at least an immunogenic portion of WT1 wherein the immunogenic portion is contained within amino acids 2-281 of WT1. Within certain embodiments, the polypeptide comprises no more than 16 consecutive amino acid residues of a native WT1 polypeptide. Within other embodiments, the polypeptide comprises an immunogenic portion of amino acid residues 1-174 of a native WT1 polypeptide or a variant thereof, wherein the polypeptide comprises no more than 16 consecutive amino acid residues present within amino acids 175 to 449 of the native WT1 polypeptide. The immunogenic portion preferably binds to an MHC class I and/or class II molecule. Within certain embodiments, the polypeptide comprises a sequence selected from the group consisting of (a) sequences recited in any one or more of Tables II-XLVI, (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished.

Within other embodiments, the polypeptide comprises a sequence selected from the group consisting of (a) ALL-PAVPSL (SEQ ID NO:34), GATLKGVAA (SEQ ID NO:88), CMTWNQMNL (SEQ ID NOs: 49 and 258), SCLESQPTI (SEQ ID NOs: 199 and 296), SCLESQPAI (SEQ ID NO:198), NLYQMTSQL (SEQ ID NOs: 147 and 284), ALL-PAVSSL (SEQ ID NOs: 35 and 255), RMFPNAPYL (SEQ ID NOs: 185 and 293), VLDFAPPGA (SEQ ID NO:241), VLD-FAPPGAS (SEQ ID NO:411), SEQ ID NOs: 414-450, ALL-PAVPSL (SEQ ID NO:451) (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished. Mimetics may comprises amino acids in combination with one or more amino acid mimetics or may be entirely nonpeptide mimetics.

Within further aspects, the present invention provides polypeptides comprising a variant of an immunogenic portion of a WT1 protein, wherein the variant differs from the immunogenic portion due to substitutions at between 1 and 3 amino acid positions within the immunogenic portion such that the ability of the variant to react with antigen-specific antisera and/or T-cell lines or clones is not substantially reduced or is enhanced relative to a native WT1 protein.

The present invention further provides WT1 polynucleotides that encode a WT1 polypeptide as described above.

Within other aspects, the present invention provides pharmaceutical compositions and vaccines. Pharmaceutical compositions may comprise a polypeptide or mimetic as described above and/or one or more of (i) a WT1 polynucleotide; (ii) an antibody or antigen-binding fragment thereof that specifically binds to a WT1 polypeptide; (iii) a T cell that specifically reacts with a WT1 polypeptide or (iv) an antigen-presenting cell that expresses a WT1 polypeptide, in combination with a pharmaceutically acceptable carrier or excipient. Vaccines comprise a polypeptide as described above and/or one or more of (i) a WT1 polynucleotide, (ii) an antigen-presenting cell that expresses a WT1 polypeptide or (iii) an anti-idiotypic antibody, and a non-specific immune response enhancer. Within certain embodiments, less than 23 consecutive amino acid residues, preferably less than 17 amino acid residues, of a native WT1 polypeptide are present within a WT1 polypeptide employed within such pharmaceutical compositions and vaccines. The immune response enhancer may be an adjuvant. Preferably, an immune response enhancer enhances a T cell response.

The present invention further provides methods for enhancing or inducing an immune response in a patient, comprising administering to a patient a pharmaceutical composition or vaccine as described above. In certain embodiments, the patient is a human.

The present invention further provides methods for inhibiting the development of a malignant disease in a patient, comprising administering to a patient a pharmaceutical composition or vaccine as described above. Malignant diseases include, but are not limited to leukemias (e.g., acute myeloid, acute lymphocytic and chronic myeloid) and cancers (e.g., breast, lung, thyroid or gastrointestinal cancer or a melanoma). The patient may, but need not, be afflicted with the malignant disease, and the administration of the pharmaceutical composition or vaccine may inhibit the onset of such a disease, or may inhibit progression and/or metastasis of an existing disease.

The present invention further provides, within other aspects, methods for removing cells expressing WT1 from bone marrow and/or peripheral blood or fractions thereof, comprising contacting bone marrow, peripheral blood or a fraction of bone marrow or peripheral blood with T cells that specifically react with a WT1 polypeptide, wherein the step of contacting is performed under conditions and for a time sufficient to permit the removal of WT1 positive cells to less than 10%, preferably less than 5% and more preferably less than 1%, of the number of myeloid or lymphatic cells in the bone marrow, peripheral blood or fraction. Bone marrow, peripheral blood and fractions may be obtained from a patient afflicted with a disease associated with WT1 expression, or may be obtained from a human or non-human mammal not afflicted with such a disease.

Within related aspects, the present invention provides methods for inhibiting the development of a malignant disease in a patient, comprising administering to a patient bone marrow, peripheral blood or a fraction of bone marrow or peripheral blood prepared as described above. Such bone marrow, peripheral blood or fractions may be autologous, or may be derived from a related or unrelated human or non-human animal (e.g., syngeneic or allogeneic).

In other aspects, the present invention provides methods for stimulating (or priming) and/or expanding T cells, comprising contacting T cells with a WT1 polypeptide under conditions and for a time sufficient to permit the stimulation and/or expansion of T cells. Such T cells may be autologous, allogeneic, syngeneic or unrelated WT1-specific T cells, and may be stimulated in vitro or in vivo. Expanded T cells may, within certain embodiments, be present within bone marrow, peripheral blood or a fraction of bone marrow or peripheral blood, and may (but need not) be clonal. Within certain embodiments, T cells may be present in a mammal during stimulation and/or expansion. WT1-specific T cells may be used, for example, within donor lymphocyte infusions.

Within related aspects, methods are provided for inhibiting the development of a malignant disease in a patient, comprising administering to a patient T cells prepared as described above. Such T cells may, within certain embodiments, be autologous, syngeneic or allogeneic.

The present invention further provides, within other aspects, methods for monitoring the effectiveness of an immunization or therapy for a malignant disease associated with WT1 expression in a patient. Such methods are based on monitoring antibody, CD4+ T cell and/or CD8+ T cell responses in the patient. Within certain such aspects, a method may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the first biological sample is obtained from a patient prior to a therapy or immunization, and wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample obtained from the same patient following therapy or immunization; and (d) comparing the number of immunocomplexes detected in the first and second biological samples, and therefrom monitoring the effectiveness of the therapy or immunization in the patient.

Within certain embodiments of the above methods, the step of detecting comprises (a) incubating the immunocomplexes with a detection reagent that is capable of binding to the immunocomplexes, wherein the detection reagent comprises a reporter group, (b) removing unbound detection reagent, and (c) detecting the presence or absence of the reporter group. The detection reagent may comprise, for example, a second antibody, or antigen-binding fragment thereof, capable of binding to the antibodies that specifically bind to the WT1 polypeptide or a molecule such as Protein A. Within other embodiments, a reporter group is bound to the WT1 polypeptide, and the step of detecting comprises removing unbound WT1 polypeptide and subsequently detecting the presence or absence of the reporter group.

Within further aspects, methods for monitoring the effectiveness of an immunization or therapy for a malignant disease associated with WT1 expression in a patient may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the biological sample comprises CD4+ and/or CD8+ T cells and is obtained from a patient prior to a therapy or immunization, and wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, wherein the second biological sample is obtained from the same patient following therapy or immunization; and (d) comparing the amount of activation, proliferation and/or lysis of T cells in the first and second biological samples, and therefrom monitoring the effectiveness of the therapy or immunization in the patient.

The present invention further provides methods for inhibiting the development of a malignant disease associated with WT1 expression in a patient, comprising the steps of: (a) incubating CD4+ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; and (b) administering to the patient an effective amount of the proliferated T cells, and therefrom inhibiting the development of a malignant disease in the patient. Within certain embodiments, the step of incubating the T cells may be repeated one or more times.

Within other aspects, the present invention provides methods for inhibiting the development of a malignant disease associated with WT1 expression in a patient, comprising the steps of: (a) incubating CD4+ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; (b) cloning one or more cells that proliferated; and (c) administering to the patient an effective amount of the cloned T cells.

Within other aspects, methods are provided for determining the presence or absence of a malignant disease associated with WT1 expression in a patient, comprising the steps of: (a) incubating CD4+ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide; and (b) detecting the presence or absence of specific activation of the T cells, therefrom determining the presence or absence of a malignant disease associated with WT1 expression. Within certain embodiments, the step of detecting comprises detecting the presence or absence of proliferation of the T cells.

Within further aspects, the present invention provides methods for determining the presence or absence of a malignant disease associated with WT1 expression in a patient, comprising the steps of: (a) incubating a biological sample obtained from a patient with one or more of: (i) a WT1 polypeptide; (ii) a polynucleotide encoding a WT1 polypeptide; or (iii) an antigen presenting cell that expresses a WT1 polypeptide, wherein the incubation is performed under conditions and for a time sufficient to allow immunocomplexes to form; and (b) detecting immunocomplexes formed between the WT1 polypeptide and antibodies in the biological sample that specifically bind to the WT1 polypeptide; and therefrom determining the presence or absence of a malignant disease associated with WT1 expression.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 depicts a comparison of the mouse (MO) and human (HU) WT1 protein sequences (SEQ ID NOS: 320 and 319 respectively).

FIG. 6A) or p287-301 (p287), p299-313 (p299), p421-435 (p421) (Vaccine B; FIG. 6B) and spleen cells pulsed with an irrelevant control peptide (irrelevant peptide) at 25 ug/ml and were assayed after 96 hr for proliferation by ($^3$H) thymidine incorporation. Bars represent the stimulation index (SI), which is calculated as the mean of the experimental wells divided by the mean of the control (B6 spleen cells with no antigen).

FIGS. 8A and 8B present the results of TSITES Analysis of human WT1 (SEQ ID NO:319) for peptides that have the potential to elicit Th responses. Regions indicated by "A" are AMPHI midpoints of blocks, "R" indicates residues matching the Rothbard/'Taylor motif, "D" indicates residues matching the IAd motif, and 'd' indicates residues matching the IEd motif.

FIG. 9A illustrates the lysis of target cells by allogeneic cell lines and FIG. 9B shows the lysis of peptide coated cell lines. In each case, the % lysis (as determined by standard chromium release assays) is shown at three indicated effector: target ratios. Results are provided for lymphoma cells (LSTRA and E10), as well as E10+p235-243 (E10+P235). E10 cells are also referred to herein as EL-4 cells.

FIG. 10A illustrates that T-cells of non-immunized B6 mice do not kill WT1 positive tumor cell lines.

FIG. 10B illustrates the lysis of the target cells by allogeneic cell lines. FIGS. 10C and 10D demonstrate the lysis of WT1 positive tumor cell lines, as compared to WT1 negative cell lines in two different experiments. In addition, FIGS. 10C and 10D show the lysis of peptide-coated cell lines (WT1 negative cell line E10 coated with the relevant WT1 peptide P117) In each case, the % lysis (as determined by standard chromium release assays) is shown at three indicated effector: target ratios. Results are provided for lymphoma cells (E10), prostate cancer cells (TRAMP-C), a transformed fibroblast cell line (BLK-SV40), as well as E10+p117.

FIGS. 11A and 11B are histograms illustrating the ability of representative peptide P117-139 specific CTL to lyse WT1 positive tumor cells. Three weeks after the third immunization, spleen cells of mice that had been inoculated with the peptides p235-243 or p117-139 were stimulated in vitro with the relevant peptide and tested for ability to lyse targets incubated with WT1 peptides as well as WT1 positive and negative tumor cells. The bars represent the mean % specific lysis in chromium release assays performed in triplicate with an E:T ratio of 25:1. FIG. 11A shows the cytotoxic activity of the p235-243 specific T cell line against the WT1 negative cell line EL-4 (EL-4, WT1 negative); EL-4 pulsed with the relevant (used for immunization as well as for restimulation) peptide p235-243 (EL-4+p235); EL-4 pulsed with the irrelevant peptides p117-139 (EL-4+p117), p126-134 (EL-4+p126) or p130-138 (EL-4+p130) and the WT1 positive tumor cells BLK-SV40 (BLK-SV40, WT1 positive) and TRAMP-C (TRAMP-C, WT1 positive), as indicated. FIG. 11B shows cytotoxic activity of the p117-139 specific T cell line against EL-4; EL-4 pulsed with the relevant peptide P117-139 (EL-4+p117) and EL-4 pulsed with the irrelevant peptides p123-131 (EL-4+p123), or p128-136 (EL-4+p128); BLK-SV40 and TRAMP-C, as indicated.

FIGS. 12A and 12B are histograms illustrating the specificity of lysis of WT1 positive tumor cells, as demonstrated by cold target inhibition. The bars represent the mean % specific lysis in chromium release assays performed in triplicate with an E:T ratio of 25:1. FIG. 12A shows the cytotoxic activity of the p117-139 specific T cell line against the WT1 negative cell line EL-4 (EL-4, WT1 negative); the WT1 positive tumor cell line TRAMP-C (TRAMP-C, WT1 positive); TRAMP-C cells incubated with a ten-fold excess (compared to the hot target) of EL-4 cells pulsed with the relevant peptide p117-139 (TRAMP-C+p117 cold target) without $^{51}$Cr labeling and TRAMP-C cells incubated with EL-4 pulsed with an irrelevant peptide without $^{51}$Cr labeling (TRAMP-C+irrelevant cold target), as indicated. FIG. 12B shows the cytotoxic activity of the p117-139 specific T cell line against the WT1 negative cell line EL-4 (EL-4, WT1 negative); the WT1 positive tumor cell line BLK-SV40 (BLK-SV40, WT1 positive); BLK-SV40 cells incubated with the relevant cold target (BLK-SV40+p117 cold target) and BLK-SV40 cells incubated with the irrelevant cold target (BLK-SV40+irrelevant cold target), as indicated.

FIG. 13A shows the cytotoxic activity of the p117-139 specific T cell line against the WT1 negative cell line EL-4 (EL-4, WT1 negative) and EL-4 cells pulsed with the peptides p117-139 (EL-4+p117), p119-127 (EL-4+p119), p120-128 (EL-4+p120), p123-131 (EL-4+p123), p126-134 (EL-4+p126), p128-136 (EL-4+p128), and p130-138 (EL-4+p130). FIG. 13B shows the cytotoxic activity of the CTL line after restimulation with p126-134 against the WT1 negative cell line EL-4, EL-4 cells pulsed with p117-139 (EL-4+p117), p126-134 (EL-4+p126) and the WT1 positive tumor cell line TRAMP-C. FIG. 13C shows the cytotoxic activity of the CTL line after restimulation with p130-138 against EL-4, EL-4 cells pulsed with p117-139 (EL-4+p117), p130-138 (EL-4+p130) and the WT1 positive tumor cell line TRAMP-C.

Figure 17:
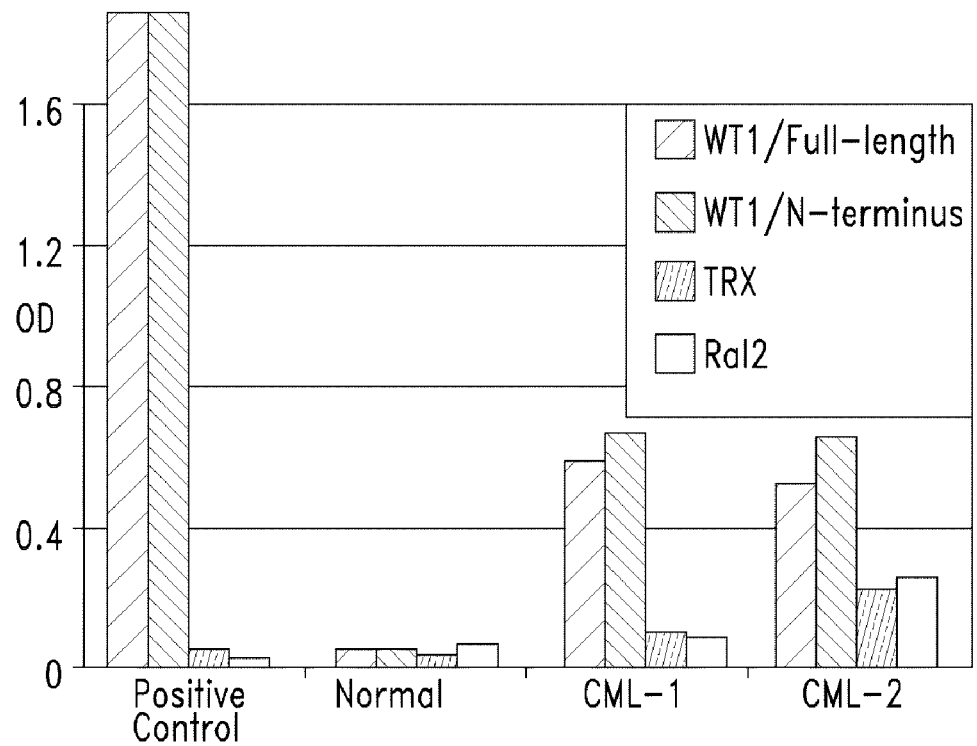

FIG. 17 depicts serum antibody reactivity to WT1 proteins and control proteins in 2 patients with CML. Reactivity of serum antibody to WT1/full-length, WT1/N-terminus, TRX and Ra12 proteins was evaluated by ELISA in 2 patients with CML. The OD values depicted were from ELISA using a 1:500 serum dilution. CML-1 and CML-2 denote serum from 2 of the individual patients in FIG. 3 with demonstrated antibody reactivity to WT1/full-length. The WT1/full-length protein was expressed as a fusion protein with Ra12. The WT1/N-terminus protein was expressed as a fusion protein with TRX. The control Ra12 and TRX proteins were purified in a similar manner. The results confirm that the serum antibody reactivity against the WT1 fusion proteins is directed against the WT1 portions of the protein.

FIG. 18 provides the characteristics of the recombinant WT1 proteins used for serological analysis.

FIGS. 19A1-19E3 is a bar graph depicting the antibody responses in mice elicited by vaccination with different doses of WT1 protein.

Figure 20A:
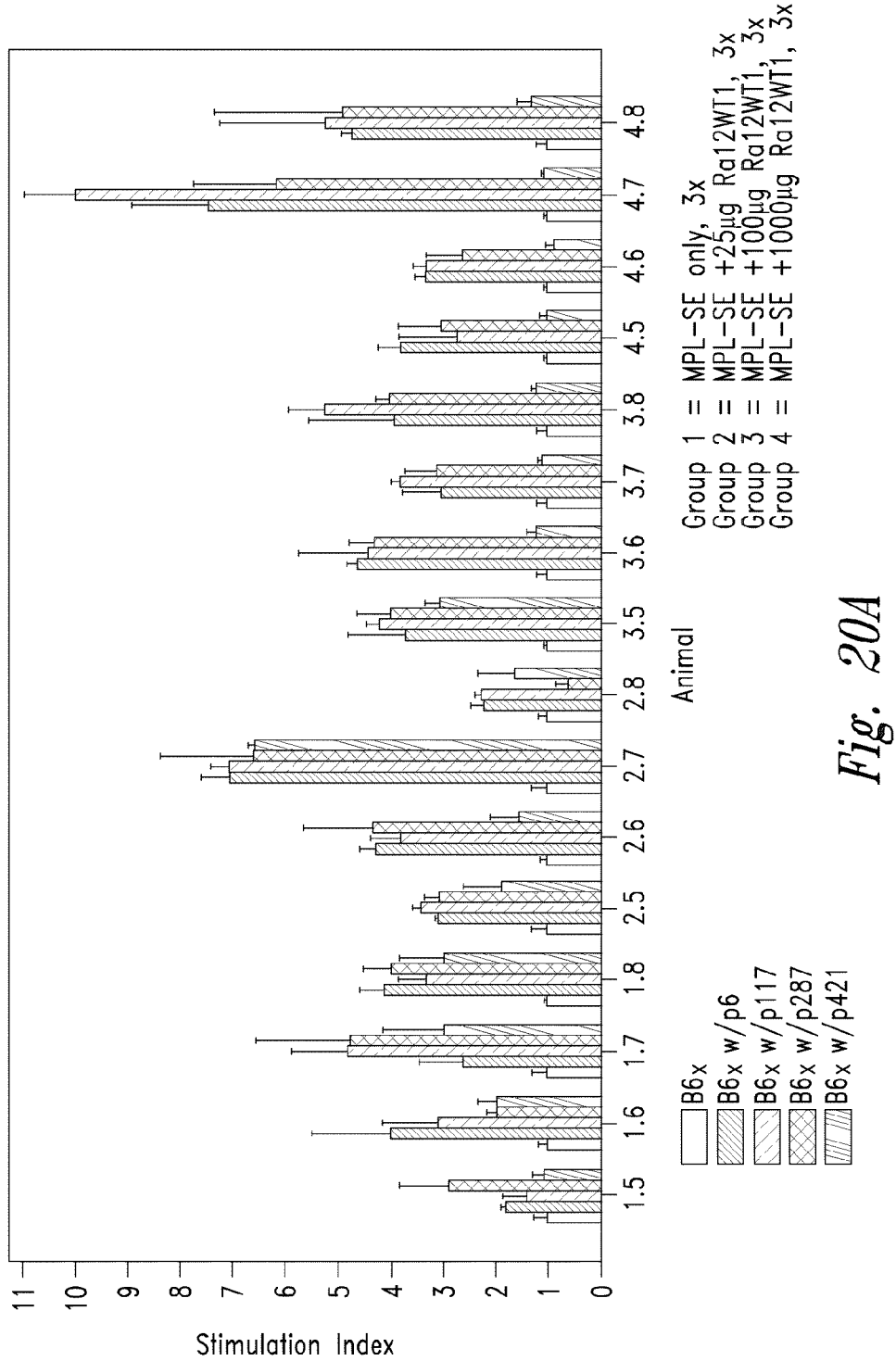

FIGS. 20A and B is a bar graph of the proliferative T-cell responses in mice immunized with WT1 protein.

FIG. 21 is a photograph of human DC, examined by fluorescent microscopy, expressing WT1 following adeno WT1 and Vaccinia WT1 infection.

FIG. 22 is a photograph that demonstrates that WT1 expression in human DC is reproducible following adeno WT1 infection and is not induced by a control Adeno infection.

Figure 23:
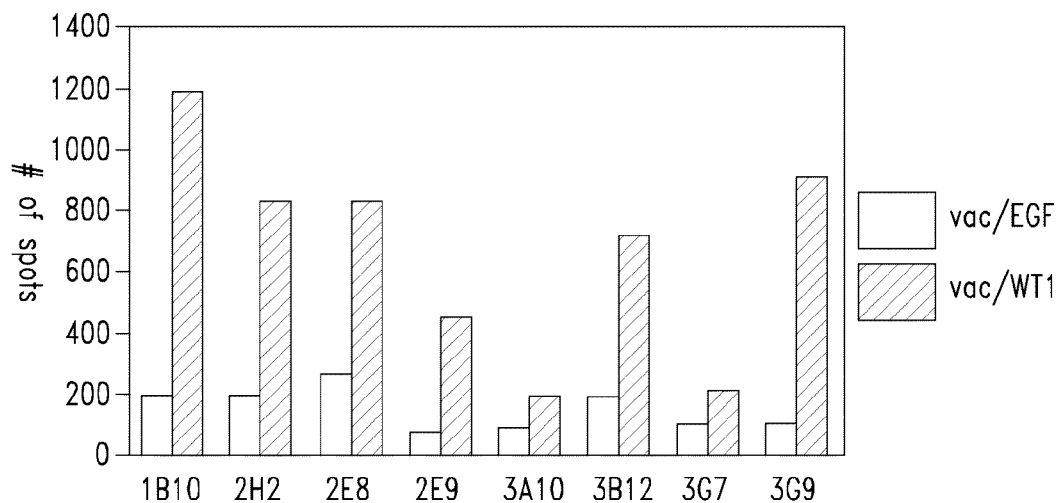

FIG. 23 is a graph of an IFN-gamma ELISPOT assay showing that WT1 whole gene in vitro priming elicits WT1 specific T-cell responses.

FIG. 24 shows amino acids 2-281 (SEQ ID NO:461) of the WT1 protein and the cDNA encoding these amino acid residues (SEQ ID NO:460). This truncated WT1 protein is referred to as WT1-F.

DETAILED DESCRIPTION OF THE INVENTION

U.S. patents, U.S. patent application publications, U.S. patent applications, foreign patents, foreign patent applications and non-patent publications referred to in this specification and/or listed in the Application Data Sheet, are incorporated herein by reference, in their entirety.

As noted above, the present invention is generally directed to compositions and methods for the immunotherapy and diagnosis of malignant diseases. The compositions described herein may include WT1 polypeptides, WT1 polynucleotides, antigen-presenting cells (APC, e.g., dendritic cells) that express a WT1 polypeptide, agents such as antibodies that bind to a WT1 polypeptide and/or immune system cells (e.g., T cells) specific for WT1. WT1 Polypeptides of the present invention generally comprise at least a portion of a Wilms Tumor gene product (WT1) or a variant thereof. Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a WT1 polypeptide. T cells that may be employed within such compositions are generally T cells (e.g., CD4$^+$ and/or CD8$^+$) that are specific for a WT1 polypeptide. Certain methods described herein further employ antigen-presenting cells that express a WT1 polypeptide as provided herein.

The present invention is based on the discovery that an immune response raised against a Wilms Tumor (WT) gene product (e.g., WT1) can provide prophylactic and/or therapeutic benefit for patients afflicted with malignant diseases characterized by increased WT1 gene expression. Such diseases include, but are not limited to, leukemias (e.g., acute myeloid leukemia (AML), chronic myeloid leukemia (CML), acute lymphocytic leukemia (ALL) and childhood ALL), as well as many cancers such as lung, breast, thyroid and gastrointestinal cancers and melanomas. The WT1 gene was originally identified and isolated on the basis of a cytogenetic deletion at chromosome 11p13 in patients with Wilms' tumor (see Call et al., U.S. Pat. No. 5,350,840). The gene consists of 10 exons and encodes a zinc finger transcription factor, and sequences of mouse and human WT1 proteins are provided in FIG. 1 and SEQ ID NOs: 319 and 320.

WT1 Polypeptides

Within the context of the present invention, a WT1 polypeptide is a polypeptide that comprises at least an immunogenic portion of a native WT1 (i.e., a WT1 protein expressed by an organism that is not genetically modified), or a variant thereof, as described herein. A WT1 polypeptide may be of any length, provided that it comprises at least an immunogenic portion of a native protein or a variant thereof. In other words, a WT1 polypeptide may be an oligopeptide (i.e., consisting of a relatively small number of amino acid residues, such as 8-10 residues, joined by peptide bonds), a full length WT1 protein (e.g., present within a human or non-human animal, such as a mouse) or a polypeptide of intermediate size. Within certain embodiments, the use of WT1 polypeptides that contain a small number of consecutive amino acid residues of a native WT1 polypeptide is preferred. Such polypeptides are preferred for certain uses in which the generation of a T cell response is desired. For example, such a WT1 polypeptide may contain less than 23, preferably no more than 18, and more preferably no more than 15 consecutive amino acid residues, of a native WT1 polypeptide. Polypeptides comprising nine consecutive amino acid residues of a native WT1 polypeptide are generally suitable for such purposes. Additional sequences derived from the native protein and/or heterologous sequences may be present within any WT1 polypeptide, and such sequences may (but need not) possess further immunogenic or antigenic properties. Polypeptides as provided herein may further be associated (covalently or noncovalently) with other polypeptide or non-polypeptide compounds.

An "immunogenic portion," as used herein is a portion of a polypeptide that is recognized (i.e., specifically bound) by a B-cell and/or T-cell surface antigen receptor. Certain preferred immunogenic portions bind to an MHC class I or class II molecule. As used herein, an immunogenic portion is said to "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., *J. Immunol.* 152:163, 1994). Alternatively, functional peptide competition assays that are known in the art may be employed. Certain immunogenic portions have one or more of the sequences recited within one or more of Tables II-XIV. Representative immunogenic portions include, but are not limited to, RDLNALLPAVPSLGGGG (human WT1 residues 6-22; SEQ ID NO:1), PSQASSGQARMFPNAPY- LPSCLE (human and mouse WT1 residues 117-139; SEQ ID NOs: 2 and 3 respectively), GATLKGVAAGSSSSVKWTE (human WT1 residues 244-262; SEQ ID NO:4), GATLKGVAA (human WT1 residues 244-252; SEQ ID NO:88), CMTWNQMNL (human and mouse WT1 residues 235-243; SEQ ID NOs: 49 and 258 respectively), SCLESQPTI (mouse WT1 residues 136-144; SEQ ID NO:296), SCLESQPAI (human WT1 residues 136-144; SEQ ID NO:198), NLYQMTSQL (human and mouse WT1 residues 225-233; SEQ ID NOs: 147 and 284 respectively); ALL-PAVSSL (mouse WT1 residues 10-18; SEQ ID NO:255); RMFPNAPYL (human and mouse WT1 residues 126-134; SEQ ID NOs: 185 and 293 respectively), VLDFAPPGA (human WT1 residues 37-45; SEQ ID NO:241), or VLDFAPPGAS (human WT1 residues 37-46; SEQ ID NO:411). Further immunogenic portions are provided in SEQ ID NOs:414-451. Further immunogenic portions are provided herein, and others may generally be identified using well known techniques, such as those summarized in Paul, *Fundamental Immunology*, 3rd ed., 243-247 (Raven Press, 1993) and references cited therein. Representative techniques for identifying immunogenic portions include screening polypeptides for the ability to react with antigen-specific antisera and/or T-cell lines or clones. An immunogenic portion of a native WT1 polypeptide is a portion that reacts with such antisera and/or T-cells at a level that is not substantially less than the reactivity of the full length WT1 (e.g., in an ELISA and/or T-cell reactivity assay). In other words, an immunogenic portion may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988.

Alternatively, immunogenic portions may be identified using computer analysis, such as the Tsites program (see Rothbard and Taylor, *EMBO J.* 7:93-100, 1988; Deavin et al., *Mol. Immunol.* 33:145-155, 1996), which searches for peptide motifs that have the potential to elicit Th responses. CTL peptides with motifs appropriate for binding to murine and human class I or class II MHC may be identified according to BIMAS (Parker et al., *J. Immunol.* 152:163, 1994) and other HLA peptide binding prediction analyses. Alternatively, immungenic portions that bind to a particular MHC molecule can be identified by using defined peptide binding motifs such as those described in Rammensee et al., Immunogenetics 41:178-228, 1995. To confirm peptide binding to murine and human class I or class II MHC molecules, peptide binding assays known in the art may be used. To confirm immunogenicity, a peptide may be tested using an HLA A2 or other transgenic mouse model and/or an in vitro stimulation assay using dendritic cells, fibroblasts or peripheral blood cells.

As noted above, a composition may comprise a variant of a native WT1 protein. A polypeptide "variant," as used herein, is a polypeptide that differs from a native polypeptide in one or more substitutions, deletions, additions and/or insertions, such that the immunogenicity of the polypeptide is retained (i.e., the ability of the variant to react with antigen-specific antisera and/or T-cell lines or clones is not substantially diminished relative to the native polypeptide). In other words, the ability of a variant to react with antigen-specific antisera and/or T-cell lines or clones may be enhanced or unchanged, relative to the native polypeptide, or may be diminished by less than 50%, and preferably less than 20%, relative to the native polypeptide. In one embodiment the ability of a variant to react with antigen-specific antisera and/or T-cell lines or clones may be diminished by less than 10%, 5%, 4%, 3%, 2%, 1%, or 0.5%, relative to the native polypeptide. Such variants may generally be identified by modifying one of the above polypeptide sequences and evaluating the reactivity of the modified polypeptide with antisera and/or T-cells as described herein. In one embodiment of the present invention, a variant may be identified by evaluating its ability to bind to a human or a muring HLA molecule. In one preferred embodiment, a variant polypeptide has a modification such that the ability of the variant polypeptide to bind to a class I or class II MHC molecule, for example HLA-A2, HLA-A24, HLA-A1, HLA-A3, HLA-A-68, HLA-A11, HLA-A31, HLA-A33, HLA-B14, HLA-B40, HLA-B60, HLA-B62, HLA-B7, HLA-B8, HLA-B27, HLA-B3501, HLA-B37, HLA-B38, HLA-B39, HLA-B44, HLA-B51, HLA-B52, HLA-B58, HLA-CW03, HLA-CW04, HLA-CW06, or HLA-CW07, is increased relative to that of a wild type (unmodified) WT1 polypeptide. In a further embodiment, the N-terminal portion of WT1 from amino acids 1-281 is modified such that the ability of any number of polypeptides therein that can bind to HLA-A2, HLA-A24, HLA-A1, HLA-A3, HLA-A68, HLA-A11, HLA-A31, HLA-A33, HLA-B14, HLA-B40, HLA-B60, HLA-B62, HLA-B7, HLA-B8, HLA-B27, HLA-B3501, HLA-B37, HLA-B38, HLA-B39, HLA-B44, HLA-B51, HLA-B52, HLA-B58, HLA-CW03, HLA-CW04, HLA-CW06, or HLA-CW07 is increased relative to that of the wild type (unmodified) WT1 polypeptide sequence. In a further embodiment, a polypeptide comprising at least one immunogenic portion (epitope) is modified such that its ability to bind to an MHC molecule, such as HLA-A2, HLA-A24, HLA-A1, HLA-A3, HLA-A68, HLA-A11, HLA-A31, HLA-A33, HLA-B14, HLA-B40, HLA-B60, HLA-B62, HLA-B7, HLA-B8, HLA-B27, HLA-B3501, HLA-B37, HLA-B38, HLA-B39, HLA-B44, HLA-B51, HLA-B52, HLA-B58, HLA-CW03, HLA-CW04, HLA-CW06, or HLA-CW07 is increased. Example 30 describes illustrative variants that can be generated. The skilled artisan would readily recognize that these are illustrative variants and that other variants can be generated in a similar manner for peptides that bind to HLA molecules other than HLA-A2. In a further embodiment, the ability of the variant polypeptide to bind to a HLA molecule is increased by at least 2 fold, preferably at least 3 fold, 4 fold, or 5 fold relative to that of a native WT1 polypeptide. It has been found, within the context of the present invention, that a relatively small number of substitutions (e.g., 1 to 3) within an immunogenic portion of a WT1 polypeptide may serve to enhance the ability of the polypeptide to elicit an immune response. Suitable substitutions may generally be identified by using computer programs, as described above, and the effect confirmed based on the reactivity of the modified polypeptide with antisera and/or T-cells as described herein. Accordingly, within certain preferred embodiments, a WT1 polypeptide comprises a variant in which 1 to 3 amino acid resides within an immunogenic portion are substituted such that the ability to react with antigen-specific antisera and/or T-cell lines or clones is statistically greater than that for the unmodified polypeptide. Such substitutions are preferably located within an MHC binding site of the polypeptide, which may be identified as described above. Preferred substitutions allow increased binding to MHC class I or class II molecules.

Certain variants contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

In a preferred embodiment, a variant polypeptide of the WT1 N-terminus (amino acids 1-249) is constructed, wherein the variant polypeptide is capable of binding to an antibody that recognizes full-length WT1 and/or WT1 N-terminus polypeptide. A non-limiting example of an antibody is anti WT1 antibody WT180 (Santa Cruz Biotechnology, Inc., Santa Cruz, Calif.).

As noted above, WT1 polypeptides may be conjugated to a signal (or leader) sequence at the N-terminal end of the protein which co-translationally or post-translationally directs transfer of the protein. A polypeptide may also, or alternatively, be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

WT1 polypeptides may be prepared using any of a variety of well known techniques. Recombinant polypeptides encoded by a WT1 polynucleotide as described herein may be readily prepared from the polynucleotide. In general, any of a variety of expression vectors known to those of ordinary skill in the art may be employed to express recombinant WT1 polypeptides. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line such as COS or CHO. Supernatants from suitable host/vector systems which secrete recombinant protein or polypeptide into culture media may be first concentrated using a commercially available filter. The concentrate may then be applied to a suitable purification matrix such as an affinity matrix or an ion exchange resin. Finally, one or more reverse phase HPLC steps can be employed to further purify a recombinant polypeptide. Such techniques may be used to prepare native polypeptides or variants thereof. For example, polynucleotides that encode a variant of a native polypeptide may generally be prepared using standard mutagenesis techniques, such as oligonucleotide-directed site-specific mutagenesis, and sections of the DNA sequence may be removed to permit preparation of truncated polypeptides.

Certain portions and other variants may also be generated by synthetic means, using techniques well known to those of ordinary skill in the art. For example, polypeptides having fewer than about 500 amino acids, preferably fewer than about 100 amino acids, and more preferably fewer than about 50 amino acids, may be synthesized. Polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Applied BioSystems, Inc. (Foster City, Calif.), and may be operated according to the manufacturer's instructions.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Within further aspects, the present invention provides mimetics of WT1 polypeptides. Such mimetics may comprise amino acids linked to one or more amino acid mimetics (i.e., one or more amino acids within the WT1 protein may be replaced by an amino acid mimetic) or may be entirely non-peptide mimetics. An amino acid mimetic is a compound that is conformationally similar to an amino acid such that it can be substituted for an amino acid within a WT1 polypeptide without substantially diminishing the ability to react with antigen-specific antisera and/or T cell lines or clones. A non-peptide mimetic is a compound that does not contain amino acids, and that has an overall conformation that is similar to a WT1 polypeptide such that the ability of the mimetic to react with WT1-specific antisera and/or T cell lines or clones is not substantially diminished relative to the ability of a WT1 polypeptide. Such mimetics may be designed based on standard techniques (e.g., nuclear magnetic resonance and computational techniques) that evaluate the three dimensional structure of a peptide sequence. Mimetics may be designed where one or more of the side chain functionalities of the WT1 polypeptide are replaced by groups that do not necessarily have the same size or volume, but have similar chemical and/or physical properties which produce similar biological responses. It should be understood that, within embodiments described herein, a mimetic may be substituted for a WT1 polypeptide.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. patent application 60/158,585, now issued as U.S. Pat. No. 7,009,042, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application 60/158,585, now issued as U.S. Pat. No. 7,009,042; see also, Skeiky et al., *Infection and Immun.* (1999) 67:3998-4007, incorporated herein by reference). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Within another illustrative embodiment the fusion partner comprises a twin arginine translocation (TAT) signal peptide from the TorA signal peptide in *E. coli* on the N-terminus; see J. Mol. Microbiol. (2000) 2(2): 179-189; Journal of Bacteriology, January 2001 p604-610 Vol 183, No 2; Journal of Biochemistry Vol 276, Mar. 16, 2001 pp 8159-8164), hereby incorporated herein in its entirety.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4+ T-cells specific for the polypeptide.

The invention provides truncated forms of WT1 polypeptides that can be recombinantly expressed in *E. coli* without the addition of a fusion partner. Examples of these truncated forms are shown in SEQ ID NOs:342-346, and are encoded by polynucleotides shown in SEQ ID NOs:337-341. In variations of these truncations, the first 76 amino acids of WT1 can be fused to the C-terminus of the protein, creating a recombinant protein that is easier to express in *E. coli*. Other hosts in addition to *E. coli* can also be used, such as, for example, *B. megaterium*. The protein can further be prepared without a histidine tag.

In other embodiments, different subunits can be made and fused together in an order which differs from that of native WT1. In addition, fusions can be made with, for example, Ra12. Exemplary fusion proteins are shown in SEQ ID NOs: 332-336 and can be encoded by polynucleotides shown in SEQ ID NOs: 327-331.

WT1 Polynucleotides

Any polynucleotide that encodes a WT1 polypeptide as described herein is a WT1 polynucleotide encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

WT1 polynucleotides may encode a native WT1 protein, or may encode a variant of WT1 as described herein. Polynucleotide variants may contain one or more substitutions, additions, deletions and/or insertions such that the immunogenicity of the encoded polypeptide is not diminished, relative to a native WT1 protein. The effect on the immunogenicity of the encoded polypeptide may generally be assessed as described herein. Preferred variants contain nucleotide substitutions, deletions, insertions and/or additions at no more than 20%, preferably at no more than 10%, of the nucleotide positions that encode an immunogenic portion of a native WT1 sequence. Certain variants are substantially homologous to a native gene, or a portion thereof. Such polynucleotide variants are capable of hybridizing under moderately stringent conditions to a naturally occurring DNA sequence encoding a WT1 polypeptide (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a WT1 polypeptide. Some of these polynucleotides bear minimal homology to the nucleotide sequence of any native gene. Nonetheless, polynucleotides that vary due to differences in codon usage are specifically contemplated by the present invention.

Therefore, according to another aspect of the present invention, polynucleotide compositions are provided that comprise some or all of a polynucleotide sequence set forth herein, complements of a polynucleotide sequence set forth herein, and degenerate variants of a polynucleotide sequence set forth herein. In certain preferred embodiments, the polynucleotide sequences set forth herein encode immunogenic polypeptides, as described above.

Once an immunogenic portion of WT1 is identified, as described above, a WT1 polynucleotide may be prepared using any of a variety of techniques. For example, a WT1 polynucleotide may be amplified from cDNA prepared from cells that express WT1. Such polynucleotides may be amplified via polymerase chain reaction (PCR). For this approach, sequence-specific primers may be designed based on the sequence of the immunogenic portion and may be purchased or synthesized. For example, suitable primers for PCR amplification of a human WT1 gene include: first step—P118: 1434-1414: 5' GAG AGT CAG ACT TGA AAG CAGT 3' (SEQ ID NO:5) and P135: 5' CTG AGC dC AGC AAA TGG GC 3' (SEQ ID NO:6); second step—P136: 5' GAG CAT GCA TGG GCT CCG ACG TGC GGG 3' (SEQ ID NO:7) and P137: 5' GGG GTA CCC ACT GAA CGG TCC CCG A 3' (SEQ ID NO:8). Primers for PCR amplification of a mouse WT1 gene include: first step—P138: 5' TCC GAG CCG CAC CTC ATG 3' (SEQ ID NO:9) and P139: 5' GCC TGG GAT GCT GGA CTG 3' (SEQ ID NO:10), second step—P140: 5' GAG CAT GCG ATG GGT TCC GAC GTG CGG 3' (SEQ ID NO:11) and P141: 5' GGG GTA CCT CAA AGC GCC ACG TGG AGT TT 3' (SEQ ID NO:12).

An amplified portion may then be used to isolate a full length gene from a human genomic DNA library or from a suitable cDNA library, using well known techniques. Alternatively, a full length gene can be constructed from multiple PCR fragments. WT1 polynucleotides may also be prepared by synthesizing oligonucleotide components, and ligating components together to generate the complete polynucleotide.

WT1 polynucleotides may also be synthesized by any method known in the art, including chemical synthesis (e.g., solid phase phosphoramidite chemical synthesis). Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a WT1 polypeptide, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells such as dendritic cells with a cDNA construct encoding a WT1 polypeptide, and administering the transfected cells to the patient).

Polynucleotides that encode a WT1 polypeptide may generally be used for production of the polypeptide, in vitro or in vivo. WT1 polynucleotides that are complementary to a coding sequence (i.e., antisense polynucleotides) may also be used as a probe or to inhibit WT1 expression. cDNA constructs that can be transcribed into antisense RNA may also be introduced into cells of tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art. In particular, one embodiment of the invention comprises expression vectors which incorporate the nucleic acid molecules of the invention, in operable linkage (i.e., "operably linked") to an expression control sequence (promoter). Illustrative vectors include, but are not limited, those described herein in Examples 20 and 40. Construction of vaccinia virus or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda* or Sf-9 cells), NIH 3T3 cells, and so forth. Prokaryotic cells, such as *E. coli* and other bacteria may also be used.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. cDNA constructs within such a vector may be used, for example, to transfect human or animal cell lines for use in establishing WT1 positive tumor models which may be used to perform tumor protection and adoptive immunotherapy experiments to demonstrate tumor or leukemia-growth inhibition or lysis of such cells.

Other therapeutic formulations for polynucleotides include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antibody Compositions, Fragments thereof and Other Binding Agents

According to another aspect, the present invention further provides binding agents, such as antibodies and antigen-binding fragments thereof, that exhibit immunological binding to a WT1 polypeptide disclosed herein, or to a portion, variant or derivative thereof. An antibody, or antigen-binding fragment thereof, is said to "specifically bind," "immunogically bind," and/or is "immunologically reactive" to a WT1 polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a WT1-associated cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) Proc. Nat. Acad. Sci. USA 86:4220-4224; Shaw et al. (1987) J. Immunol. 138:4534-

4538; and Brown et al. (1987) Cancer Res. 47:3577-3583), rodent CDRs grafted into a human supporting FR prior to fusion with an appropriate human antibody constant domain (Riechmann et al. (1988) Nature 332:323-327; Verhoeyen et al. (1988) Science 239:1534-1536; and Jones et al. (1986) Nature 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cells

Immunotherapeutic compositions may also, or alternatively, comprise T cells specific for WT1. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. Nos. 5,240,856; 5,215,926; WO 89/06280; WO 91/16116 and WO 92/07243). Alternatively, T cells may be derived from related or unrelated humans, non-human animals, cell lines or cultures.

T cells may be stimulated with WT1 polypeptide, polynucleotide encoding a WT1 polypeptide and/or an antigen presenting cell (APC) that expresses a WT1 polypeptide. Such stimulation is performed under conditions and for a time sufficient to permit the generation of T cells that are specific for the WT1 polypeptide. Preferably, a WT1 polypeptide or polynucleotide is present within a delivery vehicle, such as a microsphere, to facilitate the generation of antigen-specific T cells. Briefly, T cells, which may be isolated from a patient or a related or unrelated donor by routine techniques (such as by FICOLL®/HYPAQUE® density gradient centrifugation of peripheral blood lymphocytes), are incubated with WT1 polypeptide. For example, T cells may be incubated in vitro for 2-9 days (typically 4 days) at 37° C. with WT1 polypeptide (e.g., 5 to 25 µg/ml) or cells synthesizing a comparable amount of WT1 polypeptide. It may be desirable to incubate a separate aliquot of a T cell sample in the absence of WT1 polypeptide to serve as a control.

T cells are considered to be specific for a WT1 polypeptide if the T cells kill target cells coated with a WT1 polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a WT1 polypeptide may be quantified. Contact with a WT1 polypeptide (200 ng/ml-100 µg/ml, preferably 100 ng/ml-25 µg/ml) for 3-7 days should result in at least a two fold increase in proliferation of the T cells and/or contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). WT1 specific T cells may be expanded using standard techniques. Within preferred embodiments, the T cells are derived from a patient or a related or unrelated donor and are administered to the patient following stimulation and expansion.

T cells that have been activated in response to a WT1 polypeptide, polynucleotide or WT1-expressing APC may be $CD4^+$ and/or $CD8^+$. Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for WT1). For CD4+ T cells, a preferred method for detecting specific T cell activation is the detection of the proliferation of T cells. For CD8+ T cells, a preferred method for detecting specific T cell activation is the detection of the generation of cytolytic activity.

For therapeutic purposes, $CD4^+$ or $CD8^+$ T cells that proliferate in response to the WT1 polypeptide, polynucleotide or APC can be expanded in number either in vitro or in vivo. Proliferation of such T cells in vitro may be accomplished in a variety of ways. For example, the T cells can be re-exposed to WT1 polypeptide, with or without the addition of T cell growth factors, such as interleukin-2, and/or stimulator cells that synthesize a WT1 polypeptide. The addition of stimulator cells is preferred where generating $CD8^+$ T cell responses. T cells can be grown to large numbers in vitro with retention of specificity in response to intermittent restimulation with WT1 polypeptide. Briefly, for the primary in vitro stimulation (IVS), large numbers of lymphocytes (e.g., greater than $4 \times 10^7$) may be placed in flasks with media containing human serum. WT1 polypeptide (e.g., peptide at 10 µg/ml) may be added directly, along with tetanus toxoid (e.g., 5 µg/ml). The flasks may then be incubated (e.g., 37° C. for 7 days). For a second IVS, T cells are then harvested and placed in new flasks with $2-3 \times 10^7$ irradiated peripheral blood mononuclear cells. WT1 polypeptide (e.g., 10 µg/ml) is added directly. The flasks are incubated at 37° C. for 7 days. On day 2 and day 4 after the second IVS, 2-5 units of interleukin-2 (IL-2) may be added. For a third IVS, the T cells may be placed in wells and stimulated with the individual's own EBV transformed B cells coated with the peptide. IL-2 may be added on days 2 and 4 of each cycle. As soon as the cells are shown to be specific cytotoxic T cells, they may be expanded using a 10 day stimulation cycle with higher IL-2 (20 units) on days 2, 4 and 6.

Alternatively, one or more T cells that proliferate in the presence of WT1 polypeptide can be expanded in number by cloning. Methods for cloning cells are well known in the art, and include limiting dilution. Responder T cells may be purified from the peripheral blood of sensitized patients by density gradient centrifugation and sheep red cell rosetting and established in culture by stimulating with the nominal antigen in the presence of irradiated autologous filler cells. In order to generate CD4+ T cell lines, WT1 polypeptide is used as the antigenic stimulus and autologous peripheral blood lymphocytes (PBL) or lymphoblastoid cell lines (LCL) immortalized by infection with Epstein Barr virus are used as antigen presenting cells. In order to generate CD8+ T cell lines, autologous antigen-presenting cells transfected with an expression vector which produces WT1 polypeptide may be used as stimulator cells. Established T cell lines may be cloned 2-4 days following antigen stimulation by plating stimulated T cells at a frequency of 0.5 cells per well in 96-well flat-bottom plates with $1\times10^6$ irradiated PBL or LCL cells and recombinant interleukin-2 (rIL2) (50 U/ml). Wells with established clonal growth may be identified at approximately 2-3 weeks after initial plating and restimulated with appropriate antigen in the presence of autologous antigen-presenting cells, then subsequently expanded by the addition of low doses of rIL2 (10 U/ml) 2-3 days following antigen stimulation. T cell clones may be maintained in 24-well plates by periodic restimulation with antigen and rIL2 approximately every two weeks.

Within certain embodiments, allogeneic T-cells may be primed (i.e., sensitized to WT1) in vivo and/or in vitro. Such priming may be achieved by contacting T cells with a WT1 polypeptide, a polynucleotide encoding such a polypeptide or a cell producing such a polypeptide under conditions and for a time sufficient to permit the priming of T cells. In general, T cells are considered to be primed if, for example, contact with a WT1 polypeptide results in proliferation and/or activation of the T cells, as measured by standard proliferation, chromium release and/or cytokine release assays as described herein. A stimulation index of more than two fold increase in proliferation or lysis, and more than three fold increase in the level of cytokine, compared to negative controls, indicates T-cell specificity. Cells primed in vitro may be employed, for example, within a bone marrow transplantation or as donor lymphocyte infusion.

T cells specific for WT1 can kill cells that express WT1 protein. Introduction of genes encoding T-cell receptor (TCR) chains for WT1 are used as a means to quantitatively and qualitatively improve responses to WT1 bearing leukemia and cancer cells. Vaccines to increase the number of T cells that can react to WT1 positive cells are one method of targeting WT1 bearing cells. T cell therapy with T cells specific for WT1 is another method. An alternative method is to introduce the TCR chains specific for WT1 into T cells or other cells with lytic potential. In a suitable embodiment, the TCR alpha and beta chains are cloned out from a WT1 specific T cell line and used for adoptive T cell therapy, such as described in WO96/30516, incorporated herein by reference.

T Cell Receptor Compositions

The T cell receptor (TCR) consists of 2 different, highly variable polypeptide chains, termed the T-cell receptor α and β chains, that are linked by a disulfide bond (Janeway, Travers, Walport. Immunobiology. Fourth Ed., 148-159. Elsevier Science Ltd/Garland Publishing. 1999). The α/β heterodimer complexes with the invariant CD3 chains at the cell membrane. This complex recognizes specific antigenic peptides bound to MHC molecules. The enormous diversity of TCR specificities is generated much like immunoglobulin diversity, through somatic gene rearrangement. The β chain genes contain over 50 variable (V), 2 diversity (D), over 10 joining (J) segments, and 2 constant region segments (C). The α chain genes contain over 70 V segments, and over 60 J segments but no D segments, as well as one C segment. During T cell development in the thymus, the D to J gene rearrangement of the β chain occurs, followed by the V gene segment rearrangement to the DJ. This functional VDJβ exon is transcribed and spliced to join to a Cβ. For the α chain, a Vα gene segment rearranges to a Jα gene segment to create the functional exon that is then transcribed and spliced to the Cα. Diversity is further increased during the recombination process by the random addition of P and N-nucleotides between the V, D, and J segments of the β chain and between the V and J segments in the α chain (Janeway, Travers, Walport. Immunobiology. Fourth Ed., 98 and 150. Elsevier Science Ltd/Garland Publishing. 1999).

The present invention, in another aspect, provides TCRs specific for a polypeptide disclosed herein, or for a variant or derivative thereof. In accordance with the present invention, polynucleotide and amino acid sequences are provided for the V-J or V-D-J junctional regions or parts thereof for the alpha and beta chains of the T-cell receptor which recognize tumor polypeptides described herein. In general, this aspect of the invention relates to T-cell receptors which recognize or bind tumor polypeptides presented in the context of MHC. In a preferred embodiment the tumor antigens recognized by the T-cell receptors comprise a polypeptide of the present invention. For example, cDNA encoding a TCR specific for a WT1 peptide can be isolated from T cells specific for a tumor polypeptide using standard molecular biological and recombinant DNA techniques.

This invention further includes the T-cell receptors or analogs thereof having substantially the same function or activity as the T-cell receptors of this invention which recognize or bind tumor polypeptides. Such receptors include, but are not limited to, a fragment of the receptor, or a substitution, addition or deletion mutant of a T-cell receptor provided herein. This invention also encompasses polypeptides or peptides that are substantially homologous to the T-cell receptors provided herein or that retain substantially the same activity. The term "analog" includes any protein or polypeptide having an amino acid residue sequence substantially identical to the T-cell receptors provided herein in which one or more residues, preferably no more than 5 residues, more preferably no more than 25 residues have been conservatively substituted with a functionally similar residue and which displays the functional aspects of the T-cell receptor as described herein.

The present invention further provides for suitable mammalian host cells, for example, non-specific T cells, that are transfected with a polynucleotide encoding TCRs specific for a polypeptide described herein, thereby rendering the host cell specific for the polypeptide. The α and β chains of the TCR may be contained on separate expression vectors or alternatively, on a single expression vector that also contains an internal ribosome entry site (IRES) for cap-independent translation of the gene downstream of the IRES. Said host cells expressing TCRs specific for the polypeptide may be used, for example, for adoptive immunotherapy of WT1-associated cancer as discussed further below.

In further aspects of the present invention, cloned TCRs specific for a polypeptide recited herein may be used in a kit for the diagnosis of WT1-associated cancer. For example, the nucleic acid sequence or portions thereof, of tumor-specific TCRs can be used as probes or primers for the detection of expression of the rearranged genes encoding the specific TCR in a biological sample. Therefore, the present invention further provides for an assay for detecting messenger RNA or DNA encoding the TCR specific for a polypeptide.

Peptide-MHC Tetrameric Complexes

The present invention, in another aspect, provides peptide-MHC tetrameric complexes (tetramers) specific for T cells that recognize a polypeptide disclosed herein, or for a variant or derivative thereof. In one embodiment, tetramers may be used in the detection of WT1 specific T-cells. Tetramers may be used in monitoring WT1 specific immune responses, early detection of WT1 associated malignancies and for monitoring minimal residual disease. Tetramer staining is typically carried out with flow cytometric analysis and can be used to identify groups within a patient population suffering from a WT1 associated disease at a higher risk for relapse or disease progression.

Pharmaceutical Compositions

In additional embodiments, the present invention concerns formulation of one or more of the polynucleotide, polypeptide, T-cell, TCR, and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, TCR, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and therapeutic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, Crit. Rev. Therap. Drug Carrier Systems 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipoxviruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545. A number of pox viruses have been developed as live viral vectors for the expression of heterologous proteins (Cepko et al., Cell 37:1053-1062 (1984); Morin et al., Proc. Natl. Acad. Sci. USA 84:4626-4630 (1987); Lowe et al., Proc. Natl. Acad. Sci. USA, 84:3896-3900 (1987); Panicali & Paoletti, Proc. Natl. Acad. Sci. USA, 79:4927-4931 (1982); Machett et al., Proc. Natl. Acad. Sci. USA, 79:7415-7419 (1982)). Representative fowlpox and swinepox virus are available through the ATCC under accession numbers VR-229 and VR-363, respectively. A recombinant vaccinia—CEA is available through the ATCC under accession number VR2323. Other illustrative viral vectors also include, but are not limited to, those described by Therion Biologics (Cambridge, Mass., USA), for example, in U.S. Pat. Nos. 6,051, 410, 5,858,726, 5,656,465, 5,804,196, 5,747,324, 6,319,496, 6,165,460.

Any of a number of alphavirus vectors can also be used for delivery of polynucleotide compositions of the present invention, such as those vectors described in U.S. Pat. Nos. 5,843, 723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

As would be readily appreciated by the skilled artisan, any number of additional components may be present in a DNA or retroviral vector expressing a WT1 polypeptide or any portion thereof, as described herein. For example, an expression vector for delivery of a polynucleotide or peptide of the present invention may include any number of a variety of costimulatory molecules, including, but not limited to CD28, B7-1, ICAM-1, and LFA-3. A delivery vector may also include any number of cytokines, for example IFN-γ, GM-CSF, or IL-2. In one illustrative embodiment, a recombinant viral vector, e.g. a vaccinia or fowlpox vector, includes B7-1, ICAM-1, and LFA-3.

The present invention also comprises the use of any combination of the DNA and/or viral vectors described herein for use in the treatment of malignancies associated with the expression of WT1. In one illustrative embodiment, a recombinant vaccinia viral vector is administered to an animal or human patient afflicted with a WT1-associated malignancy, followed by administration of a recombinant fowlpox vector. In another embodiment of the present invention, the recombinant fowlpox is adminstered twice following administration of the vaccinia vector (e.g. a prime/boost/boost vaccination regimen).

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell, TCR, and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

Certain preferred adjuvants for eliciting a predominantly Th1-type response include, for example, a combination of monophosphoryl lipid A (MPL®), preferably 3-de-O-acylated monophosphoryl lipid A (3D-MPL™), together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium* quinoa saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOM®s (saponins, cholesterol and phospholipids). Furthermore, the saponins may be formulated together with a polyoxyethylene ether or ester, in either a non-particulate solution or suspension, or in a particulate structure such as a paucilamelar liposome or ISCOM®. The saponins may also be formulated with excipients such as CARBOPOL® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include MONTANIDE® ISA 720 (Seppic, France), SAF™ (Chiron, Calif., United States), ISCOM®s (CSL), MF-59™ (Chiron), the SBAS™ series of adjuvants (e.g., SBAS™-2 or SBAS™-4, available from SmithKline Beecham, Rixensart, Belgium), Detox (ENHANZYN®) (Corixa, Hamilton, Mont.), RC-529™ (Corixa, Hamilton, Mont.) and other aminoalkyl glucosaminide 4-phosphates (AGPs), such as those described in U.S. patent application Ser. No. 08/853,826, now issued as U.S. Pat. No. 6,113,918 and U.S. patent application Ser. No. 09/074,720, now issued as U.S. Pat. No. 6,355,257 and in U.S. Pat. No. 6,303,347 the disclosures of which are incorporated herein by reference in their entireties, and polyoxyethylene ether adjuvants such as those described in WO 99/52549A1. Additional illustrative adjuvants for use in the pharmaceutical compositions of the invention include isotucerosol.

Other preferred adjuvants include adjuvant molecules of the general formula $$HO(CH_2CH_2O)_n\text{-A-R,} \qquad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12$^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1 BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class 1-restricted cytotoxic T lymphocyte responses in a host.

In another illustrative embodiment, calcium phosphate core particles are employed as carriers, vaccine adjuvants, or as controlled release matrices for the compositions of this invention. Exemplary calcium phosphate particles are disclosed, for example, in published patent application No. WO/0046147.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit. Rev Ther Drug Carrier Syst 1998; 15(3):243-84; U.S. Pat. Nos. 5,641,515; 5,580,579 and 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation.

Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. Nos. 5,756,353 and 5,804,212. Likewise, the delivery of drugs using intranasal microparticle resins (Takenaga et al., J Controlled Release 1998 Mar. 2;52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit. Rev Ther Drug Carrier Syst. 1995; 12(2-3):233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol. Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit. Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2;50 (1-3):31-40; and U.S. Pat. No. 5,145,684.

Therapy of Malignant Diseases

Immunologic approaches to cancer therapy are based on the recognition that cancer cells can often evade the body's defenses against aberrant or foreign cells and molecules, and that these defenses might be therapeutically stimulated to regain the lost ground, e.g. pgs. 623-648 in Klein, Immunology (Wiley-Interscience, New York, 1982). Numerous recent observations that various immune effectors can directly or indirectly inhibit growth of tumors has led to renewed interest in this approach to cancer therapy, e.g. Jager, et al., Oncology 2001; 60(1):1-7; Renner, et al., Ann Hematol 2000 December; 79(12):651-9.

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins that are responsible for lysing and processing the immunoglobulin-coated target invader cells; iii) natural killer lymphocytes having two mechanisms for the destruction of tumor cells, antibody-dependent cellular cytotoxicity and natural killing; and iv) T-lymphocytes possessing antigen-specific receptors and having the capacity to recognize a tumor cell carrying complementary marker molecules (Schreiber, H., 1989, in Fundamental Immunology (ed). W. E. Paul, pp. 923-955).

Cancer immunotherapy generally focuses on inducing humoral immune responses, cellular immune responses, or both. Moreover, it is well established that induction of $CD4^+$ T helper cells is necessary in order to secondarily induce either antibodies or cytotoxic $CD8^+$ T cells. Polypeptide antigens that are selective or ideally specific for cancer cells, particularly cancer cells associated with WT1 expression, offer a powerful approach for inducing immune responses against cancer associated with WT1 expression, and are an important aspect of the present invention.

In further aspects of the present invention, the compositions and vaccines described herein may be used to inhibit the development of malignant diseases (e.g., progressive or metastatic diseases or diseases characterized by small tumor burden such as minimal residual disease). In general, such methods may be used to prevent, delay or treat a disease associated with WT1 expression. In other words, therapeutic methods provided herein may be used to treat an existing WT1-associated disease, or may be used to prevent or delay the onset of such a disease in a patient who is free of disease or who is afflicted with a disease that is not yet associated with WT1 expression.

As used herein, a disease is "associated with WT1 expression" if diseased cells (e.g., tumor cells) at some time during the course of the disease generate detectably higher levels of a WT1 polypeptide than normal cells of the same tissue. Association of WT1 expression with a malignant disease does not require that WT1 be present on a tumor. For example, overexpression of WT1 may be involved with initiation of a tumor, but the protein expression may subsequently be lost. Alternatively, a malignant disease that is not characterized by an increase in WT1 expression may, at a later time, progress to a disease that is characterized by increased WT1 expression. Accordingly, any malignant disease in which diseased cells formerly expressed, currently express or are expected to subsequently express increased levels of WT1 is considered to be "associated with WT1 expression."

Immunotherapy may be performed using any of a variety of techniques, in which compounds or cells provided herein function to remove WT1-expressing cells from a patient. Such removal may take place as a result of enhancing or inducing an immune response in a patient specific for WT1 or a cell expressing WT1. Alternatively, WT1-expressing cells may be removed ex vivo (e.g., by treatment of autologous bone marrow, peripheral blood or a fraction of bone marrow or peripheral blood). Fractions of bone marrow or peripheral blood may be obtained using any standard technique in the art.

Within such methods, pharmaceutical compositions and vaccines may be administered to a patient. As used herein, a "patient" refers to any warm-blooded animal, preferably a human. A patient may or may not be afflicted with a malignant disease. Accordingly, the above pharmaceutical compositions and vaccines may be used to prevent the onset of a disease (i.e., prophylactically) or to treat a patient afflicted with a disease (e.g., to prevent or delay progression and/or metastasis of an existing disease). A patient afflicted with a disease may have a minimal residual disease (e.g., a low tumor burden in a leukemia patient in complete or partial remission or a cancer patient following reduction of the tumor burden after surgery radiotherapy and/or chemotherapy). Such a patient may be immunized to inhibit a relapse (i.e., prevent or delay the relapse, or decrease the severity of a relapse). Within certain preferred embodiments, the patient is afflicted with a leukemia (e.g., AML, CML, ALL or childhood ALL), a myelodysplastic syndrome (MDS) or a cancer (e.g., gastrointestinal, lung, thyroid or breast cancer or a melanoma), where the cancer or leukemia is WT1 positive (i.e., reacts detectably with an anti-WT1 antibody, as provided herein or expresses WT1 mRNA at a level detectable by RT-PCR, as described herein) or suffers from an autoimmune disease directed against WT1-expressing cells.

Other diseases associated with WT1 overexpression include kidney cancer (such as renal cell carcinoma, or Wilms tumor), as described in Satoh F., et al., *Pathol. Int.* 50(6):458-71 (2000), and Campbell C. E. et al., *Int. J. Cancer* 78(2): 182-8 (1998); and mesothelioma, as described in Amin, K. M. et al., *Am. J. Pathol.* 146(2):344-56 (1995). Harada et al. (*Mol. Urol.* 3(4):357-364 (1999) describe WT1 gene expression in human testicular germ-cell tumors. Nonomura et al. *Hinyokika Kiyo* 45(8):593-7 (1999) describe molecular staging of testicular cancer using polymerase chain reaction of the testicular cancer-specific genes. Shimizu et al., *Int. J. Gynecol. Pathol.* 19(2):158-63 (2000) describe the immunohistochemical detection of the Wilms' tumor gene (WT1) in epithelial ovarian tumors.

WT1 overexpression was also described in desmoplastic small round cell tumors, by Barnoud, R. et al., *Am. J. Surg. Pathol.* 24(6):830-6 (2000); and *Pathol. Res. Pract.* 194(10): 693-700 (1998). WT1 overexpression in glioblastoma and other cancer was described by Menssen, H. D. et al., *J. Cancer Res. Clin. Oncol.* 126(4):226-32 (2000), "Wilms' tumor gene (WT1) expression in lung cancer, colon cancer and glioblastoma cell lines compared to freshly isolated tumor specimens." Other diseases showing WT1 overexpression include EBV associated diseases, such as Burkitt's lymphoma and nasopharyngeal cancer (Spinsanti P. et al., *Leuk. Lymphoma* 38(5-6):611-9 (2000), "Wilms' tumor gene expression by normal and malignant human B lymphocytes."

In *Leukemia* 14(9):1634-4 (2000), Pan et al., describe in vitro IL-12 treatment of peripheral blood mononuclear cells from patients with leukemia or myelodysplastic syndromes, and reported an increase in cytotoxicity and reduction in WT1 gene expression. In *Leukemia* 13(6):891-900 (1999), Patmasiriwat et al. reported WT1 and GATA1 expression in myelodysplastic syndrome and acute leukemia. In *Leukemia* 13(3): 393-9 (1999), Tamaki et al. reported that the Wilms' tumor gene WT1 is a good marker for diagnosis of disease progression of myelodysplastic syndromes. Expression of the Wilms' tumor gene WT1 in solid tumors, and its involvement in tumor cell growth, was discussed in relation to gastric cancer, colon cancer, lung cancer, breast cancer cell lines, germ cell tumor cell line, ovarian cancer, the uterine cancer, thyroid cancer cell line, hepatocellular carcinoma, in Oji et al., *Jpn. J. Cancer Res.* 90(2):194-204 (1999).

The compositions provided herein may be used alone or in combination with conventional therapeutic regimens such as surgery, irradiation, chemotherapy and/or bone marrow transplantation (autologous, syngeneic, allogeneic or unrelated). As discussed in greater detail below, binding agents and T cells as provided herein may be used for purging of autologous stem cells. Such purging may be beneficial prior to, for example, bone marrow transplantation or transfusion of blood or components thereof. Binding agents, T cells, antigen presenting cells (APC) and compositions provided herein may further be used for expanding and stimulating (or priming) autologous, allogeneic, syngeneic or unrelated WT1-specific T-cells in vitro and/or in vivo. Such WT1-specific T cells may be used, for example, within donor lymphocyte infusions.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. In some tumors, pharmaceutical compositions or vaccines may be administered locally (by, for example, rectocoloscopy, gastroscopy, videoendoscopy, angiography or other methods known in the art). Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response that is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent complete or partial remissions, or longer disease-free and/or overall survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent complete or partial remissions, or longer disease-free and/or overall survival) in treated patients as compared to non-treated patients. Increases in preexisting immune responses to WT1 generally correlate with an improved clinical outcome. Such immune responses may generally be evaluated using standard proliferation, cytotoxicity or cytokine assays, which may be performed using samples obtained from a patient before and after treatment.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Monoclonal antibodies may be labeled with any of a variety of labels for desired selective usages in detection, diagnostic assays or therapeutic applications (as described in U.S. Pat. Nos. 6,090,365; 6,015,542; 5,843,398; 5,595,721; and 4,708,930, hereby incorporated by reference in their entirety as if each was incorporated individually). In each case, the binding of the labelled monoclonal antibody to the determinant site of the antigen will signal detection or delivery of a particular therapeutic agent to the antigenic determinant on the non-normal cell. A further object of this invention is to provide the specific monoclonal antibody suitably labelled for achieving such desired selective usages thereof.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Within further aspects, methods for inhibiting the development of a malignant disease associated with WT1 expression involve the administration of autologous T cells that have been activated in response to a WT1 polypeptide or WT1-expressing APC, as described above. Such T cells may be $CD4^+$ and/or $CD8^+$, and may be proliferated as described above. The T cells may be administered to the individual in an amount effective to inhibit the development of a malignant disease. Typically, about $1\times10^9$ to $1\times10^{11}$ T cells/$M^2$ are administered intravenously, intracavitary or in the bed of a resected tumor. It will be evident to those skilled in the art that the number of cells and the frequency of administration will be dependent upon the response of the patient.

Within certain embodiments, T cells may be stimulated prior to an autologous bone marrow transplantation. Such stimulation may take place in vivo or in vitro. For in vitro stimulation, bone marrow and/or peripheral blood (or a fraction of bone marrow or peripheral blood) obtained from a patient may be contacted with a WT1 polypeptide, a polynucleotide encoding a WT1 polypeptide and/or an APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within related embodiments, T cells of a related or unrelated donor may be stimulated prior to a syngeneic or allogeneic (related or unrelated) bone marrow transplantation. Such stimulation may take place in vivo or in vitro. For in vitro stimulation, bone marrow and/or peripheral blood (or a fraction of bone marrow or peripheral blood) obtained from a related or unrelated donor may be contacted with a WT1 polypeptide, WT1 polynucleotide and/or APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within other embodiments, WT1-specific T cells as described herein may be used to remove cells expressing WT1 from autologous bone marrow, peripheral blood or a fraction of bone marrow or peripheral blood (e.g., $CD34^+$ enriched peripheral blood (PB) prior to administration to a patient). Such methods may be performed by contacting bone marrow or PB with such T cells under conditions and for a time sufficient to permit the reduction of WT1 expressing cells to less than 10%, preferably less than 5% and more preferably less than 1%, of the total number of myeloid or lymphatic cells in the bone marrow or peripheral blood. The extent to which such cells have been removed may be readily determined by standard methods such as, for example, qualitative and quantitative PCR analysis, morphology, immunohistochemistry and FACS analysis. Bone marrow or PB (or a fraction thereof) may then be administered to a patient using standard techniques.

Cancer Detection and Diagnostic Compositions, Methods and Kits

In general, a cancer associated with WT1 expression may be detected in a patient based on the presence of one or more WT1 proteins and/or polynucleotides encoding such proteins in a biological sample (for example, blood, sera, sputum urine and/or tumor biopsies) obtained from the patient. In other words, such WT1 proteins may be used as markers to indicate the presence or absence of a cancer. The binding agents provided herein generally permit detection of the level of antigen that binds to the agent in the biological sample.

Polynucleotide primers and probes may be used to detect the level of mRNA encoding a WT1 protein, which is also indicative of the presence or absence of a cancer. In general, a WT1 sequence should be present at a level that is at least two-fold, preferably three-fold, and more preferably five-fold or higher in tumor tissue than in normal tissue of the same type from which the tumor arose. Expression levels of WT1 in tissue types different from that in which the tumor arose are irrelevant in certain diagnostic embodiments since the presence of tumor cells can be confirmed by observation of predetermined differential expression levels, e.g., 2-fold, 5-fold, etc, in tumor tissue to expression levels in normal tissue of the same type.

Other differential expression patterns can be utilized advantageously for diagnostic purposes. For example, in one aspect of the invention, overexpression of WT1 sequence in tumor tissue and normal tissue of the same type, but not in other normal tissue types, e.g. PBMCs, can be exploited diagnostically. In this case, the presence of metastatic tumor cells, for example in a sample taken from the circulation or some other tissue site different from that in which the tumor arose, can be identified and/or confirmed by detecting expression of the tumor sequence in the sample, for example using RT-PCR analysis. In many instances, it will be desired to enrich for tumor cells in the sample of interest, e.g., PBMCs, using cell capture or other like techniques.

There are a variety of assay formats known to those of ordinary skill in the art for using a binding agent to detect WT1 polypeptide markers in a sample. See, e.g., Harlow and Lane, *Antibodies: A Laboratory Manual*, Cold Spring Harbor Laboratory, 1988. In general, the presence or absence of a cancer associated with WT1 in a patient may be determined by (a) contacting a biological sample obtained from a patient with a binding agent; (b) detecting in the sample a level of WT1 polypeptide that binds to the binding agent; and (c) comparing the level of WT1 polypeptide with a predetermined cut-off value.

In a preferred embodiment, the assay involves the use of binding agent immobilized on a solid support to bind to and remove the WT1 polypeptide from the remainder of the sample. The bound WT1 polypeptide may then be detected using a detection reagent that contains a reporter group and specifically binds to the binding agent/WT1 polypeptide complex. Such detection reagents may comprise, for example, a binding agent that specifically binds to a WT1 polypeptide or an antibody or other agent that specifically binds to the binding agent, such as an anti-immunoglobulin, protein G, protein A or a lectin. Alternatively, a competitive assay may be utilized, in which a WT1 polypeptide is labeled with a reporter group and allowed to bind to the immobilized binding agent after incubation of the binding agent with the sample. The extent to which components of the sample inhibit the binding of the labeled WT1 polypeptide to the binding agent is indicative of the reactivity of the sample with the immobilized binding agent. Suitable polypeptides for use within such assays include full length WT1 proteins and polypeptide portions thereof to which the binding agent binds, as described above.

The solid support may be any material known to those of ordinary skill in the art to which the WT1 protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that WT1 polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or TWEEN® 20 (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of WT1 polypeptide within a sample obtained from an individual with a cancer associated with WT1 least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% TWEEN® 20. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer associated with WT1 expression the signal detected from the reporter group that remains bound to the solid support is generally compared to a signal that corresponds to a predetermined cut-off value. In one preferred embodiment, the cut-off value for the detection of a cancer associated with WT1 is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the WT1 proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such WT1-specific antibodies may correlate with the presence of a cancer associated with WT1 expression.

A cancer associated with WT1 expression may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a WT1 polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37 C with polypeptide (e.g., 5-25 g/ml). It may be desirable to incubate another aliquot of a T cell sample in the absence of WT1 polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer associated with WT1 expression in the patient.

As noted above, a cancer may also, or alternatively, be detected based on the level of mRNA encoding a WT1 protein in a biological sample. For example, at least two oligonucleotide primers may be employed in a polymerase chain reaction (PCR) based assay to amplify a portion of a WT1 cDNA derived from a biological sample, wherein at least one of the oligonucleotide primers is specific for (i.e., hybridizes to) a polynucleotide encoding the WT1 protein. The amplified cDNA is then separated and detected using techniques well known in the art, such as gel electrophoresis.

Similarly, oligonucleotide probes that specifically hybridize to a polynucleotide encoding a WT1 protein may be used in a hybridization assay to detect the presence of polynucleotide encoding the WT1 protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a WT1 protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., PCR *Technology,* Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another aspect of the present invention, cell capture technologies may be used in conjunction with, for example, real-time PCR to provide a more sensitive tool for detection of metastatic cells expressing WT1 antigens. Detection of WT1-associated cancer cells in biological samples, e.g., bone marrow samples, peripheral blood, and small needle aspiration samples is desirable for diagnosis and prognosis in patients with cancer associated with WT1 expression.

Immunomagnetic beads coated with specific monoclonal antibodies to surface cell markers, or tetrameric antibody complexes, may be used to first enrich or positively select cancer cells in a sample. Various commercially available kits may be used, including DYNABEADS® Epithelial Enrich (Dynal Biotech, Oslo, Norway), STEMSEP® (StemCell Technologies, Inc., Vancouver, BC), and ROSETTESEP® (StemCell Technologies). A skilled artisan will recognize that other methodologies and kits may also be used to enrich or positively select desired cell populations. DYNABEADS® Epithelial Enrich contains magnetic beads coated with mAbs specific for two glycoprotein membrane antigens expressed on normal and neoplastic epithelial tissues. The coated beads may be added to a sample and the sample then applied to a magnet, thereby capturing the cells bound to the beads. The unwanted cells are washed away and the magnetically isolated cells eluted from the beads and used in further analyses.

ROSETTESEP® can be used to enrich cells directly from a blood sample and consists of a cocktail of tetrameric antibodies that targets a variety of unwanted cells and cross-links them to glycophorin A on red blood cells (RBC) present in the sample, forming rosettes. When centrifuged over FICOLL®, targeted cells pellet along with the free RBC. The combination of antibodies in the depletion cocktail determines which cells will be removed and consequently which cells will be recovered. Antibodies that are available include, but are not limited to: CD2, CD3, CD4, CD5, CD8, CD10, CD11b, CD14, CD15, CD16, CD19, CD20, CD24, CD25, CD29, CD33, CD34, CD36, CD38, CD41, CD45, CD45RA, CD45RO, CD56, CD66B, CD66e, HLA-DR, IgE, and TCRαβ.

In another embodiment, the compositions described herein may be used as markers for the progression of cancer. In this embodiment, assays as described above for the diagnosis of a cancer associated with WT1 expression may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of WT1 polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a WT1 protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a WT1 protein in a biological sample. Such kits generally comprise at least one oligonucleotide probe or primer, as described above, that hybridizes to a polynucleotide encoding a WT1 protein. Such an oligonucleotide may be used, for example, within a PCR or hybridization assay. Additional components that may be present within such kits include a second oligonucleotide and/or a diagnostic reagent or container to facilitate the detection of a polynucleotide encoding a WT1 protein.

The following Examples are offered by way of illustration and not by way of limitation.

EXAMPLES

Example 1

Identification of an Immune Response to WT1 in Patients with Hematological Malignancies This Example illustrates the identification of an existent immune response in patients with a hematological malignancy.

Figure 2:
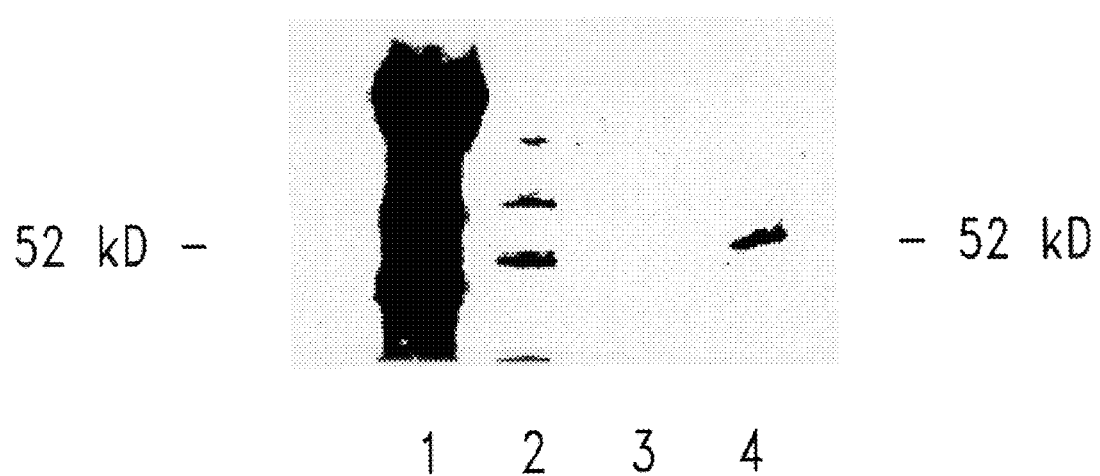
FIG. 2 is a Western blot illustrating the detection of WT1 specific antibodies in patients with hematological malignancy (AML). Lane 1 shows molecular weight markers; lane 2 shows a positive control (WT1 positive human leukemia cell line immunoprecipitated with a WT1 specific antibody); lane 3 shows a negative control (WT1 positive cell line immunoprecipitated with mouse sera); and lane 4 shows a WT1 positive cell line immunoprecipitated with sera of a patient with AML. For lanes 2-4, the immunoprecipitate was separated by gel electrophoresis and probed with a WT1 specific antibody.

To evaluate the presence of preexisting WT1 specific antibody responses in patients, sera of patients with acute myelogenous leukemia (AML), acute lymphocytic leukemia (ALL), chronic myelogenous leukemia (CML) and severe aplastic anemia were analyzed using Western blot analysis. Sera were tested for the ability to immunoprecipitate WT1 from the human leukemic cell line K562 (American Type Culture Collection, Manassas, Va.). In each case, immunoprecipitates were separated by gel electrophoresis, transferred to membrane and probed with the anti WT1 antibody WT180 (Santa Cruz Biotechnology, Inc., Santa Cruz, Calif.). This Western blot analysis identified potential WT1 specific antibodies in patients with hematological malignancy. A representative Western blot showing the results for a patient with AML is shown in FIG. 2. A 52 kD protein in the immunoprecipitate generated using the patient sera was recognized by the WT1 specific antibody. The 52 kD protein migrated at the same size as the positive control.

Additional studies analyzed the sera of patients with AML and CML for the presence of antibodies to full-length and truncated WT1 proteins. cDNA constructs representing the human WT1/full-length (aa 1-449), the N-terminus (aa 1-249) (WT1/N-terminus) and C-terminus (aa 267-449) (WT1/C-terminus) region were subcloned into modified pET28 vectors. The WT1/full-length and WT1/N-terminus proteins were expressed as Ra12 fusion proteins. Ra12 is the C-terminal fragment of a secreted *Mycobacterium tuberculosis* protein, denoted as MTB32B. (Skeiky et al., *Infect Immun.* 67; 3998, 1999). The Ra12-WT1/full-length fusion region was cloned 3' to a histidine-tag in a histidine-tag modified pET28 vector. The WT1/N-terminus region was subcloned into a modified pET28 vector that has a 5' histidine-tag followed by the thioredoxin (TRX)-WT1/N-terminus fusion region followed by a 3' histidine-tag. The WT1/C-terminus coding region was subcloned into a modified pET28 vector without a fusion partner containing only the 5' and 3' histidine-tag, followed by a Thrombin and EK site.

BL21 pLysS *E. coli* (Stratagene, La Jolla, Calif.) were transformed with the three WT1 expression constructs, grown overnight and induced with isopropyl-β-D-thiogalactoside (IPTG). WT1 proteins were purified as follows: Cells were harvested and lysed by incubation in 10 mM Tris, pH 8.0 with Complete Protease Inhibitor Tablets (Boehringer Mannheim Biochemicals, Indianapolis, Ind.) at 37° C. followed by repeated rounds of sonication. Inclusion bodies were washed twice with 10 mM Tris, pH 8.0. Proteins were then purified by metal chelate affinity chromatography over nickel-nitrilotriacetic acid resin (QIAGEN Inc., Valencia, Calif.; Hochuli et al., *Biologically Active Molecules:*217, 1989) followed by chromatography on a Source Q anion exchange resin (Amersham Pharmacia Biotech, Upsala, Sweden). The identity of the WT1 proteins was confirmed by N-terminal sequencing.

Sera from adult patients with de nova AML or CML were studied for the presence of WT1 specific Ab. Recombinant proteins were adsorbed to TC microwell plates (Nunc, Roskilde, Denmark). Plates were washed with PBS/0.5% TWEEN® 20 and blocked with 1% BSA/PBS/0.1% TWEEN® 20. After washing, serum dilutions were added and incubated overnight at 4° C. Plates were washed and Donkey anti-human IgG-HRP secondary antibody was added (Jackson-Immunochem, West Grove, Pa.) and incubated for 2 h at room temperature. Plates were washed, incubated with TMB Peroxidase substrate solution (Kirkegaard and Perry Laboratories, Mass.), quenched with 1N $H_2SO_4$, and immediately read (Cyto-Fluor 2350; Millipore, Bedford, Mass.).

For the serological survey, human sera were tested by ELISA over a range of serial dilutions from 1:50 to 1:20,000. A positive reaction was defined as an OD value of a 1:500 diluted serum that exceeded the mean OD value of sera from normal donors (n=96) by three (WT1/full-length, WT1C-terminus) standard deviations. Due to a higher background in normal donors to the WT1/N-terminus protein a positive reaction to WT1/N-terminus was defined as an OD value of 1:500 diluted serum that exceeded the mean OD value of sera from normal donors by four standard deviations. To verify that the patient Ab response was directed against WT1 and not to the Ra12 or TRX fusion part of the protein or possible *E. coli* contaminant proteins, controls included the Ra12 and TRX protein alone purified in a similar manner. Samples that showed reactivity against the Ra12 and/or TRX proteins were excluded from the analysis.

To evaluate for the presence of immunity to WT1, Ab to recombinant full-length and truncated WT1 proteins in the sera of normal individuals and patients with leukemia were determined. Antibody reactivity was analyzed by ELISA reactivity to WT1/full-length protein, WT1/N-terminus protein and WT1/C-terminus protein.

Figure 16:
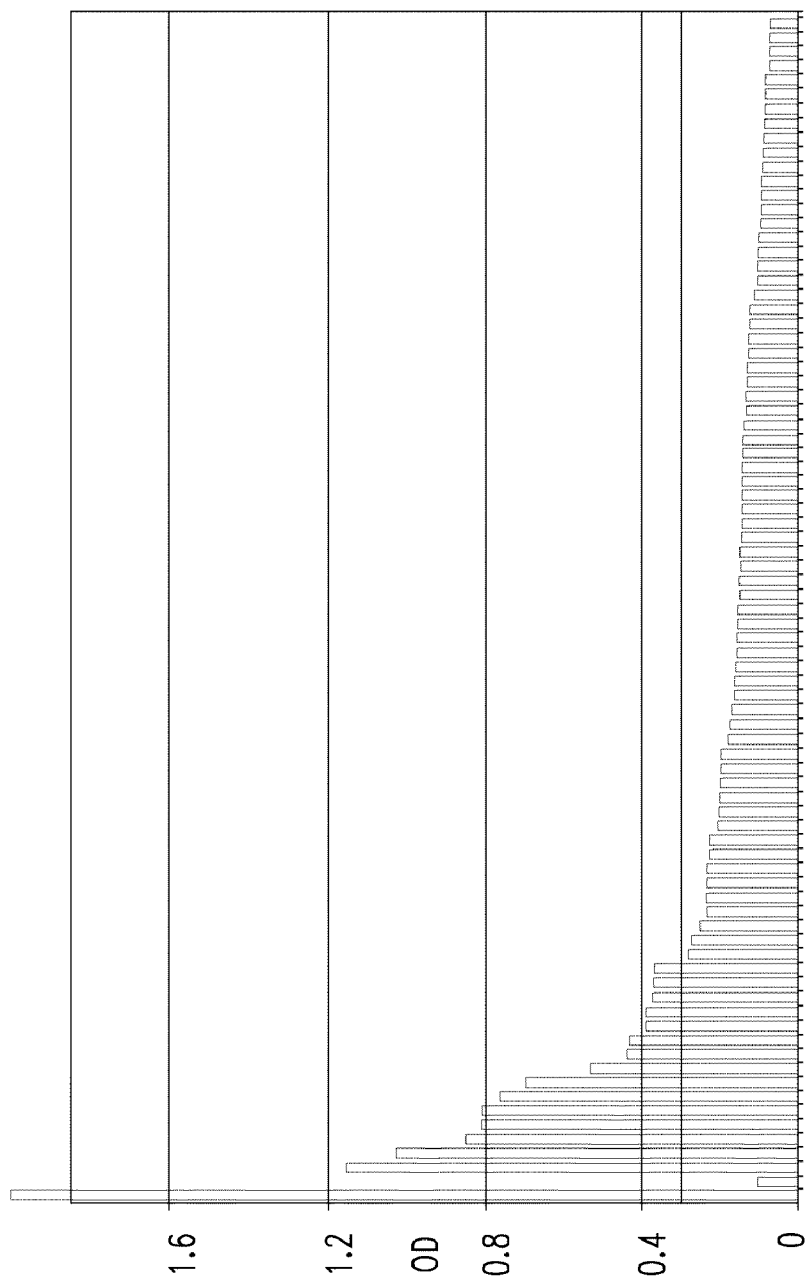
FIG. 16 depicts serum antibody reactivity to WT1 in 81 patients with CML. Reactivity of serum antibody to WT1/full-length protein was evaluated by ELISA in patients with AML. The first and second lanes represent the positive and negative controls, respectively. Commercially obtained WT1 specific antibody WT180 was used for the positive control. The next 81 lanes represent results using sera from each individual patient. The OD values depicted were from ELISA using a 1:500 serum dilution. The figure includes cumulative data from 3 separate experiments.

Only 2 of 96 normal donors had serum antibodies reactive with WT1/full-length protein (FIG. 18). One of those individuals had antibody to WT1/N-terminus protein and one had antibody to WT1/C-terminus protein. In contrast, 16 of 63 patients (25%) with AML had serum antibodies reactive with WT1/full-length protein. By marked contrast, only 2 of 63 patients (3%) had reactivity to WT1/C-terminus protein. Fifteen of 81 patients (19%) with CML had serum antibodies reactive with WT1/full-length protein and 12 of 81 patients (15%) had serum antibodies reactive with WT1/N-terminus. Only 3 of 81 patients (3%) had reactivity to WT1/C-terminus protein. (FIGS. 16 and 17.)

These data demonstrate that Ab responses to WT1 are detectable in some patients with AML and CML. The greater incidence of antibody in leukemia patients provides strong evidence that immunization to the WT1 protein occurred as a result of patients bearing malignancy that expresses or at some time expressed WT1. Without being limited to a specific theory, it is believed that the observed antibody responses to WT1 most probably result from patients becoming immune to WT1 on their own leukemia cells and provide direct evidence that WT1 can be immunogenic despite being a "self" protein.

The presence of antibody to WT1 strongly implies that concurrent helper T cell responses are also present in the same patients. WT1 is an internal protein. Thus, CTL responses are likely to be the most effective in terms of leukemia therapy and the most toxic arm of immunity. Thus, these data provide evidence that therapeutic vaccines directed against WT1 will be able to elicit an immune response to WT1.

The majority of the antibodies detected were reactive with epitopes within the N-terminus while only a small subgroup of patients showed a weak antibody response to the C-terminus. This is consistent with observations in the animal model, where immunization with peptides derived from the N-terminus elicited antibody, helper T cell and CTL responses, whereas none of the peptides tested from the C-terminus elicited antibody or T cell responses (Gaiger et al., *Blood* 96:1334, 2000).

Example 2

Induction of Antibodies to WT1 in Mice Immunized with Cell Lines Expressing WT1

This Example illustrates the use of cells expressing WT1 to induce a WT1 specific antibody response in vivo.

Detection of existent antibodies to WT1 in patients with leukemia strongly implied that it is possible to immunize to WT1 protein to elicit immunity to WT1. To test whether immunity to WT1 can be generated by vaccination, mice were injected with TRAMP-C, a WT1 positive tumor cell line of B6 origin. Briefly, male B6 mice were immunized with $5 \times 10^6$ TRAMP-C cells subcutaneously and boosted twice with $5 \times 10^6$ cells at three week intervals. Three weeks after the final immunization, sera were obtained and single cell suspensions of spleens were prepared in RPMI 1640 medium (GIBCO®) with 25µM β-2-mercaptoethanol, 200 units of penicillin per ml, 10 mM L-glutamine, and 10% fetal bovine serum.

Figure 3:
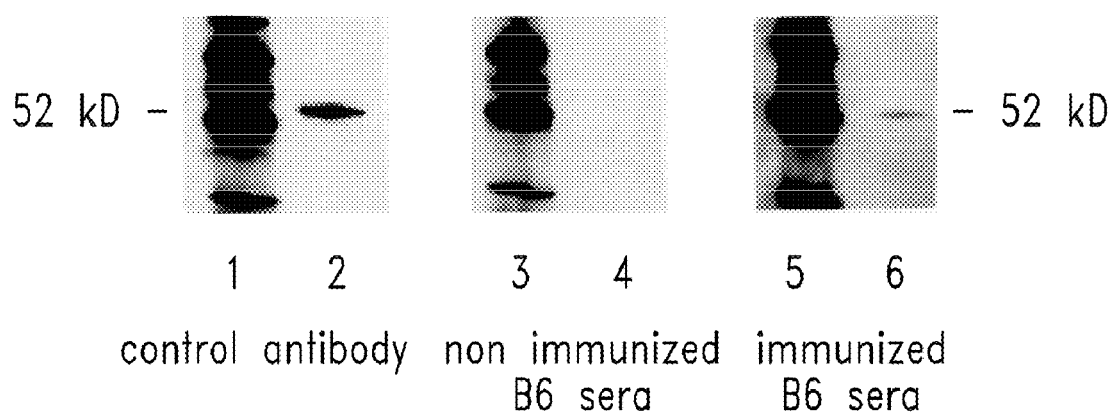
FIG. 3 is a Western blot illustrating the detection of a WT1 specific antibody response in B6 mice immunized with TRAMP-C, a WT1 positive tumor cell line. Lanes 1, 3 and 5 show molecular weight markers, and lanes 2, 4 and 6 show a WT1 specific positive control (N180, Santa Cruz Biotechnology, polypeptide spanning 180 amino acids of the N-terminal region of the WT1 protein, migrating on the Western blot at 52 kD). The primary antibody used was WT180 in lane 2, sera of non-immunized B6 mice in lane 4 and sera of the immunized B6 mice in lane 6.

Following immunization to TRAMP-C, a WT1 specific antibody response in the immunized animals was detectable. A representative Western blot is shown in FIG. 3. These results show that immunization to WT1 protein can elicit an immune response to WT1 protein.

Example 3

Induction of Th and Antibody Responses in Mice Immunized with WT1 Peptides

This Example illustrates the ability of immunization with WT1 peptides to elicit an immune response specific for WT1.

Peptides suitable for eliciting Ab and proliferative T cell responses were identified according to the Tsites program (Rothbard and Taylor, *EMBO J.* 7:93-100, 1988; Deavin et al., *Mol. Immunol.* 33:145-155, 1996), which searches for peptide motifs that have the potential to elicit Th responses. Peptides shown in Table I were synthesized and sequenced.

TABLE I

| WT1 Peptides | | |
|---|---|---|
| Peptide | Sequence | Comments |
| Mouse: p6-22 | RDLNALLPAVSSLGGGG (SEQ ID NO: 13) | 1 mismatch relative to human WT1 sequence |
| Human: p6-22 | RDLNALLPAVPSLGGGG (SEQ ID NO: 1) | |
| Human/mouse: p117-139 | PSQASSGQARMFPNAPYLPSCLE (SEQ ID NOs: 2 and 3) | |

TABLE I-continued

| WT1 Peptides | | |
|---|---|---|
| Peptide | Sequence | Comments |
| Mouse: p244-262 | GATLKGMAAGSSSSVKWTE (SEQ ID NO: 14) | 1 mismatch relative to human WT1 sequence |
| Human: p244-262 | GATLKGVAAGSSSSVKWTE (SEQ ID NO: 4) | |
| Human/mouse: p287-301 | RIHTHGVFRGIQDVR (SEQ ID NOs: 15 and 16) | |
| Mouse: p299-313 | VRRVSGVAPTLVRS (SEQ ID NO: 17) | 1 mismatch relative to human WT1 sequence |
| Human/mouse: p421-435 | CQKKFARSDELVRHH (SEQ ID NOs: 19 and 20) | |

For immunization, peptides were grouped as follows:
Group A: p6-22 human: 10.9 mg in 1 ml (10 µl=100 µg)
  p117-139 human/mouse: 7.6 mg in 1 ml (14 µl=100 µg)
  p244-262 human: 4.6 mg in 1 ml (22 µl=100 µg)
Group B: p287-301 human/mouse: 7.2 mg in 1 ml (14 µl=100 µg)
  mouse p299-313: 6.6.mg in 1 ml (15 µl=100 µg)
  p421-435 human/mouse: 3.3 mg in 1 ml (30 µl=100 µg)
Control: (FBL peptide 100 µg)+CFA/IFA
Control: (CD45 peptide 100 µg)+CFA/IFA Group A contained peptides present within the amino terminus portion of WT1 (exon 1) and Group B contained peptides present within the carboxy terminus, which contains a four zinc finger region with sequence homology to other DNA-binding proteins. Within group B, p287-301 and p299-313 were derived from exon 7, zinc finger 1, and p421-435 was derived from exon 10, zinc finger IV.

B6 mice were immunized with a group of WT1 peptides or with a control peptide. Peptides were dissolved in 1 ml sterile water for injection, and B6 mice were immunized 3 times at time intervals of three weeks. Adjuvants used were CFA/IFA, GM-CSF, and MONTANIDE®. The presence of antibodies specific for WT1 was then determined as described in Examples 1 and 2, and proliferative T cell responses were evaluated using a standard thymidine incorporation assay, in which cells were cultured in the presence of antigen and proliferation was evaluated by measuring incorporated radioactivity (Chen et al., *Cancer Res.* 54:1065-1070, 1994). In particular, lymphocytes were cultured in 96-well plates at $2 \times 10^5$ cells per well with $4 \times 10^5$ irradiated (3000 rads) syngeneic spleen cells and the designated peptide.

Figure 4:
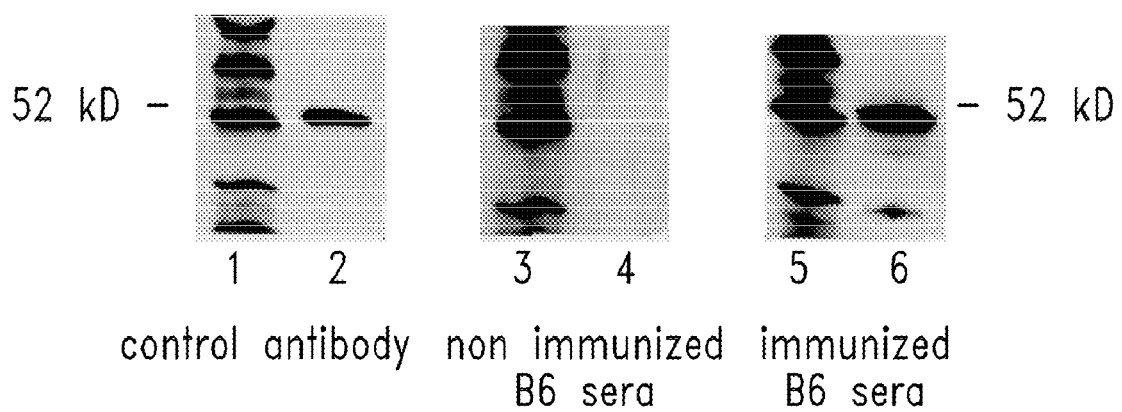
FIG. 4 is a Western blot illustrating the detection of WT1 specific antibodies in mice immunized with representative WT1 peptides. Lanes 1, 3 and 5 show molecular weight markers and lanes 2, 4 and 6 show a WT1 specific positive control (N180, Santa Cruz Biotechnology, polypeptide spanning 180 amino acids of the N-terminal region of the WT1 protein, migrating on the Western blot at 52 kD). The primary antibody used was WT180 in lane 2, sera of non-immunized B6 mice in lane 4 and sera of the immunized B6 mice in lane 6.
Figure 5A:
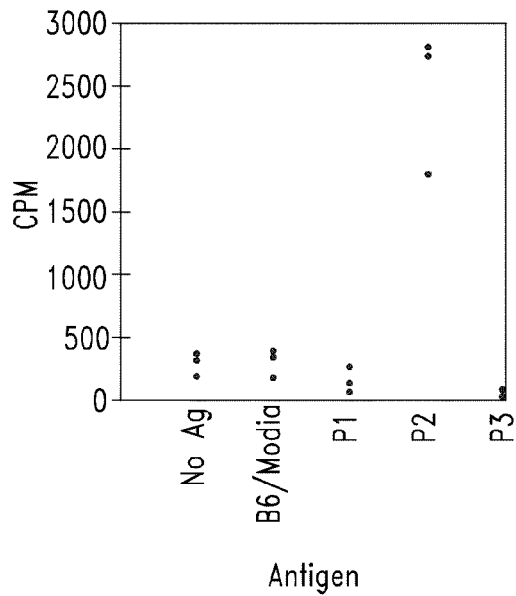
FIGS. 5A to 5C are graphs illustrating the stimulation of proliferative T cell responses in mice immunized with representative WT1 peptides. Thymidine incorporation assays were performed using one T cell line and two different clones, as indicated, and results were expressed as cpm. Controls indicated on the x axis were no antigen (No Ag) and B6/media; antigens used were p6-22 human (p1), p117-139 (p2) or p244-262 human (p3).
Figure 5B:
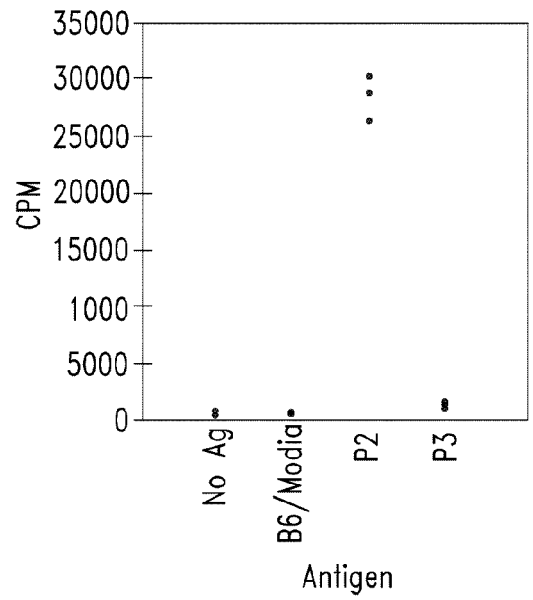
Figure 5C:
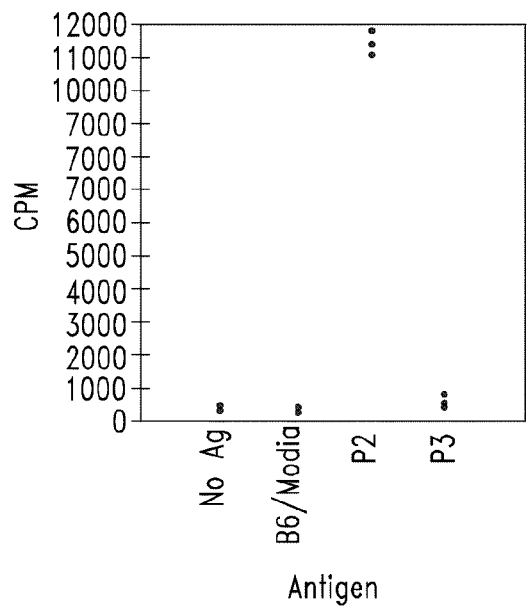

Immunization of mice with the group of peptides designated as Group A elicited an antibody response to WT1 (FIG. 4). No antibodies were detected following immunization to Vaccine B, which is consistent with a lack of helper T cell response from immunization with Vaccine B. P117-139 elicited proliferative T cell responses (FIGS. 5A-5C). The stimulation indices (SI) varied between 8 and 72. Other peptides (P6-22 and P299-313) also were shown to elicit proliferative T cell responses. Immunization with P6-22 resulted in a stimulation index (SI) of 2.3 and immunization with P299-313 resulted in a SI of 3.3. Positive controls included ConA stimulated T cells, as well as T cells stimulated with known antigens, such as CD45 and FBL, and allogeneic T cell lines (DeBruijn et al., *Eur. J. Immunol.* 21:2963-2970, 1991).

Figures 6A, 6B:
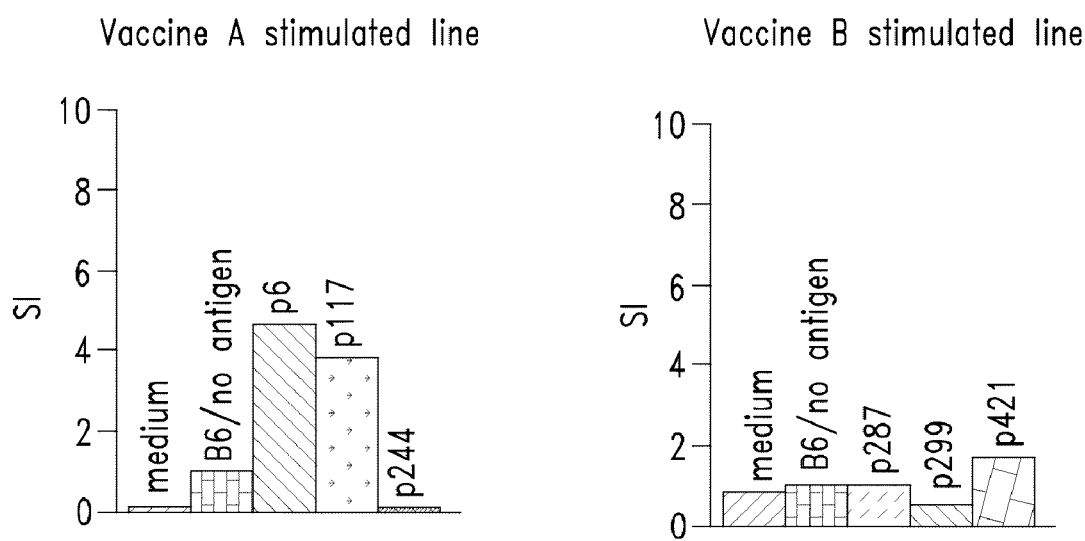
FIGS. 6A and 6B are histograms illustrating the stimulation of proliferative T cell responses in mice immunized with representative WT1 peptides. Three weeks after the third immunization, spleen cells of mice that had been inoculated with Vaccine A or Vaccine B were cultured with medium alone (medium) or spleen cells and medium (B6/no antigen), B6 spleen cells pulsed with the peptides p6-22 (p6), p117-139 (p117), p244-262 (p244) (Vaccine A.

FIGS. 6A and 6B show the proliferative response observed for each of the three peptides within vaccine A (FIG. 6A) and vaccine B (FIG. 6B). Vaccine A elicited proliferative T cell responses to the immunizing peptides p6-22 and p117-139, with stimulation indices (SI) varying between 3 and 8 (bulk lines). No proliferative response to p244-262 was detected (FIG. 6A).

Figure 7A:
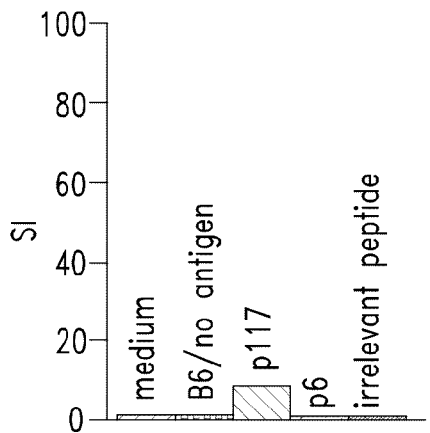
FIGS. 7A-7D are histograms illustrating the generation of proliferative T-cell lines and clones specific for p117-139 and p6-22. Following in vivo immunization, the initial three in vitro stimulations (IVS) were carried out using all three peptides of Vaccine A or B, respectively. Subsequent IVS were carried out as single peptide stimulations using only the two relevant peptides p117-139 and p6-22. Clones were derived from both the p6-22 and p117-139 specific T cell lines, as indicated. T cells were cultured with medium alone (medium) or spleen cells and medium (B6/no antigen), B6 spleen cells pulsed with the peptides p6-22 (p6), p117-139 (p117) or an irrelevant control peptide (irrelevant peptide) at 25 ug/ml and were assayed after 96 hr for proliferation by ($^3$H) thymidine incorporation. Bars represent the stimulation index (SI), which is calculated as the mean of the experimental wells divided by the mean of the control (B6 spleen cells with no antigen).
Figure 7B:
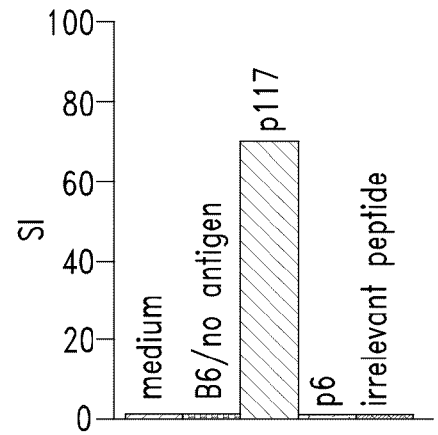
Figure 7C:
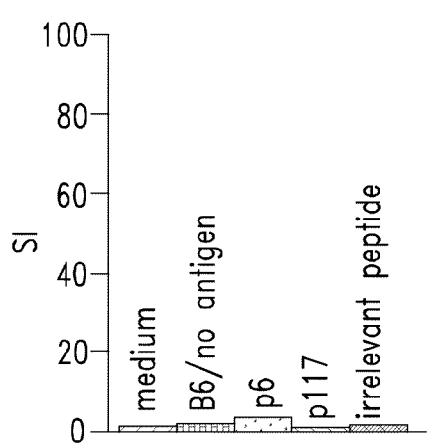
Figure 7D:
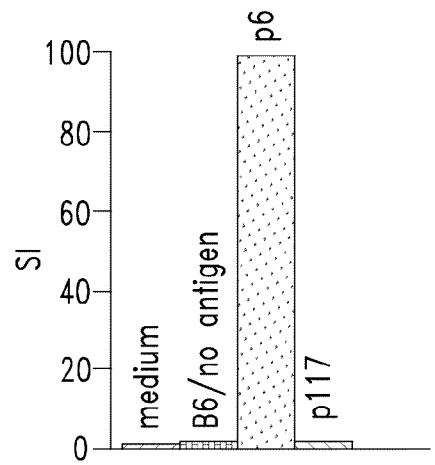

Subsequent in vitro stimulations were carried out as single peptide stimulations using only p6-22 and p117-139. Stimulation of the Vaccine A specific T cell line with p117-139 resulted in proliferation to p117-139 with no response to p6-22 (FIG. 7A). Clones derived from the line were specific for p117-139 (FIG. 7B). By contrast, stimulation of the Vaccine A specific T cell line with p6-22 resulted in proliferation to p6-22 with no response to p117-139 (FIG. 7C). Clones derived from the line were specific for p6-22 (FIG. 7D).

These results show that vaccination with WT1 peptides can elicit antibody responses to WT1 protein and proliferative T cell responses to the immunizing peptides.

Example 4

Induction of CTL Responses in Mice Immunized with WT1 Peptides

This Example illustrates the ability of WT1 peptides to elicit CTL immunity.

Peptides (9-mers) with motifs appropriate for binding to class I MHC were identified using a BIMAS HLA peptide binding prediction analysis (Parker et al., *J. Immunol.* 152: 163, 1994). Peptides identified within such analyses are shown in Tables II-XLIV. In each of these tables, the score reflects the theoretical binding affinity (half-time of dissociation) of the peptide to the MHC molecule indicated. Also indicated in the tables are the defined peptide binding motifs as described by Rammensee, et al., Immunogenetics 41:178-228, 1995, incorporated herein in its entirety. The peptide binding motif for HLA-B14 is described in DiBrino et al., J. Biol. Chem. 269:23426-23434, 1994, also incorporated herein it its entirety. Peptide positions are abbreviated as P1, P2, P3, P4, P5, P6, P7, P8, and P9.

Peptides identified using the Tsites program (Rothbard and Taylor, *EMBO J.* 7:93-100, 1988; Deavin et al., *Mol. Immunol.* 33:145-155, 1996), which searches for peptide motifs that have the potential to elicit Th responses are further shown in FIGS. 8A and 8B, and Table XLV.

TABLE II

Results of BIMAS HLA Peptide Binding Prediction Analysis for Binding of Human WT1 Peptides to Human HLA A1 (HLA-A1 peptide binding motif anchor residues are D or E at position 3 (P3); Y at P9; with auxiliary anchors being P at P4 and L at P7)

| Rank | Start Position | Subsequence Residue Listing | Score (Estimate of Half Time of Disassociation of a Molecule Containing This Subsequence) |
|---|---|---|---|
| 1 | 137 | CLESQPAIR (SEQ ID NO: 47) | 18.000 |
| 2 | 80 | GAEPHEEQC (SEQ ID NO: 87) | 9.000 |
| 3 | 40 | FAPPGASAY (SEQ ID NO: 74) | 5.000 |
| 4 | 354 | QCDFKDCER (SEQ ID NO: 162) | 5.000 |
| 5 | 2 | GSDVRDLNA (SEQ ID NO: 101) | 3.750 |
| 6 | 152 | VTFDGTPSY (SEQ ID NO: 244) | 2.500 |
| 7 | 260 | WTEGQSNHS (SEQ ID NO: 247) | 2.250 |
| 8 | 409 | TSEKPFSCR (SEQ ID NO: 232) | 1.350 |
| 9 | 73 | KQEPSWGGA (SEQ ID NO: 125) | 1.350 |
| 10 | 386 | KTCQRKFSR (SEQ ID NO: 128) | 1.250 |
| 11 | 37 | VLDFAPPGA (SEQ ID NO: 241) | 1.000 |
| 12 | 325 | CAYPGCNKR (SEQ ID NO: 44) | 1.000 |
| 13 | 232 | QLECMTWNQ (SEQ ID NO: 167) | 0.900 |
| 14 | 272 | ESDNHTTPI (SEQ ID NO: 71) | 0.750 |
| 15 | 366 | RSDQLKRHQ (SEQ ID NO: 193) | 0.750 |
| 16 | 222 | SSDNLYQMT (SEQ ID NO: 217) | 0.750 |
| 17 | 427 | RSDELVRHH (SEQ ID NO: 191) | 0.750 |
| 18 | 394 | RSDHLKTHT (SEQ ID NO: 192) | 0.750 |
| 19 | 317 | TSEKRPFMC (SEQ ID NO: 233) | 0.675 |
| 20 | 213 | QALLLRTPY (SEQ ID NO: 160) | 0.500 |

TABLE III

Results of BIMAS HLA Peptide Binding Prediction Analysis for Binding of Human WT1 Peptides to Human HLA A 0201 (HLA-A0201 peptide binding motif anchor residues are L or M at P2; V or L at P9; with an auxiliary anchor being V at P6)

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO: 185) | 313.968 |
| 2 | 187 | SLGEQQYSV (SEQ ID NO: 214) | 285.163 |
| 3 | 10 | ALLPAVPSL (SEQ ID NO: 34) | 181.794 |
| 4 | 242 | NLGATLKGV (SEQ ID NO: 146) | 159.970 |
| 5 | 225 | NLYQMTSQL (SEQ ID NO: 147) | 68.360 |
| 6 | 292 | GVFRGIQDV (SEQ ID NO: 103) | 51.790 |
| 7 | 191 | QQYSVPPPV (SEQ ID NO: 171) | 22.566 |
| 8 | 280 | ILCGAQYRI (SEQ ID NO: 116) | 17.736 |
| 9 | 235 | CMTWNQMNL (SEQ ID NO: 49) | 15.428 |
| 10 | 441 | NMTKLQLAL (SEQ ID NO: 149) | 15.428 |
| 11 | 7 | DLNALLPAV (SEQ ID NO: 58) | 11.998 |
| 12 | 227 | YQMTSQLEC (SEQ ID NO: 251) | 8.573 |
| 13 | 239 | NQMNLGATL (SEQ ID NO: 151) | 8.014 |
| 14 | 309 | TLVRSASET (SEQ ID NO: 226) | 7.452 |
| 15 | 408 | KTSEKPFSC (SEQ ID NO: 129) | 5.743 |
| 16 | 340 | LQMHSRKHT (SEQ ID NO: 139) | 4.752 |
| 17 | 228 | QMTSQLECM (SEQ ID NO: 169) | 4.044 |
| 18 | 93 | TVHFSGQFT (SEQ ID NO: 235) | 3.586 |
| 19 | 37 | VLDFAPPGA (SEQ ID NO: 241) | 3.378 |
| 20 | 86 | EQCLSAFTV (SEQ ID NO: 69) | 3.068 |

TABLE IV

Results of BIMAS HLA Peptide Binding Prediction Analysis for Binding of Human WT1 Peptides to Human HLA A 0205 (HLA-A0205 peptide binding motif anchor residues are L at P9 with auxiliary anchors being V, L, I, M at P2 and I, V, L, A, at P6)

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO: 34) | 42.000 |
| 2 | 292 | GVFRGIQDV (SEQ ID NO: 103) | 24.000 |
| 3 | 126 | RMFPNAPYL (SEQ ID NO: 185) | 21.000 |
| 4 | 225 | NLYQMTSQL (SEQ ID NO: 147) | 21.000 |
| 5 | 239 | NQMNLGATL (SEQ ID NO: 151) | 16.800 |
| 6 | 302 | RVPGVAPTL (SEQ ID NO: 195) | 14.000 |
| 7 | 441 | NMTKLQLAL (SEQ ID NO: 149) | 7.000 |
| 8 | 235 | CMTWNQMNL (SEQ ID NO: 49) | 7.000 |
| 9 | 187 | SLGEQQYSV (SEQ ID NO: 214) | 6.000 |
| 10 | 191 | QQYSVPPPV (SEQ ID NO: 171) | 4.800 |
| 11 | 340 | LQMHSRKHT (SEQ ID NO: 139) | 4.080 |
| 12 | 242 | NLGATLKGV (SEQ ID NO: 146) | 4.000 |
| 13 | 227 | YQMTSQLEC (SEQ ID NO: 251) | 3.600 |
| 14 | 194 | SVPPPVYGC (SEQ ID NO: 218) | 2.000 |
| 15 | 93 | TVHFSGQFT (SEQ ID NO: 235) | 2.000 |
| 16 | 280 | ILCGAQYRI (SEQ ID NO: 116) | 1.700 |
| 17 | 98 | GQFTGTAGA (SEQ ID NO: 99) | 1.200 |
| 18 | 309 | TLVRSASET (SEQ ID NO: 226) | 1.000 |
| 19 | 81 | AEPHEEQCL (SEQ ID NO: 30) | 0.980 |
| 20 | 73 | KQEPSWGGA (SEQ ID NO: 125) | 0.960 |

TABLE V

Results of BIMAS HLA Peptide Binding Prediction Analysis for Binding of Human WT1 Peptides to Human HLA A24 (HLA-A24 peptide binding motif anchor residues are Y at P2; I, L, or F at P9; with auxiliary anchors I or V at P5 and F at P6)

| Rank | Start Position | Subsequence Residue Listing | Score (Estimate of Half Time of Disassociation of a Molecule Containing This Subsequence) |
|---|---|---|---|
| 1 | 302 | RVPGVAPTL (SEQ ID NO: 195) | 16.800 |
| 2 | 218 | RTPYSSDNL (SEQ ID NO: 194) | 12.000 |
| 3 | 356 | DFKDCERRF (SEQ ID NO: 55) | 12.000 |
| 4 | 126 | RMFPNAPYL (SEQ ID NO: 185) | 9.600 |
| 5 | 326 | AYPGCNKRY (SEQ ID NO: 42) | 7.500 |
| 6 | 270 | GYESDNHTT (SEQ ID NO: 106) | 7.500 |
| 7 | 239 | NQMNLGATL (SEQ ID NO: 151) | 7.200 |
| 8 | 10 | ALLPAVPSL (SEQ ID NO: 34) | 7.200 |
| 9 | 130 | NAPYLPSCL (SEQ ID NO: 144) | 7.200 |
| 10 | 329 | GCNKRYFKL (SEQ ID NO: 90) | 6.600 |
| 11 | 417 | RWPSCQKKF (SEQ ID NO: 196) | 6.600 |
| 12 | 47 | AYGSLGGPA (SEQ ID NO: 41) | 6.000 |
| 13 | 180 | DPMGQQGSL (SEQ ID NO: 59) | 6.000 |
| 14 | 4 | DVRDLNALL (SEQ ID NO: 62) | 5.760 |
| 15 | 285 | QYRIHTHGV (SEQ ID NO: 175) | 5.000 |
| 16 | 192 | QYSVPPPVY (SEQ ID NO: 176) | 5.000 |
| 17 | 207 | DSCTGSQAL (SEQ ID NO: 61) | 4.800 |
| 18 | 441 | NMTKLQLAL (SEQ ID NO: 149) | 4.800 |
| 19 | 225 | NLYQMTSQL (SEQ ID NO: 147) | 4.000 |
| 20 | 235 | CMTWNQMNL (SEQ ID NO: 49) | 4.000 |

TABLE VI

Results of BIMAS HLA Peptide Binding Prediction Analysis for Binding of Human WT1 Peptides to Human HLA A3 (HLA-A3 peptide binding motif anchor residues are L, V, or M at P2; K, Y, or F at P9; auxiliary anchors are F or Y at P3, I, M, F, V, or L at P6; I, L, M, F at P7)

| Rank | Start Position | Subsequence Residue Listing | Score (Estimate of Half Time of Disassociation of a Molecule Containing This Subsequence) |
|---|---|---|---|
| 1 | 436 | NMHQRNMTK (SEQ ID NO: 148) | 40.000 |
| 2 | 240 | QMNLGATLK (SEQ ID NO: 168) | 20.000 |
| 3 | 88 | CLSAFTVHF (SEQ ID NO: 48) | 6.000 |
| 4 | 126 | RMFPNAPYL (SEQ ID NO: 185) | 4.500 |
| 5 | 169 | AQFPNHSFK (SEQ ID NO: 36) | 4.500 |
| 6 | 10 | ALLPAVPSL (SEQ ID NO: 34) | 4.050 |
| 7 | 137 | CLESQPAIR (SEQ ID NO: 47) | 4.000 |
| 8 | 225 | NLYQMTSQL (SEQ ID NO: 147) | 3.000 |
| 9 | 32 | AQWAPVLDF (SEQ ID NO: 37) | 2.700 |
| 10 | 280 | ILCGAQYRI (SEQ ID NO: 116) | 2.700 |
| 11 | 386 | KTCQRKFSR (SEQ ID NO: 128) | 1.800 |
| 12 | 235 | CMTWNQMNL (SEQ ID NO: 49) | 1.200 |
| 13 | 441 | NMTKLQLAL (SEQ ID NO: 149) | 1.200 |
| 14 | 152 | VTFDGTPSY (SEQ ID NO: 244) | 1.000 |
| 15 | 187 | SLGEQQYSV (SEQ ID NO: 214) | 0.900 |
| 16 | 383 | FQCKTCQRK (SEQ ID NO: 80) | 0.600 |
| 17 | 292 | GVFRGIQDV (SEQ ID NO: 103) | 0.450 |
| 18 | 194 | SVPPPVYGC (SEQ ID NO: 218) | 0.405 |
| 19 | 287 | RIHTHGVFR (SEQ ID NO: 182) | 0.400 |
| 20 | 263 | GQSNHSTGY (SEQ ID NO: 100) | 0.360 |

TABLE VII

Results of BIMAS HLA Peptide Binding Prediction Analysis for Binding of Human WT1 Peptides to Human HLA A68.1 (HLA-A68.1 peptide binding motif anchor residues are V or T at P2; R or K at P9

| Rank | Start Position | Subsequence Residue Listing | Score (Estimate of Half Time of Disassociation of a Molecule Containing This Subsequence) |
|---|---|---|---|
| 1 | 100 | FTGTAGACR (SEQ ID NO: 84) | 100.000 |
| 2 | 386 | KTCQRKFSR (SEQ ID NO: 128) | 50.000 |
| 3 | 368 | DQLKRHQRR (SEQ ID NO: 60) | 30.000 |
| 4 | 312 | RSASETSEK (SEQ ID NO: 190) | 18.000 |
| 5 | 337 | LSHLQMHSR (SEQ ID NO: 141) | 15.000 |
| 6 | 364 | FSRSDQLKR (SEQ ID NO: 83) | 15.000 |
| 7 | 409 | TSEKPFSCR (SEQ ID NO: 232) | 15.000 |
| 8 | 299 | DVRRVPGVA (SEQ ID NO: 63) | 12.000 |
| 9 | 4 | DVRDLNALL (SEQ ID NO: 62) | 12.000 |
| 10 | 118 | SQASSGQAR (SEQ ID NO: 216) | 10.000 |
| 11 | 343 | HSRKHTGEK (SEQ ID NO: 111) | 9.000 |
| 12 | 169 | AQFPNHSFK (SEQ ID NO: 36) | 9.000 |
| 13 | 292 | GVFRGIQDV (SEQ ID NO: 103) | 8.000 |
| 14 | 325 | CAYPGCNKR (SEQ ID NO: 44) | 7.500 |
| 15 | 425 | FARSDELVR (SEQ ID NO: 75) | 7.500 |
| 16 | 354 | QCDFKDCER (SEQ ID NO: 162) | 7.500 |
| 17 | 324 | MCAYPGCNK (SEQ ID NO: 142) | 6.000 |
| 18 | 251 | AAGSSSSVK (SEQ ID NO: 28) | 6.000 |
| 19 | 379 | GVKPFQCKT (SEQ ID NO: 104) | 6.000 |
| 20 | 137 | CLESQPAIR (SEQ ID NO: 47) | 5.000 |

TABLE VIII

Results of BIMAS HLA Peptide Binding Prediction Analysis for Binding of Human WT1 Peptides to Human HLA A 1101 (HLA-A1101 peptide binding motif anchor residues are K at P9; auxiliary anchor residues are V, I, F, Y at P2, M, L, F, Y, I, A, at P3, L, I, Y, V, or F at P7)

| Rank | Start Position | Subsequence Residue Listing | Score (Estimate of Half Time of Disassociation of a Molecule Containing This Subsequence) |
|---|---|---|---|
| 1 | 386 | KTCQRKFSR (SEQ ID NO: 128) | 1.800 |
| 2 | 169 | AQFPNHSFK (SEQ ID NO: 36) | 1.200 |
| 3 | 436 | NMHQRNMTK (SEQ ID NO: 148) | 0.800 |
| 4 | 391 | KFSRSDHLK (SEQ ID NO: 120) | 0.600 |
| 5 | 373 | HQRRHTGVK (SEQ ID NO: 109) | 0.600 |
| 6 | 383 | FQCKTCQRK (SEQ ID NO: 80) | 0.600 |
| 7 | 363 | RFSRSDQLK (SEQ ID NO: 178) | 0.600 |
| 8 | 240 | QMNLGATLK (SEQ ID NO: 168) | 0.400 |
| 9 | 287 | RIHTHGVFR (SEQ ID NO: 182) | 0.240 |
| 10 | 100 | FTGTAGACR (SEQ ID NO: 84) | 0.200 |
| 11 | 324 | MCAYPGCNK (SEQ ID NO: 142) | 0.200 |
| 12 | 251 | AAGSSSSVK (SEQ ID NO: 28) | 0.200 |
| 13 | 415 | SCRWPSCQK (SEQ ID NO: 201) | 0.200 |
| 14 | 118 | SQASSGQAR (SEQ ID NO: 216) | 0.120 |
| 15 | 292 | GVFRGIQDV (SEQ ID NO: 103) | 0.120 |
| 16 | 137 | CLESQPAIR (SEQ ID NO: 47) | 0.080 |
| 17 | 425 | FARSDELVR (SEQ ID NO: 75) | 0.080 |
| 18 | 325 | CAYPGCNKR (SEQ ID NO: 44) | 0.080 |
| 19 | 312 | RSASETSEK (SEQ ID NO: 190) | 0.060 |
| 20 | 65 | PPPPHSFIK (SEQ ID NO: 156) | 0.060 |

TABLE IX

Results of BIMAS HLA Peptide Binding Prediction Analysis for Binding of Human WT1 Peptides to Human HLA A 3101
(HLA-A3101 peptide binding motif anchor residues are R at P9; auxiliary anchors L, V, Y, or F at P2; F, L, Y, W at P3, L, F, V, I, at P6)

| Rank | Start Position | Subsequence Residue Listing | Score (Estimate of Half Time of Disassociation of a Molecule Containing This Subsequence) |
|---|---|---|---|
| 1 | 386 | KTCQRKFSR (SEQ ID NO: 128) | 9.000 |
| 2 | 287 | RIHTHGVFR (SEQ ID NO: 182) | 6.000 |
| 3 | 137 | CLESQPAIR (SEQ ID NO: 47) | 2.000 |
| 4 | 118 | SQASSGQAR (SEQ ID NO: 216) | 2.000 |
| 5 | 368 | DQLKRHQRR (SEQ ID NO: 60) | 1.200 |
| 6 | 100 | FTGTAGACR (SEQ ID NO: 84) | 1.000 |
| 7 | 293 | VFRGIQDVR (SEQ ID NO: 238) | 0.600 |
| 8 | 325 | CAYPGCNKR (SEQ ID NO: 44) | 0.600 |
| 9 | 169 | AQFPNHSFK (SEQ ID NO: 36) | 0.600 |
| 10 | 279 | PILCGAQYR (SEQ ID NO: 155) | 0.400 |
| 11 | 436 | NMHQRNMTK (SEQ ID NO: 148) | 0.400 |
| 12 | 425 | FARSDELVR (SEQ ID NO: 75) | 0.400 |
| 13 | 32 | AQWAPVLDF (SEQ ID NO: 37) | 0.240 |
| 14 | 240 | QMNLGATLK (SEQ ID NO: 168) | 0.200 |
| 15 | 354 | QCDFKDCER (SEQ ID NO: 162) | 0.200 |
| 16 | 373 | HQRRHTGVK (SEQ ID NO: 109) | 0.200 |
| 17 | 383 | FQCKTCQRK (SEQ ID NO: 80) | 0.200 |
| 18 | 313 | SASETSEKR (SEQ ID NO: 197) | 0.200 |
| 19 | 358 | KDCERRFSR (SEQ ID NO: 118) | 0.180 |
| 20 | 391 | KFSRSDHLK (SEQ ID NO: 120) | 0.180 |

TABLE X

Results of BIMAS HLA Peptide Binding Prediction Analysis for Binding of Human WT1 Peptides to Human HLA A 3302
(HLA-A3302 peptide binding motif anchor residues are R at P9; auxiliary anchors A, I, L, F, Y, or V at P2)

| Rank | Start Position | Subsequence Residue Listing | Score (Estimate of Half Time of Disassociation of a Molecule Containing This Subsequence) |
|---|---|---|---|
| 1 | 337 | LSHLQMHSR (SEQ ID NO: 141) | 15.000 |
| 2 | 409 | TSEKPFSCR (SEQ ID NO: 232) | 15.000 |
| 3 | 364 | FSRSDQLKR (SEQ ID NO: 83) | 15.000 |
| 4 | 137 | CLESQPAIR (SEQ ID NO: 47) | 9.000 |
| 5 | 368 | DQLKRHQRR (SEQ ID NO: 60) | 9.000 |
| 6 | 287 | RIHTHGVFR (SEQ ID NO: 182) | 4.500 |
| 7 | 210 | TGSQALLLR (SEQ ID NO: 223) | 3.000 |
| 8 | 425 | FARSDELVR (SEQ ID NO: 75) | 3.000 |
| 9 | 313 | SASETSEKR (SEQ ID NO: 197) | 3.000 |
| 10 | 293 | VFRGIQDVR (SEQ ID NO: 238) | 3.000 |
| 11 | 354 | QCDFKDCER (SEQ ID NO: 162) | 3.000 |
| 12 | 100 | FTGTAGACR (SEQ ID NO: 84) | 3.000 |
| 13 | 118 | SQASSGQAR (SEQ ID NO: 216) | 3.000 |
| 14 | 325 | CAYPGCNKR (SEQ ID NO: 44) | 3.000 |
| 15 | 207 | DSCTGSQAL (SEQ ID NO: 61) | 1.500 |
| 16 | 139 | ESQPAIRNQ (SEQ ID NO: 72) | 1.500 |
| 17 | 299 | DVRRVPGVA (SEQ ID NO: 63) | 1.500 |
| 18 | 419 | PSCQKKFAR (SEQ ID NO: 159) | 1.500 |
| 19 | 272 | ESDNHTTPI (SEQ ID NO: 71) | 1.500 |
| 20 | 4 | DVRDLNALL (SEQ ID NO: 62) | 1.500 |

TABLE XI

Results of BIMAS HLA Peptide Binding Prediction Analysis for Binding of Human WT1 Peptides to Human HLA B14
(HLA-B14 peptide binding motif anchor residues are R at P2, Y at P3, R at P5, L at P9. Three of the 4 anchor residues is sufficient)

| Rank | Start Position | Subsequence Residue Listing | Score (Estimate of Half Time of Dissociation of a Molecule Containing This Subsequence) |
|---|---|---|---|
| 1 | 362 | RRFSRSDQL (SEQ ID NO: 187) | 1000.000 |
| 2 | 332 | KRYFKLSHL (SEQ ID NO: 127) | 300.000 |
| 3 | 423 | KKFARSDEL (SEQ ID NO: 122) | 150.000 |
| 4 | 390 | RKFSRSDHL (SEQ ID NO: 183) | 150.000 |
| 5 | 439 | QRNMTKLQL (SEQ ID NO: 173) | 20.000 |
| 6 | 329 | GCNKRYFKL (SEQ ID NO: 90) | 10.000 |
| 7 | 10 | ALLPAVPSL (SEQ ID NO: 34) | 10.000 |
| 8 | 180 | DPMGQQGSL (SEQ ID NO: 59) | 9.000 |
| 9 | 301 | RRVPGVAPT (SEQ ID NO: 189) | 6.000 |
| 10 | 126 | RMFPNAPYL (SEQ ID NO: 185) | 5.000 |
| 11 | 371 | KRHQRRHTG (SEQ ID NO: 126) | 5.000 |
| 12 | 225 | NLYQMTSQL (SEQ ID NO: 147) | 5.000 |
| 13 | 144 | IRNQGYSTV (SEQ ID NO: 117) | 4.000 |
| 14 | 429 | DELVRHHNM (SEQ ID NO: 53) | 3.000 |
| 15 | 437 | MHQRNMTKL (SEQ ID NO: 143) | 3.000 |
| 16 | 125 | ARMFPNAPY (SEQ ID NO: 38) | 3.000 |
| 17 | 239 | NQMNLGATL (SEQ ID NO: 151) | 3.000 |
| 18 | 286 | YRIHTHGVF (SEQ ID NO: 252) | 3.000 |
| 19 | 174 | HSFKHEDPM (SEQ ID NO: 110) | 3.000 |
| 20 | 372 | RHQRRHTGV (SEQ ID NO: 181) | 3.000 |

TABLE XII

Results of BIMAS HLA Peptide Binding Prediction Analysis for Binding of Human WT1 Peptides to Human HLA B40
(HLA-B40 peptide binding motif anchor residues are E at P2, L, W, M, or A at P9; auxiliary anchors are F, I, or V at P3)

| Rank | Start Position | Subsequence Residue Listing | Score (Estimate of Half Time of Dissociation of a Molecule Containing This Subsequence) |
|---|---|---|---|
| 1 | 81 | AEPHEEQCL (SEQ ID NO: 30) | 40.000 |
| 2 | 429 | DELVRHHNM (SEQ ID NO: 53) | 24.000 |
| 3 | 410 | SEKPFSCRW (SEQ ID NO: 207) | 20.000 |
| 4 | 318 | SEKRPFMCA (SEQ ID NO: 208) | 15.000 |
| 5 | 233 | LECMTWNQM (SEQ ID NO: 131) | 12.000 |
| 6 | 3 | SDVRDLNAL (SEQ ID NO: 206) | 10.000 |
| 7 | 349 | GEKPYQCDF (SEQ ID NO: 91) | 8.000 |
| 8 | 6 | RDLNALLPA (SEQ ID NO: 177) | 5.000 |
| 9 | 85 | EEQCLSAFT (SEQ ID NO: 65) | 4.000 |
| 10 | 315 | SETSEKRPF (SEQ ID NO: 209) | 4.000 |
| 11 | 261 | TEGQSNHST (SEQ ID NO: 221) | 4.000 |
| 12 | 23 | GCALPVSGA (SEQ ID NO: 89) | 3.000 |
| 13 | 38 | LDFAPPGAS (SEQ ID NO: 130) | 3.000 |
| 14 | 273 | SDNHTTPIL (SEQ ID NO: 204) | 2.500 |
| 15 | 206 | TDSCTGSQA (SEQ ID NO: 220) | 2.500 |
| 16 | 24 | CALPVSGAA (SEQ ID NO: 43) | 2.000 |
| 17 | 98 | GQFTGTAGA (SEQ ID NO: 99) | 2.000 |
| 18 | 30 | GAAQWAPVL (SEQ ID NO: 86) | 2.000 |
| 19 | 84 | HEEQCLSAF (SEQ ID NO: 107) | 2.000 |
| 20 | 26 | LPVSGAAQW (SEQ ID NO: 138) | 2.000 |

TABLE XIII

Results of BIMAS HLA Peptide Binding Prediction Analysis for Binding of Human WT1 Peptides to Human HLA B60
(HLA-B60 peptide binding motif anchor residues are E at P2, L at P9; auxiliary anchors are I or V at P7)

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO: 30) | 160.000 |
| 2 | 3 | SDVRDLNAL (SEQ ID NO: 206) | 40.000 |
| 3 | 429 | DELVRHHNM (SEQ ID NO: 53) | 40.000 |
| 4 | 233 | LECMTWNQM (SEQ ID NO: 131) | 22.000 |
| 5 | 273 | SDNHTTPIL (SEQ ID NO: 204) | 20.000 |
| 6 | 209 | CTGSQALLL (SEQ ID NO: 52) | 8.000 |
| 7 | 30 | GAAQWAPVL (SEQ ID NO: 86) | 8.000 |
| 8 | 318 | SEKRPFMCA (SEQ ID NO: 208) | 8.000 |
| 9 | 180 | DPMGQQGSL (SEQ ID NO: 59) | 8.000 |
| 10 | 138 | LESQPAIRN (SEQ ID NO: 132) | 5.280 |
| 11 | 239 | NQMNLGATL (SEQ ID NO: 151) | 4.400 |
| 12 | 329 | GCNKRYFKL (SEQ ID NO: 90) | 4.400 |
| 13 | 130 | NAPYLPSCL (SEQ ID NO: 144) | 4.400 |
| 14 | 85 | EEQCLSAFT (SEQ ID NO: 65) | 4.400 |
| 15 | 208 | SCTGSQALL (SEQ ID NO: 202) | 4.000 |
| 16 | 207 | DSCTGSQAL (SEQ ID NO: 61) | 4.000 |
| 17 | 218 | RTPYSSDNL (SEQ ID NO: 194) | 4.000 |
| 18 | 261 | TEGQSNHST (SEQ ID NO: 221) | 4.000 |
| 19 | 18 | LGGGGGCAL (SEQ ID NO: 134) | 4.000 |
| 20 | 221 | YSSDNLYQM (SEQ ID NO: 253) | 2.200 |

TABLE XIV

Results of BIMAS HLA Peptide Binding Prediction Analysis for Binding of Human WT1 Peptides to Human HLA B61
(HLA-B61 peptide binding motif anchor residues are E at P2, V at P9; auxiliary anchors are F, I, L, V, Y, W at P3, I at P6)

| Rank | Start Position | Subsequence Residue Listing | Score (Estimate of Half Time of Disassociation of a Molecule Containing This Subsequence) |
|---|---|---|---|
| 1 | 318 | SEKRPFMCA (SEQ ID NO: 208) | 20.000 |
| 2 | 429 | DELVRHHNM (SEQ ID NO: 53) | 16.000 |
| 3 | 298 | QDVRRVPGV (SEQ ID NO: 164) | 10.000 |
| 4 | 81 | AEPHEEQCL (SEQ ID NO: 30) | 8.000 |
| 5 | 233 | LECMTWNQM (SEQ ID NO: 131) | 8.000 |
| 6 | 6 | RDLNALLPA (SEQ ID NO: 177) | 5.500 |
| 7 | 85 | EEQCLSAFT (SEQ ID NO: 65) | 4.000 |
| 8 | 261 | TEGQSNHST (SEQ ID NO: 221) | 4.000 |
| 9 | 206 | TDSCTGSQA (SEQ ID NO: 220) | 2.500 |
| 10 | 295 | RGIQDVRRV (SEQ ID NO: 179) | 2.200 |
| 11 | 3 | SDVRDLNAL (SEQ ID NO: 206) | 2.000 |
| 12 | 250 | VAAGSSSSV (SEQ ID NO: 236) | 2.000 |
| 13 | 29 | SGAAQWAPV (SEQ ID NO: 211) | 2.000 |
| 14 | 315 | SETSEKRPF (SEQ ID NO: 209) | 1.600 |
| 15 | 138 | LESQPAIRN (SEQ ID NO: 132) | 1.200 |
| 16 | 244 | GATLKGVAA (SEQ ID NO: 88) | 1.100 |
| 17 | 20 | GGGGCALPV (SEQ ID NO: 92) | 1.100 |
| 18 | 440 | RNMTKLQLA (SEQ ID NO: 186) | 1.100 |
| 19 | 23 | GCALPVSGA (SEQ ID NO: 89) | 1.100 |
| 20 | 191 | QQYSVPPPV (SEQ ID NO: 171) | 1.000 |

TABLE XV

Results of BIMAS HLA Peptide Binding Prediction Analysis for Binding of Human WT1 Peptides to Human HLA B62 (HLA-B62 peptide binding motif anchor residues are Q or L at P2, F or Y at P9; auxiliary anchors are I or V at P5)

| Rank | Start Position | Subsequence Residue Listing | Score (Estimate of Half Time of Dis- association of a Molecule Containing This Sub- sequence) |
|---|---|---|---|
| 1 | 146 | NQGYSTVTF (SEQ ID NO: 150) | 211.200 |
| 2 | 32 | AQWAPVLDF (SEQ ID NO: 37) | 96.000 |
| 3 | 263 | GQSNHSTGY (SEQ ID NO: 100) | 96.000 |
| 4 | 88 | CLSAFTVHF (SEQ ID NO: 48) | 96.000 |
| 5 | 17 | SLGGGGGCA (SEQ ID NO: 215) | 9.600 |
| 6 | 239 | NQMNLGATL (SEQ ID NO: 151) | 8.800 |
| 7 | 191 | QQYSVPPPV (SEQ ID NO: 171) | 8.000 |
| 8 | 98 | GQFTGTAGA (SEQ ID NO: 99) | 8.000 |
| 9 | 384 | QCKTCQRKF (SEQ ID NO: 163) | 6.000 |
| 10 | 40 | FAPPGASAY (SEQ ID NO: 74) | 4.800 |
| 11 | 227 | YQMTSQLEC (SEQ ID NO: 251) | 4.800 |
| 12 | 187 | SLGEQQYSV (SEQ ID NO: 214) | 4.400 |
| 13 | 86 | EQCLSAFTV (SEQ ID NO: 69) | 4.400 |
| 14 | 152 | VTFDGTPSY (SEQ ID NO: 244) | 4.400 |
| 15 | 101 | TGTAGACRY (SEQ ID NO: 224) | 4.000 |
| 16 | 242 | NLGATLKGV (SEQ ID NO: 146) | 4.000 |
| 17 | 92 | FTVHFSGQF (SEQ ID NO: 85) | 4.000 |
| 18 | 7 | DLNALLPAV (SEQ ID NO: 58) | 4.000 |
| 19 | 123 | GQARMFPNA (SEQ ID NO: 98) | 4.000 |
| 20 | 280 | ILCGAQYRI (SEQ ID NO: 116) | 3.120 |

TABLE XVI

Results of BIMAS HLA Peptide Binding Prediction Analysis for Binding of Human WT1 Peptides to Human HLA B7 (HLA-B7 peptide binding motif anchor residues are P at P2, L or F at P9; auxiliary anchor is R at P2)

| Rank | Start Position | Subsequence Residue Listing | Score (Estimate of Half Time of Dis- association of a Molecule Containing This Sub- sequence) |
|---|---|---|---|
| 1 | 180 | DPMGQQGSL (SEQ ID NO: 59) | 240.000 |
| 2 | 4 | DVRDLNALL (SEQ ID NO: 62) | 200.000 |
| 3 | 302 | RVPGVAPTL (SEQ ID NO: 195) | 20.000 |
| 4 | 30 | GAAQWAPVL (SEQ ID NO: 86) | 12.000 |
| 5 | 239 | NQMNLGATL (SEQ ID NO: 151) | 12.000 |
| 6 | 130 | NAPYLPSCL (SEQ ID NO: 144) | 12.000 |
| 7 | 10 | ALLPAVPSL (SEQ ID NO: 34) | 12.000 |
| 8 | 299 | DVRRVPGVA (SEQ ID NO: 63) | 5.000 |
| 9 | 208 | SCTGSQALL (SEQ ID NO: 202) | 4.000 |
| 10 | 303 | VPGVAPTLV (SEQ ID NO: 242) | 4.000 |
| 11 | 18 | LGGGGCAL (SEQ ID NO: 134) | 4.000 |
| 12 | 218 | RTPYSSDNL (SEQ ID NO: 194) | 4.000 |
| 13 | 207 | DSCTGSQAL (SEQ ID NO: 61) | 4.000 |
| 14 | 209 | CTGSQALLL (SEQ ID NO: 52) | 4.000 |
| 15 | 329 | GCNKRYFKL (SEQ ID NO: 90) | 4.000 |
| 16 | 235 | CMTWNQMNL (SEQ ID NO: 49) | 4.000 |
| 17 | 441 | NMTKLQLAL (SEQ ID NO: 149) | 4.000 |
| 18 | 126 | RMFPNAPYL (SEQ ID NO: 185) | 4.000 |
| 19 | 225 | NLYQMTSQL (SEQ ID NO: 147) | 4.000 |
| 20 | 143 | AIRNQGYST (SEQ ID NO: 33) | 3.000 |

TABLE XVII

Results of BIMAS HLA Peptide Binding Prediction Analysis for Binding of Human WT1 Peptides to Human HLA B8
(HLA-B8 peptide binding motif anchor residues are K at P3, K or R at P5, L at P9)

| Rank | Start Position | Subsequence Residue Listing | Score (Estimate of Half Time of Dis-association of a Molecule Containing This Sub-sequence) |
|---|---|---|---|
| 1 | 329 | GCNKRYFKL (SEQ ID NO: 90) | 16.000 |
| 2 | 4 | DVRDLNALL (SEQ ID NO: 62) | 12.000 |
| 3 | 316 | ETSEKRPFM (SEQ ID NO: 73) | 3.000 |
| 4 | 180 | DPMGQQGSL (SEQ ID NO: 59) | 1.600 |
| 5 | 208 | SCTGSQALL (SEQ ID NO: 202) | 0.800 |
| 6 | 130 | NAPYLPSCL (SEQ ID NO: 144) | 0.800 |
| 7 | 244 | GATLKGVAA (SEQ ID NO: 88) | 0.800 |
| 8 | 30 | GAAQWAPVL (SEQ ID NO: 86) | 0.800 |
| 9 | 299 | DVRRVPGVA (SEQ ID NO: 63) | 0.400 |
| 10 | 420 | SCQKKFARS (SEQ ID NO: 200) | 0.400 |
| 11 | 387 | TCQRKFSRS (SEQ ID NO: 219) | 0.400 |
| 12 | 225 | NLYQMTSQL (SEQ ID NO: 147) | 0.400 |
| 13 | 141 | QPAIRNQGY (SEQ ID NO: 170) | 0.400 |
| 14 | 10 | ALLPAVPSL (SEQ ID NO: 34) | 0.400 |
| 15 | 207 | DSCTGSQAL (SEQ ID NO: 61) | 0.400 |
| 16 | 384 | QCKTCQRKF (SEQ ID NO: 163) | 0.400 |
| 17 | 136 | SCLESQPAI (SEQ ID NO: 198) | 0.300 |
| 18 | 347 | HTGEKPYQC (SEQ ID NO: 112) | 0.300 |
| 19 | 401 | HTRTHTGKT (SEQ ID NO: 114) | 0.200 |
| 20 | 332 | KRYFKLSHL (SEQ ID NO: 127) | 0.200 |

TABLE XVIII

Results of BIMAS HLA Peptide Binding Prediction Analysis for Binding of Human WT1 Peptides to Human HLA B 2702
(HLA-B2702 peptide binding motif anchor residues are R at P2; F, Y, I, L, or W at P9)

| Rank | Start Position | Subsequence Residue Listing | Score (Estimate of Half Time of Dis-association of a Molecule Containing This Sub-sequence) |
|---|---|---|---|
| 1 | 332 | KRYFKLSHL (SEQ ID NO: 127) | 900.000 |
| 2 | 362 | RRFSRSDQL (SEQ ID NO: 187) | 900.000 |
| 3 | 286 | YRIHTHGVF (SEQ ID NO: 252) | 200.000 |
| 4 | 125 | ARMFPNAPY (SEQ ID NO: 38) | 200.000 |
| 5 | 375 | RRHTGVKPF (SEQ ID NO: 188) | 180.000 |
| 6 | 32 | AQWAPVLDF (SEQ ID NO: 37) | 100.000 |
| 7 | 301 | RRVPGVAPT (SEQ ID NO: 189) | 60.000 |
| 8 | 439 | QRNMTKLQL (SEQ ID NO: 173) | 60.000 |
| 9 | 126 | RMFPNAPYL (SEQ ID NO: 185) | 22.500 |
| 10 | 426 | ARSDELVRH (SEQ ID NO: 39) | 20.000 |
| 11 | 146 | NQGYSTVTF (SEQ ID NO: 150) | 20.000 |
| 12 | 144 | IRNQGYSTV (SEQ ID NO: 117) | 20.000 |
| 13 | 389 | QRKFSRSDH (SEQ ID NO: 172) | 20.000 |
| 14 | 263 | GQSNHSTGY (SEQ ID NO: 100) | 20.000 |
| 15 | 416 | CRWPSCQKK (SEQ ID NO: 50) | 20.000 |
| 16 | 191 | QQYSVPPPV (SEQ ID NO: 171) | 10.000 |
| 17 | 217 | LRTPYSSDN (SEQ ID NO: 140) | 10.000 |
| 18 | 107 | CRYGPFGPP (SEQ ID NO: 51) | 10.000 |
| 19 | 98 | GQFTGTAGA (SEQ ID NO: 99) | 10.000 |
| 20 | 239 | NQMNLGATL (SEQ ID NO: 151) | 6.000 |

TABLE XIX

Results of BIMAS HLA Peptide Binding Prediction Analysis for Binding of Human WT1 Peptides to Human HLA B 2705
(HLA-B2705 peptide binding motif anchor residues are R at P2; L or F at P9; Y, R, H, and K, have also been found at P9 for naturally processed epitopes)

| Rank | Start Position | Subsequence Residue Listing | Score (Estimate of Half Time of Dis-association of a Molecule Containing This Sub-sequence) |
|---|---|---|---|
| 1 | 332 | KRYFKLSHL (SEQ ID NO: 127) | 30000.000 |
| 2 | 362 | RRFSRSDQL (SEQ ID NO: 187) | 30000.000 |
| 3 | 416 | CRWPSCQKK (SEQ ID NO: 50) | 10000.000 |
| 4 | 439 | QRNMTKLQL (SEQ ID NO: 173) | 2000.000 |
| 5 | 286 | YRIHTHGVF (SEQ ID NO: 252) | 1000.000 |
| 6 | 125 | ARMFPNAPY (SEQ ID NO: 38) | 1000.000 |
| 7 | 294 | FRGIQDVRR (SEQ ID NO: 81) | 1000.000 |
| 8 | 432 | VRHHNMHQR (SEQ ID NO: 243) | 1000.000 |
| 9 | 169 | AQFPNHSFK (SEQ ID NO: 36) | 1000.000 |
| 10 | 375 | RRHTGVKPF (SEQ ID NO: 188) | 900.000 |
| 11 | 126 | RMFPNAPYL (SEQ ID NO: 185) | 750.000 |
| 12 | 144 | IRNQGYSTV (SEQ ID NO: 117) | 600.000 |
| 13 | 301 | RRVPGVAPT (SEQ ID NO: 189) | 600.000 |
| 14 | 32 | AQWAPVLDF (SEQ ID NO: 37) | 500.000 |
| 15 | 191 | QQYSVPPPV (SEQ ID NO: 171) | 300.000 |
| 16 | 373 | HQRRHTGVK (SEQ ID NO: 109) | 200.000 |
| 17 | 426 | ARSDELVRH (SEQ ID NO: 39) | 200.000 |
| 18 | 383 | FQCKTCQRK (SEQ ID NO: 80) | 200.000 |
| 19 | 239 | NQMNLGATL (SEQ ID NO: 151) | 200.000 |
| 20 | 389 | QRKFSRSDH (SEQ ID NO: 172) | 200.000 |

TABLE XX

Results of BIMAS HLA Peptide Binding Prediction Analysis for Binding of Human WT1 Peptides to Human HLA B 3501
(HLA-B3501 peptide binding motif anchor residues are P at P2; Y, F, M, L, or I at P9)

| Rank | Start Position | Subsequence Residue Listing | Score (Estimate of Half Time of Dis-association of a Molecule Containing This Sub-sequence) |
|---|---|---|---|
| 1 | 278 | TPILCGAQY (SEQ ID NO: 227) | 40.000 |
| 2 | 141 | QPAIRNQGY (SEQ ID NO: 170) | 40.000 |
| 3 | 219 | TPYSSDNLY (SEQ ID NO: 231) | 40.000 |
| 4 | 327 | YPGCNKRYF (SEQ ID NO: 250) | 20.000 |
| 5 | 163 | TPSHHAAQF (SEQ ID NO: 228) | 20.000 |
| 6 | 180 | DPMGQQGSL (SEQ ID NO: 59) | 20.000 |
| 7 | 221 | YSSDNLYQM (SEQ ID NO: 253) | 20.000 |
| 8 | 26 | LPVSGAAQW (SEQ ID NO: 138) | 10.000 |
| 9 | 174 | HSFKHEDPM (SEQ ID NO: 110) | 10.000 |
| 10 | 82 | EPHEEQCLS (SEQ ID NO: 68) | 6.000 |
| 11 | 213 | QALLLRTPY (SEQ ID NO: 160) | 6.000 |
| 12 | 119 | QASSGQARM (SEQ ID NO: 161) | 6.000 |
| 13 | 4 | DVRDLNALL (SEQ ID NO: 62) | 6.000 |
| 14 | 40 | FAPPGASAY (SEQ ID NO: 74) | 6.000 |
| 15 | 120 | ASSGQARMF (SEQ ID NO: 40) | 5.000 |
| 16 | 207 | DSCTGSQAL (SEQ ID NO: 61) | 5.000 |
| 17 | 303 | VPGVAPTLV (SEQ ID NO: 242) | 4.000 |
| 18 | 316 | ETSEKRPFM (SEQ ID NO: 73) | 4.000 |
| 19 | 152 | VTFDGTPSY (SEQ ID NO: 244) | 4.000 |
| 20 | 412 | KPFSCRWPS (SEQ ID NO: 123) | 4.000 |

TABLE XXI

Results of BIMAS HLA Peptide Binding Prediction Analysis for Binding of Human WT1 Peptides to Human HLA B 3701
(HLA-B3701 peptide binding motif anchor residues are F, M, or L at P8; I or L at P9; auxiliary anchors are D, E at P2 and V, I at P5)

| Rank | Start Position | Subsequence Residue Listing | Score (Estimate of Half Time of Dis-association of a Molecule Containing This Sub-sequence) |
|---|---|---|---|
| 1 | 3 | SDVRDLNAL (SEQ ID NO: 206) | 40.000 |
| 2 | 273 | SDNHTTPIL (SEQ ID NO: 204) | 40.000 |
| 3 | 81 | AEPHEEQCL (SEQ ID NO: 30) | 10.000 |
| 4 | 298 | QDVRRVPGV (SEQ ID NO: 164) | 8.000 |
| 5 | 428 | SDELVRHHN (SEQ ID NO: 203) | 6.000 |
| 6 | 85 | EEQCLSAFT (SEQ ID NO: 65) | 5.000 |
| 7 | 208 | SCTGSQALL (SEQ ID NO: 202) | 5.000 |
| 8 | 4 | DVRDLNALL (SEQ ID NO: 62) | 5.000 |
| 9 | 209 | CTGSQALLL (SEQ ID NO: 52) | 5.000 |
| 10 | 38 | LDFAPPGAS (SEQ ID NO: 130) | 4.000 |
| 11 | 223 | SDNLYQMTS (SEQ ID NO: 205) | 4.000 |
| 12 | 179 | EDPMGQQGS (SEQ ID NO: 64) | 4.000 |
| 13 | 206 | TDSCTGSQA (SEQ ID NO: 220) | 4.000 |
| 14 | 6 | RDLNALLPA (SEQ ID NO: 177) | 4.000 |
| 15 | 84 | HEEQCLSAF (SEQ ID NO: 107) | 2.000 |
| 16 | 233 | LECMTWNQM (SEQ ID NO: 131) | 2.000 |
| 17 | 429 | DELVRHHNM (SEQ ID NO: 53) | 2.000 |
| 18 | 315 | SETSEKRPF (SEQ ID NO: 209) | 2.000 |
| 19 | 349 | GEKPYQCDF (SEQ ID NO: 91) | 2.000 |
| 20 | 302 | RVPGVAPTL (SEQ ID NO: 195) | 1.500 |

TABLE XXII

Results of BIMAS HLA Peptide Binding Prediction Analysis for Binding of Human WT1 Peptides to Human HLA B 3801
(HLA-B3801 peptide binding motif anchor residues are F or L at P9; Auxiliary anchors are H at P2 and D or E at P3)

| Rank | Start Position | Subsequence Residue Listing | Score (Estimate of Half Time of Dis-association of a Molecule Containing This Sub-sequence) |
|---|---|---|---|
| 1 | 437 | MHQRNMTKL (SEQ ID NO: 143) | 36.000 |
| 2 | 434 | HHNMHQRNM (SEQ ID NO: 108) | 6.000 |
| 3 | 372 | RHQRRHTGV (SEQ ID NO: 181) | 6.000 |
| 4 | 180 | DPMGQQGSL (SEQ ID NO: 59) | 4.000 |
| 5 | 433 | RHHNMHQRN (SEQ ID NO: 180) | 3.900 |
| 6 | 165 | SHHAAQFPN (SEQ ID NO: 213) | 3.900 |
| 7 | 202 | CHTPTDSCT (SEQ ID NO: 45) | 3.000 |
| 8 | 396 | DHLKTHTRT (SEQ ID NO: 57) | 3.000 |
| 9 | 161 | GHTPSHHAA (SEQ ID NO: 94) | 3.000 |
| 10 | 302 | RVPGVAPTL (SEQ ID NO: 195) | 2.600 |
| 11 | 417 | RWPSCQKKF (SEQ ID NO: 196) | 2.400 |
| 12 | 327 | YPGCNKRYF (SEQ ID NO: 250) | 2.400 |
| 13 | 208 | SCTGSQALL (SEQ ID NO: 202) | 2.000 |
| 14 | 163 | TPSHHAAQF (SEQ ID NO: 228) | 2.000 |
| 15 | 120 | ASSGQARMF (SEQ ID NO: 40) | 2.000 |
| 16 | 18 | LGGGGGCAL (SEQ ID NO: 134) | 2.000 |
| 17 | 177 | KHEDPMGQQ (SEQ ID NO: 121) | 1.800 |
| 18 | 83 | PHEEQCLSA (SEQ ID NO: 154) | 1.800 |
| 19 | 10 | ALLPAVPSL (SEQ ID NO: 34) | 1.300 |
| 20 | 225 | NLYQMTSQL (SEQ ID NO: 147) | 1.300 |

TABLE XXIII

Results of BIMAS HLA Peptide Binding Prediction Analysis for Binding of Human WT1 Peptides to Human HLA B 3901
(HLA-B3901 peptide binding motif anchor residues are R or H at P2; L at P9; auxiliary anchors are I, V, or L at P6)

| Rank | Start Position | Subsequence Residue Listing | Score (Estimate of Half Time of Dis-association of a Molecule Containing This Subsequence) |
|---|---|---|---|
| 1 | 437 | MHQRNMTKL (SEQ ID NO: 143) | 135.000 |
| 2 | 332 | KRYFKLSHL (SEQ ID NO: 127) | 45.000 |
| 3 | 434 | HHNMHQRNM (SEQ ID NO: 108) | 30.000 |
| 4 | 362 | RRFSRSDQL (SEQ ID NO: 187) | 30.000 |
| 5 | 372 | RHQRRHTGV (SEQ ID NO: 181) | 30.000 |
| 6 | 10 | ALLPAVPSL (SEQ ID NO: 34) | 9.000 |
| 7 | 439 | QRNMTKLQL (SEQ ID NO: 173) | 7.500 |
| 8 | 390 | RKFSRSDHL (SEQ ID NO: 183) | 6.000 |
| 9 | 396 | DHLKTHTRT (SEQ ID NO: 57) | 6.000 |
| 10 | 239 | NQMNLGATL (SEQ ID NO: 151) | 6.000 |
| 11 | 423 | KKFARSDEL (SEQ ID NO: 122) | 6.000 |
| 12 | 126 | RMFPNAPYL (SEQ ID NO: 185) | 6.000 |
| 13 | 225 | NLYQMTSQL (SEQ ID NO: 147) | 6.000 |
| 14 | 180 | DPMGQQGSL (SEQ ID NO: 59) | 6.000 |
| 15 | 144 | IRNQGYSTV (SEQ ID NO: 117) | 5.000 |
| 16 | 136 | SCLESQPAI (SEQ ID NO: 198) | 4.000 |
| 17 | 292 | GVFRGIQDV (SEQ ID NO: 103) | 3.000 |
| 18 | 302 | RVPGVAPTL (SEQ ID NO: 195) | 3.000 |
| 19 | 208 | SCTGSQALL (SEQ ID NO: 202) | 3.000 |
| 20 | 207 | DSCTGSQAL (SEQ ID NO: 61) | 3.000 |

TABLE XXIV

Results of BIMAS HLA Peptide Binding Prediction Analysis for Binding of Human WT1 Peptides to Human HLA B 3902 (HLA-B3902 peptide binding motif anchor residues are K or Q at P2; L at P9; auxiliary anchors are I, L, F, or V at P5)

| Rank | Start Position | Subsequence Residue Listing | Score (Estimate of Half Time of Disassociation of a Molecule Containing This Subsequence) |
|---|---|---|---|
| 1 | 239 | NQMNLGATL (SEQ ID NO: 151) | 24.000 |
| 2 | 390 | RKFSRSDHL (SEQ ID NO: 183) | 20.000 |
| 3 | 423 | KKFARSDEL (SEQ ID NO: 122) | 20.000 |
| 4 | 32 | AQWAPVLDF (SEQ ID NO: 37) | 5.000 |
| 5 | 146 | NQGYSTVTF (SEQ ID NO: 150) | 5.000 |
| 6 | 130 | NAPYLPSCL (SEQ ID NO: 144) | 2.400 |
| 7 | 225 | NLYQMTSQL (SEQ ID NO: 147) | 2.400 |
| 8 | 30 | GAAQWAPVL (SEQ ID NO: 86) | 2.400 |
| 9 | 441 | NMTKLQLAL (SEQ ID NO: 149) | 2.400 |
| 10 | 302 | RVPGVAPTL (SEQ ID NO: 195) | 2.400 |
| 11 | 126 | RMFPNAPYL (SEQ ID NO: 185) | 2.000 |
| 12 | 218 | RTPYSSDNL (SEQ ID NO: 194) | 2.000 |
| 13 | 209 | CTGSQALLL (SEQ ID NO: 52) | 2.000 |
| 14 | 332 | KRYFKLSHL (SEQ ID NO: 127) | 2.000 |
| 15 | 180 | DPMGQQGSL (SEQ ID NO: 59) | 2.000 |
| 16 | 437 | MHQRNMTKL (SEQ ID NO: 143) | 2.000 |
| 17 | 207 | DSCTGSQAL (SEQ ID NO: 61) | 2.000 |
| 18 | 208 | SCTGSQALL (SEQ ID NO: 202) | 2.000 |
| 19 | 329 | GCNKRYFKL (SEQ ID NO: 90) | 2.000 |
| 20 | 10 | ALLPAVPSL (SEQ ID NO: 34) | 2.000 |

TABLE XXV

Results of BIMAS HLA Peptide Binding Prediction Analysis for Binding of Human WT1 Peptides to Human HLA B 4403 (HLA-B4403 peptide binding motif anchor residues are E at P2; Y or F at P9)

| Rank | Start Position | Subsequence Residue Listing | Score (Estimate of Half Time of Disassociation of a Molecule Containing This Subsequence) |
|---|---|---|---|
| 1 | 315 | SETSEKRPF (SEQ ID NO: 209) | 80.000 |
| 2 | 349 | GEKPYQCDF (SEQ ID NO: 91) | 80.000 |
| 3 | 84 | HEEQCLSAF (SEQ ID NO: 107) | 60.000 |
| 4 | 410 | SEKPFSCRW (SEQ ID NO: 207) | 48.000 |
| 5 | 429 | DELVRHHNM (SEQ ID NO: 53) | 24.000 |
| 6 | 278 | TPILCGAQY (SEQ ID NO: 227) | 15.000 |
| 7 | 141 | QPAIRNQGY (SEQ ID NO: 170) | 9.000 |
| 8 | 40 | FAPPGASAY (SEQ ID NO: 74) | 9.000 |
| 9 | 213 | QALLLRTPY (SEQ ID NO: 160) | 9.000 |
| 10 | 318 | SEKRPFMCA (SEQ ID NO: 208) | 8.000 |
| 11 | 81 | AEPHEEQCL (SEQ ID NO: 30) | 8.000 |
| 12 | 152 | VTFDGTPSY (SEQ ID NO: 244) | 4.500 |
| 13 | 101 | TGTAGACRY (SEQ ID NO: 224) | 4.500 |
| 14 | 120 | ASSGQARMF (SEQ ID NO: 40) | 4.500 |
| 15 | 261 | TEGQSNHST (SEQ ID NO: 221) | 4.000 |
| 16 | 85 | EEQCLSAFT (SEQ ID NO: 65) | 4.000 |
| 17 | 233 | LECMTWNQM (SEQ ID NO: 131) | 4.000 |
| 18 | 104 | AGACRYGPF (SEQ ID NO: 31) | 4.000 |
| 19 | 3 | SDVRDLNAL (SEQ ID NO: 206) | 3.000 |
| 20 | 185 | QGSLGEQQY (SEQ ID NO: 166) | 3.000 |

TABLE XXVI

Results of BIMAS HLA Peptide Binding Prediction Analysis for Binding of Human WT1 Peptides to Human HLA B 5101 (HLA-B5101 peptide binding motif anchor residues are A, P, or G at P2; F or I at P9)

| Rank | Start Position | Subsequence Residue Listing | Score (Estimate of Half Time of Disassociation of a Molecule Containing This Subsequence) |
|---|---|---|---|
| 1 | 303 | VPGVAPTLV (SEQ ID NO: 242) | 314.600 |
| 2 | 180 | DPMGQQGSL (SEQ ID NO: 59) | 242.000 |
| 3 | 250 | VAAGSSSSV (SEQ ID NO: 236) | 157.300 |
| 4 | 130 | NAPYLPSCL (SEQ ID NO: 144) | 50.000 |
| 5 | 30 | GAAQWAPVL (SEQ ID NO: 86) | 50.000 |
| 6 | 20 | GGGGCALPV (SEQ ID NO: 92) | 44.000 |
| 7 | 64 | PPPPPHSFI (SEQ ID NO: 157) | 40.000 |
| 8 | 29 | SGAAQWAPV (SEQ ID NO: 211) | 40.000 |
| 9 | 18 | LGGGGGCAL (SEQ ID NO: 134) | 31.460 |
| 10 | 295 | RGIQDVRRV (SEQ ID NO: 179) | 22.000 |
| 11 | 119 | QASSGQARM (SEQ ID NO: 161) | 18.150 |
| 12 | 418 | WPSCQKKFA (SEQ ID NO: 246) | 12.100 |
| 13 | 82 | EPHEEQCLS (SEQ ID NO: 68) | 12.100 |
| 14 | 110 | GPFGPPPPS (SEQ ID NO: 96) | 11.000 |
| 15 | 272 | ESDNHTTPI (SEQ ID NO: 71) | 8.000 |
| 16 | 306 | VAPTLVRSA (SEQ ID NO: 237) | 7.150 |
| 17 | 280 | ILCGAQYRI (SEQ ID NO: 116) | 6.921 |
| 18 | 219 | TPYSSDNLY (SEQ ID NO: 231) | 6.600 |
| 19 | 128 | FPNAPYLPS (SEQ ID NO: 79) | 6.500 |
| 20 | 204 | TPTDSCTGS (SEQ ID NO: 230) | 6.050 |

TABLE XXVII

Results of BIMAS HLA Peptide Binding Prediction Analysis for Binding of Human WT1 Peptides to Human HLA B 5102 (HLA-B5102 peptide binding motif anchor residues are P, A, or G at P2; I or V at P9; auxiliary anchor is Y at P3)

| Rank | Start Position | Subsequence Residue Listing | Score (Estimate of Half Time of Disassociation of a Molecule Containing This Subsequence) |
|---|---|---|---|
| 1 | 295 | RGIQDVRRV (SEQ ID NO: 179) | 290.400 |
| 2 | 303 | VPGVAPTLV (SEQ ID NO: 242) | 200.000 |
| 3 | 180 | DPMGQQGSL (SEQ ID NO: 59) | 133.100 |
| 4 | 250 | VAAGSSSSV (SEQ ID NO: 236) | 110.000 |
| 5 | 30 | GAAQWAPVL (SEQ ID NO: 86) | 55.000 |
| 6 | 130 | NAPYLPSCL (SEQ ID NO: 144) | 50.000 |
| 7 | 20 | GGGGCALPV (SEQ ID NO: 92) | 44.000 |
| 8 | 29 | SGAAQWAPV (SEQ ID NO: 211) | 44.000 |
| 9 | 64 | PPPPPHSFI (SEQ ID NO: 157) | 40.000 |
| 10 | 119 | QASSGQARM (SEQ ID NO: 161) | 36.300 |
| 11 | 110 | GPFGPPPPS (SEQ ID NO: 96) | 27.500 |
| 12 | 412 | KPFSCRWPS (SEQ ID NO: 123) | 25.000 |
| 13 | 18 | LGGGGGCAL (SEQ ID NO: 134) | 24.200 |
| 14 | 24 | CALPVSGAA (SEQ ID NO: 43) | 16.500 |
| 15 | 219 | TPYSSDNLY (SEQ ID NO: 231) | 15.000 |
| 16 | 292 | GVFRGIQDV (SEQ ID NO: 103) | 14.641 |
| 17 | 136 | SCLESQPAI (SEQ ID NO: 198) | 14.520 |
| 18 | 418 | WPSCQKKFA (SEQ ID NO: 246) | 12.100 |
| 19 | 269 | TGYESDNHT (SEQ ID NO: 225) | 11.000 |
| 20 | 351 | KPYQCDFKD (SEQ ID NO: 124) | 11.000 |

TABLE XXVIII

Results of BIMAS HLA Peptide Binding Prediction Analysis for Binding of Human WT1 Peptides to Human HLA B 5201 (HLA-B5201 peptide binding motif anchor residues are I or V at P8; I or V at P9; auxiliary anchors are Q at P2, F, Y, or W at P3, L, I, or V at P5)

| Rank | Start Position | Subsequence Residue Listing | Score (Estimate of Half Time of Disassociation of a Molecule Containing This Subsequence) |
|---|---|---|---|
| 1 | 191 | QQYSVPPPV (SEQ ID NO: 171) | 100.000 |
| 2 | 32 | AQWAPVLDF (SEQ ID NO: 37) | 30.000 |
| 3 | 243 | LGATLKGVA (SEQ ID NO: 133) | 16.500 |
| 4 | 303 | VPGVAPTLV (SEQ ID NO: 242) | 13.500 |
| 5 | 86 | EQCLSAFTV (SEQ ID NO: 69) | 12.000 |
| 6 | 295 | RGIQDVRRV (SEQ ID NO: 179) | 10.000 |
| 7 | 98 | GQFTGTAGA (SEQ ID NO: 99) | 8.250 |
| 8 | 292 | GVFRGIQDV (SEQ ID NO: 103) | 8.250 |
| 9 | 29 | SGAAQWAPV (SEQ ID NO: 211) | 6.000 |
| 10 | 146 | NQGYSTVTF (SEQ ID NO: 150) | 5.500 |
| 11 | 20 | GGGGCALPV (SEQ ID NO: 92) | 5.000 |
| 12 | 239 | NQMNLGATL (SEQ ID NO: 151) | 4.000 |
| 13 | 64 | PPPPPHSFI (SEQ ID NO: 157) | 3.600 |
| 14 | 273 | SDNHTTPIL (SEQ ID NO: 204) | 3.300 |
| 15 | 286 | YRIHTHGVF (SEQ ID NO: 252) | 3.000 |
| 16 | 269 | TGYESDNHT (SEQ ID NO: 225) | 3.000 |
| 17 | 406 | TGKTSEKPF (SEQ ID NO: 222) | 2.750 |
| 18 | 327 | YPGCNKRYF (SEQ ID NO: 250) | 2.750 |
| 19 | 7 | DLNALLPAV (SEQ ID NO: 58) | 2.640 |
| 20 | 104 | AGACRYGPF (SEQ ID NO: 31) | 2.500 |

TABLE XXIX

Results of BIMAS HLA Peptide Binding Prediction Analysis for Binding of Human WT1 Peptides to Human HLA B 5801 (HLA-B5801 peptide binding motif anchor residues are A, S, or T at P2; F or W at P9; auxiliary anchors are P, E, or K at P4, V, I, L, M, of F, at P5)

| Rank | Start Position | Subsequence Residue Listing | Score (Estimate of Half Time of Disassociation of a Molecule Containing This Subsequence) |
|---|---|---|---|
| 1 | 230 | TSQLECMTW (SEQ ID NO: 234) | 96.800 |
| 2 | 92 | FTVHFSGQF (SEQ ID NO: 85) | 60.000 |
| 3 | 120 | ASSGQARMF (SEQ ID NO: 40) | 40.000 |
| 4 | 168 | AAQFPNHSF (SEQ ID NO: 29) | 20.000 |
| 5 | 408 | KTSEKPFSC (SEQ ID NO: 129) | 12.000 |
| 6 | 394 | RSDHLKTHT (SEQ ID NO: 192) | 9.900 |
| 7 | 276 | HTTPILCGA (SEQ ID NO: 115) | 7.200 |
| 8 | 218 | RTPYSSDNL (SEQ ID NO: 194) | 6.600 |
| 9 | 152 | VTFDGTPSY (SEQ ID NO: 244) | 6.000 |
| 10 | 40 | FAPPGASAY (SEQ ID NO: 74) | 6.000 |
| 11 | 213 | QALLLRTPY (SEQ ID NO: 160) | 4.500 |
| 12 | 347 | HTGEKPYQC (SEQ ID NO: 112) | 4.400 |
| 13 | 252 | AGSSSSVKW (SEQ ID NO: 32) | 4.400 |
| 14 | 211 | GSQALLLRT (SEQ ID NO: 102) | 4.356 |
| 15 | 174 | HSFKHEDPM (SEQ ID NO: 110) | 4.000 |
| 16 | 317 | TSEKRPFMC (SEQ ID NO: 233) | 4.000 |
| 17 | 26 | LPVSGAAQW (SEQ ID NO: 138) | 4.000 |
| 18 | 289 | HTHGVFRGI (SEQ ID NO: 113) | 3.600 |
| 19 | 222 | SSDNLYQMT (SEQ ID NO: 217) | 3.300 |
| 20 | 96 | FSGQFTGTA (SEQ ID NO: 82) | 3.300 |

TABLE XXX

Results of BIMAS HLA Peptide Binding Prediction Analysis for Binding of Human WT1 Peptides to Human HLA CW0301 (HLA-CW0301 peptide binding motif anchor residues are L, F, M, or I at P9; auxiliary anchors are V, I, Y, L, or M, at P3, P at P4, F or Y at P6)

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO: 34) | 100.000 |
| 2 | 332 | KRYFKLSHL (SEQ ID NO: 127) | 48.000 |
| 3 | 126 | RMFPNAPYL (SEQ ID NO: 185) | 36.000 |
| 4 | 3 | SDVRDLNAL (SEQ ID NO: 206) | 30.000 |
| 5 | 239 | NQMNLGATL (SEQ ID NO: 151) | 24.000 |
| 6 | 225 | NLYQMTSQL (SEQ ID NO: 147) | 24.000 |
| 7 | 180 | DPMGQQGSL (SEQ ID NO: 59) | 20.000 |
| 8 | 362 | RRFSRSDQL (SEQ ID NO: 187) | 12.000 |
| 9 | 329 | GCNKRYFKL (SEQ ID NO: 90) | 10.000 |
| 10 | 286 | YRIHTHGVF (SEQ ID NO: 252) | 10.000 |
| 11 | 301 | RRVPGVAPT (SEQ ID NO: 189) | 10.000 |
| 12 | 24 | CALPVSGAA (SEQ ID NO: 43) | 10.000 |
| 13 | 136 | SCLESQPAI (SEQ ID NO: 198) | 7.500 |
| 14 | 437 | MHQRNMTKL (SEQ ID NO: 143) | 7.200 |
| 15 | 390 | RKFSRSDHL (SEQ ID NO: 183) | 6.000 |
| 16 | 423 | KKFARSDEL (SEQ ID NO: 122) | 6.000 |
| 17 | 92 | FTVHFSGQF (SEQ ID NO: 85) | 5.000 |
| 18 | 429 | DELVRHHNM (SEQ ID NO: 53) | 5.000 |
| 19 | 130 | NAPYLPSCL (SEQ ID NO: 144) | 4.800 |
| 20 | 30 | GAAQWAPVL (SEQ ID NO: 86) | 4.000 |

TABLE XXXI

Results of BIMAS HLA Peptide Binding Prediction Analysis for Binding of Human WT1 Peptides to Human HLA CW0401 (HLA-CW0401 peptide binding motif anchor residues are Y, P, or F at P2; L, F, or M at P9; auxiliary anchors are V, I, or L at P6)

| Rank | Start Position | Subsequence Residue Listing | Score (Estimate of Half Time of Disassociation of a Molecule Containing This Subsequence) |
|---|---|---|---|
| 1 | 356 | DFKDCERRF (SEQ ID NO: 55) | 120.000 |
| 2 | 334 | YFKLSHLQM (SEQ ID NO: 248) | 100.000 |
| 3 | 180 | DPMGQQGSL (SEQ ID NO: 59) | 88.000 |
| 4 | 163 | TPSHHAAQF (SEQ ID NO: 228) | 52.800 |
| 5 | 327 | YPGCNKRYF (SEQ ID NO: 250) | 40.000 |
| 6 | 285 | QYRIHTHGV (SEQ ID NO: 175) | 27.500 |
| 7 | 424 | KFARSDELV (SEQ ID NO: 119) | 25.000 |
| 8 | 326 | AYPGCNKRY (SEQ ID NO: 42) | 25.000 |
| 9 | 192 | QYSVPPPVY (SEQ ID NO: 176) | 25.000 |
| 10 | 417 | RWPSCQKKF (SEQ ID NO: 196) | 22.000 |
| 11 | 278 | TPILCGAQY (SEQ ID NO: 227) | 12.000 |
| 12 | 10 | ALLPAVPSL (SEQ ID NO: 34) | 11.616 |
| 13 | 141 | QPAIRNQGY (SEQ ID NO: 170) | 11.000 |
| 14 | 303 | VPGVAPTLV (SEQ ID NO: 242) | 11.000 |
| 15 | 219 | TPYSSDNLY (SEQ ID NO: 231) | 10.000 |
| 16 | 39 | DFAPPGASA (SEQ ID NO: 54) | 7.920 |
| 17 | 99 | QFTGTAGAC (SEQ ID NO: 165) | 6.000 |
| 18 | 4 | DVRDLNALL (SEQ ID NO: 62) | 5.760 |
| 19 | 70 | SFIKQEPSW (SEQ ID NO: 210) | 5.500 |
| 20 | 63 | PPPPPPHSF (SEQ ID NO: 158) | 5.280 |

TABLE XXXII

Results of BIMAS HLA Peptide Binding Prediction Analysis for Binding of Human WT1 Peptides to Human HLA CW0602 (HLA-CW0602 peptide binding motif anchor residues are L, I, V, or Y at P9; auxiliary anchors are I, L, F, or M at P5, V, I, or L at P6)

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO: 127) | 9.680 |
| 2 | 239 | NQMNLGATL (SEQ ID NO: 151) | 6.600 |
| 3 | 130 | NAPYLPSCL (SEQ ID NO: 144) | 6.600 |
| 4 | 7 | DLNALLPAV (SEQ ID NO: 58) | 6.000 |
| 5 | 441 | NMTKLQLAL (SEQ ID NO: 149) | 6.000 |
| 6 | 225 | NLYQMTSQL (SEQ ID NO: 147) | 6.000 |
| 7 | 4 | DVRDLNALL (SEQ ID NO: 62) | 6.000 |
| 8 | 3 | SDVRDLNAL (SEQ ID NO: 206) | 4.400 |
| 9 | 10 | ALLPAVPSL (SEQ ID NO: 34) | 4.000 |
| 10 | 213 | QALLLRTPY (SEQ ID NO: 160) | 3.300 |
| 11 | 319 | EKRPFMCAY (SEQ ID NO: 67) | 3.000 |
| 12 | 30 | GAAQWAPVL (SEQ ID NO: 86) | 2.200 |
| 13 | 242 | NLGATLKGV (SEQ ID NO: 146) | 2.200 |
| 14 | 292 | GVFRGIQDV (SEQ ID NO: 103) | 2.200 |
| 15 | 207 | DSCTGSQAL (SEQ ID NO: 61) | 2.200 |
| 16 | 362 | RRFSRSDQL (SEQ ID NO: 187) | 2.200 |
| 17 | 439 | QRNMTKLQL (SEQ ID NO: 173) | 2.200 |
| 18 | 295 | RGIQDVRRV (SEQ ID NO: 179) | 2.200 |
| 19 | 423 | KKFARSDEL (SEQ ID NO: 122) | 2.200 |
| 20 | 180 | DPMGQQGSL (SEQ ID NO: 59) | 2.200 |

TABLE XXXIII

Results of BIMAS HLA Peptide Binding Prediction Analysis for Binding of Human WT1 Peptides to Human HLA CW0702 (HLA-CW0702 peptide binding motif anchor residues are Y, F, or L at P9; auxiliary anchors are Y or P at P2, V, Y, I, L, F, or M at P5, V, I, L, or M at P6)

| Rank | Start Position | Subsequence Residue Listing | Score (Estimate of Half Time of Disassociation of a Molecule Containing This Subsequence) |
|---|---|---|---|
| 1 | 319 | EKRPFMCAY (SEQ ID NO: 67) | 26.880 |
| 2 | 326 | AYPGCNKRY (SEQ ID NO: 42) | 24.000 |
| 3 | 40 | FAPPGASAY (SEQ ID NO: 74) | 14.784 |
| 4 | 192 | QYSVPPPVY (SEQ ID NO: 176) | 12.000 |
| 5 | 278 | TPILCGAQY (SEQ ID NO: 227) | 12.000 |
| 6 | 219 | TPYSSDNLY (SEQ ID NO: 231) | 12.000 |
| 7 | 213 | QALLLRTPY (SEQ ID NO: 160) | 8.800 |
| 8 | 125 | ARMFPNAPY (SEQ ID NO: 38) | 8.000 |
| 9 | 327 | YPGCNKRYF (SEQ ID NO: 250) | 6.600 |
| 10 | 152 | VTFDGTPSY (SEQ ID NO: 244) | 5.600 |
| 11 | 141 | QPAIRNQGY (SEQ ID NO: 170) | 4.800 |
| 12 | 345 | RKHTGEKPY (SEQ ID NO: 184) | 4.000 |
| 13 | 185 | QGSLGEQQY (SEQ ID NO: 166) | 4.000 |
| 14 | 101 | TGTAGACRY (SEQ ID NO: 224) | 4.000 |
| 15 | 375 | RRHTGVKPF (SEQ ID NO: 188) | 4.000 |
| 16 | 263 | GQSNHSTGY (SEQ ID NO: 100) | 4.000 |
| 17 | 163 | TPSHHAAQF (SEQ ID NO: 228) | 3.000 |
| 18 | 33 | QWAPVLDFA (SEQ ID NO: 174) | 2.688 |
| 19 | 130 | NAPYLPSCL (SEQ ID NO: 144) | 2.640 |
| 20 | 84 | HEEQCLSAF (SEQ ID NO: 107) | 2.400 |

TABLE XXXIV

Results of BIMAS HLA Peptide Binding Prediction Analysis for Binding of Human WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 1 | 235 | CMTWNQMNL (SEQ ID NO: 49) | 5255.712 |
| 2 | 126 | RMFPNAPYL (SEQ ID NO: 185) | 1990.800 |
| 3 | 221 | YSSDNLYQM (SEQ ID NO: 253) | 930.000 |
| 4 | 228 | QMTSQLECM (SEQ ID NO: 169) | 33.701 |
| 5 | 239 | NQMNLGATL (SEQ ID NO: 151) | 21.470 |
| 6 | 441 | NMTKLQLAL (SEQ ID NO: 149) | 19.908 |
| 7 | 437 | MHQRNMTKL (SEQ ID NO: 143) | 19.837 |
| 8 | 136 | SCLESQPAI (SEQ ID NO: 198) | 11.177 |
| 9 | 174 | HSFKHEDPM (SEQ ID NO: 110) | 10.800 |
| 10 | 302 | RVPGVAPTL (SEQ ID NO: 195) | 10.088 |
| 11 | 130 | NAPYLPSCL (SEQ ID NO: 144) | 8.400 |
| 12 | 10 | ALLPAVPSL (SEQ ID NO: 34) | 5.988 |
| 13 | 208 | SCTGSQALL (SEQ ID NO: 202) | 4.435 |
| 14 | 209 | CTGSQALLL (SEQ ID NO: 52) | 3.548 |
| 15 | 238 | WNQMNLGAT (SEQ ID NO: 245) | 3.300 |
| 16 | 218 | RTPYSSDNL (SEQ ID NO: 194) | 3.185 |
| 17 | 24 | CALPVSGAA (SEQ ID NO: 43) | 2.851 |
| 18 | 18 | LGGGGGCAL (SEQ ID NO: 134) | 2.177 |
| 19 | 142 | PAIRNQGYS (SEQ ID NO: 152) | 2.160 |
| 20 | 30 | GAAQWAPVL (SEQ ID NO: 86) | 1.680 |

TABLE XXXV

Results of BIMAS HLA Peptide Binding Prediction Analysis for Binding of Human WT1 Peptides to Mouse MHC Class I Dd

| Rank | Start Position | Subsequence Residue Listing | Score (Estimate of Half Time of Disassociation of a Molecule Containing This Subsequence) |
|---|---|---|---|
| 1 | 112 | FGPPPPSQA (SEQ ID NO: 76) | 48.000 |
| 2 | 122 | SGQARMFPN (SEQ ID NO: 212) | 36.000 |
| 3 | 104 | AGACRYGPF (SEQ ID NO: 31) | 30.000 |
| 4 | 218 | RTPYSSDNL (SEQ ID NO: 194) | 28.800 |
| 5 | 130 | NAPYLPSCL (SEQ ID NO: 144) | 20.000 |
| 6 | 302 | RVPGVAPTL (SEQ ID NO: 195) | 20.000 |
| 7 | 18 | LGGGGGCAL (SEQ ID NO: 134) | 20.000 |
| 8 | 81 | AEPHEEQCL (SEQ ID NO: 30) | 10.000 |
| 9 | 29 | SGAAQWAPV (SEQ ID NO: 211) | 7.200 |
| 10 | 423 | KKFARSDEL (SEQ ID NO: 122) | 7.200 |
| 11 | 295 | RGIQDVRRV (SEQ ID NO: 179) | 7.200 |
| 12 | 390 | RKFSRSDHL (SEQ ID NO: 183) | 6.000 |
| 13 | 332 | KRYFKLSHL (SEQ ID NO: 127) | 6.000 |
| 14 | 362 | RRFSRSDQL (SEQ ID NO: 187) | 6.000 |
| 15 | 417 | RWPSCQKKF (SEQ ID NO: 196) | 6.000 |
| 16 | 160 | YGHTPSHHA (SEQ ID NO: 249) | 6.000 |
| 17 | 20 | GGGGCALPV (SEQ ID NO: 92) | 6.000 |
| 18 | 329 | GCNKRYFKL (SEQ ID NO: 90) | 5.000 |
| 19 | 372 | RHQRRHTGV (SEQ ID NO: 181) | 4.500 |
| 20 | 52 | GGPAPPPAP (SEQ ID NO: 93) | 4.000 |

TABLE XXXVI

Results of BIMAS HLA Peptide Binding Prediction Analysis for Binding of Human WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO: 90) | 24.000 |
| 2 | 225 | NLYQMTSQL (SEQ ID NO: 147) | 10.000 |
| 3 | 420 | SCQKKFARS (SEQ ID NO: 200) | 3.960 |
| 4 | 218 | RTPYSSDNL (SEQ ID NO: 194) | 3.630 |
| 5 | 437 | MHQRNMTKL (SEQ ID NO: 143) | 3.600 |
| 6 | 387 | TCQRKFSRS (SEQ ID NO: 219) | 3.600 |
| 7 | 302 | RVPGVAPTL (SEQ ID NO: 195) | 3.300 |
| 8 | 130 | NAPYLPSCL (SEQ ID NO: 144) | 3.000 |
| 9 | 289 | HTHGVFRGI (SEQ ID NO: 113) | 3.000 |
| 10 | 43 | PGASAYGSL (SEQ ID NO: 153) | 2.400 |
| 11 | 155 | DGTPSYGHT (SEQ ID NO: 56) | 2.400 |
| 12 | 273 | SDNHTTPIL (SEQ ID NO: 204) | 2.200 |
| 13 | 126 | RMFPNAPYL (SEQ ID NO: 185) | 2.200 |
| 14 | 128 | FPNAPYLPS (SEQ ID NO: 79) | 2.000 |
| 15 | 3 | SDVRDLNAL (SEQ ID NO: 206) | 1.584 |
| 16 | 207 | DSCTGSQAL (SEQ ID NO: 61) | 1.584 |
| 17 | 332 | KRYFKLSHL (SEQ ID NO: 127) | 1.500 |
| 18 | 18 | LGGGGGCAL (SEQ ID NO: 134) | 1.320 |
| 19 | 233 | LECMTWNQM (SEQ ID NO: 131) | 1.320 |
| 20 | 441 | NMTKLQLAL (SEQ ID NO: 149) | 1.200 |

TABLE XXXVII

Results of BIMAS HLA Peptide Binding Prediction Analysis for Binding of Human WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTHGV (SEQ ID NO: 175) | 600.000 |
| 2 | 424 | KFARSDELV (SEQ ID NO: 119) | 288.000 |
| 3 | 334 | YFKLSHLQM (SEQ ID NO: 248) | 120.000 |
| 4 | 136 | SCLESQPTI (SEQ ID NO: 199) | 115.200 |
| 5 | 239 | NQMNLGATL (SEQ ID NO: 151) | 115.200 |
| 6 | 10 | ALLPAVSSL (SEQ ID NO: 35) | 115.200 |
| 7 | 47 | AYGSLGGPA (SEQ ID NO: 41) | 86.400 |
| 8 | 180 | DPMGQQGSL (SEQ ID NO: 59) | 80.000 |
| 9 | 270 | GYESDNHTA (SEQ ID NO: 105) | 72.000 |
| 10 | 326 | AYPGCNKRY (SEQ ID NO: 42) | 60.000 |
| 11 | 192 | QYSVPPPVY (SEQ ID NO: 176) | 60.000 |
| 12 | 272 | ESDNHTAPI (SEQ ID NO: 70) | 57.600 |
| 13 | 289 | HTHGVFRGI (SEQ ID NO: 113) | 57.600 |
| 14 | 126 | DVRDLNALL (SEQ ID NO: 62) | 57.600 |
| 15 | 4 | CTGSQALLL (SEQ ID NO: 52) | 57.600 |
| 16 | 208 | SCTGSQALL (SEQ ID NO: 202) | 48.000 |
| 17 | 441 | NMTKLQLAL (SEQ ID NO: 149) | 48.000 |
| 18 | 207 | DSCTGSQAL (SEQ ID NO: 61) | 48.000 |
| 19 | 130 | NAPYLPSCL (SEQ ID NO: 144) | 48.000 |
| 20 | 235 | CMTWNQMNL (SEQ ID NO: 49) | 48.000 |

TABLE XXXVIII

Results of BIMAS HLA Peptide Binding Prediction Analysis for Binding of Human WT1 Peptides to Mouse MHC Class I Kk

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO: 30) | 40.000 |
| 2 | 85 | EEQCLSAFT (SEQ ID NO: 65) | 40.000 |
| 3 | 429 | DELVRHHNM (SEQ ID NO: 53) | 20.000 |
| 4 | 315 | SETSEKRPF (SEQ ID NO: 209) | 20.000 |
| 5 | 261 | TEGQSNHST (SEQ ID NO: 221) | 20.000 |
| 6 | 410 | SEKPFSCRW (SEQ ID NO: 207) | 10.000 |
| 7 | 272 | ESDNHTTPI (SEQ ID NO: 71) | 10.000 |
| 8 | 318 | SEKRPFMCA (SEQ ID NO: 208) | 10.000 |
| 9 | 138 | LESQPAIRN (SEQ ID NO: 132) | 10.000 |
| 10 | 233 | LECMTWNQM (SEQ ID NO: 131) | 10.000 |
| 11 | 298 | QDVRRVPGV (SEQ ID NO: 164) | 10.000 |
| 12 | 84 | HEEQCLSAF (SEQ ID NO: 107) | 10.000 |
| 13 | 349 | GEKPYQCDF (SEQ ID NO: 91) | 10.000 |
| 14 | 289 | HTHGVFRGI (SEQ ID NO: 113) | 10.000 |
| 15 | 179 | EDPMGQQGS (SEQ ID NO: 64) | 8.000 |
| 16 | 136 | SCLESQPAI (SEQ ID NO: 198) | 5.000 |
| 17 | 280 | ILCGAQYRI (SEQ ID NO: 116) | 5.000 |
| 18 | 273 | SDNHTTPIL (SEQ ID NO: 204) | 4.000 |
| 19 | 428 | SDELVRHHN (SEQ ID NO: 203) | 4.000 |
| 20 | 3 | SDVRDLNAL (SEQ ID NO: 206) | 4.000 |

TABLE XXXIX

Results of BIMAS HLA Peptide Binding Prediction Analysis for Binding of Human WT1 Peptides to Mouse MHC Class I Ld

| Rank | Start Position | Subsequence Residue Listing | Score (Estimate of Half Time of Disassociation of a Molecule Containing This Subsequence) |
|---|---|---|---|
| 1 | 163 | TPSHHAAQF (SEQ ID NO: 228) | 360.000 |
| 2 | 327 | YPGCNKRYF (SEQ ID NO: 250) | 300.000 |
| 3 | 180 | DPMGQQGSL (SEQ ID NO: 59) | 150.000 |
| 4 | 26 | LPVSGAAQW (SEQ ID NO: 138) | 93.600 |
| 5 | 278 | TPILCGAQY (SEQ ID NO: 227) | 72.000 |
| 6 | 141 | QPAIRNQGY (SEQ ID NO: 170) | 60.000 |
| 7 | 219 | TPYSSDNLY (SEQ ID NO: 231) | 60.000 |
| 8 | 303 | VPGVAPTLV (SEQ ID NO: 242) | 60.000 |
| 9 | 120 | ASSGQARMF (SEQ ID NO: 40) | 50.000 |
| 10 | 63 | PPPPPPHSF (SEQ ID NO: 158) | 45.000 |
| 11 | 113 | GPPPPSQAS (SEQ ID NO: 97) | 45.000 |
| 12 | 157 | TPSYGHTPS (SEQ ID NO: 229) | 39.000 |
| 13 | 207 | DSCTGSQAL (SEQ ID NO: 61) | 32.500 |
| 14 | 110 | GPFGPPPPS (SEQ ID NO: 96) | 30.000 |
| 15 | 82 | EPHEEQCLS (SEQ ID NO: 68) | 30.000 |
| 16 | 412 | KPFSCRWPS (SEQ ID NO: 123) | 30.000 |
| 17 | 418 | WPSCQKKFA (SEQ ID NO: 246) | 30.000 |
| 18 | 221 | YSSDNLYQM (SEQ ID NO: 253) | 30.000 |
| 19 | 204 | TPTDSCTGS (SEQ ID NO: 230) | 30.000 |
| 20 | 128 | FPNAPYLPS (SEQ ID NO: 79) | 30.000 |

TABLE XL

Results of BIMAS HLA Peptide Binding Prediction Analysis for Binding of Human WT1 Peptides to Cattle HLA A20

| Rank | Start Position | Subsequence Residue Listing | Score (Estimate of Half Time of Disassociation of a Molecule Containing This Subsequence) |
|---|---|---|---|
| 1 | 350 | EKPYQCDFK (SEQ ID NO: 66) | 1000.00 |
| 2 | 319 | EKRPFMCAY (SEQ ID NO: 67) | 500.000 |
| 3 | 423 | KKFARSDEL (SEQ ID NO: 122) | 500.000 |
| 4 | 345 | RKHTGEKPY (SEQ ID NO: 184) | 500.000 |
| 5 | 390 | RKFSRSDHL (SEQ ID NO: 183) | 500.000 |
| 6 | 137 | CLESQPAIR (SEQ ID NO: 47) | 120.000 |
| 7 | 380 | VKPFQCKTC (SEQ ID NO: 239) | 100.000 |
| 8 | 407 | GKTSEKPFS (SEQ ID NO: 95) | 100.000 |
| 9 | 335 | FKLSHLQMH (SEQ ID NO: 78) | 100.000 |
| 10 | 247 | LKGVAAGSS (SEQ ID NO: 135) | 100.000 |
| 11 | 370 | LKRHQRRHT (SEQ ID NO: 136) | 100.000 |
| 12 | 258 | VKWTEGQSN (SEQ ID NO: 240) | 100.000 |
| 13 | 398 | LKTHTRTHT (SEQ ID NO: 137) | 100.000 |
| 14 | 331 | NKRYFKLSH (SEQ ID NO: 145) | 100.000 |
| 15 | 357 | FKDCERRFS (SEQ ID NO: 77) | 100.000 |
| 16 | 385 | CKTCQRKFS (SEQ ID NO: 46) | 100.000 |
| 17 | 294 | FRGIQDVRR (SEQ ID NO: 81) | 80.000 |
| 18 | 368 | DQLKRHQRR (SEQ ID NO: 60) | 80.000 |
| 19 | 432 | VRHHNMHQR (SEQ ID NO: 243) | 80.000 |
| 20 | 118 | SQASSGQAR (SEQ ID NO: 216) | 80.000 |

TABLE XLI

Results of BIMAS HLA Peptide Binding Prediction Analysis for Binding of Mouse WT1 Peptides to Human HLA A 0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO: 293) | 313.968 |
| 2 | 187 | SLGEQQYSV (SEQ ID NO: 299) | 285.163 |
| 3 | 10 | ALLPAVSSL (SEQ ID NO: 255) | 181.794 |
| 4 | 225 | NLYQMTSQL (SEQ ID NO: 284) | 68.360 |
| 5 | 292 | GVFRGIQDV (SEQ ID NO: 270) | 51.790 |

TABLE XLI-continued

Results of BIMAS HLA Peptide Binding Prediction Analysis for Binding of Mouse WT1 Peptides to Human HLA A 0201

| Rank | Start Position | Subsequence Residue Listing | Score (Estimate of Half Time of Dis-association of a Molecule Containing This Subsequence) |
|---|---|---|---|
| 6 | 93 | TLHFSGQFT (SEQ ID NO: 302) | 40.986 |
| 7 | 191 | QQYSVPPPV (SEQ ID NO: 290) | 22.566 |
| 8 | 280 | ILCGAQYRI (SEQ ID NO: 274) | 17.736 |
| 9 | 441 | NMTKLHVAL (SEQ ID NO: 285) | 15.428 |
| 10 | 235 | CMTWNQMNL (SEQ ID NO: 258) | 15.428 |
| 11 | 7 | DLNALLPAV (SEQ ID NO: 261) | 11.998 |
| 12 | 242 | NLGATLKGM (SEQ ID NO: 283) | 11.426 |
| 13 | 227 | YQMTSQLEC (SEQ ID NO: 307) | 8.573 |
| 14 | 239 | NQMNLGATL (SEQ ID NO: 286) | 8.014 |
| 15 | 309 | TLVRSASET (SEQ ID NO: 303) | 7.452 |
| 16 | 408 | KTSEKPFSC (SEQ ID NO: 277) | 5.743 |
| 17 | 340 | LQMHSRKHT (SEQ ID NO: 280) | 4.752 |
| 18 | 228 | QMTSQLECM (SEQ ID NO: 289) | 4.044 |
| 19 | 37 | VLDFAPPGA (SEQ ID NO: 304) | 3.378 |
| 20 | 302 | RVSGVAPTL (SEQ ID NO: 295) | 1.869 |

TABLE XLII

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Dis-association of a Molecule Containing This Subsequence) |
|---|---|---|---|
| 1 | 221 | YSSDNLYQM (SEQ ID NO: 308) | 312.000 |
| 2 | 126 | RMFPNAPYL (SEQ ID NO: 293) | 260.000 |
| 3 | 235 | CMTWNQMNL (SEQ ID NO: 258) | 260.000 |
| 4 | 437 | MHQRNMTKL (SEQ ID NO: 281) | 200.000 |
| 5 | 238 | WNQMNLGAT (SEQ ID NO: 305) | 12.000 |
| 6 | 130 | NAPYLPSCL (SEQ ID NO: 282) | 8.580 |
| 7 | 3 | SDVRDLNAL (SEQ ID NO: 298) | 7.920 |
| 8 | 136 | SCLESQPTI (SEQ ID NO: 296) | 7.920 |

TABLE XLII-continued

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Dis-association of a Molecule Containing This Subsequence) |
|---|---|---|---|
| 9 | 81 | AEPHEEQCL (SEQ ID NO: 254) | 6.600 |
| 10 | 10 | ALLPAVSSL (SEQ ID NO: 255) | 6.600 |
| 11 | 218 | RTPYSSDNL (SEQ ID NO: 294) | 6.000 |
| 12 | 441 | NMTKLHVAL (SEQ ID NO: 285) | 3.432 |
| 13 | 228 | QMTSQLECM (SEQ ID NO: 289) | 3.120 |
| 14 | 174 | HSFKHEDPM (SEQ ID NO: 272) | 3.120 |
| 15 | 242 | NLGATLKGM (SEQ ID NO: 283) | 2.640 |
| 16 | 261 | TEGQSNHGI (SEQ ID NO: 301) | 2.640 |
| 17 | 225 | NLYQMTSQL (SEQ ID NO: 284) | 2.640 |
| 18 | 207 | DSCTGSQAL (SEQ ID NO: 263) | 2.600 |
| 19 | 119 | QASSGQARM (SEQ ID NO: 288) | 2.600 |
| 20 | 18 | LGGGGGCGL (SEQ ID NO: 279) | 2.600 |

TABLE XLIII

Results of BIMAS HLA Peptide Binding Prediction Analysis for Binding of Mouse WT1 Peptides to Mouse MHC Class I Kb

| Rank | Start Position | Subsequence Residue Listing | Score (Estimate of Half Time of Dis-association of a Molecule Containing This Subsequence) |
|---|---|---|---|
| 1 | 329 | GCNKRYFKL (SEQ ID NO: 268) | 24.000 |
| 2 | 225 | NLYQMTSQL (SEQ ID NO: 284) | 10.000 |
| 3 | 420 | SCQKKFARS (SEQ ID NO: 297) | 3.960 |
| 4 | 218 | RTPYSSDNL (SEQ ID NO: 294) | 3.630 |
| 5 | 437 | MHQRNMTKL (SEQ ID NO: 281) | 3.600 |
| 6 | 387 | TCQRKFSRS (SEQ ID NO: 300) | 3.600 |
| 7 | 289 | HTHGVFRGI (SEQ ID NO: 273) | 3.000 |
| 8 | 130 | NAPYLPSCL (SEQ ID NO: 282) | 3.000 |
| 9 | 43 | PGASAYGSL (SEQ ID NO: 287) | 2.400 |
| 10 | 155 | DGAPSYGHT (SEQ ID NO: 260) | 2.400 |

TABLE XLIII-continued

Results of BIMAS HLA Peptide Binding Prediction Analysis for Binding of Mouse WT1 Peptides to Mouse MHC Class I Kb

| Rank | Start Position | Subsequence Residue Listing | Score (Estimate of Half Time of Dis-association of a Molecule Containing This Subsequence) |
|---|---|---|---|
| 11 | 126 | RMFPNAPYL (SEQ ID NO: 293) | 2.200 |
| 12 | 128 | FPNAPYLPS (SEQ ID NO: 267) | 2.000 |
| 13 | 207 | DSCTGSQAL (SEQ ID NO: 263) | 1.584 |
| 14 | 3 | SDVRDLNAL (SEQ ID NO: 298) | 1.584 |
| 15 | 332 | KRYFKLSHL (SEQ ID NO: 276) | 1.500 |
| 16 | 233 | LECMTWNQM (SEQ ID NO: 278) | 1.320 |
| 17 | 18 | LGGGGGCGL (SEQ ID NO: 279) | 1.320 |
| 18 | 242 | NLGATLKGM (SEQ ID NO: 283) | 1.200 |
| 19 | 123 | GQARMFPN (SEQ ID NO: 269)A | 1.200 |
| 20 | 441 | NMTKLHVAL (SEQ ID NO: 285) | 1.200 |

TABLE XLIV

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Dis-association of a Molecule Containing This Subsequence) |
|---|---|---|---|
| 1 | 285 | QYRIHTHGV (SEQ ID NO: 291) | 600.000 |
| 2 | 424 | KFARSDELV (SEQ ID NO: 275) | 288.000 |
| 3 | 334 | YFKLSHLQM (SEQ ID NO: 306) | 120.000 |
| 4 | 136 | SCLESQPTI (SEQ ID NO: 296) | 115.200 |
| 5 | 239 | NQMNLGATL (SEQ ID NO: 286) | 115.200 |
| 6 | 10 | ALLPAVSSL (SEQ ID NO: 255) | 115.200 |
| 7 | 47 | AYGSLGGPA (SEQ ID NO: 256) | 86.400 |
| 8 | 180 | DPMGQQGSL (SEQ ID NO: 262) | 80.000 |
| 9 | 270 | GYESDNHTA (SEQ ID NO: 271) | 72.000 |
| 10 | 192 | QYSVPPPVY (SEQ ID NO: 292) | 60.000 |
| 11 | 326 | AYPGCNKRY (SEQ ID NO: 257) | 60.000 |
| 12 | 289 | HTHGVFRGI (SEQ ID NO: 273) | 57.600 |
| 13 | 4 | DVRDLNALL (SEQ ID NO: 264) | 57.600 |

TABLE XLIV-continued

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Dis-association of a Molecule Containing This Subsequence) |
|---|---|---|---|
| 14 | 126 | RMFPNAPYL (SEQ ID NO: 293) | 57.600 |
| 15 | 209 | CTGSQALLL (SEQ ID NO: 259) | 48.000 |
| 16 | 86 | EQCLSAFTL (SEQ ID NO: 265) | 48.000 |
| 17 | 302 | RVSGVAPTL (SEQ ID NO: 295) | 48.000 |
| 18 | 218 | RTPYSSDNL (SEQ ID NO: 294) | 48.000 |
| 19 | 272 | ESDNHTAPI (SEQ ID NO: 266) | 48.000 |
| 20 | 225 | NLYQMTSQL (SEQ ID NO: 284) | 48.000 |

TABLE XLV

Results of TSites Peptide Binding Prediction Analysis for Human WT1 Peptides Capable of Eliciting a Helper T cell Response

| Peptide | Sequence |
|---|---|
| p6-23 | RDLNALLPAVPSLGGGG (SEQ ID NO: 1) |
| p30-35 | GAAQWA (SEQ ID NO: 309) |
| p45-56 | ASAYGSLGGPAP (SEQ ID NO: 310) |
| p91-105 | AFTVHFSGQFTGTAG (SEQ ID NO: 311) |
| p117-139 | PSQASSGQARMFPNAPYLPSCLE (SEQ ID NO: 2) |
| p167-171 | HAAQF (SEQ ID NO: 312) |
| p202-233 | CHTPTDSCTGSQALLLRTPYSSDNLYQMTSQL (SEQ ID NO: 313) |
| p244-262 | GATLKGVAAGSSSSVKWTE (SEQ ID NO: 4) |
| p287-318 | RIHTHGVFRGIQDVRRVPGVAPTLVRSASETS (SEQ ID NO: 314) |
| p333-336 | RYFK (SEQ ID NO: 315) |
| p361-374 | ERRFSRSDQLKRHQ (SEQ ID NO: 316) |
| p389-410 | QRKFSRSDHLKTHTRTHTGKTS (SEQ ID NO: 317) |
| p421-441 | CQKKFARSDELVRHHNMHQRN (SEQ ID NO: 318) |

Certain CTL peptides (shown in Table XLVI) were selected for further study. For each peptide in Table XLVI, scores obtained using BIMAS HLA peptide binding prediction analysis are provided.

TABLE XLVI

WT1 Peptide Sequences and HLA Peptide Binding Predictions

| Peptide | Sequence | Comments |
|---|---|---|
| p329-337 | GCNKRYFKL (SEQ ID NOs: 90 and 268) | Score 24,000 |
| p225-233 | NLYQMTSQL (SEQ ID NOs: 147 and 284) | binds also to class II and HLA A2, Kd, score 10,000 |
| p235-243 | CMTWNQMNL (SEQ ID NOs: 49 and 258) | binds also to HLA A2, score 5,255,712 |
| p126-134 | RMFPNAPYL (SEQ ID NOs: 185 and 293) | binds also to Kd, class II and HLA A2, score 1,990,800 |
| p221-229 | YSSDNLYQM (SEQ ID NOs: 253 and 308) | binds also to Ld, score 312,000 |
| p228-236 | QMTSQLECM (SEQ ID NOs: 169 and 289) | score 3,120 |
| p239-247 | NQMNLGATL (SEQ ID NOs: 151 and 286) | binds also to HLA A 0201, Kd, score 8,015 |
| mouse p136-144 | SCLESQPTI (SEQ ID NO: 296) | binds also to Kd, 1 mismatch to human |
| human p136-144 | SCLESQPAI (SEQ ID NO: 198) | score 7,920 |
| mouse p10-18 | ALLPAVSSL (SEQ ID NO: 255) | binds also to Kd, HLA A2, 1 mismatch to human |
| human p10-18 | ALLPAVPSL (SEQ ID NO: 34) | score 6,600 |

Peptide binding to C57Bl/6 murine MHC was confirmed using the leukemia cell line RMA-S, as described by Ljunggren et al., Nature 346:476-480, 1990. In brief, RMA-S cells were cultured for 7 hours at 26° C. in complete medium supplemented with 1% FCS. A total of $10^6$ RMA-S cells were added into each well of a 24-well plate and incubated either alone or with the designated peptide (25 ug/ml) for 16 hours at 26° C. and additional 3 hours at 37° C. in complete medium. Cells were then washed three times and stained with fluorescein isothiocyanate-conjugated anti $D^b$ or anti-$K^b$ antibody (PharMingen, San Diego, Calif.). Labeled cells were washed twice, resuspended and fixed in 500 ul of PBS with 1% paraformaldehyde and analyzed for fluorescence intensity in a flow cytometer (Becton-Dickinson FACSCALIBUR™). The percentage of increase of $D^b$ or $K^b$ molecules on the surface of the RMA-S cells was measured by increased mean fluorescent intensity of cells incubated with peptide compared with that of cells incubated in medium alone.

Mice were immunized with the peptides capable of binding to murine class I MHC. Following immunization, spleen cells were stimulated in vitro and tested for the ability to lyse targets incubated with WT1 peptides. CTL were evaluated with a standard chromium release assay (Chen et al., Cancer Res. 54:1065-1070, 1994). $10^6$ target cells were incubated at 37° C. with 150 μCi of sodium $^{51}$Cr for 90 minutes, in the presence or absence of specific peptides. Cells were washed three times and resuspended in RPMI with 5% fetal bovine serum. For the assay, $10^4$ $^{51}$Cr-labeled target cells were incubated with different concentrations of effector cells in a final volume of 200 μl in U-bottomed 96-well plates. Supernatants were removed after 4 to 7 hours at 37° C., and the percentage specific lysis was determined by the formula:

% specific lysis=100×(experimental release−spontaneous release)/(maximum release−spontaneous release).

Figure 9A:
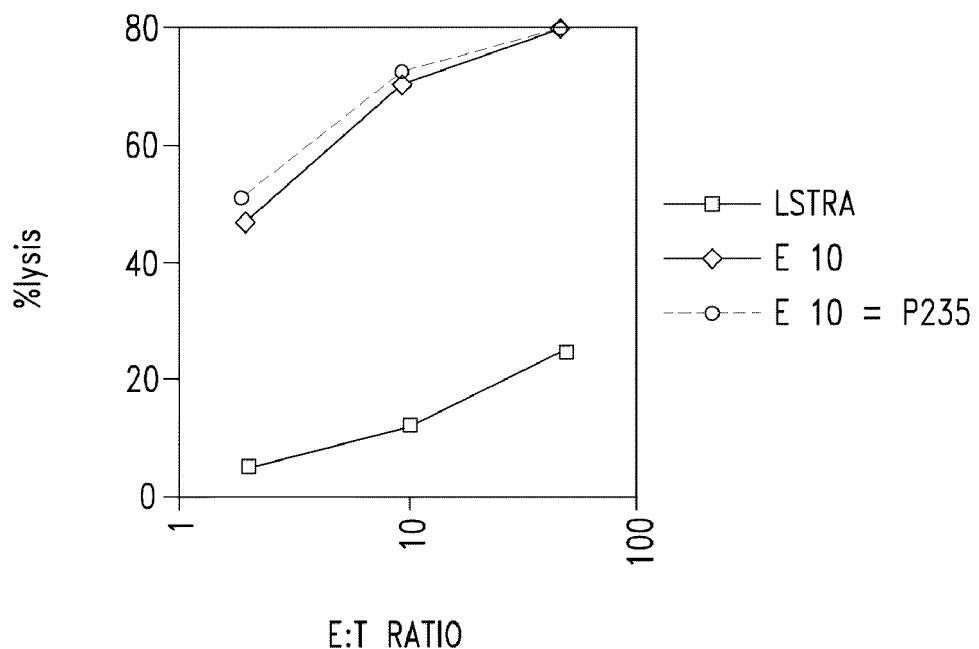
FIGS. 9A and 9B are graphs illustrating the elicitation of WT1 peptide-specific CTL in mice immunized with WT1 peptides.
Figure 9B:
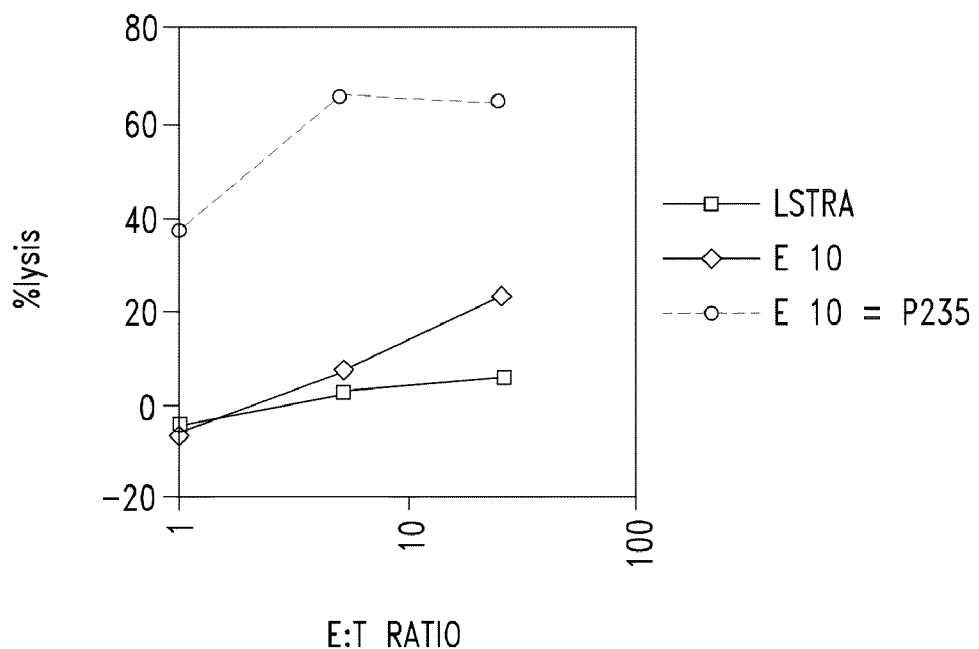
Figure 10A:
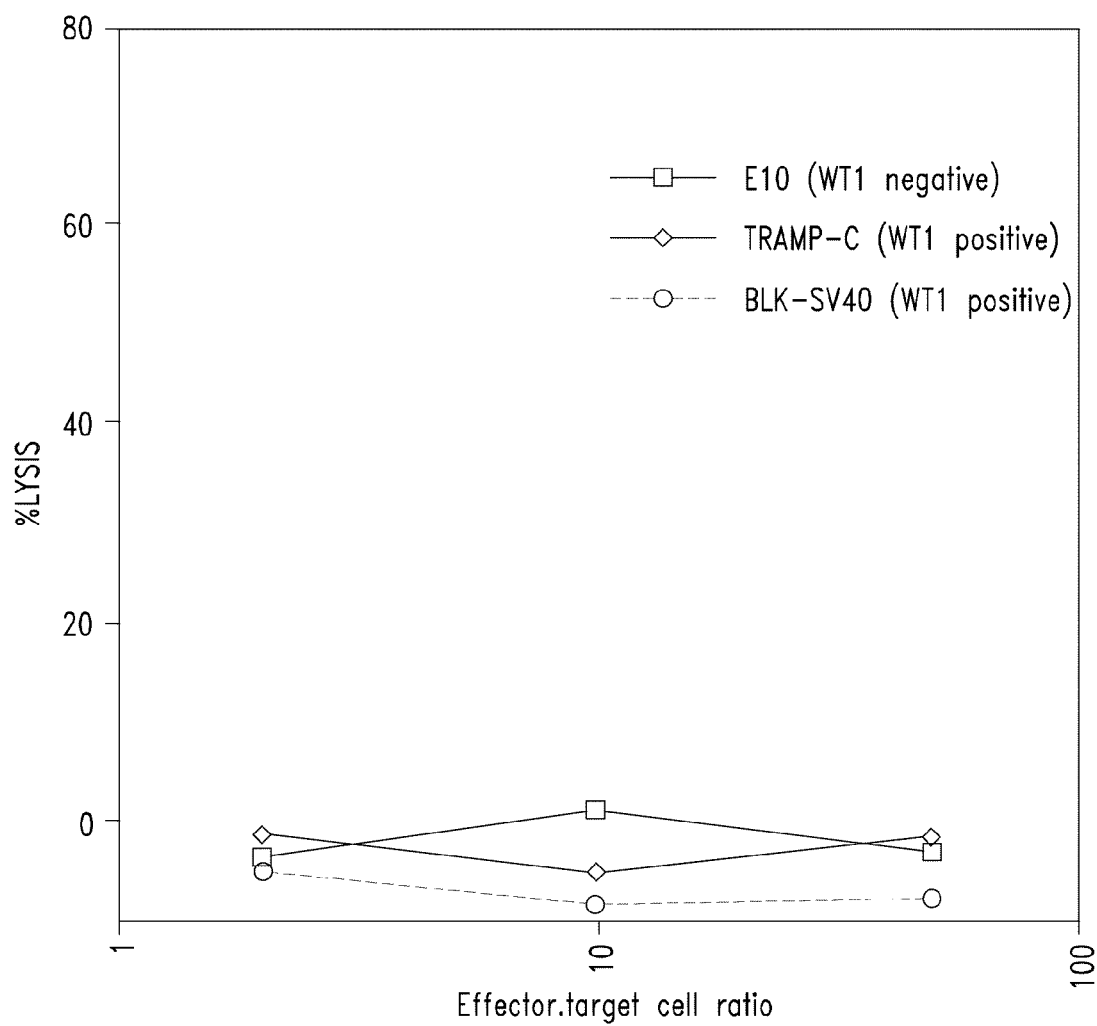
FIGS. 10A-10D are graphs illustrating the elicitation of WT1 specific CTL, which kill WT1 positive tumor cell lines but do not kill WT1 negative cell lines, following vaccination of B6 mice with WT1 peptide P117.
Figure 10B:
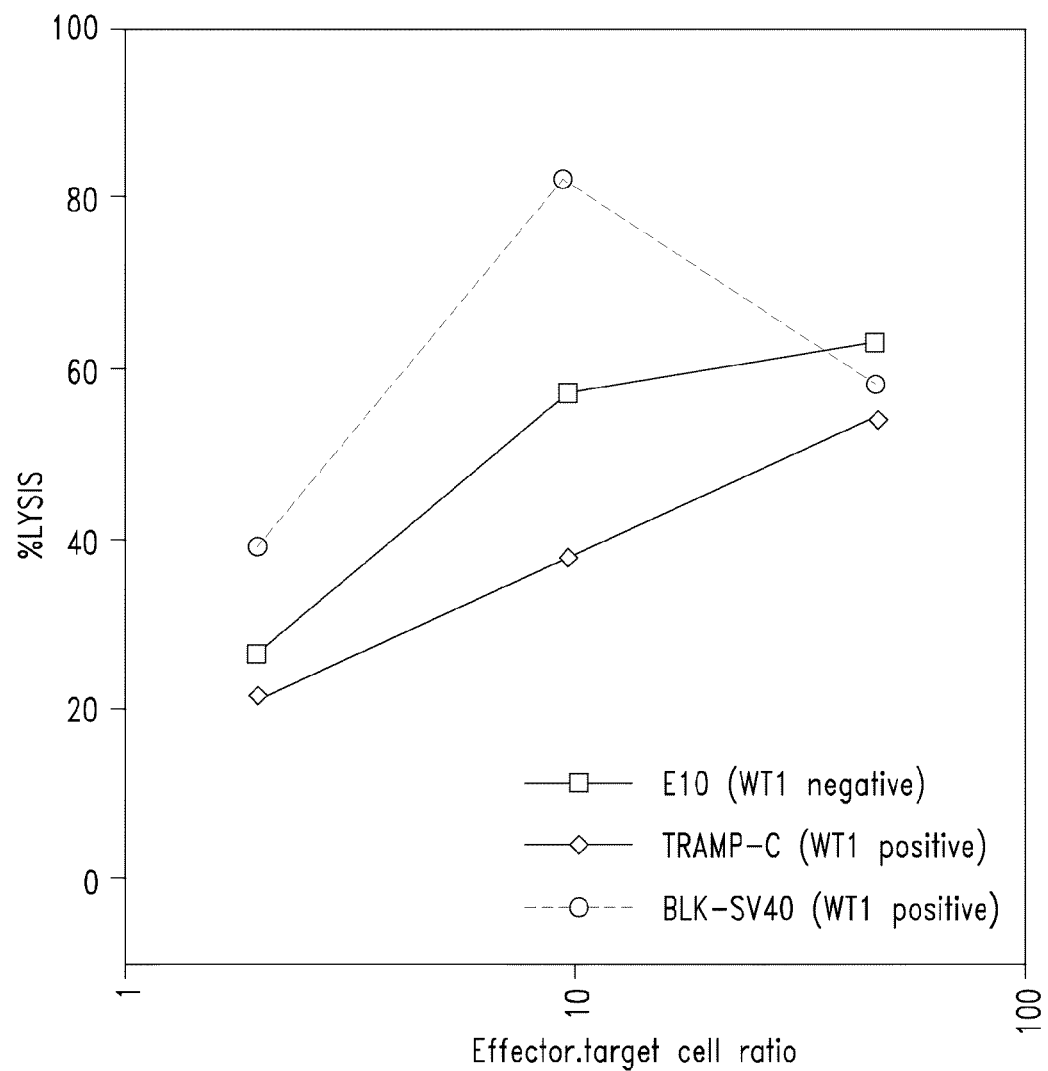
Figure 10C:
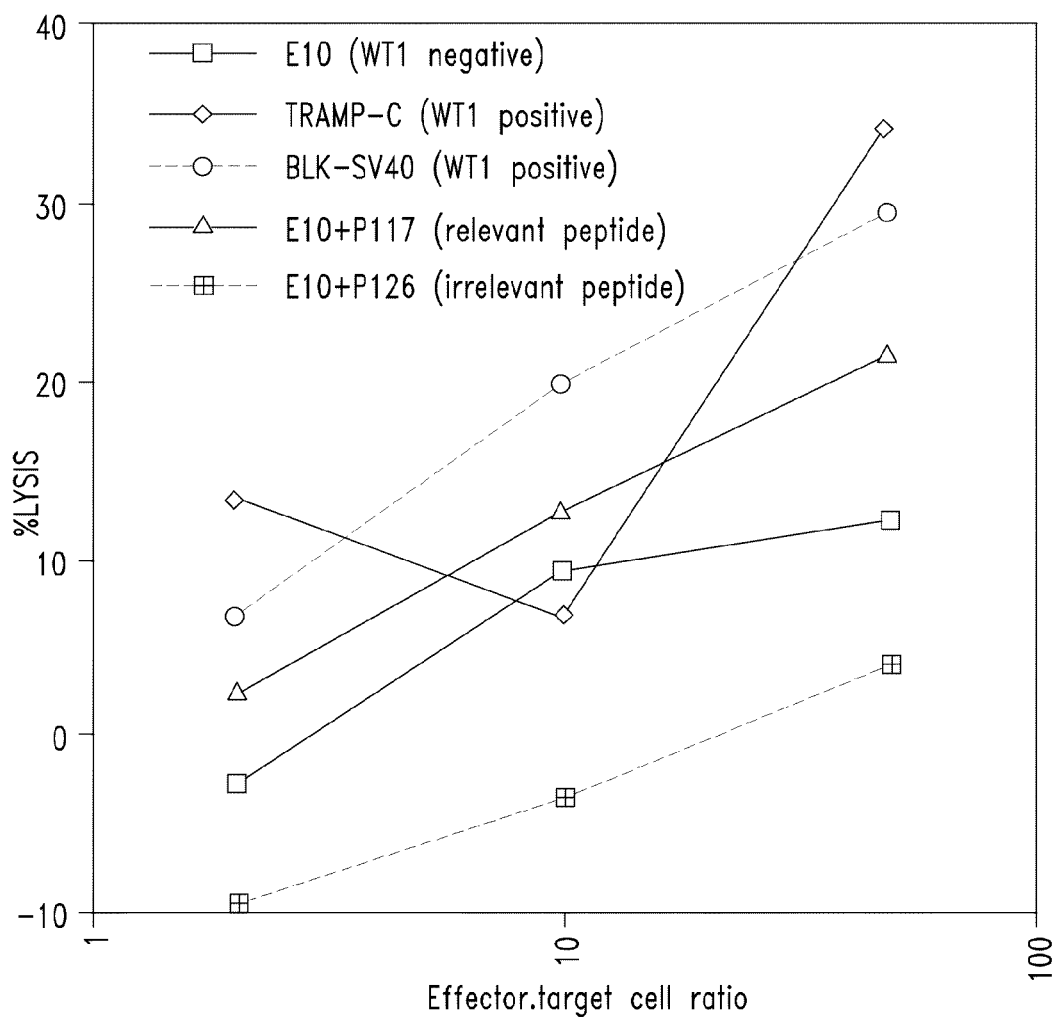
Figure 10D:
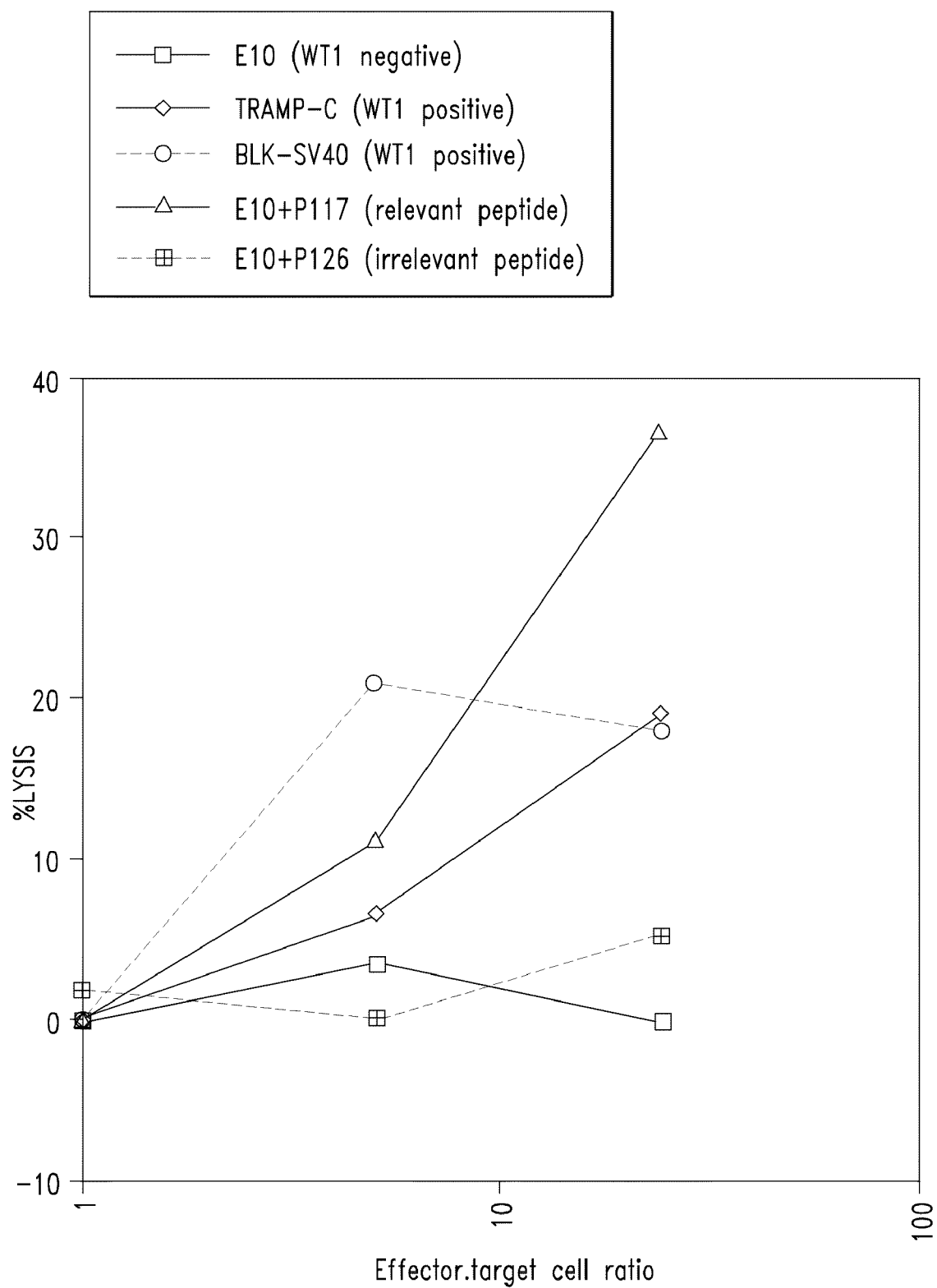

The results, presented in Table XLVII, show that some WT1 peptides can bind to class I MHC molecules, which is essential for generating CTL. Moreover, several of the peptides were able to elicit peptide specific CTL (FIGS. 9A and 9B), as determined using chromium release assays. Following immunization to CTL peptides p10-18 human, p136-144 human, p136-144 mouse and p235-243, peptide specific CTL lines were generated and clones were established. These results indicate that peptide specific CTL can kill malignant cells expressing WT1.

TABLE XLVII

Binding of WT1 CTL Peptides to mouse B6 class I antigens

| Peptide | Binding Affinity to Mouse MHC Class I |
|---|---|
| Positive control | 91% |
| negative control | 0.5.-1.3% |
| p235-243 | 33.6% |
| p136-144 mouse | 27.9% |
| p136-144 human | 52% |
| p10-18: human | 2.2% |
| p225-233 | 5.8% |
| p329-337 | 1.2% |
| p126-134 | 0.9% |
| p221-229 | 0.8% |
| p228-236 | 1.2% |
| p239-247 | 1% |

Example 5

Use of A WT1 Polypeptide to Elicit WT1 Specific CTL in Mice

This Example illustrates the ability of a representative WT1 polypeptide to elicit CTL immunity capable of killing WT1 positive tumor cell lines.

P117-139, a peptide with motifs appropriate for binding to class I and class II MHC, was identified as described above using TSITES and BIMAS HLA peptide binding prediction analyses. Mice were immunized as described in Example 3. Following immunization, spleen cells were stimulated in vitro and tested for the ability to lyse targets incubated with WT1 peptides, as well as WT1 positive and negative tumor cells. CTL were evaluated with a standard chromium release assay. The results, presented in FIGS. 10A-10D, show that P117 can elicit WT1 specific CTL capable of killing WT1 positive tumor cells, whereas no killing of WT1 negative cells was observed. These results demonstrate that peptide specific CTL in fact kill malignant cells expressing WT1 and that vaccine and T cell therapy are effective against malignancies that express WT1.

Similar immunizations were performed using the 9-mer class I MHC binding peptides p136-144, p225-233, p235-243 as well as the 23-mer peptide p117-139. Following immunization, spleen cells were stimulated in vitro with each of the 4 peptides and tested for ability to lyse targets incubated with WT1 peptides. CTL were generated specific for p136-144, p235-243 and p117-139, but not for p225-233. CTL data for p235-243 and p117-139 are presented in FIGS. 11A and 11B. Data for peptides p136-144 and p225-233 are not depicted.

CTL lysis demands that the target WT1 peptides are endogenously processed and presented in association with tumor cell class I MHC molecules. The above WT1 peptide specific CTL were tested for ability to lyse WT1 positive versus negative tumor cell lines. CTL specific for p235-243 lysed targets incubated with the p235-243 peptides, but failed to lyse cell lines that expressed WT1 proteins (FIG. 11A). By marked contrast, CTL specific for p117-139 lysed targets incubated with p117-139 peptides and also lysed malignant cells expressing WT1 (FIG. 11B). As a negative control, CTL specific for p117-139 did not lyse WT1 negative EL-4 (also referred to herein as E10).

Specificity of WT1 specific lysis was confirmed by cold target inhibition (FIGS. 12A-12B). Effector cells were plated for various effector: target ratios in 96-well U-bottom plates. A ten-fold excess (compared to hot target) of the indicated peptide-coated target without $^{51}$Cr labeling was added. Finally, $10^4$ $^{51}$Cr-labeled target cells per well were added and the plates incubated at 37° C. for 4 hours. The total volume per well was 200 µl.

Lysis of TRAMP-C by p117-139 specific CTL was blocked from 58% to 36% by EL-4 incubated with the relevant peptide p117-139, but not with EL-4 incubated with an irrelevant peptide (FIG. 12A). Similarly, lysis of BLK-SV40 was blocked from 18% to 0% by EL-4 incubated with the relevant peptide p117-139 (FIG. 12B). Results validate that WT1 peptide specific CTL specifically kill malignant cells by recognition of processed WT1.

Figure 13A:
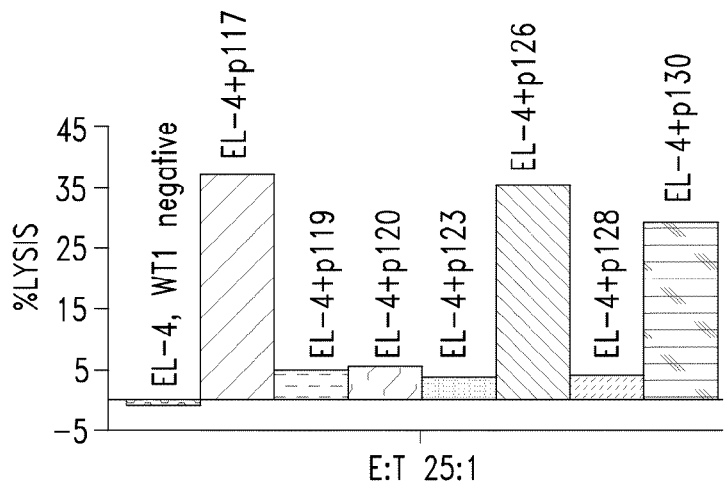
FIGS. 13A-13C are histograms depicting an evaluation of the 9mer CTL epitope within p117-139. The p117-139 tumor specific CTL line was tested against peptides within aa117-139 containing or lacking an appropriate H-2$^b$ class I binding motif and following restimulation with p126-134 or p130-138. The bars represent the mean % specific lysis in chromium release assays performed in triplicate with an E:T ratio of 25:1.

Several segments with putative CTL motifs are contained within p117-139. To determine the precise sequence of the CTL epitope all potential 9-mer peptides within p117-139 were synthesized (Table XLVIII). Two of these peptides (p126-134 and p130-138) were shown to bind to H-2$^b$ class I molecules (Table XLVIII). CTL generated by immunization with p117-139 lysed targets incubated with p126-134 and p130-138, but not the other 9-mer peptides within p117-139 (FIG. 13A).

Figure 13B:
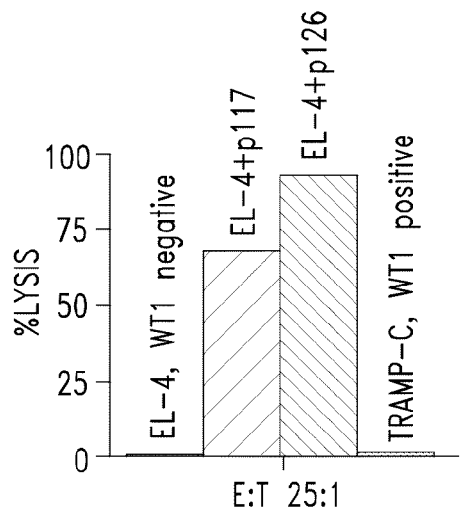
Figure 13C:
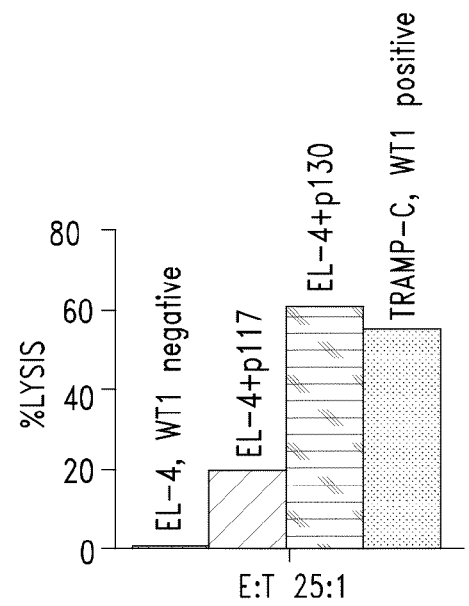
Figure 14:
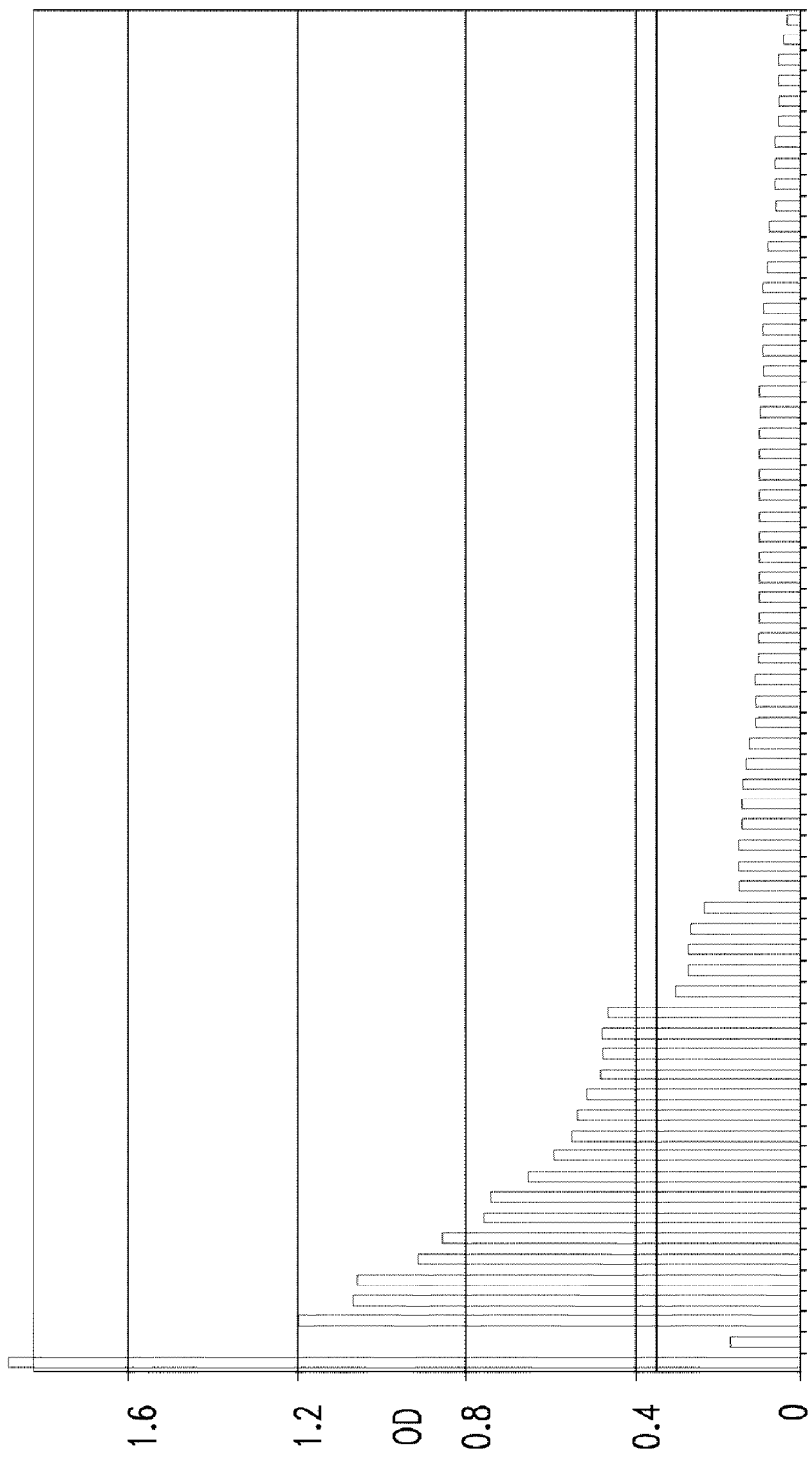
FIG. 14 depicts serum antibody reactivity to WT1 in 63 patients with AML. Reactivity of serum antibody to WT1/N-terminus protein was evaluated by ELISA in patients with AML. The first and second lanes represent the positive and negative controls, respectively. The first and second lanes represent the positive and negative controls, respectively. Commercially obtained WT1 specific antibody WT180 was used for the positive control. The next 63 lanes represent results using sera from each individual patient. The OD values depicted were from ELISA using a 1:500 serum dilution. The figure includes cumulative data from 3 separate experiments.
Figure 15:
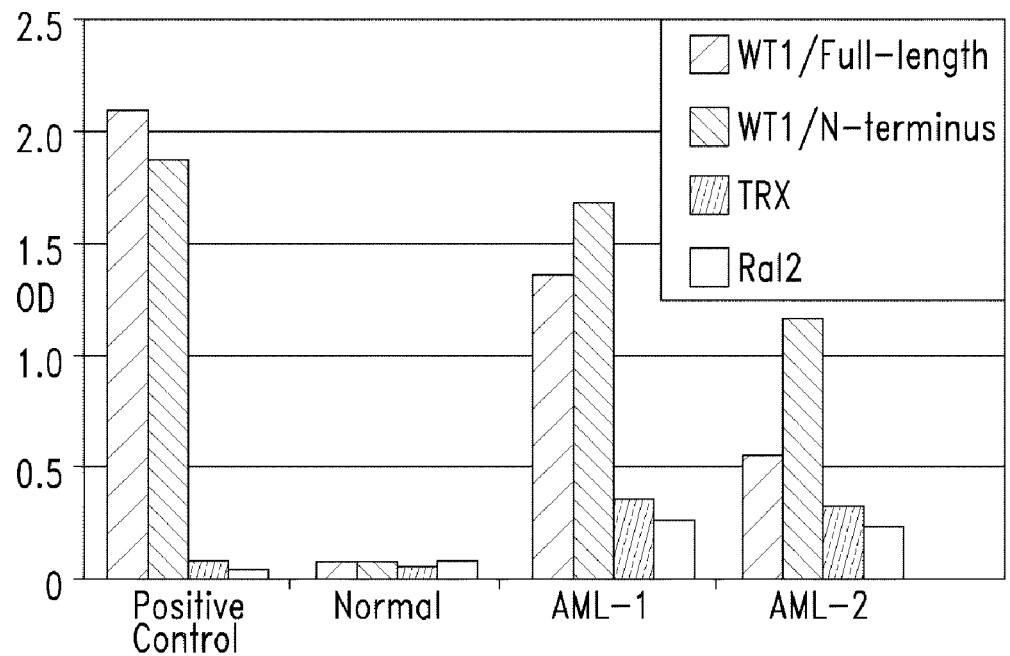
FIG. 15 depicts serum antibody reactivity to WT1 proteins and control proteins in 2 patients with AML. Reactivity of serum antibody to WT1/full-length, WT1N-terminus, TRX and Ra12 proteins was evaluated by ELISA in 2 patients with AML. The OD values depicted were from ELISA using a 1:500 serum dilution. AML-1 and AML-2 denote serum from 2 of the individual patients in FIG. 1 with demonstrated antibody reactivity to WT1/full-length. The WT1 full-length protein was expressed as a fusion protein with Ra12. The WT1/N-terminus protein was expressed as a fusion protein with TRX. The control Ra12 and TRX proteins were purified in a similar manner. The results confirm that the serum antibody reactivity against the WT1 fusion proteins is directed against the WT1 portions of the protein.

The p117-139 specific CTL line was restimulated with either p126-134 or p130-138. Following restimulation with p126-134 or p130-138, both T cell lines demonstrated peptide specific lysis, but only p130-138 specific CTL showed lysis of a WT1 positive tumor cell line (FIGS. 13B and 13C). Thus, p130-138 appears to be the naturally processed epitope.

TABLE XLVIII

Binding of WT1 CTL 9mer Peptides within p117-139 to mouse B6 class I antigens

| Peptide | Binding Affinity to Mouse MHC Class I |
|---|---|
| P117-125 PSQASSGQA (SEQ ID NO: 221) | 2% |
| P118-126 SQASSGQAR (SEQ ID NO: 216) | 2% |
| P119-127 QASSGQARM (SEQ ID Nos: 161 and 288) | 2% |
| P120-128 ASSGQARMF (SEQ ID NO: 40) | 1% |
| P121-129 SSGQARMFP (SEQ ID NO: 222) | 1% |

TABLE XLVIII-continued

Binding of WT1 CTL 9mer Peptides within p117-139 to mouse B6 class I antigens

| Peptide | Binding Affinity to Mouse MHC Class I |
|---|---|
| P122-130 SGQARMFPN (SEQ ID NO: 212) | 1% |
| P123-131 GQARMFPNA (SEQ ID Nos: 98 and 269) | 1% |
| P124-132 QARMFPNAP (SEQ ID NO: 223) | 1% |
| P125-133 ARMFPNAPY (SEQ ID NO: 38) | 1% |
| P126-134 RMFPNAPYL (SEQ ID Nos: 185 and 293) | 79% |
| P127-135 MFPNAPYLP (SEQ ID NO: 224) | 2% |
| P128-136 FPNAPYLPS (SEQ ID Nos: 79 and 267) | 1% |
| P129-137 PNAPYLPSC (SEQ ID NO: 225) | 1% |
| P130-138 NAPYLPSCL (SEQ ID Nos: 144 and 282) | 79% |
| P131-139 APYLPSCLE (SEQ ID NO: 226) | 1% |

Example 6

Identification of WT1 Specific mRNA in Mouse Tumor Cell Lines

This Example illustrates the use of RT-PCR to detect WT1 specific mRNA in cells and cell lines.

Mononuclear cells were isolated by density gradient centrifugation, and were immediately frozen and stored at −80° C. until analyzed by RT-PCR for the presence of WT1 specific mRNA. RT-PCR was generally performed as described by Fraizer et al., Blood 86:4704-4706, 1995. Total RNA was extracted from $10^7$ cells according to standard procedures. RNA pellets were resuspended in 25 µL diethylpyrocarbonate treated water and used directly for reverse transcription. The zinc-finger region (exons 7 to 10) was amplified by PCR as a 330 bp mouse cDNA. Amplification was performed in a thermocycler during one or, when necessary, two sequential rounds of PCR. AMPLITAQ® DNA Polymerase (Perkin Elmer Cetus, Norwalk, Conn.), 2.5 mM MgCl$_2$ and 20 µmol of each primer in a total reaction volume of 50 µl were used. Twenty µL aliquots of the PCR products were electrophoresed on 2% agarose gels stained with ethidium bromide. The gels were photographed with POLAROID® film (Polaroid 667, Polaroid Ltd., Hertfordshire, England). Precautions against cross contamination were taken following the recommendations of Kwok and Higuchi, Nature 339:237-238, 1989. Negative controls included the cDNA- and PCR-reagent mixes with water instead of cDNA in each experiment. To avoid false negatives, the presence of intact RNA and adequate cDNA generation was evaluated for each sample by a control PCR using β-actin primers. Samples that did not amplify with these primers were excluded from analysis.

Primers for amplification of WT1 in mouse cell lines were: P115: 1458-1478: 5'CCC AGG CTG CM TAA GAG ATA 3' (forward primer; SEQ ID NO:21); and P116: 1767-1787: 5' ATG TTG TGA TGG CGG ACC AAT 3' (reverse primer;

SEQ ID NO:22) (see Inoue et al, *Blood* 88:2267-2278, 1996; Fraizer et al., *Blood* 86:4704-4706, 1995).

Beta Actin primers used in the control reactions were: 5' GTG GGG CGC CCC AGG CAC CA 3' (sense primer; SEQ ID NO:23); and 5' GTC CTT MT GTC ACG CAC GAT TTC 3' (antisense primer; SEQ ID NO:24)

Primers for use in amplifying human WT1 include: P117: 954-974: 5' GGC ATC TGA GAC CAG TGA GAA 3' (SEQ ID NO:25); and P118: 1434-1414: 5' GAG AGT CAG ACT TGA AAG CAGT 3' (SEQ ID NO:5). For nested RT-PCR, primers may be: P119: 1023-1043: 5' GCT GTC CCA CTT ACA GAT GCA 3' (SEQ ID NO:26); and P120: 1345-1365: 5' TCA MG CGC CAG CTG GAG TTT 3' (SEQ ID NO:27).

Table XLVIII shows the results of WT1 PCR analysis of mouse tumor cell lines. Within Table IV, (+++) indicates a strong WT1 PCR amplification product in the first step RT PCR, (++) indicates a WT1 amplification product that is detectable by first step WT1 RT PCR, (+) indicates a product that is detectable only in the second step of WT1 RT PCR, and (−) indicates WT1 PCR negative.

TABLE XLIX

Detection of WT1 mRNA in Mouse Tumor Cell Lines

| Cell Line | WT1 mRNA |
|---|---|
| K562 (human leukemia; ATCC): Positive control; (Lozzio and Lozzio, Blood 45: 321-334, 1975) | +++ |
| TRAMPC (SV40 transformed prostate, B6); Foster et al., Cancer Res. 57: 3325-3330, 1997 | +++ |
| BLK-SV40 HD2 (SV40-transf. fibroblast, B6; ATCC); Nature 276: 510-511, 1978 | ++ |
| CTLL (T-cell, B6; ATCC); Gillis, Nature 268: 154-156, 1977) | + |
| FM (FBL-3 subline, leukemia, B6); Glynn and Fefer, Cancer Res. 28: 434-439, 1968 | + |
| BALB 3T3 (ATCC); Aaroston and Todaro, J. Cell. Physiol. 72: 141-148, 1968 | + |
| S49.1 (Lymphoma, T-cell like, B/C; ATCC); Horibata and Harris, Exp. Cell. Res. 60: 61, 1970 | + |
| BNL CL.2 (embryonic liver, B/C; ATCC); Nature 276: 510-511, 1978 | + |
| MethA (sarcoma, B/C); Old et al., Ann. NY Acad. Sci. 101: 80-106, 1962 | − |
| P3.6.2.8.1 (myeloma, B/C; ATCC); Proc. Natl. Acad. Sci. USA 66: 344, 1970 | − |
| P2N (leukemia, DBA/2; ATCC); Melling et al., J. Immunol. 117: 1267-1274, 1976 | − |
| BCL1 (lymphoma, B/C; ATCC); Slavin and Strober, Nature 272: 624-626, 1977 | − |
| LSTRA (lymphoma, B/C); Glynn et al., Cancer Res. 28: 434-439, 1968 | − |
| E10/EL-4 (lymphoma, B6); Glynn et al., Cancer Res. 28: 434-439, 1968 | − |

Example 7

Expression in *E. Coli* of WT1 TRX Fusion Construct

The truncated open reading frame of WT1 (WT1B) was PCR amplified with the following primers:

```
Forward Primer starting at amino acid 2
P-37
                                   (SEQ ID NO. 347)
5' ggctccgacgtgcgggacctg 3' Tm 64° C.

Reverse Primer creating EcoRI site after stop
codon
P-23
                                   (SEQ ID NO. 348)
5' gaattctcaaagcgccagctggagtttggt 3' Tm 63° C.
```

The PCR was performed under the following conditions:

```
10 µl   10X Pfu buffer
 1 µl   10 mM dNTPs
 2 µl   10 µM each oligo
83 µL   sterile water
1.5 µl  Pfu DNA polymerase (Stratagene, La Jolla, CA)
 50 ng  DNA (pPDM FL WT1)
96° C.  2 minutes
96° C.  20 seconds   63° C. 15 seconds   72° C. 3 minutes × 40 cycles
72° C.  4 minutes
```

The PCR product was digested with EcoRI restriction enzyme, gel purified and then cloned into pTrx 2H vector (a modified pET28 vector with a Trx fusion on the N-terminal and two His tags surrounding the Trx fusion. After the Trx fusion there exists protease cleavage sites for thrombin and enterokinase). The pTrx2H construct was digested with StuI and EcoRI restriction enzymes. The correct constructs were confirmed by DNA sequence analysis and then transformed into BL21 (DE3) pLys S and BL21 (DE3) CodonPlus expression host cells.

Example 8

Expression in *E. Coli* of WT1 A His Tag Fusion Constructs

The N-terminal open reading frame of WT1 (WT1A) was PCR amplified with the following primers:

```
Forward Primer starting at amino acid 2
P-37
                                   (SEQ ID NO. 347)
5'ggctccgacgtgcgggacctg 3' Tm 64° C.

Reverse Primer creating EcoRI site after an
artificial stop codon put after amino acid 249.
PDM-335
                                   (SEQ ID NO. 348)
5'gaattctcaaagcgccagctggagtttggt 3' Tm 64° C.
```

The PCR was performed under the following conditions:

```
10 µl   10X Pfu buffer
 1 µl   10 mM dNTPs
 2 µl   10 µM each oligo
83 µL   sterile water
1.5 µl  Pfu DNA polymerase (Stratagene, La Jolla, CA)
 50 ng  DNA (pPDM FL WT1)
96° C.  2 minutes
96° C.  20 seconds   63° C. 15 seconds   72° C. 1 minute 20 seconds ×
                                                  40 cycles
72° C.  4 minutes
```

The PCR product was digested with EcoRI restriction enzyme, gel purified and then cloned into pPDM, a modified pET28 vector with a His tag in frame, which had been digested with Eco72I and EcoRI restriction enzymes. The PCR product was also transformed into pTrx 2H vector. The pTrx2H construct was digested with StuI and EcoRI restriction enzymes. The correct constructs were confirmed by DNA sequence analysis and then transformed into BL21 (DE3) pLys S and BL21 (DE3) CodonPlus expression host cells.

Example 9

Expression in *E. Coli* of WT1 B His Tag Fusion Constructs

The truncated open reading frame of WT1 (WT1A) was PCR amplified with the following primers:

```
Forward Primer starting at amino acid 250
PDM-346
                                   (SEQ ID NO. 351)
5' cacagcacagggtacgagagc 3' Tm 58° C.

Reverse Primer creating EcoRI site after stop
codon
P-23
                                   (SEQ ID NO. 348)
5'gaattctcaaagcgccagctggagtttggt 3' Tm 63° C.
```

The PCR was performed under the following conditions:

| | |
|---|---|
| 10 μl | 10X Pfu buffer |
| 1 μl | 10 mM dNTPs |
| 2 μl | 10 μM each oligo |
| 83 μL | sterile water |
| 1.5 μl | Pfu DNA polymerase (Stratagene, La Jolla, CA) |
| 50 ng | DNA (pPDM FL WT1) |
| 96° C. 2 minutes | |
| 96° C. 20 seconds   63° C. 15 seconds   72° C. 1 minute 30 seconds × 40 cycles | |
| 72° C. 4 minutes | |

The PCR product was digested with EcoRI restriction enzyme, gel purified and then cloned into pPDM, a modified pET28 vector with a His tag in frame, which had been digested with Eco72I and EcoRI restriction enzymes. The PCR product was also transformed into pTrx 2H vector. The pTrx 2H construct was digested with StuI and EcoRI restriction enzymes. The correct constructs were confirmed by DNA sequence analysis and then transformed into BL21 (DE3) pLys S and BL21 (DE3) CodonPlus expression host cells.

For Examples 7-9, the following SEQ ID NOs. are disclosed:

SEQ ID NO. 327 is the determined cDNA sequence for Trx_WT1_B
SEQ ID NO. 328 is the determined cDNA sequence for Trx_WT1_A
SEQ ID NO. 329 is the determined cDNA sequence for Trx_WT1
SEQ ID NO. 330 is the determined cDNA sequence for WT1_A
SEQ ID NO. 331 is the determined cDNA sequence for WT1_B
SEQ ID NO. 332 is the predicted amino acid sequence encoded by SEQ ID No.
SEQ ID NO. 333 is the predicted amino acid sequence encoded by SEQ ID No. 328
SEQ ID NO. 334 is the predicted amino acid sequence encoded by SEQ ID No. 329
SEQ ID NO. 335 is the predicted amino acid sequence encoded by SEQ ID No. 330
SEQ ID NO. 336 is the predicted amino acid sequence encoded by SEQ ID No. 331

Example 10

Truncated Forms of WT1 Expressed in *E. Coli*

Three reading frames of WT1 were amplified by PCR using the following primers:

```
For WT1 Tr2:
PDM-441
                                   (SEQ ID NO. 353)
5' cacgaagaacagtgcctgagcgcattcac 3' Tm 63° C.

PDM-442
                                   (SEQ ID NO. 354)
5' ccggcgaattcatcagtataaattgtcactgc 3' TM 62° C.

For WT1 Tr3:
PDM-443
                                   (SEQ ID NO. 355)
5' caggctttgctgctgaggacgccc 3' Tm 64° C.

PDM-444
                                   (SEQ ID NO. 356)
5' cacggagaattcatcactggtatggtttctcacc Tm 64° C.

For WT1 Tr4:
PDM-445
                                   (SEQ ID NO. 357)
5' cacagcaggaagcacactggtgagaaac 3' Tm 63° C.

PDM-446
                                   (SEQ ID NO. 358)
5' ggatatctgcagaattctcaaagcgccagc 3' TM 63° C.
```

The PCR was performed under the following conditions:

| | |
|---|---|
| 10 μl | 10X Pfu buffer |
| 1 μl | 10 mM dNTPs |
| 2 μl | 10 μM each oligo |
| 83 μL | sterile water |
| 1.5 μl | Pfu DNA polymerase (Stratagene, La Jolla, CA) |
| 50 ng | DNA (pPDM FL WT1) |
| 96° C. 2 minutes | |
| 96° C. 20 seconds   63° C. 15 seconds   72° C. 30 seconds × 40 cycles | |
| 72° C. 4 minutes | |

The PCR products were digested with EcoRI and cloned into pPDM His (a modified pET28 vector with a His tag in frame on the 5' end) which has been digested with Eco72I and EcoRI. The constructs were confirmed to be correct through sequence analysis and transformed into BL21 pLys S and BL21-CODONPLUS® cells or BLR pLys S and BL21-CODONPLUS® cells.

Example 11

WT1 C (Amino Acids 76-437) and WT1 D (Amino Acids 91-437) Expression in *E. Coli*

The WT1 C reading frame was amplified by PCR using the following primers:

```
PDM-504
                                   (SEQ ID NO. 359)
5' cactccttcatcaaacaggaac 3' Tm 61° C.

PDM-446
                                   (SEQ ID NO. 358)
5' ggatatctgcagaattctcaaagcgccagc 3' Tm 63° C.
```

The PCR was performed under the following conditions:

| | |
|---|---|
| 10 μl | 10X Pfu buffer |
| 1 μl | 10 mM dNTPs |
| 2 μl | 10 μM each oligo |
| 83 μL | sterile water |
| 1.5 μl | Pfu DNA polymerase (Stratagene, La Jolla, CA) |

```
50 ng DNA (pPDM FL WT1)
96° C. 2 minutes
96° C. 20 seconds    63° C. 15 seconds   72° C. 2 minutes × 40 cycles
72° C. 4 minutes
```

The PCR product was digested with EcoRI and cloned into pPDM His which had been digested with Eco72I and EcoRI. The sequence was confirmed through sequence analysis and then transformed into BLR pLys S and BLR which is co-transformed with CODONPLUS® RP.

Example 12

Synthetic Production of WT1 TR-1 by Annealing Overlapping Oligos

This example was performed to determine the effect of changing proline codon usage on expression.

The following pairs of oligos were annealed:

```
1. PDM-505
                                            (SEQ ID NO. 361)
5' ggttccgacgtgcgggacctgaacgcactgctg 3'

PDM-506
                                            (SEQ ID NO. 362)
5' ctgccggcagcagtgcgttcaggtcccgcacgtcggaacc 3'

2. PDM-507
                                            (SEQ ID NO. 363)
5' ccggcagttccatccctgggtggcggtggaggctg 3'

PDM-508
                                            (SEQ ID NO. 364)
5' cggcagtgcgcagcctccaccgccacccagggatggaa 3'

3. PDM-509
                                            (SEQ ID NO. 365)
5' cgcactgccggttagcggtgcagcacagtgggctc 3'

PDM-510
                                            (SEQ ID NO. 366)
5' cagaactggagcccactgtgctgcaccgctaac 3'

4. PDM-511
                                            (SEQ ID NO. 367)
5' cagttctggacttcgcaccgcctggtgcatccgcatac 3'

PDM-512
                                            (SEQ ID NO. 368)
5' cagggaaccgtatgcggatgcaccaggcggtgcgaagtc 3'

5. PDM-513
                                            (SEQ ID NO. 369)
5' ggttccctgggtggtccagcacctccgcccgcaacgcc 3'

PDM-514
                                            (SEQ ID NO. 370)
5' ggcggtggggcgttgcgggcggaggtgctggaccacc 3'

6. PDM-515
                                            (SEQ ID NO. 371)
5' cccaccgcctccaccgccccgcactccttcatcaaacag 3'

PDM-516
                                            (SEQ ID NO. 372)
5' ctaggttcctgtttgatgaaggagtgcggggcggtgga 3'

7. PDM-517
                                            (SEQ ID NO. 373)
5' gaacctagctgggtggtgcagaaccgcacgaagaaca 3'

PDM-518
                                            (SEQ ID NO. 374)
5' ctcaggcactgttcttcgtgcggttctgcaccaccccag 3'

8. PDM-519
                                            (SEQ ID NO. 375)
5' gtgcctgagcgcattctgagaattctgcagat 3'

PDM-520
                                            (SEQ ID NO. 376)
5' gtgtgatggatatctgcagaattctcagaatgcg 3'
```

Each oligo pair was separately combined then annealed. The pairs were then ligated together and one µl of ligation mix was used for PCR conditions below:

```
10 µl   10X Pfu buffer
 1 µl   10 mM dNTPs
 2 µl   10 µM each oligo
83 µL   sterile water
1.5 µl  Pfu DNA polymerase (Stratagene, La Jolla, CA)
96° C. 2 minutes
96° C. 20 seconds    63° C. 15 seconds   72° C. 30 seconds × 40 cycles
72° C. 4 minutes
```

The PCR product was digested with EcoRI and cloned into pPDM His which had been digested with Eco72I and EcoRI. The sequence was confirmed and then transformed into BLR pLys S and BLR which is co-transformed with CODONPLUS® RP.

For examples 10-12, the following SEQ ID NOs. are disclosed:

SEQ ID NO:337 is the determined cDNA sequence for WT1_Tr1

SEQ ID NO:338 is the determined cDNA sequence for WT1_Tr2

SEQ ID NO:339 is the determined cDNA sequence for WT1_Tr3

SEQ ID NO:340 is the determined cDNA sequence for WT1_Tr4

SEQ ID NO:341 is the determined cDNA sequence for WT1_C

SEQ ID NO:342 is the predicted amino acid sequence encoded by SEQ ID NO:337

SEQ ID NO:343 is the predicted amino acid sequence encoded by SEQ ID NO:338

SEQ ID NO:344 is the predicted amino acid sequence encoded by SEQ ID NO:339

SEQ ID NO:345 is the predicted amino acid sequence encoded by SEQ ID NO:340

SEQ ID NO:346 is the predicted amino acid sequence encoded by SEQ ID NO:341

The WT1 C sequence represents a polynucleotide having the coding regions of TR2, TR3 and TR4.

The WT1 TR-1 synthetic sequence represents a polynucleotide in which alternative codons for proline were substituted for the native codons, producing a polynucleotide capable of expressing WT1 TR-1 in E. coli.

Example 13

Evaluation of the Systemic Histopathological and Toxicological Effects of WT1 Immunization in Mice The purpose of this example is to analyze the immunogenicity and potential systemic histopathological and toxicological effects of WT1 protein immunization in a multiple dose titration in mice.

The experimental design for immunization of mice with WT1 protein is outlined in Table L.

TABLE L

Experimental Design of WT1 Immunization in Mice

| Histology Group | Corixa Group | Treatment Description | Dose Level | Total No. (Females) |
|---|---|---|---|---|
| 1 | 0 | No treatment | 0 | 4 |
| 2 | 1.1 | MPL ®-SE (adjuvants alone), 6x, 1 week apart | 10 ug | 4 |
| 3 | 1.2 | MPL ®-SE, 3x, 2 weeks apart | 10 ug | 4 |
| 4 | 2.1 | Ra12-WT1 + MPL ®-SE, 6x | 25 ug | 4 |
| 5 | 2.2 | Ra12-WT1 + MPL ®-SE, 3x | 25 ug | 4 |
| 6 | 3.1 | Ra12-WT1 + MPL ®-SE, 6x | 100 ug | 4 |
| 7 | 3.2 | Ra12-WT1 + MPL ®-SE, 3x | 100 ug | 4 |
| 8 | 4.1 | Ra12-WT1 + MPL ®-SE, 6x | 1000 ug | 4 |
| 9 | 4.2 | Ra12-WT1 + MPL ®-SE, 3x | 1000 ug | 4 |

Figure 20B:
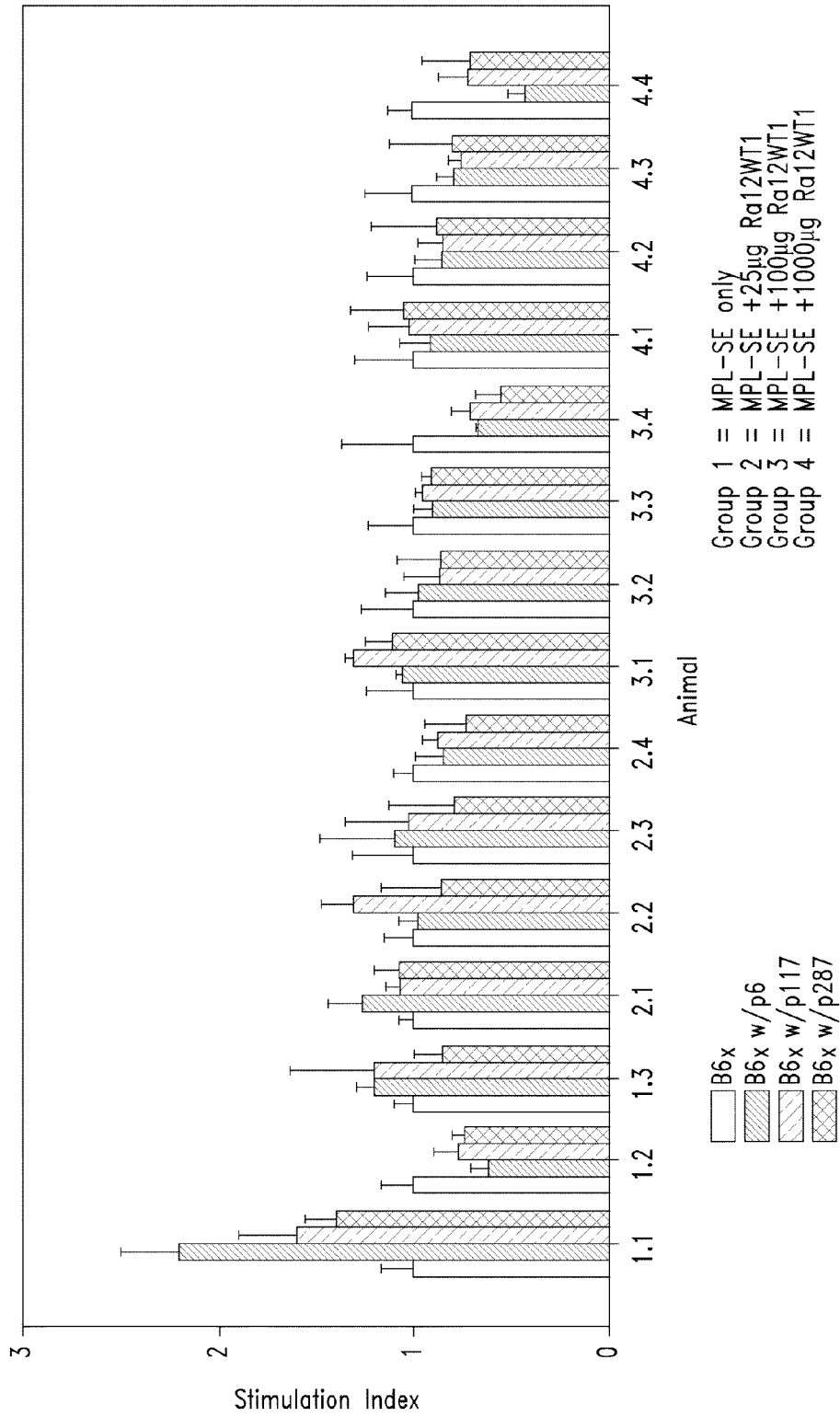

Vaccination to WT1 protein using MPL ®-SE as adjuvant, in a multiple dose titration study (doses ranging from 25 µg, 100 µg to 1000 µg WT1 protein) in female C57/B6 mice elicited a strong WT1-specific antibody response (FIG. 19) and cellular T-cell responses (FIG. 20).

No systemic histopathological or toxicological effects of immunization with WT1 protein was observed. No histological evidence for toxicity was seen in the following tissues: adrenal gland, brain, cecum, colon, duodenum, eye, femur and marrow, gall bladder, heart, ileum, jejunum, kidney, larynx, lacrimal gland, liver, lung, lymph node, muscle, esophagus, ovary, pancreas, parathyroid, salivary gland, sternum and marrow, spleen, stomach, thymus, trachea, thyroid, urinary bladder and uterus.

Special emphasis was put on evaluation of potential hematopoietic toxicity. The myeloid/erythroid ratio in sternum and femur marrow was normal. All evaluable blood cell counts and blood chemistry (BUN, creatinine, bilirubin, albumin, globulin) were within the normal range (Table LI).

Given that existent immunity to WT1 is present in some patients with leukemia and that vaccination to WT1 protein can elicit WT1 specific Ab and cellular T-cell responses in mice without toxicity to normal tissues, these experiments validate WT1 as a tumor/leukemia vaccine.

TABLE LI

Clinical Chemistry and Hematology Analysis
Table LI: WT1 Dose Titration Study
Clinical Chemistry and Hematology Analysis

| Animal # | K/uL WBC | M/uL RBC | g/dl Hg. | % HCT Normal | fL MCV | pg MCH | % MCHC |
|---|---|---|---|---|---|---|---|
|  | 5.4-16.0 | 6.7-12.5 | 10.2-16.6 | 32-54 | 31-62 | 9.2-20.8 | 22.0-35.5 |
| Group 1 | | | | | | | |
| 1 (0) | 5.6 | 8.41 | 12.8 | 43.5 | 53 | 15.2 | 29.4 |
| 2 (0) | 5.5 | 9.12 | 13.4 | 47.5 | 53 | 14.7 | 28.2 |
| 3 (0) | 7.5 | 9.22 | 13.5 | 48 | 54 | 14.7 | 28.1 |
| 4 (0) | 3.9 | 9.27 | 13.6 | 46 | 52 | 14.7 | 29.6 |
| Mean | 5.6 | 9.0 | 13.3 | 46.3 | 53.0 | 14.8 | 28.8 |
| STD | 1.5 | 0.4 | 0.4 | 2.0 | 0.8 | 0.3 | 0.8 |
| Group 2 | | | | | | | |
| 5 (1.5) | 6.6 | 9 | 13.1 | 46 | 54 | 14.5 | 28.5 |
| 6 (1.6) | 5.2 | 8.58 | 12.6 | 44 | 53 | 14.7 | 28.6 |
| 7 (1.7) | 7.8 | 9.21 | 13.6 | 46 | 53 | 14.7 | 29.6 |
| 8 (1.8) | 6.3 | NA | NA | 41 | NA | NA | NA |
| Mean | 6.5 | 8.9 | 13.1 | 44.3 | 53.3 | 14.6 | 28.9 |
| STD | 1.1 | 0.3 | 0.5 | 2.4 | 0.6 | 0.1 | 0.6 |
| Group 3 | | | | | | | |
| 9 (2.5) | 8.3 | 9.16 | 13.6 | 50.3 | 55 | 14.9 | 27.1 |
| 10 (2.6) | 5 | 8.78 | 13 | 44.2 | 50 | 14.8 | 29.3 |
| 11 (2.7) | 4 | 8.94 | 13.2 | 48.3 | 54 | 14.7 | 27.3 |
| 12 (2.8) | 8.2 | NA | NA | 41 | NA | NA | NA |
| Mean | 6.4 | 9.0 | 13.3 | 46.0 | 53.0 | 14.8 | 27.9 |
| STD | 2.2 | 0.2 | 0.3 | 4.2 | 2.6 | 0.1 | 1.2 |
| Group 4 | | | | | | | |
| 13 (3.5) | 6.1 | 8.82 | 13.1 | 46 | 54 | 14.9 | 28.5 |
| 14 (3.6) | 6.1 | 8.64 | 12.9 | 46 | 54 | 15 | 28 |
| 15 (3.7) | 9.3 | 8.93 | 13.2 | 48 | 55 | 14.8 | 27.5 |
| 16 (3.8) | 4.8 | 8.19 | 12.6 | 44 | 55 | 15.3 | 28.6 |
| Mean | 6.6 | 8.6 | 13.0 | 46.0 | 54.5 | 15.0 | 28.2 |
| STD | 1.9 | 0.3 | 0.3 | 1.6 | 0.6 | 0.2 | 0.5 |
| Group 5 | | | | | | | |
| 17 (4.5) | 3.1 | 8.48 | 12.6 | 46 | 54 | 14.9 | 27.5 |
| 18 (4.6) | 5.7 | 9.12 | 13.7 | 48 | 54 | 15 | 28.5 |
| 19 (4.7) | 5.3 | 8.58 | 13 | 44.5 | 55 | 15.2 | 29.2 |
| 20 (4.8) | 5.3 | NA | NA | 40 | NA | NA | NA |
| Mean | 4.9 | 8.7 | 13.1 | 44.6 | 54.3 | 15.0 | 28.4 |
| STD | 1.2 | 0.3 | 0.6 | 3.4 | 0.6 | 0.2 | 0.9 |

TABLE LI-continued

Clinical Chemistry and Hematology Analysis
Table LI: WT1 Dose Titration Study
Clinical Chemistry and Hematology Analysis

| Group 6 | | | | | | | |
|---|---|---|---|---|---|---|---|
| 21 (1.1) | 3.5 | 9.36 | 13.5 | 37.6 | 40 | 14.4 | 35.9 |
| 22 (1.2) | 6.9 | 8.93 | 13.6 | 37.3 | 42 | 15.3 | 36.6 |
| 23 (1.3) | 3.6 | 8.3 | 12.5 | 35.3 | 43 | 15.1 | 35.5 |
| 24 (1.4) | NA | NA | NA | NA | NA | NA | NA |
| Mean | 4.7 | 8.9 | 13.2 | 36.7 | 41.7 | 14.9 | 36.0 |
| STD | 1.9 | 0.5 | 0.6 | 1.3 | 1.5 | 0.5 | 0.6 |
| Group 7 | | | | | | | |
| 25 (2.1) | 4 | NA | NA | 40 | NA | NA | NA |
| 26 (2.2) | 7.4 | 9.12 | 13.2 | 38.5 | 42 | 14.5 | 34.3 |
| 27 (2.3) | 4.5 | 8.19 | 12.1 | 34.5 | 42 | 14.8 | 35.1 |
| 28 (2.4) | 5.8 | 8.25 | 12.3 | 34.1 | 41 | 14.9 | 36.1 |
| Mean | 5.4 | 8.5 | 12.5 | 36.8 | 41.7 | 14.7 | 35.2 |
| STD | 1.5 | 0.5 | 0.6 | 2.9 | 0.6 | 0.2 | 0.9 |
| Group 8 | | | | | | | |
| 29 (3.1) | 5.1 | 8.53 | 12.6 | 34.9 | 41 | 14.7 | 36 |
| 30 (3.2) | 7.6 | 8.42 | 13 | 36.1 | 43 | 15.4 | 35.9 |
| 31 (3.3) | 3.4 | 8.45 | 12.6 | 34.9 | 41 | 14.9 | 36.1 |
| 32 (3.4) | 6.1 | 8.11 | 12.3 | 34.8 | 43 | 15.2 | 35.5 |
| Mean | 5.6 | 8.4 | 12.6 | 35.2 | 42.0 | 15.1 | 35.9 |
| STD | 1.8 | 0.2 | 0.3 | 0.6 | 1.2 | 0.3 | 0.3 |
| Group 9 | | | | | | | |
| 33 (4.1) | NA | NA | NA | NA | NA | NA | NA |
| 34 (4.2) | 4.5 | 8.63 | 12.8 | 36.2 | 42 | 14.8 | 35.2 |
| 35 (4.3) | 3.9 | 8.85 | 13 | 36.6 | 41 | 14.7 | 35.6 |
| 36 (4.4) | 4.7 | 8.14 | 12.3 | 33.8 | 42 | 15.1 | 36.3 |
| Mean | 4.4 | 8.5 | 12.7 | 35.5 | 41.7 | 14.9 | 35.7 |
| STD | 0.4 | 0.4 | 0.4 | 1.5 | 0.6 | 0.2 | 0.6 |

| Animal # | yes/no Plt. clump | K/uL Platelets 150-1500 | Abs. Baso 0.0-0.15 K/uL | Abs. Eos Normal 0.0-0.51 K/uL | Abs. Bands 0.0-0.32 K/uL | Abs. Polys 8.0-42.9 K/uL | Abs. Lymph 8.0-18.0 K/uL | Abs. Mono 0.0-1.5 K/uL |
|---|---|---|---|---|---|---|---|---|
| Group 1 | | | | | | | | |
| 1 (0) | yes | 726 | 0 | 56 | 0 | 336 | 5208 | 0 |
| 2 (0) | no | 860 | 0 | 0 | 0 | 55 | 5445 | 0 |
| 3 (0) | no | 875 | 0 | 375 | 0 | 525 | 6525 | 75 |
| 4 (0) | yes | 902 | 0 | 0 | 0 | 156 | 3744 | 0 |
| Mean | | 840.8 | 0.0 | 107.8 | 0.0 | 268.0 | 5230.5 | 18.8 |
| STD | | 78.4 | 0.0 | 180.1 | 0.0 | 207.0 | 1144.8 | 37.5 |
| Group 2 | | | | | | | | |
| 5 (1.5) | no | 1193 | 0 | 132 | 0 | 792 | 5214 | 462 |
| 6 (1.6) | no | 1166 | 0 | 52 | 0 | 624 | 4472 | 52 |
| 7 (1.7) | no | 1087 | 0 | 234 | 0 | 1170 | 6396 | 0 |
| 8 (1.8) | yes | NA | 0 | 126 | 0 | 126 | 5922 | 126 |
| Mean | | 1148.7 | 0.0 | 136.0 | 0.0 | 678.0 | 5501.0 | 160.0 |
| STD | | 55.1 | 0.0 | 74.8 | 0.0 | 433.1 | 840.5 | 207.9 |
| Group 3 | | | | | | | | |
| 9 (2.5) | no | 705 | 0 | 166 | 0 | 664 | 7387 | 83 |
| 10 (2.6) | no | 1140 | 0 | 150 | 0 | 500 | 4350 | 0 |
| 11 (2.7) | no | 952 | 0 | 120 | 0 | 680 | 3200 | 0 |
| 12 (2.8) | yes | NA | 0 | 164 | 0 | 656 | 7216 | 164 |
| Mean | | 932.3 | 0.0 | 150.0 | 0.0 | 625.0 | 5538.3 | 61.8 |
| STD | | 218.2 | 0.0 | 21.2 | 0.0 | 83.9 | 2090.6 | 78.6 |
| Group 4 | | | | | | | | |
| 13 (3.5) | no | 785 | 0 | 488 | 0 | 732 | 4636 | 244 |
| 14 (3.6) | yes | 973 | 0 | 0 | 0 | 488 | 5307 | 305 |
| 15 (3.7) | yes | 939 | 0 | 465 | 0 | 558 | 7812 | 465 |
| 16 (3.8) | yes | 1622 | 0 | 192 | 0 | 480 | 4080 | 48 |
| Mean | | 1079.8 | 0.0 | 286.3 | 0.0 | 564.5 | 5458.8 | 265.5 |
| STD | | 370.6 | 0.0 | 233.4 | 0.0 | 117.0 | 1647.1 | 172.4 |
| Group 5 | | | | | | | | |
| 17 (4.5) | no | 892 | 0 | 31 | 0 | 620 | 2449 | 0 |
| 18 (4.6) | yes | 966 | 57 | 114 | 0 | 855 | 4674 | 0 |

TABLE LI-continued

Clinical Chemistry and Hematology Analysis
Table LI: WT1 Dose Titration Study
Clinical Chemistry and Hematology Analysis

| | | | | | | | |
|---|---|---|---|---|---|---|---|
| 19 (4.7) | yes | 883 | 0 | 53 | 0 | 742 | 4452 | 53 |
| 20 (4.8) | yes | NA | 0 | 106 | 0 | 53 | 5141 | 0 |
| Mean | | 913.7 | 14.3 | 76.0 | 0.0 | 567.5 | 4179.0 | 13.3 |
| STD | | 45.5 | 28.5 | 40.4 | 0.0 | 356.2 | 1188.5 | 26.5 |
| Group 6 | | | | | | | | |
| 21 (1.1) | yes | 784 | 0 | 35 | 0 | 385 | 2870 | 210 |
| 22 (1.2) | yes | 806 | 0 | 69 | 0 | 207 | 6486 | 138 |
| 23 (1.3) | yes | 790 | 0 | 180 | 0 | 396 | 2988 | 36 |
| 24 (1.4) | NA | NA | NA | NA | NA | NA | NA | NA |
| Mean | | 793.3 | 0.0 | 94.7 | 0.0 | 329.3 | 4114.7 | 128.0 |
| STD | | 11.4 | 0.0 | 75.8 | 0.0 | 106.1 | 2054.5 | 87.4 |
| Group 7 | | | | | | | | |
| 25 (2.1) | yes | NA | 0 | 80 | 0 | 200 | 3720 | 0 |
| 26 (2.2) | yes | 753 | 0 | 0 | 0 | 518 | 6734 | 148 |
| 27 (2.3) | yes | 725 | 0 | 90 | 0 | 225 | 4140 | 45 |
| 28 (2.4) | yes | 792 | 0 | 232 | 0 | 754 | 4814 | 0 |
| Mean | | 756.7 | 0.0 | 100.5 | 0.0 | 424.3 | 4852.0 | 48.3 |
| STD | | 33.7 | 0.0 | 96.5 | 0.0 | 263.0 | 1333.1 | 69.8 |
| Group 8 | | | | | | | | |
| 29 (3.1) | yes | 784 | 0 | 153 | 0 | 561 | 4233 | 153 |
| 30 (3.2) | yes | 512 | 0 | 152 | 0 | 304 | 6992 | 152 |
| 31 (3.3) | yes | 701 | 0 | 0 | 0 | 238 | 3094 | 68 |
| 32 (3.4) | yes | 631 | 0 | 305 | 0 | 305 | 5368 | 122 |
| Mean | | 657.0 | 0.0 | 152.5 | 0.0 | 352.0 | 4921.8 | 123.8 |
| STD | | 115.1 | 0.0 | 124.5 | 0.0 | 142.8 | 1663.3 | 39.9 |
| Group 9 | | | | | | | | |
| 33 (4.1) | NA | NA | NA | NA | NA | NA | NA | NA |
| 34 (4.2) | yes | 724 | 0 | 125 | 0 | 540 | 3780 | 45 |
| 35 (4.3) | yes | 758 | 0 | 117 | 0 | 429 | 3315 | 39 |
| 36 (4.4) | yes | 808 | 0 | 47 | 0 | 329 | 4089 | 235 |
| Mean | | 763.3 | 0.0 | 96.3 | 0.0 | 432.7 | 3728.0 | 106.3 |
| STD | | 42.3 | 0.0 | 42.9 | 0.0 | 105.5 | 389.6 | 111.5 |

| | mg/dl BUN | mg/dl Creatinine | g/dl T. protein | g/dl Albumin | g/dl Globulin | mg/dl T. Bilirubin |
|---|---|---|---|---|---|---|
| | | | Normal | | | |
| Animal # | 13.9-28.3 | 0.3-1.0 | 4.0-8.6 | 2.5-4.8 | 1.5-3.8 | 0.10-0.90 |
| Group 1 | | | | | | |
| 1 (0) | NA | NA | NA | NA | NA | NA |
| 2 (0) | 28 | 0.5 | 4.9 | 3.7 | 1.2 | 0.3 |
| 3 (0) | 25 | 0.5 | 4.9 | 3.8 | 1.1 | 0.2 |
| 4 (0) | 27 | 0.5 | 4.7 | 3.7 | 1 | 0.2 |
| Mean | 26.7 | 0.5 | 4.8 | 3.7 | 1.1 | 0.2 |
| STD | 1.5 | 0.0 | 0.1 | 0.1 | 0.1 | 0.1 |
| Group 2 | | | | | | |
| 5 (1.5) | 34 | 0.5 | 4.6 | 3.6 | 1 | 0.2 |
| 6 (1.6) | 31 | 0.4 | 4.6 | 3.3 | 1.3 | 0.2 |
| 7 (1.7) | 34 | 0.6 | 4.9 | 4 | 0.9 | 0.3 |
| 8 (1.8) | NA | NA | NA | NA | NA | NA |
| Mean | 33.0 | 0.5 | 4.7 | 3.6 | 1.1 | 0.2 |
| STD | 1.7 | 0.1 | 0.2 | 0.4 | 0.2 | 0.1 |
| Group 3 | | | | | | |
| 9 (2.5) | NA | NA | NA | NA | NA | NA |
| 10 (2.6) | 33 | 0.5 | 4.6 | 3.6 | 1 | 0.3 |
| 11 (2.7) | NA | NA | NA | NA | NA | NA |
| 12 (2.8) | 31 | 0.5 | 4.8 | 3.7 | 1.1 | 0.2 |
| Mean | 32.0 | 0.5 | 4.7 | 3.7 | 1.1 | 0.3 |
| STD | 1.4 | 0.0 | 0.1 | 0.1 | 0.1 | 0.1 |
| Group 4 | | | | | | |
| 13 (3.5) | 32 | 0.7 | 4.6 | 3.4 | 1.2 | 0.2 |
| 14 (3.6) | 34 | 0.4 | 4.8 | 3.8 | 1 | 0.2 |
| 15 (3.7) | 30 | 0.4 | 4.7 | 3.4 | 1.3 | 0.2 |
| 16 (3.8) | 24 | 0.3 | 5.1 | 3.8 | 1.3 | 0.2 |
| Mean | 30.0 | 0.5 | 4.8 | 3.6 | 1.2 | 0.2 |
| STD | 4.3 | 0.2 | 0.2 | 0.2 | 0.1 | 0.0 |

TABLE LI-continued

Clinical Chemistry and Hematology Analysis
Table LI: WT1 Dose Titration Study
Clinical Chemistry and Hematology Analysis

| Group 5 | | | | | | |
|---|---|---|---|---|---|---|
| 17 (4.5) | 22 | 0.4 | 4.6 | 3.3 | 1.3 | 0.2 |
| 18 (4.6) | 31 | 0.5 | 4.9 | 3.7 | 1.2 | 0.2 |
| 19 (4.7) | 23 | 0.6 | 4.8 | 3.6 | 1.2 | 0.2 |
| 20 (4.8) | 28 | 0.5 | 4.5 | 3.4 | 1.1 | 0.2 |
| Mean | 26.0 | 0.5 | 4.7 | 3.5 | 1.2 | 0.2 |
| STD | 4.2 | 0.1 | 0.2 | 0.2 | 0.1 | 0.0 |
| Group 6 | | | | | | |
| 21 (1.1) | 28 | 0.3 | 5.1 | 3.4 | 1.7 | 0.2 |
| 22 (1.2) | 36 | 0.3 | 5.1 | 3.8 | 1.3 | 0.2 |
| 23 (1.3) | 32 | 0.4 | 4.9 | 3.5 | 1.4 | 0.1 |
| 24 (1.4) | NA | NA | NA | NA | NA | NA |
| Mean | 32.0 | 0.3 | 5.0 | 3.6 | 1.5 | 0.2 |
| STD | 4.0 | 0.1 | 0.1 | 0.2 | 0.2 | 0.1 |
| Group 7 | | | | | | |
| 25 (2.1) | 32 | 0.2 | 5 | 3.4 | 1.6 | 0.2 |
| 26 (2.2) | 24 | 0.3 | 4.2 | 2.8 | 1.4 | 0.1 |
| 27 (2.3) | 28 | 0.3 | 4.8 | 3.2 | 1.6 | 0.2 |
| 28 (2.4) | 27 | 0.3 | 5 | 3.4 | 1.6 | 0.1 |
| Mean | 27.8 | 0.3 | 4.8 | 3.2 | 1.6 | 0.2 |
| STD | 3.3 | 0.0 | 0.4 | 0.3 | 0.1 | 0.1 |
| Group 8 | | | | | | |
| 29 (3.1) | 32 | 0.3 | 4.9 | 3.3 | 1.6 | 0.2 |
| 30 (3.2) | NA | NA | NA | NA | NA | NA |
| 31 (3.3) | 18 | 0.3 | 4.8 | 3.1 | 1.7 | 0.2 |
| 32 (3.4) | 26 | 0.2 | 4.2 | 2.9 | 1.3 | 0 |
| Mean | 25.3 | 0.3 | 4.6 | 3.1 | 1.5 | 0.1 |
| STD | 7.0 | 0.1 | 0.4 | 0.2 | 0.2 | 0.1 |
| Group 9 | | | | | | |
| 33 (4.1) | 25 | 0.2 | 4.1 | 2.7 | 1.4 | 0.3 |
| 34 (4.2) | NA | NA | NA | NA | NA | NA |
| 35 (4.3) | 23 | 0.2 | 4.7 | 3.1 | 1.6 | 0.2 |
| 36 (4.4) | 29 | 0.3 | 4.7 | 3.2 | 1.5 | 0.3 |
| Mean | 25.7 | 0.2 | 4.5 | 3.0 | 1.5 | 0.3 |
| STD | 3.1 | 0.1 | 0.3 | 0.3 | 0.1 | 0.1 |

Abbreviations:
WBC: white blood cells;
RBC: red blood cells;
Hg.: hemoglobin;
HCT: hematocrit;
MCV: Mean corpuscular volume;
MCH: mean corpuscular hemoglobin;
MCHC: mean corpuscular hemoglobin concentration;
Plt.: platelets;
Abs.: Absolute;
Baso: basophils;
Eos: eosinophils;
Abs. Bands: immature neutrophils;
Polys: polymorphonuclear cells;
Lymph: lymphocytes;
Mono: monocytes;
BUN: blood urea nitrogen.

Example 14

Elicitation of Human WT1-Specific T-Cell Responses by Whole Gene In Vitro Priming This example demonstrates that WT1 specific T-cell responses can be generated from the blood of normal individuals.

Dendritic cells (DC) were differentiated from monocyte cultures derived from PBMC of normal donors by growth for 4-10 days in RPMI medium containing 10% human serum, 50 ng/ml GMCSF and 30 ng/ml IL-4. Following culture, DC were infected 16 hours with recombinant WT1-expressing vaccinia virus at an M.O.I. of 5, or for 3 days with recombinant WT1-expressing adenovirus at an M.O.I. of 10 (FIGS. 21 and 22). Vaccinia virus was inactivated by U.V. irradiation. CD8+ T-cells were isolated by positive selection using magnetic beads, and priming cultures were initiated in 96-well plates. Cultures were restimulated every 7-10 days using autologous dendritic cells adeno or vaccinia infected to express WT1. Following 3-6 stimulation cycles, CD8+ lines could be identified that specifically produced interferon-gamma when stimulated with autologous-WT1-expressing dendritic cells or fibroblasts. The WT1-specific activity of these lines could be maintained following additional stimulation cycles. These lines were demonstrated to specifically recognize adeno or vaccinia WT1 infected autologous dendritic cells but not adeno or vaccinia EGFP-infected autologous dendritic cells by Elispot assays (FIG. 23).

Example 15

Formulation of RA12-WT1 for Injection: Use of Excipients to Stabilize Lyophilized Product This example describes the formulation that allows the complete solubilization of lyophilized Ra12-WT1.

The following formulation allowed for the recombinant protein Ra12-WT1 to be dissolved into an aqueous medium after being lyophylized to dryness:

Recombinant Ra12-WT1 concentration: 0.5-1.0 mg/ml; Buffer: 10-20 mM Ethanolamine, pH 10.0; 1.0-5.0 mM Cysteine; 0.05% TWEEN®-80 (Polysorbate-80); Sugar: 10% Trehalose (T5251, Sigma, Mo.) 10% Maltose (M9171, Sigma, Mo.) 10% Sucrose (S7903, Sigma, Mo.) 10% Fructose (F2543, Sigma, Mo.) 10% Glucose (G7528, Sigma, Mo.).

The lyophilized protein with the sugar excipient was found to dissolve significantly more than without the sugar excipient. Analysis by coomassie stained SDS-PAGE showed no signs of remaining solids in the dissolved material.

Example 16

Formulation of a WT1 Protein Vaccine

This example describes the induction of WT1-specific immune responses following immunization with WT1 protein and 2 different adjuvant formulations.

According to this example, WT1 protein in combination with MPL®-SE induces a strong Ab and Interferon-γ(IFN-γ) response to WT1. Described in detail below are the methods used to induce WT1 specific immune responses following WT1 protein immunization using MPL®-SE or ENHANZYN® as adjuvant in C57/B6 mice. C57BL/6 mice were immunized with 20 µg rRa2-WT1 combined with either MPL®-SE or ENHANZYN® adjuvants. One group of control mice was immunized with rRa12-WT1 without adjuvant and one group was immunized with saline alone. Three intramuscular (IM) immunizations were given, three weeks apart. Spleens and sera were harvested 2 weeks post-final immunization. Sera were analyzed for antibody responses by ELISA on plates coated with Ra12-WT1 fusion, Ra12 or WT1 TRX. Similar levels of IgG2a and IgG1 antibody titers were observed in mice immunized with Ra12-WT1+MPL®-SE and Ra12-WT1+ENHANZYN®. Mice immunized with rRa12-WT1 without adjuvant showed lower levels of IgG2a antibodies.

CD4 responses were assessed by measuring Interferon-γ production following stimulation of splenocytes in vitro with rRa12-WT1, rRa12 or with WT1 peptides p6, p117 and p287. Both adjuvants improved the CD4 responses over mice immunized with rRA12-WT1 alone. Additionally, the results indicate that rRA12-WT1+MPL®-SE induced a stronger CD4 response than did rRA12-WT1+ENHANZYN®. IFN-γOD readings ranged from 1.4-1.6 in the mice immunized with rRA12-WT1+MPL®-SE as compared to 1-1.2 in the mice immunized with rRA12-WT1+ENHANZYN®. Peptide responses were only observed against p117, and then only in mice immunized with rRa12-WT1+MPL®-SE. Strong IFN-γ responses to the positive control, ConA, were observed in all mice. Only responses to ConA were observed in the negative control mice immunized with saline indicating that the responses were specific to rRA12-WT1.

Example 17

Construction of a Randomly Mutated WT1 Library

The nucleic acid sequence of human WT1 was randomly mutated using a polymerase chain reaction method in the presence of 8-oxo dGTP and dPTP (journal of Molecular Biology 1996; 255:589-603). The complete unspliced human WT1 gene is disclosed in SEQ ID NO:380 and the corresponding protein sequence is set forth in SEQ ID NO:404. A splice variant of WT1 was used as a template for the PCR reactions and is disclosed in SEQ ID NOs:381 (DNA) and 408 (protein). Conditions were selected so that the frequency of nucleic acid alterations led to a targeted change in the amino acid sequence, usually 5-30% of the PCR product. The mutated PCR product was then amplified in the absence of the nucleotide analogues using the four normal dNTPs. This PCR product was subcloned into mammalian expression vectors and viral vectors for immunization. This library, therefore, contains a mixed population of randomly mutated WT1 clones. Several clones were selected and sequenced. The mutated WT1 variant DNA sequences are disclosed in SEQ ID NOs:377-379 and the predicted amino acid sequences of the variants are set forth in SEQ ID NOs:405-407. These altered sequences, and others from the library, can be used as immunogens to induce stronger T cell responses against WT1 protein in cancer cells.

Example 18

Construction of WT1-Lamp Fusions

A tripartite fusion was constructed using the polymerase chain reaction and synthetic oligonucleotides containing the desired junctions of human lysosomal associated membrane protein-1 (LAMP-1) and a splice variant of the human WT1 sequence. The splice variant of WT1 and the LAMP-1 sequence used for these fusions are disclosed in SEQ ID NOs:381 and 383. Specifically, the signal peptide of LAMP-1 (base pairs 1-87 of LAMP) was fused to the 5-prime end of the human WT1 open reading frame (1,290 base pairs in length), then the transmembrane and cytoplasmic domain of LAMP-1 (base pairs 1161 to 1281 of LAMP) was fused to the 3-prime end of the WT1 sequence. The sequence of the resulting WT1-LAMP construct is set forth in SEQ ID NO:382 (DNA) and SEQ ID NO:409 (protein). The construct was designed so that when it is expressed in eukaryotic cells, the signal peptide directs the protein to the endoplasmic reticulum (ER) where the localization signals in the transmembrane and cytoplasmic domain of LAMP-1 direct transport of the fusion protein to the lysosomal location where peptides are loaded on to Class II MHC molecules.

Example 19

Construction of WT1-Ubiquitin Fusions for Enhanced MHC Class I Presentation

The human ubiquitin open reading frame (SEQ ID NO:384) was mutated such that the nucleotides encoding the last amino acid encode an alanine instead of a glycine. This mutated open reading frame was cloned in frame just upstream of the first codon of a splice variant of human WT1 (SEQ ID NOs:381 and 408, DNA and protein, respectively). The G->A mutation prevents co-translational cleavage of the ancient protein by the proteases that normally process polyubiquitin during translation. The DNA and predicted amino acid sequence for the resulting construct are set forth in SEQ ID NOs:385 and 410, respectively. The resulting protein demonstrated decreased cellular cytotoxicity when it was expressed in human cells. Whereas it was not possible to generate stable lines expressing native WT1, cell lines expressing the fusion protein were readily obtained. The resulting protein is predicted to be targeted to the proteosome by virtue of the added ubiquitin molecule. This should result in more efficient recognition of the protein by WT1 specific CD8+ T cells.

Example 20

Construction of an Adenovirus Vector Expressing Human WT1

A splice variant of human WT1 (SEQ ID NO:381) was cloned into an E1 and E3 deleted adenovirus serotype 5 vector. The expression of the WT1 gene is controlled by the CMV promoter mediating high levels of WT1 protein expression. Infection of human cells with this reagent leads to a high level of expression of the WT1 protein. The antigenic nature of the adenoviral proteins introduced into the host cell during and produced at low levels subsequent to infection can act to increase immune surveillance and immune recognition of WT1 as an immunological target. This vector can be also used to generate immune responses against the WT1 protein when innoculated into human subjects. If these subjects are positive for WT1 expressing tumor cells the immune response could have a therapeutic or curative effect on the course of the disease.

Example 21

Construction of a Vaccinia Virus Vector Expressing Human WT1

A splice variant of the full length human WT1 gene (SEQ ID NO:381) was cloned into the thymidine kinase locus of the Western Reserve strain of the vaccinia virus using the pSC11 shuttle vector. The WT1 gene is under the control of a hybrid vaccinia virus promoter that mediates gene expression throughout the course of vaccinia virus infection. This reagent can be used to express the WT1 protein in human cells in vivo or in vitro. WT1 is a self protein that is overexpressed on some human tumor cells. Thus, immunological responses to WT1 delivered as a protein are unlikely to lead to Major Histocompatibility Class I (MHC class I)-mediated recognition of WT1. However, expression of the protein in the intracellular compartment by the vaccinia virus vector will allow high level MHC class I presentation and recognition of the WT1 protein by CD8+ T cells. Expression of the WT1 protein by the vaccinia virus vector will also lead to presentation of WT1 peptides in the context of MHC class II and thus to recognition by CD4+ T cells.

The uses of this invention include its use as a cancer vaccine. Immunization of human subjects bearing WT1 positive tumors could lead to a therapeutic or curative response. The expression of WT1 within the cell will lead to recognition of the protein by both CD4 and CD8 positive T cells.

Example 22

Generation of WT1-Specific CD8+ T-Cell Clones Using Whole Gene Priming

Dendritic cells (DC) were differentiated from monocyte cultures derived from PBMC of normal donors by growth for 4-6 days in RPMI medium containing 10% human serum, 50 ng/ml GM-CSF and 30 ng/ml IL-4. Following culture, DC were infected 16 hours with recombinant WT1-expressing vaccinia virus (described in Example 21) at a multiplicity of infection (MOI) of 5 or for 3 days with recombinat WT1-expressing adenovirus at an MOI of 10. Vaccinia virus was inactivated by U.V. irradiation. CD8+ T-cells were isolated by negative depletion using magnetic beads, and priming cultures were initiated in 96-well plates. Cultures were restimulated every 7-10 days using autologous dendritic cells infected with adeno or vaccinia virus engineered to express WT1. Following 4-5 stimulation cycles, CD8+ T-cell lines could be identified that specifically produced interferon-gamma when stimulated with autologous-WT1 expressing dendritic cells or fibroblasts. These lines were cloned and demonstrated to specifically recognize WT1 transduced autologous fibroblasts but not EGFP transduced fibroblasts by Elispot assays.

The Wilms' tumor (WT1) gene participates in leukemogenesis and is overexpressed in most human leukemias as well as in several solid tumors. Previous studies in humans have demonstrated the presence of WT1 specific antibody (Ab) responses in 16/63 (25%) of AML and in 15/81 (19%) of CML patients studied. Previous studies in mice have shown that WT1 peptide based vaccines elicit WT1 specific Ab, Th and CTL responses. The use of peptides as vaccines in humans is limited by their HLA restriction and the tendency to elicit peptide specific responses and only in a minority of patients tumor specific CTL. The advantages of whole gene immunization are that several helper and CTL epitopes can be included in a single vaccine, thus not restricting the vaccine to specific HLA types. The data disclosed herein demonstrate the induction of WT1 specific immune responses using whole gene in vitro priming and that WT1 specific CD8+ T-cell clones can be generated. Given that existent immunity to WT1 is present in some patients with leukemia and that murine and human WT1 are 96% identical at the amino acid level and vaccination to WT1 protein, DNA or peptides can elicit WT1 specific Ab, and cellular T-cell responses in mice without toxicity to normal tissues in mice, these human in vitro priming experiments provide further validation of WT1 as a tumor/leukemia vaccine. Furthermore, the ability to generate WT1 specific CD8+ T-cell clones may lead to the treatment of malignancies associated with WT1 overexpression using genetically engineered T-cells.

Example 23

Recombinant Constructs for Clinical Manufacturing of WT1

Five constructs were made as described in detail below, for the production of clinical grade WT1.

Design of Ra12/WT-E (SEQ ID NOs:388 (cDNA) and 391 (protein)) and WT-1 E (SEQ ID NOs:386 (cDNA) and 395 (protein)) with No His tag:

The WT-1 E reading frame was PCR amplified with the following primers for the non-His non fusion construct:

```
PDM-780
                                      (SEQ ID NO: 396)
5' gacgaaagcatatgcactccttcatcaaac 3'  Tm 6° C.
PDM-779
                                      (SEQ ID NO: 397)
5' cgcgtgaattcatcactgaatgcctctgaag 3' Tm 63° C.
```

The following PCR cycling conditions were used: 1 μl 10×Pfu buffer, 1 μl 10 mM dNTPs, 2 μl 1M each oligo, 83 μl sterile water 1.5 μl Pfu DNA polymerase (Stratagene, La Jolla, Calif.), 50 μg DNA (pPDMRa12WT-1 No His). The reaction was denatured initially at 96° C. for 2 minutes, followed by 40 cycles of 96° C. for 20 seconds, 62° C. for 15 seconds, and 72° C. for 1 minute and 40 seconds. This was followed by a final extension of 72° C. for 4 minutes. The PCR product was digested with NdeI and EcoRI and cloned into pPDM His (a modified pET28 vector) that had been digested with NdeI and EcoRI. The construct was confirmed through sequence analysis and then transformed into BLR (DE3) pLys S and HMS 174 (DE3) pLys S cells. This construct—pPDM WT-1 E was then digested with NcoI and XbaI and used as the vector backbone for the NcoI and XbaI insert from pPDM Ra12 WT-1 F (see below). The construct was confirmed through sequence analysis and then transformed into BLR (DE3) pLys S and HMS174 (DE3) pLys S cells. Protein expression was confirmed by Coomassie stained SDS-PAGE and N-terminal protein sequence analysis.

Design of Ra12-WT-1-F (a.a. 1-281) with No His tag (SEQ ID NOs:389 (cDNA) and 393 (protein)):

The Ra12 WT-1 reading frame was PCR amplified with the following primers:

```
PDM-777
                                        (SEQ ID NO: 398)
5' cgataagcatatgacggccgcgtccgataac 3' Tm 66° C.

PDM-779
                                        (SEQ ID NO: 399)
5' cgcgtgaattcatcactgaatgcctctgaag 3' Tm 63° C.
```

The following PCR cycling conditions were used: 1 μl 10×Pfu buffer, 1 μl 10 mM dNTPs, 2 μl 1 μM each oligo, 83 μl sterile water 1.5 μl Pfu DNA polymerase (Stratagene, La Jolla, Calif.), 50 ηg DNA (pPDMRa12 WT-1 No His). The reaction was denatured initially at 96° C. for 2 minutes, followed by 40 cycles of 96° C. for 20 seconds, 58° C. for 15 seconds, and 72° C. for 3 minutes. This was followed by a final extension of 72° C. for 4 minutes. The PCR product was digested with NdeI and cloned into pPDM His that had been digested with NdeI and Eco72I. The sequence was confirmed through sequence analysis and then transformed into BLR (DE3) pLys S and HMS174 (DE3) pLysS cells. Protein expression was confirmed by Coomassie stained SDS-PAGE and N-terminal protein sequence analysis.

Design of Ra12-WT-1 with No His tag (SEQ ID NOs:390 (cDNA) and 392 (protein)):

The Ra12WT-1 reading frame was PCR amplified with the following primers:

```
PDM-777
                                        (SEQ ID NO: 400)
5' cgataagcatatgacggccgcgtccgataac 3' Tm 66° C.

PDM-778
                                        (SEQ ID NO: 401)
5' gtctgcagcggccgctcaaagcgccagc 3' Tm 7° C.
```

The following PCR cycling conditions were used: 1 μl 10×Pfu buffer, 1 μl 10 mM dNTPs, 2 μl 1 μM each oligo, 83 μl sterile water 1.5 μl Pfu DNA polymerase (Stratagene, La Jolla, Calif.), 50 ηg DNA (pPDMRa12 WT-1 No His). The reaction was denatured initially at 96° C. for 2 minutes, followed by 40 cycles of 96° C. for 20 seconds, 68° C. for 15 seconds, and 72° C. for 2 minutes and 30 seconds. This was followed by a final extension of 72° C. for 4 minutes. The PCR product was digested with NotI and NdeI and cloned into pPDM His that had been digested with NdeI and NotI. The sequence was confirmed through sequence analysis and then transformed into BLR (DE3) pLys S and HMS174 (DE3) pLysS cells. Protein expression was confirmed by Coomassie stained SDS-PAGE and N-terminal protein sequence analysis.

Design of WT-1 C (a.a. 69-430) in *E. coli* without His tag (SEQ ID NOs:387 (cDNA) and 394 (protein)):

The WT-1 C reading frame was PCR amplified with the following primers:

```
PDM-780
                                        (SEQ ID NO: 402)
5' gacgaaagcatatgcactccttcatcaaac 3' Tm 6° C.

PDM-778
                                        (SEQ ID NO: 403)
5' gtctgcagcggccgctcaaagcgccagc 3' Tm 7° C.
```

The following PCR cycling conditions were used: 1 μl 10×Pfu buffer, 1 μl 10 mM dNTPs, 2 μl 1 μM each oligo, 83 μl sterile water 1.5 μl Pfu DNA polymerase (Stratagene, La Jolla, Calif.), 50 ηg DNA (pPDMRa12WT-1 No His). The reaction was denatured initially at 96° C. for 2 minutes, followed by 40 cycles of 96° C. for 20 seconds, 62° C. for 15 seconds, and 72° C. for 2 minutes. This was followed by a final extension of 72° C. for 4 minutes. The PCR product was digested with NdeI and cloned into pPDM His that had been digested with NdeI and Eco72I. The sequence was confirmed through sequence analysis and then transformed into BLR (DE3) pLys S and HMS174 (DE3) pLys S cells. Protein expression was confirmed by Coomassie stained SDS-PAGE and N-terminal protein sequence analysis.

Example 24

Generation of WT1-Specific CD8+ T Cell Clones Using Whole Gene Priming and Identification of an HLA-A2-Restricted WT1 Epitope In this example, Adeno and Vaccinia virus delivery vehicles were used to generate WT1-specific T cell lines. A T cell clone from the line was shown to be specific for WT1 and further, the epitope recognized by this clone was identified.

Dendritic cells (DC) were differentiated from monocyte cultures derived from PBMC of normal donors by growth for 4-6 days in RPMI medium containing 10% human serum, 50 ng/ml GM-CSF and 30 ng/ml IL-4. Following culture, DC were infected 16 hours with recombinant WT1-expressing vaccinia virus at a multiplicity of infection (MOI) of 5 or for 2-3 days with recombinant WT1-expressing adeno virus at an MOI of 3-10. Vaccinia virus was inactivated by U.V. irradiation. CD8+ T-cells were isolated by negative depletion using antibodies to CD4, CD14, CD16, CD19 and CD56+ cells, followed by magnetic beads specific for the Fc portion of these Abs.

Priming cultures were initiated in 96-well plates. Cultures were restimulated every 7-14 days using autologous dendritic cells infected with adeno or vaccinia virus engineered to express WT1. Following 4-5 stimulation cycles, CD8+ T cell lines could be identified that specifically produced interferon-γ (IFN-γ) when stimulated with autologous-WT1 expressing dendritic cells or fibroblasts. These lines were cloned and demonstrated to specifically recognize WT1 transduced autologous fibroblasts but not control transduced fibroblasts by Elispot assays.

To further analyze HLA restriction of these WT1 specific CD8+ T-cell clones, fibroblasts derived from an additional donor (D475), sharing only the HLA-A2 allele with the donor (D349) from which the T-cell clone was established, were transduced with WT1. ELISPOT analysis demonstrated recognition of these D475 target cells by the T-cell clone. To further demonstrate HLA A2 restriction and demonstrate that this epitope is expressed by tumor cells "naturally" overexpressing WT1 (as part of their malignant transformation), the leukemia cell line K562 was tested. K562 was transduced with the HLA A2 molecule, and HLA-A2 negative K562 cells were used as controls for nonspecific IFN-γ release. ELISPOT analysis demonstrated that the T cells recognized the A2 positive K562 cell line, but not the A2 negative K562 cells. Further proof of specificity and HLA-A2 restriction of the recognition was documented by HLA-A2 antibody blocking experiments.

To further define the WT1 epitope, 4 truncated WT1 retroviral constructs were generated. Donor 475 fibroblasts were then transduced with these constructs. ELISPOT assays demonstrated recognition of D475 fibroblasts transduced with the WT1 Tr1 construct (aa2-aa92), thus demonstrating that the WT1 epitope is localized within the first 91 N-terminal amino acids of the WT1 protein. To fine map the epitope, 15mer peptides of the WT1 protein, overlapping by 11 amino acids, were synthesized. The WT1 specific T-cell clone recognized two overlapping 15mer peptides, peptide 9 (QWAPVLDFAPPGASA) (SEQ ID NO: 412) and peptide 10 (VLDFAPPGASAYGSL) (SEQ ID NO: 413). To further characterize the minimal epitope recognized, shared 9mer and 10 mer peptides of the 15mers (5 total) were used to analyse the specificity of the clone. The clone specifically recognized the 9mer, VLDFAPPGA (SEQ ID NO:241), and the 10 mer, VLDFAPPGAS (SEQ ID NO:411).

Example 25

Cloning and Sequencing of TCR Alpha and Beta Chains Derived from a CD8 T Cell Specific for WT1

T cell receptor (TCR) alpha and beta chains from CD8+ T cell clones specific for WT1 are cloned. Sequence analysis is carried to demonstrate the family origin of the alpha and beta chains of the TCR. Additionally, unique diversity and joining segments (contributing to the specificity of the response) are identified.

Total mRNA from $2 \times 10^6$ cells from a WT1 specific CD8+ T cell clone is isolated using TRIZOL® reagent (a monophasic solution of phenol and guanidine isothiocyanate) and cDNA is synthesized using READY-TO-GO® kits (Pharmacia). To determine Vα and Vβ sequences in a clone, a panel of Vα and Vβ subtype specific primers are synthesized (based on primer sequences generated by Clontech, Palo Alto, Calif.) and used in RT-PCR reactions with cDNA generated from each clone. The RT-PCR reactions demonstrate which Vβ and Vα sequence is expressed by each clone.

To clone the full-length TCR alpha and beta chains from a clone, primers are designed that span the initiator and terminator-coding TCR nucleotides. Standard 35 cycle RT-PCR reactions are established using cDNA synthesized from the CTL clone and the above primers using the proofreading thermostable polymerase PWO (Roche, Basel, Switzerland). The resultant specific bands (~850 bp for alpha and ~950 for beta) are ligated into the PCR blunt vector (Invitrogen, Carlsbad, Calif.) and transformed into E. coli. E. coli transformed with plasmids containing full-length alpha and beta chains are identified, and large scale preparations of the corresponding plasmids are generated. Plasmids containing full-length TCR alpha and beta chains are then sequenced using standard methods. The diversity-joining (DJ) region that contributes to the specificity of the TCR is thus determined.

Example 26

WT1 Specific CD8+ T-Cell Clone Lyses WT1-Expressing Leukemic Blasts

The CD8+ T cell clone initially disclosed in Example 24 that recognizes peptide sequence VLDFAPPGA (human WT1 residues 37-45; SEQ ID NO:241) was further tested for the ability to kill (lyse) WT1 expressing leukemia target cells in an HLA A2 restricted fashion. K562 target cells transduced with the HLA A2 molecule, GFP, A2 Kb, or untransduced, were used in a standard 4.5 hour $^{51}$Chromium release assay with effector to target cell (E:T) ratios of 25:1 and 5:1. At an E:T ratio of 25:1, the CD8+ T-cell clone lysed the K562/A2 and K562/A2 Kb cells (40% and 49% specific lysis, respectively) while the control GFP transduced and the K562 cells were not lysed. At an E:T of 5:1, specific lysis of the K562/A2 and K562/A2 Kb cells was 21% and 24%, respectively. Thus, this CD8+ T cell clone recognizes and lyses leukemic cells expressing WT1 in an HLA-A2-restricted fashion. The ability to generate WT1 specific CD8+ T-cell clones has utility in the treatment of malignancies associated with WT1 overexpression using genetically engineered T-cells.

Example 27

Construction of HLA-A2-Peptide-MHC Tetrameric Complexes

This example describes the cloning and expression of soluble HLA-A2 in insect cells, and the purification and assembly of HLA-A2 into fluorescent, multivalent peptide-MHC tetramer complexes for the detection and isolation of antigen-specific CD8 T cells.

This system is similar to that developed and described by Altman, et al. (Altman, J., et al., Science, 1996 274(5284): 94-6) in that soluble HLA-A2 was singly biotinylated at a birA recognition sequence and was subsequently assembled into multimers on a phycoerythrin-conjugated streptavidin scaffolding. The materials described herein differ in that the HLA-A2 was expressed in a glycosylated, soluble form from insect cells and the heterodimer was purified using an anti-human class I MHC antibody affinity column.

The HLA-A2 heavy chain gene, appended with the birA biotinylation sequence, and the human beta-2-microglobulin gene were cloned into the baculovirus expression vector pFASTBAC-dual. Upon infection of insect cells the genes were concomitantly transcribed from divergent promoters and fully assembled, glycosylated soluble HLA-A2 heterodimer was secreted into the growth medium. The infected insect cells were cultured in cell factories for 4 days at 21° C. before the supernatants were harvested. HLA-A2 production was monitored by a capture ELISA employing the W6/32 and biotinylated B9.12.1 antibodies. HLA-A2 was purified from the culture supernatant to >90% purity in one step by affinity chromatography using 2 anti-human class I MHC monoclonal antibodies linked to Sepharose beads. The antibodies used were PA2.1 and W6/32. Purified HLA-A2 was singly biotinylated on the birA recognition sequence on the C-terminus of the heavy chain using the commercially available birA enzyme. The efficiency of biotinylation was evaluated essentially as described (Crawford et al (1998) Immunity June; 8(6):675-82.), and the material was further purified by size exclusion chromatography (SEC). Phycoerythrin-conjugated streptavidin was saturated with bio-HLA-A2 and the multivalent staining reagent was purified from free HLA-A2 by SEC. HLA-A2 tetramer was incubated for 48 hours at room temperature with a 10-fold molar excess of Her-2/neu E75 peptide or Influenza matrix MI peptide before the specific T cell clones were stained at 4° C. for 30 minutes in the presence of peptide loaded tetramer and anti-CD8 antibody. Results indicated that the tetramers incubated in the presence of molar excess of the M1 58-66 M1 influenza peptide specifically stained an influenza-specific T cell clone and the tetramers incubated with an excess of the Her-2/neu E75 peptide specifically stained the Her-2/new specific T cell clone.

Example 28

Detection of WT1 Specific T-Cells Using WT1 MHC-Peptide Tetramers

HLA-A2 tetramers described in Example 27 were incubated with a molar excess of the WT1 p37-45 peptide (VLD-FAPPGA) (human WT1 residues 37-45; SEQ ID NO:241) previously shown in Example 24 to be restricted by HLA-A2. This tetramer was used to stain the WT1-specific CD8+ T cell clone described in Example 24. This clone was shown to specifically recognize the p37-45 epitope. When the tetramers were incubated with an excess of p37-45 peptide, they specifically stained the CD8+ T cell clone while those tetramers incubated with an excess of irrelevant HLA-A2 peptides (Her2/neu, WT1 p38-46, WT1 p39-47), the tetramers did not stain the CD8+ T cell clone. Thus, the WT1 p37-45-specific CD8+ T cell clone is specifically recognized by the HLA-A2-p37-45 peptide MHC tetramer.

A WT1-specific T cell line generated as described in Example 24 was then stained with the HLA-A2-p37-45, irrelevant Her2/neu or WT1 p37-46 tetramers. The HLA-A2-p37-45 tetramers stained 1% of the total population of this WT1-specific T cell line and 7% of the gated CD8+ population while the control HLA-A2-p37-46 tetramer stained at the same background levels as the control HLA-A2-Her2/neu tetramers.

These results indicate that MHC-peptide tetramers are a highly sensitive and specific tool for detecting WT1 specific immune responses. The peptide-MHC tetramers can be used for early detection of WT1 associated malignancies, monitoring WT1-specific responses, and for monitoring minimal residual disease. Detection of WT1 specific T-cells by tetramer staining is also a useful tool to identify groups within a patient population suffering from a WT1 associated disease at a higher risk for relapse or disease progression.

Example 29

Generation of a WT1-Specific CD8$^+$ T Cell Line from an HLA-A24-Positive Donor Using Whole Gene Priming In this example, Adeno and Vaccinia virus delivery vehicles were used to generate WT1-specific T cell lines from an HLA-A24 positive donor. This T cell line was shown to be MHC class I restricted. These experiments further confirm the immunogenicity of the WT1 protein and support its use as a target for vaccine and/or other immunotherapeutic approaches.

Dendritic cells (DC) were differentiated from monocyte cultures derived from PBMC of a normal HLA-A24-positive donor by growth for 4-6 days in RPMI medium containing 10% human serum, 50 ng/ml GM-CSF and 30 ng/ml IL-4. Following culture, DC were infected 16 hours with recombinant WT1-expressing vaccinia virus at a multiplicity of infection (MOI) of 5 or for 2-3 days with recombinant WT1-expressing adeno virus at an MOI of 3-10. Vaccinia virus was inactivated by U.V. irradiation. CD8+ T-cells were isolated by negative depletion using antibodies to CD4, CD14, CD16, CD19 and CD56+ cells, followed by magnetic beads specific for the Fc portion of these Abs.

Priming cultures were initiated in 96-well plates. Cultures were restimulated every 7-14 days using autologous dendritic cells infected with adeno or vaccinia virus engineered to express WT1. Following 4-5 stimulation cycles, CD8+ T cell lines could be identified that specifically produced interferon-γ (IFN-γ) when stimulated with autologous-WT1 expressing dendritic cells or fibroblasts. These lines were cloned and shown by Elispot assays to specifically recognize WT1 transduced autologous fibroblasts but not control transduced fibroblasts in an MHC class I-restricted manner.

These experiments show that the WT1 protein can be used to generate a T cell response and thus, further confirm the immunogenicity of the WT1 antigen and support its use as a target for vaccine and other immunotherapeutic approaches.

Example 30

Identification of HLA-A2 High Affinity WT1 Epitopes

This experiment describes the in silico identification of WT1 epitopes predicted to bind to HLA-A2 with higher affinity than naturally processed epitopes. The epitopes identified herein have utility in vaccine and/or immunotherapeutic strategies for the treatment of cancers associated with WT1 expression.

Peptide analogs of the naturally processed HLA A2 restricted WT1 epitope p37-45 (VLDFAPPGA; human WT1 residues 37-45; SEQ ID NO:241; previously shown in Example 24 to be restricted by HLA-A2) with motifs for binding to HLA-A2.1 with higher affinity than the naturally processed peptide were constructed as described in further detail below.

A peptide motif searching program based on algorithms developed by Rammensee, et al (Hans-Georg Rammensee, Jutta Bachmann, Niels Nikolaus Emmerich, Oskar Alexander Bachor, Stefan Stevanovic: SYFPEITHI: database for MHC ligands and peptide motifs. Immunogenetics (1999) 50: 213-219) and by Parker, et al (Parker, K. C., M. A. Bednarek, and J. E. Coligan. 1994. Scheme for ranking potential HLA-A2 binding peptides based on independent binding of individual peptide side-chains. J. Immunol. 152:163.) was used to identify analogs of the WT1 p37-45 peptide epitope that are predicted to bind to HLA-A2 with higher affinity than the natural p37-45 peptide. The peptides shown in Table LII have predicted peptide binding scores equal to or greater than the naturally processed p37-45 peptide. The binding score is derived from a predicted half-time of dissociation to the HLA-A2 class I molecule. The analysis is based on coefficient tables deduced from the published literature by Dr. Kenneth Parker kparker@atlas.niaid.nih.gov, NIAID, NIH.

TABLE LII p37-45 Peptide Analogs

| Position Modified | Sequence | Theoretical Binding Score | SEQ ID NO: |
|---|---|---|---|
| Wild Type | VLDFAPPGA | 3.378 | 241 |
| P1 | ILDFAPPGA | 3.378 | 414 |
| P1 | LLDFAPPGA | 3.378 | 415 |
| P1 | FLDFAPPGA | 9.141 | 416 |
| P1 | KLDFAPPGA | 6.955 | 417 |
| P1 | MLDFAPPGA | 3.378 | 418 |
| P1 | YLDFAPPGA | 9.141 | 419 |
| P2 | VMDFAPPGA | 2.44 | 420 |
| P4 | VLDEAPPGA | 13.85 | 421 |
| P4 | VLDKAPPGA | 3.378 | 422 |
| P6 | VLDFAVPGA | 7.77 | 423 |
| P8 | VLDFAPPKA | 3.378 | 424 |
| P9 | VLDFAPPGV | 47.3 | 425 |
| P9 | VLDFAPPGL | 14.53 | 426 |
| P1 and P4 | FLDEAPPGA | 37.48 | 427 |
| P1 and P4 | KLDEAPPGA | 28.52 | 428 |
| P1 and P4 | YLDEAPPGA | 37.48 | 429 |
| P1 and P4 | FLDKAPPGA | 9.141 | 430 |
| P1 and P4 | KLDKAPPGA | 6.955 | 431 |
| P1 and P4 | YLDKAPPGA | 9.141 | 432 |
| P1 and P9 | FLDFAPPGV | 128 | 433 |
| P1 and P9 | KLDFAPPGV | 97.37 | 434 |
| P1 and P9 | YLDFAPPGV | 128 | 435 |
| P1 and P9 | FLDFAPPGL | 39.31 | 436 |
| P1 and P9 | KLDFAPPGL | 29.91 | 437 |
| P1 and P9 | YLDFAPPGL | 39.31 | 438 |
| P1, P4 and P9 | FLDEAPPGV | 524.7 | 439 |
| P1, P4 and P9 | KLDEAPPGV | 399.2 | 440 |
| P1, P4 and P9 | YLDEAPPGV | 524.7 | 441 |
| P1, P4 and P9 | FLDEAPPGL | 161.2 | 442 |
| P1, P4 and P9 | KLDEAPPGL | 122.6 | 443 |
| P1, P4 and P9 | YLDEAPPGL | 161.2 | 444 |

In a separate analysis, computer modeling was used to identify peptide epitope analogs of the p37-45 WT1 epitope. The coordinates of the HLA-A2 native structure were downloaded from the Brookhaven protein database (pdb I.D.: 3HLA) (L. L. Walsh, "Annotated PDB File Listing", Protein Science 1:5, Diskette Appendix (1992). This file was used as a template for manipulations with the SwissModel (Peitsch MC (1996) ProMod and Swiss-Model: Internet-based tools for automated comparative protein modeling. *Biochem. Soc. Trans.* 24:274-279.) program available through the Expasy web site (Appel R. D., Bairoch A., Hochstrasser D. F. A new generation of information retrieval tools for biologists: the example of the ExPASy WWW server. *Trends Biochem. Sci.* 19:258-260(1994). The peptide bound to the protein was mutated manually to yield the bound WT p37-45 peptide. The new structure was submitted for three rounds of energy minimization with the GROMOS96 implementation of the Swiss-PdbViewer; two energy minimizations were performed on the whole structure, followed by one round with unfavorable residues selected. A final evaluation showed an overall favorable energy state for the model. Ramachandran plotting indicated that only one non-glycinyl residue is far in disallowed regions. Peptides identified using the modeling method described herein are set forth in Table LIII below.

TABLE LIII p37-45 Peptide Analogs Identified by Computer Modeling

| Position Modified | Sequence | SEQ ID NO: |
|---|---|---|
| Wild Type | VLDFAPPGA | 241 |
| P6 | VLDFAGPGA | 445 |
| P6 | VLDFATPGA | 446 |
| P6 and P9 | VLDFATPGV | 447 |
| P6 and P9 | VLDFATPGL | 448 |
| P6 and P9 | VLDFATPGS | 449 |
| P6 and P9 | VLDFATPGA | 450 |

Several peptides identified using the two methods described above were then tested for the ability to be recognized by the p37-45 specific CTL clone (see Example 24). ELISPOT analysis showed that peptides p37-1 (SEQ ID NO:426) and model-1 (SEQ ID NO:445) were recognized by the p37-45 CTL clone. These results suggest that these 2 peptide analogs are predicted to bind to HLA-A2 with higher affinity than the naturally processed epitope and still be recognized by a native T cell receptor.

Thus, this experiment describes the in silico identification of WT1 epitopes predicted to bind to HLA-A2 with higher affinity than naturally processed epitopes. Two of the epitopes identified were tested and shown to be recognized by a CTL clone generated with the native WT1 p37-45 epitope. The epitopes identified herein have utility in vaccine and/or immunotherapeutic strategies for the treatment of cancers associated with WT1 expression.

Example 31

The In Vivo Immunogenicity of the WT1 Antigen

This example describes three in vivo immunogenicity studies to evaluate vaccination strategies with WT1 in mice. The three strategies comprised: 1) a naked DNA vaccine prime and boost; 2) an attenuated adenovirus prime followed by an attenuated alphavirus boost; or 3) a naked DNA prime followed by an adenovirus boost. The full-length cDNA of the splice variant of WT1 used in these studies is set forth in SEQ ID NO:381. The results described herein provide support for the use of WT1 DNA/DNA, DNA/adenovirus or adenovirus/ alphavirus prime/boost regimens as vaccine strategies for treating cancers associated with WT1 expression.

In the first study, C57/BI6 mice were immunized 3 times at 2 week intervals with 100 μg of naked DNA encoding for WT1. Mice were sacrificed 2-3 weeks after the final immunization and CTL were evaluated by standard Chromium release assay. This first study showed that WT1 DNA immunization elicits WT1-specific cytotoxic T cell responses in these mice with a 25:1 E:T ratio showing 40% lysis.

In the second study, HLA-A2/Kb transgenic mice were immunized once with $5 \times 10^8$ PFU of attenuated adenovirus encoding WT1 (as described in Example 20) followed 4 weeks later by one boost with $5 \times 10^6$ PFU of alphavirus (AlphaVax) encoding WT1. Mice were sacrificed 2-3 weeks after the final immunization and CTL were evaluated by standard Chromium release assay. The results showed that WT1-specific CTL in HLA-A2/Kb transgenic mice specifically lysed dendritic cells (DC) transduced with WT1-expressing viral construct as well as DC pulsed with WT1 peptides. Thus, this immunization strategy also effectively elicits WT1-specific CTL in vivo.

In the third study, C57/BI6 and HLA-A2/Kb transgenic mice were immunized twice with 100 μg of naked WT1 DNA 2 weeks apart followed 3 weeks later by a boost with $7 \times 10^8$ PFU adenovirus encoding WT1. Mice were sacrificed 2-3 weeks after the final immunization and CTL were evaluated by IFN-γ ELISPOT assay. The results showed that the WT1 DNA and adenovirus prime-boost generates a WT1-specific CD8 T cell response in HLA-A2/Kb transgenic mice. About 42% of CD8 positive cells stained positive for IFN-γ following a 7 day stimulation with DCs transduced with WT-1. The results from the C57/BL6 mice showed that this immunization strategy generates CD8 responses detectable in fresh splenocytes. Splenocytes were stimulated for 6 hours with pools of 10 15-mer peptides overlapping by 11 amino acids that span the entire WT1 protein. Only cells stimulated with the p121-171 showed IFN-γ staining. About 1.1% of those CD8 T cells stimulated with the p121-171 peptide pool stained positive for IFN-γ. This peptide contains the p117-139 peptide (SEQ ID NO:2) shown in Example 3 to elicit CTL, T helper cell and antibody responses in mice.

In summary, these results show that the three immunization strategies tested herein generate T cell responses in vivo. Thus, these studies further confirm the immunogenicity of the WT1 protein and provide support for the use of WT1 DNA/DNA, DNA/adenovirus or adenovirus/alphavirus prime/boost regimens as vaccine strategies for treating cancers associated with WT1 expression.

Example 32

Reduction in WT1+Tumor Growth in HLA-A2/kb Transgenic Mice Immunized with WT1 Protein This example describes the reduction of WT1+ tumors in transgenic mice immunized with a WT1 vaccine. These results further validate WT1 as a vaccine target and provide support for the use of WT1 in vaccine strategies for treating cancers associated with WT1 expression.

The murine dendritic cell (DC) line DC2.4. was stably transduced with a WT1-LAMP construct (see Example 18, cDNA and protein sequences set forth in SEQ ID NO:382 and 409, respectively). Mice were then inoculated either subcutaneously (s.c.) or intraperitoneally (i.p.) with $2 \times 10^6$ cells. This resulted in tumor growth in 80-100% of the mice. The tumors established in mice in vivo retained their WT1 expression. Thus, this model provides a system in which to validate the efficacy of WT1 vaccine strategies.

Three groups of A2/Kb mice were then immunized 3 times, 2 weeks apart as follows:
Group 1: saline alone s.c. (control, n=10 mice)
Group 2: MPL®-SE 10 μg alone s.c. (control, n=10 mice)
Group 3: Raa12/WT1 protein 100 μg+10 μg MPL®-SE s.c. (n=9 mice)

Two to three weeks after the last WT1 immunization, mice were inoculated with $2 \times 10^6$ A2/Kb DC2.4 tumor cells overexpressing WT1. After tumor challenge mice were monitored and tumor size measured twice per week up to 4 weeks after tumor challenge.

The results showed that the percentage of mice with tumor growth in the group that received the WT1 protein vaccine was reduced from about 100% (saline control) or 90% (MPL®-SE adjuvant control) to 45% (WT1 protein immunized group). Further, the average tumor volume was reduced in this group from an average tumor size of 1233 cmm (saline control) or 753 cmm (MPL®-SE adjuvant control) observed in the control group to 226 cmm in the WT1 protein immunized group. Histopathological analyses showed that tumor margins in vaccinated animals were mixed with host immunological reactions including histiocytes, eosinophils, lymphocytes, mast cells and plasmacytes. Taken together, the results demonstrate that WT1 protein immunization protects against or delays the growth of WT1-positive tumors in the animals immunized with WT1. Thus, these results support the use of WT1 protein as a vaccine for malignancies associated with WT1 expression.

Example 33

Identification of a Naturally Processed WT1 Cytotoxic T Cell Epitope

This example describes the identification of a naturally processed epitope of the WT1 protein recognized by cytotoxic T cells. This experiment further confirms the immunogenicity of the WT1 protein and provides support for its use as a target for vaccine and/or other immunotherapeutic approaches. Additionally, this experiment identifies epitopes of the WT1 protein that may be used in these applications.

HLA-A2/Kb transgenic mice were immunized twice with 100 ug of naked WT1 DNA 2 weeks apart followed 3 weeks later by a boost with $10^7$ PFU adenovirus encoding WT1. Mice were sacrificed 2-3 weeks after the final immunization and CTL were evaluated by standard chromium release assay. As observed in previous experiments, immunization with WT1 DNA followed by adenoviral boost elicited a WT1-specific CTL response in HLA-A2 transgenic mice. In order to identify which epitopes were recognized by the T cells, CTL lines were generated and cloned by limiting dilution using standard protocols. A positive clone was then tested using as target cells DC2.4 A2/Kb cells pulsed with peptides corresponding to the top 20 predicted HLA-A2 restricted CTL epitopes. The results showed that the WT1 p10-18 9mer peptide (amino acids: ALLPAVPSL, set forth in SEQ ID NO:451) was recognized by this CTL clone. This epitope was previously predicted to be an epitope, as described in Table XLVI, SEQ ID NO:34. In an additional experiment, CTL responses to the p10 peptide were observed in 4 of 5 WT1 immunized animals tested. Thus, this experiment demonstrates that the predicted p10-18 WT1 epitope is naturally processed and recognized by CTLs. Moreover, this experiment confirms the immunogenicity of the WT1 protein and further defines a naturally processed HLA-A2-restricted CTL epitope that can be used in vaccine and immunotherapeutic strategies for the treatment of malignancies associated with WT1 overexpression.

Example 34

WT1 Expression Constructs Using Twin Arginine Translocator (TAT) Signal Peptide

This example describes the construction of WT1-TAT vectors and expression of WT1-TAT from these vectors. These constructs have utility in the expression of WT1-TAT molecules for the use in vaccination strategies.

WT-1-F (a.a. 2-281 of the WT1 protein; cDNA and amino acid sequence of 2-281 of WT1 are set forth in SEQ ID NOs:460 and 461, respectively) and full-length WT-1 were constructed as pTAT fusions with no His tag as described below. The cDNA sequence of the resulting fusion contructs pTAT-WT1F and the pTAT-WT1 full-length are set forth in SEQ ID NOs 452 and 453 respectively. The amino acid sequences of the resulting fusions are set forth in SEQ ID NOs:455 and 454, respectively.

The WT-1-F open reading frame was PCR amplified with the following primers:

```
PDM-439 (SEQ ID NO: 456):
5' GGCTCCGACGTGCGGGACCTGAAC 3' Tm 66° C.

PDM-779 (SEQ ID NO: 457):
5' CGCGTGAATTCATCACTGAATGCCTCTGAAG 3' Tm 63° C.
```

The WT-1 full-length open reading frame was amplified with the following primers:

```
p37 (SEQ ID NO: 458):
5' GGCTCCGACGTGCGGGACCTG 3' p23 (SEQ ID NO: 459):
5' GAATTCTCAAAGCGCCAGCTGGAGTTTGGT 3'
```

The PCR conditions were as follows: 1 µl 10×Pfu buffer, 1 µl 10 mM dNTPs 2 µl 1 µM each oligo 83 µl sterile water 1.5 µl Pfu DNA polymerase (Stratagene, La Jolla, Calif.) 50 ng DNA (pPDM FL WT-1). The reaction was denatured at 96° C. for 2 minutes followed by 40 cycles of 96° C. for 20 seconds, 64° C. for 15 seconds, and 72° C. for 2 minutes, 30 seconds and a single, final extension of 4 minutes at 72° C.

The PCR products were digested with EcoRI and cloned into pTAT (a modified pET28 vector with a Twin Arginine Translocation (TAT) signal peptide from the TorA signal peptide in *E. coli* on the N-terminus; see J. Mol. Microbiol. (2000) 2(2): 179-189; Journal of Bacteriology, January 2001 p604-610 Vol 183, No 2; Journal of Biochemistry Vol 276, Mar. 16, 2001 pp 8159-8164) at the Eco72I and EcoRI sites. The sequences were confirmed through sequence analysis and then transformed into BLR (DE3) pLys S and HMS174 (DE3) pLysS cells. Expression of the WT1-TAT proteins was confirmed by Western analysis.

Example 35

The N-Terminus of WT1 is the Dominant In Vivo Immunogenic Portion of the Protein In this Example, mice were immunized with different protein constructs of WT-1, (F truncation (2-281) and full length (2-430) as described in Example 34)) formulated with MPL®-SE adjuvant. Improved CD4 responses were elicited by the truncated constructs relative to the full length protein. Thus, this example demonstrates that the N-terminal portion of the WT1 protein spanning from amino acid 2 to 281 is the dominant immunogenic portion of the WT1 protein in vivo.

Groups of four C57BL/6 mice were immunized subcutaneously with 20 µg WT-1 proteins: WT-1-F or WT-1 full length (FL), with Ra12, HIS or TAT fusions. Immunizations were performed at weeks 0, 3 and 9, and spleens were harvested at week 11. Splenocytes were then stimulated in vitro for 6 hours with medium alone, with a 15-mer peptide "p32" (ARMFPNAPYLPSCLE, amino acids 125-139 of WT-1; found within the p117-139 peptide set forth in SEQ ID NO:2), with the DC2.4-WT-1/LAMP cell line, or with rRa12. CD4 cells were then stained for intracellular interferon-gamma and quantified by FACS analysis. A portion of these splenocytes were then stimulated in vitro for 8 days, after which CD4+ IFN+ cells were enumerated. After the 6 hour stimulation with p32, 0.33% of CD4-positive cells were positive for intracellular IFN-gamma staining in mice immunized with the truncated N-terminal construct rWT1-F-TAT. By contrast, only 0.10% of CD4-positive cells stained positive for intracellular IFN-gamma in mice immunized with rWT1-FL-TAT. After the 8 day stimulation, mice immunized with the rWT1-F-TAT construct showed IFN-gamma staining in 10.72% of the CD4+ cells. By contrast, 0.24% of CD4-positive cells from mice immunized with the full-length WT1-TAT construct stained positive for intracellular IFN-gamma. These data indicate that improved CD4 responses were elicited by the truncated rWT1-TAT construct relative to the full-length rWT1-TAT construct.

In a second assay splenocytes were stimulated in vitro with the 23-mer peptide, p117-139 (SEQ ID NO:2; PSQASS-GQARMFPNAPYLPSCLE, containing a known CD4 epitope and encompassing "p32"), for 3 days, after which supernatants were assayed for secreted IFN-gamma by ELISA. There was no detectable IFN-gamma secretion from splenocytes from mice immunized with the full-length WT1 constructs. By contrast, an average of 2477 pg/ml IFN-gamma was detected from splenocytes from mice immunized with rWT1-F without a HIS tag. An average of 4658 pg/ml IFN-gamma was detected from splenocytes from mice immunized with rWT1-F-TAT. These data further support the observation that improved CD4 responses were elicited by the truncated N-terminal WT1 constructs relative to the full length protein.

The WT1 protein is a transcription factor which is composed of two functional domains: a proline-glutamine rich domain at the N-terminus, and a zinc finger domain composed of four zinc fingers at the C-terminus with homology to the EGR1/Sp1 family of transcription factors. WT1 is a self-protein. The C-terminus is homologous to other self-proteins and is thus less immunogenic, i.e. the subject of a greater degree of immunological tolerance. Of note, the 4 zinc-finger domains within the C-terminus have homology to EGR family members. The results described in this example indicate that tolerance will vary between different portions of a protein, possibly depending on sequence homologies and functional domains.

In summary, the data described in this example support the notion that the most efficient WT1 vaccine will comprise the WT1 N-terminus, either as a recombinant protein or gene-based construct.

Example 36

Baculovirus Expression Constructs for Expression of the N-Terminal Fragment of WT1 (WT-1-F: Amino Acids 1-281) and Large Scale Production of Protein Using Insect Cells The cDNA for the N-terminal fragment of WT-1, together with a Kozak consensus sequence, were obtained by PCR using the WT1-F plasmid as a template (WT-1-F: amino acids 2-281 of the WT1 protein cloned downstream of a start methionine; cDNA and amino acid sequence of 2-281 of WT1 are set forth in SEQ ID NOs:460 and 461, respectively. The pTAT fusion construct used as template in the experiments described herein is described in Example 34. The cDNA of this construct is set forth in SEQ ID NO:452). The following primers were used for amplification:

```
WT1F1 (SEQ ID NO: 466):
5' CGGCTCTAGAGCCGCCACCATGGGCTCCGACGTGCG

WT1RV4 (SEQ ID NO: 467):
5' CGGCTCTAGACTACTGAATGCCTCTGAAGACACCGTG
```

The cDNA for the same ORF plus a C-terminal 10 residue His Tag was obtained by PCR similarly as above except using WT1 RV3 (SEQ ID NO:468) as reverse primer (5' CGGCTCTAGACTAATGGTGATGGTGAT-GATGATGGTGATGATGCTGAATGCC TCTGAAGA-CACCGTG).

The purified PCR products were cloned into the Xba I site of the donor plasmid, pFastBac1. The recombinant donor plasmid pFBWT1-F (cDNA and amino acid sequences set forth in SEQ ID NOs:463 and 465, respectively) and pFBWT1-FH (with the 10×His Tag; cDNA and amino acid sequence set forth in SEQ ID NOs:462 and 464, respectively) were transformed into E. coli strain DH10Bac (Invitrogen, Carlsbad, Calif.) to make recombinant bacmids in E. coli through site-specific transposition. The recombinant bacmids were confirmed by PCR analysis and then transfected into Sf-9 insect cells to make recombinant baculoviruses BVWT1-F and BVWT1-FH. The recombinant viruses were amplified to high titer viral stock in Sf-9 cells.

The HIGH FIVE insect cell line was used to optimize conditions for the protein expression and for the large-scale production of the recombinant proteins. To optimize the conditions for protein expression, High 5 insect cell monolayers were infected with the recombinant baculoviruses BVWT1-F and BVWT1-FH at different multiplicities of infection (MOI) and harvested the transduced cells at different periods of time. The identities of the proteins were confirmed by Western blot analysis with a rabbit anti-WT1 polyclonal antibody [#942-32 (799L)]. Both WT1-F and WT1-FH recombinant proteins were well expressed at either 48 hours or 54 hours post-infection when HIGH FIVE cells were infected by the recombinant viruses at MOI 1.0 or 2.0.

The amplification of the recombinant baculoviruses and the expression of the recombinant WT1-F and WT1-FH proteins was then further optimized. Both BVWT1-F and BVWT1-FH were amplified in the Sf9 insect cell line in ESF921 medium containing 2% fatal calf serum and 0.5× PSF. The amplification was carried out for 4 days at MOI 0.05 at 28° C. The HIGH FIVE insect cell line was used to optimize conditions for the protein expression. High 5 insect cells were infected by the recombinant baculoviruses at MOIs of 0.5, 1 or 2 for 30, 48, 54, or 72 hours before harvesting. The identity of the recombinant protein was confirmed by Western blot analysis with a specific rabbit polyclonal antibody against WT1 (Antibody #942-32), and by capillary LC-ESI-tandem mass spectrometry. These experiments indicate that optimal protein expression for large scale production of WT1-F and WT1-FH occurs at 43 hours post-infection when HIGH FIVE cells were infected by the recombinant viruses at an MOI 0.5-1.0.

In summary, the above WT1 baculovirus can be used for large-scale protein production of the N-terminal portion of WT1 for use in a variety of vaccine strategies for the treatment of malignancies associated with WT1 expression.

Example 37

Induction of In Vivo CD4 and CD8 T Cell Responses in Mice Using Recombinant Tricom Vaccinia and Fowl Pox Vectors This example describes in vivo immunogenicity studies to evaluate vaccination strategies with WT1 in mice. The purpose of these experiments was to test the ability to rV-WT1/TRICOM® and rF-WT1/TRICOM® to induce immunity, in particular T cell immunity, to WT1. The results described herein provide support for the use of TRICOM® vaccinia and fowlpox vectors expressing WT1 and containing a triad of costimulatory molecules (B7-1, ICAM-1 and LFA-3) in vaccine strategies for treating cancers associated with WT1 expression.

In the first study, C57BI/6 mice (12 mice per group) were immunized two or three times with 14 days between the primary, secondary and tertiary immunizations as shown below in Table 1. Mice were harvested at 21 days following the secondary and tertiary immunizations. CD8 and CD4 T cell responses were assayed by IFN-γ intracellular cytokine staining of WT1-peptide activated spleen cells as described in further detail below. CD4 T cell responses were additionally assayed by IFN-γ release from rWT1 protein stimulated spleen cells. Serum $IgG_1$ and $IgG_{2b}$ antibody responses were assayed by ELISA. T cell responses were evaluated using pooled splenocyte cultures (4 mice/group/time point). Antibody titers were determined for individual mice (4 mice/group/time point).

TABLE 1

| Vaccination Strategy |
|---|
| Groups: |
| A. Non-immune |
| B. rWT1 + SE-Vehicle |
| C. rWT1 + MPL ®-SE |
| D. 1°: WT1-DNA, 2°: WT1-DNA, 3°: WT1-Adeno |
| E. rF-WT1/TRICOM ® |
| F. 1°: rV-WT1/TRICOM ®, 2°: rF-WT1/TRICOM ®, 3°: rF-WT1/TRICOM ® |
| Dose: |
| rWT1: 50 ug |
| MPL ®-SE: 10 ug |
| WT1-DNA: 100 ug |
| WT1-Adeno: 5 × $10^5$ pfu |
| rF-WT1/TRICOM ®: 1 × $10^8$ pfu |
| rV-WT1/TRICOM ®: 1 × $10^8$ pfu |
| Route: |
| Subcutaneous (200 ul) immunization for protein/adjuvant and vectors. |
| Intramuscular immunization (50 ul) for WT1-DNA. |

The full-length cDNA of the splice variant of WT1 used in these studies is set forth in SEQ ID NO:381. The WT1-adenovirus used herein is as described in Example 20. The rF-WT1/TRICOM® recombinant fowlpox and the rV-WT1/TRICOM® recombinant vaccinia vectors both expressing WT1 and containing a triad of costimulatory molecules (B7-1, ICAM-1 and LFA-3) were generated by Therion Biologics (Cambridge, Mass., USA).

To evaluate T cell responses, splenocytes were stimulated in vitro with WT1 peptide "p32" (ARMFPNAPYLPSCLE [SEQ ID NO:509], amino acids 125-139 of WT-1; found within the p117-139 peptide set forth in SEQ ID NO:2) known to contain a CTL and a helper T cell epitope. Intracellular cytokine staining for IFN-γ of p125-139 activated splenocytes at 21 days following the secondary immunization showed a significant percentage WT1 responsive CD4$^+$ and CD8$^+$ T cells in mice immunized with rV-WT1/TRICOM® (prime) and rF-WT1/TRICOM® (boost) whereas no other groups showed significant WT1 specific T cell immune responses. Note that the DNA group was primed and boosted with DNA only. The same group subsequently had an rWT1-Adv tertiary immunization.

Following tertiary immunization, responses to pools of overlapping 15-mer peptides were evaluated rather than responses to the single peptide #32. WT1 peptide CD8$^+$ and CD4$^+$ T-cells specific for peptide pool #32-36 were found to respond at levels similar to the responses following secondary immunization in mice vaccinated with rV-WT1/TRICOM® (prime) and rF-WT1/TRICOM® (boost X2). In addition, CD4$^+$ and CD8$^+$ T-cells from these mice were found to respond, albeit at a much lower level than peptide #32, to a second WT1 epitope contained within two overlapping 15-mer peptides #57-58 (Peptide 57: DNLYQMTSQLECMTWN (amino acids 224-239; SEQ ID NO:510); Peptide 58: MTSQLECMTWNQMNL (amino acids 229-243; SEQ ID NO:511; overlap corresponds to amino acid residues 224-243 of WT1).

Antibody responses were evaluated using a standard ELISA. Low levels of serum IgG$_{2b}$ antibodies to WT1 were measurable in all 8 mice 21 days post secondary immunization (titer of 1:1350) and 21 days post tertiary immunization (titer of 1:3325) in mice immunized with rWT1+MPL®-SE. By contrast, in all other groups serum IgG$_{2b}$ antibodies titers were <1:100 (Table 2).

TABLE 2

Antibody Responses in WT1-Immunized Mice

| | Serum Titers* | | | |
|---|---|---|---|---|
| | Secondary | | Tertiary | |
| Group | IgG$_1$ | IgG$_{2b}$ | IgG$_1$ | IgG$_{2b}$ |
| Non-immune | ND | ND | ND | ND |
| WT1 + Vehicle-SE | <75 | <100 | 475 | <50 |
| WT1 + MPL ®-SE | <50 | 1350 | 338 | 3325 |
| WT1-DNA, WT1-DNA, WT1-Adeno | ND | ND | ND | ND |
| rF-WT1/TRICOM ® | ND | ND | <50 | <50 |
| rV-WT/TRICOM ®, rFWT1/TRICOM ® | ND | <50 | <50 | ND |

*Serum titers are the average of 4 mice per group. Titers written as <50, <75, or <100 were also averages, but in all instances less than 4 mice had detectable titers.
ND indicates antibody was not detected in any of the mice.

In summary, immunization of C57Bl/6 mice with rV-WT1/TRICOM® (prime) followed by rF-WT1/TRICOM® (boost) or by WT1-DNA (prime) followed by WT1-Adeno (boost) elicited both CD8 and CD4 T cell responses against WT1. The T cell responses to rV-WT1/TRICOM® followed by rF-WT1/TRICOM® versus WT1-DNA followed by WT1-Adeno were equivalent within the power of the experimental design. Without being bound by theory, a major advantage of rF-WT1/TRICOM® is that multiple boosts can continue to increase the level of immunity. Thus, these studies further confirm the immunogenicity of the WT1 protein and provide support for the use of WT1 DNA/adenovirus or rv-WT1/TRICOM®/rF-WT1/TRICOM® immunization regimens in vaccine strategies for treating cancers associated with WT1 expression.

Example 38

Construction of the Stumpy-WT1-F Vector for Expression of WT1-F in *E. Coli*

This example describes the construction of an expression vector containing a truncated twin arginine translocator (TAT) signal peptide fused to the WT1-F reading frame (2-281 N-terminal portion of the WT1 protein). This vector can be used to produce a single species truncated TAT-WT1-F protein for use in immunization strategies for the treatment of malignancies associated with expression of WT1.

As described previously in Example 34, the TAT signal sequence was used to make various WT1 vectors. When these TAT vectors were used in expression, multiple forms of the protein were observed. N-terminal sequencing of these forms showed that each of the three separate proteins being expressed were truncations of the TAT peptide. These cleavages were occurring at each of the twin arginine sites. Thus, a truncated TAT vector was constructed to shorten the TAT signal peptide from 39 amino acids to 12 amino acids to avoid generation of these cleavage products during expression. The TAT "Stumpy" vector was generated by maintaining the first 12 residues of the TAT signal peptide up to the first twin arginine. This vector was constructed as follows:

The following pairs of oligonucleotides were combined and then annealed.

```
Pair 1:
Stumpy 1 (SEQ ID NO: 486):
5' tatgaacaataacgatctgtttcaggc 3'

Stumpy 3 (SEQ ID NO: 487):
5' CTGAAACAGATCGTTATTGTTCA 3'

Pair 2:
Stumpy 4 (SEQ ID NO: 488):
5' aattcttggtcattcacgtggcggctcgc 3'

Stumpy 2 (SEQ ID NO: 489):
5' gagccgccacgtgaatgaccaag 3'
```

The pairs were then ligated together with pPDM, a modified pET28 vector, that had been digested with NdeI and EcoRI. The resulting plasmid, pStumpy, is set forth in SEQ ID NO:471. The amino acid sequence of the truncated TAT protein is set forth in SEQ ID NO:506. The full-length TAT polynucleotide is set forth in SEQ ID NO:503 and encodes the amino acid sequence of the TAT polypeptide set forth in SEQ ID NO:504.

The pStumpy vector was then used to construct the Stumpy-WT1-F vector to express the N-terminal portion of WT1 without cleavage products. The Stumpy-WT1-F vector was constructed as follows:

The coding region of WT1-F was PCR amplified with the following primer set:

PDM-1005 (SEQ ID NO: 484):
5' GGCTCCGACGTTCGGGACCTGAACGCACTG 3'

PDM-1004 (SEQ ID NO: 485):
5' CTGCAGAATTCATCACTGAATGCCTCTGAAG 3'

The amplification reaction contained 10 ul 10×Pfu buffer, 1 ul 10 mM dNTPs, 2 ul each 10 uM primer, 83 ul sterile water, and 1.5 ul Pfu DNA polymerase (Stratagene, La Jolla, Calif.). The reaction was first denatured for 2 minutes at 96° C. followed by 40 cycles of 96° C. for 20 seconds, 63° C. for 15 seconds, and 72° C. for 30 seconds. The reaction was then extended for a final extension of 72° C. for 4 minutes.

The PCR product was then digested with EcoRI and cloned into the pStumpy vector that had been digested with Eco72I and EcoRI. The construct was confirmed through sequence analysis and then transformed into BLR (DE3) pLys S cells. The resulting truncated TAT WT1-F fusion protein expressed as a single species. The polynucleotide sequence of the coding region of pStumpy WT1-F is set forth in SEQ ID NO:469 which encodes the amino acid sequence set forth in SEQ ID NO:470.

Example 39

Construction of WT1-F GMP, WT1-G, and WT1-Delta G Vectors for Expression in *E. Coli*

This example describes the construction of WT1-F, WT1-G, and WT1-Delta G vectors optimized for protein production in *E. coli*.

The TAT WT-1 F DNA sequence was codon optimized and synthetically engineered by Blue Heron Biotechnology (Bothel, Wash.) to be optimized for expression in *E. coli*. This codon optimized cDNA sequence of WT1-F is set forth in SEQ ID NOs:477 and encodes the amino acid sequence set forth in SEQ ID NO:479. The plasmid containing this sequence was then digested with NdeI and EcoRI and sub-cloned into a modified pET28 vector that had been digested with NdeI and EcoRI for expression in *E. coli*. This construct was confirmed to be correct by DNA sequence analysis and then transformed into BLR (DE3) pLys S cells for expression. This construct is a purely synthetic traceable source of TAT WT1-F template DNA.

The codon optimized sequence was then used as template for PCR to delete a proline rich region of fourteen amino acids from the N-terminal region (deletion of amino acids 54-67 of WT-1 F sequence set forth in SEQ ID NO:461; corresponding to amino acids 55-68 of full-length WT1), creating the WT-1 G cDNA sequence set forth in SEQ ID NO:473 which encodes the amino acid sequence set forth in SEQ ID NO:478. This was done by first generating the pTAT-WT-1 G construct as follows:

The 5' coding region of WT-1 G was PCR amplified using the following primer set:

PDM-1007
(SEQ ID NO: 490)
5' caagcgctcatgagcccgaagtggcgagcc 3' Tm 76° C.

PDM-1006
(SEQ ID NO: 491)
5' cataaatttgcccgggcccgcccagagagccg 3' Tm 76° C.

The 3' coding region of the WT-1 G region was PCR amplified using the following primer set:

PDM-1008
(SEQ ID NO: 492)
5' cattcattcatcaaacaggagcc 3' Tm 61° C.

PDM-1009
(SEQ ID NO: 493)
5' ccattaagaattcatcactgaataccc 3' Tm 60° C.

The PCR reaction for amplification of WT1-G contained 10 ul 10×Pfu buffer, 1 ul 10 mM dNTPs, 2 ul each 10 uM primer, 83 ul sterile water, 1.5 ul Pfu DNA polymerase (Stratagene, La Jolla, Calif.), and 50 ng DNA template (pTAT WT1-F codon optimized as set forth in SEQ ID NO: 477). The reaction was first denatured for 2 minutes at 96° C. followed by 40 cycles of 96° C. for 20 seconds, 63° C. for 15 seconds, and 72° C. for 30 seconds. The reaction was then extended for a final extension of 72° C. for 4 minutes.

The first PCR product was then digested with XbaI and cloned into pPDM (a modified pET28 vector) that had been digested with XbaI and Eco72I. The resulting construct (pTAT WT1-GA) was then digested with SrfI and EcoRI. The second PCR construct was digested with EcoRI and cloned into the pTAT WT1-GA plasmid construct. At the same time a three-way ligation was carried out by digesting the first PCR construct with XbaI and SrfI and digesting the second PCR construct with EcoRI and cloning into pPDM that had been digested with XbaI and EcoRI. The resulting pTAT-WT1-G construct was confirmed to be correct through sequence analysis and then transformed into an expression host. The cDNA of pTAT-WT1-G is set forth in SEQ ID NO:475 and encodes the amino acid sequence of SEQ ID NO:482.

Due to incomplete SrfI digestion during the second method described above, an unexpected form of WT-1 G (WT-1 Delta G was created that deleted 14 amino acids (amino acids 55-68 of WT-1 F) and added three additional amino acids (WT-1 Delta G polynucleotide sequence set forth in SEQ ID NO:505 which encodes the polypeptide sequence set forth in SEQ ID NO:502). This TAT WT-1 Delta G construct resulted in an unexpected 5-fold over expression as compared to the TAT WT-1 F constructs. The cDNA of the pTAT-WT1 Delta G construct is set forth in SEQ ID NO:476 and encodes the amino acid sequence set forth in SEQ ID NO:481.

Following generation of the pTAT-WT-1 G, pStumpy-WT1 G and WT1-G with and without a His tag were constructed using the pTAT-WT1 G as a template in the PCR reactions described below.

The coding region of the WT1-G region was PCR amplified using the following primer sets:

PCR 1:
PDM-1010
(SEQ ID NO: 494)
5' ggttcggatgtacgcgatctgaacg 3' Tm 68° C.

PDM-1011
(SEQ ID NO: 495)
5' caaagaattcatcactgaataccgcg 3' Tm 63° C.

PCR 2:
PDM-1023
(SEQ ID NO: 496)
5' gcttttggcatatgggttcggatgtacgcgatc 3' Tm 71° C.

PDM-1011
(SEQ ID NO: 497)
5' caaagaattcatcactgaataccgcg 3' Tm 63° C.

The PCR reaction and amplification conditions were as described above using the pTAT-WT1 G set forth in SEQ ID NO:475 as template. The first PCR product was digested with EcoRI and cloned into pPDM (a modified pET28 vector with a his tag in-frame) and pSTUMPY (a modified pET28 vector with a 12 amino acid truncated TAT leader peptide in frame set forth in SEQ ID NO:471) that were digested with EcoRI and Eco72I. The second PCR product was digested with NdeI and EcoRI and cloned into a modified pET28 vector (pPDM) that had been digested with NdeI and EcoRI. The constructs were confirmed to be correct through sequence analysis and then transformed into an expression host. The resulting constructs are as follows: The polynucleotide of WT1-G with His tag is set forth in SEQ ID NO:472 and encodes the amino acid sequence set forth in SEQ ID NO:480. The polynucleotide of WT1-G without His tag is set forth in SEQ ID NO:473 which encodes the amino acid sequence set forth in SEQ ID NO:478. The pStumpy-WT1-G polynucleotide sequence is set forth in SEQ ID NO:474 and encodes the amino acid sequence set forth in SEQ ID NO:483.

In a related experiment, the pStumpy WT-1 F GMP (codon optimized) vector was constructed as follows:

The coding region of the WT-1 F region was amplified using the following primers

```
PDM-1010
                                         (SEQ ID NO: 500)
5' ggttcggatgtacgcgatctgaacg 3' Tm 68° C.

PDM-1011
                                         (SEQ ID NO: 501)
5' caaagaattcatcactgaataccgcg 3' Tm 63° C.
```

The PCR reaction and amplification conditions were as described above using pTAT WT-1F GMP as template. The PCR product was digested with EcoRI and cloned into the pStumpy vector described in Example 38 that was digested with EcoRI and Eco72I. The construct was confirmed to be correct through sequence analysis and then transformed into an expression host. The polynucleotide sequence of pStumpy WT-1 F GMP is set forth in SEQ ID NO:498 which encodes the amino acid sequence of SEQ ID NO:499.

In summary, the expression vectors described herein can be used for optimal expression and production of WT1, truncated WT1, and WT1 fusion proteins for use in vaccine strategies for the treatment of malignancies associated with expression of WT1.

Example 40

Construction of an Adenovirus Vector Expressing Human WT1-F

WT1-F including a start codon (the DNA sequence of WT1-F including the start codon is set forth in SEQ ID NO:508) was cloned into an E1 and E3 deleted adenovirus serotype 5 vector. The resulting adenovirus vector is set forth in SEQ ID NO:507. The expression of WT1-F is controlled by the CMV promoter mediating high levels of WT1-F protein expression. Infection of human cells with this reagent leads to a high level of expression of the WT1-F protein. The antigenic nature of the adenoviral proteins introduced into the host cell during and produced at low levels subsequent to infection can act to increase immune surveillance and immune recognition of WT1 as an immunological target. This vector can be also used to generate immune responses against the WT1 protein when innoculated into mammalian subjects. If these subjects are positive for WT1 expressing tumor cells the immune response could have a therapeutic or curative effect on the course of the disease.

Example 41

CTL Responses in HLA-A2 Transgenic Mice WITH WT-1 Protein Plus Various Adjuvants Groups of four HLA-A2/Kb transgenic mice were immunized intradermally three times at three week intervals with 20 µg of WT1-F truncation protein (see Example 35) admixed with one of the following adjuvants, 10 µg RC-529™-SE, 10 µg ENHANZYN®, or 10 µg RC-529™-AF+10 µg QuilA. A positive control group were immunized twice with WT1-F DNA followed by a boost with $10^7$ PFU adenovirus encoding WT1-F (see example 40). Mice were sacrificed 2 weeks after the final immunization and CTL were measured. Spleens were harvested and stimulated in vitro with CD.24-A2 Kb-WT-1-LAMP cells (see Example 18) and assayed against Jurkat A2Kb cells expressing full length WT1-F or pulsed with WT-1 CD8 epitope peptides (p10-18 (ALLPAVPSL, SEQ ID NO:451), p32 (ARMFPNAPYLPSCLE [SEQ ID NO:509], aa 125-139 found within p117-139 SEQ ID NO:2, and WT1 p37-45 peptide (VLDFAPPGA, human WT1 residues 37-45; SEQ ID NO:241). A standard chromium release assay was used to assay for CTL activity. As observed in previous experiments, immunization with WT1 DNA followed by adenoviral boost elicited a WT1-specific CTL response in HLA-A2 transgenic mice. CTL responses were also detected from the spleens of mice immunized with WT1-F protein in combination with ENHANZYN®, RC-529™-SE and the combination of RC-529™-AF and QuilA. The magnitude of the responses induced was comparable to that seen in the DNA-Adenovirus immunization.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polynucleotide encoding a polypeptide comprising an amino acid sequence selected from the group consisting of SEQ ID Nos:470, 479, 480, 481, 482, and 483.

2. The isolated polynucleotide of claim 1 wherein the polynucleotide has been codon optimized for expression in *E. coli*.

3. The isolated polynucleotide of claim 1 wherein the polynucleotide comprises a sequence selected from the group consisting of SEQ ID NO:469, SEQ ID NO:471, SEQ ID NO:472, SEQ ID NO:473, SEQ ID NO:474, SEQ ID NO:475, SEQ ID NO:476, SEQ ID NO:477, SEQ ID NO:503, and SEQ ID NO:505.

4. A pharmaceutical composition comprising the isolated polynucleotide of claim 1 and a pharmaceutically acceptable carrier or excipient.

5. An expression vector comprising the isolated polynucleotide of claim 1 operably linked to an expression control sequence.

6. A host cell transformed or transfected with the expression vector according to claim 5.

7. An isolated polynucleotide encoding a polypeptide comprising SEQ ID NO:470.

8. The isolated polynucleotide according to claim 7 wherein the polynucleotide has been codon optimized for expression in *E. coli*.

9. The isolated polynucleotide according to claim 7 wherein the polynucleotide comprises a sequence selected from the group consisting of SEQ ID NO:469 and SEQ ID NO:471.

10. A pharmaceutical composition comprising the isolated polynucleotide according to claim 7 and a pharmaceutically acceptable carrier or excipient.

11. An expression vector comprising the isolated polynucleotide according to claim 7 operably linked to an expression control sequence.

12. A host cell transformed or transfected with the expression vector according to claim 11.

13. An isolated polynucleotide encoding a polypeptide comprising SEQ ID NO:479.

14. The isolated polynucleotide according to claim 13 wherein the polynucleotide has been codon optimized for expression in *E. coli*.

15. The isolated polynucleotide according to claim 13 wherein the polynucleotide comprises SEQ ID NO:477.

16. A pharmaceutical composition comprising the isolated polynucleotide according to claim 13 and a pharmaceutically acceptable carrier or excipient.

17. An expression vector comprising the isolated polynucleotide according to claim 13 operably linked to an expression control sequence.

18. A host cell transformed or transfected with the expression vector according to claim 17.

* * * * *

UNITED STATES PATENT AND TRADEMARK OFFICE
CERTIFICATE OF CORRECTION

PATENT NO. : 7,915,393 B2  
APPLICATION NO. : 12/470408  
DATED : March 29, 2011  
INVENTOR(S) : Alexander Gaiger et al.

Page 1 of 1

It is certified that error appears in the above-identified patent and that said Letters Patent is hereby corrected as shown below:

Title Page 4  
Item 56:  
"Genbank Database, Accession No. 574529, May 16, 1995." should read, --Genbank Database, Accession No. S74529, May 16, 1995.--.

Signed and Sealed this  
Fourth Day of October, 2011

David J. Kappos  
*Director of the United States Patent and Trademark Office*